US009963448B2

(12) United States Patent
Devraj et al.

(10) Patent No.: US 9,963,448 B2
(45) Date of Patent: May 8, 2018

(54) BICYCLIC INHIBITORS OF PAD4

(71) Applicant: Padlock Therapeutics, Inc., Princeton, NJ (US)

(72) Inventors: Rajesh Devraj, Chesterfield, MO (US); Gnanasambandam Kumaravel, Lexington, MA (US); Michael F. Parker, Higganum, CT (US); Edward Beaumont, Abingdon (GB); Lee Bowles, Abingdon (GB); Steve Bromidge, Abingdon (GB); Sophie Cooper, Abingdon (GB); Elise Gadouleau, Abingdon (GB); Laura Gleave, Abingdon (GB); Philip Kerry, Abingdon (GB); Adrian Kotey, Abingdon (GB); Thomas Krulle, Abingdon (GB); Cristina Lecci, Abingdon (GB); Pui Loke, Abingdon (GB); Mirco Meniconi, Abingdon (GB); Nat Monck, Abingdon (GB); Carl North, Abingdon (GB); Jordan Palfrey, Abingdon (GB); Shelley Parrott, Abingdon (GB); Mark Ridgill, Abingdon (GB); Heather Tye, Abingdon (GB)

(73) Assignee: Padlock Therapeutics, Inc., Princeton, NJ (US)

( * ) Notice: Subject to any disclaimer, the term of this patent is extended or adjusted under 35 U.S.C. 154(b) by 0 days. days.

(21) Appl. No.: 15/374,159

(22) Filed: Dec. 9, 2016

(65) Prior Publication Data
US 2017/0166565 A1 Jun. 15, 2017

Related U.S. Application Data

(60) Provisional application No. 62/264,925, filed on Dec. 9, 2015.

(51) Int. Cl.
| | | |
|---|---|---|
| *A61K 31/4184* | (2006.01) |
| *C07D 471/04* | (2006.01) |
| *A61K 31/437* | (2006.01) |
| *A61K 31/439* | (2006.01) |
| *A61K 31/519* | (2006.01) |
| *A61K 31/5383* | (2006.01) |
| *C07D 403/14* | (2006.01) |
| *C07D 519/00* | (2006.01) |

(52) U.S. Cl.
CPC ........ *C07D 471/04* (2013.01); *A61K 31/4184* (2013.01); *A61K 31/437* (2013.01); *A61K 31/439* (2013.01); *A61K 31/519* (2013.01); *A61K 31/5383* (2013.01); *C07D 403/14* (2013.01); *C07D 519/00* (2013.01)

(58) Field of Classification Search
CPC .......... C07D 471/04; A61K 31/4184
See application file for complete search history.

(56) References Cited

U.S. PATENT DOCUMENTS

| 6,897,208 B2 | 5/2005 | Edwards et al. |
| 7,622,592 B2 | 11/2009 | Kim et al. |
| 8,288,425 B2 | 10/2012 | Edwards et al. |
| 2004/0048868 A1 | 3/2004 | Edwards et al. |
| 2006/0036098 A1 | 2/2006 | Kim et al. |
| 2011/0052562 A1 | 3/2011 | Feng et al. |
| 2014/0005183 A1 | 1/2014 | Galatsis et al. |

FOREIGN PATENT DOCUMENTS

| JP | 2012193149 A2 | 10/2012 |
| WO | WO-2013052263 A2 | 4/2013 |
| WO | WO-2013157021 A1 | 10/2013 |
| WO | WO-2013186229 A1 | 12/2013 |
| WO | WO-2014015905 A1 | 1/2014 |
| WO | WO-2016185279 A1 | 11/2016 |

OTHER PUBLICATIONS

Berge et al., "Pharmaceutical Salts," Journal of Pharmaceutical Sciences, vol. 66, No. 1, Jan. 1977 (pp. 1-19).
Brinkmann et al., "Neutrophil extracellular traps kill bacteria," Science vol. 303, No. 5663, Mar. 2004 (pp. 1532-1535).
Chang et al., "Increased PADI4 expression in blood and tissues of patients with malignant tumors," BMC Cancer, vol. 9, No. 40, Jan. 2009 (11 pages).
Chumanevich et al., "Suppression of colitis in mice by Cl-amidine: a novel peptidylarginine deiminase inhibitor," American Journal of Physiology. Gastrointestinal and Liver Physiology, vol. 300, No. 6, Jun. 2011 (pp. G929-G938).
Clark et al., "Platelet TLR4 activates neutrophil extracellular traps to ensnare bacteria in septic blood," Nature Medicine, vol. 13, No. 4, Apr. 2007 (pp. 463-469).
Dworski et al., "Eosinophil and neutrophil extracellular DNA traps in human allergic asthmatic airways," The Journal of Allergy and Clinical Immunology, vol. 127, No. 5, May 2011 (pp. 1260-1266).
Fuchs et al., "Extracellular DNA traps promote thrombosis," The Proceedings of the National Academy of Sciences U.S.A., vol. 107, No. 36, Sep. 2010 (pp. 15880-15885).
Hakkim et al., "Impairment of neutrophil extracellular trap degradation is associated with lupus nephritis," The Proceedings of the National Academy of Sciences U.S.A., vol. 107, No. 21, May 2010 (pp. 9813-9818).
International Search Report and Written Opinion issued by the United States Patent and Trademark Office as International Searching Authority for International Application No. PCT/US2016/065857 dated Apr. 17, 2017 (10 pages).
Jones et al., "Protein arginine deiminase 4 (PAD4): Current understanding and future therapeutic potential," Current Opinion in Drug Discovery & Development, vol. 12, No. 5, Sep. 2009 (pp. 616-627).
Kessenbrock et al., "Netting neutrophils in autoimmune small-vessel vasculitis," Nature Medicine, vol. 15, No. 6, Jun. 2009 (pp. 623-625).

(Continued)

*Primary Examiner* — Rebecca L Anderson
*Assistant Examiner* — Karen Cheng
(74) *Attorney, Agent, or Firm* — Andrea L.C. Reid; Dechert LLP

(57) ABSTRACT

The present invention provides compounds useful as inhibitors of PAD4, compositions thereof, and methods of treating PAD4-related disorders.

20 Claims, No Drawings

(56) References Cited

OTHER PUBLICATIONS

Kochi et al., "*PADI4* polymorphism predisposes male smokers to rheumatoid arthritis," Annals of the Rheumatic Diseases, vol. 70, No. 3, Mar. 2011 (pp. 512-515).

Lange et al., "Protein deiminases: new players in the developmentally regulated loss of neural regenerative ability," Developmental Biology, vol. 355, No. 2, Jul. 2011 (pp. 205-214).

Lewis et al., "Inhibition of PAD4 activity is sufficient to disrupt mouse and human NET formation," Nature Chemical Biology, vol. 11, No. 3, Jan. 26, 2015 (pp. 189-191).

Li et al., "PAD4 is essential for antibacterial innate immunity mediated by neutrophil extracellular traps," The Journal of Experimental Medicine, vol. 207, No. 9, Aug. 2010 (1853-1862).

Li et al., "Regulation of p53 Target Gene Expression by Peptidylarginine Deiminase 4," Molecular and Cellular Biology, vol. 28, No. 15, Aug. 2008 (pp. 4745-4758).

Lin et al., "Mast cells and neutrophils release IL-17 through extracellular trap formation in psoriasis," The Journal of Immunology, vol. 187, No. 1, Jul. 2011 (pp. 490-500).

Neeli et al., "Histone Deimination as a Response to Inflammatory Stimuli in Neutrophils," The Journal of Immunology, vol. 108, No. 3, Feb. 2008 (pp. 1895-1902).

PubChem, "Substance Record for SID 1730220505," retrieved from <http://pubchem.ncbi/nlm.nih.gov/substance/173022050#section=Top> accessed on Mar. 24, 2017 (5 pages).

Savchenko et al., "Long pentraxin 3 (PTX3) expression and release by neutrophils in vitro and in ulcerative colitis," Pathology International, vol. 61, No. 5, May 2011 (pp. 290-297).

Slack et al., "Protein Arginine Deiminase 4: a target for an epigenetic cancer therapy," Cellular and Molecular Life Sciences, vol. 68, No. 4, Feb. 2011 (pp. 709-720).

Villanueva et al., "Netting neutrophils induce endothelial damage, infiltrate tissues, and expose immunostimulatory molecules in systemic lupus erythematosus," The Journal of Immunology, vol. 187, No. 1, Jul. 2011 (pp. 538-552).

Vitkov et al., "Neutrophil Fate in Gingival Crevicular Fluid," Ultrastructural Pathology, vol. 34, No. 1, Jan. 2010 (6 pages).

Wegner et al., "Autoimmunity to specific citrullinated proteins gives the first clues to the etiology of rheumatoid arthritis," Immunological Reviews, vol. 233, No. 1, Jan. 2010 (pp. 34-54).

Willis et al., "N-α-Benzoyl-N5-(2-Chloro-1-Iminoethyl)-L-Ornithine Amide, a Protein Arginine Deiminase Inhibitor, Reduces the Severity of Murine Collagen-Induced Arthritis," The Journal of Immunology, vol. 186, No. 7, Apr. 2011 (pp. 4396-4404).

BICYCLIC INHIBITORS OF PAD4

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, *Curr. Opin. Drug Discov. Devel.*, 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an autoimmune disease affecting approximately 1% of the population (Wegner N. et al, *Immunol. Rev.*, 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, *Ann. Rheum. Dis.*, 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrullination and is deficient in PAD4 knockout mice (Neeli I. et al, *J. Immunol.*, 180, (2008), 1895-1902 and Li P. et al, *J. Exp. Med.*, 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, *Nat. Med.*, 15(6), (2009), 623-625), systemic lupus erythematosus (Hakkim A. et al, *Proc. Natl. Acad. Sci. USA*, 107(21), (2010), 9813-9818 and Villanueva E. et al, *J. Immunol.*, 187(1), (2011), 538-52), ulcerative colitis (Savchenko A. et al, *Pathol. Int.*, 61(5), (2011), 290-7), cystic fibrosis, asthma (Dworski R. et al, *J. Allergy Clin. Immunol.*, 127(5), (2011), 1260-6), deep vein thrombosis (Fuchs T. et al, *Proc. Natl. Acad. Sci. USA*, 107(36), (2010), 15880-5), periodontitis (Vitkov L. et al, *Ultrastructural Pathol.*, 34(1), (2010), 25-30), sepsis (Clark S. R. et al, *Nat. Med.*, 13(4), (2007), 463-9), appendicitis (Brinkmann V. et al, *Science*, 303, (2004), 1532-5), and stroke. In addition, there is evidence that NETs may contribute to pathology in diseases affecting the skin, eg in cutaneous lupus erythematosus (Villanueva E. et al, *J. Immunol.*, 187(1), (2011), 538-52) and psoriasis (Lin A. M. et al., *J. Immunol.*, 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, *J. Immunol.*, 186(7), (2011), 4396-4404), dextran sulfate sodium (DSS)-induced experimental colitis (Chumanevich A. A. et al, *Am. J. Physiol. Gastrointest. Liver Physiol.*, 300(6), (2011), G929-G938), spinal cord repair (Lange S. et al, *Dev. Biol.*, 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, *Cell. Mol. Life Sci.*, 68(4), (2011), 709-720). Over-expression of PAD4 has been demonstrated in numerous cancers (Chang X. et al, *BMC Cancer*, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, *Mol. Cell Biol.*, 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formula I are useful as inhibitors of PAD4:

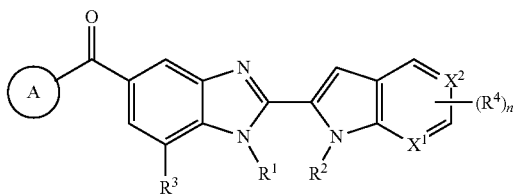

or a pharmaceutically acceptable salt thereof, wherein each of Ring A, $R^1$, $R^2$, $R^3$, $R^4$, $X^1$, and $X^2$ is as defined herein.

It has also been found that compounds of formula I' are useful as inhibitors of PAD4:

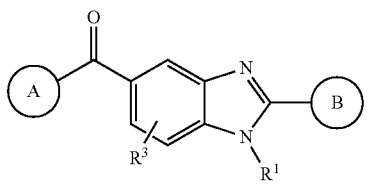

or a pharmaceutically acceptable salt thereof, wherein each of Ring A, Ring B, $R^1$, and $R^3$ is as defined herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosis, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of formula I:

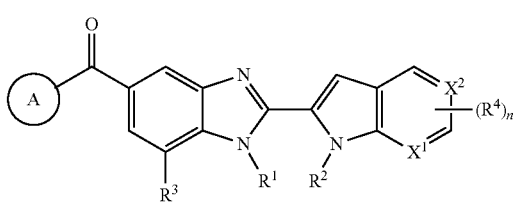

or a pharmaceutically acceptable salt thereof, wherein:

Ring A is

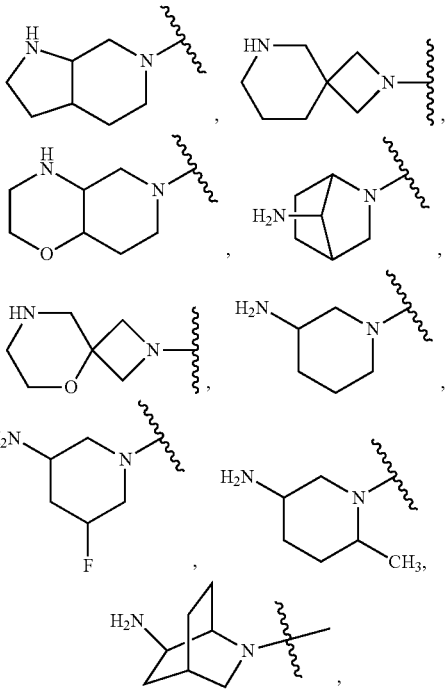

wherein Ring A is optionally substituted with 1-4 groups selected from fluorine, —CN, —OR, or $C_{1-6}$ aliphatic optionally substituted with 1-3 fluorine atoms;

$R^1$ is hydrogen, —CN, —OR, or $C_{1-6}$ aliphatic optionally substituted with 1-4 groups selected from fluorine, —CN, or OR;

$R^2$ is hydrogen or $C_{1-10}$ aliphatic optionally substituted with 1-5 groups selected from fluorine, —CN, or —OR;

each of $X^1$ and $X^2$ is independently selected from N or $C(R^4)$;

each of $R^3$ and $R^4$ is independently halogen, —CN, —R, or —OR;

n is 0-4; and each R is independently hydrogen or $C_{1-6}$ aliphatic optionally substituted with 1-3 fluorine atoms.

In some embodiments, such compounds include those of the formulae described herein, or a pharmaceutically acceptable salt thereof, wherein each variable is as defined herein and described in embodiments. Such compounds have the structure of formula I':

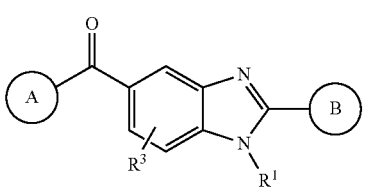

or a pharmaceutically acceptable salt thereof, wherein:
Ring A is
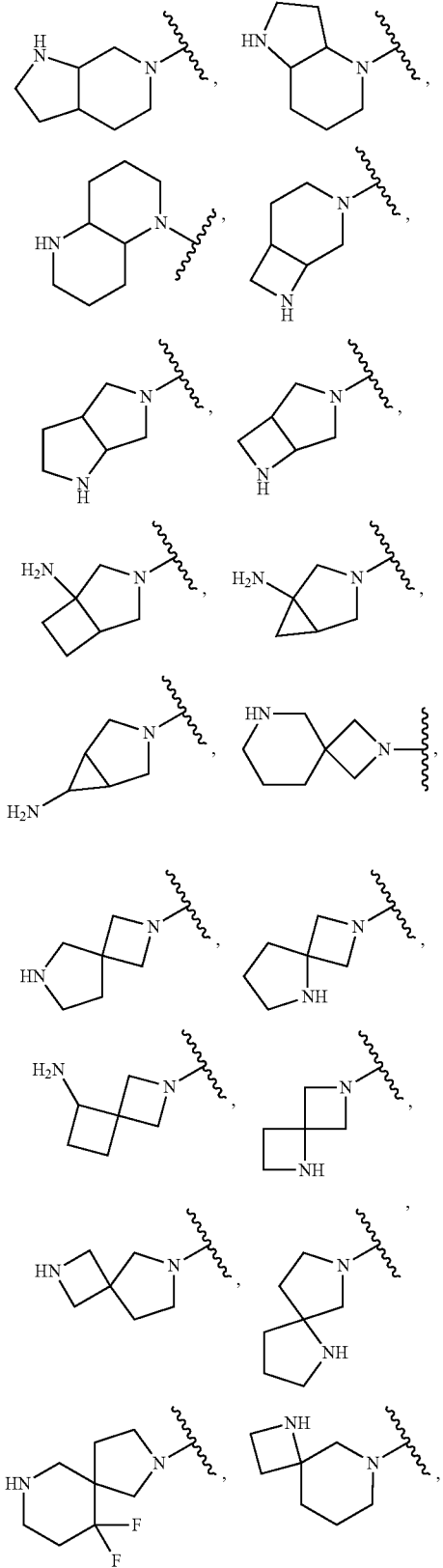
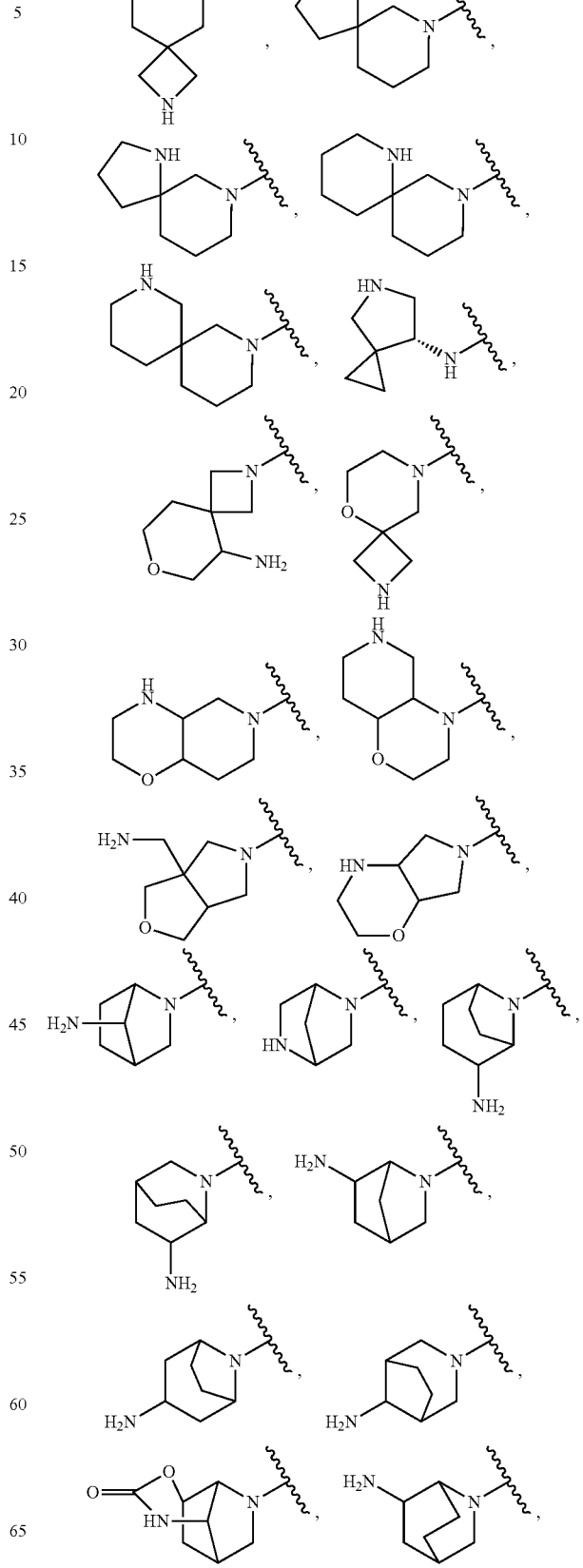

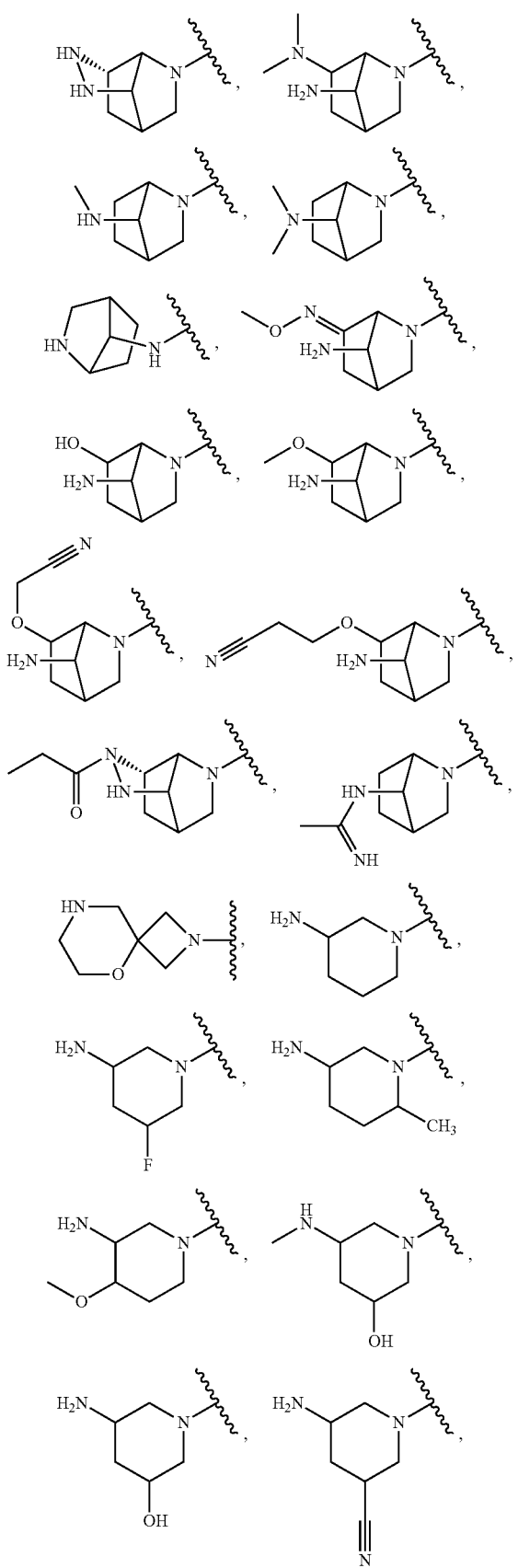
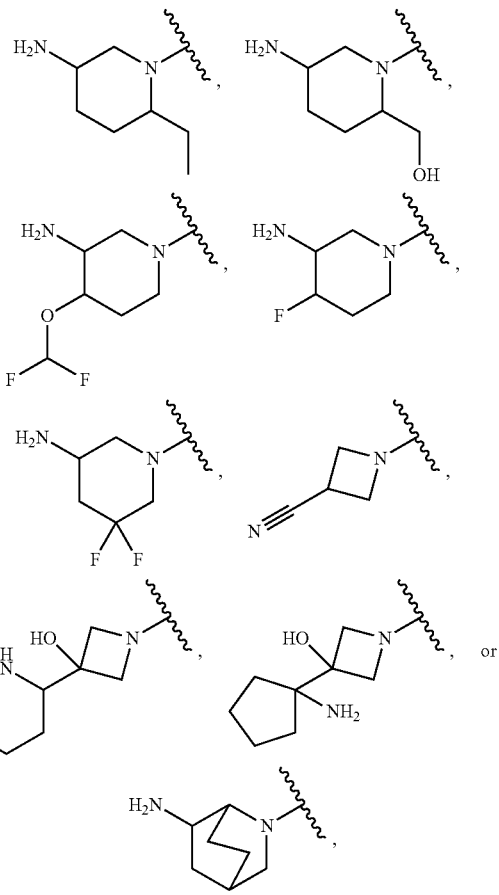
wherein Ring A is optionally substituted with 1-4 groups selected from fluorine, —CN, —OR, or $C_{1-6}$ aliphatic optionally substituted with 1-3 fluorine atoms;
Ring B is
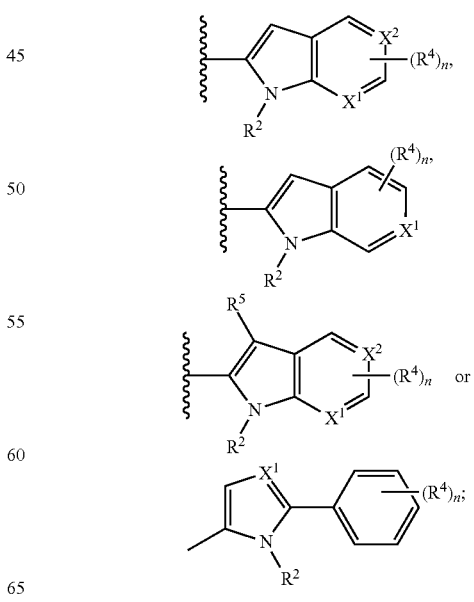

$R^1$ is hydrogen, —CN, —OR,

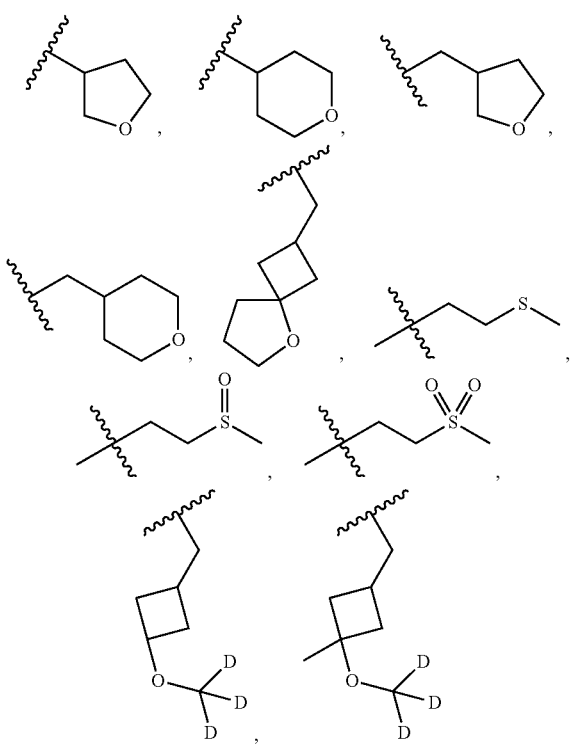

or $C_{1-6}$ aliphatic optionally substituted with 1-4 groups selected from fluorine, —CN, or —OR;
$R^2$ is hydrogen or $C_{1-10}$ aliphatic optionally substituted with 1-5 groups selected from fluorine, —CN, or —OR;
each of $X^1$ and $X^2$ is independently selected from N or $C(R^4)$;
$R^3$ is halogen, —CN, —R, or —OR;

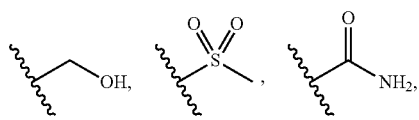

each $R^4$ is independently halogen, —CN, —R,

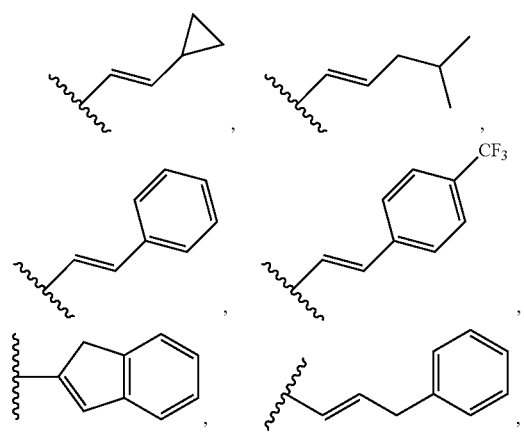

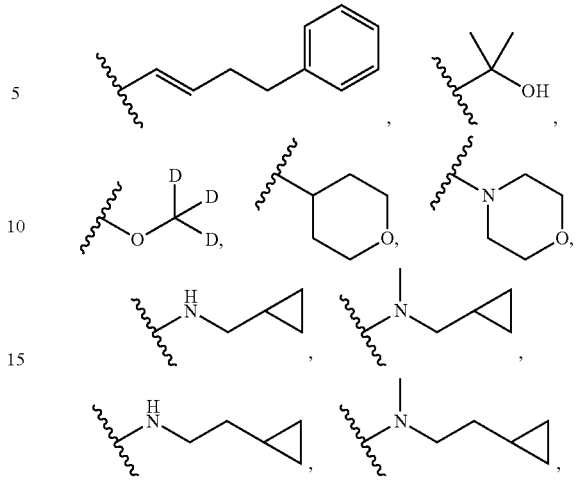

or —OR;
$R^5$ is hydrogen or halogen;
n is 0-4; and
each R is independently hydrogen or $C_{1-6}$ aliphatic optionally substituted with 1-3 fluorine atoms.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

3. Description of Exemplary Compounds

According to one aspect, the present invention provides a compound of formula I:

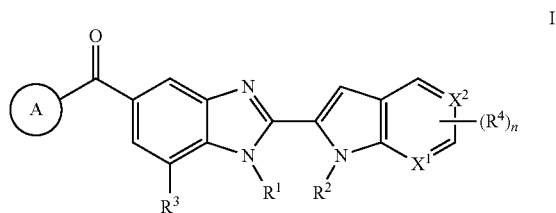

or a pharmaceutically acceptable salt thereof, wherein:
Ring A is

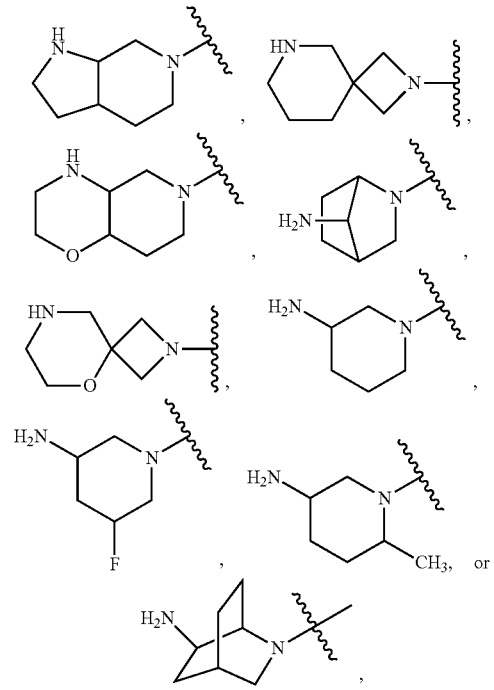

wherein Ring A is optionally substituted with 1-4 groups selected from fluorine, —CN, —OR, or $C_{1-6}$ aliphatic optionally substituted with 1-3 fluorine atoms;
$R^1$ is hydrogen, —CN, —OR, or $C_{1-6}$ aliphatic optionally substituted with 1-4 groups selected from fluorine, —CN, or —OR;
$R^2$ is hydrogen or $C_{1-10}$ aliphatic optionally substituted with 1-5 groups selected from fluorine, —CN, or —OR;
each of $X^1$ and $X^2$ is independently selected from N or $C(R^4)$;
each of $R^3$ and $R^4$ is independently halogen, —CN, —R, or —OR;
n is 0-4; and
each R is independently hydrogen or $C_{1-6}$ aliphatic optionally substituted with 1-3 fluorine atoms.

According to another aspect, the present invention provides a compound of formula I':

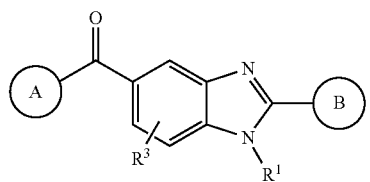
or a pharmaceutically acceptable salt thereof, wherein:
Ring A is
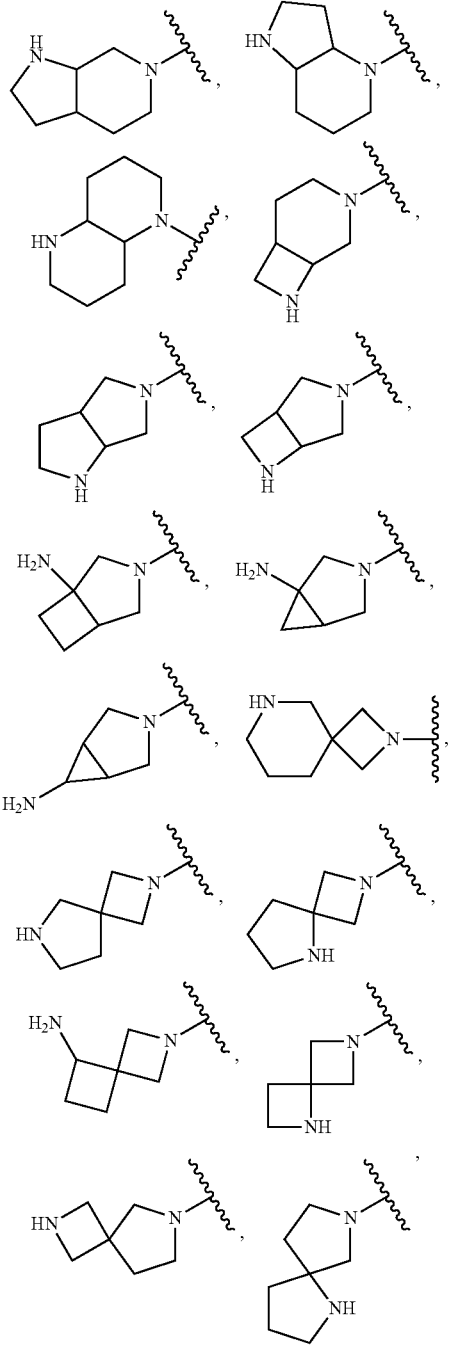
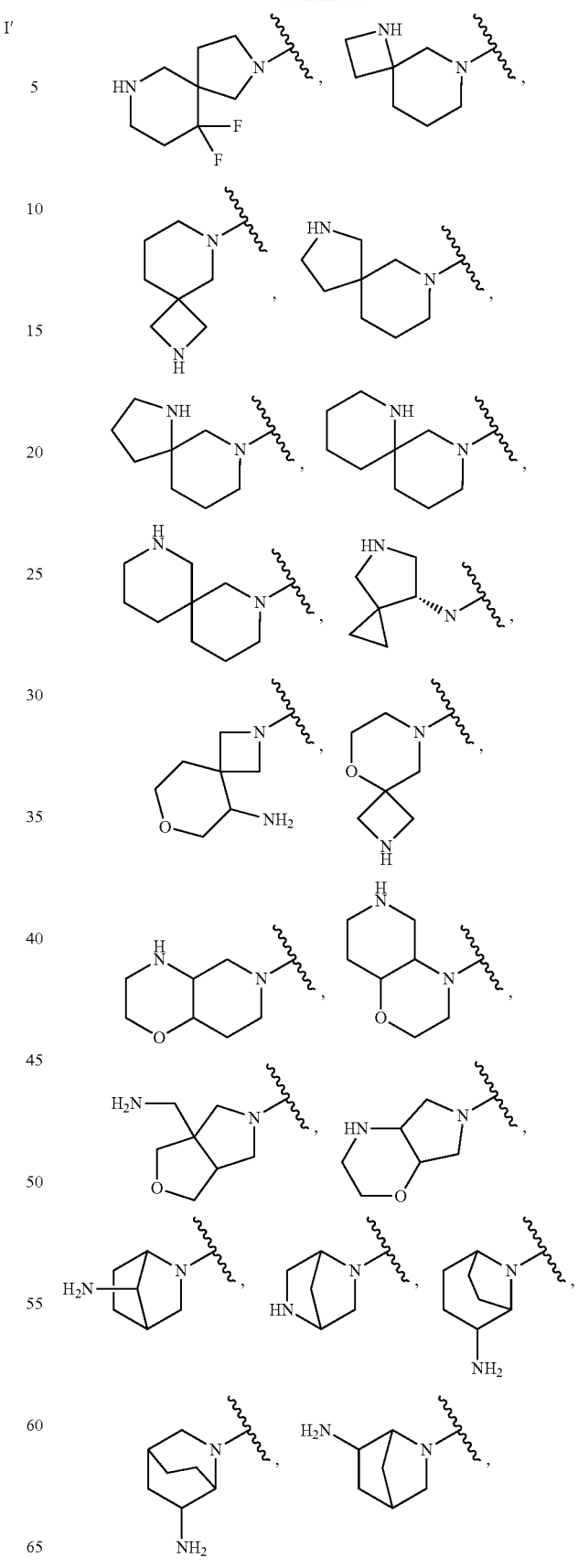

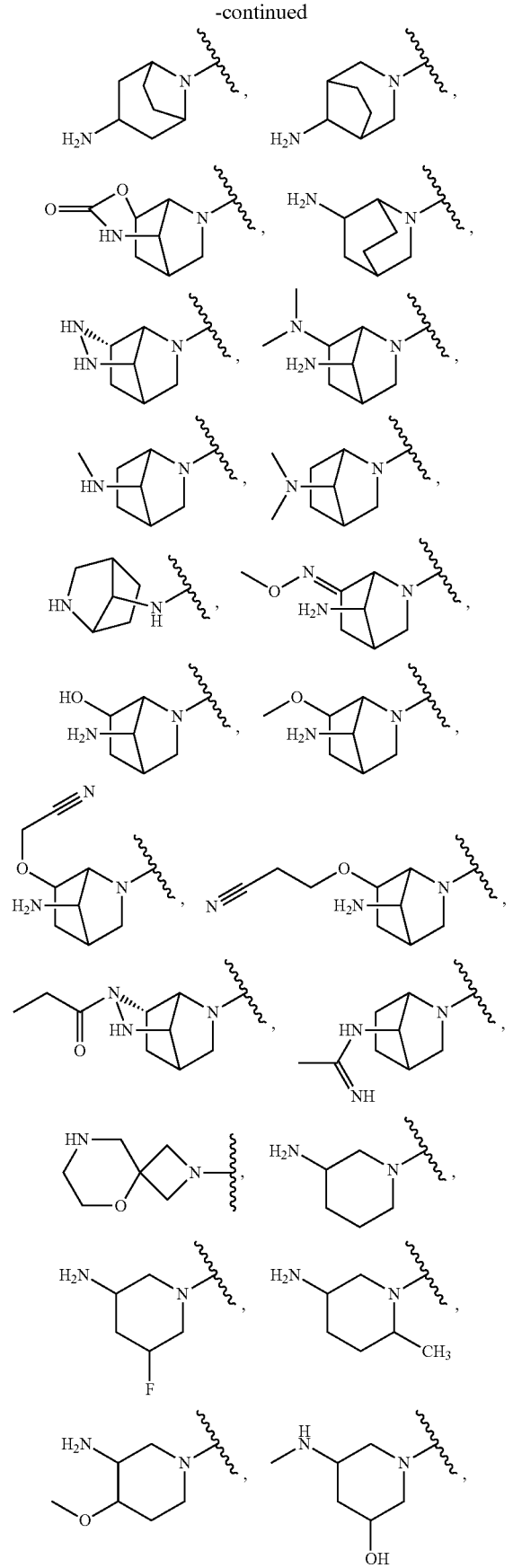
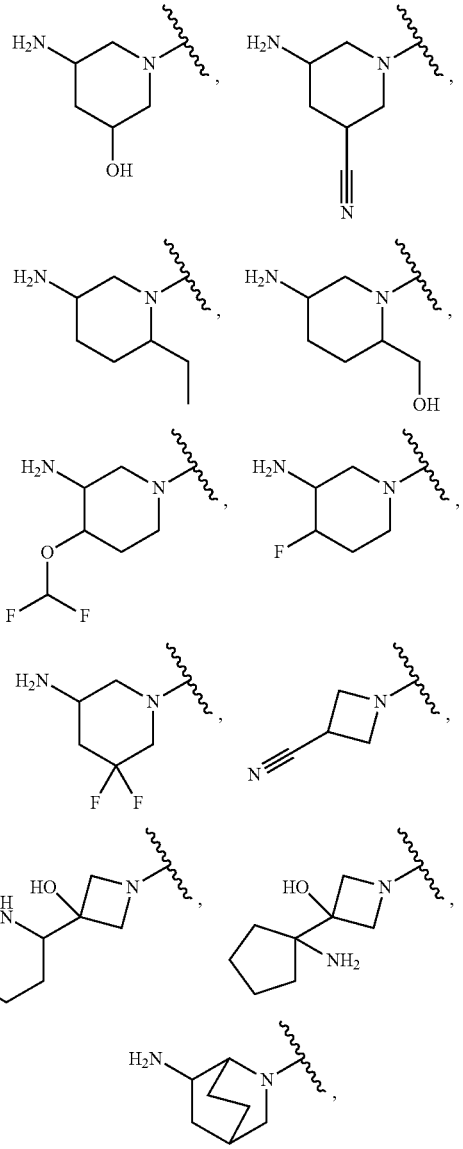
wherein Ring A is optionally substituted with 1-4 groups selected from fluorine, —CN, —OR, or $C_{1-6}$ aliphatic optionally substituted with 1-3 fluorine atoms;
Ring B is
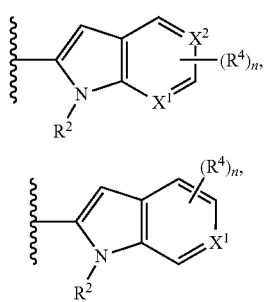

-continued

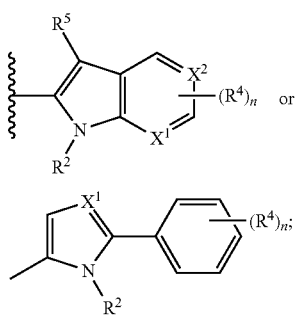

$R^1$ is hydrogen, —CN, —OR,

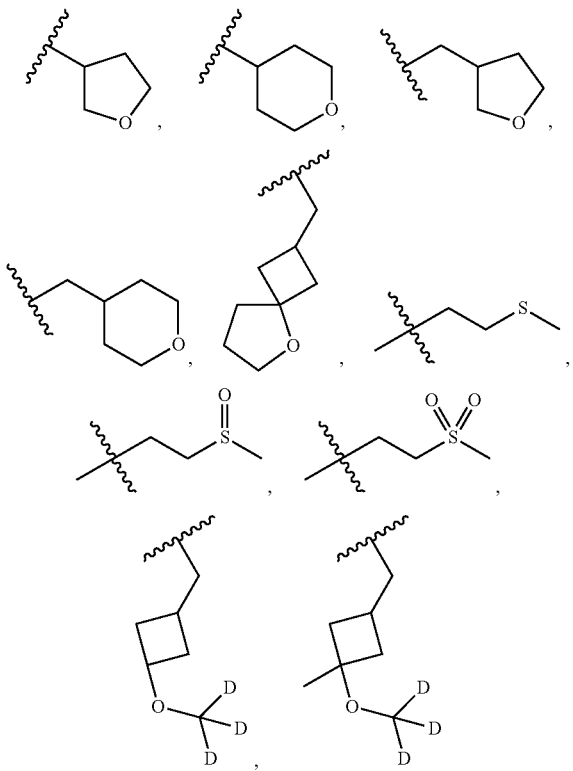

or $C_{1-6}$ aliphatic optionally substituted with 1-4 groups selected from fluorine, —CN, or —OR;

$R^2$ is hydrogen or $C_{1-10}$ aliphatic optionally substituted with 1-5 groups selected from fluorine, —CN, or —OR;

each of $X^1$ and $X^2$ is independently selected from N or $C(R^4)$;

$R^3$ is halogen, —CN, —R,

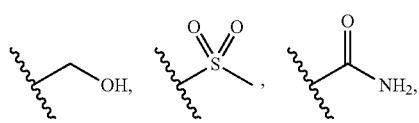

or —OR;

each $R^4$ is independently halogen, —CN, —R,

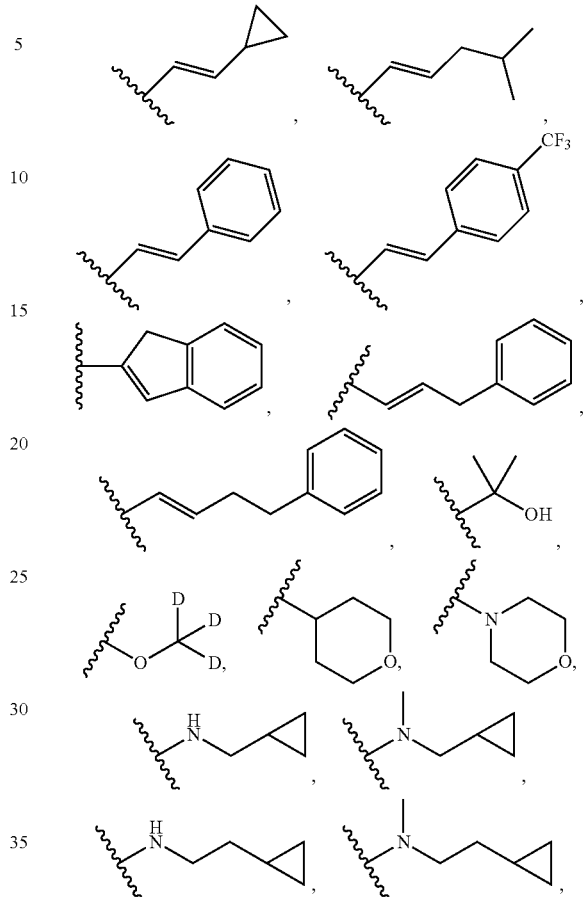

or —OR;

$R^5$ is hydrogen or halogen;

n is 0-4; and each R is independently hydrogen or $C_{1-6}$ aliphatic optionally substituted with 1-3 fluorine atoms.

As defined above and described herein, $R^1$ is hydrogen, —CN, —OR, or $C_{1-6}$ aliphatic optionally substituted with 1-4 groups selected from fluorine, —CN, or —OR. In some embodiments, $R^1$ is hydrogen. In some embodiments, $R^1$ is —CN. In some embodiments, $R^1$ is —OR. In some embodiments, $R^1$ is $C_{1-6}$ aliphatic optionally substituted with 1-4 groups selected from fluorine, —CN, or OR. In some embodiments, $R^1$ is $C_{1-3}$ aliphatic. In some embodiments, $R^1$ is methyl. In some embodiments, $R^1$ is ethyl. In some embodiments, $R^1$ is propyl. In some embodiments, $R^1$ is —$CH_2$-cyclobutyl optionally substituted with methyl and —OH. In some embodiments, $R^1$ is

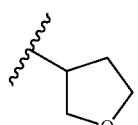

In some embodiments, R¹ is
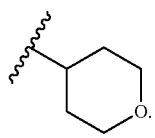 [SMILES: *C1CCOCC1]
In some embodiments, R¹ is
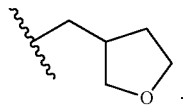 [SMILES: *CC1CCOC1]
In some embodiments, R¹ is
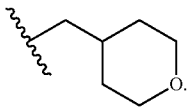 [SMILES: *CC1CCOCC1]
In some embodiments, R¹ is
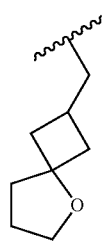
In some embodiments, R¹ is
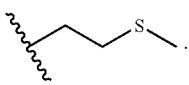 [SMILES: *CCSC]
In some embodiments, R¹ is

In some embodiments, R¹ is
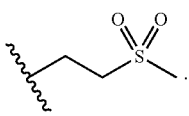
In some embodiments, R¹ is
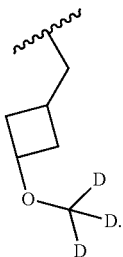
In some embodiments, R¹ is
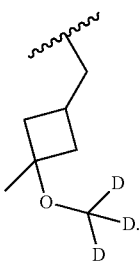
In some embodiments, R¹ is
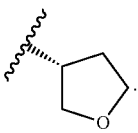
In some embodiments, R¹ is
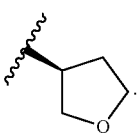 [SMILES: *[C@H]1CCOC1]
In some embodiments, R¹ is
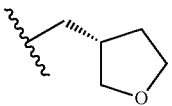
In some embodiments, R¹ is
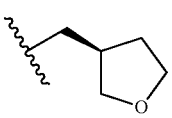

In some embodiments, $R^1$ is

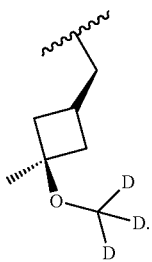

In some embodiments, $R^1$ is

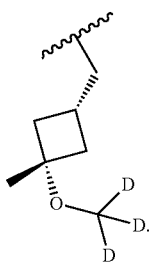

In some embodiments, $R^1$ is

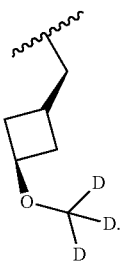

In some embodiments, $R^1$ is

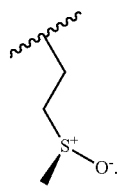

In some embodiments, $R^1$ is

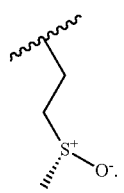

In certain embodiments, $R^1$ is selected from those depicted in Table 1, below.

As defined above and described herein, $R^2$ is hydrogen or $C_{1-10}$ aliphatic optionally substituted with 1-5 groups selected from fluorine, —CN, or —OR. In some embodiments, $R^2$ is hydrogen. In some embodiments, $R^2$ is $C_{1-10}$ aliphatic optionally substituted with 1-5 groups selected from fluorine, —CN, or —OR. In some embodiments, $R^2$ is methyl. In some embodiments, $R^2$ is ethyl. In some embodiments, $R^2$ is propyl. In some embodiments, $R^2$ is butyl. In some embodiments, $R^2$ is pentyl. In some embodiments, $R^2$ is hexyl. In some embodiments, $R^2$ is cyclopropyl. In some embodiments, $R^2$ is cyclobutyl. In some embodiments, $R^2$ is cyclopentyl. In some embodiments, $R^2$ is cyclohexyl. In some embodiments, $R^2$ is cyclopropylmethyl. In some embodiments, $R^2$ is cyclobutylmethyl. In some embodiments, $R^2$ is cyclopentylmethyl. In some embodiments, $R^2$ is cyclohexylmethyl. In some embodiments, $R^2$ is cyclopropylethyl. In some embodiments, $R^2$ is cyclobutylethyl. In some embodiments, $R^2$ is cyclopentylethyl. In some embodiments, $R^2$ is cyclohexylethyl. In some embodiments, $R^2$ is —CH$_2$-cyclopropyl or —CH$_2$-cyclobutyl. In some embodiments, $R^1$ is —CH$_2$-cyclobutyl optionally substituted with methyl and —OH.

In some embodiments, $R^2$ is $C_{1-10}$ aliphatic, substituted with 1-5 fluorine atoms. In some embodiments, $R^2$ is $C_{1-10}$ aliphatic, substituted with 1-5 fluorine atoms. In some embodiments, $R^2$ is $C_{1-10}$ aliphatic, substituted with 1 fluorine atom. In some embodiments, $R^2$ is $C_{1-10}$ aliphatic, substituted with 2 fluorine atoms. In some embodiments, $R^2$ is $C_{1-10}$ aliphatic, substituted with 3 fluorine atoms. In some embodiments, $R^2$ is $C_{1-10}$ aliphatic, substituted with 4 fluorine atoms. In some embodiments, $R^2$ is $C_{1-10}$ aliphatic, substituted with 5 fluorine atoms. In some embodiments, $R^2$ is methyl, substituted with 1-3 fluorine atoms. In some embodiments, $R^2$ is trifluoromethyl. In some embodiments, $R^2$ is ethyl, substituted with 1-5 fluorine atoms. In some embodiments, $R^2$ is 2,2,2-trifluoroethyl. In some embodiments, $R^2$ is propyl, substituted with 1-5 fluorine atoms. In some embodiments, $R^2$ is 3,3,3-trifluoropropyl. In some embodiments, $R^2$ is butyl, substituted with 1-5 fluorine atoms. In some embodiments, $R^2$ is 4,4,4-trifluorobutyl. In some embodiments, $R^2$ is pentyl, substituted with 1-5 fluorine atoms. In some embodiments, $R^2$ is 5,5,5-trifluoropentyl. In some embodiments, $R^2$ is hexyl, substituted with 1-5 fluorine atoms. In some embodiments, $R^2$ is 6,6,6-trifluorohexyl. In certain embodiments, $R^2$ is selected from those depicted in Table 1, below.

As defined above and described herein, each $X^1$ and $X^2$ is independently selected from N or $C(R^4)$. In some embodiments, both of $X^1$ and $X^2$ are N. In some embodiments, $X^1$ is N, and $X^2$ is CH. In some embodiments, $X^1$ is CH, and $X^2$ is N. In some embodiments, both of $X^1$ and $X^2$ are CH. In some embodiments, $X^1$ is N, and $X^2$ is $C(R^4)$. In some embodiments, $X^1$ is $C(R^4)$, and $X^2$ is N. In some embodiments, both of $X^1$ and $X^2$ are $C(R^4)$. In certain embodiments, $X^1$ and $X^2$ are selected from those depicted in Table 1, below.

As defined above and described herein, $R^3$ is halogen, —CN, —R, or —OR and each R is independently hydrogen or $C_{1-6}$ aliphatic optionally substituted with 1-3 fluorine atoms.

In some embodiments, $R^3$ is hydrogen. In some embodiments, $R^3$ is halogen. In some embodiments, $R^3$ is —CN. In some embodiments, $R^3$ is $C_{1-3}$ aliphatic. In some embodiments, $R^3$ is methyl. In some embodiments, $R^3$ is ethyl. In some embodiments, $R^3$ is propyl. In some embodiments, $R^3$ is —OR. In some embodiments, $R^3$ is —OCH$_3$. In some embodiments, $R^3$ is —$OCH_2CH_3$. In some embodiments, $R^3$ is —$OCH_2CH_2CH_3$. In certain embodiments, $R^3$ is —$OCH(F)_2$.

In some embodiments, $R^3$ is

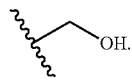

In some embodiments, $R^3$ is

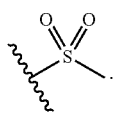

In some embodiments, $R^3$ is

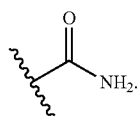

In certain embodiments, $R^3$ is selected from those depicted in Table 1, below.

As defined above and described herein, each $R^4$ is independently halogen, —CN, —R,

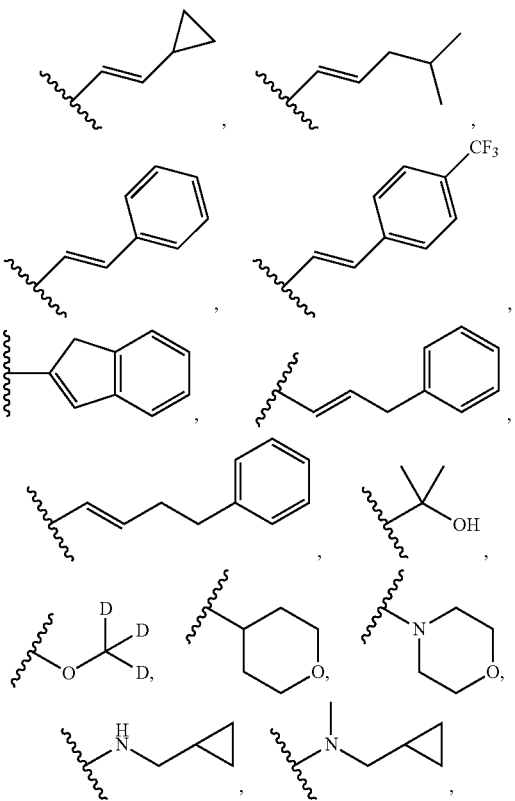

or —OR.

In some embodiments, $R^4$ is hydrogen. In some embodiments, $R^4$ is halogen. In some embodiments, $R^4$ is —CN. In some embodiments, $R^4$ is $C_{1-6}$ aliphatic or —OR. In some embodiments, $R^4$ is —$OCH_3$. In some embodiments, $R^4$ is ethyl.

In some embodiments, $R^4$ is

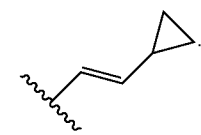 [SMILES: */C=C/C1CC1]

In some embodiments, $R^4$ is

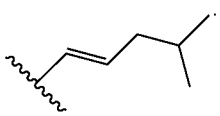 [SMILES: */C=C/CC(C)C]

In some embodiments, $R^4$ is

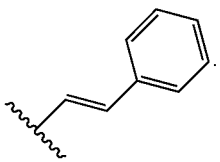 [SMILES: */C=C/c1ccccc1]

In some embodiments, $R^4$ is

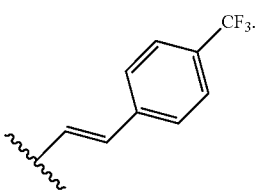 [SMILES: */C=C/c1ccc(C(F)(F)F)cc1]

In some embodiments, $R^4$ is

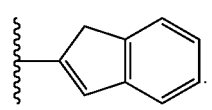 [SMILES: *C1=Cc2ccccc2C1]

In some embodiments, R⁴ is

In some embodiments, R⁴ is

In some embodiments, R⁴ is

In some embodiments, R⁴ is

In some embodiments, R⁴ is

In some embodiments, R⁴ is

In some embodiments, R⁴ is

In some embodiments, R⁴ is

In some embodiments, R⁴ is

In some embodiments, R⁴ is

In some embodiments, R⁴ is

In certain embodiments, R⁴ is selected from those depicted in Table 1, below.

As defined above, Ring A is wherein Ring A is optionally substituted with 1-4 groups selected from fluorine or $C_{1-6}$ aliphatic optionally substituted with 1-3 fluorine atoms.

In some embodiments, Ring A is
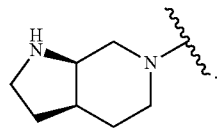 [SMILES: *N1CC[C@H]2CCN[C@H]2C1]
In some embodiments, Ring A is
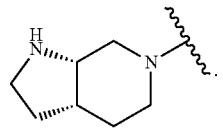 [SMILES: *N1CC[C@@H]2CCN[C@@H]2C1]
In some embodiments, Ring A is
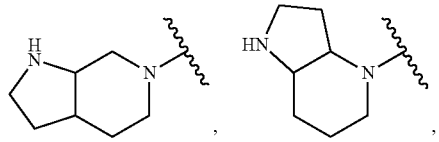
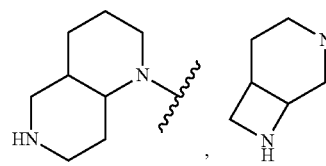
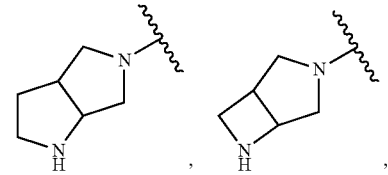
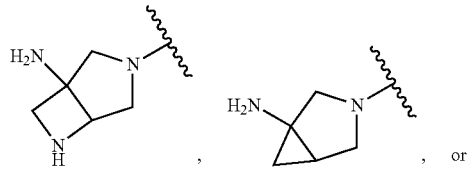, or
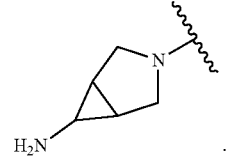
In some embodiments, Ring A is
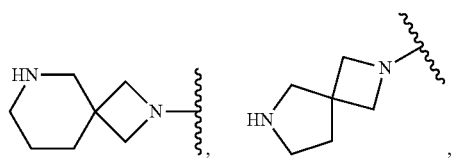,
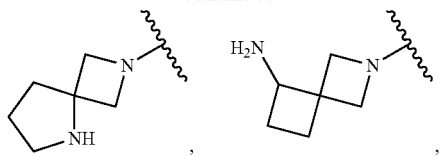,
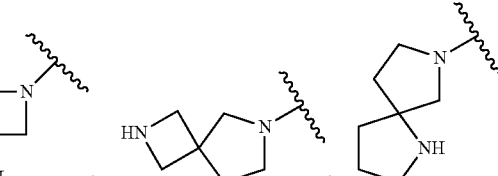,
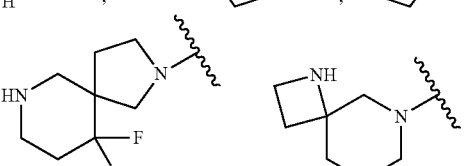,
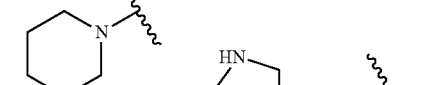,
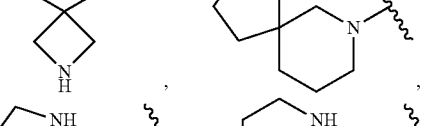,
,
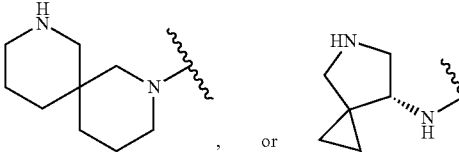, or
In some embodiments, Ring A is
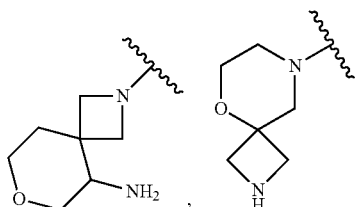,
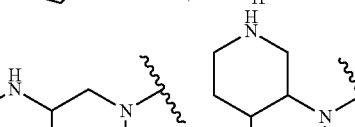,
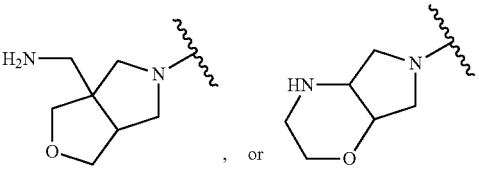, or In some embodiments, Ring A is
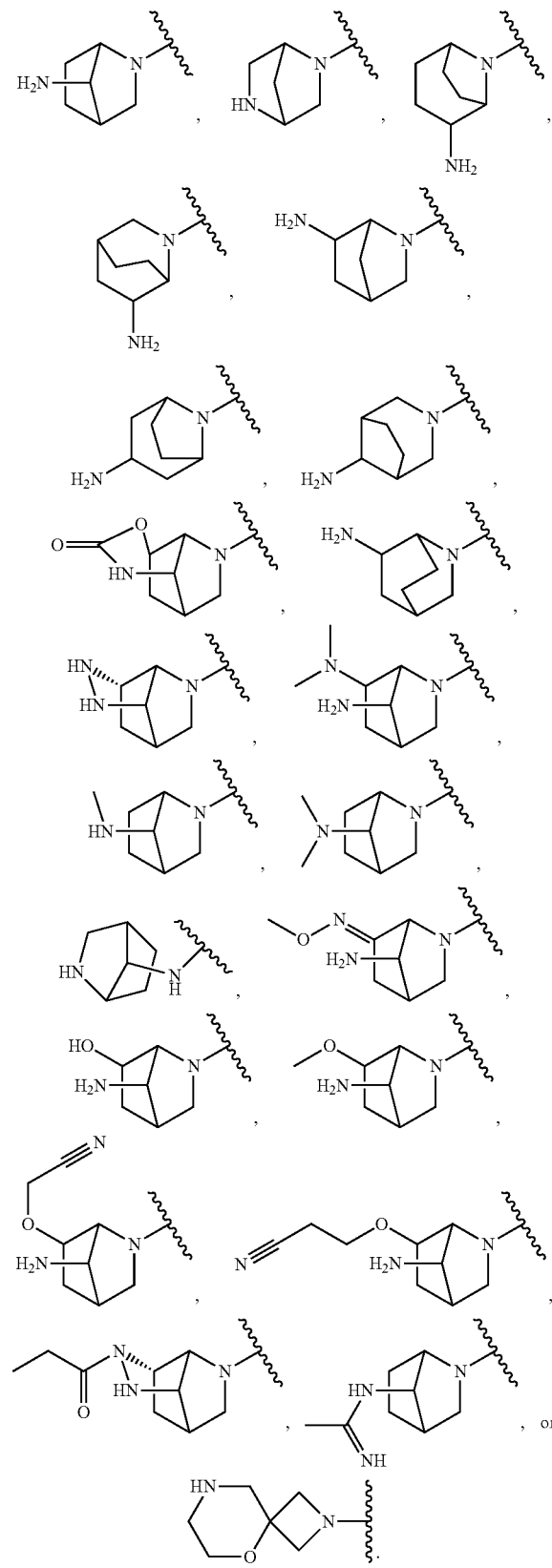
In some embodiments, Ring A is
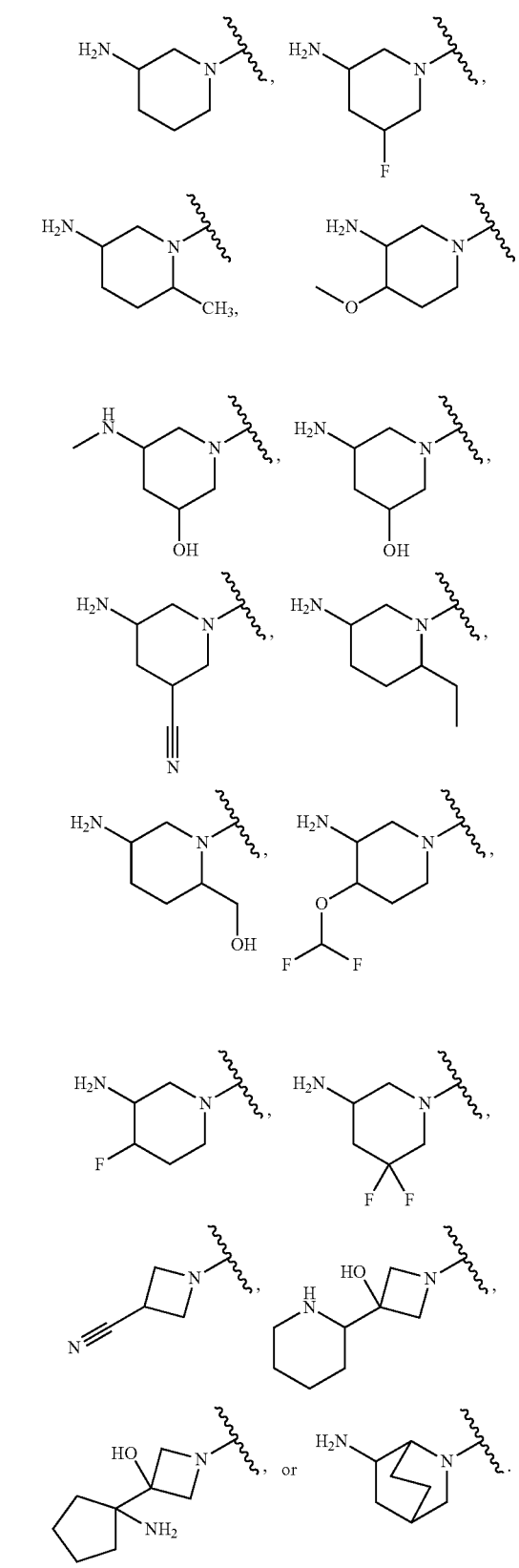

In some embodiments, Ring A is
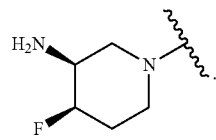 [SMILES: *N1CC[C@@H](F)[C@@H](N)C1]
In some embodiments, Ring A is
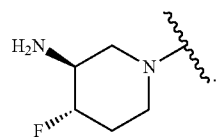 [SMILES: *N1CC[C@H](F)[C@@H](N)C1]
In some embodiments, Ring A is
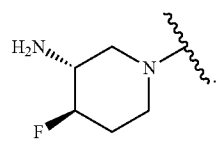 [SMILES: *N1CC[C@@H](F)[C@H](N)C1]
In some embodiments, Ring A is
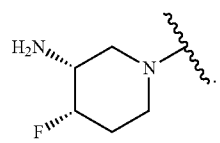
In some embodiments, Ring A is
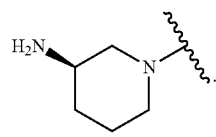
In some embodiments, Ring A is
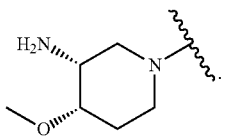 [SMILES: *N1CC[C@H](OC)[C@H](N)C1]
In some embodiments, Ring A is
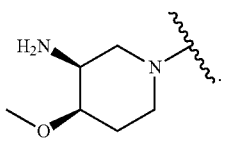 [SMILES: *N1CC[C@@H](OC)[C@@H](N)C1]
In some embodiments, Ring A is
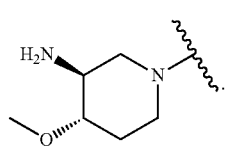 [SMILES: *N1CC[C@H](OC)[C@@H](N)C1]
In some embodiments, Ring A is
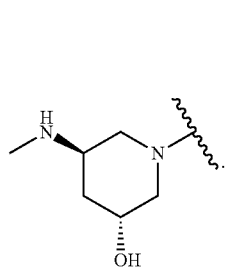 [SMILES: *N1C[C@H](O)C[C@@H](NC)C1]
In some embodiments, Ring A is
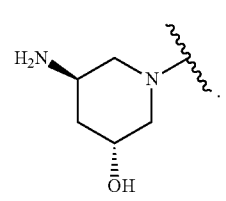
In some embodiments, Ring A is
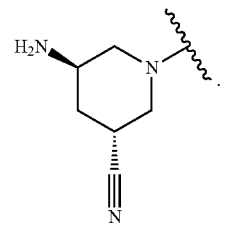
In some embodiments, Ring A is
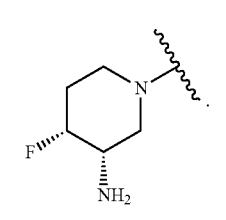

In some embodiments, Ring A is
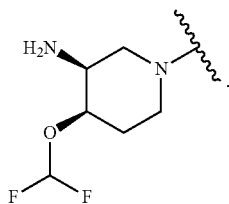
In some embodiments, Ring A is
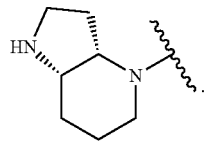
In some embodiments, Ring A is
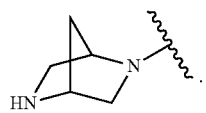
In some embodiments, Ring A is
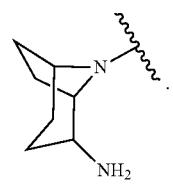 [SMILES: *N1C2CCC(N)C1CC2]
In some embodiments, Ring A is
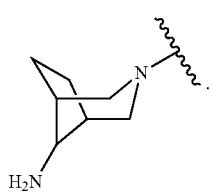
In some embodiments, Ring A is
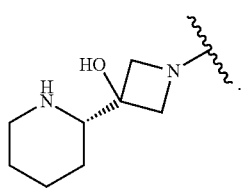 [SMILES: *N1CC(O)([C@@H]2CCCCN2)C1]
In some embodiments, Ring A is
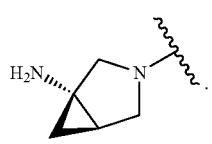
In some embodiments, Ring A is
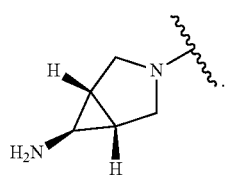 [SMILES: *N1C[C@@H]2[C@@H](N)[C@@H]2C1]
In some embodiments, Ring A is
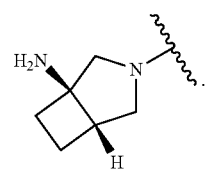
In some embodiments, Ring A is
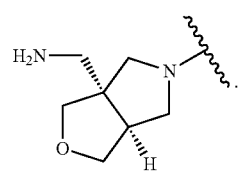 [SMILES: *N1C[C@H]2COC[C@@]2(CN)C1]
In some embodiments, Ring A is
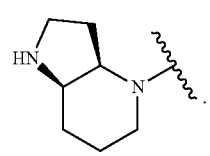
In some embodiments, Ring A is
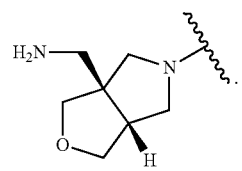 [SMILES: *N1C[C@@H]2COC[C@]2(CN)C1]

In some embodiments, Ring A is

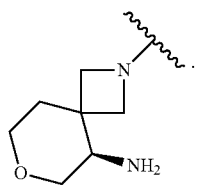 [SMILES: *N1CC2(CCOC[C@@H]2N)C1]

In some embodiments, Ring A is

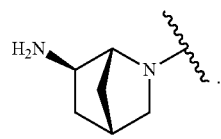 [SMILES: *N1C[C@@H]2C[C@@H](N)[C@H]1C2]

In some embodiments, Ring A is

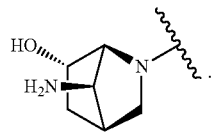 [SMILES: *N1C[C@H]2C[C@H](O)[C@@H]1[C@@H]2N]

In some embodiments, Ring A is

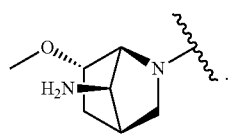 [SMILES: *N1C[C@H]2C[C@H](OC)[C@@H]1[C@@H]2N]

In some embodiments, Ring A is

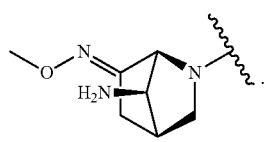 [SMILES: *N1C[C@H]2C/C(=N\OC)[C@@H]1[C@@H]2N]

In some embodiments, Ring A is

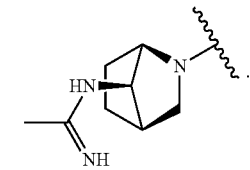 [SMILES: *N1C[C@H]2CC[C@@H]1[C@@H]2NC(C)=N]

In some embodiments, Ring A is

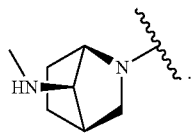 [SMILES: *N1C[C@H]2CC[C@@H]1[C@@H]2NC]

In some embodiments, Ring A is

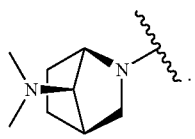 [SMILES: *N1C[C@H]2CC[C@@H]1[C@@H]2N(C)C]

In some embodiments, Ring A is

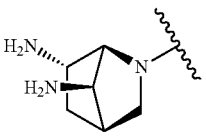

In some embodiments, Ring A is

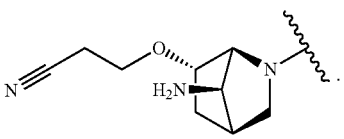 [SMILES: *N1C[C@H]2C[C@H](OCCC#N)[C@@H]1[C@@H]2N]

In some embodiments, Ring A is

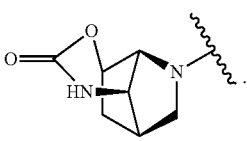 [SMILES: *N1C[C@H]2CC3OC(=O)N[C@H]2[C@@H]31]

In some embodiments, Ring A is

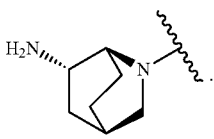 [SMILES: *N1C[C@@H]2CC[C@H]1[C@@H](N)C2]

In some embodiments, Ring A is

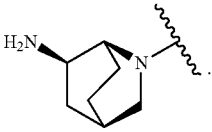 [SMILES: *N1C[C@@H]2CC[C@H]1[C@H](N)C2]

In some embodiments, Ring A is
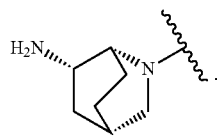
In some embodiments, Ring A is
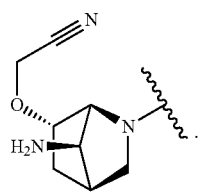 [SMILES: *N1C[C@H]2C[C@H](OCC#N)[C@@H]1[C@@H]2N]
In some embodiments, Ring A is
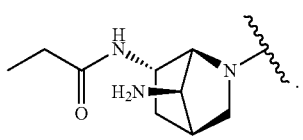 [SMILES: *N1C[C@H]2C[C@H](NC(=O)CC)[C@@H]1[C@@H]2N]
In some embodiments, Ring A is
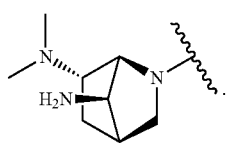 [SMILES: *N1C[C@H]2C[C@H](N(C)C)[C@@H]1[C@@H]2N]
In some embodiments, Ring A is
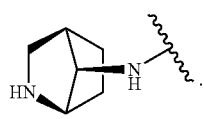
In some embodiments, Ring A is
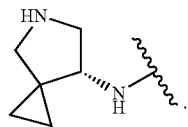 [SMILES: *N[C@H]1CNCC12CC2]
In some embodiments, Ring A is
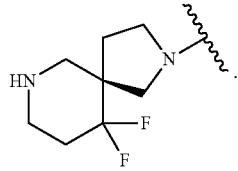 [SMILES: *N1CC[C@]2(CNCCC2(F)F)C1]
In some embodiments, Ring A is
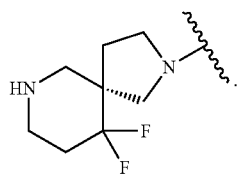
In some embodiments, Ring A is
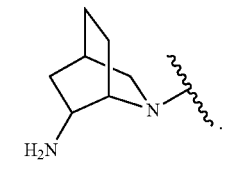
In some embodiments, Ring A is
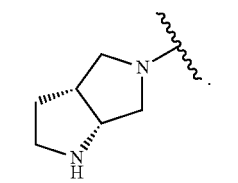 [SMILES: *N1C[C@H]2CCN[C@H]2C1]
In some embodiments, Ring A is
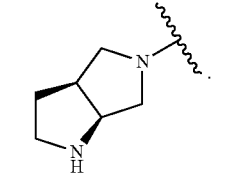 [SMILES: *N1C[C@@H]2CCN[C@@H]2C1]
In some embodiments, Ring A is
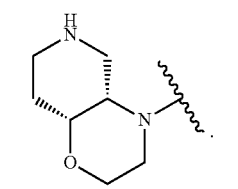 [SMILES: *N1CCO[C@@H]2CCNC[C@@H]21]

In some embodiments, Ring A is

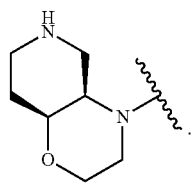 [SMILES: *N1CCO[C@H]2CCNC[C@H]21]

In some embodiments, Ring A is

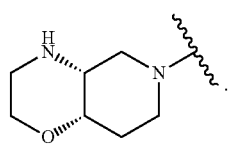 [SMILES: *N1CC[C@@H]2OCCN[C@@H]2C1]

In some embodiments, Ring A

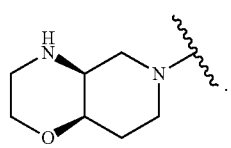 [SMILES: *N1CC[C@H]2OCCN[C@H]2C1]

In some embodiments, Ring A is

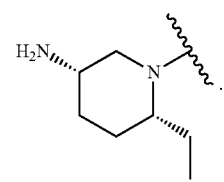

In some embodiments, Ring A is

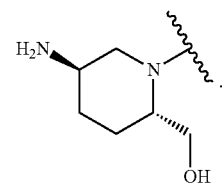 [SMILES: *N1C[C@H](N)CC[C@H]1CO]

In some embodiments, Ring A is

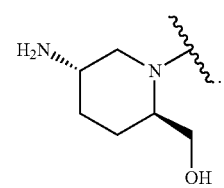

In some embodiments, Ring A is

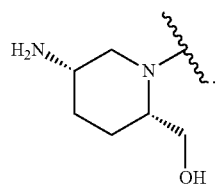

In some embodiments, Ring A is

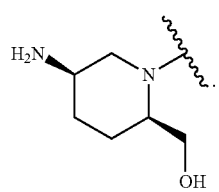 [SMILES: *N1C[C@H](N)CC[C@@H]1CO]

In some embodiments, Ring A is

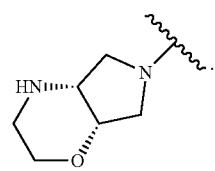 [SMILES: *N1C[C@@H]2OCCN[C@@H]2C1]

In some embodiments, Ring A is

In certain embodiments, Ring A is selected from those depicted in Table 1, below.

As defined above and described herein, Ring B is

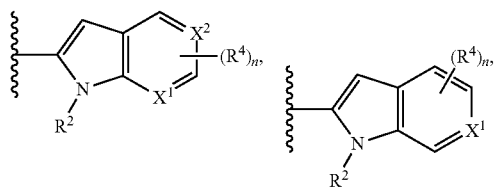

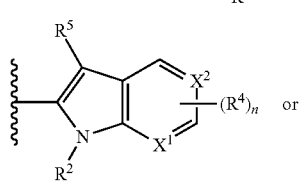 or

-continued

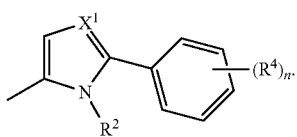

In some embodiments, Ring B is

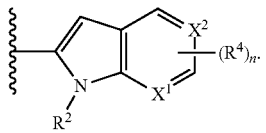

In some embodiments, Ring B is

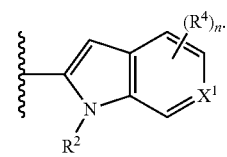

In some embodiments, Ring B is

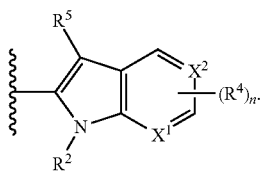

In some embodiments, Ring B is

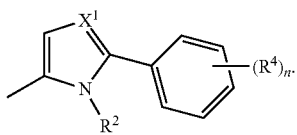

In certain embodiments, Ring B is selected from those depicted in Table 1, below.

As defined above and described herein, $R^5$ is hydrogen or halogen. In some embodiments, $R^5$ is hydrogen. In some embodiments, $R^5$ is halogen. In some embodiments, $R^5$ is fluoro. In certain embodiments, $R^5$ is selected from those depicted in Table 1, below.

As defined above and described herein, n is 0-4. In some embodiments, n is 0. In some embodiments, n is 1. In some embodiments, n is 2. In some embodiments, n is 3. In some embodiments, n is 4. In certain embodiments, n is selected from those depicted in Table 1, below.

In some embodiments, $R^1$ is methyl, $R^2$ is ethyl, $X^1$ is N, $X^2$ is CH, $R^3$ is hydrogen, and Ring A is

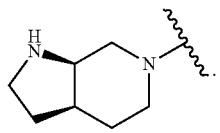 [SMILES: *N1CC[C@H]2CCN[C@H]2C1]

In some embodiments, $R^1$ is methyl, $R^2$ is 2,2,2-trifluoroethyl, $X^1$ is N, $X^2$ is CH, and Ring A is

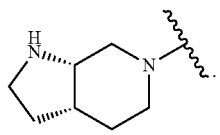 [SMILES: *N1CC[C@@H]2CCN[C@@H]2C1]

In some embodiments, $R^1$ is methyl, $R^2$ is cyclopropylmethyl, $X^1$ is N, $X^2$ is N, $R^3$ is —OCH$_3$, and Ring A is

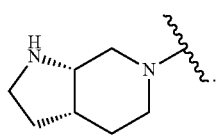 [SMILES: *N1CC[C@@H]2CCN[C@@H]2C1]

In some embodiments, $R^1$ is methyl, $R^2$ is ethyl, $X^1$ is N, $X^2$ is CH, $R^3$ is hydrogen, and Ring A is

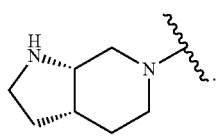 [SMILES: *N1CC[C@@H]2CCN[C@@H]2C1]

In some embodiments, $R^1$ is methyl, $R^2$ is cyclopropylmethyl, $X^1$ is N, $X^2$ is N, $R^3$ is hydrogen, and Ring A is

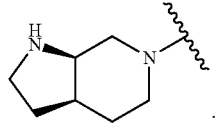

In some embodiments, $R^1$ is methyl, $R^2$ is 2,2,2-trifluoroethyl, $X^1$ is N, $X^2$ is CH, and Ring A is In some embodiments, $R^1$ is methyl, $R^2$ is cyclopropylmethyl, $X^1$ is N, $X^2$ is N, $R^3$ is —OCH$_3$, and

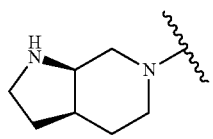

In some embodiments, $R^1$ is methyl, $R^2$ is 2,2,2-trifluoroethyl, $X^1$ is N, $X^2$ is CH, and Ring A is

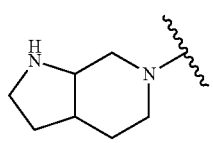

In some embodiments, $R^1$ is methyl, $R^2$ is cyclopropylmethyl, $X^1$ is N, $X^2$ is N, $R^3$ is —OCH$_3$, and Ring A is

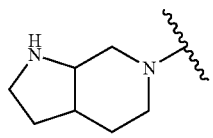

In some embodiments $R^1$ is methyl, $R^2$ is cyclopropylmethyl, X' is N, $X^2$ is CH, and Ring A is

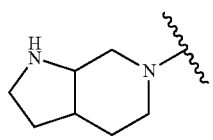

In some embodiments, $R^1$ is methyl, $R^2$ is ethyl, X' is N, $X^2$ is CH, $R^3$ is hydrogen, and Ring A is

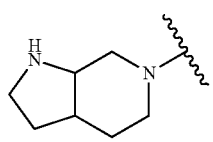

In some embodiments, $R^1$ is methyl, $R^2$ is cyclopropylmethyl, X' is N, $X^2$ is CH, $R^3$ is —OCH$_3$, and Ring A is

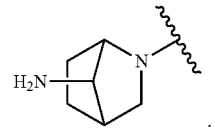

In some embodiments, $R^1$ is methyl, $R^2$ is cyclopropylmethyl, $X^1$ is N, $X^2$ is CH, $R^3$ is —OCH$_3$, and Ring A is

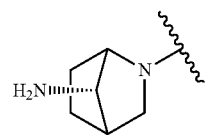

In some embodiments, $R^1$ is methyl, $R^2$ is cyclopropylmethyl, $X^1$ is N, $X^2$ is CH, $R^3$ is —OCH$_3$ and Ring A is

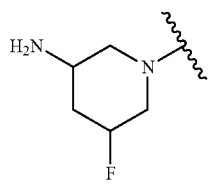

In some embodiments, $R^1$ is methyl, $R^2$ is cyclopropylmethyl, $X^1$ is N, $X^2$ is CH, $R^3$ is —OCH$_3$ and Ring A is

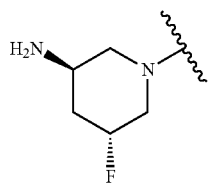

In some embodiments, $R^1$ is methyl, $R^2$ is cyclopropylmethyl, $X^1$ is N, $X^2$ is CH, $R^3$ is —OCH$_3$, and Ring A is

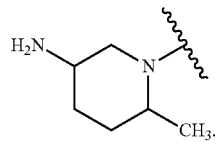

In some embodiments, $R^1$ is methyl, $R^2$ is cyclopropylmethyl, $X^1$ is N, $X^2$ is CH, $R^3$ is —OCH$_3$, and Ring A is

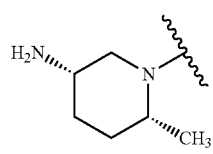

In some embodiments, Ring A is

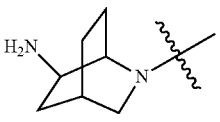

In some embodiments, the compound of formula I is selected from those depicted below in Table 1.

TABLE 1
Exemplary Compounds of Formula I
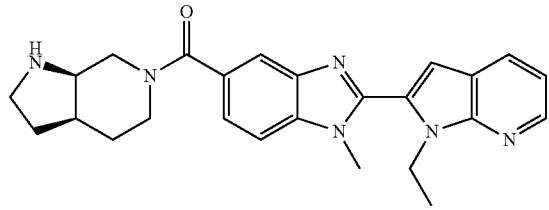 [SMILES: CCn1c(-c2nc3cc(C(=O)N4CC[C@H]5CCN[C@H]5C4)ccc3n2C)cc2cccnc21]
I-1
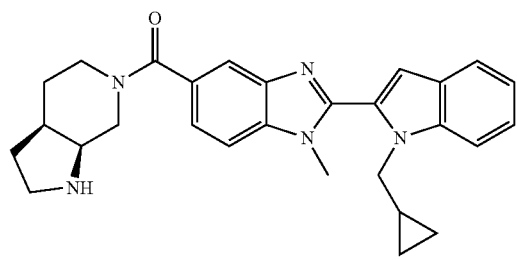 [SMILES: Cn1c(-c2cc3ccccc3n2CC2CC2)nc2cc(C(=O)N3CC[C@@H]4CCN[C@@H]4C3)ccc21]
I-2
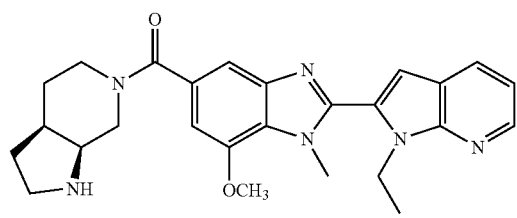 [SMILES: CCn1c(-c2nc3cc(C(=O)N4CC[C@@H]5CCN[C@@H]5C4)cc(OC)c3n2C)cc2cccnc21]
I-3
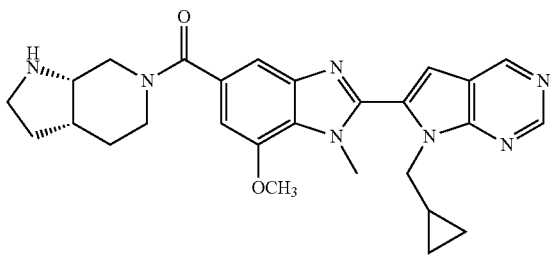 [SMILES: COc1cc(C(=O)N2CC[C@@H]3CCN[C@@H]3C2)cc2nc(-c3cc4cncnc4n3CC3CC3)n(C)c12]
I-4
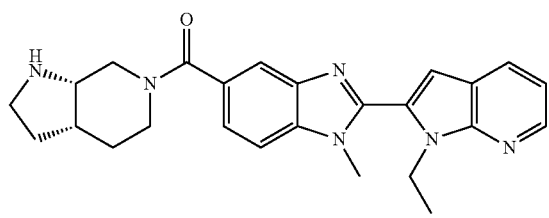 [SMILES: CCn1c(-c2nc3cc(C(=O)N4CC[C@@H]5CCN[C@@H]5C4)ccc3n2C)cc2cccnc21]
I-5
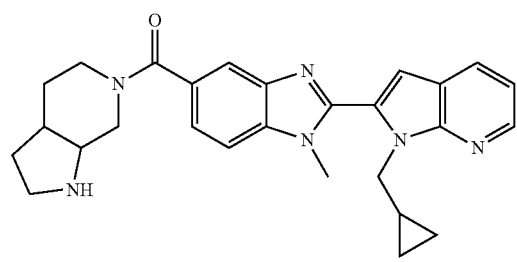 [SMILES: Cn1c(-c2cc3cccnc3n2CC2CC2)nc2cc(C(=O)N3CCC4CCNC4C3)ccc21]
I-6

TABLE 1-continued
Exemplary Compounds of Formula I
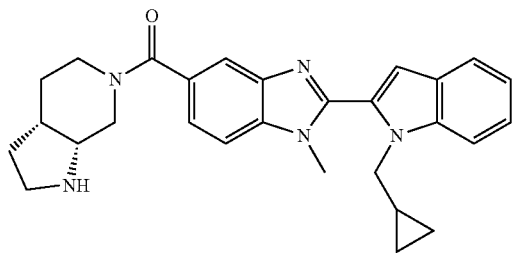 [SMILES: Cn1c(-c2cc3ccccc3n2CC2CC2)nc2cc(C(=O)N3CC[C@H]4CCN[C@H]4C3)ccc21]
I-7
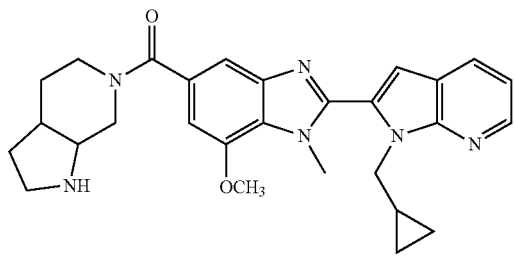 [SMILES: COc1cc(C(=O)N2CCC3CCNC3C2)cc2nc(-c3cc4cccnc4n3CC3CC3)n(C)c12]
I-8
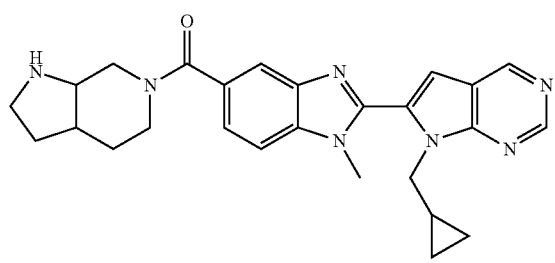 [SMILES: Cn1c(-c2cc3cncnc3n2CC2CC2)nc2cc(C(=O)N3CCC4CCNC4C3)ccc21]
I-9
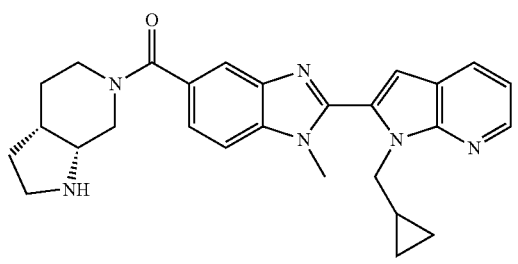 [SMILES: Cn1c(-c2cc3cccnc3n2CC2CC2)nc2cc(C(=O)N3CC[C@H]4CCN[C@H]4C3)ccc21]
I-10
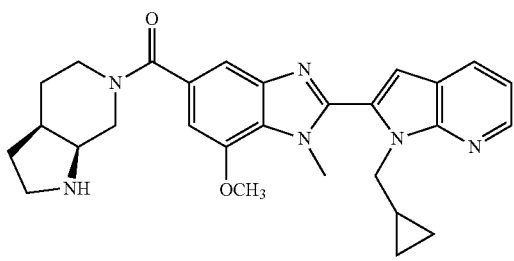 [SMILES: COc1cc(C(=O)N2CC[C@@H]3CCN[C@@H]3C2)cc2nc(-c3cc4cccnc4n3CC3CC3)n(C)c12]
I-11
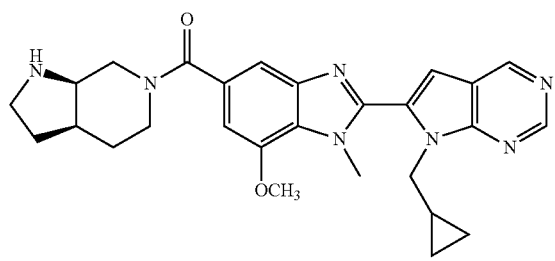 [SMILES: COc1cc(C(=O)N2CC[C@H]3CCN[C@H]3C2)cc2nc(-c3cc4cncnc4n3CC3CC3)n(C)c12]
I-12

TABLE 1-continued
Exemplary Compounds of Formula I
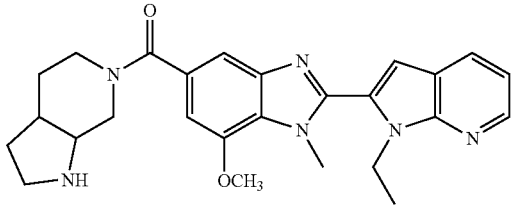
I-13
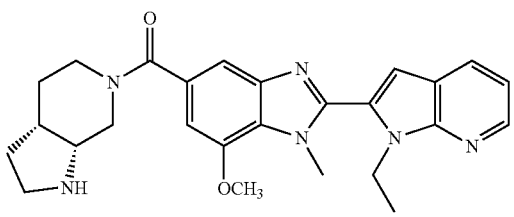 [SMILES: CCn1c(-c2nc3cc(C(=O)N4CCC5CCNC5C4)cc(OC)c3n2C)cc2cccnc21]
I-14
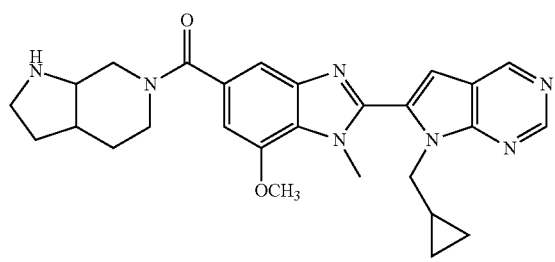 [SMILES: COc1cc(C(=O)N2CCC3CCNC3C2)cc2nc(-c3cc4cncnc4n3CC3CC3)n(C)c12]
I-15
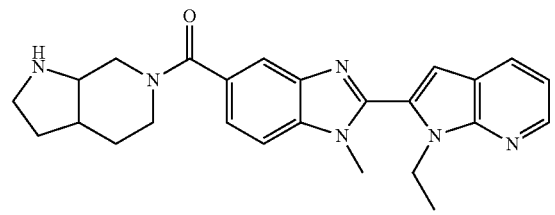 [SMILES: CCn1c(-c2nc3cc(C(=O)N4CCC5CCNC5C4)ccc3n2C)cc2cccnc21]
I-16
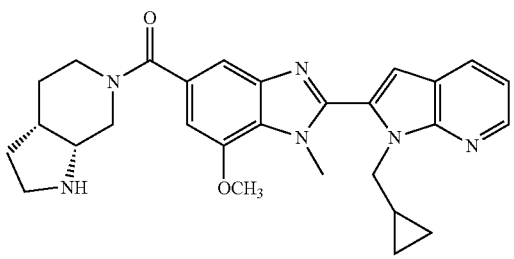 [SMILES: COc1cc(C(=O)N2CC[C@H]3CCN[C@H]3C2)cc2nc(-c3cc4cccnc4n3CC3CC3)n(C)c12]
I-17
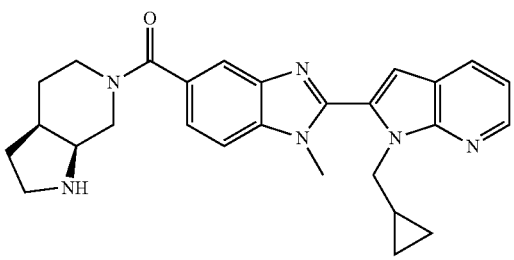 [SMILES: Cn1c(-c2cc3cccnc3n2CC2CC2)nc2cc(C(=O)N3CC[C@@H]4CCN[C@@H]4C3)ccc21]
I-18

TABLE 1-continued
Exemplary Compounds of Formula I
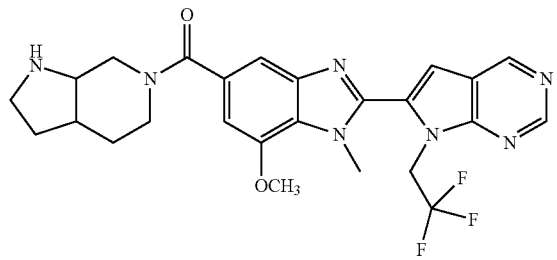 [SMILES: COc1cc(C(=O)N2CCC3CCNC3C2)cc2nc(-c3cc4cncnc4n3CC(F)(F)F)n(C)c12]
I-19
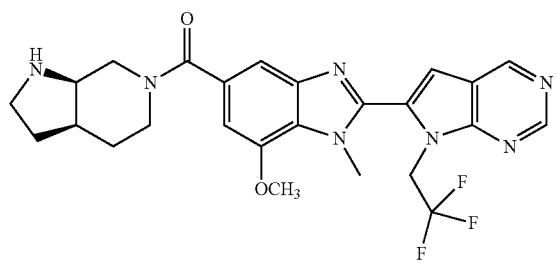 [SMILES: COc1cc(C(=O)N2CC[C@H]3CCN[C@H]3C2)cc2nc(-c3cc4cncnc4n3CC(F)(F)F)n(C)c12]
I-20
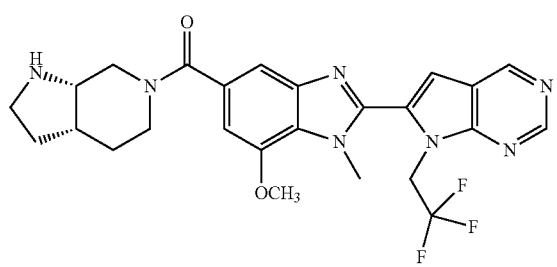 [SMILES: COc1cc(C(=O)N2CC[C@@H]3CCN[C@@H]3C2)cc2nc(-c3cc4cncnc4n3CC(F)(F)F)n(C)c12]
I-21
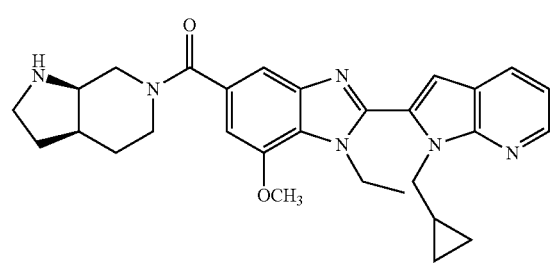 [SMILES: CCn1c(-c2cc3cccnc3n2CC2CC2)nc2cc(C(=O)N3CC[C@H]4CCN[C@H]4C3)cc(OC)c21]
I-22
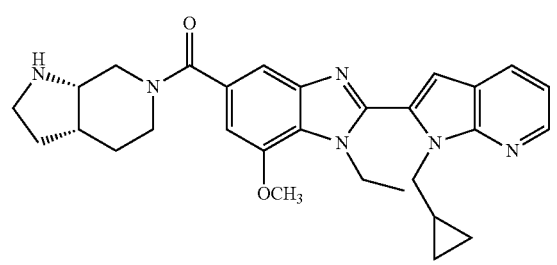 [SMILES: CCn1c(-c2cc3cccnc3n2CC2CC2)nc2cc(C(=O)N3CC[C@@H]4CCN[C@@H]4C3)cc(OC)c21]
I-23
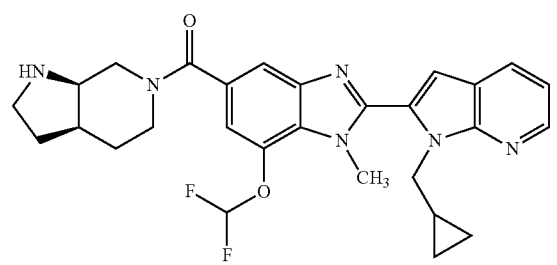 [SMILES: Cn1c(-c2cc3cccnc3n2CC2CC2)nc2cc(C(=O)N3CC[C@H]4CCN[C@H]4C3)cc(OC(F)F)c21]
I-24

TABLE 1-continued
Exemplary Compounds of Formula I
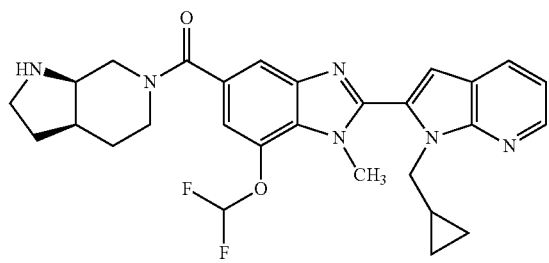 [SMILES: Cn1c(-c2cc3cccnc3n2CC2CC2)nc2cc(C(=O)N3CC[C@H]4CCN[C@H]4C3)cc(OC(F)F)c21]
I-25
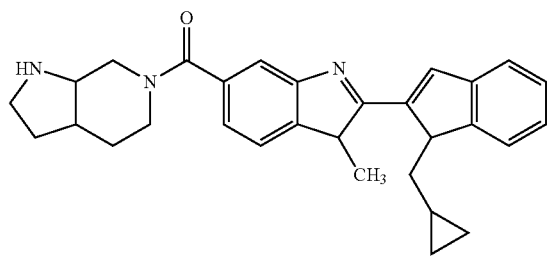 [SMILES: CC1C(C2=Cc3ccccc3C2CC2CC2)=Nc2cc(C(=O)N3CCC4CCNC4C3)ccc21]
I-26
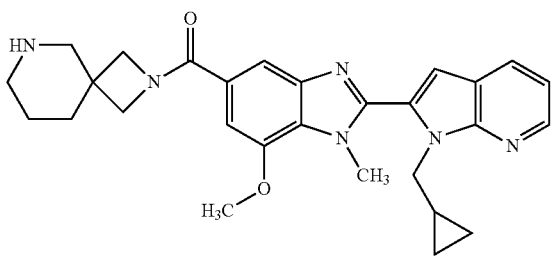 [SMILES: COc1cc(C(=O)N2CC3(CCCNC3)C2)cc2nc(-c3cc4cccnc4n3CC3CC3)n(C)c12]
I-27
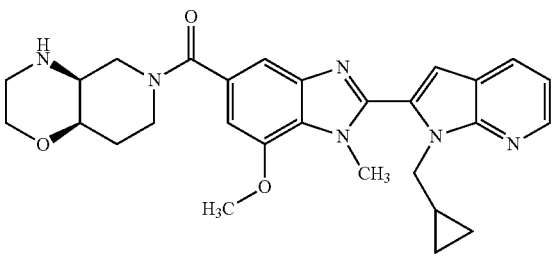 [SMILES: COc1cc(C(=O)N2CC[C@H]3OCCN[C@H]3C2)cc2nc(-c3cc4cccnc4n3CC3CC3)n(C)c12]
I-28
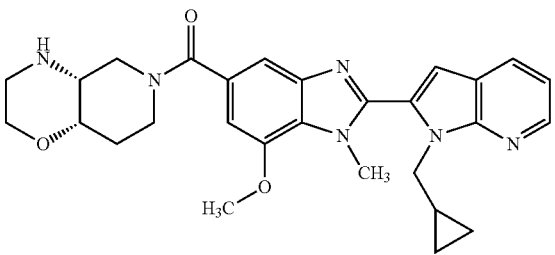
I-29
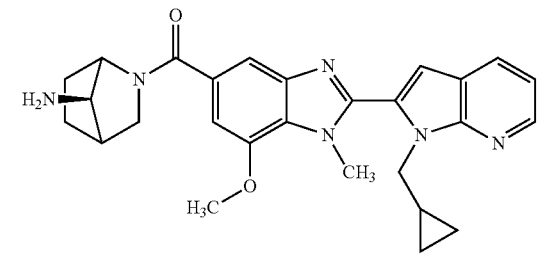 [SMILES: COc1cc(C(=O)N2CC3CCC2[C@@H]3N)cc2nc(-c3cc4cccnc4n3CC3CC3)n(C)c12]
I-30

TABLE 1-continued
Exemplary Compounds of Formula I
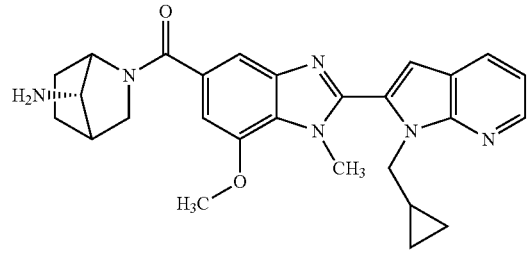 [SMILES: COc1cc(C(=O)N2CC3CCC2[C@H]3N)cc2nc(-c3cc4cccnc4n3CC3CC3)n(C)c12]
I-31
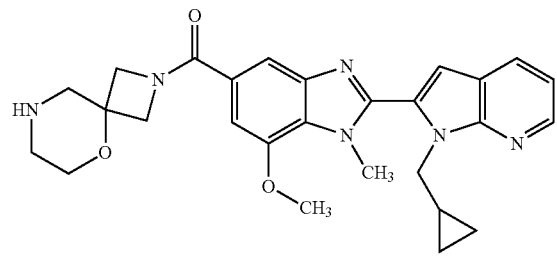 [SMILES: COc1cc(C(=O)N2CC3(CNCCO3)C2)cc2nc(-c3cc4cccnc4n3CC3CC3)n(C)c12]
I-32
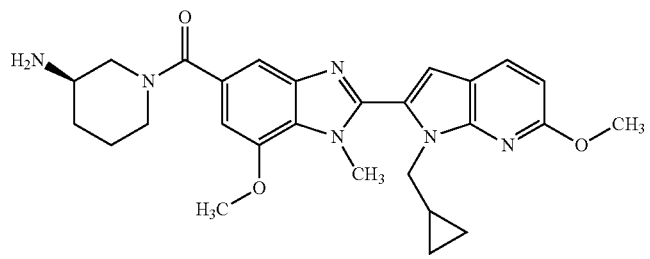 [SMILES: COc1ccc2cc(-c3nc4cc(C(=O)N5CCC[C@@H](N)C5)cc(OC)c4n3C)n(CC3CC3)c2n1]
I-33
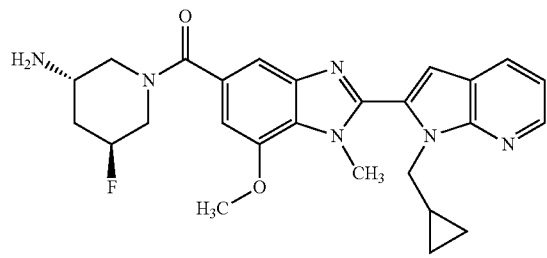 [SMILES: COc1cc(C(=O)N2C[C@@H](N)C[C@H](F)C2)cc2nc(-c3cc4cccnc4n3CC3CC3)n(C)c12]
I-34
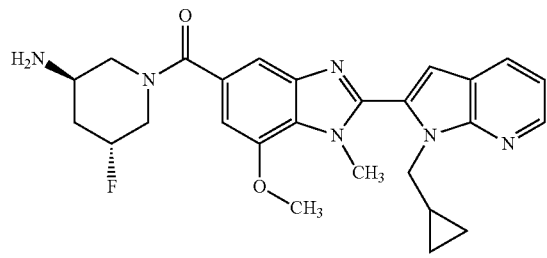 [SMILES: COc1cc(C(=O)N2C[C@H](N)C[C@@H](F)C2)cc2nc(-c3cc4cccnc4n3CC3CC3)n(C)c12]
I-35

TABLE 1-continued
Exemplary Compounds of Formula I
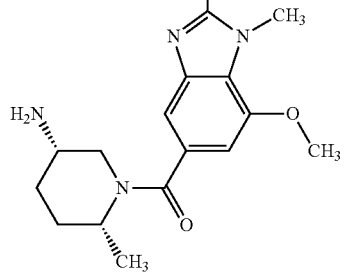
I-36
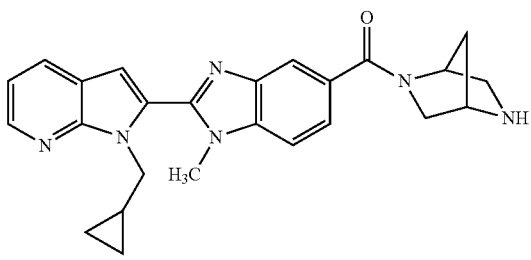 [SMILES: Cn1c(-c2cc3cccnc3n2CC2CC2)nc2cc(C(=O)N3CC4CC3CN4)ccc21]
I-37
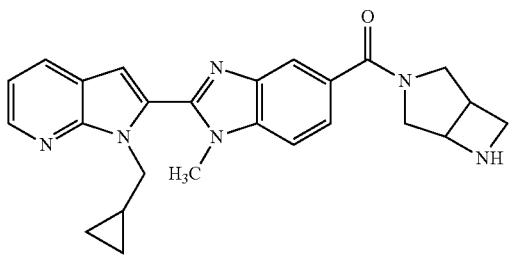 [SMILES: Cn1c(-c2cc3cccnc3n2CC2CC2)nc2cc(C(=O)N3CC4CNC4C3)ccc21]
I-38
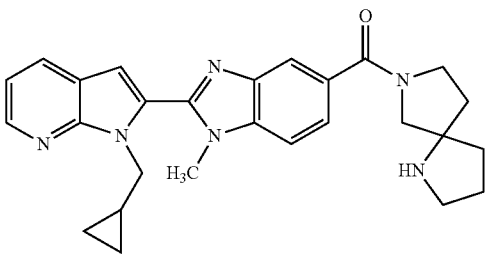 [SMILES: Cn1c(-c2cc3cccnc3n2CC2CC2)nc2cc(C(=O)N3CCC4(CCCN4)C3)ccc21]
I-39
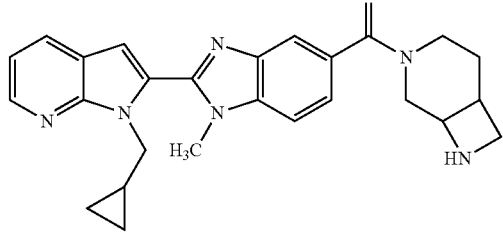
I-40

TABLE 1-continued
Exemplary Compounds of Formula I
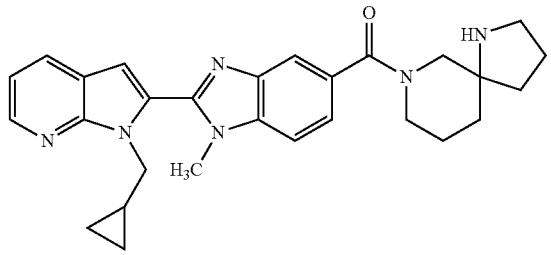 [SMILES: Cn1c(-c2cc3cccnc3n2CC2CC2)nc2cc(C(=O)N3CCCC4(CCCN4)C3)ccc21]
I-41
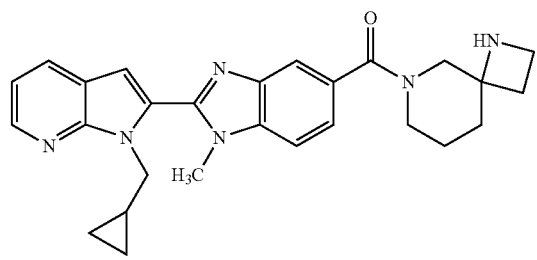 [SMILES: Cn1c(-c2cc3cccnc3n2CC2CC2)nc2cc(C(=O)N3CCCC4(CCN4)C3)ccc21]
I-42
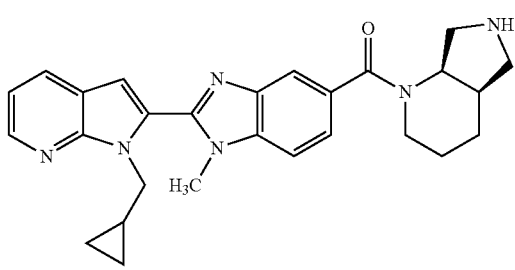 [SMILES: Cn1c(-c2cc3cccnc3n2CC2CC2)nc2cc(C(=O)N3CCC[C@@H]4CNC[C@@H]43)ccc21]
I-43
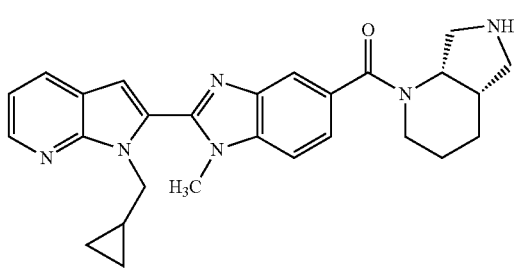 [SMILES: Cn1c(-c2cc3cccnc3n2CC2CC2)nc2cc(C(=O)N3CCC[C@H]4CNC[C@H]43)ccc21]
I-44
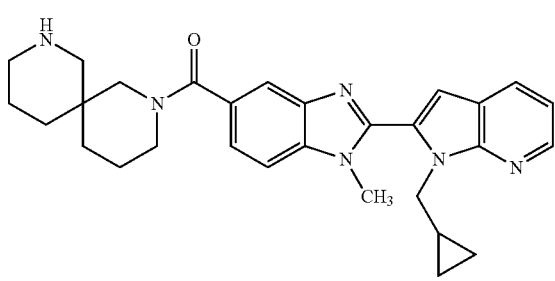 [SMILES: Cn1c(-c2cc3cccnc3n2CC2CC2)nc2cc(C(=O)N3CCCC4(CCCNC4)C3)ccc21]
I-45
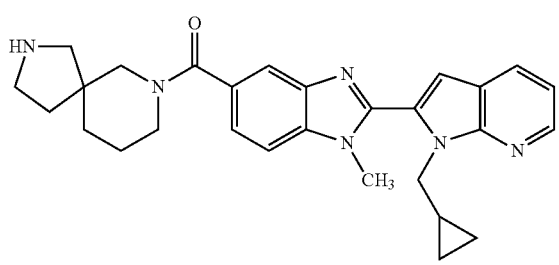 [SMILES: Cn1c(-c2cc3cccnc3n2CC2CC2)nc2cc(C(=O)N3CCCC4(CCNC4)C3)ccc21]
I-46

TABLE 1-continued
Exemplary Compounds of Formula I
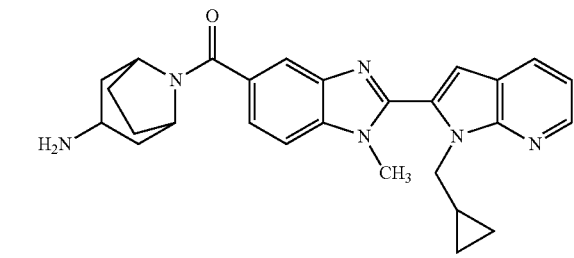 [SMILES: Cn1c(-c2cc3cccnc3n2CC2CC2)nc2cc(C(=O)N3C4CCC3CC(N)C4)ccc21]
I-47
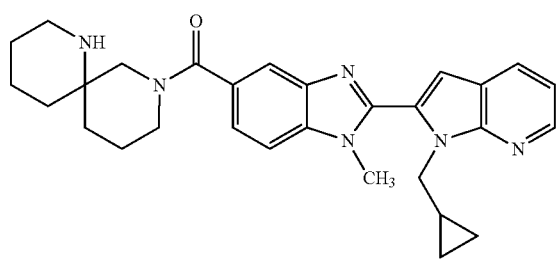 [SMILES: Cn1c(-c2cc3cccnc3n2CC2CC2)nc2cc(C(=O)N3CCCC4(CCCCN4)C3)ccc21]
I-48
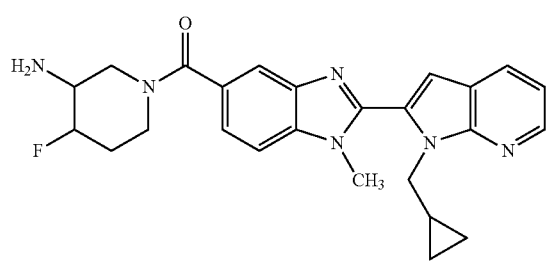 [SMILES: Cn1c(-c2cc3cccnc3n2CC2CC2)nc2cc(C(=O)N3CCC(F)C(N)C3)ccc21]
I-49
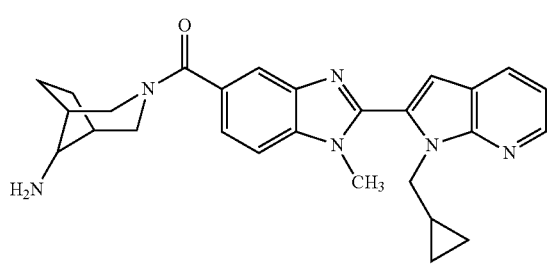 [SMILES: Cn1c(-c2cc3cccnc3n2CC2CC2)nc2cc(C(=O)N3CC4CCC(C3)C4N)ccc21]
I-50
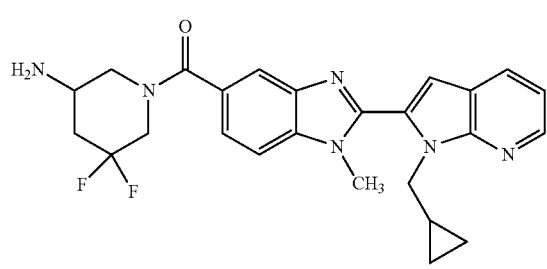 [SMILES: Cn1c(-c2cc3cccnc3n2CC2CC2)nc2cc(C(=O)N3CC(N)CC(F)(F)C3)ccc21]
I-51
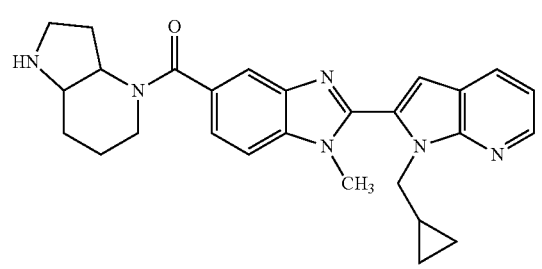
I-52

TABLE 1-continued
Exemplary Compounds of Formula I
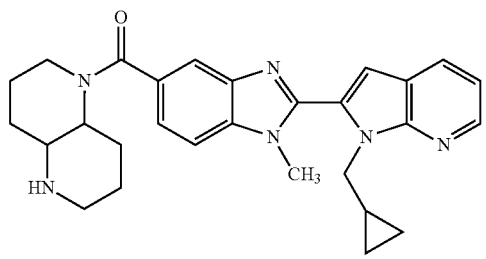 [SMILES: Cn1c(-c2cc3cccnc3n2CC2CC2)nc2cc(C(=O)N3CCCC4NCCCC43)ccc21]
I-53
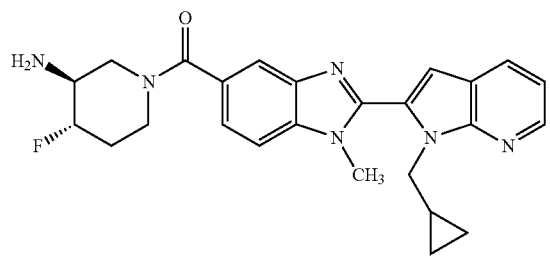 [SMILES: Cn1c(-c2cc3cccnc3n2CC2CC2)nc2cc(C(=O)N3CC[C@H](F)[C@@H](N)C3)ccc21]
I-54
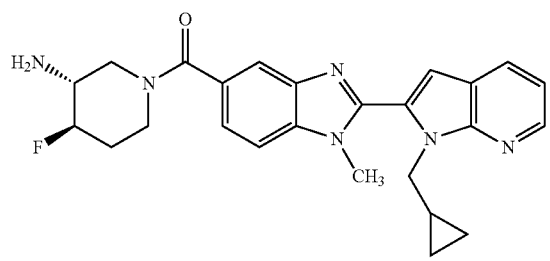 [SMILES: Cn1c(-c2cc3cccnc3n2CC2CC2)nc2cc(C(=O)N3CC[C@@H](F)[C@H](N)C3)ccc21]
I-55
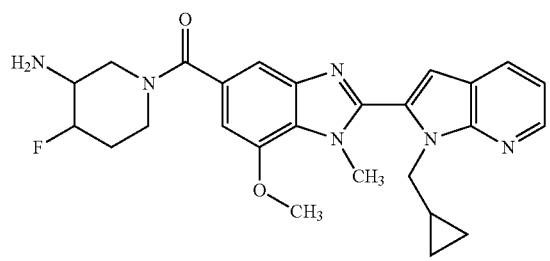 [SMILES: COc1cc(C(=O)N2CCC(F)C(N)C2)cc2nc(-c3cc4cccnc4n3CC3CC3)n(C)c12]
I-56
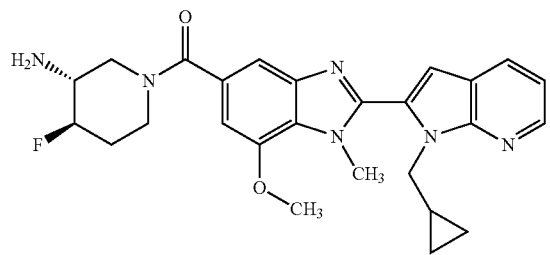 [SMILES: COc1cc(C(=O)N2CC[C@@H](F)[C@H](N)C2)cc2nc(-c3cc4cccnc4n3CC3CC3)n(C)c12]
I-57
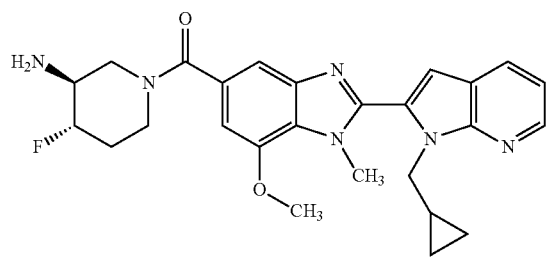 [SMILES: COc1cc(C(=O)N2CC[C@H](F)[C@@H](N)C2)cc2nc(-c3cc4cccnc4n3CC3CC3)n(C)c12]
I-58

TABLE 1-continued
Exemplary Compounds of Formula I
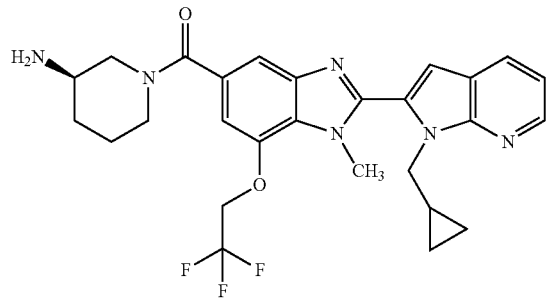 [SMILES: Cn1c(-c2cc3cccnc3n2CC2CC2)nc2cc(C(=O)N3CCC[C@@H](N)C3)cc(OCC(F)(F)F)c21]
I-59
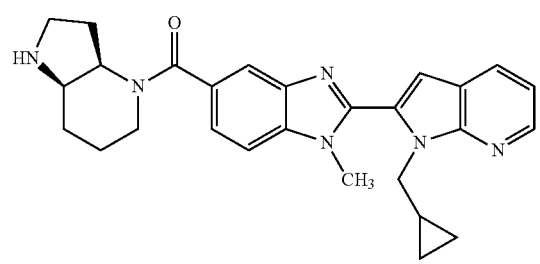 [SMILES: Cn1c(-c2cc3cccnc3n2CC2CC2)nc2cc(C(=O)N3CCC[C@H]4NCC[C@H]43)ccc21]
I-60
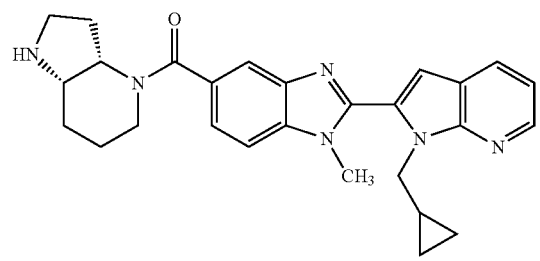 [SMILES: Cn1c(-c2cc3cccnc3n2CC2CC2)nc2cc(C(=O)N3CCC[C@@H]4NCC[C@@H]43)ccc21]
I-61
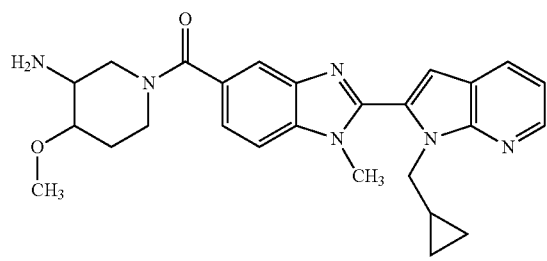 [SMILES: COC1CCN(C(=O)c2ccc3c(c2)nc(-c2cc4cccnc4n2CC2CC2)n3C)CC1N]
I-62
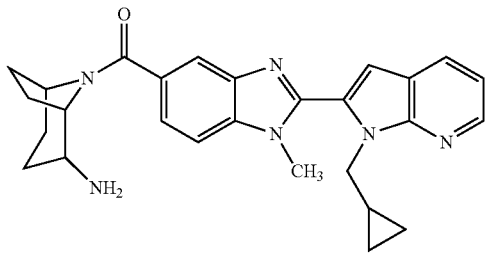 [SMILES: Cn1c(-c2cc3cccnc3n2CC2CC2)nc2cc(C(=O)N3C4CCC(N)C3CC4)ccc21]
I-63

TABLE 1-continued
Exemplary Compounds of Formula I
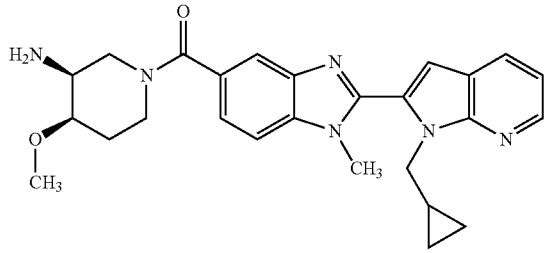 [SMILES: CO[C@@H]1CCN(C(=O)c2ccc3c(c2)nc(-c2cc4cccnc4n2CC2CC2)n3C)C[C@@H]1N]
I-64
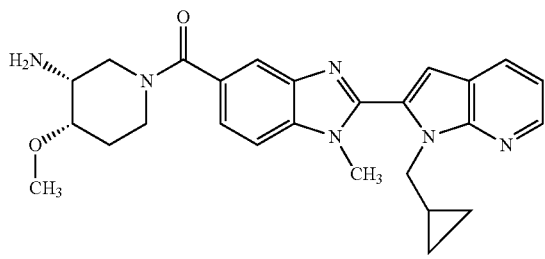 [SMILES: CO[C@H]1CCN(C(=O)c2ccc3c(c2)nc(-c2cc4cccnc4n2CC2CC2)n3C)C[C@H]1N]
I-65
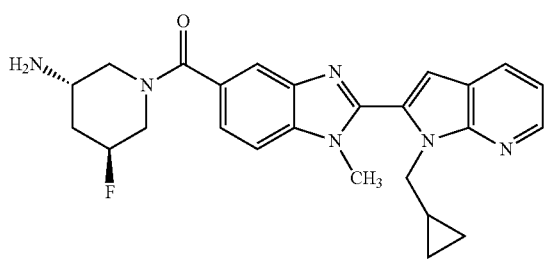 [SMILES: Cn1c(-c2cc3cccnc3n2CC2CC2)nc2cc(C(=O)N3C[C@@H](N)C[C@H](F)C3)ccc21]
I-66
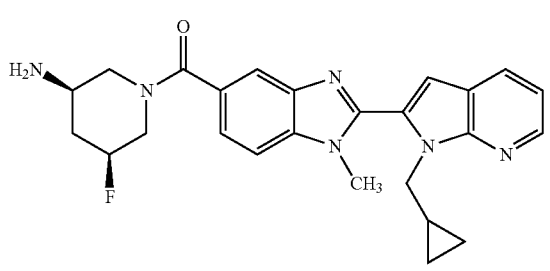 [SMILES: Cn1c(-c2cc3cccnc3n2CC2CC2)nc2cc(C(=O)N3C[C@H](N)C[C@H](F)C3)ccc21]
I-67
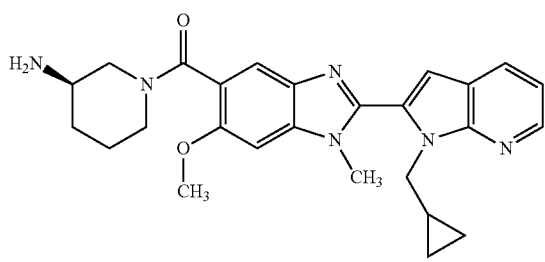 [SMILES: COc1cc2c(cc1C(=O)N1CCC[C@@H](N)C1)nc(-c1cc3cccnc3n1CC1CC1)n2C]
I-68

TABLE 1-continued
Exemplary Compounds of Formula I
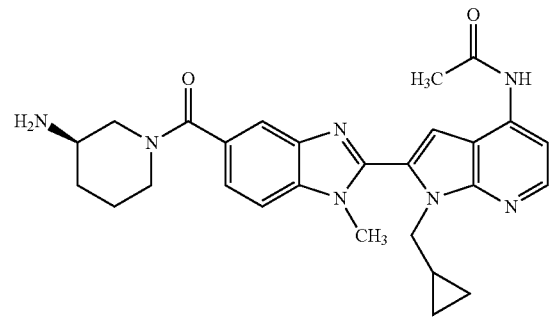 [SMILES: CC(=O)Nc1ccnc2c1cc(-c1nc3cc(C(=O)N4CCC[C@@H](N)C4)ccc3n1C)n2CC1CC1] I-69
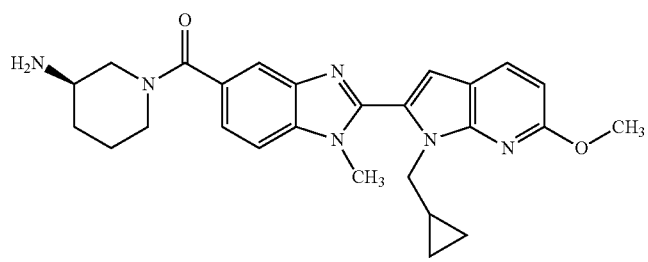 [SMILES: COc1ccc2cc(-c3nc4cc(C(=O)N5CCC[C@@H](N)C5)ccc4n3C)n(CC3CC3)c2n1] I-70
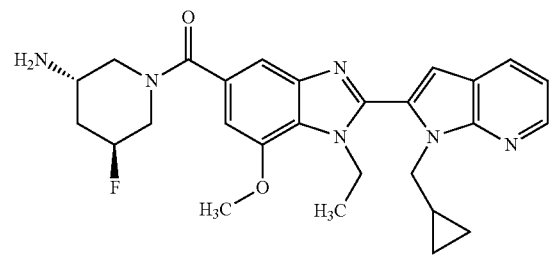 [SMILES: CCn1c(-c2cc3cccnc3n2CC2CC2)nc2cc(C(=O)N3C[C@@H](N)C[C@H](F)C3)cc(OC)c21] I-71
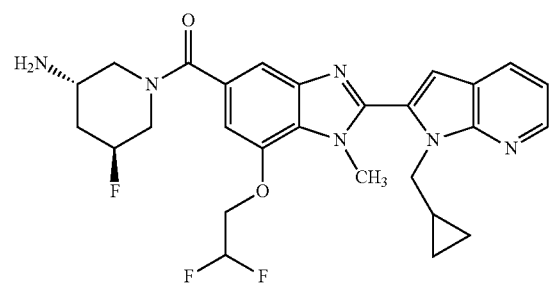 [SMILES: Cn1c(-c2cc3cccnc3n2CC2CC2)nc2cc(C(=O)N3C[C@@H](N)C[C@H](F)C3)cc(OCC(F)F)c21] I-72
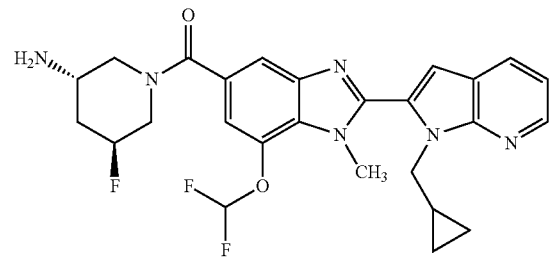 [SMILES: Cn1c(-c2cc3cccnc3n2CC2CC2)nc2cc(C(=O)N3C[C@@H](N)C[C@H](F)C3)cc(OC(F)F)c21] I-73

TABLE 1-continued
Exemplary Compounds of Formula I
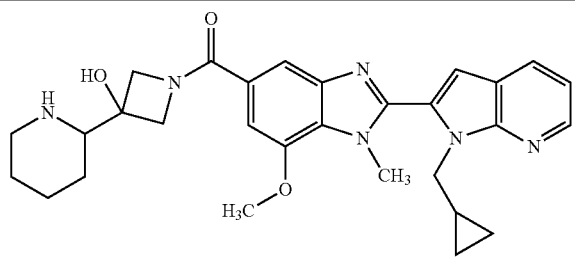
I-74
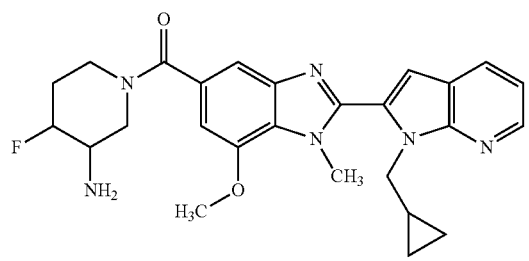 [SMILES: COc1cc(C(=O)N2CCC(F)C(N)C2)cc2nc(-c3cc4cccnc4n3CC3CC3)n(C)c12]
I-75
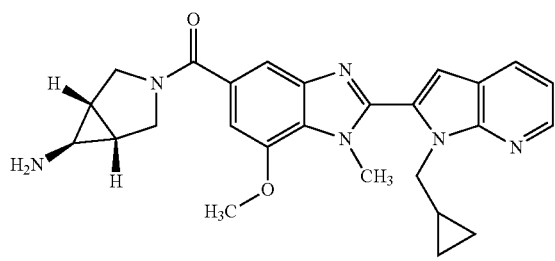 [SMILES: COc1cc(C(=O)N2C[C@@H]3[C@@H](N)[C@@H]3C2)cc2nc(-c3cc4cccnc4n3CC3CC3)n(C)c12]
I-76
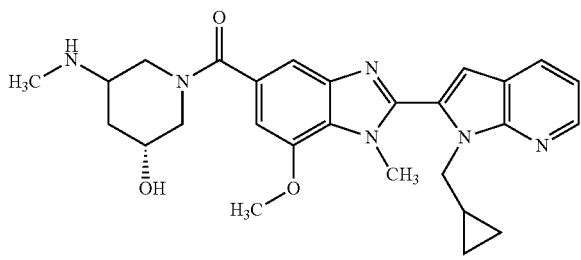 [SMILES: CNC1C[C@@H](O)CN(C(=O)c2cc(OC)c3c(c2)nc(-c2cc4cccnc4n2CC2CC2)n3C)C1]
I-77
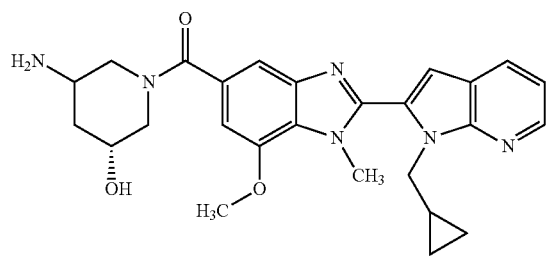 [SMILES: COc1cc(C(=O)N2CC(N)C[C@@H](O)C2)cc2nc(-c3cc4cccnc4n3CC3CC3)n(C)c12]
I-80
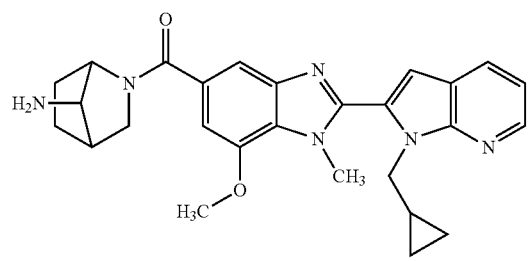 [SMILES: COc1cc(C(=O)N2CC3CCC2C3N)cc2nc(-c3cc4cccnc4n3CC3CC3)n(C)c12]
I-81

TABLE 1-continued

Exemplary Compounds of Formula I

I-82
I-83
I-84
I-85
I-86
I-87

US 9,963,448 B2
75　　　　　　　　　　　　　　　　　　　76
TABLE 1-continued
Exemplary Compounds of Formula I
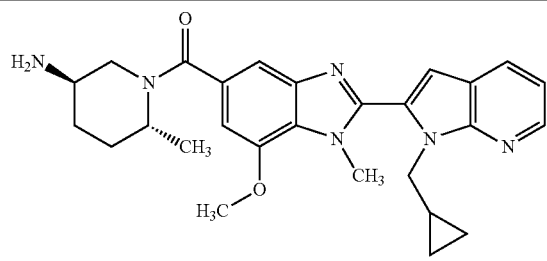
I-88
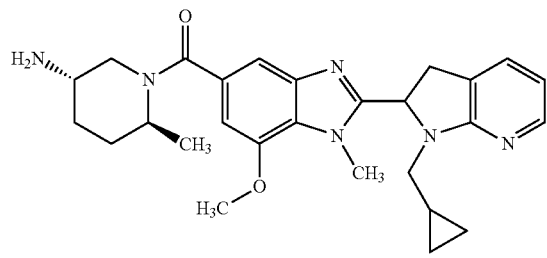 [SMILES: COc1cc(C(=O)N2C[C@@H](N)CC[C@@H]2C)cc2nc(C3Cc4cccnc4N3CC3CC3)n(C)c12]
I-89
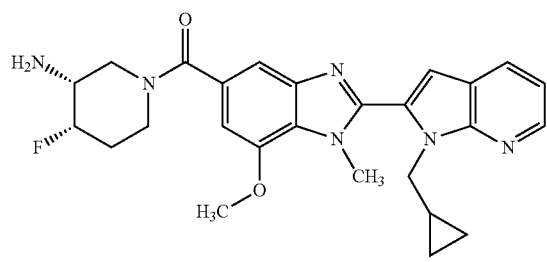 [SMILES: COc1cc(C(=O)N2CC[C@H](F)[C@H](N)C2)cc2nc(-c3cc4cccnc4n3CC3CC3)n(C)c12]
I-90
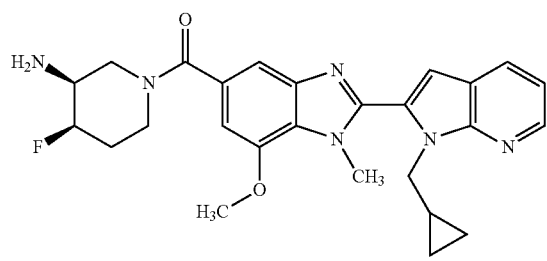 [SMILES: COc1cc(C(=O)N2CC[C@@H](F)[C@@H](N)C2)cc2nc(-c3cc4cccnc4n3CC3CC3)n(C)c12]
I-91
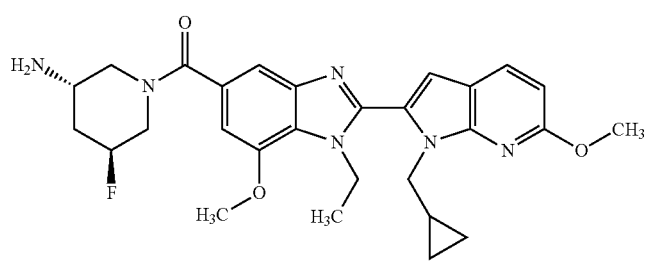 [SMILES: CCn1c(-c2cc3ccc(OC)nc3n2CC2CC2)nc2cc(C(=O)N3C[C@@H](N)C[C@H](F)C3)cc(OC)c21]
I-92
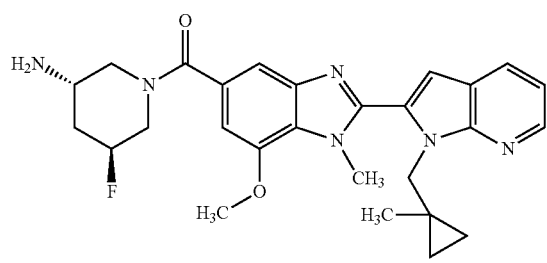 [SMILES: COc1cc(C(=O)N2C[C@@H](N)C[C@H](F)C2)cc2nc(-c3cc4cccnc4n3CC3(C)CC3)n(C)c12]
I-93

TABLE 1-continued
Exemplary Compounds of Formula I
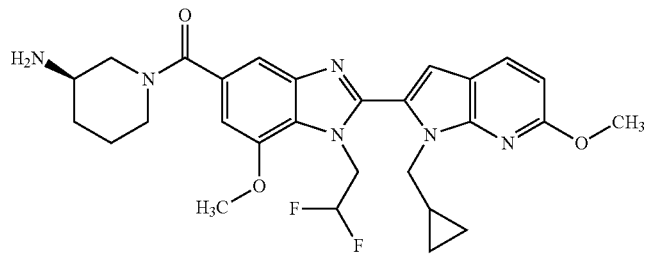 [SMILES: COc1ccc2cc(-c3nc4cc(C(=O)N5CCC[C@@H](N)C5)cc(OC)c4n3CC(F)F)n(CC3CC3)c2n1]
I-94
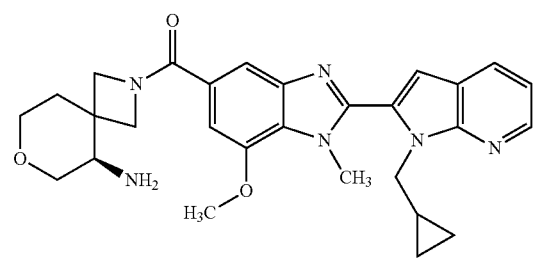 [SMILES: COc1cc(C(=O)N2CC3(CCOC[C@@H]3N)C2)cc2nc(-c3cc4cccnc4n3CC3CC3)n(C)c12]
I-95
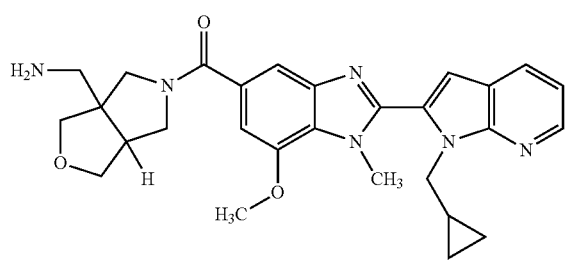 [SMILES: COc1cc(C(=O)N2CC3COCC3(CN)C2)cc2nc(-c3cc4cccnc4n3CC3CC3)n(C)c12]
I-96
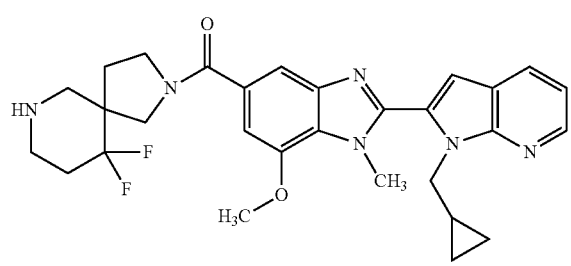 [SMILES: COc1cc(C(=O)N2CCC3(CNCCC3(F)F)C2)cc2nc(-c3cc4cccnc4n3CC3CC3)n(C)c12]
I-97
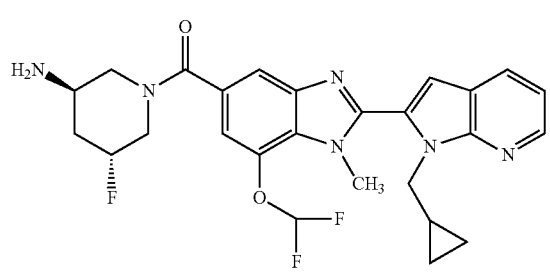 [SMILES: Cn1c(-c2cc3cccnc3n2CC2CC2)nc2cc(C(=O)N3C[C@H](N)C[C@@H](F)C3)cc(OC(F)F)c21]
I-98
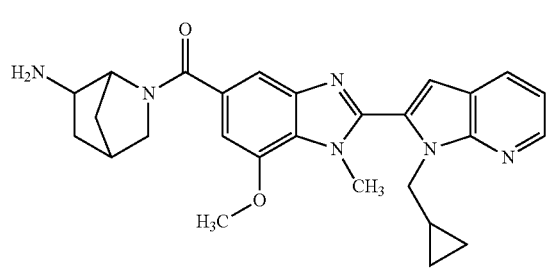 [SMILES: COc1cc(C(=O)N2CC3CC(N)C2C3)cc2nc(-c3cc4cccnc4n3CC3CC3)n(C)c12]
I-99

TABLE 1-continued

Exemplary Compounds of Formula I

I-100
I-101
I-102
I-103
I-104
I-105

TABLE 1-continued
Exemplary Compounds of Formula I
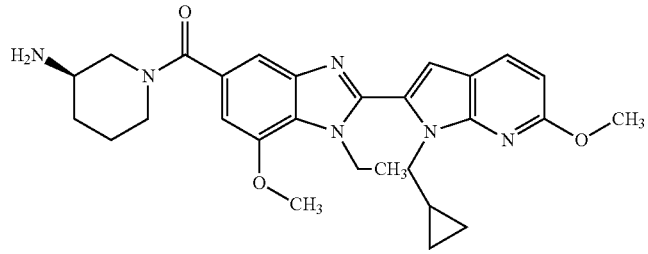 [SMILES: CCn1c(-c2cc3ccc(OC)nc3n2CC2CC2)nc2cc(C(=O)N3CCC[C@@H](N)C3)cc(OC)c21]
I-106
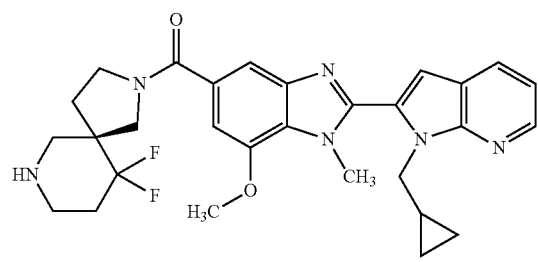 [SMILES: COc1cc(C(=O)N2CC[C@]3(CNCCC3(F)F)C2)cc2nc(-c3cc4cccnc4n3CC3CC3)n(C)c12]
I-107
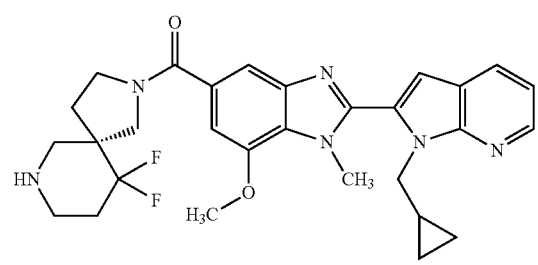 [SMILES: COc1cc(C(=O)N2CC[C@@]3(CNCCC3(F)F)C2)cc2nc(-c3cc4cccnc4n3CC3CC3)n(C)c12]
I-108
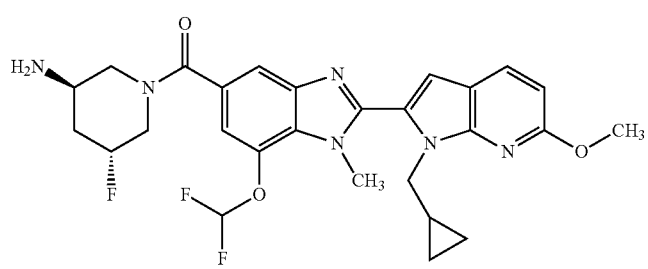 [SMILES: COc1ccc2cc(-c3nc4cc(C(=O)N5C[C@H](N)C[C@@H](F)C5)cc(OC(F)F)c4n3C)n(CC3CC3)c2n1]
I-109
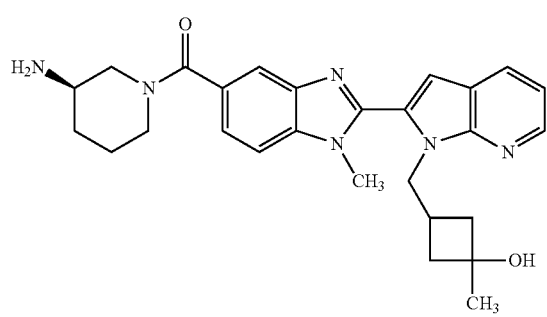 [SMILES: Cn1c(-c2cc3cccnc3n2CC2CC(C)(O)C2)nc2cc(C(=O)N3CCC[C@@H](N)C3)ccc21]
I-110

TABLE 1-continued
Exemplary Compounds of Formula I
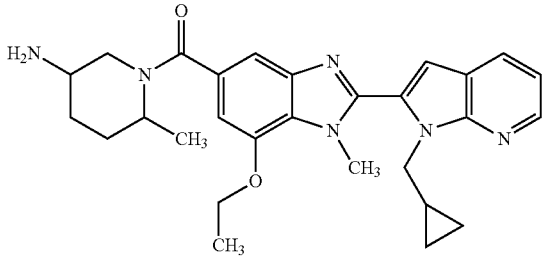 [SMILES: CCOc1cc(C(=O)N2CC(N)CCC2C)cc2nc(-c3cc4cccnc4n3CC3CC3)n(C)c12]
I-111
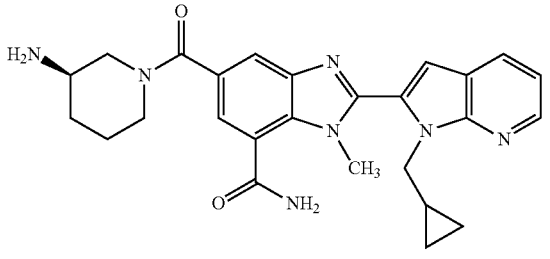 [SMILES: Cn1c(-c2cc3cccnc3n2CC2CC2)nc2cc(C(=O)N3CCC[C@@H](N)C3)cc(C(N)=O)c21]
I-112
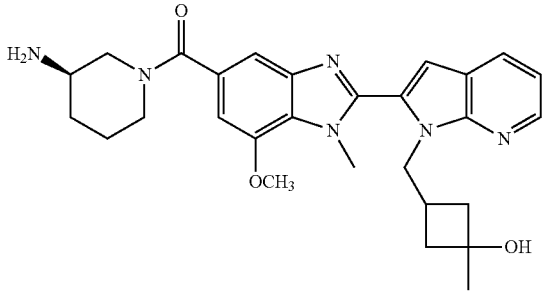 [SMILES: COc1cc(C(=O)N2CCC[C@@H](N)C2)cc2nc(-c3cc4cccnc4n3CC3CC(C)(O)C3)n(C)c12]
I-113
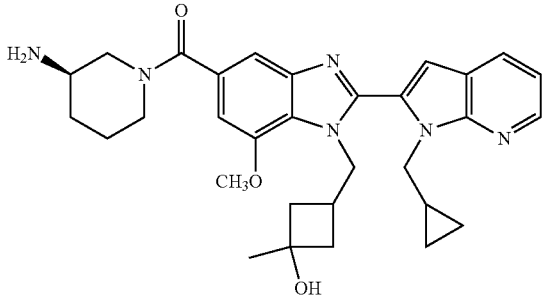
I-114
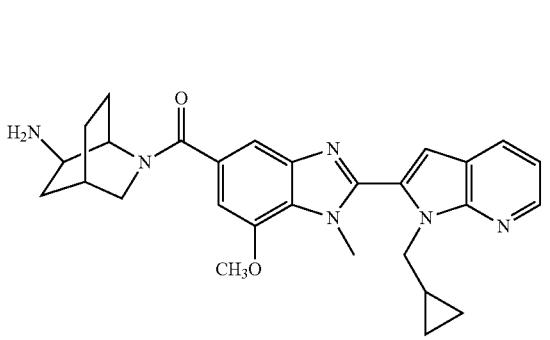
I-115

TABLE 1-continued
Exemplary Compounds of Formula I
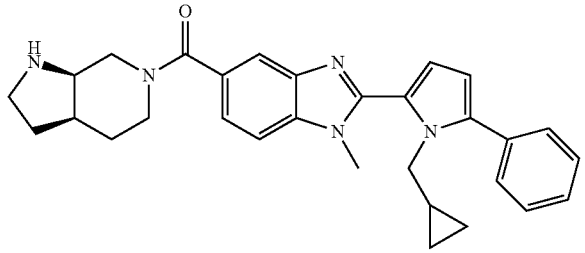 [SMILES: Cn1c(-c2ccc(-c3ccccc3)n2CC2CC2)nc2cc(C(=O)N3CC[C@H]4CCN[C@H]4C3)ccc21]
I-116
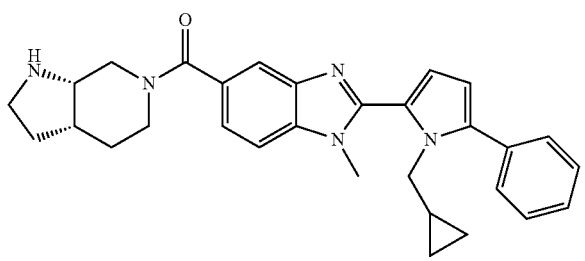 [SMILES: Cn1c(-c2ccc(-c3ccccc3)n2CC2CC2)nc2cc(C(=O)N3CC[C@@H]4CCN[C@@H]4C3)ccc21]
I-117
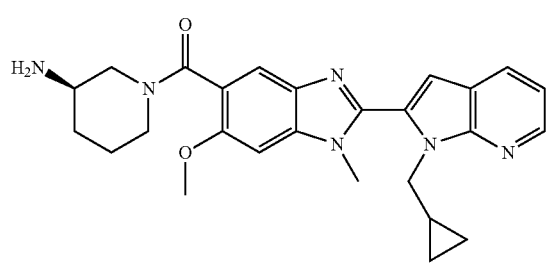 [SMILES: COc1cc2c(cc1C(=O)N1CCC[C@@H](N)C1)nc(-c1cc3cccnc3n1CC1CC1)n2C]
I-119
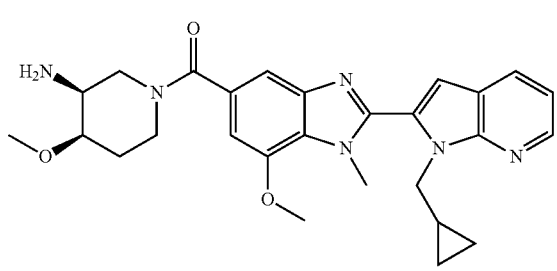 [SMILES: COc1cc(C(=O)N2CC[C@@H](OC)[C@@H](N)C2)cc2nc(-c3cc4cccnc4n3CC3CC3)n(C)c12]
I-121
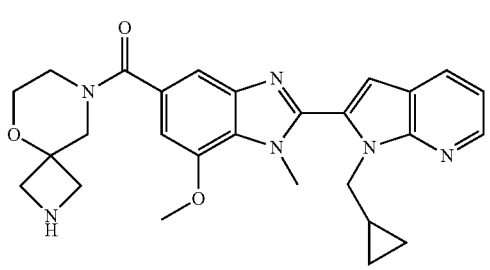 [SMILES: COc1cc(C(=O)N2CCOC3(CNC3)C2)cc2nc(-c3cc4cccnc4n3CC3CC3)n(C)c12]
I-122
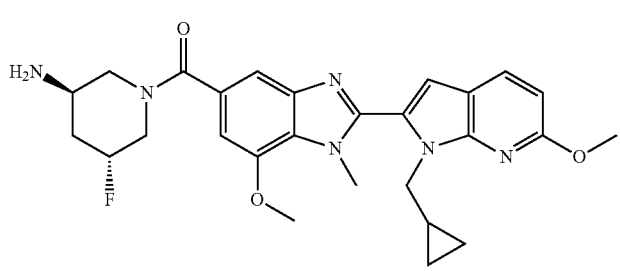 [SMILES: COc1ccc2cc(-c3nc4cc(C(=O)N5C[C@H](N)C[C@@H](F)C5)cc(OC)c4n3C)n(CC3CC3)c2n1]
I-123

TABLE 1-continued

Exemplary Compounds of Formula I

| | |
|---|---|
| (structure) | I-124 |
| (structure) | I-125 |
| (structure) | I-126 |
| (structure) | I-127 |
| (structure) | I-128 |
| (structure) | I-129 |

TABLE 1-continued
Exemplary Compounds of Formula I
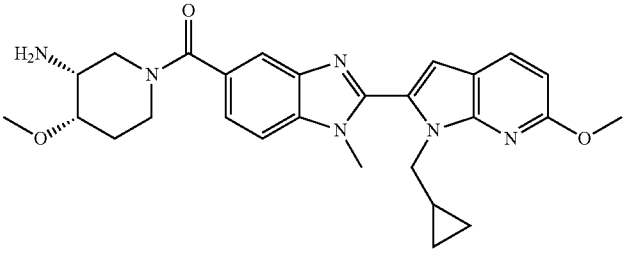
I-130
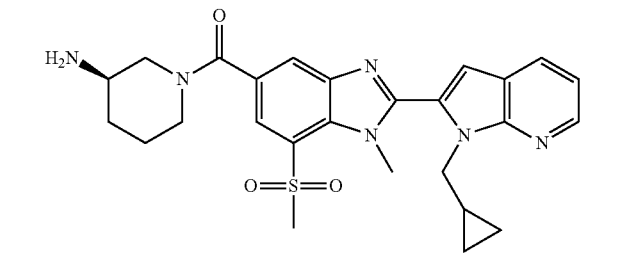 [SMILES: Cn1c(-c2cc3cccnc3n2CC2CC2)nc2cc(C(=O)N3CCC[C@@H](N)C3)cc(S(C)(=O)=O)c21]
I-131
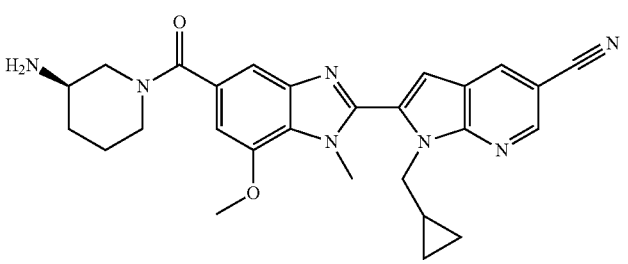 [SMILES: COc1cc(C(=O)N2CCC[C@@H](N)C2)cc2nc(-c3cc4cc(C#N)cnc4n3CC3CC3)n(C)c12]
I-132
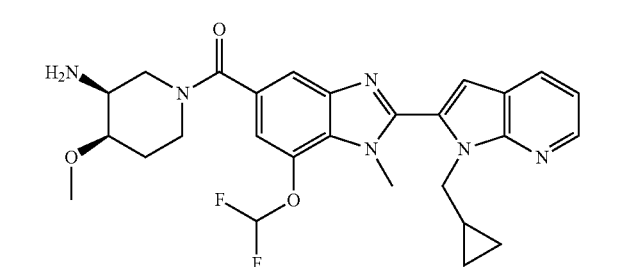 [SMILES: CO[C@@H]1CCN(C(=O)c2cc(OC(F)F)c3c(c2)nc(-c2cc4cccnc4n2CC2CC2)n3C)C[C@@H]1N]
I-133
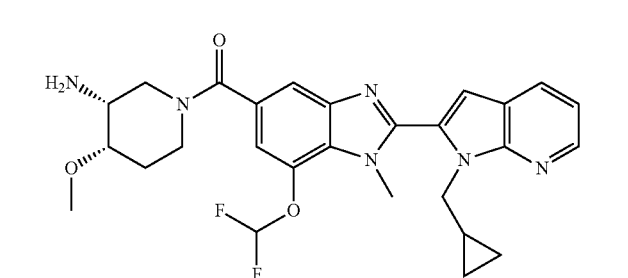
I-134
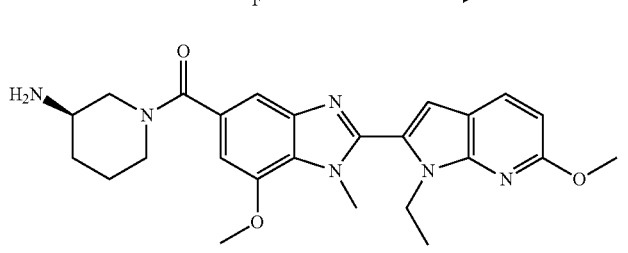
I-135

TABLE 1-continued
Exemplary Compounds of Formula I
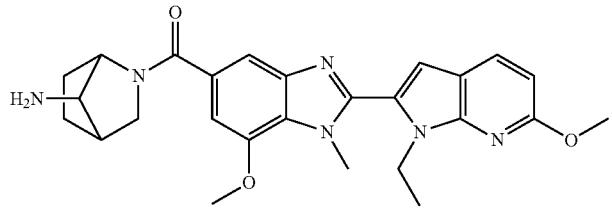 [SMILES: CCn1c(-c2nc3cc(C(=O)N4CC5CCC4C5N)cc(OC)c3n2C)cc2ccc(OC)nc21]
I-136
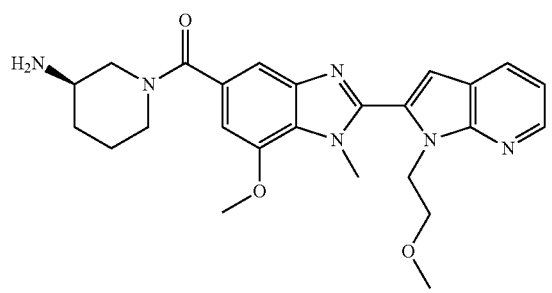 [SMILES: COCCn1c(-c2nc3cc(C(=O)N4CCC[C@@H](N)C4)cc(OC)c3n2C)cc2cccnc21]
I-137
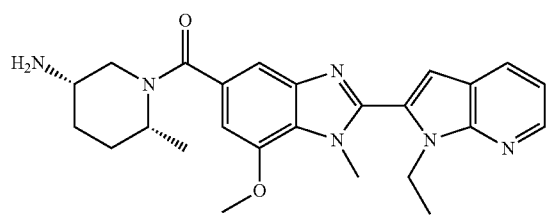 [SMILES: CCn1c(-c2nc3cc(C(=O)N4C[C@@H](N)CC[C@H]4C)cc(OC)c3n2C)cc2cccnc21]
I-138
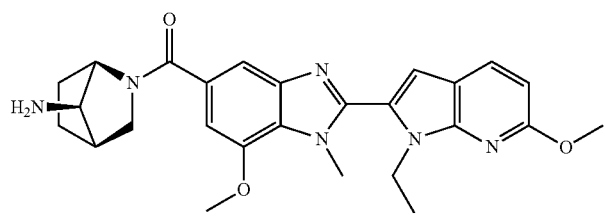 [SMILES: CCn1c(-c2nc3cc(C(=O)N4C[C@H]5CC[C@@H]4[C@@H]5N)cc(OC)c3n2C)cc2ccc(OC)nc21]
I-139
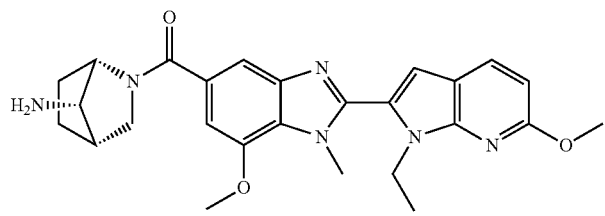 [SMILES: CCn1c(-c2nc3cc(C(=O)N4C[C@@H]5CC[C@H]4[C@H]5N)cc(OC)c3n2C)cc2ccc(OC)nc21]
I-140
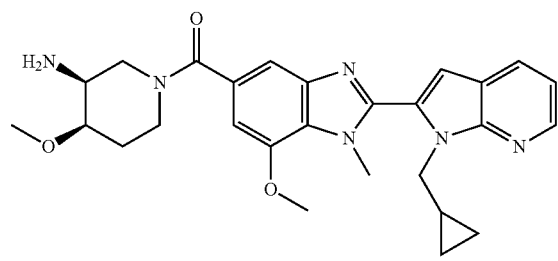 [SMILES: COc1cc(C(=O)N2CC[C@@H](OC)[C@@H](N)C2)cc2nc(-c3cc4cccnc4n3CC3CC3)n(C)c12]
I-141

TABLE 1-continued
Exemplary Compounds of Formula I
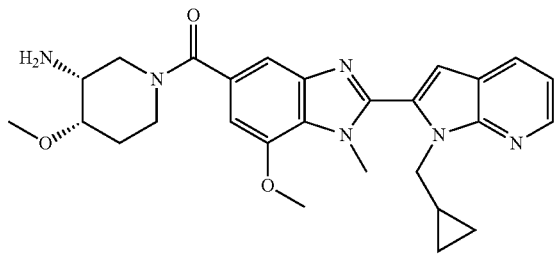 [SMILES: COc1cc(C(=O)N2CC[C@H](OC)[C@H](N)C2)cc2nc(-c3cc4cccnc4n3CC3CC3)n(C)c12]
I-142
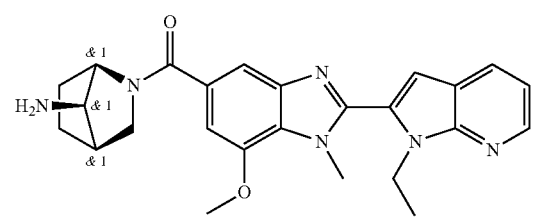 [SMILES: CCn1c(-c2nc3cc(C(=O)N4C[C@H]5CC[C@@H]4[C@@H]5N)cc(OC)c3n2C)cc2cccnc21]
I-143
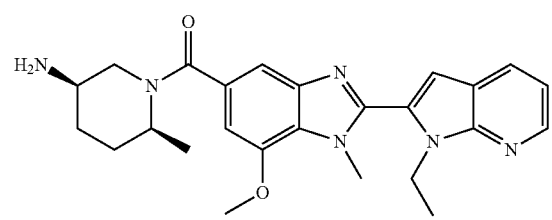 [SMILES: CCn1c(-c2nc3cc(C(=O)N4C[C@H](N)CC[C@@H]4C)cc(OC)c3n2C)cc2cccnc21]
I-144
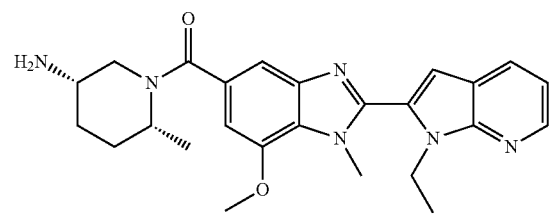 [SMILES: CCn1c(-c2nc3cc(C(=O)N4C[C@@H](N)CC[C@H]4C)cc(OC)c3n2C)cc2cccnc21]
I-145
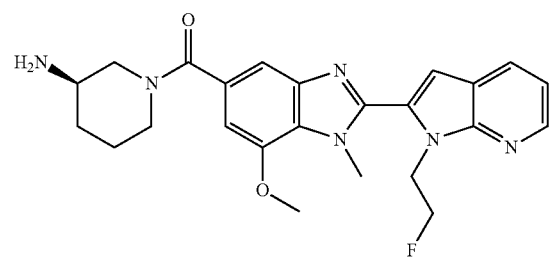 [SMILES: COc1cc(C(=O)N2CCC[C@@H](N)C2)cc2nc(-c3cc4cccnc4n3CCF)n(C)c12]
I-146
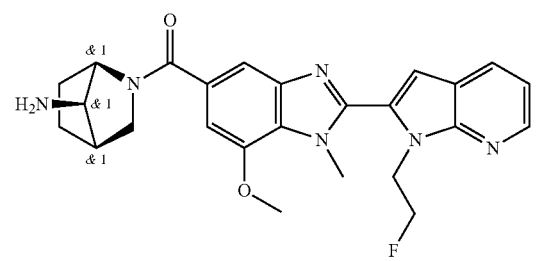 [SMILES: COc1cc(C(=O)N2C[C@H]3CC[C@@H]2[C@@H]3N)cc2nc(-c3cc4cccnc4n3CCF)n(C)c12]
I-147

TABLE 1-continued
Exemplary Compounds of Formula I
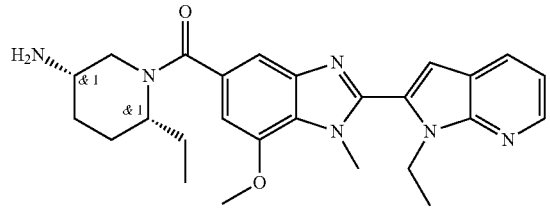 [SMILES: CC[C@@H]1CC[C@H](N)CN1C(=O)c1cc(OC)c2c(c1)nc(-c1cc3cccnc3n1CC)n2C]
I-148
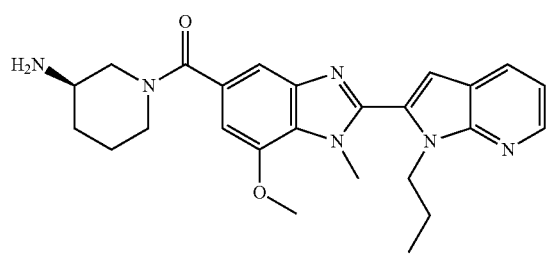 [SMILES: CCCn1c(-c2nc3cc(C(=O)N4CCC[C@@H](N)C4)cc(OC)c3n2C)cc2cccnc21]
I-149
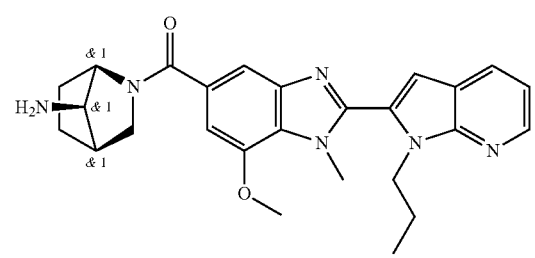 [SMILES: CCCn1c(-c2nc3cc(C(=O)N4C[C@H]5CC[C@@H]4[C@@H]5N)cc(OC)c3n2C)cc2cccnc21]
I-150
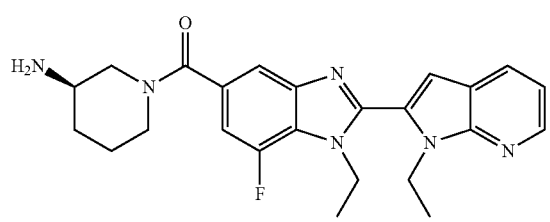 [SMILES: CCn1c(-c2nc3cc(C(=O)N4CCC[C@@H](N)C4)cc(F)c3n2CC)cc2cccnc21]
I-151
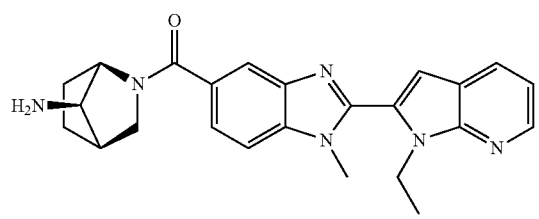 [SMILES: CCn1c(-c2nc3cc(C(=O)N4C[C@H]5CC[C@@H]4[C@@H]5N)ccc3n2C)cc2cccnc21]
I-152
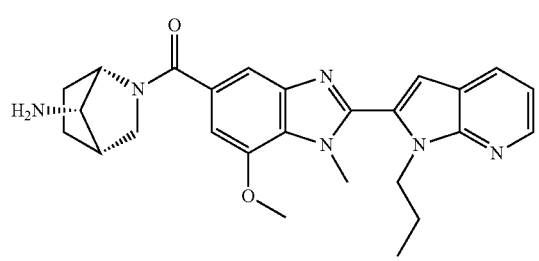 [SMILES: CCCn1c(-c2nc3cc(C(=O)N4C[C@@H]5CC[C@H]4[C@H]5N)cc(OC)c3n2C)cc2cccnc21]
I-153

TABLE 1-continued
Exemplary Compounds of Formula I
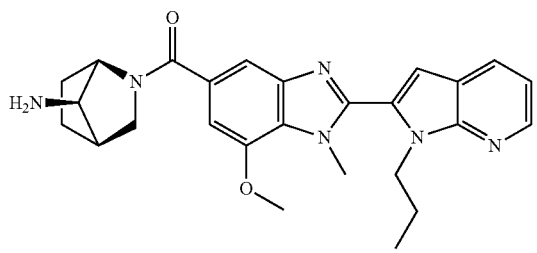 [SMILES: CCCn1c(-c2nc3cc(C(=O)N4C[C@H]5CC[C@@H]4[C@@H]5N)cc(OC)c3n2C)cc2cccnc21]
I-154
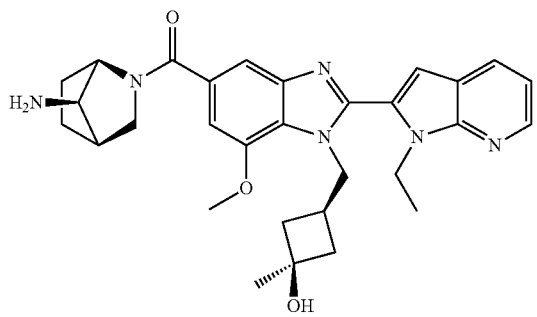 [SMILES: CCn1c(-c2nc3cc(C(=O)N4C[C@H]5CC[C@@H]4[C@@H]5N)cc(OC)c3n2C[C@H]2C[C@@](C)(O)C2)cc2cccnc21]
I-155
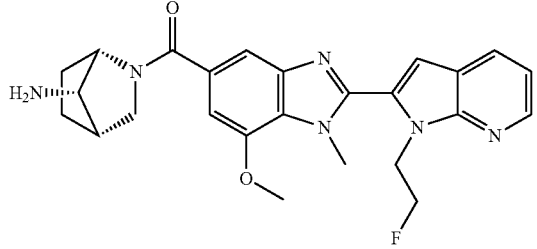 [SMILES: COc1cc(C(=O)N2C[C@@H]3CC[C@H]2[C@H]3N)cc2nc(-c3cc4cccnc4n3CCF)n(C)c12]
I-156
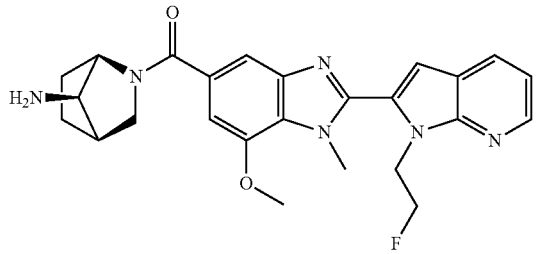 [SMILES: COc1cc(C(=O)N2C[C@H]3CC[C@@H]2[C@@H]3N)cc2nc(-c3cc4cccnc4n3CCF)n(C)c12]
I-157
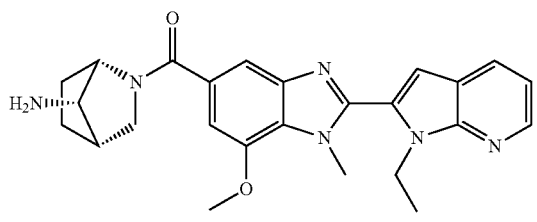 [SMILES: CCn1c(-c2nc3cc(C(=O)N4C[C@@H]5CC[C@H]4[C@H]5N)cc(OC)c3n2C)cc2cccnc21]
I-158
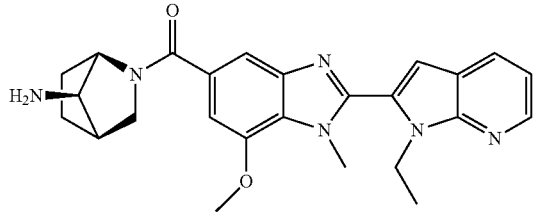 [SMILES: CCn1c(-c2nc3cc(C(=O)N4C[C@H]5CC[C@@H]4[C@@H]5N)cc(OC)c3n2C)cc2cccnc21]
I-159

TABLE 1-continued
Exemplary Compounds of Formula I
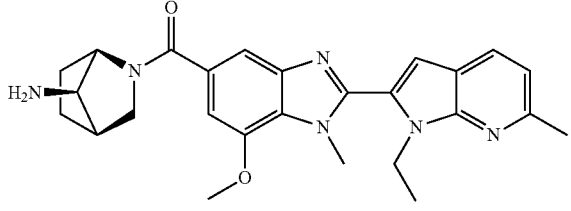 [SMILES: CCn1c(-c2nc3cc(C(=O)N4C[C@H]5CC[C@@H]4[C@@H]5N)cc(OC)c3n2C)cc2ccc(C)nc21] I-160
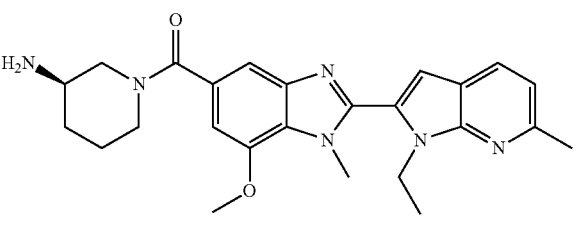 [SMILES: CCn1c(-c2nc3cc(C(=O)N4CCC[C@@H](N)C4)cc(OC)c3n2C)cc2ccc(C)nc21] I-161
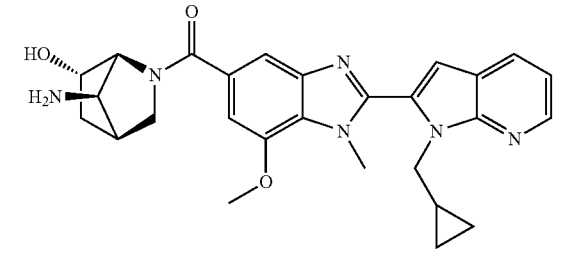 [SMILES: COc1cc(C(=O)N2C[C@H]3C[C@H](O)[C@@H]2[C@@H]3N)cc2nc(-c3cc4cccnc4n3CC3CC3)n(C)c12] I-162
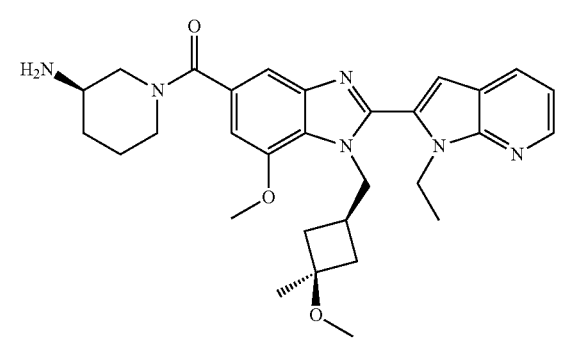 [SMILES: CCn1c(-c2nc3cc(C(=O)N4CCC[C@@H](N)C4)cc(OC)c3n2C[C@H]2C[C@@](C)(OC)C2)cc2cccnc21] I-163
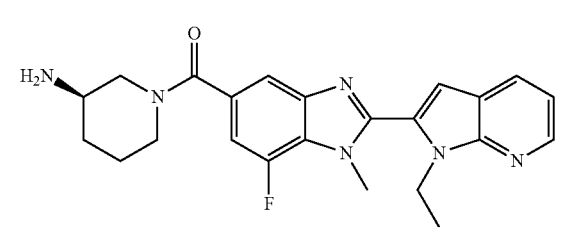 [SMILES: CCn1c(-c2nc3cc(C(=O)N4CCC[C@@H](N)C4)cc(F)c3n2C)cc2cccnc21] I-164
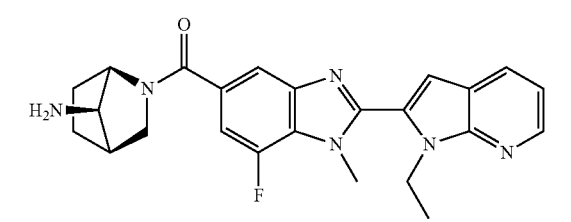 [SMILES: CCn1c(-c2nc3cc(C(=O)N4C[C@H]5CC[C@@H]4[C@@H]5N)cc(F)c3n2C)cc2cccnc21] I-165

TABLE 1-continued
Exemplary Compounds of Formula I
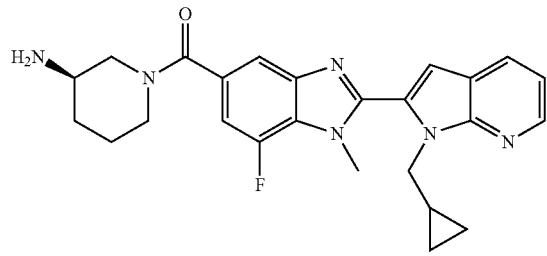 [SMILES: Cn1c(-c2cc3cccnc3n2CC2CC2)nc2cc(C(=O)N3CCC[C@@H](N)C3)cc(F)c21]
I-166
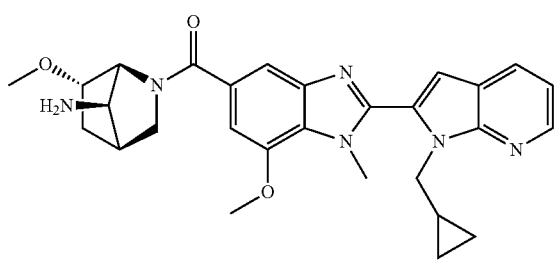 [SMILES: COc1cc(C(=O)N2C[C@H]3C[C@H](OC)[C@@H]2[C@@H]3N)cc2nc(-c3cc4cccnc4n3CC3CC3)n(C)c12]
I-167
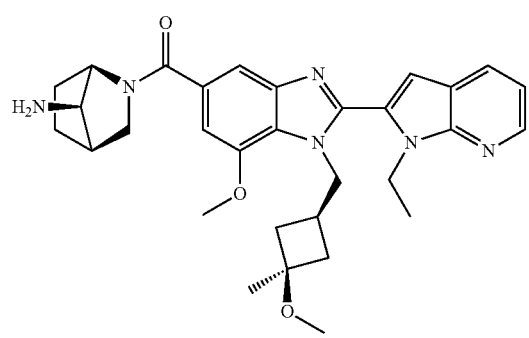 [SMILES: CCn1c(-c2nc3cc(C(=O)N4C[C@H]5CC[C@@H]4[C@@H]5N)cc(OC)c3n2C[C@H]2C[C@@](C)(OC)C2)cc2cccnc21]
I-168
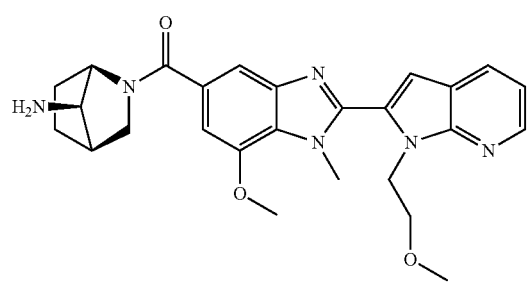 [SMILES: COCCn1c(-c2nc3cc(C(=O)N4C[C@H]5CC[C@@H]4[C@@H]5N)cc(OC)c3n2C)cc2cccnc21]
I-169
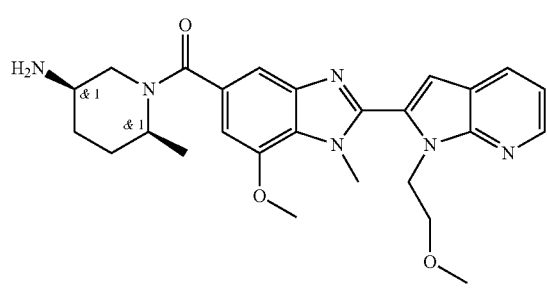 [SMILES: COCCn1c(-c2nc3cc(C(=O)N4C[C@H](N)CC[C@@H]4C)cc(OC)c3n2C)cc2cccnc21]
I-170

TABLE 1-continued

Exemplary Compounds of Formula I

| | |
|---|---|
| (structure) | I-171 |
| (structure) | I-172 |
| (structure) | I-173 |
| (structure) | I-174 |
| (structure) | I-175 |
| (structure) | I-176 |

TABLE 1-continued
Exemplary Compounds of Formula I
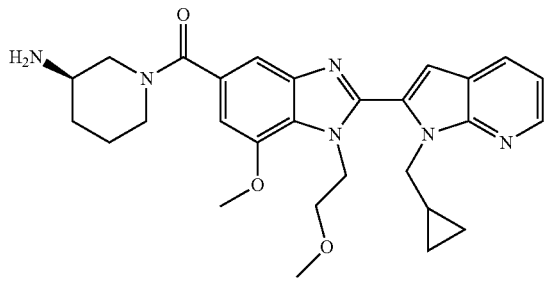 [SMILES: COCCn1c(-c2cc3cccnc3n2CC2CC2)nc2cc(C(=O)N3CCC[C@@H](N)C3)cc(OC)c21]
I-177
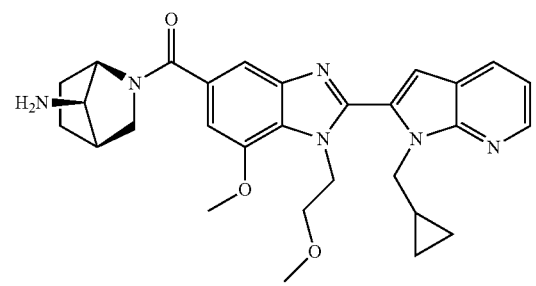 [SMILES: COCCn1c(-c2cc3cccnc3n2CC2CC2)nc2cc(C(=O)N3C[C@H]4CC[C@@H]3[C@@H]4N)cc(OC)c21]
I-178
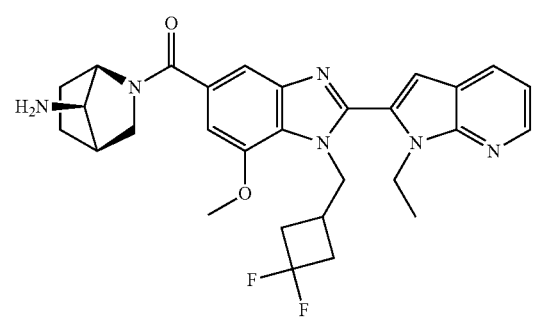 [SMILES: CCn1c(-c2nc3cc(C(=O)N4C[C@H]5CC[C@@H]4[C@@H]5N)cc(OC)c3n2CC2CC(F)(F)C2)cc2cccnc21]
I-179
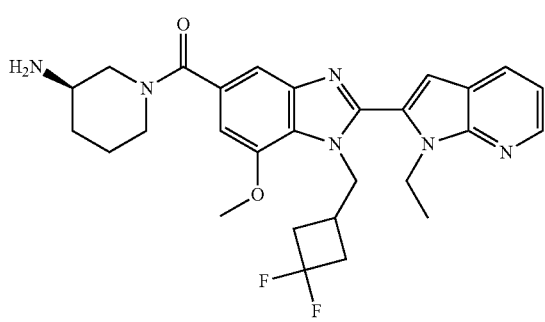 [SMILES: CCn1c(-c2nc3cc(C(=O)N4CCC[C@@H](N)C4)cc(OC)c3n2CC2CC(F)(F)C2)cc2cccnc21]
I-180
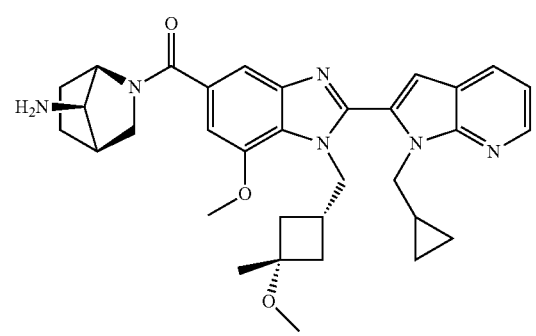 [SMILES: COc1cc(C(=O)N2C[C@H]3CC[C@@H]2[C@@H]3N)cc2nc(-c3cc4cccnc4n3CC3CC3)n(C[C@H]3C[C@@](C)(OC)C3)c12]
I-181

TABLE 1-continued
Exemplary Compounds of Formula I
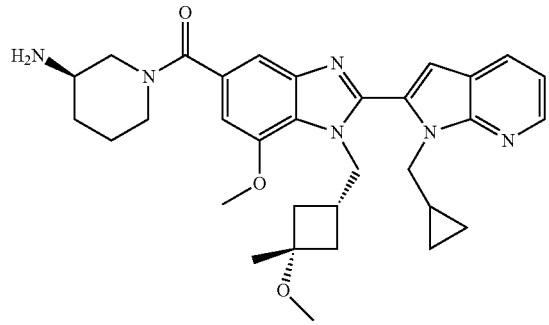 [SMILES: COc1cc(C(=O)N2CCC[C@@H](N)C2)cc2nc(-c3cc4cccnc4n3CC3CC3)n(C[C@H]3C[C@@](C)(OC)C3)c12]
I-182
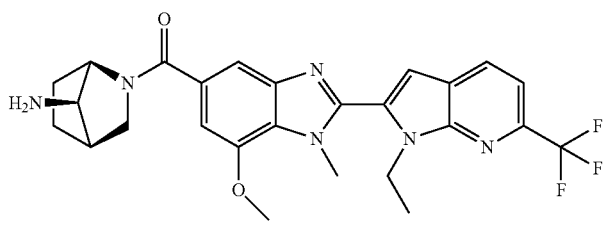 [SMILES: CCn1c(-c2nc3cc(C(=O)N4C[C@H]5CC[C@@H]4[C@@H]5N)cc(OC)c3n2C)cc2ccc(C(F)(F)F)nc21]
I-183
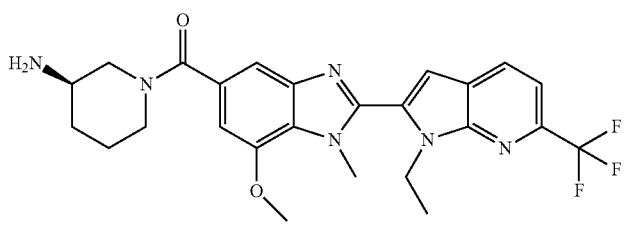 [SMILES: CCn1c(-c2nc3cc(C(=O)N4CCC[C@@H](N)C4)cc(OC)c3n2C)cc2ccc(C(F)(F)F)nc21]
I-184
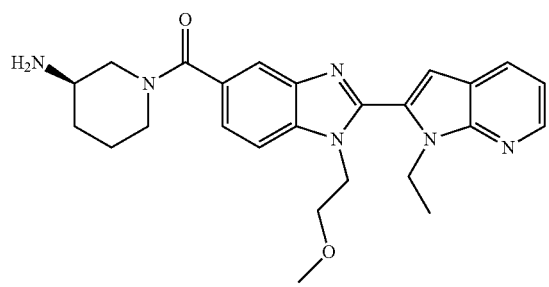 [SMILES: CCn1c(-c2nc3cc(C(=O)N4CCC[C@@H](N)C4)ccc3n2CCOC)cc2cccnc21]
I-185
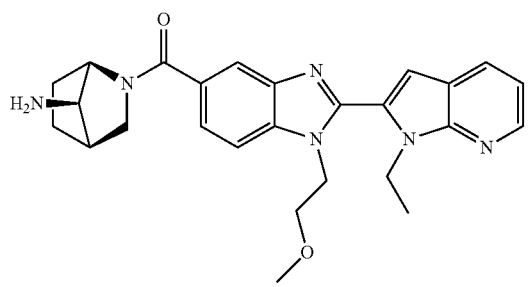 [SMILES: CCn1c(-c2nc3cc(C(=O)N4C[C@H]5CC[C@@H]4[C@@H]5N)ccc3n2CCOC)cc2cccnc21]
I-186

TABLE 1-continued
Exemplary Compounds of Formula I
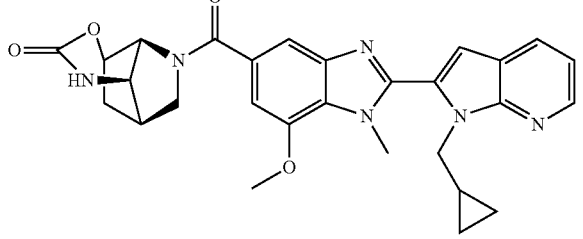 I-187
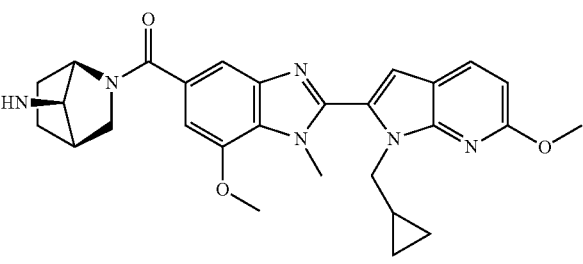 [SMILES: COc1ccc2cc(-c3nc4cc(C(=O)N5C[C@H]6CC[C@@H]5[C@@H]6N)cc(OC)c4n3C)n(CC3CC3)c2n1] I-188
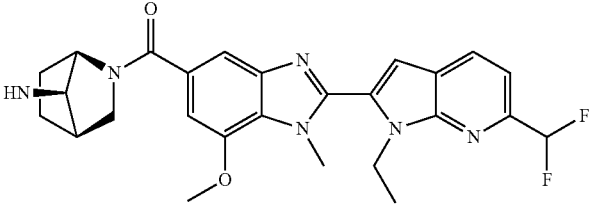 [SMILES: CCn1c(-c2nc3cc(C(=O)N4C[C@H]5CC[C@@H]4[C@@H]5N)cc(OC)c3n2C)cc2ccc(C(F)F)nc21] I-189
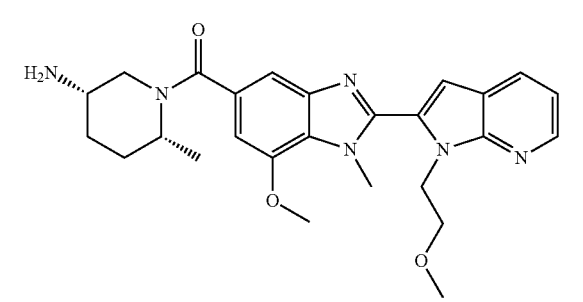 [SMILES: COCCn1c(-c2nc3cc(C(=O)N4C[C@@H](N)CC[C@H]4C)cc(OC)c3n2C)cc2cccnc21] I-190
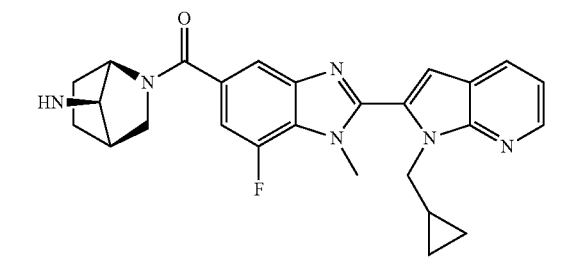 [SMILES: Cn1c(-c2cc3cccnc3n2CC2CC2)nc2cc(C(=O)N3C[C@H]4CC[C@@H]3[C@@H]4N)cc(F)c21] I-191
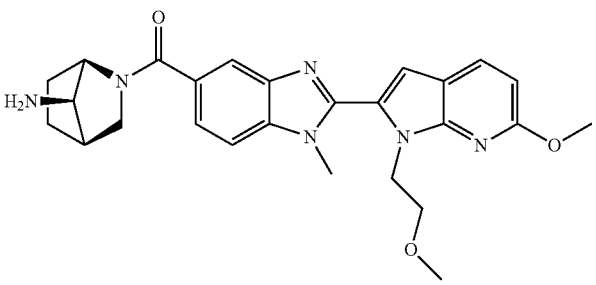 [SMILES: COCCn1c(-c2nc3cc(C(=O)N4C[C@H]5CC[C@@H]4[C@@H]5N)ccc3n2C)cc2ccc(OC)nc21] I-192

TABLE 1-continued
Exemplary Compounds of Formula I
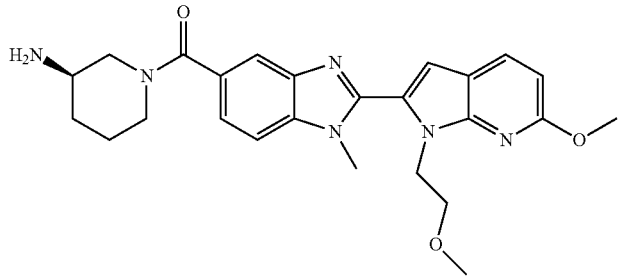 [SMILES: COCCn1c(-c2nc3cc(C(=O)N4CCC[C@@H](N)C4)ccc3n2C)cc2ccc(OC)nc21]
I-193
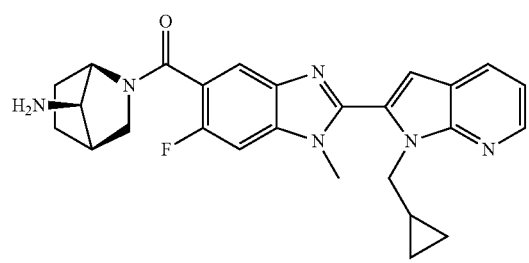 [SMILES: Cn1c(-c2cc3cccnc3n2CC2CC2)nc2cc(C(=O)N3C[C@H]4CC[C@@H]3[C@@H]4N)c(F)cc21]
I-194
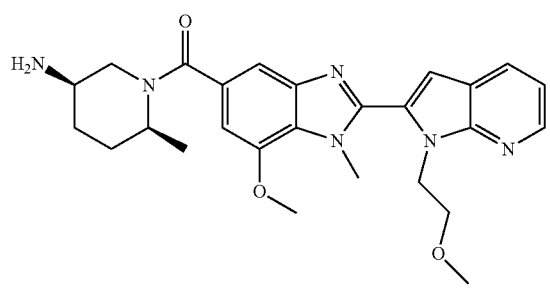 [SMILES: COCCn1c(-c2nc3cc(C(=O)N4C[C@H](N)CC[C@@H]4C)cc(OC)c3n2C)cc2cccnc21]
I-195
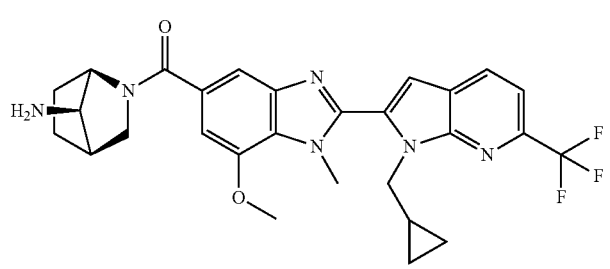 [SMILES: COc1cc(C(=O)N2C[C@H]3CC[C@@H]2[C@@H]3N)cc2nc(-c3cc4ccc(C(F)(F)F)nc4n3CC3CC3)n(C)c12]
I-196
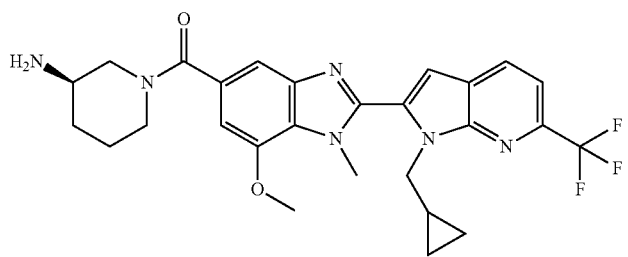 [SMILES: COc1cc(C(=O)N2CCC[C@@H](N)C2)cc2nc(-c3cc4ccc(C(F)(F)F)nc4n3CC3CC3)n(C)c12]
I-197

TABLE 1-continued

Exemplary Compounds of Formula I

| | |
|---|---|
| (structure) | I-198 |
| (structure) | I-199 |
| (structure) | I-200 |
| (structure) | I-201 |
| (structure) | I-202 |
| (structure) | I-203 |

TABLE 1-continued
Exemplary Compounds of Formula I
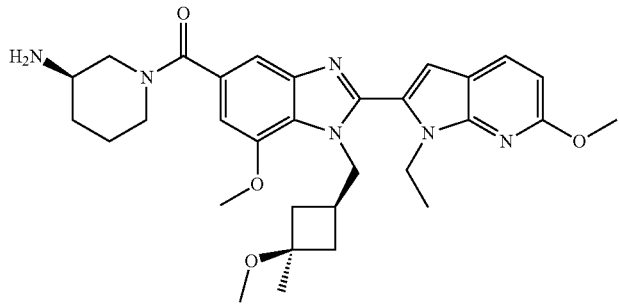 [SMILES: CCn1c(-c2nc3cc(C(=O)N4CCC[C@@H](N)C4)cc(OC)c3n2C[C@H]2C[C@@](C)(OC)C2)cc2ccc(OC)nc21]
I-204
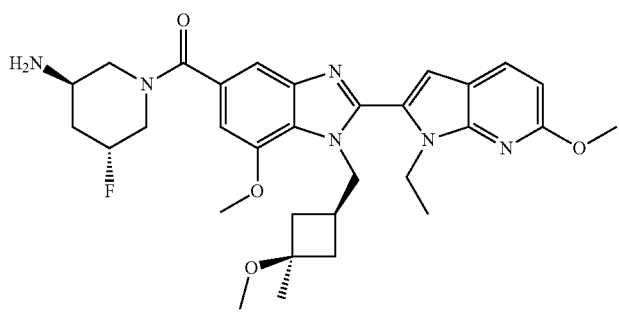 [SMILES: CCn1c(-c2nc3cc(C(=O)N4C[C@H](N)C[C@@H](F)C4)cc(OC)c3n2C[C@H]2C[C@@](C)(OC)C2)cc2ccc(OC)nc21]
I-205
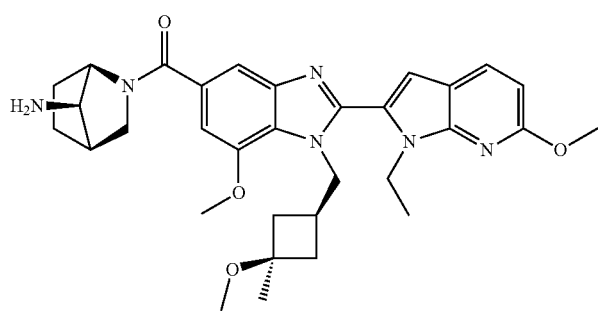 [SMILES: CCn1c(-c2nc3cc(C(=O)N4C[C@H]5CC[C@@H]4[C@@H]5N)cc(OC)c3n2C[C@H]2C[C@@](C)(OC)C2)cc2ccc(OC)nc21]
I-206
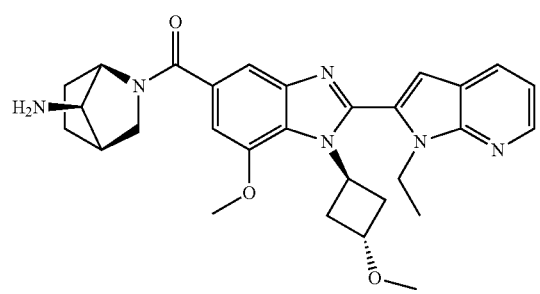 [SMILES: CCn1c(-c2nc3cc(C(=O)N4C[C@H]5CC[C@@H]4[C@@H]5N)cc(OC)c3n2[C@H]2C[C@H](OC)C2)cc2cccnc21]
I-207
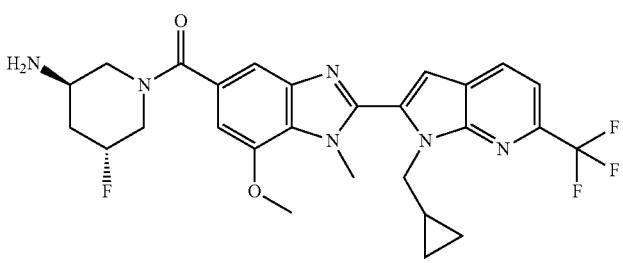 [SMILES: COc1cc(C(=O)N2C[C@H](N)C[C@@H](F)C2)cc2nc(-c3cc4ccc(C(F)(F)F)nc4n3CC3CC3)n(C)c12]
I-208

TABLE 1-continued
Exemplary Compounds of Formula I
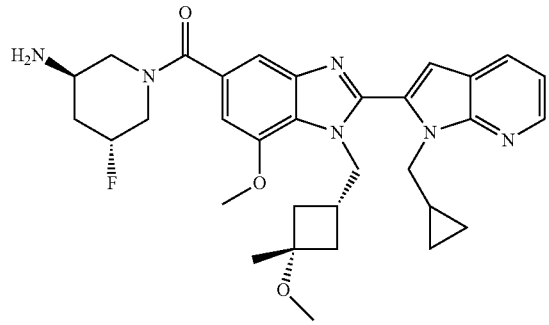 [SMILES: COc1cc(C(=O)N2C[C@H](N)C[C@@H](F)C2)cc2nc(-c3cc4cccnc4n3CC3CC3)n(C[C@H]3C[C@@](C)(OC)C3)c12] I-209
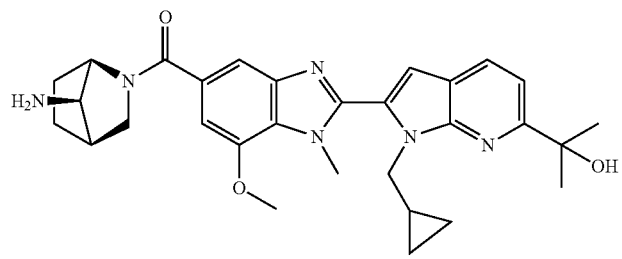 [SMILES: COc1cc(C(=O)N2C[C@H]3CC[C@@H]2[C@@H]3N)cc2nc(-c3cc4ccc(C(C)(C)O)nc4n3CC3CC3)n(C)c12] I-210
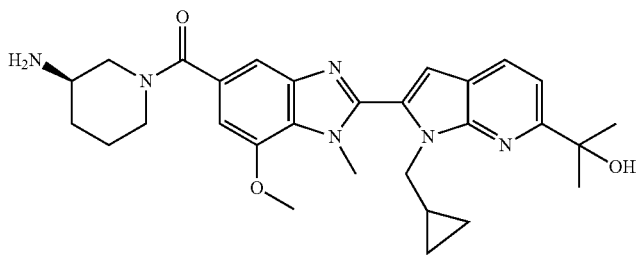 [SMILES: COc1cc(C(=O)N2CCC[C@@H](N)C2)cc2nc(-c3cc4ccc(C(C)(C)O)nc4n3CC3CC3)n(C)c12] I-211
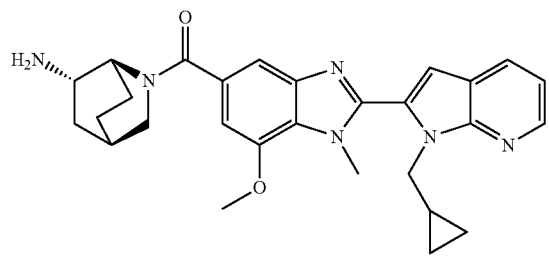 [SMILES: COc1cc(C(=O)N2C[C@@H]3CC[C@H]2[C@@H](N)C3)cc2nc(-c3cc4cccnc4n3CC3CC3)n(C)c12] I-212
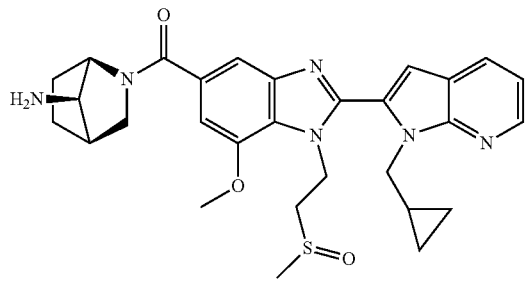 [SMILES: COc1cc(C(=O)N2C[C@H]3CC[C@@H]2[C@@H]3N)cc2nc(-c3cc4cccnc4n3CC3CC3)n(CCS(C)=O)c12] I-213

TABLE 1-continued
Exemplary Compounds of Formula I
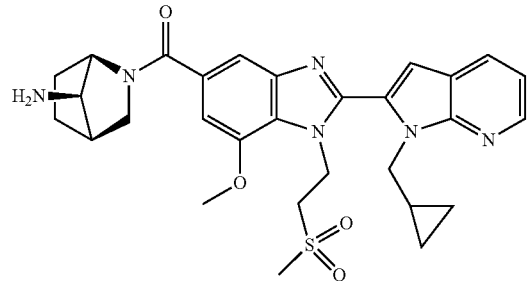 [SMILES: COc1cc(C(=O)N2C[C@H]3CC[C@@H]2[C@@H]3N)cc2nc(-c3cc4cccnc4n3CC3CC3)n(CCS(C)(=O)=O)c12]
I-214
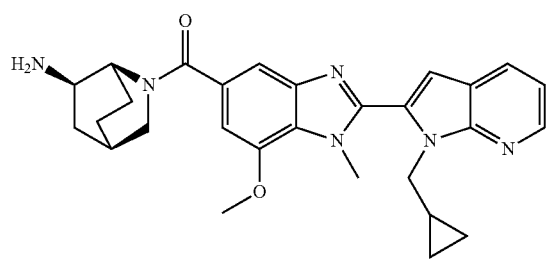 [SMILES: COc1cc(C(=O)N2C[C@@H]3CC[C@H]2[C@H](N)C3)cc2nc(-c3cc4cccnc4n3CC3CC3)n(C)c12]
I-215
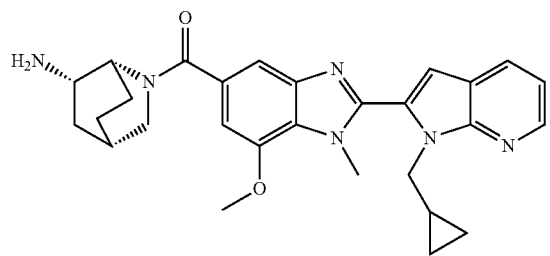 [SMILES: COc1cc(C(=O)N2C[C@H]3CC[C@@H]2[C@@H](N)C3)cc2nc(-c3cc4cccnc4n3CC3CC3)n(C)c12]
I-216
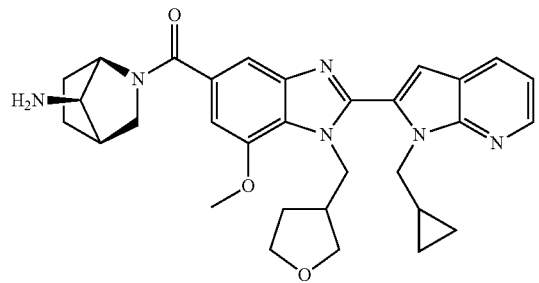 [SMILES: COc1cc(C(=O)N2C[C@H]3CC[C@@H]2[C@@H]3N)cc2nc(-c3cc4cccnc4n3CC3CC3)n(CC3CCOC3)c12]
I-217
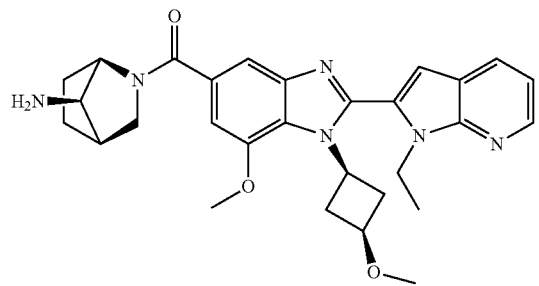 [SMILES: CCn1c(-c2nc3cc(C(=O)N4C[C@H]5CC[C@@H]4[C@@H]5N)cc(OC)c3n2[C@H]2C[C@@H](OC)C2)cc2cccnc21]
I-218

TABLE 1-continued

Exemplary Compounds of Formula I

| | |
|---|---|
| (structure) | I-219 |
| (structure) | I-220 |
| (structure) | I-221 |
| (structure) | I-222 |
| (structure) | I-223 |

TABLE 1-continued
Exemplary Compounds of Formula I
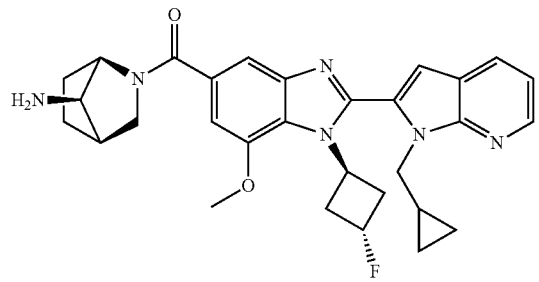 [SMILES: COc1cc(C(=O)N2C[C@H]3CC[C@@H]2[C@@H]3N)cc2nc(-c3cc4cccnc4n3CC3CC3)n([C@H]3C[C@H](F)C3)c12]
I-224
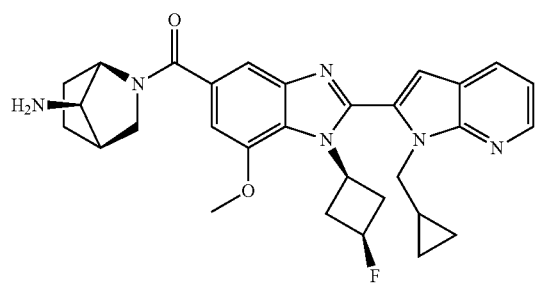 [SMILES: COc1cc(C(=O)N2C[C@H]3CC[C@@H]2[C@@H]3N)cc2nc(-c3cc4cccnc4n3CC3CC3)n([C@H]3C[C@@H](F)C3)c12]
I-225
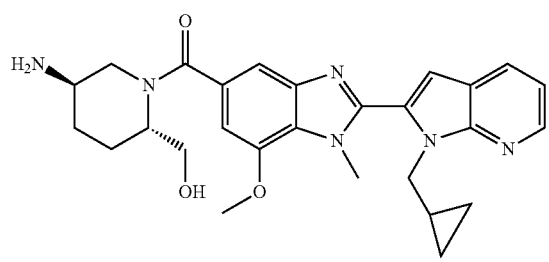 [SMILES: COc1cc(C(=O)N2C[C@H](N)CC[C@H]2CO)cc2nc(-c3cc4cccnc4n3CC3CC3)n(C)c12]
I-226
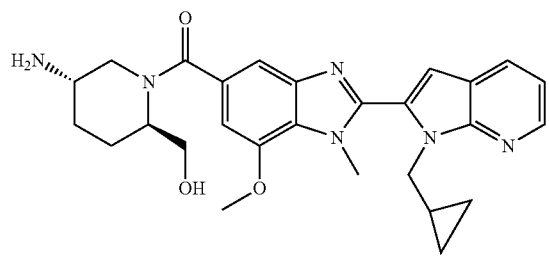 [SMILES: COc1cc(C(=O)N2C[C@@H](N)CC[C@@H]2CO)cc2nc(-c3cc4cccnc4n3CC3CC3)n(C)c12]
I-227
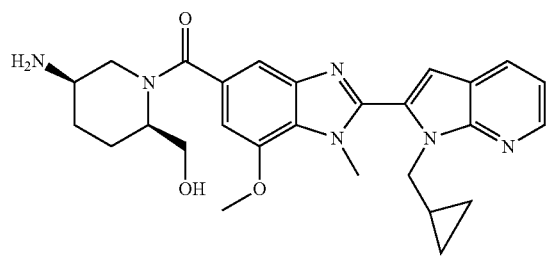 [SMILES: COc1cc(C(=O)N2C[C@H](N)CC[C@@H]2CO)cc2nc(-c3cc4cccnc4n3CC3CC3)n(C)c12]
I-228
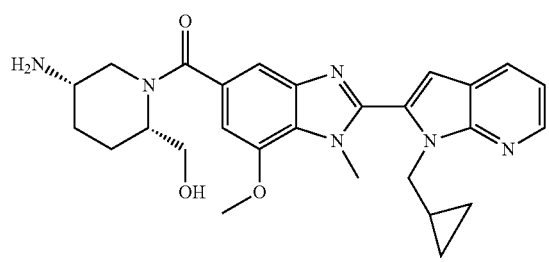 [SMILES: COc1cc(C(=O)N2C[C@@H](N)CC[C@H]2CO)cc2nc(-c3cc4cccnc4n3CC3CC3)n(C)c12]
I-229

TABLE 1-continued
Exemplary Compounds of Formula I
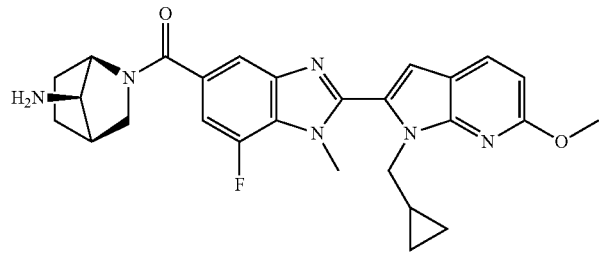 [SMILES: COc1ccc2cc(-c3nc4cc(C(=O)N5C[C@H]6CC[C@@H]5[C@@H]6N)cc(F)c4n3C)n(CC3CC3)c2n1]
I-230
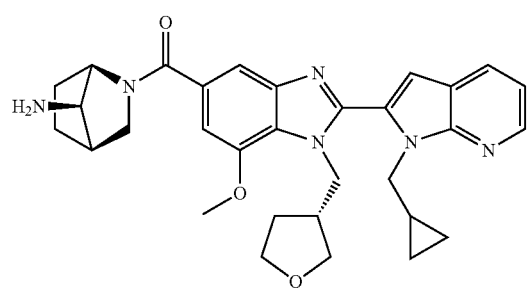 [SMILES: COc1cc(C(=O)N2C[C@H]3CC[C@@H]2[C@@H]3N)cc2nc(-c3cc4cccnc4n3CC3CC3)n(C[C@H]3CCOC3)c12]
I-231
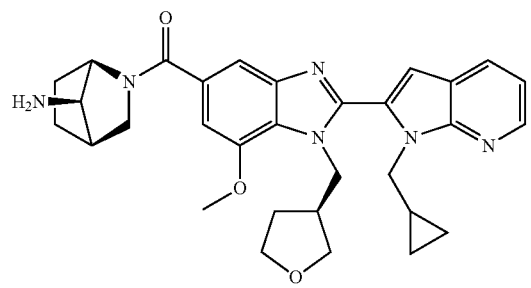 [SMILES: COc1cc(C(=O)N2C[C@H]3CC[C@@H]2[C@@H]3N)cc2nc(-c3cc4cccnc4n3CC3CC3)n(C[C@@H]3CCOC3)c12]
I-232
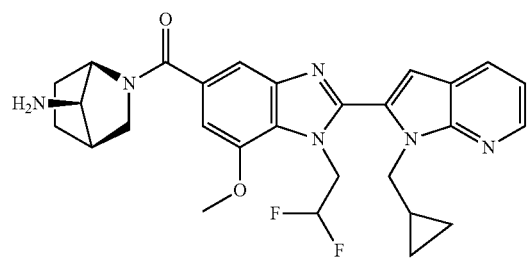 [SMILES: COc1cc(C(=O)N2C[C@H]3CC[C@@H]2[C@@H]3N)cc2nc(-c3cc4cccnc4n3CC3CC3)n(CC(F)F)c12]
I-233
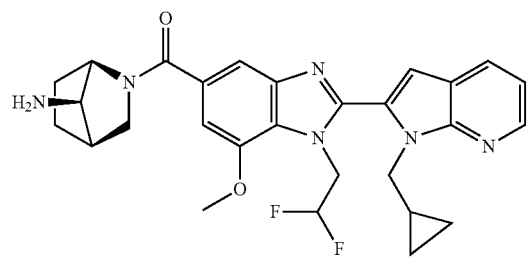 [SMILES: COc1cc(C(=O)N2C[C@H]3CC[C@@H]2[C@@H]3N)cc2nc(-c3cc4cccnc4n3CC3CC3)n(CC(F)F)c12]
I-234

TABLE 1-continued
Exemplary Compounds of Formula I
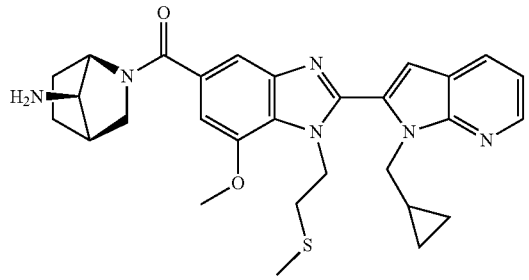 [SMILES: COc1cc(C(=O)N2C[C@H]3CC[C@@H]2[C@@H]3N)cc2nc(-c3cc4cccnc4n3CC3CC3)n(CCSC)c12]
I-235
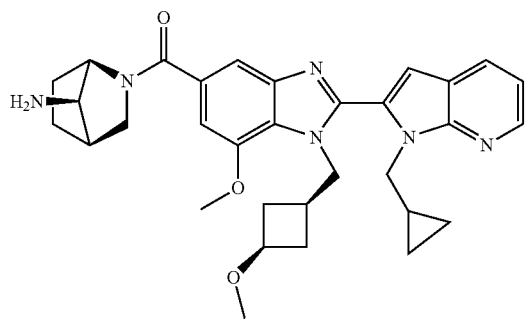 [SMILES: COc1cc(C(=O)N2C[C@H]3CC[C@@H]2[C@@H]3N)cc2nc(-c3cc4cccnc4n3CC3CC3)n(C[C@H]3C[C@@H](OC)C3)c12]
I-236
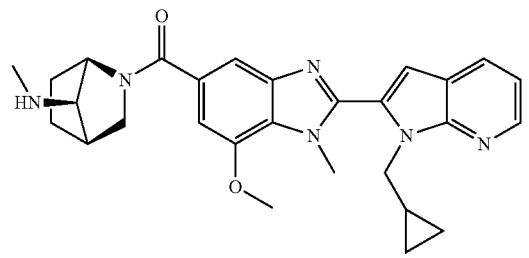
I-237
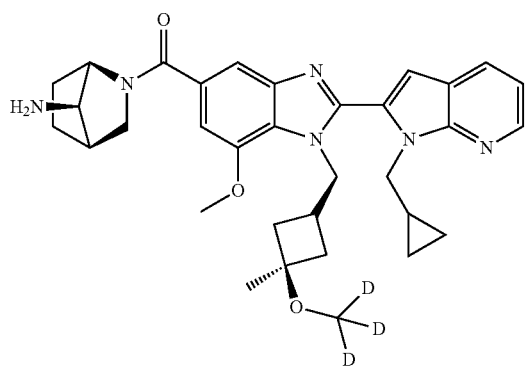
I-238
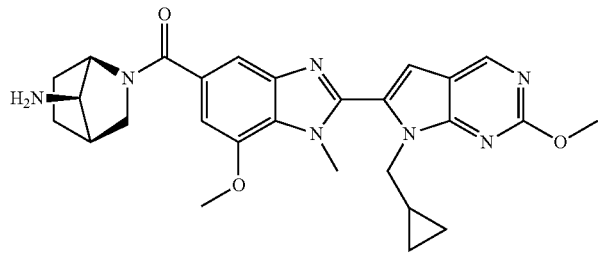 [SMILES: COc1ncc2cc(-c3nc4cc(C(=O)N5C[C@H]6CC[C@@H]5[C@@H]6N)cc(OC)c4n3C)n(CC3CC3)c2n1]
I-239

US 9,963,448 B2
TABLE 1-continued
Exemplary Compounds of Formula I
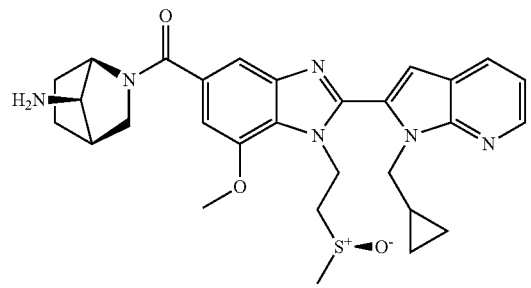 [SMILES: COc1cc(C(=O)N2C[C@H]3CC[C@@H]2[C@@H]3N)cc2nc(-c3cc4cccnc4n3CC3CC3)n(CC[S@+](C)[O-])c12] I-240
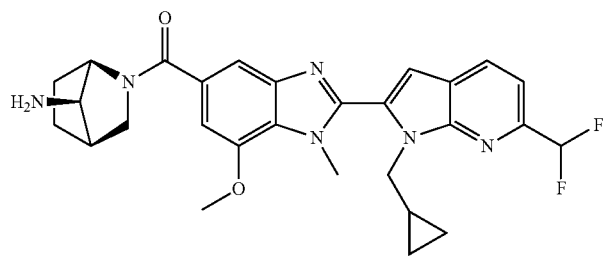 [SMILES: COc1cc(C(=O)N2C[C@H]3CC[C@@H]2[C@@H]3N)cc2nc(-c3cc4ccc(C(F)F)nc4n3CC3CC3)n(C)c12] I-241
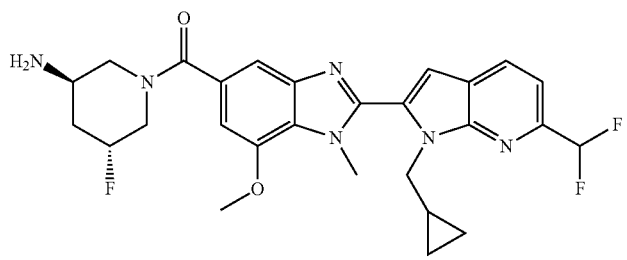 [SMILES: COc1cc(C(=O)N2C[C@H](N)C[C@@H](F)C2)cc2nc(-c3cc4ccc(C(F)F)nc4n3CC3CC3)n(C)c12] I-242
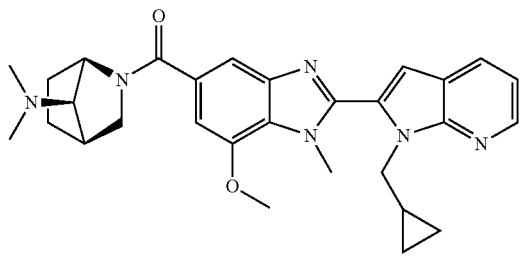 [SMILES: COc1cc(C(=O)N2C[C@H]3CC[C@@H]2[C@@H]3N(C)C)cc2nc(-c3cc4cccnc4n3CC3CC3)n(C)c12] I-243
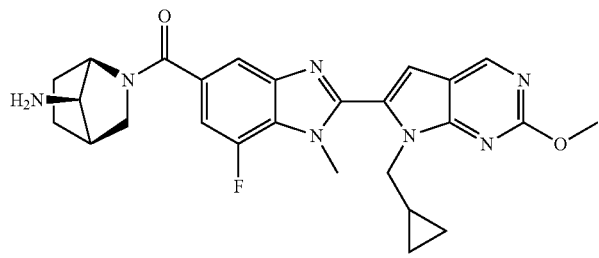 [SMILES: COc1ncc2cc(-c3nc4cc(C(=O)N5C[C@H]6CC[C@@H]5[C@@H]6N)cc(F)c4n3C)n(CC3CC3)c2n1] I-244
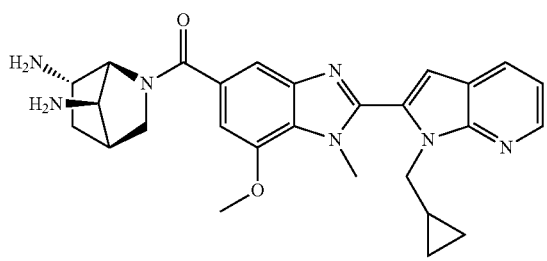 [SMILES: COc1cc(C(=O)N2C[C@H]3C[C@H](N)[C@@H]2[C@@H]3N)cc2nc(-c3cc4cccnc4n3CC3CC3)n(C)c12] I-245

TABLE 1-continued
Exemplary Compounds of Formula I
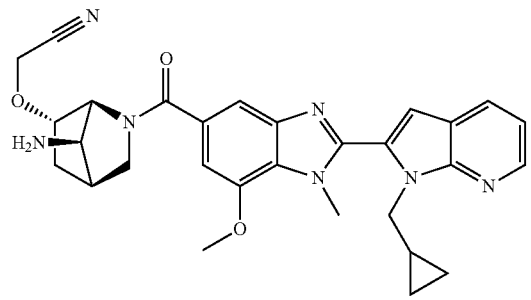 [SMILES: COc1cc(C(=O)N2C[C@H]3C[C@H](OCC#N)[C@@H]2[C@@H]3N)cc2nc(-c3cc4cccnc4n3CC3CC3)n(C)c12]
I-246
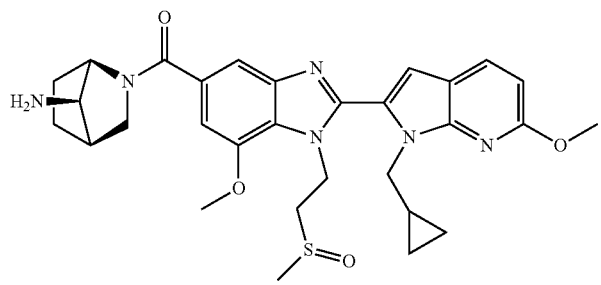 [SMILES: COc1ccc2cc(-c3nc4cc(C(=O)N5C[C@H]6CC[C@@H]5[C@@H]6N)cc(OC)c4n3CCS(C)=O)n(CC3CC3)c2n1]
I-247
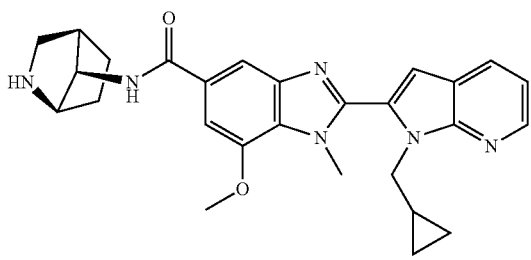 [SMILES: COc1cc(C(=O)N[C@@H]2[C@@H]3CC[C@H]2NC3)cc2nc(-c3cc4cccnc4n3CC3CC3)n(C)c12]
I-248
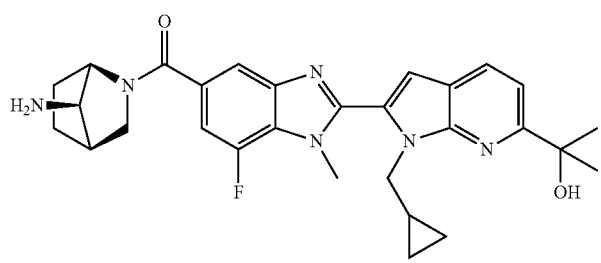 [SMILES: Cn1c(-c2cc3ccc(C(C)(C)O)nc3n2CC2CC2)nc2cc(C(=O)N3C[C@H]4CC[C@@H]3[C@@H]4N)cc(F)c21]
I-249
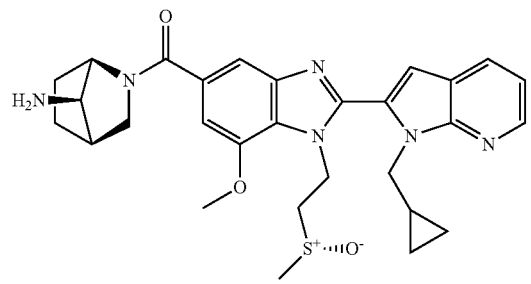 [SMILES: COc1cc(C(=O)N2C[C@H]3CC[C@@H]2[C@@H]3N)cc2nc(-c3cc4cccnc4n3CC3CC3)n(CC[S@@+](C)[O-])c12]
I-250

TABLE 1-continued
Exemplary Compounds of Formula I
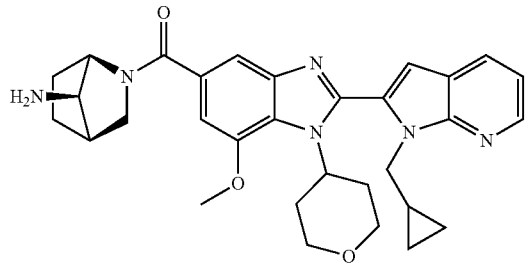 [SMILES: COc1cc(C(=O)N2C[C@H]3CC[C@@H]2[C@@H]3N)cc2nc(-c3cc4cccnc4n3CC3CC3)n(C3CCOCC3)c12]
I-251
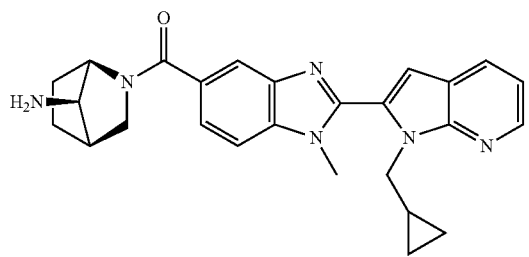 [SMILES: Cn1c(-c2cc3cccnc3n2CC2CC2)nc2cc(C(=O)N3C[C@H]4CC[C@@H]3[C@@H]4N)ccc21]
I-252
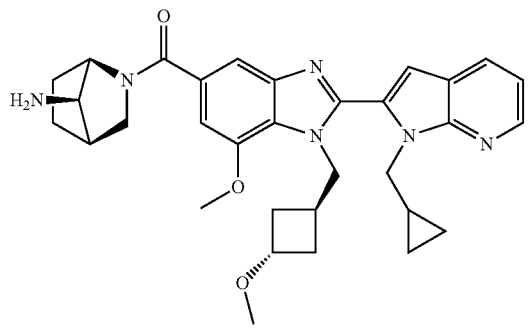 [SMILES: COc1cc(C(=O)N2C[C@H]3CC[C@@H]2[C@@H]3N)cc2nc(-c3cc4cccnc4n3CC3CC3)n(C[C@H]3C[C@H](OC)C3)c12]
I-253
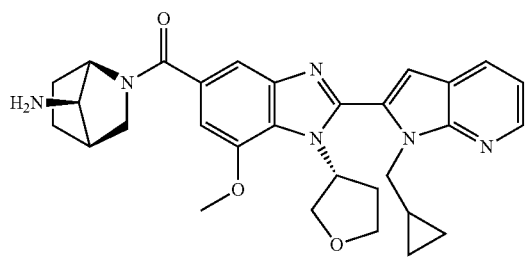 [SMILES: COc1cc(C(=O)N2C[C@H]3CC[C@@H]2[C@@H]3N)cc2nc(-c3cc4cccnc4n3CC3CC3)n([C@@H]3CCOC3)c12]
I-254
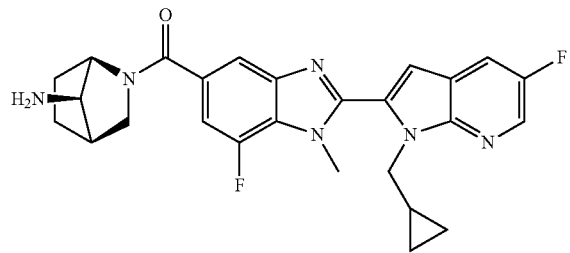 [SMILES: Cn1c(-c2cc3cc(F)cnc3n2CC2CC2)nc2cc(C(=O)N3C[C@H]4CC[C@@H]3[C@@H]4N)cc(F)c21]
I-255

TABLE 1-continued
Exemplary Compounds of Formula I
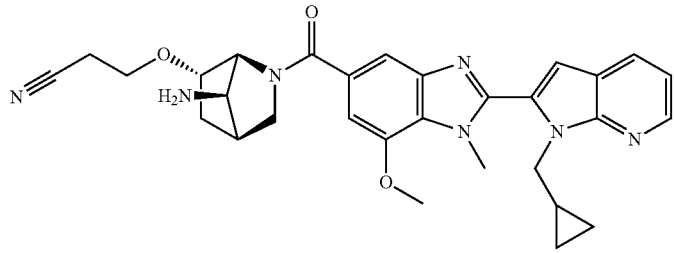 [SMILES: COc1cc(C(=O)N2C[C@H]3C[C@H](OCCC#N)[C@@H]2[C@@H]3N)cc2nc(-c3cc4cccnc4n3CC3CC3)n(C)c12]
I-256
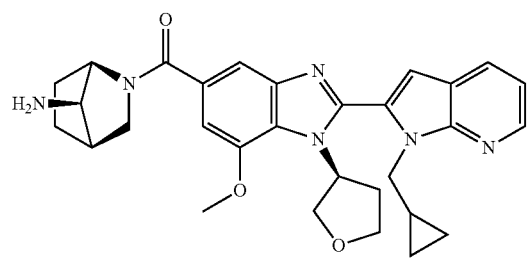 [SMILES: COc1cc(C(=O)N2C[C@H]3CC[C@@H]2[C@@H]3N)cc2nc(-c3cc4cccnc4n3CC3CC3)n([C@H]3CCOC3)c12]
I-257
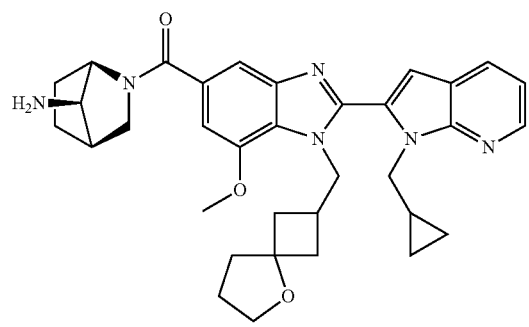 [SMILES: COc1cc(C(=O)N2C[C@H]3CC[C@@H]2[C@@H]3N)cc2nc(-c3cc4cccnc4n3CC3CC3)n(CC3CC4(CCCO4)C3)c12]
I-258
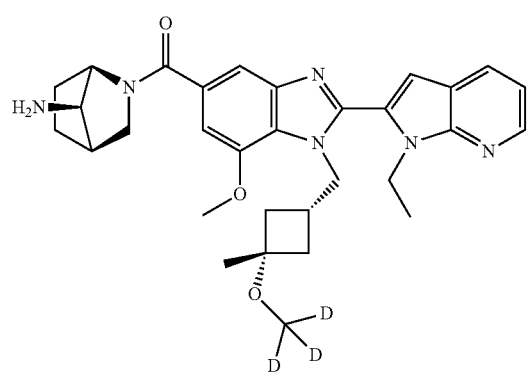 [SMILES: [2H]C([2H])([2H])O[C@]1(C)C[C@H](Cn2c(-c3cc4cccnc4n3CC)nc3cc(C(=O)N4C[C@H]5CC[C@@H]4[C@@H]5N)cc(OC)c32)C1]
I-259
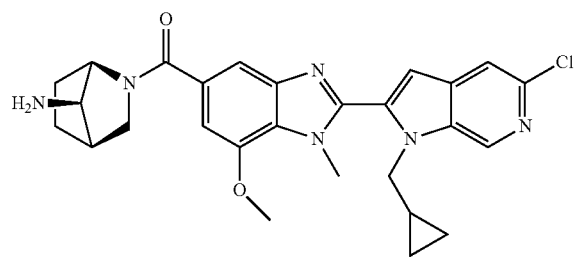 [SMILES: COc1cc(C(=O)N2C[C@H]3CC[C@@H]2[C@@H]3N)cc2nc(-c3cc4cc(Cl)ncc4n3CC3CC3)n(C)c12]
I-260

TABLE 1-continued
Exemplary Compounds of Formula I
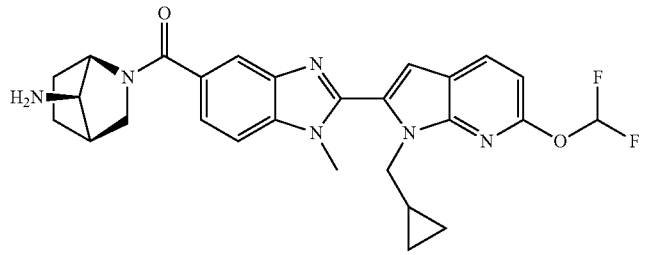 [SMILES: Cn1c(-c2cc3ccc(OC(F)F)nc3n2CC2CC2)nc2cc(C(=O)N3C[C@H]4CC[C@@H]3[C@@H]4N)ccc21]
I-261
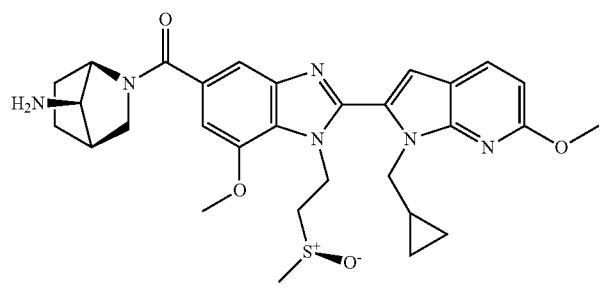 [SMILES: COc1ccc2cc(-c3nc4cc(C(=O)N5C[C@H]6CC[C@@H]5[C@@H]6N)cc(OC)c4n3CC[S@+](C)[O-])n(CC3CC3)c2n1]
I-262
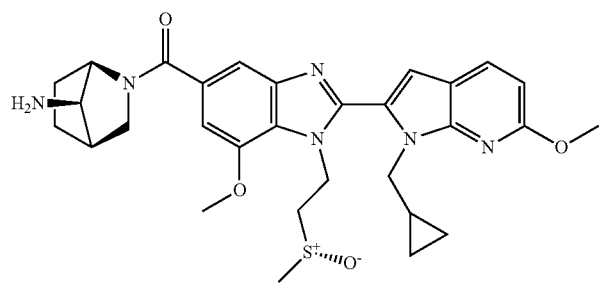 [SMILES: COc1ccc2cc(-c3nc4cc(C(=O)N5C[C@H]6CC[C@@H]5[C@@H]6N)cc(OC)c4n3CC[S@@+](C)[O-])n(CC3CC3)c2n1]
I-263
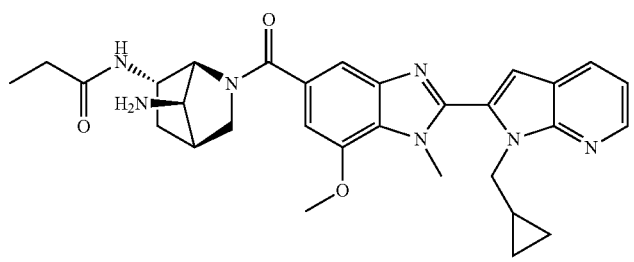 [SMILES: CCC(=O)N[C@H]1C[C@@H]2CN(C(=O)c3cc(OC)c4c(c3)nc(-c3cc5cccnc5n3CC3CC3)n4C)[C@H]1[C@@H]2N]
I-264
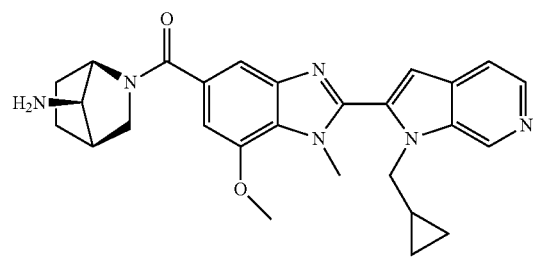 [SMILES: COc1cc(C(=O)N2C[C@H]3CC[C@@H]2[C@@H]3N)cc2nc(-c3cc4ccncc4n3CC3CC3)n(C)c12]
I-265

TABLE 1-continued
Exemplary Compounds of Formula I
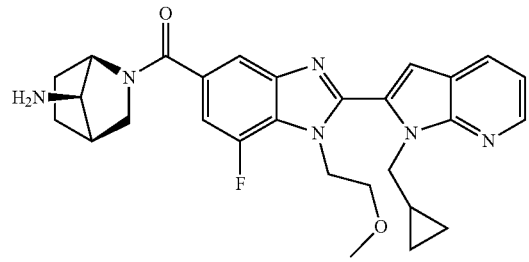 [SMILES: COCCn1c(-c2cc3cccnc3n2CC2CC2)nc2cc(C(=O)N3C[C@H]4CC[C@@H]3[C@@H]4N)cc(F)c21]
I-266
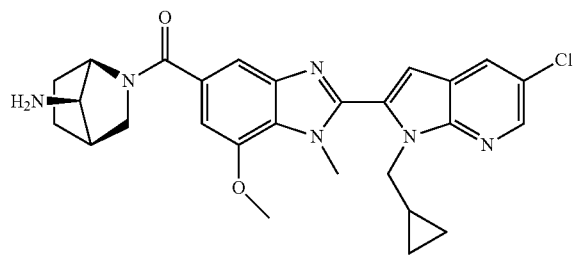 [SMILES: COc1cc(C(=O)N2C[C@H]3CC[C@@H]2[C@@H]3N)cc2nc(-c3cc4cc(Cl)cnc4n3CC3CC3)n(C)c12]
I-267
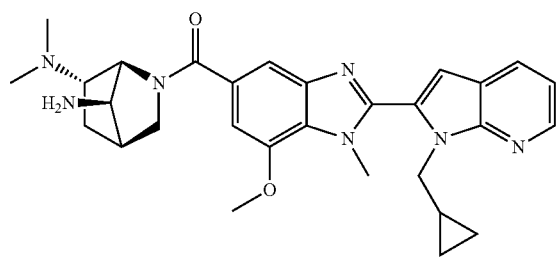 [SMILES: COc1cc(C(=O)N2C[C@H]3C[C@H](N(C)C)[C@@H]2[C@@H]3N)cc2nc(-c3cc4cccnc4n3CC3CC3)n(C)c12]
I-268
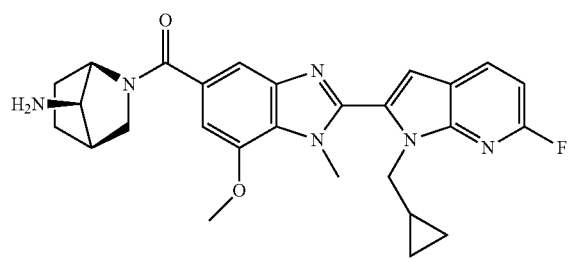 [SMILES: COc1cc(C(=O)N2C[C@H]3CC[C@@H]2[C@@H]3N)cc2nc(-c3cc4ccc(F)nc4n3CC3CC3)n(C)c12]
I-269
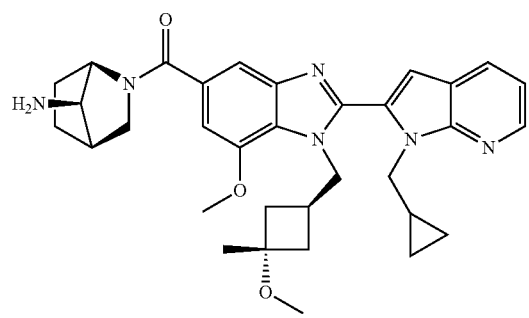 [SMILES: COc1cc(C(=O)N2C[C@H]3CC[C@@H]2[C@@H]3N)cc2nc(-c3cc4cccnc4n3CC3CC3)n(C[C@H]3C[C@](C)(OC)C3)c12]
I-270

TABLE 1-continued
Exemplary Compounds of Formula I
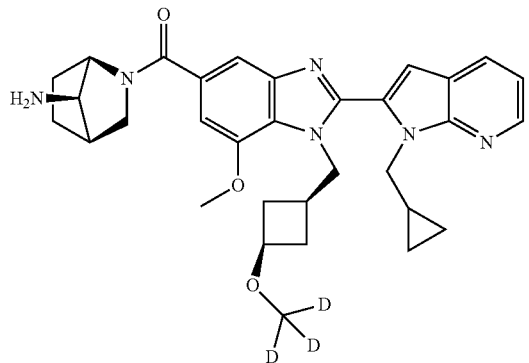 [SMILES: [2H]C([2H])([2H])O[C@H]1C[C@@H](Cn2c(-c3cc4cccnc4n3CC3CC3)nc3cc(C(=O)N4C[C@H]5CC[C@@H]4[C@@H]5N)cc(OC)c32)C1]
I-271
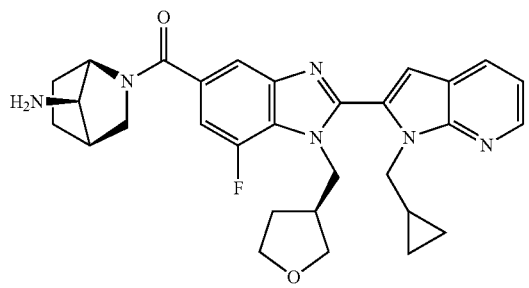 [SMILES: N[C@@H]1[C@@H]2CC[C@H]1N(C(=O)c1cc(F)c3c(c1)nc(-c1cc4cccnc4n1CC1CC1)n3C[C@@H]1CCOC1)C2]
I-272
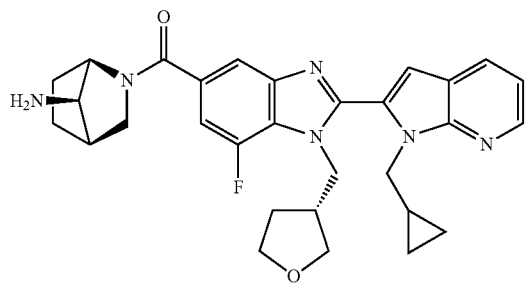 [SMILES: N[C@@H]1[C@@H]2CC[C@H]1N(C(=O)c1cc(F)c3c(c1)nc(-c1cc4cccnc4n1CC1CC1)n3C[C@H]1CCOC1)C2]
I-273
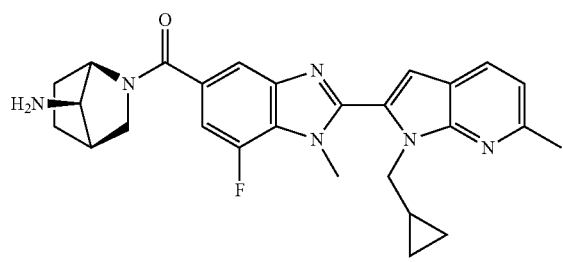 [SMILES: Cc1ccc2cc(-c3nc4cc(C(=O)N5C[C@H]6CC[C@@H]5[C@@H]6N)cc(F)c4n3C)n(CC3CC3)c2n1]
I-274
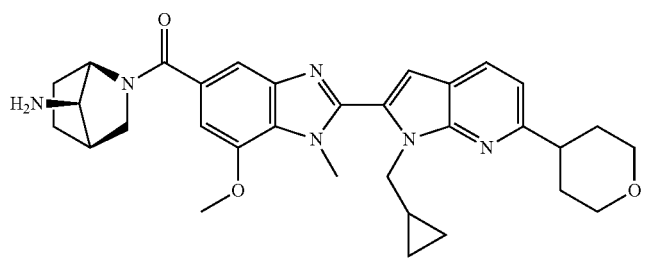 [SMILES: COc1cc(C(=O)N2C[C@H]3CC[C@@H]2[C@@H]3N)cc2nc(-c3cc4ccc(C5CCOCC5)nc4n3CC3CC3)n(C)c12]
I-275

TABLE 1-continued
Exemplary Compounds of Formula I
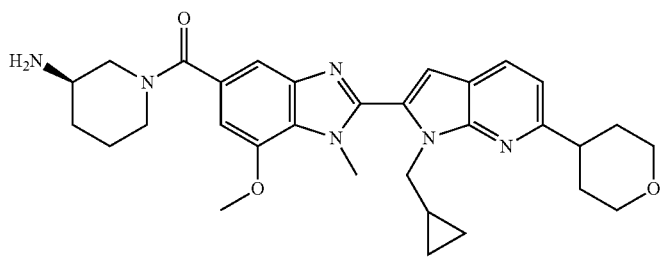 [SMILES: COc1cc(C(=O)N2CCC[C@@H](N)C2)cc2nc(-c3cc4ccc(C5CCOCC5)nc4n3CC3CC3)n(C)c12]
I-276
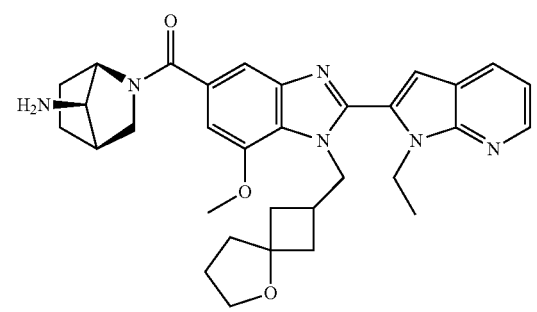 [SMILES: CCn1c(-c2nc3cc(C(=O)N4C[C@H]5CC[C@@H]4[C@@H]5N)cc(OC)c3n2CC2CC3(CCCO3)C2)cc2cccnc21]
I-277
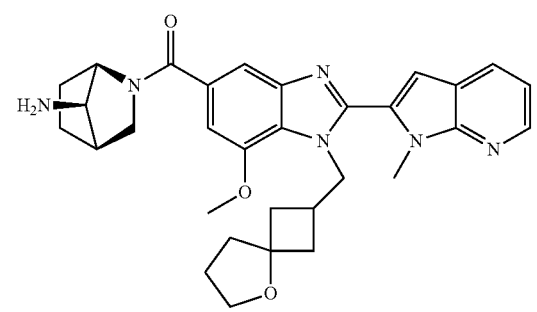 [SMILES: COc1cc(C(=O)N2C[C@H]3CC[C@@H]2[C@@H]3N)cc2nc(-c3cc4cccnc4n3C)n(CC3CC4(CCCO4)C3)c12]
I-278
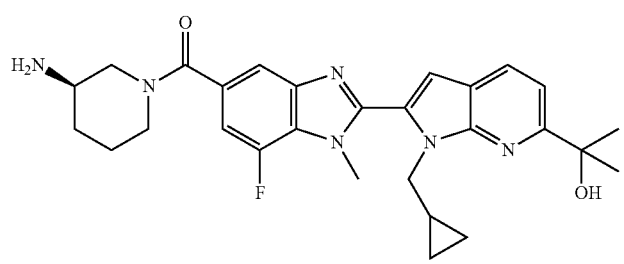 [SMILES: Cn1c(-c2cc3ccc(C(C)(C)O)nc3n2CC2CC2)nc2cc(C(=O)N3CCC[C@@H](N)C3)cc(F)c21]
I-279
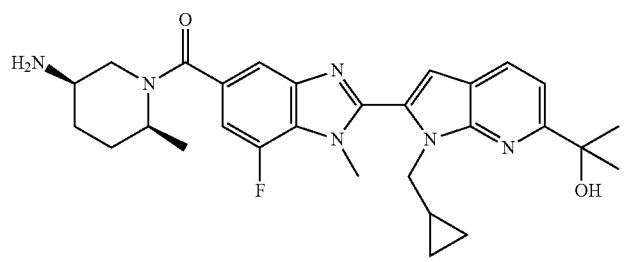 [SMILES: C[C@H]1CC[C@@H](N)CN1C(=O)c1cc(F)c2c(c1)nc(-c1cc3ccc(C(C)(C)O)nc3n1CC1CC1)n2C]
I-280

TABLE 1-continued
Exemplary Compounds of Formula I
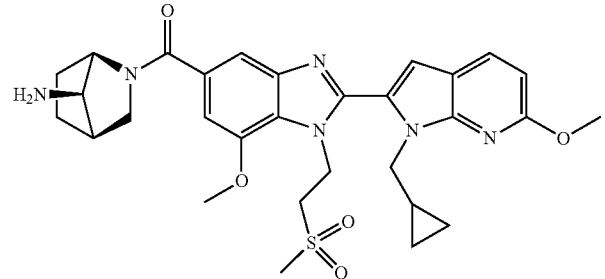 [SMILES: COc1ccc2cc(-c3nc4cc(C(=O)N5C[C@H]6CC[C@@H]5[C@@H]6N)cc(OC)c4n3CCS(C)(=O)=O)n(CC3CC3)c2n1]
I-281
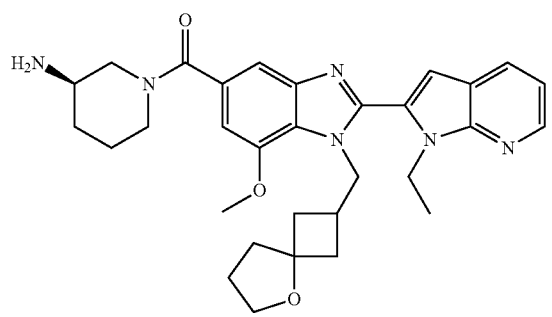 [SMILES: CCn1c(-c2nc3cc(C(=O)N4CCC[C@@H](N)C4)cc(OC)c3n2CC2CC3(CCCO3)C2)cc2cccnc21]
I-282
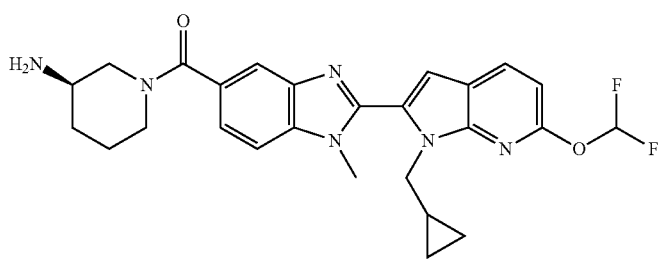 [SMILES: Cn1c(-c2cc3ccc(OC(F)F)nc3n2CC2CC2)nc2cc(C(=O)N3CCC[C@@H](N)C3)ccc21]
I-283
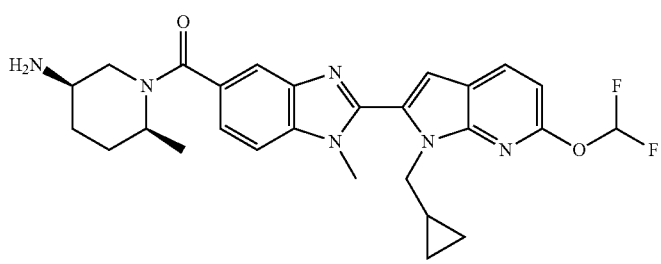 [SMILES: C[C@H]1CC[C@@H](N)CN1C(=O)c1ccc2c(c1)nc(-c1cc3ccc(OC(F)F)nc3n1CC1CC1)n2C]
I-284
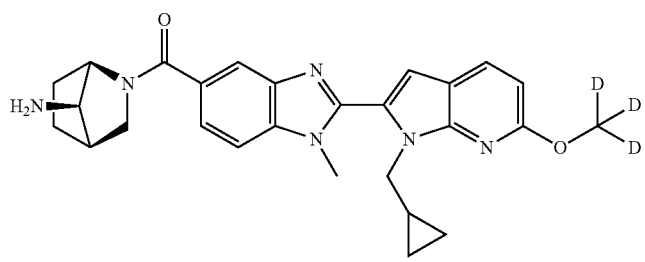 [SMILES: [2H]C([2H])([2H])Oc1ccc2cc(-c3nc4cc(C(=O)N5C[C@H]6CC[C@@H]5[C@@H]6N)ccc4n3C)n(CC3CC3)c2n1]
I-285

TABLE 1-continued
Exemplary Compounds of Formula I
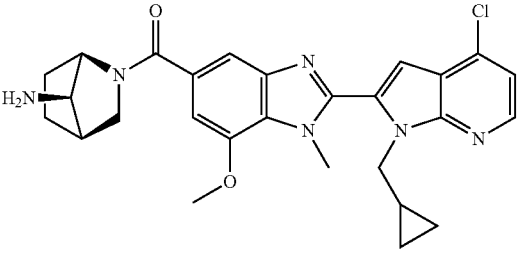 [SMILES: COc1cc(C(=O)N2C[C@H]3CC[C@@H]2[C@@H]3N)cc2nc(-c3cc4c(Cl)ccnc4n3CC3CC3)n(C)c12] I-286
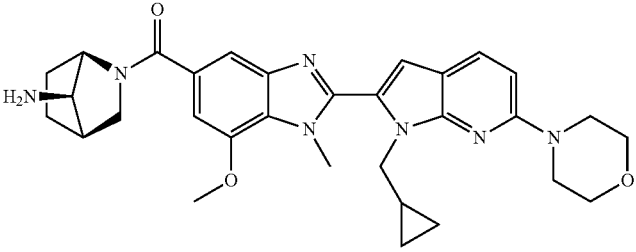 [SMILES: COc1cc(C(=O)N2C[C@H]3CC[C@@H]2[C@@H]3N)cc2nc(-c3cc4ccc(N5CCOCC5)nc4n3CC3CC3)n(C)c12] I-287
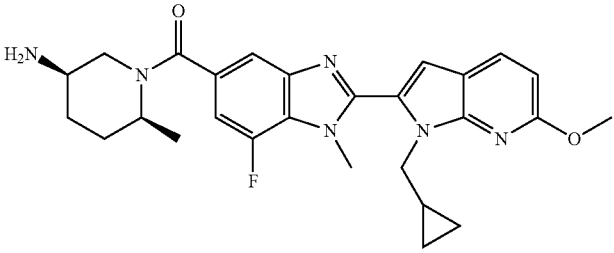 [SMILES: COc1ccc2cc(-c3nc4cc(C(=O)N5C[C@H](N)CC[C@@H]5C)cc(F)c4n3C)n(CC3CC3)c2n1] I-288
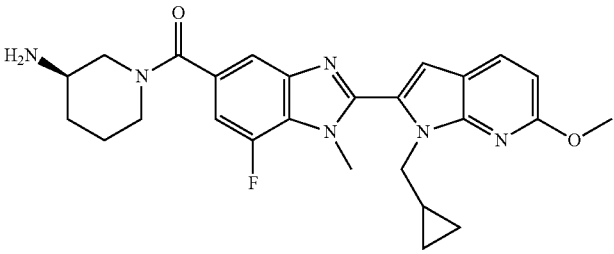 [SMILES: COc1ccc2cc(-c3nc4cc(C(=O)N5CCC[C@@H](N)C5)cc(F)c4n3C)n(CC3CC3)c2n1] I-289
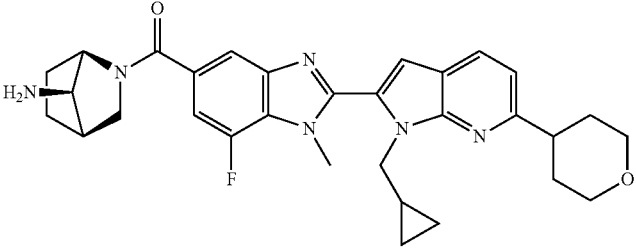 [SMILES: Cn1c(-c2cc3ccc(C4CCOCC4)nc3n2CC2CC2)nc2cc(C(=O)N3C[C@H]4CC[C@@H]3[C@@H]4N)cc(F)c21] I-290
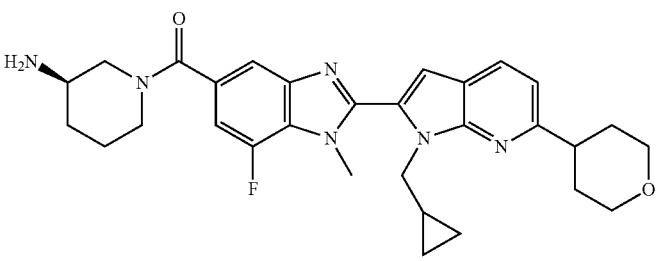 [SMILES: Cn1c(-c2cc3ccc(C4CCOCC4)nc3n2CC2CC2)nc2cc(C(=O)N3CCC[C@@H](N)C3)cc(F)c21] I-291

US 9,963,448 B2
149                                                                                                        150
TABLE 1-continued
Exemplary Compounds of Formula I
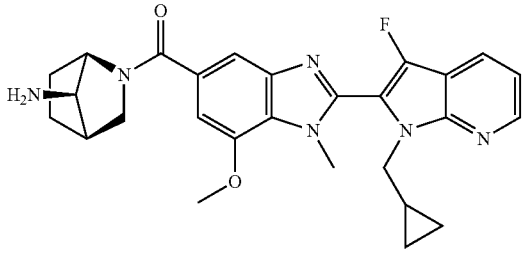 [SMILES: COc1cc(C(=O)N2C[C@H]3CC[C@@H]2[C@@H]3N)cc2nc(-c3c(F)c4cccnc4n3CC3CC3)n(C)c12] I-292
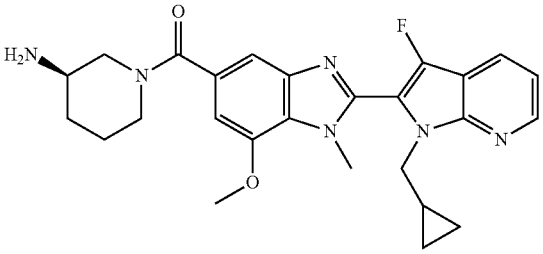 [SMILES: COc1cc(C(=O)N2CCC[C@@H](N)C2)cc2nc(-c3c(F)c4cccnc4n3CC3CC3)n(C)c12] I-293
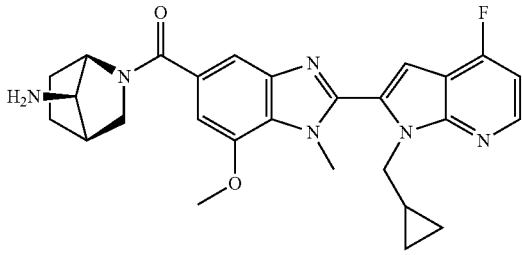 [SMILES: COc1cc(C(=O)N2C[C@H]3CC[C@@H]2[C@@H]3N)cc2nc(-c3cc4c(F)ccnc4n3CC3CC3)n(C)c12] I-294
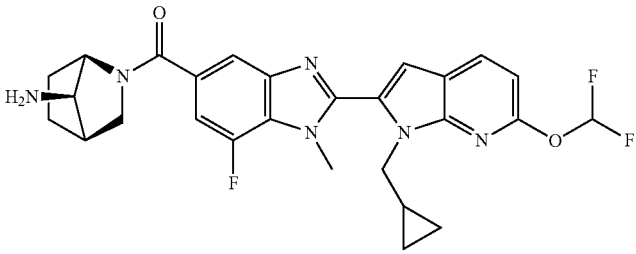 [SMILES: Cn1c(-c2cc3ccc(OC(F)F)nc3n2CC2CC2)nc2cc(C(=O)N3C[C@H]4CC[C@@H]3[C@@H]4N)cc(F)c21] I-295
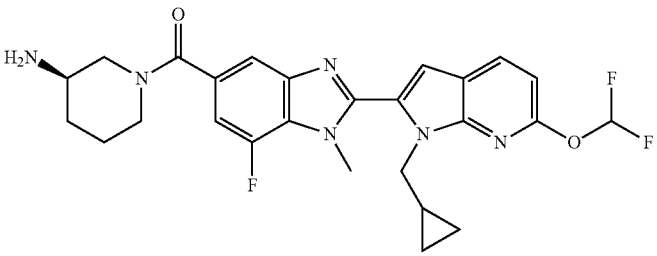 [SMILES: Cn1c(-c2cc3ccc(OC(F)F)nc3n2CC2CC2)nc2cc(C(=O)N3CCC[C@@H](N)C3)cc(F)c21] I-296
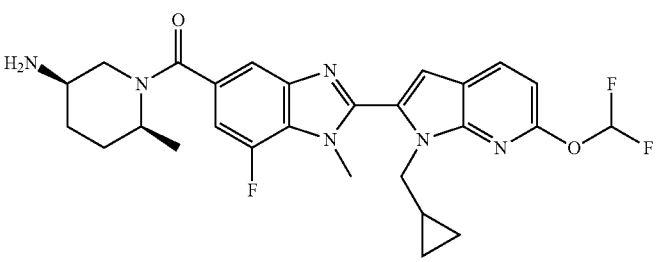 [SMILES: C[C@H]1CC[C@@H](N)CN1C(=O)c1cc(F)c2c(c1)nc(-c1cc3ccc(OC(F)F)nc3n1CC1CC1)n2C] I-297

TABLE 1-continued
Exemplary Compounds of Formula I
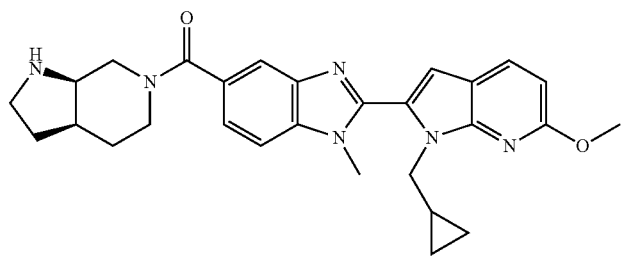 [SMILES: COc1ccc2cc(-c3nc4cc(C(=O)N5CC[C@H]6CCN[C@H]6C5)ccc4n3C)n(CC3CC3)c2n1]
I-298
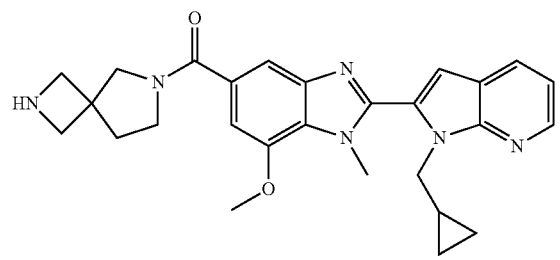 [SMILES: COc1cc(C(=O)N2CCC3(CNC3)C2)cc2nc(-c3cc4cccnc4n3CC3CC3)n(C)c12]
I-299
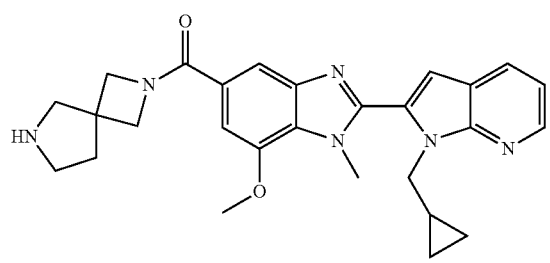 [SMILES: COc1cc(C(=O)N2CC3(CCNC3)C2)cc2nc(-c3cc4cccnc4n3CC3CC3)n(C)c12]
I-300
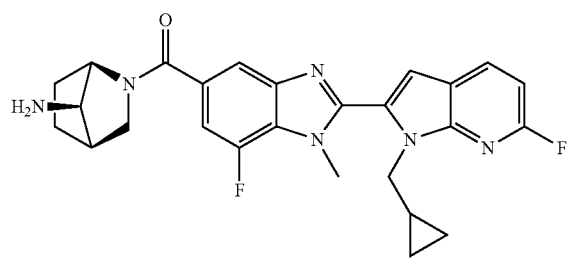 [SMILES: Cn1c(-c2cc3ccc(F)nc3n2CC2CC2)nc2cc(C(=O)N3C[C@H]4CC[C@@H]3[C@@H]4N)cc(F)c21]
I-301
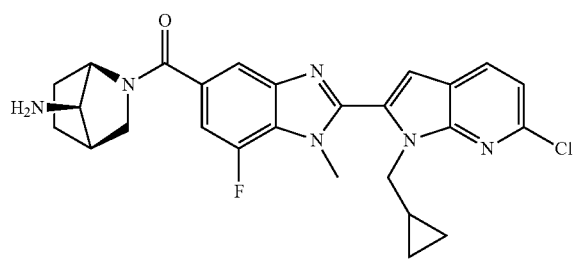 [SMILES: Cn1c(-c2cc3ccc(Cl)nc3n2CC2CC2)nc2cc(C(=O)N3C[C@H]4CC[C@@H]3[C@@H]4N)cc(F)c21]
I-302
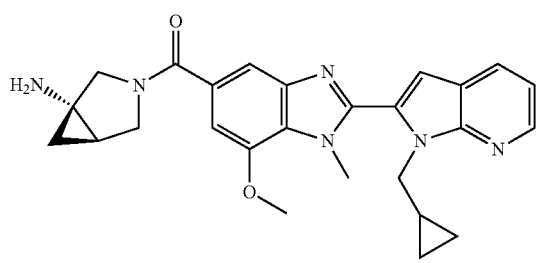 [SMILES: COc1cc(C(=O)N2C[C@H]3C[C@@]3(N)C2)cc2nc(-c3cc4cccnc4n3CC3CC3)n(C)c12]
I-303

TABLE 1-continued
Exemplary Compounds of Formula I
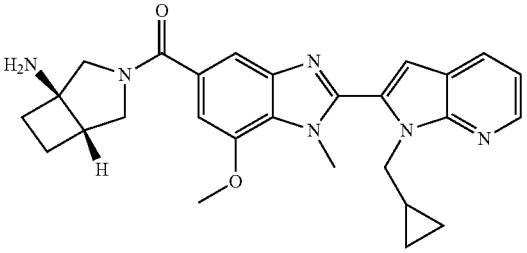 [SMILES: COc1cc(C(=O)N2C[C@@H]3CC[C@]3(N)C2)cc2nc(-c3cc4cccnc4n3CC3CC3)n(C)c12] I-304
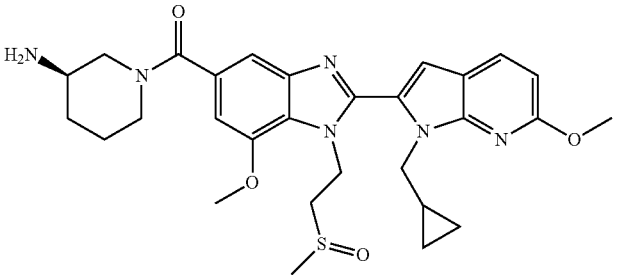 [SMILES: COc1ccc2cc(-c3nc4cc(C(=O)N5CCC[C@@H](N)C5)cc(OC)c4n3CCS(C)=O)n(CC3CC3)c2n1] I-305
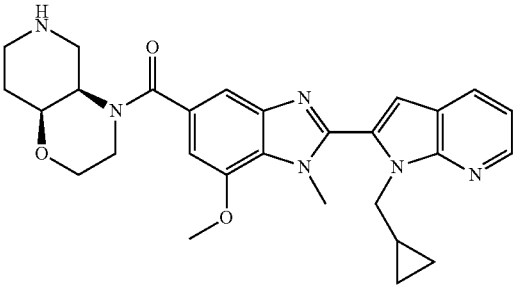 [SMILES: COc1cc(C(=O)N2CCO[C@H]3CCNC[C@H]32)cc2nc(-c3cc4cccnc4n3CC3CC3)n(C)c12] I-306
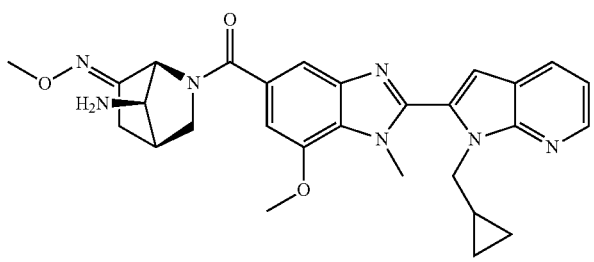 [SMILES: CO/N=C1\C[C@@H]2CN(C(=O)c3cc(OC)c4c(c3)nc(-c3cc5cccnc5n3CC3CC3)n4C)[C@H]1[C@@H]2N] I-307
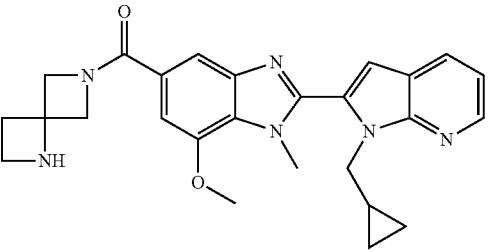 [SMILES: COc1cc(C(=O)N2CC3(CCN3)C2)cc2nc(-c3cc4cccnc4n3CC3CC3)n(C)c12] I-308

TABLE 1-continued
Exemplary Compounds of Formula I
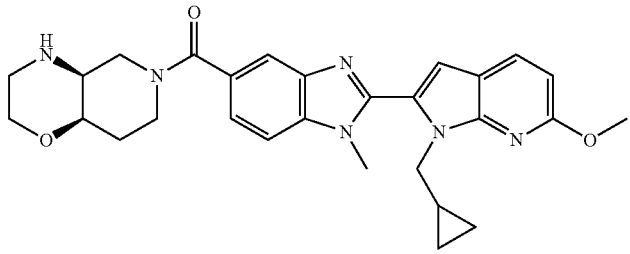 [SMILES: COc1ccc2cc(-c3nc4cc(C(=O)N5CC[C@H]6OCCN[C@H]6C5)ccc4n3C)n(CC3CC3)c2n1]
I-309
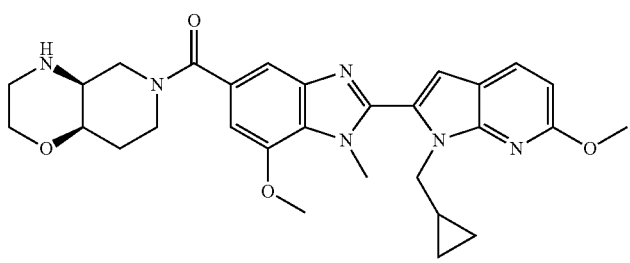 [SMILES: COc1ccc2cc(-c3nc4cc(C(=O)N5CC[C@H]6OCCN[C@H]6C5)cc(OC)c4n3C)n(CC3CC3)c2n1]
I-310
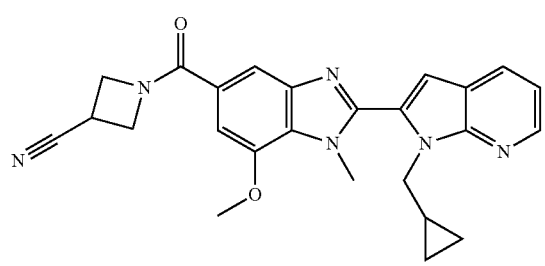 [SMILES: COc1cc(C(=O)N2CC(C#N)C2)cc2nc(-c3cc4cccnc4n3CC3CC3)n(C)c12]
I-311
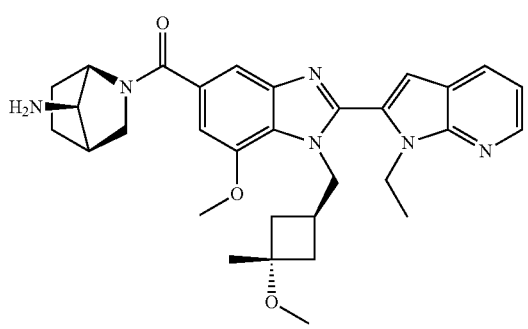 [SMILES: CCn1c(-c2nc3cc(C(=O)N4C[C@H]5CC[C@@H]4[C@@H]5N)cc(OC)c3n2C[C@H]2C[C@](C)(OC)C2)cc2cccnc21]
I-312
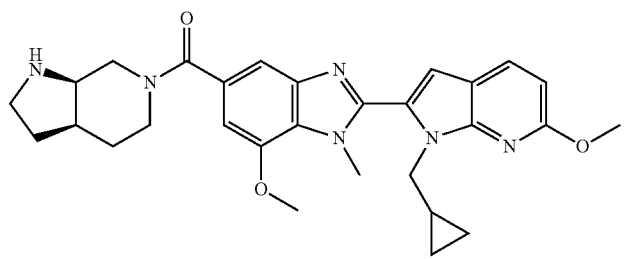 [SMILES: COc1ccc2cc(-c3nc4cc(C(=O)N5CC[C@H]6CCN[C@H]6C5)cc(OC)c4n3C)n(CC3CC3)c2n1]
I-313

TABLE 1-continued
Exemplary Compounds of Formula I
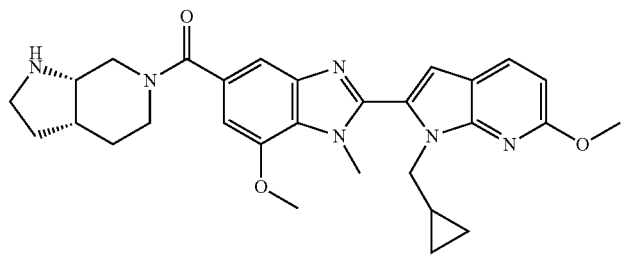 [SMILES: COc1ccc2cc(-c3nc4cc(C(=O)N5CC[C@@H]6CCN[C@@H]6C5)cc(OC)c4n3C)n(CC3CC3)c2n1]
I-314
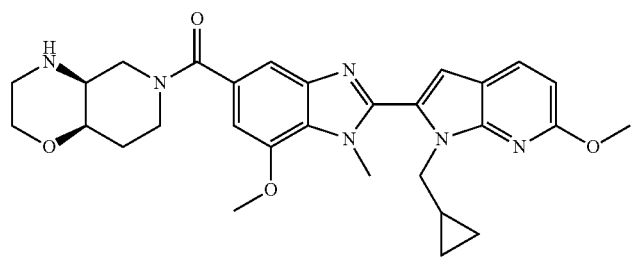 [SMILES: COc1ccc2cc(-c3nc4cc(C(=O)N5CC[C@H]6OCCN[C@H]6C5)cc(OC)c4n3C)n(CC3CC3)c2n1]
I-315
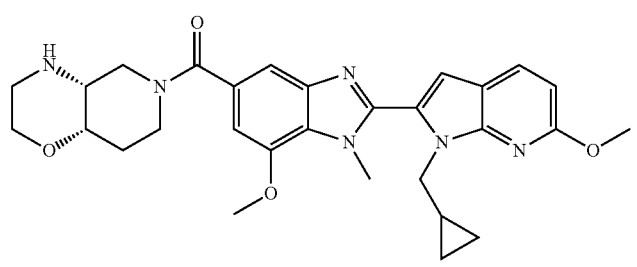 [SMILES: COc1ccc2cc(-c3nc4cc(C(=O)N5CC[C@@H]6OCCN[C@@H]6C5)cc(OC)c4n3C)n(CC3CC3)c2n1]
I-316
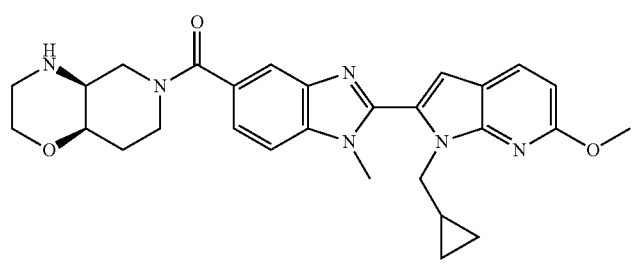 [SMILES: COc1ccc2cc(-c3nc4cc(C(=O)N5CC[C@H]6OCCN[C@H]6C5)ccc4n3C)n(CC3CC3)c2n1]
I-317
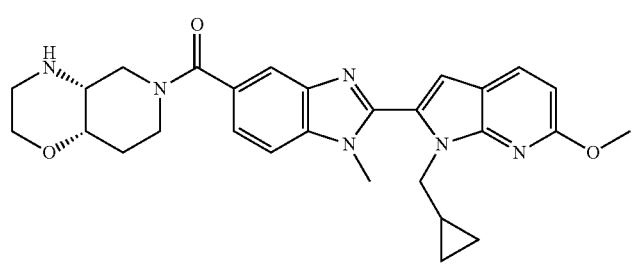 [SMILES: COc1ccc2cc(-c3nc4cc(C(=O)N5CC[C@@H]6OCCN[C@@H]6C5)ccc4n3C)n(CC3CC3)c2n1]
I-318
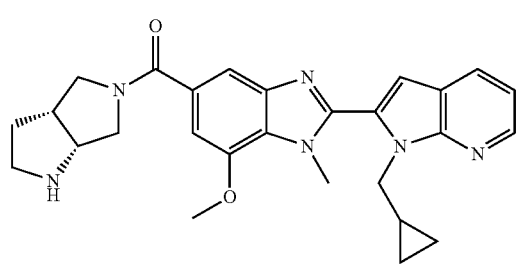 [SMILES: COc1cc(C(=O)N2C[C@H]3CCN[C@H]3C2)cc2nc(-c3cc4cccnc4n3CC3CC3)n(C)c12]
I-319

TABLE 1-continued
Exemplary Compounds of Formula I
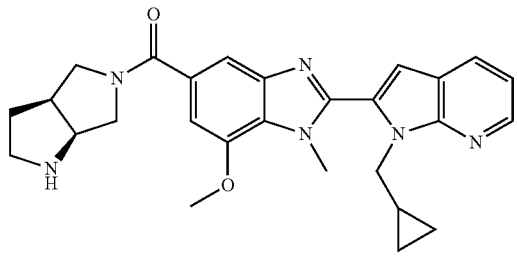 [SMILES: COc1cc(C(=O)N2C[C@@H]3CCN[C@@H]3C2)cc2nc(-c3cc4cccnc4n3CC3CC3)n(C)c12]
I-320
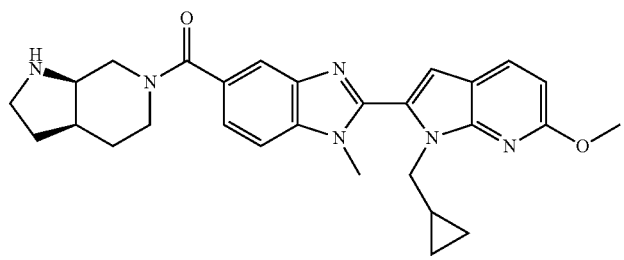 [SMILES: COc1ccc2cc(-c3nc4cc(C(=O)N5CC[C@H]6CCN[C@H]6C5)ccc4n3C)n(CC3CC3)c2n1]
I-321
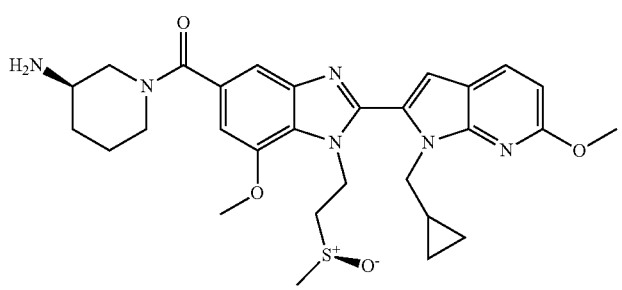 [SMILES: COc1ccc2cc(-c3nc4cc(C(=O)N5CCC[C@@H](N)C5)cc(OC)c4n3CC[S@+](C)[O-])n(CC3CC3)c2n1]
I-322
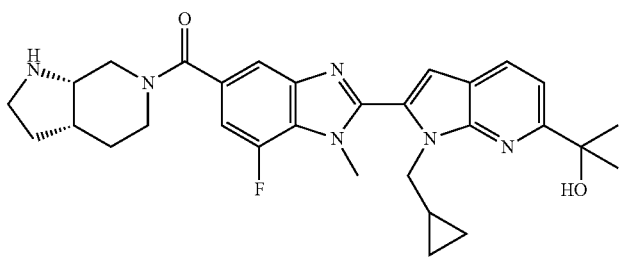 [SMILES: Cn1c(-c2cc3ccc(C(C)(C)O)nc3n2CC2CC2)nc2cc(C(=O)N3CC[C@@H]4CCN[C@@H]4C3)cc(F)c21]
I-323
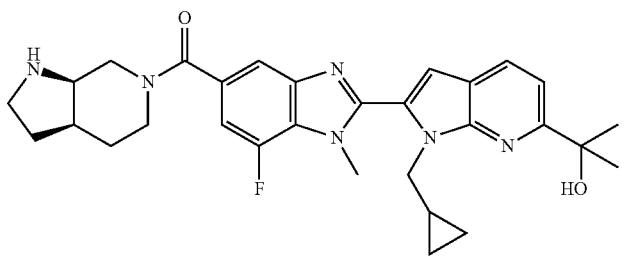 [SMILES: Cn1c(-c2cc3ccc(C(C)(C)O)nc3n2CC2CC2)nc2cc(C(=O)N3CC[C@H]4CCN[C@H]4C3)cc(F)c21]
I-324
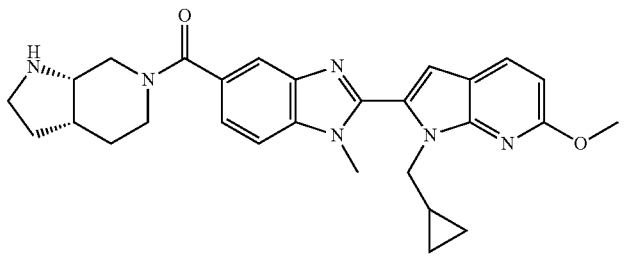 [SMILES: COc1ccc2cc(-c3nc4cc(C(=O)N5CC[C@@H]6CCN[C@@H]6C5)ccc4n3C)n(CC3CC3)c2n1]
I-325

TABLE 1-continued
Exemplary Compounds of Formula I
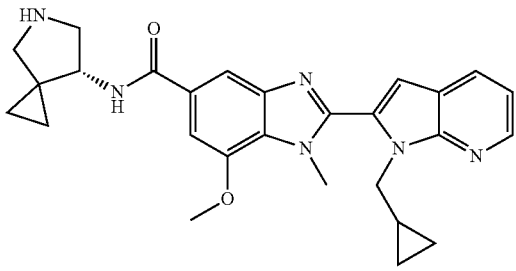 [SMILES: COc1cc(C(=O)N[C@H]2CNCC23CC3)cc2nc(-c3cc4cccnc4n3CC3CC3)n(C)c12]
I-326
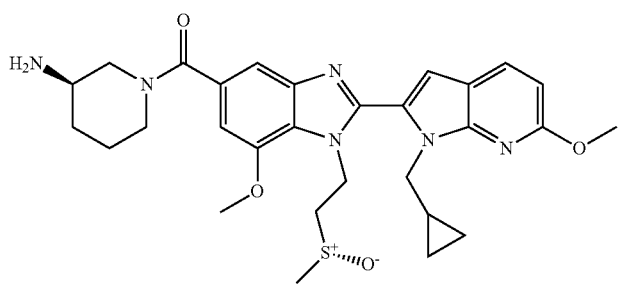 [SMILES: COc1ccc2cc(-c3nc4cc(C(=O)N5CCC[C@@H](N)C5)cc(OC)c4n3CC[S@@+](C)[O-])n(CC3CC3)c2n1]
I-327
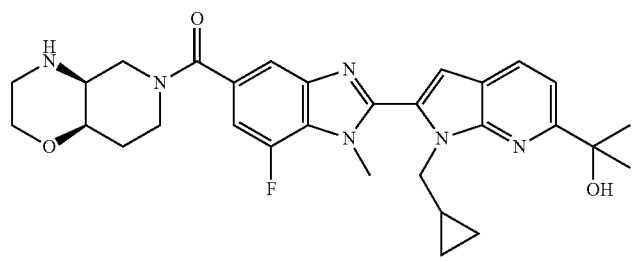 [SMILES: Cn1c(-c2cc3ccc(C(C)(C)O)nc3n2CC2CC2)nc2cc(C(=O)N3CC[C@H]4OCCN[C@H]4C3)cc(F)c21]
I-328
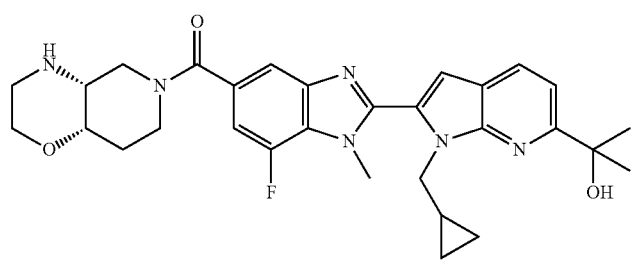 [SMILES: Cn1c(-c2cc3ccc(C(C)(C)O)nc3n2CC2CC2)nc2cc(C(=O)N3CC[C@@H]4OCCN[C@@H]4C3)cc(F)c21]
I-329
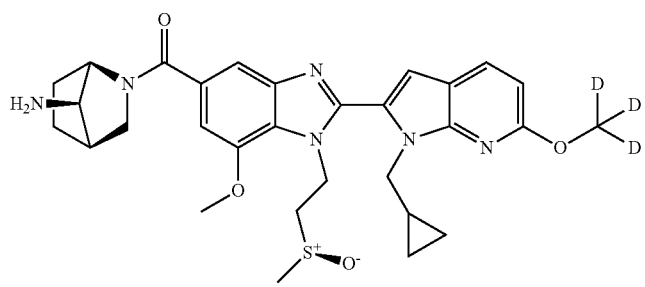 [SMILES: [2H]C([2H])([2H])Oc1ccc2cc(-c3nc4cc(C(=O)N5C[C@H]6CC[C@@H]5[C@@H]6N)cc(OC)c4n3CC[S@+](C)[O-])n(CC3CC3)c2n1]
I-330

TABLE 1-continued
Exemplary Compounds of Formula I
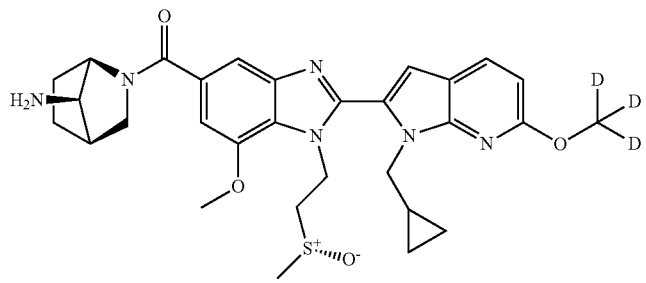 [SMILES: [2H]C([2H])([2H])Oc1ccc2cc(-c3nc4cc(C(=O)N5C[C@H]6CC[C@@H]5[C@@H]6N)cc(OC)c4n3CC[S@@+](C)[O-])n(CC3CC3)c2n1]
I-331
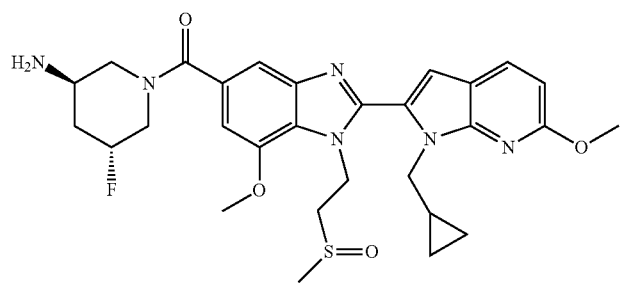 [SMILES: COc1ccc2cc(-c3nc4cc(C(=O)N5C[C@H](N)C[C@@H](F)C5)cc(OC)c4n3CCS(C)=O)n(CC3CC3)c2n1]
I-332
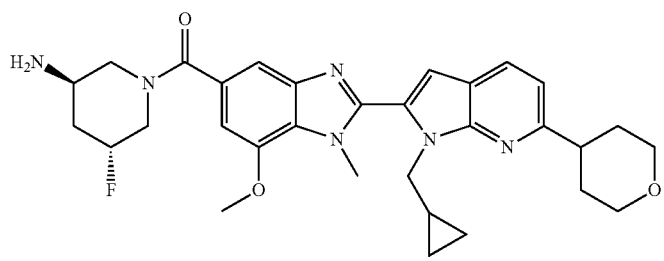 [SMILES: COc1cc(C(=O)N2C[C@H](N)C[C@@H](F)C2)cc2nc(-c3cc4ccc(C5CCOCC5)nc4n3CC3CC3)n(C)c12]
I-333
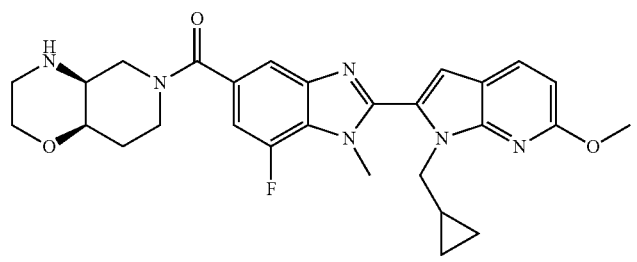 [SMILES: COc1ccc2cc(-c3nc4cc(C(=O)N5CC[C@H]6OCCN[C@H]6C5)cc(F)c4n3C)n(CC3CC3)c2n1]
I-334
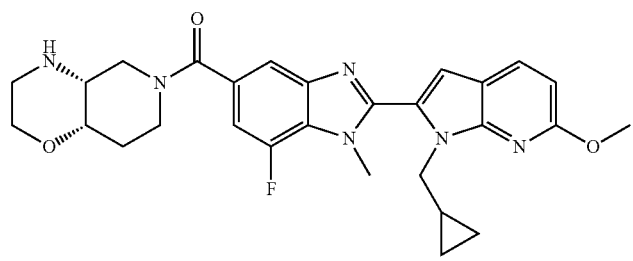 [SMILES: COc1ccc2cc(-c3nc4cc(C(=O)N5CC[C@@H]6OCCN[C@@H]6C5)cc(F)c4n3C)n(CC3CC3)c2n1]
I-335
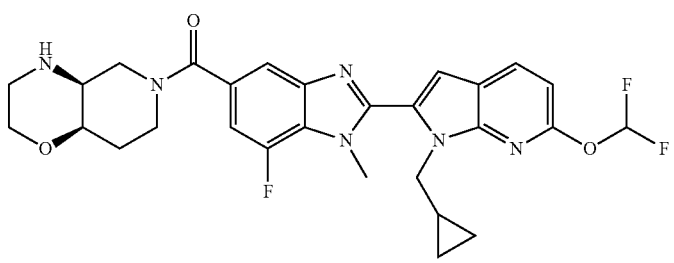 [SMILES: Cn1c(-c2cc3ccc(OC(F)F)nc3n2CC2CC2)nc2cc(C(=O)N3CC[C@H]4OCCN[C@H]4C3)cc(F)c21]
I-336

TABLE 1-continued
Exemplary Compounds of Formula I
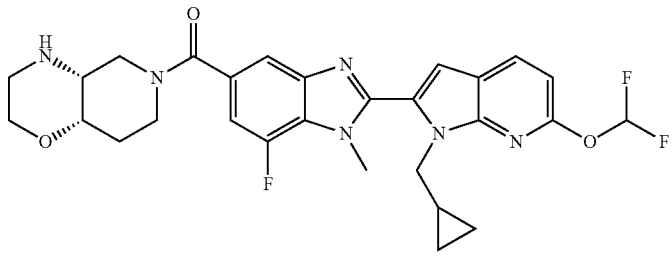 [SMILES: Cn1c(-c2cc3ccc(OC(F)F)nc3n2CC2CC2)nc2cc(C(=O)N3CC[C@@H]4OCCN[C@@H]4C3)cc(F)c21]
I-337
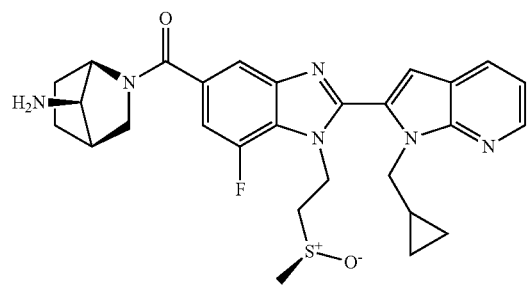 [SMILES: C[S@+]([O-])CCn1c(-c2cc3cccnc3n2CC2CC2)nc2cc(C(=O)N3C[C@H]4CC[C@@H]3[C@@H]4N)cc(F)c21]
I-338
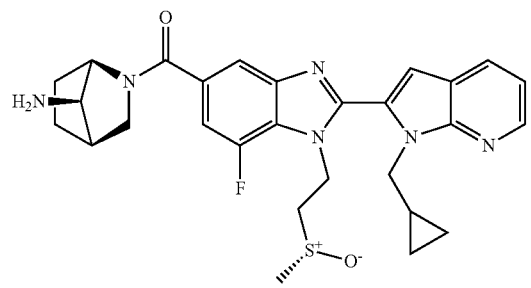 [SMILES: C[S@@+]([O-])CCn1c(-c2cc3cccnc3n2CC2CC2)nc2cc(C(=O)N3C[C@H]4CC[C@@H]3[C@@H]4N)cc(F)c21]
I-339
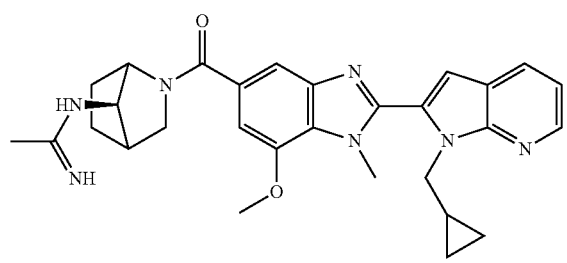 [SMILES: COc1cc(C(=O)N2CC3CCC2[C@@H]3NC(C)=N)cc2nc(-c3cc4cccnc4n3CC3CC3)n(C)c12]
I-340
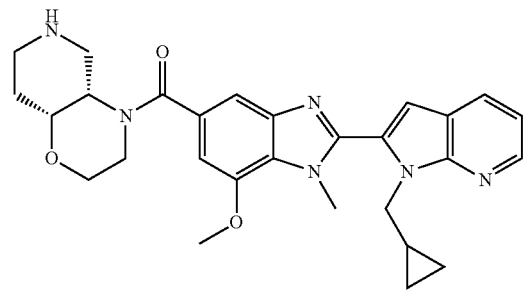 [SMILES: COc1cc(C(=O)N2CCO[C@@H]3CCNC[C@@H]32)cc2nc(-c3cc4cccnc4n3CC3CC3)n(C)c12]
I-341

TABLE 1-continued
Exemplary Compounds of Formula I
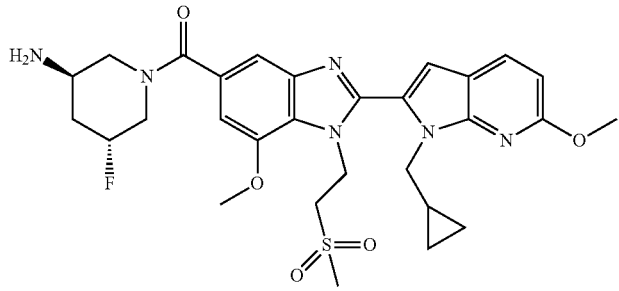 [SMILES: COc1ccc2cc(-c3nc4cc(C(=O)N5C[C@H](N)C[C@@H](F)C5)cc(OC)c4n3CCS(C)(=O)=O)n(CC3CC3)c2n1]
I-342
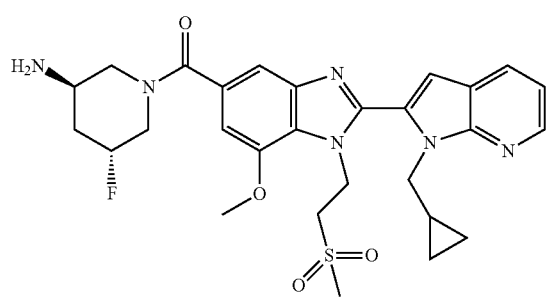 [SMILES: COc1cc(C(=O)N2C[C@H](N)C[C@@H](F)C2)cc2nc(-c3cc4cccnc4n3CC3CC3)n(CCS(C)(=O)=O)c12]
I-343
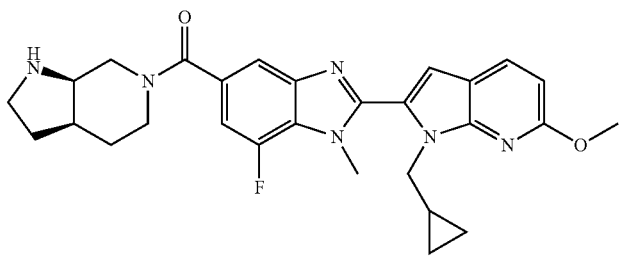 [SMILES: COc1ccc2cc(-c3nc4cc(C(=O)N5CC[C@H]6CCN[C@H]6C5)cc(F)c4n3C)n(CC3CC3)c2n1]
I-344
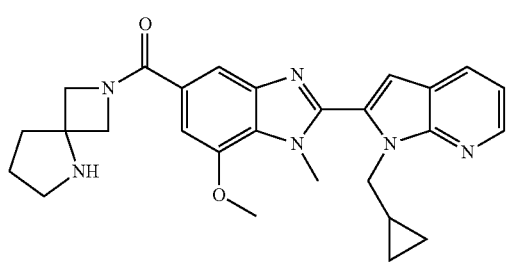 [SMILES: COc1cc(C(=O)N2CC3(CCCN3)C2)cc2nc(-c3cc4cccnc4n3CC3CC3)n(C)c12]
I-345
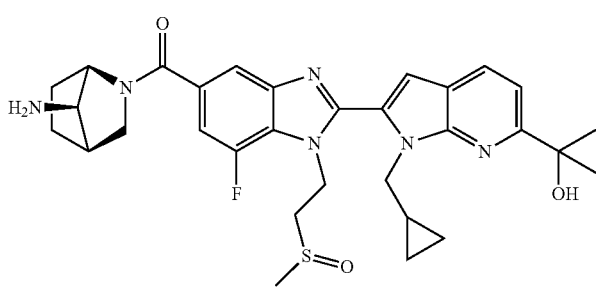 [SMILES: CS(=O)CCn1c(-c2cc3ccc(C(C)(C)O)nc3n2CC2CC2)nc2cc(C(=O)N3C[C@H]4CC[C@@H]3[C@@H]4N)cc(F)c21]
I-346

TABLE 1-continued
Exemplary Compounds of Formula I
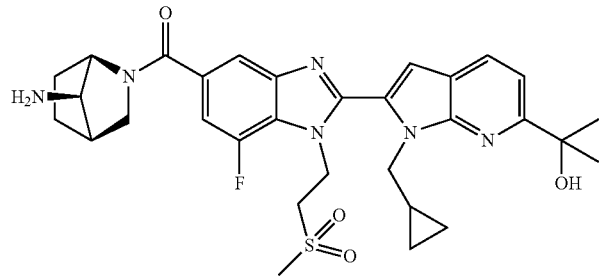 [SMILES: CC(C)(O)c1ccc2cc(-c3nc4cc(C(=O)N5C[C@H]6CC[C@@H]5[C@@H]6N)cc(F)c4n3CCS(C)(=O)=O)n(CC3CC3)c2n1] I-347
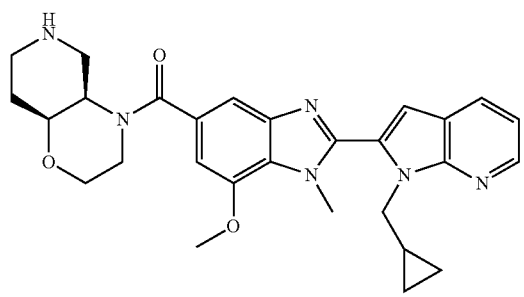 [SMILES: COc1cc(C(=O)N2CCO[C@H]3CCNC[C@H]32)cc2nc(-c3cc4cccnc4n3CC3CC3)n(C)c12] I-348
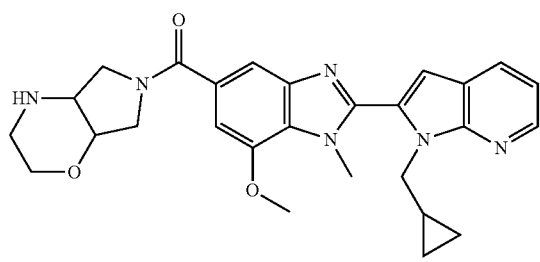 [SMILES: COc1cc(C(=O)N2CC3NCCOC3C2)cc2nc(-c3cc4cccnc4n3CC3CC3)n(C)c12] I-349
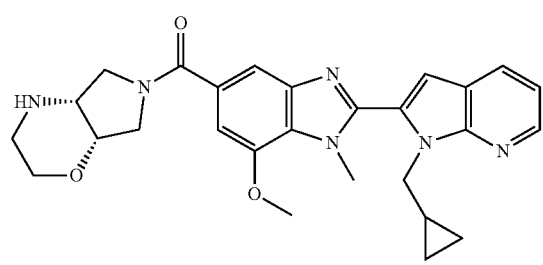 [SMILES: COc1cc(C(=O)N2C[C@@H]3OCCN[C@@H]3C2)cc2nc(-c3cc4cccnc4n3CC3CC3)n(C)c12] I-350
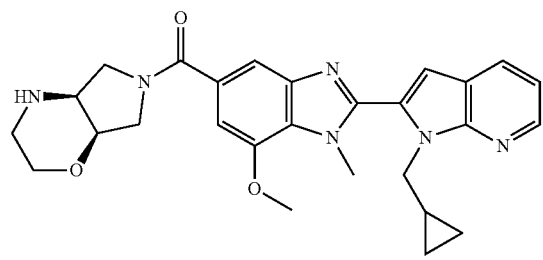 [SMILES: COc1cc(C(=O)N2C[C@@H]3NCCO[C@@H]3C2)cc2nc(-c3cc4cccnc4n3CC3CC3)n(C)c12] I-351

TABLE 1-continued
Exemplary Compounds of Formula I
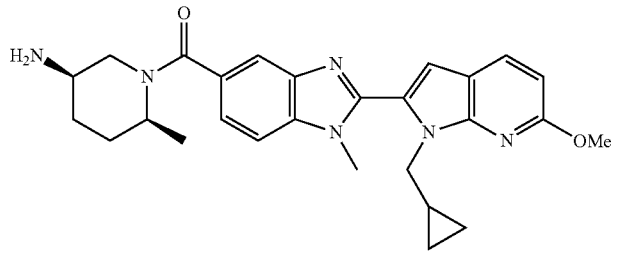 [SMILES: COc1ccc2cc(-c3nc4cc(C(=O)N5C[C@H](N)CC[C@@H]5C)ccc4n3C)n(CC3CC3)c2n1]
I-352
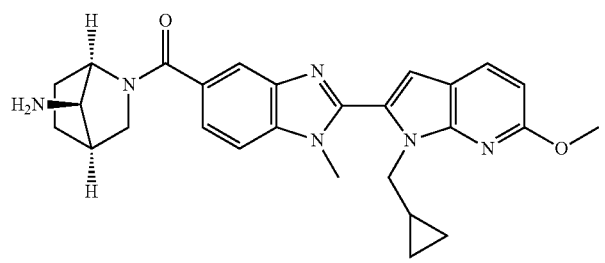 [SMILES: COc1ccc2cc(-c3nc4cc(C(=O)N5C[C@H]6CC[C@@H]5[C@@H]6N)ccc4n3C)n(CC3CC3)c2n1]
I-353
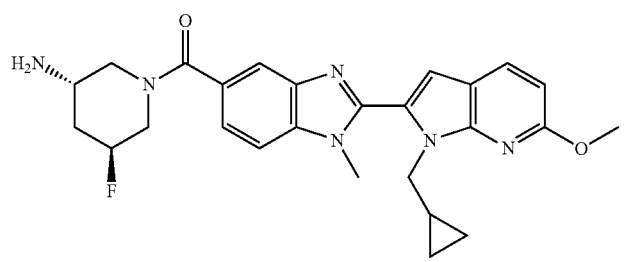 [SMILES: COc1ccc2cc(-c3nc4cc(C(=O)N5C[C@@H](N)C[C@H](F)C5)ccc4n3C)n(CC3CC3)c2n1]
I-354
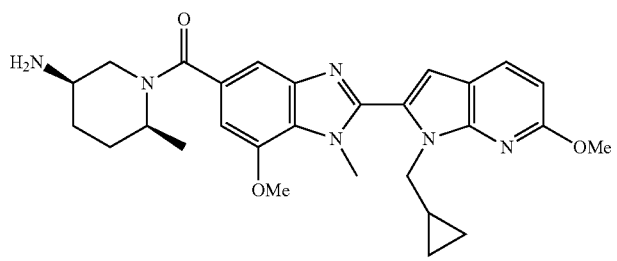 [SMILES: COc1ccc2cc(-c3nc4cc(C(=O)N5C[C@H](N)CC[C@@H]5C)cc(OC)c4n3C)n(CC3CC3)c2n1]
I-355
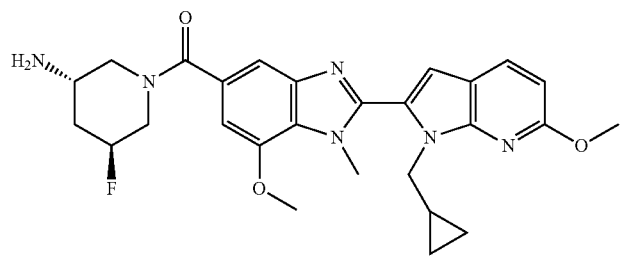 [SMILES: COc1ccc2cc(-c3nc4cc(C(=O)N5C[C@@H](N)C[C@H](F)C5)cc(OC)c4n3C)n(CC3CC3)c2n1]
I-356

TABLE 1-continued
Exemplary Compounds of Formula I
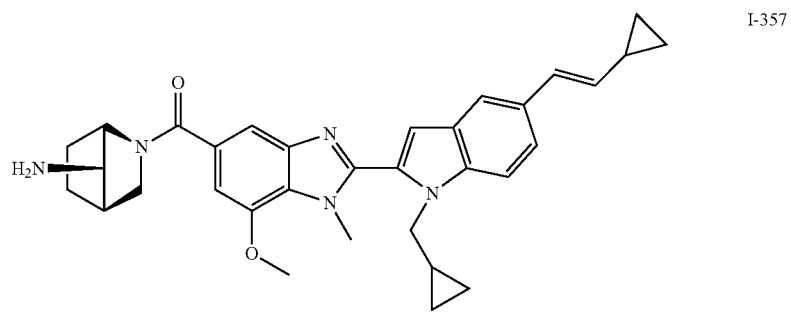
I-357
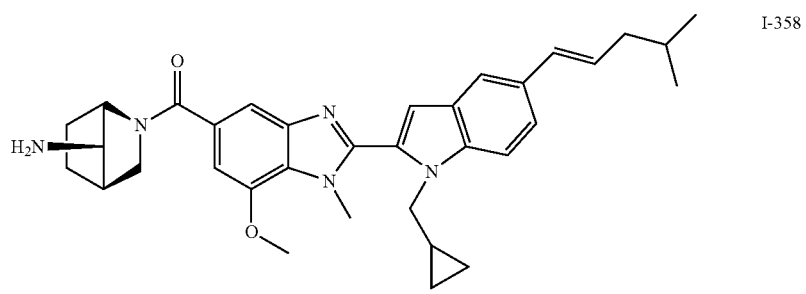
I-358
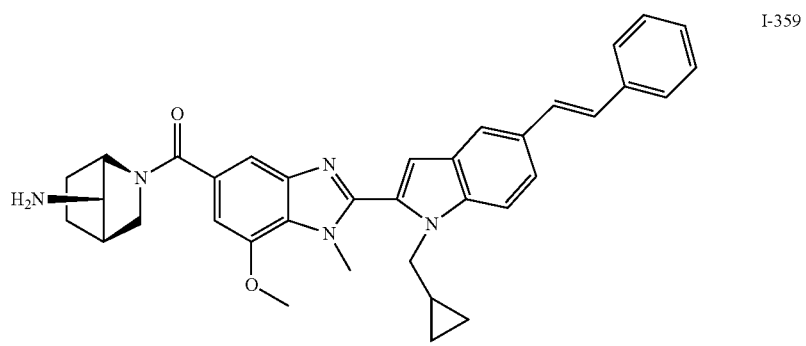
I-359
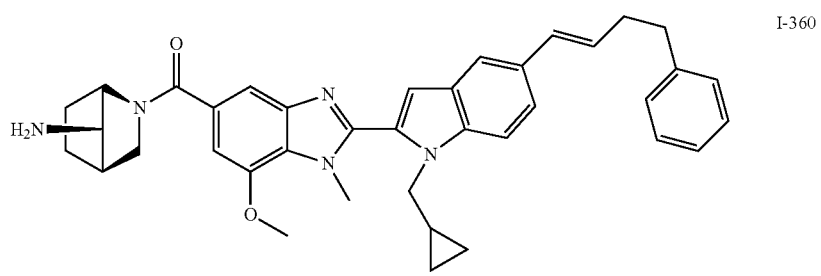
I-360
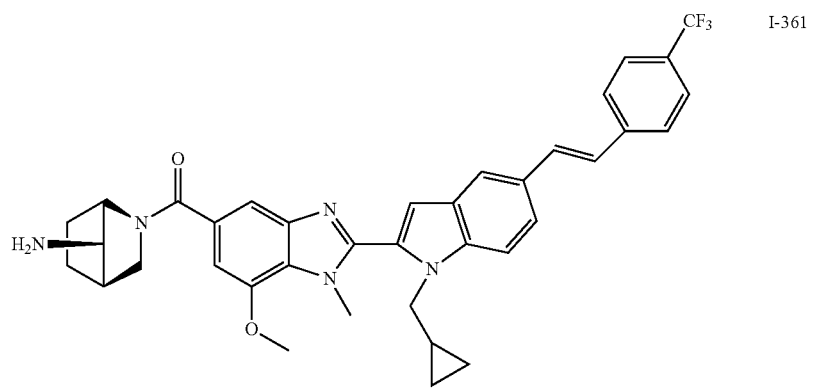
I-361

TABLE 1-continued
Exemplary Compounds of Formula I
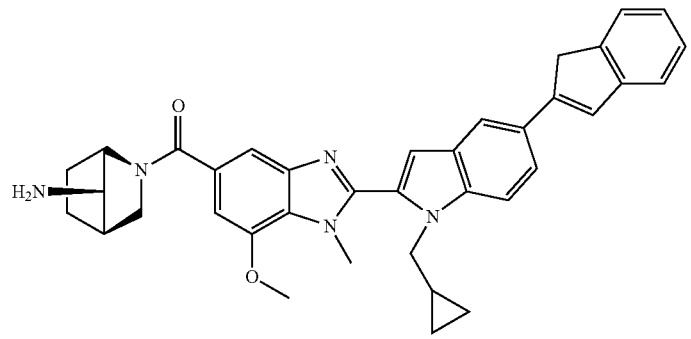
I-362
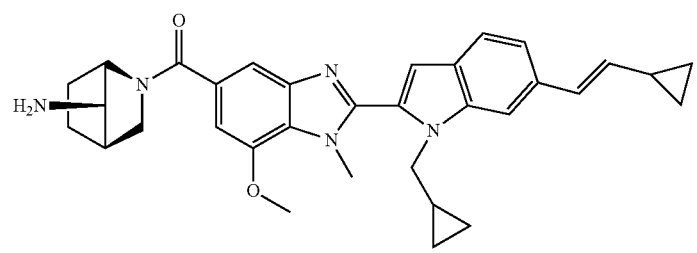
I-363
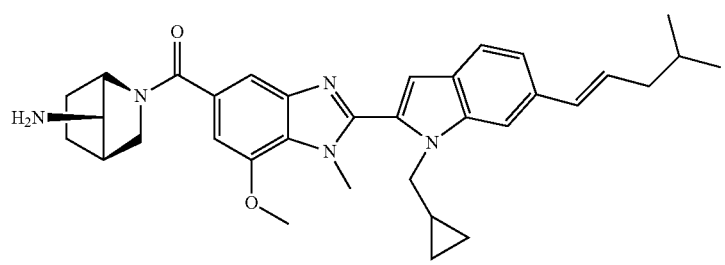
I-364
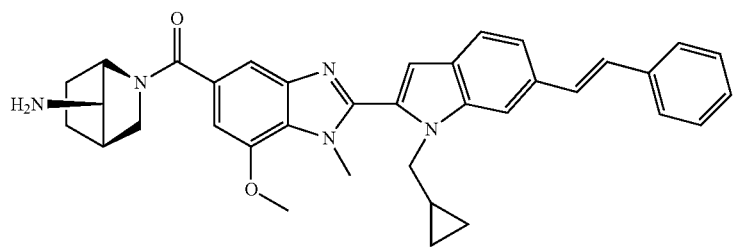
I-365
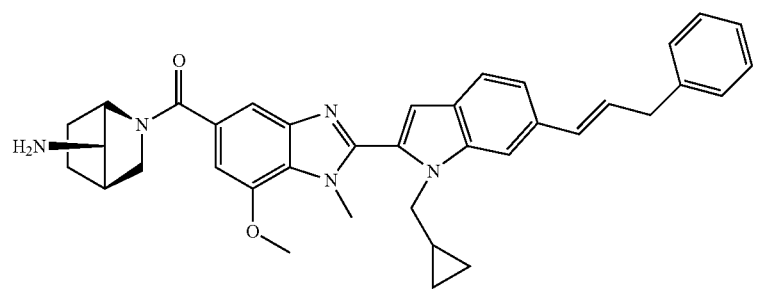
I-366

TABLE 1-continued
Exemplary Compounds of Formula I
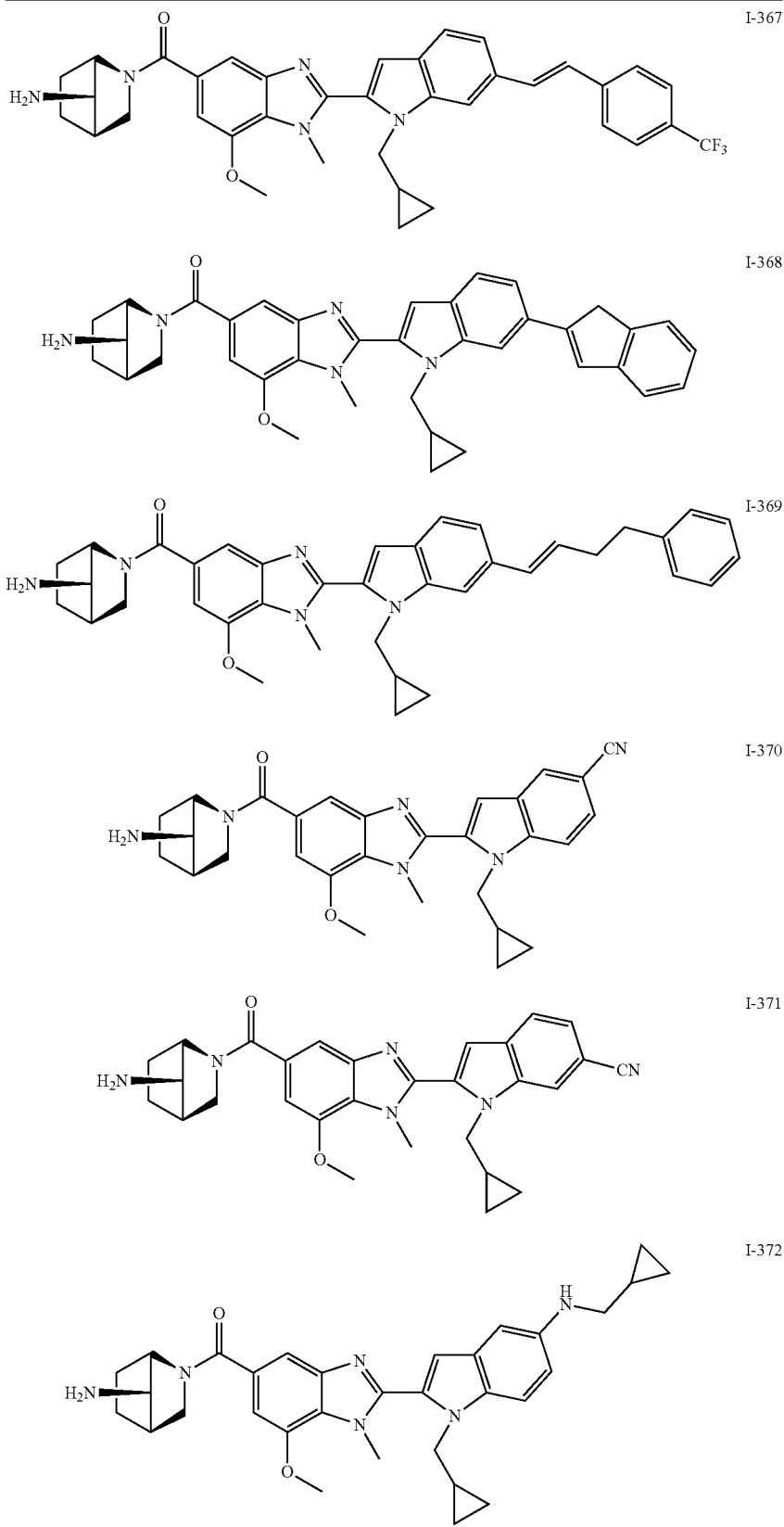
I-367
I-368
I-369
I-370
I-371
I-372

TABLE 1-continued

Exemplary Compounds of Formula I

I-373

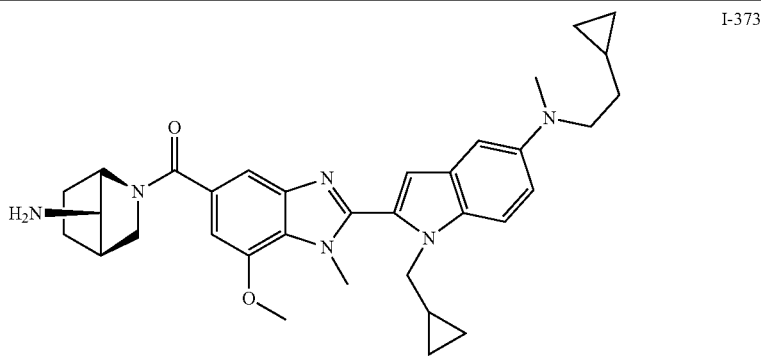

I-374

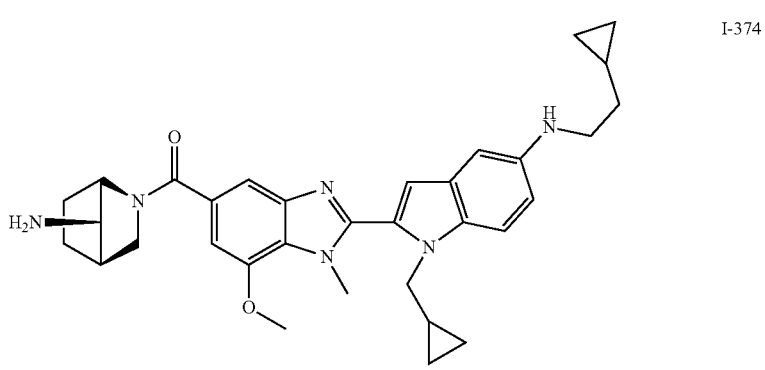

I-375

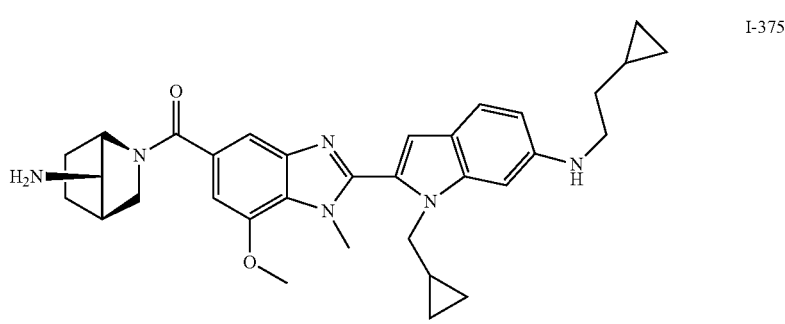

I-376

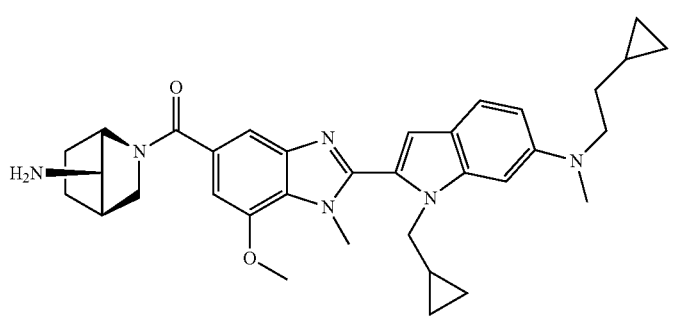

In certain embodiments, the present invention provides any compound described above and herein, or a pharmaceutically acceptable salt thereof. In some embodiments, the present invention provides a compound as depicted in Table 1, above, or a pharmaceutically acceptable salt thereof.

In some embodiments, the present invention provides any compound described above and herein in isolated form.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosis, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, behcet's disease, Behcet's syndrome, Bells Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osterarthritis, otitis media, paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis nodosa, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, and Wegener's granulomatosis.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosis. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosis. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosis comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutandis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Method A
MET/u-HPLC (low pH 7 min method)
Column: Phenomenex Kinetex-XB C18, 2.1 mm×100 mm, 1.7 μm
Flow rate: 0.6 ml/min
Mobile Phase: A, Formic acid (aqueous) 0.1% and B, Formic acid (MeCN) 0.1%
Injection Vol: 3 μl
Temp.: 40° C.
Detection: 215 nm (nominal)
Gradient Time (minutes)—% B
 0.00-5
 5.30-100
 5.80-100
 5.82-5
Method B
MET/CR/1600 (high pH 7 min method)
Column: Phenomenex Gemini C18, 2.0 mm×100 mm, 3 μm
Flow rate: 0.5 ml/min
Mobile phase:
 A: 2 mM ammonium bicarbonate in HPLC grade water pH10
 B: HPLC grade MeCN
Injection volume: 3 μl
Temperature: 50° C.
Detection: 215 nm
Gradient time: (minutes)—% B
 0.0-5
 5.50-100
 5.90-100
 5.92-5
 9.00-5
Method C
METCR 1416 (low pH Shimadzu 7 min method)
Column: Waters Atlantis dC18, 2.1 mm×100 mm, 3 μm column
Flow rate: 0.6 ml/min
Mobile Phase: A, Formic acid (aqueous) 0.1% and B, Formic acid (acetonitrile) 0.1%
Injection Vol: 3 μl
Temp.: 40° C.
Detection: 215 nm (nominal)
Gradient Time (minutes)—% B
 0.00-5
 5.00-100

5.40-100
5.42-5
Method D
METCR 1410 (low pH Shimadzu 2 min method)
Column: Kinetex Core-Shell C18, 2.1 mm×50 mm, 5 µm column
Flow rate: 1.2 ml/min
Mobile Phase: A, Formic acid (aqueous) 0.1% and B, Formic acid (acetonitrile) 0.1%
Injection Vol: 3 µl
Temp.: 40° C.
Detection: 215 nm (nominal)
Gradient Time (minutes)—% B
  0.00-5
  1.20-100
  1.30-100
  1.31-5
  Method E:
Chiral HPLC preparative method
Column: Chiralpak IC 250 mm×4.6 mm, 5 m column
Flow rate: 15 ml/min
Mobile Phase: 35% Ethanol: 65% CO2
Sample Diluent: Ethanol
Temp.: 40° C.
Detection: 215 nm (nominal)
  Method F:
Chiral purity analysis method
Column: Chiralpak IC 250 mm×4.6 mm, 5 µm column
Flow Rate: 4 ml/min
Injection Vol: 10 µL
Temp.: 40° C.
Detection: 215 nm
Isocratic Conditions 40% Ethanol: 60% CO2
  Method G
Chiral HPLC preparative method
Column: XSelect CSH C18 50×2.1 mm, 1.7 µm
Flow rate: 0.6 ml/min
Mobile Phase: Water (0.1% v/v TFA), MecN (0.1% v/v TFA)
Sample Diluent: Ethanol
Temp.: 40° C.
Detection: 240 nm (nominal)
  Method H
MET/u-HPLC (high pH MS16 7 min method)
Column: Waters UPLC CSH C18, 2.1 mm×100 mm 5 µm column
Flow rate: 0.6 ml/min
Mobile Phase: A, 2 mM Ammonium bicarbonate modified to pH 10 with Ammonium hydroxide (aqueous) and B, acetonitrile
Injection Vol: 3 µl
Temp.: 40° C.
Detection: 215 nm (nominal)
Gradient Time (minutes)—% B
  0.00-5
  5.30-100
  5.80-100
  5.82-5
  Method I:
Chiral purity analysis method
Column: Lux C4 (21.2 mm×250 mm, 5 µm)
Flow Rate: 21 ml/min
Injection Vol: 350 µL
Detection: 222 nm
Isocratic Conditions: MeOH (0.1% v/v NH3)
  Method J
MET/CR/0990 (high pH 3 min method)
Column: Phenomenex Gemini C18, 2.0 mm×100 mm, 3 m
Flow rate: 1 ml/min
Mobile phase: A, 2 mM ammonium bicarbonate in HPLC grade water pH10
  B HPLC grade MeCN
Injection volume: 3 µl
Temperature: 60° C.
Detection: 215 nm
Gradient time: (minutes)—% B
  0.0-1
  1.80-100
  2.10-100
  2.30-1
  Method K:
Chiral HPLC preparative method
Column: Amy-C 20 mm×250 mm, 5 µm
Flow Rate: 21 ml/min
Mobile Phase: 4:6 heptane:ethanol (0.1% v/v ammonia)
Sample Diluent: Methanol
Temp.: Ambient
Detection: 254 nm
  Method L:
Chiral purity analysis method
Column: Amy-C 4.6 mm×250 mm, 5 µm
Flow Rate: 21 ml/min
Injection Vol: 1.0 µL
Temp.: Ambient
UV Detection: 254 nm
Isocratic Conditions 4:6 heptane:ethanol (0.1% v/v ammonia)

Certain compounds of the present invention were prepared according to Scheme 1, below.

Scheme 1

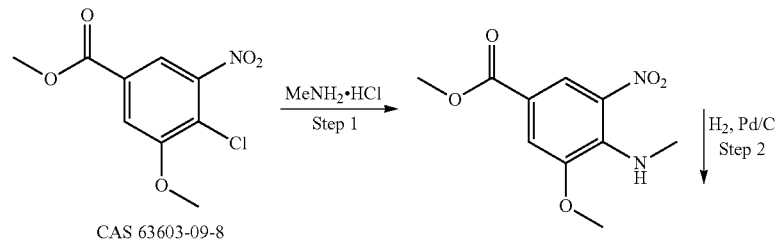

CAS 63603-09-8

193
194
-continued
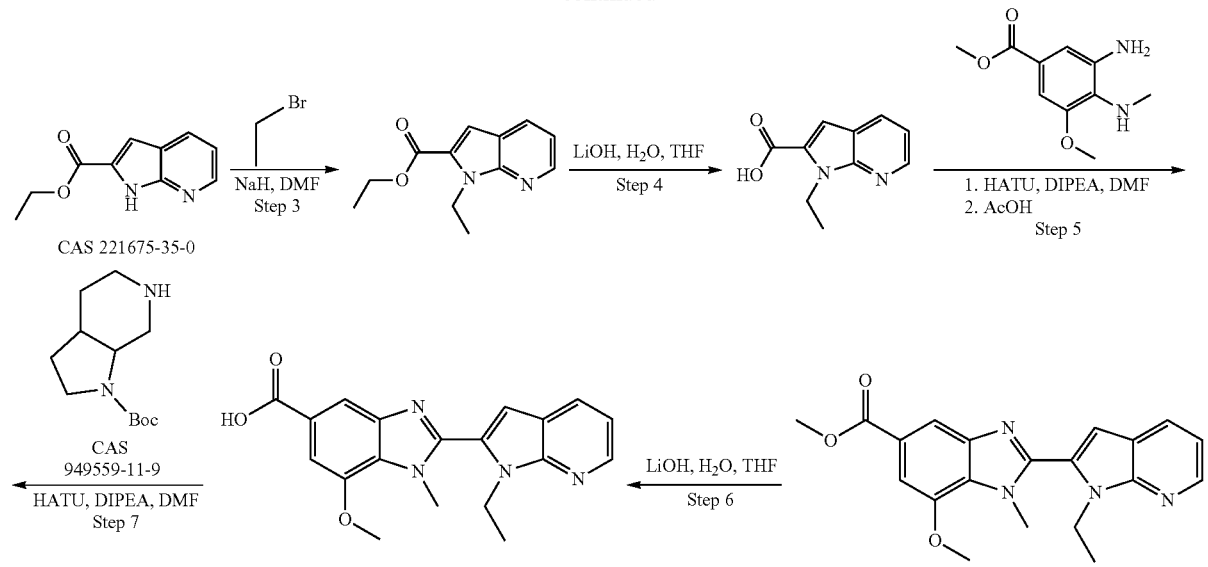
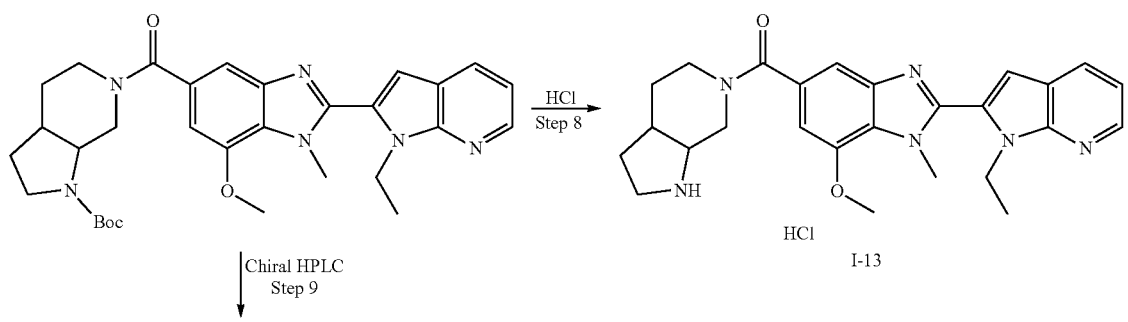
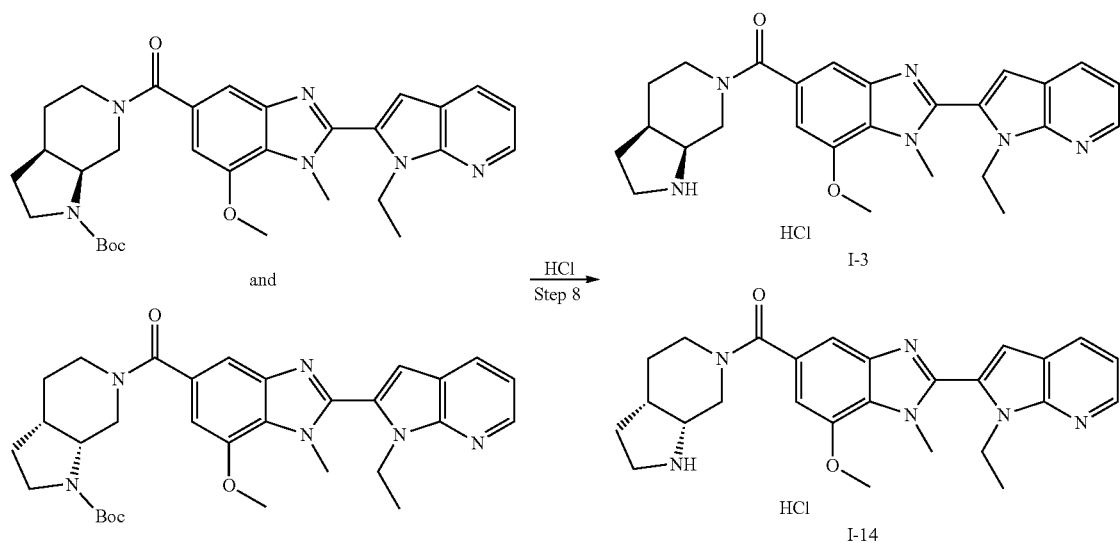

Synthesis of 2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole EV-AR0076-002 (EOAI3428370), I-13

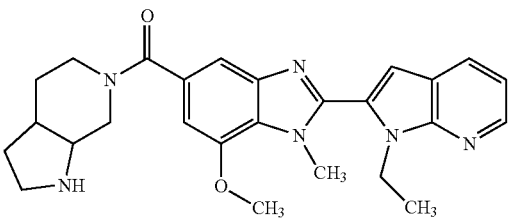

Methyl 3-methoxy-4-(methylamino)-5-nitrobenzoate EV-AR0065-002—step 1

To a stirred solution of methyl 4-chloro-3-methoxy-5-nitrobenzoate (CAS 63603-09-8, 2.0 g, 8.14 mmol) in DMF (10 ml) was added K$_2$CO$_3$ (99%, 1.37 g, 9.81 mmol). To this solution was added methanamine hydrochloride (1:1) (0.62 g, 9.18 mmol) and the mixture was stirred in a sealed tube under nitrogen at 80° C. for 16 h. The reaction crude was concentrated in vacuo and partitioned between DCM (100 ml) and water (10 ml). The organic layer was washed further with water (2×10 ml) and saturated aqueous sodium chloride (10 ml). The organic layer was dried over sodium sulfate, filtered and concentrated in vacuo to afford an orange powder which was purified by flash column chromatography (15-40% EtOAc/heptane) to obtain 1.49 g (76%) of methyl 3-methoxy-4-(methylamino)-5-nitrobenzoate EV-AR0065-002 as an orange powder. LCMS (method D): retention time 1.13 min, M/z=241 (M+1).

Methyl 3-amino-5-methoxy-4-(methylamino)benzoate EV-AR0068-002—step 2

To a stirred solution of methyl 3-methoxy-4-(methylamino)-5-nitrobenzoate (EV-AR0065-002, 1.49 g, 6.20 mmol) in ethanol (100 ml) under nitrogen was added 10% Pd/C (0.18 g, 0.17 mmol) and the resulting mixture was stirred at room temperature under an atmosphere of hydrogen for 16 h. The reaction mixture was filtered through Kieselguhr and the filter was washed through with methanol (150 ml). The filtrate was concentrated in vacuo to afford 1.21 g (89%) of methyl 3-amino-5-methoxy-4-(methylamino)benzoate EV-AR0068-002 as a pale purple powder. LCMS (method D): retention time 0.63 min, M/z=211 (M+1).

Ethyl 1-ethyl-1H-pyrrolo[2,3-b]pyridine-2-carboxylate EV-AQ1957-001—step 3

Sodium hydride (60%, 59 mg, 1.47 mmol) was added portion wise to a stirred suspension of ethyl 1H-pyrrolo[2,3-b]pyridine-2-carboxylate (CAS 221675-35-0, 200 mg, 1.05 mmol) in DMF (5 ml) at room temperature. The mixture was stirred for 20 minutes then ethyl iodide (197 mg, 1.26 mmol) was added. The reaction mixture was stirred for 20 h. The mixture was partitioned between EtOAc (20 ml) and water (20 ml). The aqueous layer was extracted further with EtOAc (1×20 ml), the combined organics were washed with water (20 ml) and evaporated to dryness. The crude product was purified by flash column chromatography (0-50% EtOAc/heptane) to obtain 135 mg (57.1%) of ethyl 1-ethyl-1H-pyrrolo[2,3-b]pyridine-2-carboxylate EV-AQ1957-001 as a colourless oil. LCMS (method D): retention time 1.18 min, M/z=219 (M+1).

1-Ethyl-1H-pyrrolo[2,3-b]pyridine-2-carboxylic acid EV-AQ1960-001—step 4

To a stirred solution of ethyl 1-ethyl-1H-pyrrolo[2,3-b]pyridine-2-carboxylate (EV-AQ1957-001, 135 mg, 0.62 mmol) in THF (2 ml) was added lithium hydroxide (74 mg, 3.09 mmol) in water (2 ml). The mixture was stirred at 50° C. for 2.5 h. The mixture was acidified with 1M HCl (3 ml) and extracted with DCM (2×5 ml). The combined organics were washed with water and evaporated to dryness to give 120 mg (99%) of 1-ethyl-1H-pyrrolo[2,3-b]pyridine-2-carboxylic acid EV-AQ1960-001 as a white solid. LCMS (method D): retention time 0.92 min, M/z=191 (M+1).

Methyl 2-{1-ethyl-1H-pyrrolo[2,3-b]pyridin-2-yl}-7-methoxy-1-methyl-1H-1,3-benzodiazole-5-carboxylate EV-AR0070-003—step 5

To a stirred solution of 1-ethyl-1H-pyrrolo[2,3-b]pyridine-2-carboxylic acid (EV-AQ1960-001, 120 mg, 0.63 mmol) in DMF (2 ml) was added DIPEA (116 µl, 0.70 mmol) followed by HATU (236 mg, 0.62 mmol) and the resulting mixture was stirred at room temperature for 15 minutes. Methyl 3-amino-5-methoxy-4-(methylamino)benzoate (EV-AR0068-002, 148 mg, 0.70 mmol) was added and the resulting mixture was stirred at room temperature for 6 h. The reaction mixture was concentrated in vacuo, dissolved in acetic acid (3 ml) and stirred at 70° C. for 16 h. The solvent was removed in vacuo and the remaining material was purified by flash column chromatography (25-40% EtOAc/heptane) to obtain 150 mg (63%) of methyl 2-{1-ethyl-1H-pyrrolo[2,3-b]pyridin-2-yl}-7-methoxy-1-methyl-1H-1,3-benzodiazole-5-carboxylate EV-AR0070-003 as a white powder. LCMS (method D): retention time 1.18 min, M/z=365 (M+1).

2-{1-Ethyl-1H-pyrrolo[2,3-b]pyridin-2-yl}-7-methoxy-1-methyl-1H-1,3-benzodiazole-5-carboxylic acid EV-AR0072-002—step 6

To a stirred solution of methyl 2-{1-ethyl-1H-pyrrolo[2,3-b]pyridin-2-yl}-7-methoxy-1-methyl-1H-1,3-benzodiazole-5-carboxylate (EV-AR0070-003, 150 mg, 0.41 mmol) in THF (3 ml) was added a solution of lithium hydroxide (30 mg, 1.25 mmol) in water (3 ml) and the mixture was stirred at room temperature for 16 h. The reaction mixture was concentrated in vacuo, taken up in water (5 ml) and acidified with 5N HCl (0.5 ml) whilst stirring. The resulting suspension was stirred for 10 minutes then the precipitate was collected by vacuum filtration and dried to obtain 130 mg (89%) of 2-{1-ethyl-1H-pyrrolo[2,3-b]pyridin-2-yl}-7-methoxy-1-methyl-1H-1,3-benzodiazole-5-carboxylic acid EV-AR0072-002 as a white powder. LCMS (method D): retention time 1.03 min, M/z=351 (M+1).

Tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002—step 7

To a stirred solution of 2-{1-ethyl-1H-pyrrolo[2,3-b]pyridin-2-yl}-7-methoxy-1-methyl-1H-1,3-benzodiazole-5-carboxylic acid (EV-AR0072-002, 130 mg, 0.37 mmol) in 2:1 DMSO/MeCN (4.5 ml) were added DIPEA (65 µl, 0.39 mmol) and HATU (148 mg, 0.39 mmol). The resulting mixture was stirred at room temperature for 15 minutes then tert-butyl octahydro-1H-pyrrolo[2,3-c]pyridine-1-carboxylate (CAS 949559-11-9, 88 mg, 0.39 mmol) was added and the mixture was stirred at room temperature for 4 h. The reaction mixture was diluted with 3:2 MeCN/water (1.5 ml) and purified by preparative HPLC (basic method) to obtain 142 mg (81%) of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002 as a white powder. LCMS (method A): retention time 3.41 min, M/z=559 (M+1).

2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole EV-AR0076-002 (EOAI3428370), I-13—step 8

To a stirred solution of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0074-002, 20 mg, 0.04 mmol) in methanol (1 ml) was added 4M HCl in 1,4-dioxane (0.5 ml) and the resulting solution was stirred at room temperature for 4 h. The reaction mixture was concentrated in vacuo and the residue was freeze-dried from water (4 ml) to obtain 13.4 mg (75%) of 2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole hydrochloride EV-AR0076-002, I-13, as a yellow solid. LCMS (method A): retention time 1.80 min, M/z=459 (M+1).

Chiral HPLC to obtain tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-001, and tert-butyl (3aS,7aR)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-002,—step 9

107 mg of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002 were dissolved in ethanol and then purified by chiral HPLC (method E) to obtain 46.6 mg (43.6%) of tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-001 (absolute stereochemistry arbitrarily assigned) and 36.8 mg (33.4%) of tert-butyl (3aS,7aR)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-002 (absolute stereochemistry arbitrarily assigned).
EV-AR0090-001, Chiral purity (UV, 254 nm): 100%, retention time: 6.30 min (method F)
EV-AR0090-002, Chiral purity (UV, 254 nm): 97%, retention time: 9.96 min (method F)

5-[(3aS,7aS)-Octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole EV-AR0091-002 (EOAI3432499, absolute stereochemistry arbitrarily assigned) I-3—step 8

Tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0090-001, 46 mg, 0.08 mmol) was treated as in step 8, Scheme 1 to obtain 40 mg (97%) of 5-[(3aS,7aS)-octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole hydrochloride EV-AR0091-002, I-3, as an orange powder. LCMS (method A): retention time 1.83 min, M/z=459 (M+1).

5-[(3aR,7aR)-Octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole EV-AR0092-002 (EOAI3432500, absolute stereochemistry arbitrarily assigned) I-14—step 8

Tert-butyl (3aS,7aR)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0090-002, 36.8 mg, 0.07 mmol) was treated as in step 8, Scheme 1 to obtain 31 mg (92.7%) of 5-[(3aR,7aR)-octahydro-1H-pyrrolo[2,3-c]pyridine-6-carbonyl]-2-{1-ethyl-1H-pyrrolo[2,3-b]pyridin-2-yl}-7-methoxy-1-methyl-1-1H-1,3-benzodiazole EV-AR0092-002, 1-14, as an orange powder. LCMS (method A): retention time 1.82 min, M/z=459 (M+1).

Scheme 2

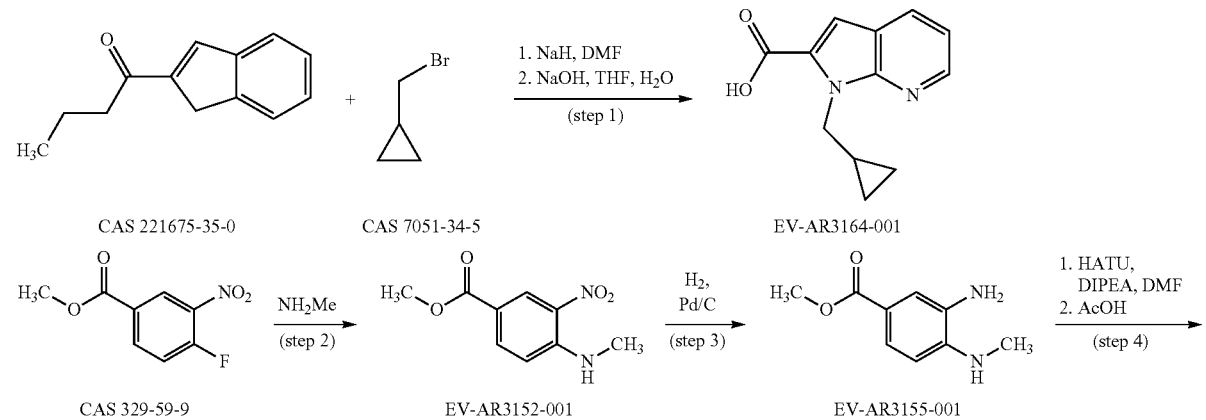

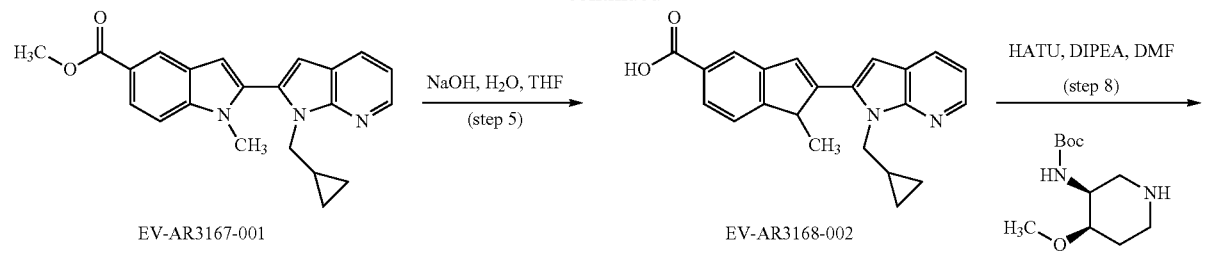
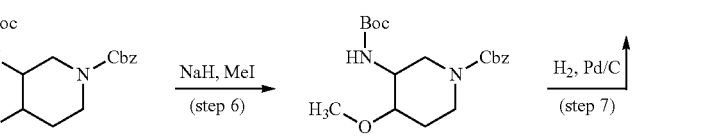
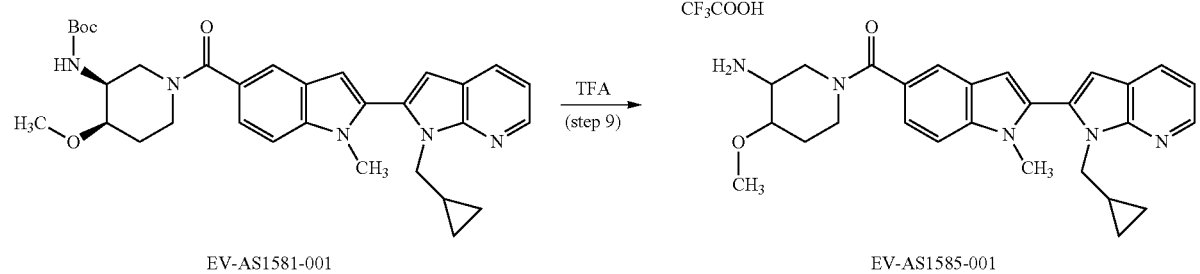
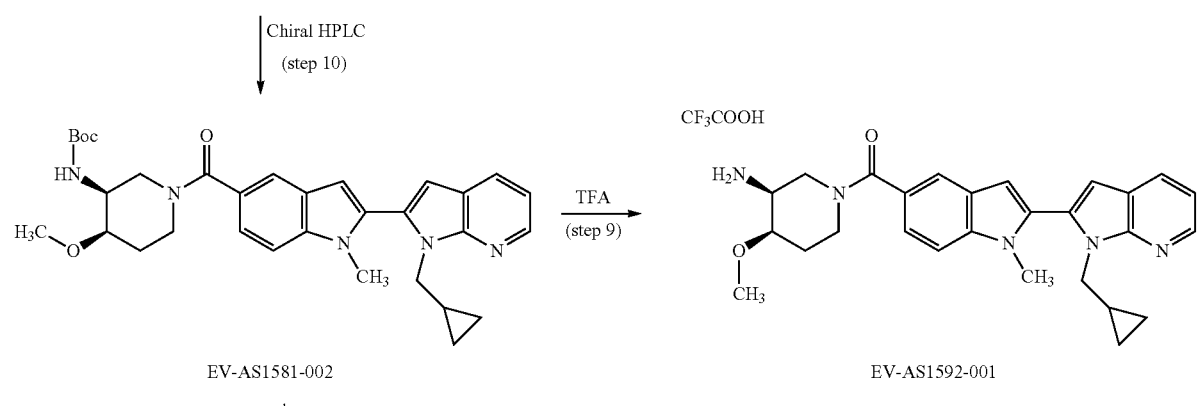
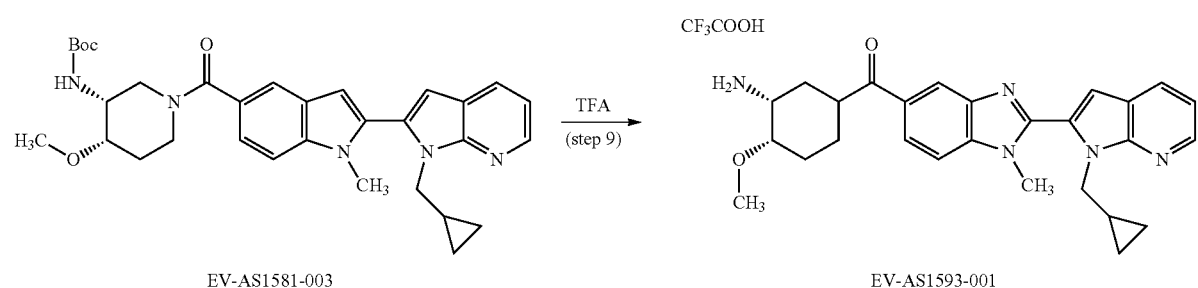

Synthesis of 1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine EV-AS1585-001 (EOAI3436357), I-62

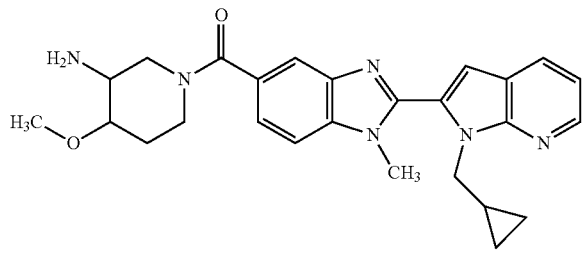

I-62

1-(Cyclopropylmethyl)-1H-pyrrolo[2,3-b]pyridine-2-carboxylic acid EV-AR3164-001—step 1

To a stirred solution of ethyl 1H-pyrrolo[2,3-b]pyridine-2-carboxylate (CAS 221675-35-0, 4.40 g, 23.1 mmol) in DMF (50 ml) was added sodium hydride (60%, 1.05 g, 26.3 mmol). The mixture was stirred under nitrogen at room temperature for 45 minutes and (bromomethyl)cyclopropane (CAS 7051-34-5, 2.70 ml, 27.8 mmol) was added. The mixture was stirred at room temperature for 2.5 h and the solvent was removed in vacuo. The residue was suspended in THF (40 ml) and 5M aqueous sodium hydroxide (22 ml, 110 mmol) was added. The mixture was stirred at 50° C. for 3.5 h. Additional THF (20 ml) and 5M aqueous sodium hydroxide (22 ml, 110 mmol) were added and the reaction was stirred at 50° C. for 16 h. The reaction crude was concentrated in vacuo and water (10 ml) and 5M aqueous hydrochloric acid (100 ml) were added. The solid was filtered off, washed with water (2×100 ml) and dried in a vac oven to obtain 3.46 g (69.2%) of 1-(cyclopropylmethyl)-1H-pyrrolo[2,3-b]pyridine-2-carboxylic acid EV-AR3164-001 as a white powder. LCMS (method D): retention time 1.03 min, M/z=217 (M+1).

Methyl 4-(methylamino)-3-nitrobenzoate EV-AR3152-001—step 2

To a stirred solution of methyl 4-fluoro-3-nitrobenzoate (CAS 329-59-9, 5.00 g, 25.1 mmol) in DMF (50 ml) was added methanamine hydrochloride (1:1) (2.00 g, 29.6 mmol) and potassium carbonate (4.50 g, 32.6 mmol). The mixture was stirred at room temperature under nitrogen for 18 h. The reaction crude was concentrated in vacuo and the residue was partitioned between in EtOAc (350 ml) and 1N aqueous hydrochloric acid (250 ml). The organic layer was washed further with 1N aqueous hydrochloric acid (150 ml) and saturated aqueous sodium chloride (100 ml). The organic layer was dried over magnesium sulfate, filtered and concentrated in vacuo to obtain 5.30 g (quantitative) of methyl 4-(methylamino)-3-nitrobenzoate EV-AR3152-001 as a yellow powder. LCMS (method D): retention time 1.07 min, M/z=211 (M+1).

Methyl 3-amino-4-(methylamino)benzoate EV-AR3155-001—step 3

To a stirred solution of methyl 4-(methylamino)-3-nitrobenzoate (EV-AR3152-001, 5.30 g, 25.2 mmol) in ethanol (100 ml) under nitrogen was added 10% Pd/C (1.30 g, 0.05 mmol). The reaction was then placed under a hydrogen atmosphere and stirred at room temperature for 4 h. The reaction mixture was diluted with methanol (100 ml) and Kieselguhr was added. The mixture was stirred at room temperature for 10 minutes and filtered under vacuum. The filter was washed with methanol (3×50 ml) and the filtrate was concentrated in vacuo to obtain 4.39 g (96.6%) of methyl 3-amino-4-(methylamino)benzoate EV-AR3155-001 as a brown powder. LCMS (method D): retention time 0.75 min, M/z=181 (M+1).

Methyl 2-[1-(cyclopropylmethyl)-1H-pyrrolo[2,3-b]pyridin-2-yl]-1-methyl-1H-1,3-benzodiazole-5-carboxylate EV-AR3167-001—step 4

To a solution of 1-(cyclopropylmethyl)-1H-pyrrolo[2,3-b]pyridine-2-carboxylic acid (EV-AR3164-001, 2.20 g, 10.2 mmol) in dry DMF (40 ml) was added HATU (4.95 g, 12.8 mmol) and DIPEA (2.25 ml, 12.8 mmol). The mixture was stirred at room temperature for 1 h then methyl 3-amino-4-(methylamino)benzoate (EV-AR3155-001, 2.02 g, 11.2 mmol) was added. The mixture was stirred at room temperature for 16 h. The solvent was removed in vacuo and the residue was dissolved in acetic acid and stirred at 80° C. for 2 h, then 85° C. for 30 minutes then 90° C. for 1 h. The solvent was removed in vacuo and the crude material was purified by flash column chromatography (12-100% EtOAc/heptane) to obtain 3.08 g (83.2%) of methyl 2-[1-(cyclopropylmethyl)-1H-pyrrolo[2,3-b]pyridin-2-yl]-1-methyl-1H-1,3-benzodiazole-5-carboxylate EV-AR3167-001 as a pink powder. LCMS (method D): retention time 1.20 min, M/z=361 (M+1).

2-[1-(cyclopropylmethyl)-1H-pyrrolo[2,3-b]pyridin-2-yl]-1-methyl-1H-1,3-benzodiazole-5-carboxylic acid EV-AR3168-002—step 5

To a suspension of methyl 2-[1-(cyclopropylmethyl)-1H-pyrrolo[2,3-b]pyridin-2-yl]-1-methyl-1H-1,3-benzodiazole-5-carboxylate (EV-AR3167-001, 3.08 g, 8.46 mmol) in methanol (60 ml) was added 2M aqueous sodium hydroxide (30 ml, 60.0 mmol). The mixture was then stirred at 50° C. for 2 h. The reaction was allowed to cool to room temperature and the solvent was removed in vacuo. Water (50 ml) was added followed by 2M aqueous HCl until pH 3 was achieved. The mixture was stirred for 15 minutes and filtered through a sinter. The solid was washed with water (2×50 ml) and air-dried for 64 h to afford 1.81 g (61.2%) of 2-[1-(cyclopropylmethyl)-1H-pyrrolo[2,3-b]pyridin-2-yl]-1-methyl-1H-1,3-benzodiazole-5-carboxylic acid EV-AR3168-001 as a beige solid. LCMS (method D): retention time 1.05 min, M/z=347 (M+1). The filtrate was further acidified by addition of 2M aqueous HCl until a precipitate started to form. The mixture was allowed to stand for 1 h and filtered through a sinter. The solid was washed with water (2×20 ml) and air-dried under vacuum for 3 h to obtain 460 mg of (15.7%) 2-[1-(cyclopropylmethyl)-1H-pyrrolo[2,3-b]pyridin-2-yl]-1-methyl-1H-1,3-benzodiazole-5-carboxylic acid EV-AR3168-002 as an off white powder LCMS (method D): retention time 1.06 min, M/z=347 (M+1).

Benzyl (3S,4R)-3-{[(tert-butoxy)carbonyl]amino}-4-methoxypiperidine-1-carboxylate EV-AT1700-001—step 6

To a stirred solution of benzyl (3S,4R)-3-{[(tert-butoxy)carbonyl]amino}-4-hydroxypiperidine-1-carboxylate (EV- AQ1997-001, synthesised as in WO2014/015905, 450 mg, 1.28 mmol) in anhydrous THF (10 ml) at 0° C. under nitrogen was added sodium hydride (60%, 62 mg, 1.54 mmol). The mixture was stirred at 0° C. for 30 minutes then iodomethane (83.94 µl, 1.35 mmol) was added and the mixture was stirred at room temperature for 16 h. Saturated aqueous ammonium chloride (2 ml) was added and the mixture was stirred for 10 minutes. The mixture was concentrated in vacuo and partitioned between water (50 ml) and DCM (50 ml). The aqueous layer was extracted further with DCM (2×50 ml) and the combined organics were concentrated in vacuo. The crude product was purified by flash column chromatography (0-100% EtOAc/heptane) to obtain 248 mg (52.9%) of benzyl (3S,4R)-3-{[(tert-butoxy)carbonyl]amino}-4-methoxypiperidine-1-carboxylate EV-AT1700-001 as a colourless oil. LCMS (method D): retention time 1.29 min, M/z=387 (M+23).

Tert-butyl N-[(3S,4R)-4-methoxypiperidin-3-yl]carbamate EV-AT1701-001—step 7

To a stirred solution of benzyl (3S,4R)-3-{[(tert-butoxy)carbonyl]amino}-4-methoxypiperidine-1-carboxylate (EV-AT1700-001, 235 mg, 0.64 mmol) in ethanol (10 ml) under nitrogen was added 10% Pd/C (34 mg, 0.03 mmol). The reaction was placed under a hydrogen atmosphere and stirred at room temperature for 16 h. The reaction mixture was filtered through Kieselguhr and the filter was washed through with ethanol (20 ml). The filtrate was concentrated in vacuo to obtain 135 mg (68.0%) of tert-butyl N-[(3S,4R)-4-methoxypiperidin-3-yl]carbamate EV-AT1701-001 as a colourless oil. LCMS (method D): retention time 0.79 min, M/z=231 (M+1).

Tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS-1581-001—step 8

To a stirred solution of 2-[1-(cyclopropylmethyl)-1H-pyrrolo[2,3-b]pyridin-2-yl]-1-methyl-1H-1,3-benzodiazole-5-carboxylic acid (EV-AR3168-002, 150 mg, 0.43 mmol) in DMF (5 ml) was added HATU (197.6 mg, 0.52 mmol) followed by DIPEA (0.15 ml, 0.87 mmol). The mixture was stirred for 1 h then tert-butyl N-[(3S,4R)-4-methoxypiperidin-3-yl]carbamate (EV-AT1701-001, 99.7 mg, 0.43 mmol) was added. The reaction was stirred at room temperature for 16 h. The solvent was removed in vacuo and the residue was partitioned between DCM (30 ml) and saturated aqueous sodium hydrogen carbonate (30 ml). The aqueous layer was extracted with DCM (20 ml) and the combined organics were washed with water (20 ml) and saturated aqueous sodium chloride (20 ml). The organic layer was dried over sodium sulfate, filtered and concentrated in vacuo to afford an orange oil which was purified by preparative HPLC (basic method) to obtain 205 mg (82.9%) of tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-001 as a white crystalline solid. LCMS (method A): retention time 3.36 min, M/z=559 (M+1).

1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine EV-AS1585-001 (EOAI3436357) I-62—step 9

To a stirred solution of tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate (EV-AS1581-001, 30 mg, 0.05 mmol) in DCM (2 ml) was added trifluoroacetic acid (1 ml, 13.0 mmol). The mixture was stirred at room temperature for 3 h. The solvent was removed under a stream of nitrogen and the residue was freeze-dried from acetonitrile:water (1:1, 4 ml) to obtain 9.6 mg (96.3%) of 1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine trifluoroacetic acid EV-AS1585-001, 1-62, as a white powder. LCMS (method A): retention time 1.86 min, M/z=459 (M+1).

Chiral HPLC to obtain tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-002 and tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-003—step 10

90.4 mg of tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-001 were dissolved in methanol and then purified by chiral HPLC (method K) to obtain 36.2 mg of tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-002 (absolute stereochemistry arbitrarily assigned) and 34.4 mg of tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate EV-AS1581-003 (absolute stereochemistry arbitrarily assigned).

EV-AS1581-002 Chiral purity (UV, 254 nm): 100%, retention time: 7.58 min (method L)
EV-AS1581-003 Chiral purity (UV, 254 nm): 100%, retention time: 10.07 min (method L)

(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine EV-AS1592-001 (EOAI3438020, absolute stereochemistry arbitrarily assigned) I-64—step 9

Tert-butyl N-[(3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate (EV-AS1581-002, 36.2 mg, 0.07 mmol) was treated as in step 9, Scheme 1 to obtain 37.1 mg (64.6%) of (3S,4R)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine trifluoroacetic acid EV-AS1592-001, I-64, as a white powder. LCMS (method A): retention time 1.86 min, M/z=459 (M+1).

(3R,4S)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine EV-AS1593-001 (EOAI3437979, absolute stereochemistry arbitrarily assigned) I-65—step 9

Tert-butyl N-[(3R,4S)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-yl]carbamate (EV- AS1581-003, 34.4 mg, 0.06 mmol) was treated as in step 9, Scheme 1 to obtain 33.6 mg (94.3%) of (3R,4S)-1-{2-[1-(cyclopropylmethyl)-1H-pyrrolo[2,3-b]pyridin-2-yl]-1-methyl-1H-1,3-benzodiazole-5-carbonyl}-4-methoxypiperidin-3-amine trifluoroacetic acid EV-AS1593-001, I-65, as a white powder. LCMS (method A): retention time 1.86 min, M/z=459 (M+1).

5-[(3aR,7aR)-Octahydro-1H-pyrrolo[2,3-c]pyridine-6-carbonyl]-2-[1-(cyclopropylmethyl)-5-phenyl-1H-pyrrol-2-yl]-1-methyl-1H-1,3-benzodiazole EV-AS5709-003 (EOAI3434977) I-116 and 5-[(3aS,7aS)-octahydro-1H-pyrrolo[2,3-c]pyridine-6-carbonyl]-2-[1-(cyclopropylmethyl)-5-phenyl-1H-pyrrol-2-yl]-1-methyl-1H-1,3-benzodiazole EV-AS5710-003 (EOAI3434978) I-117 were synthesised according to the procedures described in Scheme 2 via synthesis of methyl 5-phenyl-1H-pyrrole-2-carboxylate EV-AR0054-002 described in Scheme 2.1:

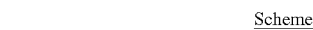

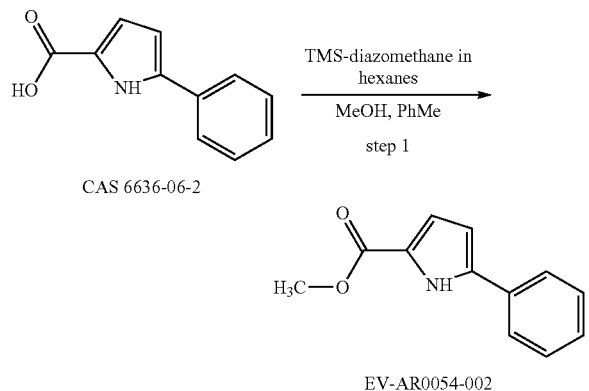

EV-AR0054-002

To a stirred solution of 5-phenyl-1H-pyrrole-2-carboxylic acid (CAS 6636-06-2, 500 mg, 2.67 mmol) in toluene (10 ml) and methanol (3 ml) was added 2M (diazomethyl)(trimethyl)silane in hexane (2 ml) and the mixture was stirred under nitrogen at room temperature for 30 minutes. To the reaction mixture was added acetic acid (1 ml) and the mixture was concentrated in vacuo to afford 530 mg (99%) of methyl 5-phenyl-1H-pyrrole-2-carboxylate (EV-AR0054-002) as a pale yellow powder. LCMS (method D): retention time 1.14 min, M/z=202 (M+1).

3-[(2-{5-[(3R)-3-Aminopiperidine-1-carbonyl]-1-methyl-1H-1,3-benzodiazol-2-yl}-1H-pyrrolo[2,3-b]pyridin-1-yl)methyl]-1-methylcyclobutan-1-ol EV-AU7275-001 (EOAI3455096) I-110 was synthesised according to the procedures described in Scheme 1 via synthesis of ethyl 1-[(3-hydroxy-3-methylcyclobutyl)methyl]-1H-pyrrolo[2,3-b]pyridine-2-carboxylate EV-AU7265-001 described in Scheme 2.2:

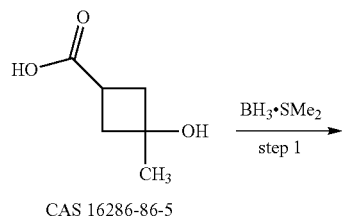

CAS 16286-86-5

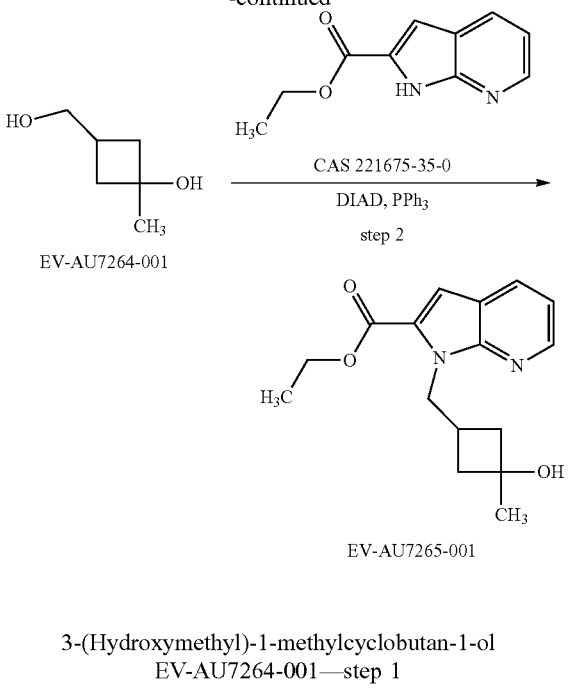

3-(Hydroxymethyl)-1-methylcyclobutan-1-ol EV-AU7264-001—step 1

To a stirred solution of 3-hydroxy-3-methylcyclobutanecarboxylic acid (CAS 16286-86-5, 950 mg, 7.30 mmol) in THF (30 ml) was added BH₃.Me₂S (4.96 ml, 9.93 mmol) drop-wise at −78° C. The reaction was allowed to warm up to room temperature and stirred for 16 h. The reaction was quenched with anhydrous MeOH (20 ml). The resulting mixture was reduced to dryness to obtain 200 mg (23.2%) of 3-(hydroxymethyl)-1-methylcyclobutan-1-ol EV-AU7264-001 as a colourless oil.

1-[(3-Hydroxy-3-methylcyclobutyl)methyl]-1H-pyrrolo[2,3-b]pyridine-2-carboxylate EV-AU7265-001—step 2

To a stirred solution of DIAD (1.10 ml, 5.26 mmol) in dry THF (10 ml) under an atmosphere of nitrogen was added a solution of triphenylphosphine (1.39 g, 5.26 mmol) in THF (10 ml) at −20° C. The reaction mixture was stirred for 30 minutes then a solution of ethyl 1H-pyrrolo[2,3-b]pyridine-2-carboxylate (CAS 221675-35-0, 500 mg, 2.63 mmol) in THF (10 ml) was added. Stirring at −20° C. was continued for a further 30 min. After this period a solution of 3-(hydroxymethyl)-1-methylcyclobutan-1-ol (EV-AU7264-001, 458 mg, 3.94 mmol in THF (5 ml) was added drop-wise at −20° C., the reaction mixture was allowed to warm to room temperature and stirred for 16 h. The mixture was concentrated in vacuo and the residue purified by flash column chromatography (5-80% EtOAc/heptane) to obtain 200 mg (23.2%) of ethyl 1-[(3-hydroxy-3-methylcyclobutyl)methyl]-1H-pyrrolo[2,3-b]pyridine-2-carboxylate EV-AU7265-001 as a pale yellow oil. LCMS (method D): retention time 1.10 min, M/z=289 (M+1).

N-(2-{5-[(3R)-3-Aminopiperidine-1-carbonyl]-1-methyl-1H-1,3-benzodiazol-2-yl}-1-(cyclopropylmethyl)-1H-pyrrolo[2,3-b]pyridin-4-yl)acetamide EV-AT0096-001 (EOAI3447170) I-69 was obtained from Boc-deprotection of tert-butyl N-[(3R)-1-{2-[1-(cyclopropylmethyl)-4-acetamido-1H-pyrrolo[2,3-b]pyridin-2-yl]-1-methyl-1H-1,3-benzodiazole-5-carbonyl}piperidin-3-yl]carbamate EV-AT0094-001 obtained according to Scheme 2.3 starting from tert-butyl N-[(3R)-1-{2-[4-bromo-1-(cyclopropylmethyl)-1H-pyrrolo[2,3-b]pyridin-2-yl]-1-methyl-1H-1,3-benzodiazole-5-carbonyl}piperidin-3-yl]carbamate EV-AT0086-001 which was synthesised according to the procedures described in Scheme 2:
Scheme 2.3
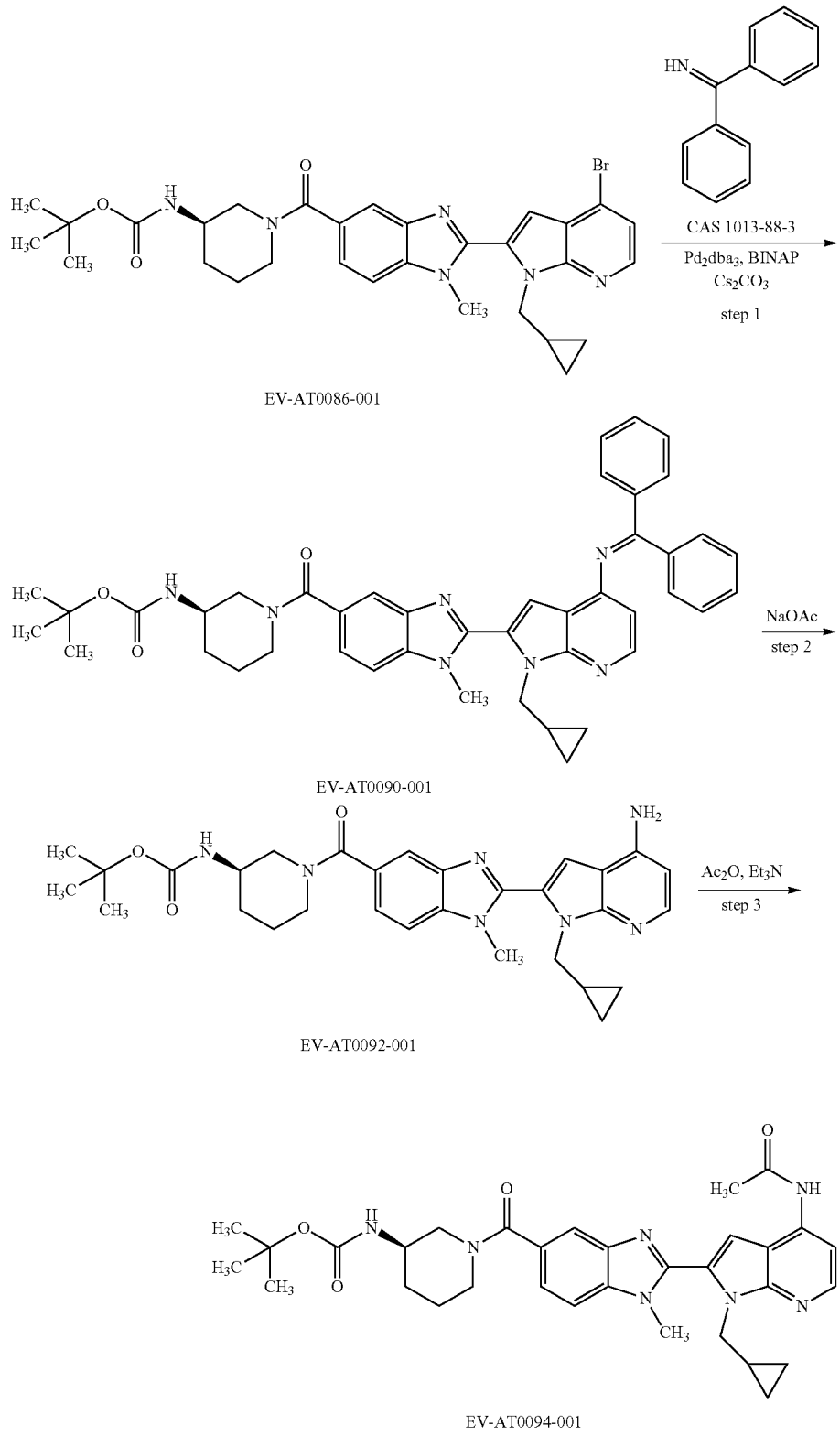

Tert-butyl N-[(3R)-1-{2-[1-(cyclopropylmethyl)-4-[(diphenylmethylidene)amino]-1H-pyrrolo[2,3-b]pyridin-2-yl]-1-methyl-1H-1,3-benzodiazole-5-carbonyl}piperidin-3-yl]carbamate EV-AT0090-001—step 1

A mixture of tert-butyl N-[(3R)-1-{2-[4-bromo-1-(cyclopropylmethyl)-1H-pyrrolo[2,3-b]pyridin-2-yl]-1-methyl-1H-1,3-benzodiazole-5-carbonyl}piperidin-3-yl]carbamate (EV-AT0086-001, 150 mg, 0.24 mmol), 1,1-diphenylmethanimine (53.2 mg, 0.29 mmol), Pd$_2$dba$_3$ (5.6 mg, 0.006 mmol), BINAP (11.4 mg, 0.018 mmol) and Cs$_2$CO$_3$ (111.5 mg, 0.34 mmol) in toluene (4.0 ml) in a sealed tube was stirred at 100° C. for 5 h. The reaction was cooled to room temperature and filtered through Kieselguhr washing with EtOAc. The filtrate was evaporated to dryness, the remaining residue was dissolved in DMSO and purified by preparative HPLC (basic method) to obtain 128 mg (73.2%) of tert-butyl N-[(3R)-1-{2-[1-(cyclopropylmethyl)-4-[(diphenylmethylidene)amino]-1H-pyrrolo[2,3-b]pyridin-2-yl]-1-methyl-1H-1,3-benzodiazole-5-carbonyl}piperidin-3-yl]carbamate EV-AT0090-001 as a yellow solid. LCMS (method D): retention time 1.38 min, M/z=708 (M+1).

Tert-butyl N-[(3R)-1-{2-[4-amino-1-(cyclopropylmethyl)-1H-pyrrolo[2,3-b]pyridin-2-yl]-1-methyl-1H-1,3-benzodiazole-5-carbonyl}piperidin-3-yl]carbamate EV-AT0092-001—step 2

Hydroxylamine hydrochloride (1:1) (58.3 mg, 0.839 mmol) and NaOAc (90 mg, 1.09 mmol) were added to a suspension of tert-butyl N-[(3R)-1-{2-[1-(cyclopropylmethyl)-4-[(diphenylmethylidene)amino]-1H-pyrrolo[2,3-b]pyridin-2-yl]-1-methyl-1H-1,3-benzodiazole-5-carbonyl}piperidin-3-yl]carbamate (EV-AT0090-001, 120 mg, 0.168 mmol) in MeOH (8 ml). The resulting mixture was stirred at room temperature for 16 h. The solvent was removed in vacuo, the remaining residue was dissolved in DMSO and purified by preparative HPLC (basic method) to obtain 86 mg (94.3%) of tert-butyl N-[(3R)-1-{2-[4-amino-1-(cyclopropylmethyl)-1H-pyrrolo[2,3-b]pyridin-2-yl]-1-methyl-1H-1,3-benzodiazole-5-carbonyl}piperidin-3-yl]carbamate EV-AT0092-001 as a white solid. LCMS (method D): retention time 0.95 min, M/z=544 (M+1).

Tert-butyl N-[(3R)-1-{2-[1-(cyclopropylmethyl)-4-acetamido-1H-pyrrolo[2,3-b]pyridin-2-yl]-1-methyl-1H-1,3-benzodiazole-5-carbonyl}piperidin-3-yl]carbamate EV-AT0094-001—step 3

To a solution of tert-butyl N-[(3R)-1-{2-[4-amino-1-(cyclopropylmethyl)-1H-pyrrolo[2,3-b]pyridin-2-yl]-1-methyl-1H-1,3-benzodiazole-5-carbonyl}piperidin-3-yl]carbamate (EV-AT0092-001, 80 mg, 0.15 mmol) in DCM (4 ml) was added acetic anhydride (18 mg, 0.18 mmol) and triethylamine (30 mg, 0.29 mmol) at room temperature and the reaction was stirred at room temperature for 16 h then at 50° C. for 24 h. The solvent was removed in vacuo, the remaining residue was dissolved in DMSO and purified by preparative HPLC (basic method) to obtain 82 mg (95.1%) of tert-butyl N-[(3R)-1-{2-[1-(cyclopropylmethyl)-4-acetamido-1H-pyrrolo[2,3-b]pyridin-2-yl]-1-methyl-1H-1,3-benzodiazole-5-carbonyl}piperidin-3-yl]carbamate EV-AT0094-001 as a white foam. LCMS (method D): retention time 1.09 min, M/z=586 (M+1).

{5-[(3R)-3-aminopiperidine-1-carbonyl]-2-[1-(cyclopropylmethyl)-1H-pyrrolo[2,3-b]pyridin-2-yl]-1-methyl-1H-1,3-benzodiazol-7-yl}methanol EV-AV9647-001 (EOAI3455579) I-128 was synthesised according to the procedures described in Scheme 2 via synthesis of tert-butyl N-[(3R)-1-{2-[1-(cyclopropylmethyl)-1H-pyrrolo[2,3-b]pyridin-2-yl]-7-(hydroxymethyl)-1-methyl-1H-1,3-benzodiazole-5-carbonyl}piperidin-3-yl]carbamate EV-AV9641-002 described in Scheme 2.4.

(3R)-1-{2-[1-(cyclopropylmethyl)-1H-pyrrolo[2,3-b]pyridin-2-yl]-7-methanesulfonyl-1-methyl-1H-1,3-benzodiazole-5-carbonyl}piperidin-3-amine EV-AV9654-001 (EOAI3455786) I-131 was synthesised according to the procedures described in Scheme 2 via synthesis of tert-butyl N-[(3R)-1-{2-[1-(cyclopropylmethyl)-1H-pyrrolo[2,3-b]pyridin-2-yl]-7-methanesulfonyl-1-methyl-1H-1,3-benzodiazole-5-carbonyl}piperidin-3-yl]carbamate EV-AV9652-001 described in Scheme 2.4:

Scheme 2.4

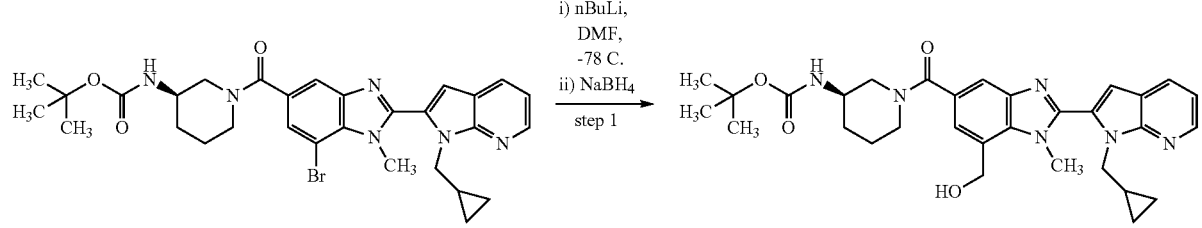

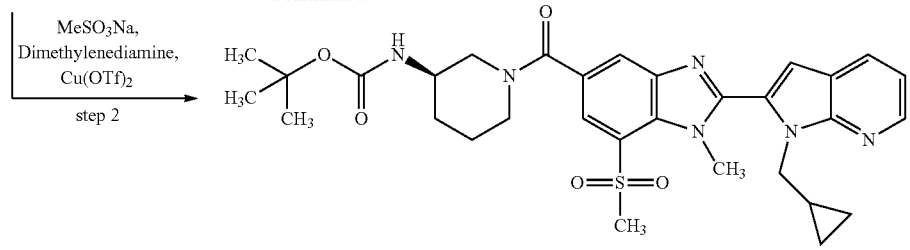

EV-AV9652-001

Tert-butyl N-[(3R)-1-{2-[1-(cyclopropylmethyl)-1H-pyrrolo[2,3-b]pyridin-2-yl]-7-(hydroxymethyl)-1-methyl-1H-1,3-benzodiazole-5-carbonyl}piperidin-3-yl]carbamate EV-AV9641-002—step 1

To a stirred solution of tert-butyl N-[(3R)-1-{7-bromo-2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AV9639-001, 50 mg, 0.08 mmol) in anhydrous THF (5.0 ml) at −78° C. was added drop-wise n-butyllithium (1.6M in hexane, 0.11 ml, 0.17 mmol). The reaction was stirred at −78° C. for 10 minutes and anhydrous DMF (0.01 ml, 0.16 mmol) was added in one portion. The reaction mixture was stirred for 10 minutes at −78° C. and allowed to warm to room temperature over 1 h. The reaction mixture was then cooled to 0° C. and saturated aqueous ammonium chloride solution (1 ml) was added. The biphasic mixture was stirred for 30 minutes and the layers were then separated. The aqueous phase was re-extracted with EtOAc (2×3 ml) and the combined organics were dried over sodium sulfate, filtered and concentrated in vacuo. The crude material was dissolved in methanol (5 ml) at 0° C. and sodium borohydride (6 mg, 0.16 mmol) was added. The reaction was stirred for 16 h at room temperature and quenched by the addition of water (2 ml) and concentrated in vacuo. The residue was partitioned between EtOAc (5 ml) and water (2 ml), the aqueous layer was extracted further with EtOAc (2×2 ml) and the combined organics were dried over sodium sulfate, filtered and concentrated in vacuo. The crude was purified by preparative HPLC (basic method) to obtain 20 mg (43%) of tert-butyl N-[(3R)-1-{2-[1-(cyclopropylmethyl)-1H-pyrrolo[2,3-b]pyridin-2-yl]-7-(hydroxymethyl)-1-methyl-1H-1,3-benzodiazole-5-carbonyl}piperidin-3-yl]carbamate EV-AV9641-002 as an off-white powder. LCMS (method D): retention time 1.10 min, M/z=559 (M+1).

Tert-butyl N-[(3R)-1-{2-[1-(cyclopropylmethyl)-1H-pyrrolo[2,3-b]pyridin-2-yl]-7-methanesulfonyl-1-methyl-1H-1,3-benzodiazole-5-carbonyl}piperidin-3-yl]carbamate EV-AV9652-001—step 2

To a pressure tube was added copper(II) triflate (45 mg, 0.12 mmol), sodium methanesulfinate (25 mg, 0.25 mmol) and N,N'-dimethylethane-1,2-diamine (0.03 ml, 0.26 mmol) and DMSO (2.0 ml) under an atmosphere of nitrogen. The deep blue reaction was stirred at room temperature for 5 minutes and tert-butyl N-[(3R)-1-{7-bromo-2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AV9639-001, 75 mg, 0.12 mmol) was added. The vessel was sealed and heated at 120° C. for 2 h. The cooled reaction was diluted with water (15 ml) and extracted with EtOAc (2×10 ml). The combined organics were dried over sodium sulfate, filtered and concentrated in vacuo. The residue was purified by preparative HPLC (acidic method) to obtain 20 mg (27%) of tert-butyl N-[(3R)-1-{2-[1-(cyclopropylmethyl)-1H-pyrrolo[2,3-b]pyridin-2-yl]-7-methanesulfonyl-1-methyl-1H-1,3-benzodiazole-5-carbonyl}piperidin-3-yl]carbamate EV-AV9652-001 as an off-white powder. LCMS (method D): 1.18 min, M/z=607 (M+1).

Scheme 3

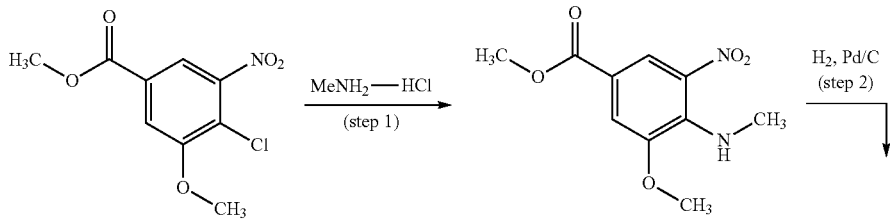

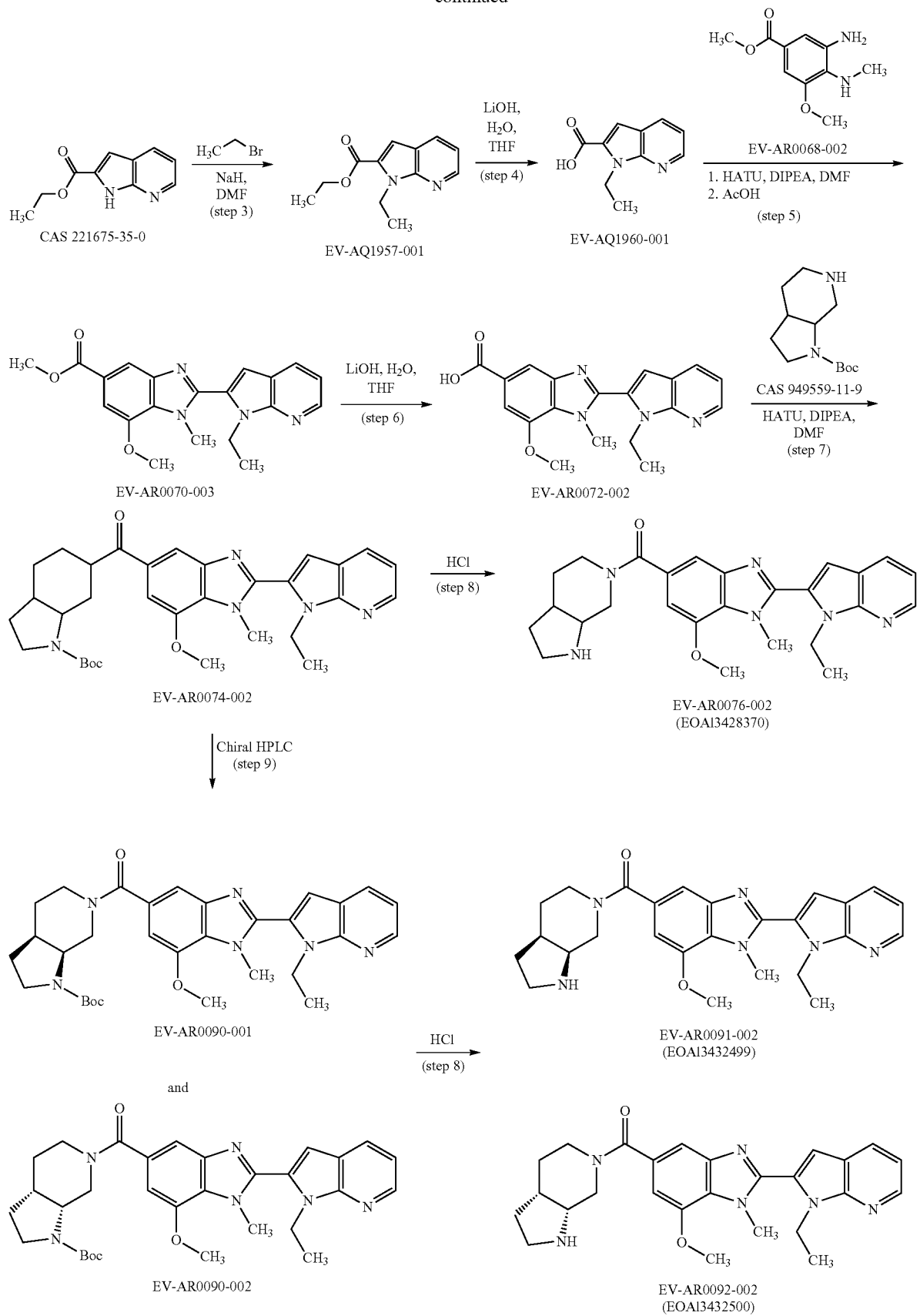

Synthesis of 2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole EV-AR0076-002 (EOAI3428370) I-13

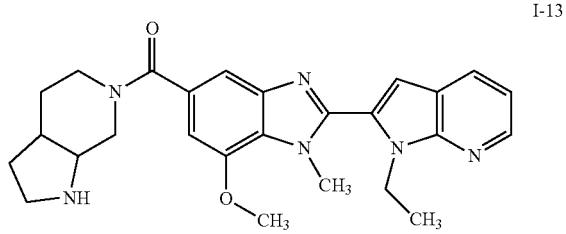 [SMILES: CCn1c(-c2nc3cc(C(=O)N4CCC5CCNC5C4)cc(OC)c3n2C)cc2cccnc21]

I-13

Methyl 3-methoxy-4-(methylamino)-5-nitrobenzoate EV-AR0065-002—step 1

To a stirred solution of methyl 4-chloro-3-methoxy-5-nitrobenzoate (CAS 63603-09-8, 2.00 g, 8.14 mmol) in DMF (10 ml) was added $K_2CO_3$ (99%, 1.37 g, 9.81 mmol). To this solution was added methanamine hydrochloride (1:1) (0.62 g, 9.18 mmol) and the mixture was stirred in a sealed tube under nitrogen at 80° C. for 16 h. The reaction crude was concentrated in vacuo and partitioned between DCM (100 ml) and water (10 ml). The organic layer was washed further with water (2×10 ml) and saturated aqueous sodium chloride (10 ml). The organic layer was dried over sodium sulfate, filtered and concentrated in vacuo to afford an orange powder which was purified by flash column chromatography (15-40% EtOAc/heptane) to obtain 1.49 g (76%) of methyl 3-methoxy-4-(methylamino)-5-nitrobenzoate EV-AR0065-002 as an orange powder. LCMS (method D): retention time 1.13 min, M/z=241 (M+1).

Methyl 3-amino-5-methoxy-4-(methylamino)benzoate EV-AR0068-002—step 2

To a stirred solution of methyl 3-methoxy-4-(methylamino)-5-nitrobenzoate (EV-AR0065-002, 1.49 g, 6.20 mmol) in ethanol (100 ml) under nitrogen was added 10% Pd/C (0.18 g, 0.17 mmol) and the resulting mixture was stirred at room temperature under an atmosphere of hydrogen for 16 h. The reaction mixture was filtered through Kieselguhr and the filter was washed through with methanol (150 ml). The filtrate was concentrated in vacuo to afford 1.21 g (89%) of methyl 3-amino-5-methoxy-4-(methylamino)benzoate EV-AR0068-002 as a pale purple powder. LCMS (method D): retention time 0.63 min, M/z=211 (M+1).

Ethyl 1-ethyl-1H-pyrrolo[2,3-b]pyridine-2-carboxylate EV-AQ1957-001—step 3

Sodium hydride (60%, 59 mg, 1.47 mmol) was added portion wise to a stirred suspension of ethyl 1H-pyrrolo[2,3-b]pyridine-2-carboxylate (CAS 221675-35-0, 200 mg, 1.05 mmol) in DMF (5 ml) at room temperature. The mixture was stirred for 20 minutes then ethyl iodide (197 mg, 1.26 mmol) was added. The reaction mixture was stirred for 20 h. The mixture was partitioned between EtOAc (20 ml) and water (20 ml). The aqueous layer was extracted further with EtOAc (1×20 ml), the combined organics were washed with water (20 ml) and evaporated to dryness. The crude product was purified by flash column chromatography (0-50% EtOAc/heptane) to obtain 135 mg (57.1%) of ethyl 1-ethyl-1H-pyrrolo[2,3-b]pyridine-2-carboxylate EV-AQ1957-001 as a colourless oil. LCMS (method D): retention time 1.18 min, M/z=219 (M+1).

1-Ethyl-1H-pyrrolo[2,3-b]pyridine-2-carboxylic acid EV-AQ1960-001—step 4

To a stirred solution of ethyl 1-ethyl-1H-pyrrolo[2,3-b]pyridine-2-carboxylate (EV-AQ1957-001, 135 mg, 0.62 mmol) in THF (2 ml) was added lithium hydroxide (74 mg, 3.09 mmol) in water (2 ml). The mixture was stirred at 50° C. for 2.5 h, acidified with 1M HCl (3 ml) and extracted with DCM (2×5 ml). The combined organics were washed with water and evaporated to dryness to give 120 mg (99%) of 1-ethyl-1H-pyrrolo[2,3-b]pyridine-2-carboxylic acid EV-AQ1960-001 as a white solid. LCMS (method D): retention time 0.92 min, M/z=191 (M+1).

Methyl 2-{1-ethyl-1H-pyrrolo[2,3-b]pyridin-2-yl}-7-methoxy-1-methyl-1H-1,3-benzodiazole-5-carboxylate EV-AR0070-003—step 5

To a stirred solution of 1-ethyl-1H-pyrrolo[2,3-b]pyridine-2-carboxylic acid (EV-AQ1960-001, 120 mg, 0.63 mmol) in DMF (2 ml) was added DIPEA (116 µl, 0.70 mmol) followed by HATU (236 mg, 0.62 mmol) and the resulting mixture was stirred at room temperature for 15 minutes. Methyl 3-amino-5-methoxy-4-(methylamino)benzoate (EV-AR0068-002, 148 mg, 0.70 mmol) was added and the resulting mixture was stirred at room temperature for 6 h. The reaction mixture was concentrated in vacuo, dissolved in acetic acid (3 ml) and stirred at 70° C. for 16 h. The solvent was removed in vacuo and the remaining material was purified by flash column chromatography (25-40% EtOAc/heptane) to obtain 150 mg (63%) of methyl 2-{1-ethyl-1H-pyrrolo[2,3-b]pyridin-2-yl}-7-methoxy-1-methyl-1H-1,3-benzodiazole-5-carboxylate EV-AR0070-003 as a white powder. LCMS (method D): retention time 1.18 min, M/z=365 (M+1).

2-{1-Ethyl-1H-pyrrolo[2,3-b]pyridin-2-yl}-7-methoxy-1-methyl-1H-1,3-benzodiazole-5-carboxylic acid EV-AR0072-002—step 6

To a stirred solution of methyl 2-{1-ethyl-1H-pyrrolo[2,3-b]pyridin-2-yl}-7-methoxy-1-methyl-1H-1,3-benzodiazole-5-carboxylate (EV-AR0070-003, 150 mg, 0.41 mmol) in THF (3 ml) was added a solution of lithium hydroxide (30 mg, 1.25 mmol) in water (3 ml) and the mixture was stirred at room temperature for 16 h. The reaction mixture was concentrated in vacuo, taken up in water (5 ml) and acidified with 5N HCl (0.5 ml) whilst stirring. The resulting suspension was stirred for 10 minutes then the precipitate was collected by vacuum filtration and dried to obtain 130 mg (89%) of 2-{1-ethyl-1H-pyrrolo[2,3-b]pyridin-2-yl}-7-methoxy-1-methyl-1H-1,3-benzodiazole-5-carboxylic acid EV-AR0072-002 as a white powder. LCMS (method D): retention time 1.03 min, M/z=351 (M+1).

Tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002—step 7

To a stirred solution of 2-{1-ethyl-1H-pyrrolo[2,3-b]pyridin-2-yl}-7-methoxy-1-methyl-1H-1,3-benzodiazole-5-carboxylic acid (EV-AR0072-002, 130 mg, 0.37 mmol) in 2:1 DMSO/MeCN (4.5 ml) were added DIPEA (65 µl, 0.39 mmol) and HATU (148 mg, 0.39 mmol). The resulting mixture was stirred at room temperature for 15 minutes then tert-butyl octahydro-1H-pyrrolo[2,3-c]pyridine-1-carboxylate (CAS 949559-11-9, 88 mg, 0.39 mmol) was added and the mixture was stirred at room temperature for 4 h. The reaction mixture was diluted with 3:2 MeCN/water (1.5 ml) and purified by preparative HPLC (basic method) to obtain 142 mg (81%) of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002 as a white powder. LCMS (method A): retention time 3.41 min, M/z=559 (M+1).

2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole EV-AR0076-002 (EOAI3428370) I-13—step 8

To a stirred solution of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0074-002, 20 mg, 0.04 mmol) in methanol (1 ml) was added 4M HCl in 1,4-dioxane (0.5 ml) and the resulting solution was stirred at room temperature for 4 h. The reaction mixture was concentrated in vacuo and the residue was freeze-dried from water (4 ml) to obtain 13.4 mg (75%) of 2-{1-ethyl-1H-pyrrolo[2,3-b]pyridin-2-yl}-7-methoxy-1-methyl-5-{octahydro-1H-pyrrolo[2,3-c]pyridine-6-carbonyl}-1H-1,3-benzodiazole hydrochloride EV-AR0076-002, I-13, as a yellow solid. LCMS (method A): retention time 1.80 min, M/z=459 (M+1).

Chiral HPLC to obtain tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-001 and tert-butyl (3aS,7aR)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-002—step 9

107 mg of tert-butyl 6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0074-002 were dissolved in ethanol and then purified by chiral HPLC (method E) to obtain 46.6 mg (43.6%) of tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate EV-AR0090-001 (absolute stereochemistry arbitrarily assigned) and 36.8 mg (33.4%) of tert-butyl (3aS,7aR)-6-(2-{1-ethyl-1H-pyrrolo[2,3-b]-pyridin-2-yl}-7-methoxy-1-methyl-1H-1,3-benzodiazole-5-carbonyl)-octahydro-1H-pyrrolo[2,3-c]pyridine-1-carboxylate EV-AR0090-002 (absolute stereochemistry arbitrarily assigned).

EV-AR0090-001 Chiral purity (UV, 254 nm): 100%, retention time: 6.30 min (method F)

EV-AR0090-002 Chiral purity (UV, 254 nm): 97%, retention time: 9.96 min (method F)

5-[(3aS,7aS)-Octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole EV-AR0091-002 (EOAI3432499, absolute stereochemistry arbitrarily assigned) I-3—step 8

Tert-butyl (3aR,7aS)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0090-001, 46 mg, 0.08 mmol) was treated as in step 8, Scheme 2 to obtain 40 mg (97%) of 5-[(3aS,7aS)-octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole hydrochloride EV-AR0091-002, 1-3, as an orange powder. LCMS (method A): retention time 1.83 min, M/z=459 (M+1).

5-[(3aR,7aR)-Octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole EV-AR0092-002 (EOAI3432500, absolute stereochemistry arbitrarily assigned) I-14—step 8

Tert-butyl (3aS,7aR)-6-(2-{1-ethyl-1H-pyrrolo[2,3-b]pyridin-2-yl}-7-methoxy-1-methyl-1H-1,3-benzodiazole-5-carbonyl)-octahydro-1H-pyrrolo[2,3-c]pyridine-1-carboxylate (EV-AR0090-002, 36.8 mg, 0.07 mmol) was treated as in step 8, Scheme 2 to obtain 31 mg (92.7%) of 5-[(3aR,7aR)-octahydro-1H-pyrrolo[2,3-c]pyridine-6-carbonyl]-2-{1-ethyl-1H-pyrrolo[2,3-b]pyridin-2-yl}-7-methoxy-1-methyl-1H-1,3-benzodiazole EV-AR0092-002, 1-14, as an orange powder. LCMS (method A): retention time 1.82 min, M/z=459 (M+1).

Special Cases for Scheme 3

(3S,5S)-5-Fluoro-1-(7-methoxy-1-methyl-2-{1-[(1-methylcyclopropyl)methyl]-1H-pyrrolo[2,3-b]pyridin-2-yl}-1H-1,3-benzodiazole-5-carbonyl)piperidin-3-amine EV-AV3056-001 (EOAI3454078) I-93 was synthesised according to the procedures described in Scheme 2 via synthesis of ethyl 1-[(1-methylcyclopropyl)methyl]-1H-pyrrolo[2,3-b]pyridine-2-carboxylate EV-AU3682-002 described in Scheme 3.1:

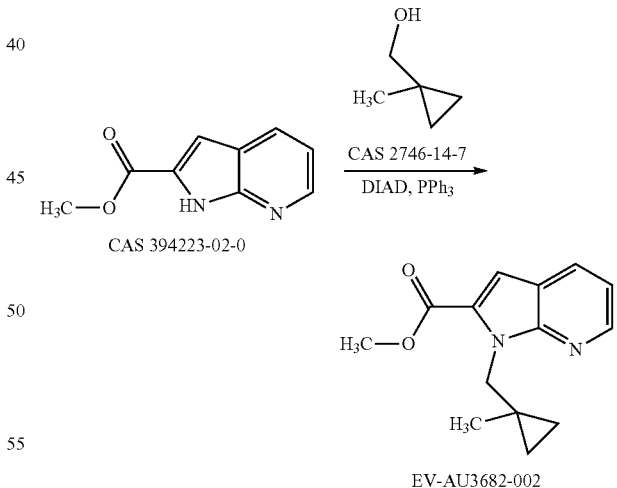

Scheme 3.1

To a solution of DIAD (0.44 ml, 2.10 mmol) in dry THF (5 ml) under nitrogen at −20° C. was added a solution of triphenylphosphine (557 mg, 2.10 mmol) in THF (5 ml) and the reaction mixture was stirred for 30 minutes. To the reaction mixture was added a solution of ethyl 1H-pyrrolo[2,3-b]pyridine-2-carboxylate (CAS 394223-02-0, 200 mg, 1.05 mmol) in THF (7.5 ml) at −20° C. and the reaction mixture was stirred at −20° C. for a further 30 minutes. (1-Methylcyclopropyl)methanol (CAS 2746-14-7, 0.15 ml, 1.58 mmol) was added dropwise at −20° C. and the reaction mixture was allowed to warm to room temperature and stirred for 1 h 15 min. The reaction mixture was concentrated in vacuo and purified by flash column chromatography (0-100% EtOAc) to obtain 240 mg (87%) of ethyl 1-[(1-methylcyclopropyl)methyl]-1H-pyrrolo[2,3-b]pyridine-2-carboxylate EV-AU3682-002 as a yellow gum. LCMS (method D): retention time 1.35 min, M/z=259 (M+1).

(3R)-1-(2-{1-[(1R)-1-cyclopropylethyl]-1H-pyrrolo[2,3-b]pyridin-2-yl}-7-methoxy-1-methyl-1H-1,3-benzodiazole-5-carbonyl)piperidin-3-amine EV-AV3097-001 (EOAI3454812) I-101 and (3R)-1-(2-{1-[(1S)-1-cyclopropylethyl]-1H-pyrrolo[2,3-b]pyridin-2-yl}-7-methoxy-1-methyl-1H-1,3-benzodiazole-5-carbonyl)piperidin-3-amine EV-AV3098-001 (EOAI3454813) I-102 were synthesised according to the procedures described in Scheme 2 via synthesis of ethyl 1-(1-cyclopropylethyl)-1H-pyrrolo[2,3-b]pyridine-2-carboxylate EV-AU3682-001 described in Scheme 3.2:

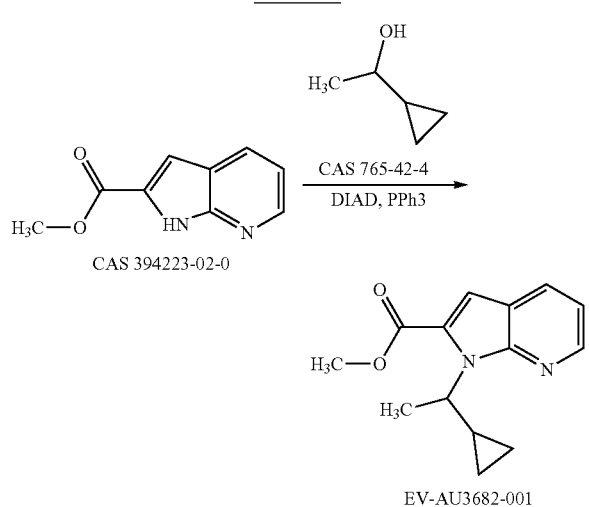

Scheme 3.2

To a solution of DIAD (0.44 ml, 2.1 mmol) in dry THF (5 ml) under nitrogen at −20° C. was added a solution of triphenylphosphine (557.18 mg, 2.1 mmol) in THF (5 ml) and the reaction mixture was stirred for 30 minutes. To the reaction mixture was added a solution of ethyl 1H-pyrrolo[2,3-b]pyridine-2-carboxylate (CAS 394223-02-0, 200 mg, 1.05 mmol) in THF (7.5 ml) at −20° C. and the reaction mixture was stirred at −20° C. for a further 30 minutes. 1-Cyclopropylethan-1-ol (CAS 765-42-4, 0.15 mL, 1.58 mmol) was added dropwise at −20° C. and the reaction mixture was allowed to warm to room temperature and stirred for 1 h 15 minutes. The reaction mixture was concentrated in vacuo and purified by purified using by flash column chromatography (0-100% EtOAc) to obtain 205 mg (75%) of ethyl 1-(1-cyclopropylethyl)-1H-pyrrolo[2,3-b]pyridine-2-carboxylate EV-AU3682-001 as a yellow gum. LCMS (method D): retention time 1.35 min, M/z=259 (M+1).

(3R)-1-{2-[1-(cyclopropylmethyl)-6-ethyl-1H-pyrrolo[2,3-b]pyridin-2-yl]-1-ethyl-7-methoxy-1H-1,3-benzodiazole-5-carbonyl}piperidin-3-amine EV-AV4845-001 (EOAI3454972) I-105 was synthesised according to the procedures described in Scheme 2 via synthesis of methyl 2-[1-(cyclopropyl methyl)-6-ethyl-1H-pyrrolo[2,3-b]pyridin-2-yl]-1-ethyl-7-methoxy-1H-1,3-benzodiazole-5-carboxylate EV-AV4834-002 described in Scheme 3.3:

Scheme 3.3

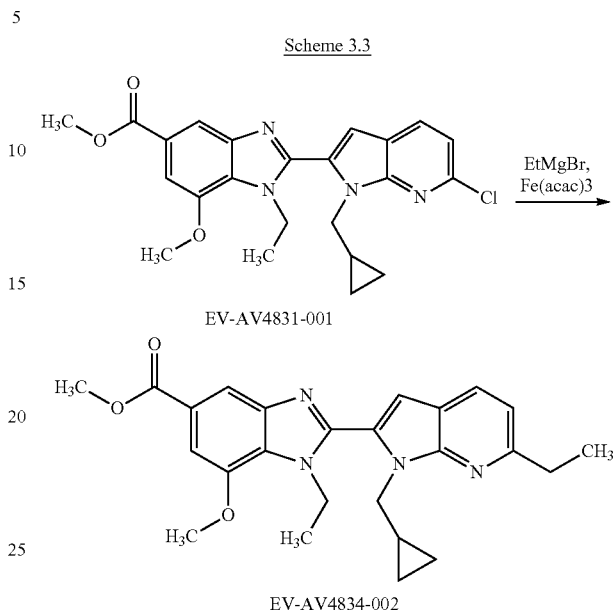

To a solution of methyl 2-[6-chloro-1-(cyclopropylmethyl)-1H-pyrrolo[2,3-b]pyridin-2-yl]-1-ethyl-7-methoxy-1H-1,3-benzodiazole-5-carboxylate EV-AV4831-001 (synthesised according to Scheme 2, 150 mg, 0.31 mmol) in anhydrous THF (5 ml) was added Fe(acac)₃ (6 mg, 0.02 mmol) and NMP (150 µl). A solution of ethylmagnesium bromide (0.9M in THF, 411 µl, 0.37 mmol) was added drop-wise over 1 minute and the reaction mixture stirred at room temperature for 3 h. Further Fe(acac)₃ (6 mg, 0.02 mmol) and ethylmagnesium bromide (0.9M in THF, 411 µl, 0.37 mmol) were added and the reaction mixture was stirred for 16 h at room temperature. The reaction mixture was quenched by the addition of 1M HCl (~1 ml) and extracted with DCM (3×15 ml). The combined organics were washed with brine (20 ml), dried over magnesium sulphate and concentrated in vacuo. The crude residue was purified by preparative HPLC (acidic method) to obtain 81 mg (55%) of methyl 2-[1-(cyclopropyl methyl)-6-ethyl-1H-pyrrolo[2,3-b]pyridin-2-yl]-1-ethyl-7-methoxy-1H-1,3-benzodiazole-5-carboxylate EV-AV4834-002 as a colourless glass. LCMS (method A): retention time 4.59 min, M/z=433 (M+1).

1-{2-[1-(Cyclopropylmethyl)-1H-pyrrolo[2,3-b]pyridin-2-yl]-7-methoxy-1-methyl-1H-1,3-benzodiazole-5-carbonyl}-5-(methylamino)piperidin-3-ol EV-AV4609-001 (EOAI3451154) I-77 was synthesised according to Scheme 3.4:

Scheme 3.4

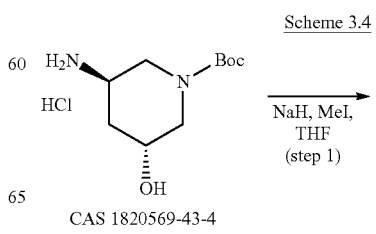

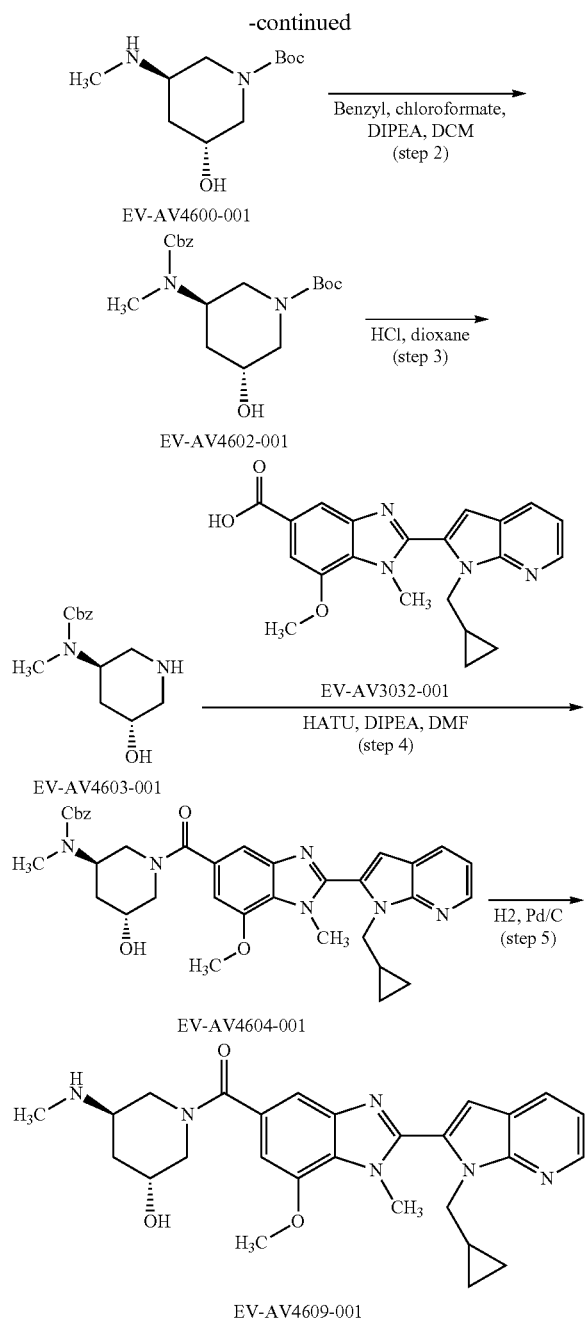

boxylate EV-AV4600-001 as a yellow oil. LCMS (method D): retention time 0.23 min, M/z=231 (M+1).

Rel-tert-butyl (3R,5R)-3-{[(benzyloxy)carbonyl](methyl)amino}-5-hydroxypiperidine-1-carboxylate EV-AV4602-001—step 2 Note: starting materials and products are trans-racemate To a stirred solution of rel-tert-butyl (3R,5R)-3-hydroxy-5-(methylamino)piperidine-1-carboxylate EV-AV4600-001 (91 mg, 0.40 mmol) in DCM (2 ml) was added DIPEA (103 µl, 0.59 mmol) followed by benzyl chloroformate (56 µl, 0.40 mmol). The reaction mixture was stirred for 1.5 h, diluted with DCM (20 ml) and washed with water (15 ml). The organic extract was dried over sodium sulfate, filtered and concentrated in vacuo. The crude residue was purified by flash column chromatography (0-100% EtOAc/heptane) to obtain 58 mg (18%) of rel-tert-butyl (3R,5R)-3-{[(benzyloxy)carbonyl](methyl)amino}-5-hydroxypiperidine-1-carboxylate EV-AV4602-001 as a transparent oil. LCMS (method D): retention time 1.12 min, M/z=387 (M+Na).

Rel-benzyl N-[(3R,5R)-5-hydroxypiperidin-3-yl]-N-methylcarbamate hydrochloride EV-AV4603-001—step 3 Note: starting materials and products are trans-racemate To a solution of rel-tert-butyl (3R,5R)-3-{[(benzyloxy)carbonyl](methyl)amino}-5-hydroxypiperidine-1-carboxylate EV-AV4602-001 (58 mg, 0.16 mmol) in dioxane (1 ml) under nitrogen was added 4M HCl in dioxane (0.16 ml, 0.64 mmol). The mixture was left standing at room temperature for 16 h. To the reaction mixture was added methanol (0.5 ml) and 4M HCl in dioxane (0.16 ml, 0.64 mmol) and the mixture was left standing at room temperature for 4 h. The reaction mixture was then concentrated in vacuo to obtain 59 mg (43%) of rel-benzyl N-[(3R,5R)-5-hydroxypiperidin-3-yl]-N-methylcarbamate hydrochloride EV-AV4603-001 as an off-white solid. LCMS (method D): retention time 0.76 min, M/z=265 (M+1).

Benzyl N-[(3R,5R)-1-{2-[1-(cyclopropylmethyl)-1H-pyrrolo[2,3-b]pyridin-2-yl]-7-methoxy-1-methyl-1H-1,3-benzodiazole-5-carbonyl}-5-hydroxypiperidin-3-yl]-N-methylcarbamate EV-AV4604-001—step 4

To a solution of 2-[1-(cyclopropylmethyl)-1H-pyrrolo[2,3-b]pyridin-2-yl]-7-methoxy-1-methyl-1H-1,3-benzodiazole-5-carboxylic acid EV-AU3032-001 (synthesised according to Scheme 2, 60 mg, 0.16 mmol) in DMF (3 ml) was added DIPEA (31 µl, 0.18 mmol), HATU (67 mg, 0.18 mmol) and rel-benzyl N-[(3R,5R)-5-hydroxypiperidin-3-yl]-N-methylcarbamate hydrochloride EV-AV4603-001 (48 mg, 0.16 mmol) and the reaction mixture was stirred at room temperature for 1 h. The mixture was then partitioned between EtOAc (40 ml) and water (40 ml) and the organic extract was dried over sodium sulfate, filtered and concentrated in vacuo. The crude residue was purified by preparative HPLC (basic method) to obtain 22 mg (22%) of benzyl N-[(3R,5R)-1-{2-[1-(cyclopropylmethyl)-1H-pyrrolo[2,3-b]pyridin-2-yl]-7-methoxy-1-methyl-1H-1,3-benzodiazole-5-carbonyl}-5-hydroxypiperidin-3-yl]-N-methylcarbamate EV-AV4604-001 as an off-white solid. LCMS (method D): retention time 1.17 min, M/z=623 (M+1).

Rel-(3R,5R)-1-{2-[1-(cyclopropylmethyl)-1H-pyrrolo[2,3-b]pyridin-2-yl]-7-methoxy-1-methyl-1H-1,3-benzodiazole-5-carbonyl}-5-(methylamino)piperidin-3-ol hydrochloride EV-AV4609-001, 1-77—step 5 Note: starting materials and products are trans racemate To a stirred solution of rel-benzyl N-[(3R,5R)-1-{2-[1-(cyclopropylmethyl)-1H-pyrrolo[2,3-b]pyridin-2-yl]-7-

Rel-tert-butyl (3R,5R)-3-hydroxy-5-(methylamino)piperidine-1-carboxylate EV-AV4600-001—step 1 Note: starting material and products are all trans-racemate.

To a solution of rel-tert-butyl (3R,5R)-3-amino-5-hydroxypiperidine-1-carboxylate hydrochloride (100 mg, 0.40 mmol) in anhydrous THF (5 ml) at 0° C., was added sodium hydride (60%, 35 mg, 0.87 mmol) and the mixture was stirred at 0° C. for 30 minutes. To the reaction mixture was added methyl iodide (26 µl, 0.41 mmol) and the mixture was allowed to warm to room temperature and left stirring for 16 h. The reaction mixture was partitioned between ethyl acetate (20 ml) and water (20 ml). The aqueous extract was washed with further ethyl acetate (2×15 ml), the combined organic extracts were dried over sodium sulfate, filtered and concentrated in vacuo to obtain 91 mg (quant) of rel-tert-butyl (3R,5R)-3-hydroxy-5-(methylamino)piperidine-1-carmethoxy-1-methyl-1H-1,3-benzodiazole-5-carbonyl}-5-hydroxypiperidin-3-yl]-N-methylcarbamate EV-AV4604-001 (22 mg, 0.04 mmol) in ethanol (1 ml) under nitrogen was added 10% Pd/C (2.3 mg, 0.001 mmol) and the resulting mixture was stirred at room temperature under an atmosphere of hydrogen for 16 h. The reaction mixture was filtered through a glass fibre sinter and the filtrate was then treated with 1.25M HCl in ethanol (0.2 ml). The mixture was left standing at room temperature for 30 minutes, concentrated in vacuo and freeze dried to obtain 10.2 mg (52%) of rel-(3R,5R)-1-{2-[1-(cyclopropylmethyl)-1H-pyrrolo[2,3-b]pyridin-2-yl]-7-methoxy-1-methyl-1H-1,3-benzodiazole-5-carbonyl}-5-(methylamino)piperidin-3-ol hydrochloride EV-AV4609-001, I-77, as an off-white powder. LCMS (method A): retention time 1.93 min, M/z=489 (M+1).

1-{2-[1-(Cyclopropylmethyl)-1H-pyrrolo[2,3-b]pyridin-2-yl]-7-methoxy-1-methyl-1H-1,3-benzodiazole-5-carbonyl}-4-(difluoromethoxy)piperidin-3-amine EV-AV4627-001 (EOAI3452884) I-86 was synthesised according to Scheme 3.5:

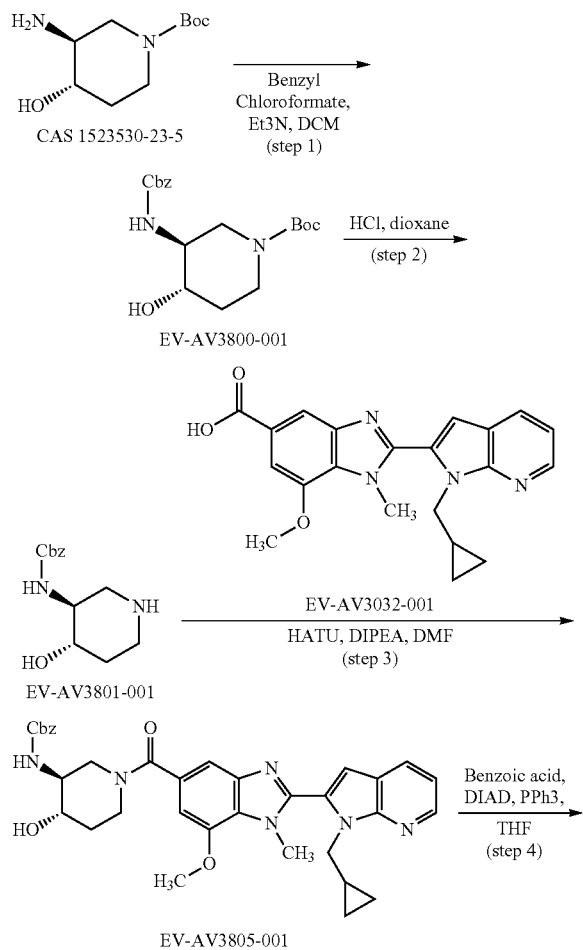

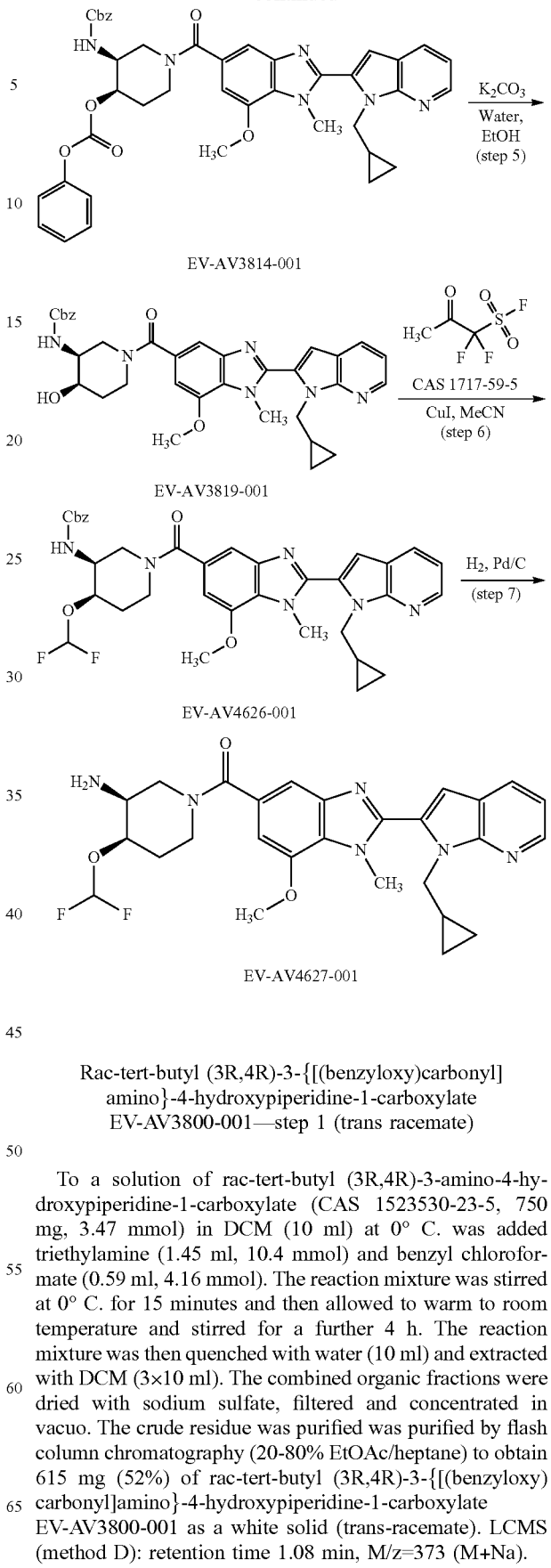

Rac-tert-butyl (3R,4R)-3-{[(benzyloxy)carbonyl]amino}-4-hydroxypiperidine-1-carboxylate EV-AV3800-001—step 1 (trans racemate)

To a solution of rac-tert-butyl (3R,4R)-3-amino-4-hydroxypiperidine-1-carboxylate (CAS 1523530-23-5, 750 mg, 3.47 mmol) in DCM (10 ml) at 0° C. was added triethylamine (1.45 ml, 10.4 mmol) and benzyl chloroformate (0.59 ml, 4.16 mmol). The reaction mixture was stirred at 0° C. for 15 minutes and then allowed to warm to room temperature and stirred for a further 4 h. The reaction mixture was then quenched with water (10 ml) and extracted with DCM (3×10 ml). The combined organic fractions were dried with sodium sulfate, filtered and concentrated in vacuo. The crude residue was purified was purified by flash column chromatography (20-80% EtOAc/heptane) to obtain 615 mg (52%) of rac-tert-butyl (3R,4R)-3-{[(benzyloxy)carbonyl]amino}-4-hydroxypiperidine-1-carboxylate EV-AV3800-001 as a white solid (trans-racemate). LCMS (method D): retention time 1.08 min, M/z=373 (M+Na).

rac-Benzyl N-[(3R,4R)-4-hydroxypiperidin-3-yl] carbamate EV-AV3801-001—step 2 (trans racemate)

Rac-tert-butyl (3R,4R)-3-{[(benzyloxy)carbonyl] amino}-4-hydroxypiperidine-1-carboxylate EV-AV3800-001 (610 mg, 1.74 mmol) was dissolved in dioxane (4M in dioxane, 8.7 ml) and left to stir at room temperature for 1 h. The reaction mixture was concentrated in vacuo to obtain 408 mg (82%) of rac-benzyl N-[(3R,4R)-4-hydroxypiperidin-3-yl]carbamate EV-AV3801-001 as a white solid. LCMS (method D): retention time 0.48 min, M/z=251 (M+1).

rac-Benzyl N-[(3R,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate EV-AV3805-001—step 3 (trans racemate)

To a solution of 2-[1-(cyclopropylmethyl)-1H-pyrrolo[2,3-b]pyridin-2-yl]-7-(difluoromethoxy)-1-methyl-1H-1,3-benzodiazole-5-carboxylic acid EV-AV3032-001 (535 mg, 1.42 mmol) in DMF (5 ml) were added HATU (595 mg, 1.57 mmol) and DIPEA (0.59 ml, 3.56 mmol) and the reaction was left to stir at room temperature for 30 minutes. rac-Benzyl N-[(3R,4R)-4-hydroxypiperidin-3-yl]carbamate EV-AV3801-001 (synthesised according to Scheme 2, 408 mg, 1.42 mmol) was then added and the reaction was left to stir at room temperature for a further 2 h. The reaction mixture was then diluted with EtOAc (10 ml), washed with water (3×10 ml) and saturated aqueous sodium chloride (10 ml). The organic fraction was then dried (sodium sulfate), filtered and concentrated in vacuo to obtain 775 mg (79%) of rac-benzyl N-[(3R,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate EV-AV3805-001 as an orange solid. LCMS (method D): retention time 1.12 min, M/z=609 (M+1).

rac-(3R,4S)-3-{[(Benzyloxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidin-4-yl benzoate EV-AV3814-001—step 4 (cis racemate)

To a solution of triphenylphosphine (411 mg, 1.55 mmol) in THF (1 mol) at 0° C. was added DIAD (325 µl, 1.55 mmol). The reaction mixture was allowed to stir for 5 minutes and rac-benzyl N-[(3R,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate EV-AV3805-001 (675 mg, 1.11 mmol) and benzoic acid (190 mg, 1.55 mmol) were added. The reaction mixture was stirred at room temperature for 3 h and then diluted with EtOAc (15 ml). The mixture was washed with water (10 ml) and saturated aqueous sodium chloride (10 ml). The organic layer was dried over sodium sulfate, filtered and concentrated in vacuo. The crude residue was purified by flash column chromatography (50-100% EtOAc/heptane) to obtain 743 mg (49%) of rac-(3R,4S)-3-{[(benzyloxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidin-4-yl benzoate EV-AV3814-001. LCMS (method D): retention time 1.36 min, M/z=713 (M+1).

rac-Benzyl N-[(3S,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate EV-AV3819-001—step 5 (cis racemate)

To a solution of rac-(3R,4S)-3-{[(benzyloxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidin-4-yl benzoate EV-AV3814-001 (0.74 g, 0.54 mmol) in ethanol (10 ml) and water (5 ml) was added $K_2CO_3$ (0.11 g, 0.81 mmol) and the solution was stirred at room temperature for 3 h. The reaction mixture was then concentrated in vacuo, the crude residue was dissolved in DCM (10 ml) and washed with water (10 ml). The organic layer was then washed with saturated aqueous sodium chloride (10 ml), dried over sodium sulfate, filtered and concentrated in vacuo. The crude was purified by flash column chromatography (0-20% methanol/EtOAc) to obtain 214 mg (64%) of rac-benzyl N-[(3S,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate EV-AV3819-001 as a white solid. LCMS (method D): retention time 1.14 min, M/z=609 (M+1).

rac-benzyl N-[(3R,4S)-1-{2-[1-(cyclopropylmethyl)-1H-pyrrolo[2,3-b]pyridin-2-yl]-7-methoxy-1-methyl-1H-1,3-benzodiazole-5-carbonyl}-4-(difluoromethoxy)piperidin-3-yl]carbamate EV-AV4626-001—step 6 (cis racemate)

To a stirred suspension of rac-benzyl N-[(3S,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate (EV-AV3819-001, 214 mg, 0.35 mmol) and copper(I) iodide (13.4 mg, 0.070 mmol) in acetonitrile (2 ml) in a pressure tube was added 2,2-difluoro-2-(fluorosulfonyl)acetic acid (125 mg, 0.70 mmol). The vessel was sealed and reaction mixture was stirred at 80° C. for 2 h. To the cooled reaction mixture was added 2,2-difluoro-2-(fluorosulfonyl)acetic acid (125 mg, 0.70 mmol), the vessel was sealed and reaction mixture was stirred at 80° C. for a further 2 h. The reaction mixture was again cooled and 2,2-difluoro-2-(fluorosulfonyl)acetic acid (125 mg, 0.70 mmol) was added, the vessel was sealed and reaction mixture was stirred at 80° C. for a further 2 h. The reaction mixture was then concentrated in vacuo and the residue was purified by flash column chromatography (20-100% EtOAc/heptane) followed by preparative HPLC (basic method) to obtain 33 mg (14%) of rac-benzyl N-[(3R,4S)-1-{2-[1-(cyclopropylmethyl)-1H-pyrrolo[2,3-b]pyridin-2-yl]-7-methoxy-1-methyl-1H-1,3-benzodiazole-5-carbonyl}-4-(difluoromethoxy)piperidin-3-yl]carbamate EV-AV4626-001 as a white solid. LCMS (method D): retention time 1.27 min, M/z=659 (M+1).

rac-(3R,4S)-1-{2-[1-(cyclopropylmethyl)-1H-pyrrolo[2,3-b]pyridin-2-yl]-7-methoxy-1-methyl-1H-1,3-benzodiazole-5-carbonyl}-4-(difluoromethoxy) piperidin-3-amine EV-AV4627-001 (EOAI3452884) I-86—step 7 (cis racemate)

To a stirred solution of rac-benzyl N-[(3R,4S)-1-{2-[1-(cyclopropylmethyl)-1H-pyrrolo[2,3-b]pyridin-2-yl]-7-methoxy-1-methyl-1H-1,3-benzodiazole-5-carbonyl}-4-(difluoromethoxy)piperidin-3-yl]carbamate (EV-AV4626-001, 33 mg, 0.05 mmol) in ethanol (2 ml) under nitrogen was added 10% Pd/C (3.2 mg, 0.002 mmol) and the resulting mixture was stirred at room temperature under an atmosphere of hydrogen for 5 h. The reaction mixture was filtered through a glass fibre sinter and the filtrate was then treated with 1.25M HCl in ethanol (0.3 ml). The mixture was left standing at room temperature for 30 minutes, concentrated in vacuo and freeze dried to obtain 28.2 mg (98%) of rac-(3R,4S)-1-{2-[1-(cyclopropylmethyl)-1H-pyrrolo[2,3-b]pyridin-2-yl]-7-methoxy-1-methyl-1H-1,3-benzodiazole-5-carbonyl}-4-(difluoromethoxy)piperidin-3-amine EV-AV4627-001 (I-86) as an off-white powder. LCMS (method A): retention time 2.20 min, M/z=524 (M+1).

1-{2-[1-(Cyclopropylmethyl)-1H-pyrrolo[2,3-b]pyridin-2-yl]-7-methoxy-1-methyl-1H-1,3-benzodiazole-5-carbonyl}-4-fluoropiperidin-3-amine EV-AV3807-001 (EOAI3451007) I-75 was synthesised according to the procedures described in Scheme 3.6:

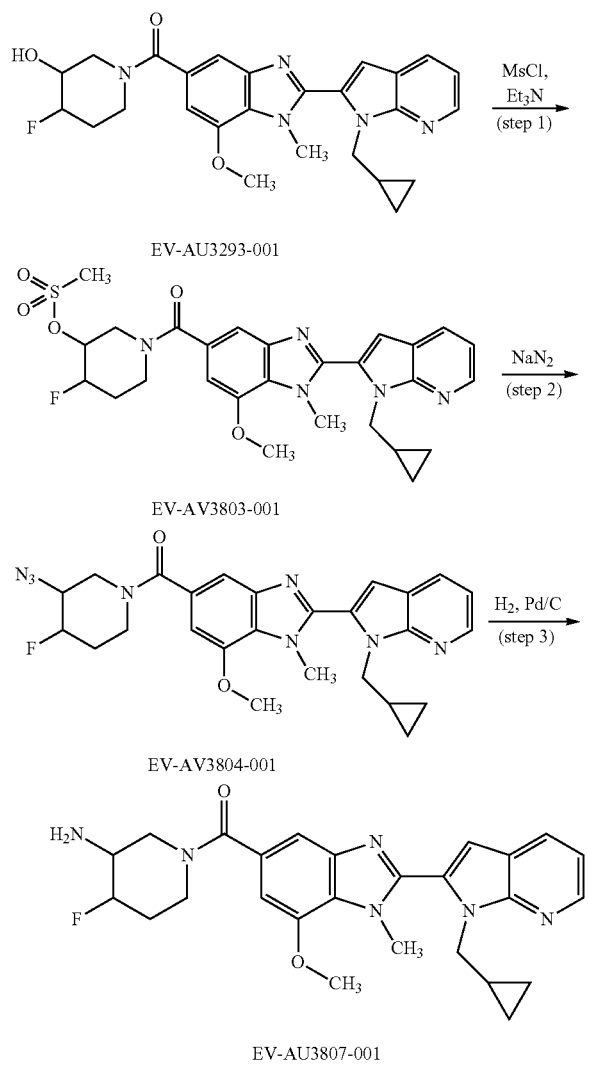

Scheme 4.6

EV-AU3293-001

EV-AV3803-001

EV-AV3804-001

EV-AU3807-001

1-{2-[1-(Cyclopropylmethyl)-1H-pyrrolo[2,3-b]pyridin-2-yl]-7-methoxy-1-methyl-1H-1,3-benzodiazole-5-carbonyl}-4-fluoropiperidin-3-yl methanesulfonate EV-AV3803-001—step 1

To a stirred solution of 1-{2-[1-(cyclopropylmethyl)-1H-pyrrolo[2,3-b]pyridin-2-yl]-7-methoxy-1-methyl-1H-1,3-benzodiazole-5-carbonyl}-4-fluoropiperidin-3-ol (EV-AU3293-001, synthesised according to Scheme 2, 570 mg, 1.19 mmol) in DCM (10 ml) at 0° C. was added triethylamine (0.25 ml, 1.79 mmol) and mesyl chloride (0.11 ml, 1.43 mmol). The reaction was stirred at room temperature for 2 h. Water (5 ml) was added to the mixture and the organic layer was collected, dried over sodium sulfate and concentrated in vacuo to obtain 663 mg (quantitative) of 1-{2-[1-(cyclopropylmethyl)-1H-pyrrolo[2,3-b]pyridin-2-yl]-7-methoxy-1-methyl-1H-1,3-benzodiazole-5-carbonyl}-4-fluoropiperidin-3-yl methanesulfonate EV-AV-3803-001. LCMS (method D): retention time 1.14 min, M/z=556 (M+1).

5-(3-Azido-4-fluoropiperidine-1-carbonyl)-2-[1-(cyclopropylmethyl)-1H-pyrrolo[2,3-b]pyridin-2-yl]-7-methoxy-1-methyl-1H-1,3-benzodiazole EV-AV3804-001—step 2

To a stirred solution of 1-{2-[1-(cyclopropylmethyl)-1H-pyrrolo[2,3-b]pyridin-2-yl]-7-methoxy-1-methyl-1H-1,3-benzodiazole-5-carbonyl}-4-fluoropiperidin-3-yl methanesulfonate (EV-AV-3803-001, 610 mg, 1.10 mmol) in DMSO (10 ml) was added sodium azide (285 mg, 4.39 mmol). The reaction was stirred at 120° C. for 14 h. The reaction was allowed to cool to room temperature then diluted with EtOAc (20 ml), washed with water (3×20 ml) and then saturated aqueous sodium chloride (20 ml). The organic layer was dried over sodium sulfate, filtered and concentrated in vacuo. The crude residue was purified by flash column chromatography (50-100% EtOAc/heptane) to obtain 191 mg (34.6%) of 5-(3-azido-4-fluoropiperidine-1-carbonyl)-2-[1-(cyclopropylmethyl)-1H-pyrrolo[2,3-b]pyridin-2-yl]-7-methoxy-1-methyl-1H-1,3-benzodiazole EV-AU3804-001 as an orange solid. LCMS (method D): retention time 1.19 min, M/z=503 (M+1).

1-{2-[1-(Cyclopropylmethyl)-1H-pyrrolo[2,3-b]pyridin-2-yl]-7-methoxy-1-methyl-1H-1,3-benzodiazole-5-carbonyl}-4-fluoropiperidin-3-amine EV-AV3807-001 (EOAI3451007) I-75—step 3

To a stirred solution of 5-(3-azido-4-fluoropiperidine-1-carbonyl)-2-[1-(cyclopropylmethyl)-1H-pyrrolo[2,3-b]pyridin-2-yl]-7-methoxy-1-methyl-1H-1,3-benzodiazole (EV-AU3804-001, 191 mg, 0.38 mmol) in EtOAc (5 ml) under nitrogen was added 10% Pd/C (81 mg, 0.04 mmol). The mixture was placed under a hydrogen atmosphere and stirred at room temperature for 12 h. The mixture was filtered through a glass fibre filter and the filter washed with methanol. The filtrate was concentrated in vacuo and the residue was purified by preparative HPLC (basic method) to obtain 80 mg (44.2%) of 1-{2-[1-(cyclopropylmethyl)-1H-pyrrolo[2,3-b]pyridin-2-yl]-7-methoxy-1-methyl-1H-1,3-benzodiazole-5-carbonyl}-4-fluoropiperidin-3-amine EV-AV3807-001 (I-75) as a white solid. LCMS (method A): retention time 2.01 min, M/z=477 (M+1).

5-Amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carbonitrile EV-AV4621-001

(EOAI3452077) I-82 was synthesised according to the procedures described in Scheme 3.7 via methyl 1-{2-[1-(cyclopropylmethyl)-1H-pyrrolo[2,3-b]pyridin-2-yl]-7-methoxy-1-methyl-1H-1,3-benzodiazole-5-carbonyl}-5-hydroxypiperidine-3-carboxylate EV-AT8698-001. This was prepared according to the procedure described in Scheme 3, step 7 using methyl 5-hydroxypiperidine-3-carboxylate. Methyl 5-hydroxypiperidine-3-carboxylate was prepared from 1-benzyl 3-methyl 5-hydroxypiperidine-1,3-dicarboxylate (CAS 1095010-45-9) according to the procedure described in Scheme 3, step 7.

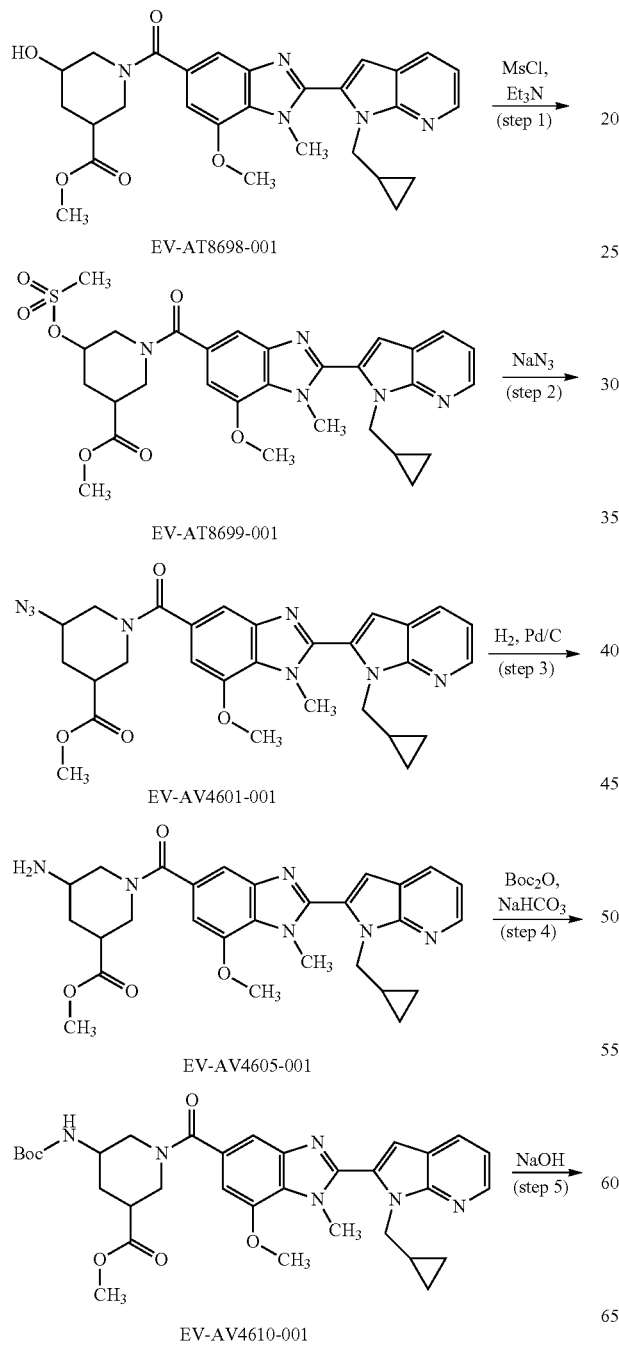

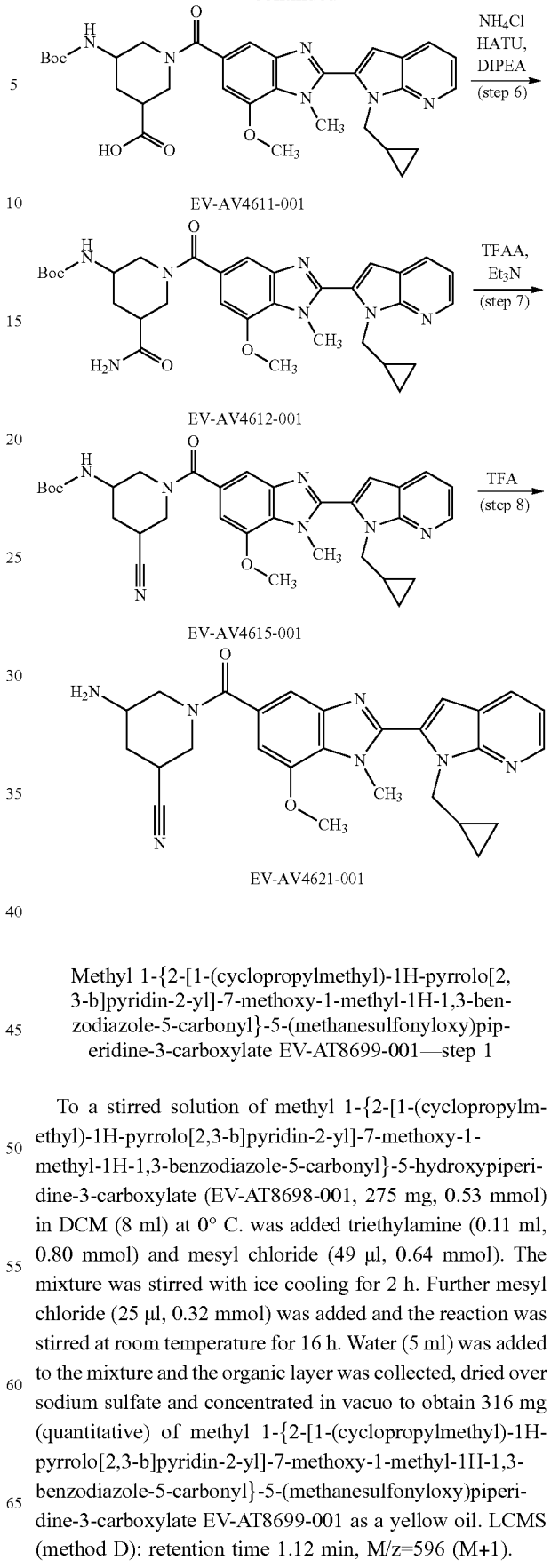

Methyl 1-{2-[1-(cyclopropylmethyl)-1H-pyrrolo[2,3-b]pyridin-2-yl]-7-methoxy-1-methyl-1H-1,3-benzodiazole-5-carbonyl}-5-(methanesulfonyloxy)piperidine-3-carboxylate EV-AT8699-001—step 1

To a stirred solution of methyl 1-{2-[1-(cyclopropylmethyl)-1H-pyrrolo[2,3-b]pyridin-2-yl]-7-methoxy-1-methyl-1H-1,3-benzodiazole-5-carbonyl}-5-hydroxypiperidine-3-carboxylate (EV-AT8698-001, 275 mg, 0.53 mmol) in DCM (8 ml) at 0° C. was added triethylamine (0.11 ml, 0.80 mmol) and mesyl chloride (49 µl, 0.64 mmol). The mixture was stirred with ice cooling for 2 h. Further mesyl chloride (25 µl, 0.32 mmol) was added and the reaction was stirred at room temperature for 16 h. Water (5 ml) was added to the mixture and the organic layer was collected, dried over sodium sulfate and concentrated in vacuo to obtain 316 mg (quantitative) of methyl 1-{2-[1-(cyclopropylmethyl)-1H-pyrrolo[2,3-b]pyridin-2-yl]-7-methoxy-1-methyl-1H-1,3-benzodiazole-5-carbonyl}-5-(methanesulfonyloxy)piperidine-3-carboxylate EV-AT8699-001 as a yellow oil. LCMS (method D): retention time 1.12 min, M/z=596 (M+1).

Methyl 5-azido-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4601-001—step 2

To a stirred solution of methyl 1-{2-[1-(cyclopropylmethyl)-1H-pyrrolo[2,3-b]pyridin-2-yl]-7-methoxy-1-methyl-1H-1,3-benzodiazole-5-carbonyl}-5-(methanesulfonyloxy)piperidine-3-carboxylate (EV-AT8699-001, 316 mg, 0.53 mmol) in DMSO (2 ml) was added sodium azide (86 mg, 1.33 mmol). The resulting mixture was stirred at 90° C. for 16 h. The reaction was allowed to cool to room temperature and partitioned between EtOAc (40 ml) and water (30 ml). The organic layer was dried over sodium sulfate and concentrated in vacuo. The crude residue was purified by flash column chromatography (50-100% EtOAc/heptane) to obtain 141 mg (43.1%) of methyl 5-azido-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4601-001 as an off white solid. LCMS (method D): retention time 1.19 min, M/z=543 (M+1).

Methyl 5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4605-001—step 3

To a stirred solution of methyl 5-azido-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate (EV-AV4601-001, 131 mg, 0.24 mmol) in ethanol under nitrogen was added 10% Pd/C (0.15 g, 0.01 mmol). The reaction mixture was placed under a hydrogen atmosphere and stirred at room temperature for 16 h. The reaction was filtered through a glass fibre filter and the filtrate concentrated in vacuo to obtain 98 mg (46.0%) of methyl 5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4605-001 as a yellow oil. LCMS (method D): retention time 0.92 min, M/z=517 (M+1).

Methyl 5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4610-001—step 4

To a stirred solution of methyl 5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate (EV-AV4605-001, 77 mg, 0.15 mmol) in dioxane (1 ml) was added saturated aqueous sodium hydrogen carbonate (1 ml) and boc anhydride (39 mg, 0.18 mmol). The resulting mixture was stirred at room temperature for 1 h. The mixture was partitioned between EtOAc (20 ml) and water (20 ml). The aqueous layer was extracted with EtOAc (15 ml) and the combined organics were dried over sodium sulfate and concentrated in vacuo. The crude residue was purified by flash column chromatography (0-100% EtOAc/heptane) to obtain 62 mg (63.2%) of methyl 5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate EV-AV4610-001 as an off white powder. LCMS (method D): retention time 1.20 min, M/z=617 (M+1).

5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylic acid EV-AV4611-001—step 5

To a stirred solution of methyl 5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylate (EV-AV4610-001, 62 mg, 0.10 mmol) in methanol (1 ml) was added 1M aqueous sodium hydroxide (0.5 ml). The resulting mixture was stirred at room temperature for 16 h. The mixture was concentrated in vacuo to remove the methanol. The resulting aqueous solution was acidified using 1M aqueous hydrochloric acid to pH ~4-5 until a precipitate was formed. The solid was filtered off and dried under vacuum to obtain 58 mg (89.4%) of 5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylic acid EV-AV4611-001 as an off white powder. LCMS (method D): retention time 1.13 min, M/z=603 (M+1).

Tert-butyl N-(5-carbamoyl-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl)carbamate EV-AV4612-001—step 6

To a stirred solution of 5-{[(tert-butoxy)carbonyl]amino}-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carboxylic acid (EV-AV4611-001, 58 mg, 0.96 mmol) in DMF (1 ml) was added DIPEA (34 µl, 0.19 mmol), HATU (46 mg, 0.12 mmol) and ammonium chloride (10 mg, 0.19 mmol). The resulting mixture was stirred at room temperature for 1 h. The mixture was partitioned between EtOAc (40 ml) and water (40 ml). The aqueous layer was further extracted with EtOAc (40 ml) and the combined organics were dried over sodium sulfate and concentrated in vacuo to obtain 65 mg (97.7%) of tert-butyl N-(5-carbamoyl-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl)carbamate EV-AV4612-001 as a yellow oil. LCMS (method D): retention time 1.09 min, M/z=602 (M+1).

Tert-butyl N-(5-cyano-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl)carbamate EV-AV4615-004—step 7

To a stirred solution of tert-butyl N-(5-carbamoyl-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl)carbamate (EV-AV4612-001, 65 mg, 0.10 mmol) in anhydrous dioxane (1 ml) was added triethylamine (44.3 µl, 0.32 mmol) and trifluoroacetic anhydride (30 µl, 0.22 mmol). The reaction was stirred at room temperature for 5 h. The mixture was re-treated with triethylamine (44.3 µl, 0.32 mmol) and trifluoroacetic anhydride (30 µl, 0.22 mmol) and stirred at room temperature for 16 h. The mixture was re-treated with triethylamine (44.3 µl, 0.32 mmol) and trifluoroacetic anhydride (30 µl, 0.22 mmol) and stirred at room temperature for 2 h. The mixture was re-treated with (44.3 µl, 0.32 mmol) and trifluoroacetic anhydride (30 µl, 0.22 mmol) and stirred for 2 h. The mixture was re-treated with triethylamine (44.3 μl, 0.32 mmol) and trifluoroacetic anhydride (30 μl, 0.22 mmol) and stirred at room temperature for 2 h. The mixture was partitioned between EtOAc (20 ml) and saturated aqueous ammonium chloride (20 ml). The aqueous layer was extracted with EtOAc (20 ml) and the combined organics were dried over sodium sulfate and concentrated in vacuo. The crude material was purified by flash column chromatography (0-100% EtOAc/heptane) to obtain 2 batches of product which were separately purified by preparative HPLC (basic method) to obtain 9 mg (14.3%) of tert-butyl N-[(3R,5S)-5-cyano-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl]carbamate EV-AV4615-003 as an off white powder. Arbitrarily assigned as racemic cis-diastereomer. LCMS (method D): retention time 1.21 min, M/z=584 (M+1). 11 mg (17.5%) of tert-butyl N-[(3R,5S)-5-cyano-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl]carbamate EV-AV4615-004 were also obtained as an off white powder. Arbitrarily assigned as a racemic trans-diastereomer. LCMS (method D): retention time 1.19 min, M/z=584 (M+1).

5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carbonitrile EV-AV4621-001 (EOAI3452077) I-82—step 8

A solution of tert-butyl N-(5-cyano-1-{2-[1-(cyclopropylmethyl)-1H-pyrrolo[2,3-b]pyridin-2-yl]-7-methoxy-1-methyl-1H-1,3-benzodiazole-5-carbonyl}piperidin-3-yl)carbamate (EV-AV4615-004, 11 mg, 0.02 mmol) in 10% trifluoroacetic acid in DCM (1 ml) was left standing at room temperature for 1 h. The reaction was concentrated in vacuo and the residue was freeze-dried from 1:1 acetonitrile:water (4 ml) to obtain 11.6 mg (quantitative) of 5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidine-3-carbonitrile trifluoroacetic acid EV-AV4621-001 (I-82) as a white powder. LCMS (method A): retention time 2.08 min, M/z=484 (M+1).

(1R,4R,7R)-2-{2-[1-(cyclopropylmethyl)-1H-pyrrolo[2,3-b]pyridin-2-yl]-7-methoxy-1-{[3-($^2$H$_3$)methoxy-3-methylcyclobutyl]methyl}-1H-1,3-benzodiazole-5-carbonyl}-2-azabicyclo[2.2.1]heptan-7-amine EV-AY5000-002 (EOAI3462946) I-238 was obtained according to the procedures described in Scheme 3 via deuteromethylation of methyl 2-[1-(cyclopropylmethyl)-1H-pyrrolo[2,3-b]pyridin-2-yl]-7-methoxy-1-{[(1r,3s)-3-hydroxy-3-ethylcyclobutyl]methyl}-1H-1,3-benzodiazole-5-carboxylate EV-AX8640-001 as described in Scheme 3.8:

Scheme 3.8

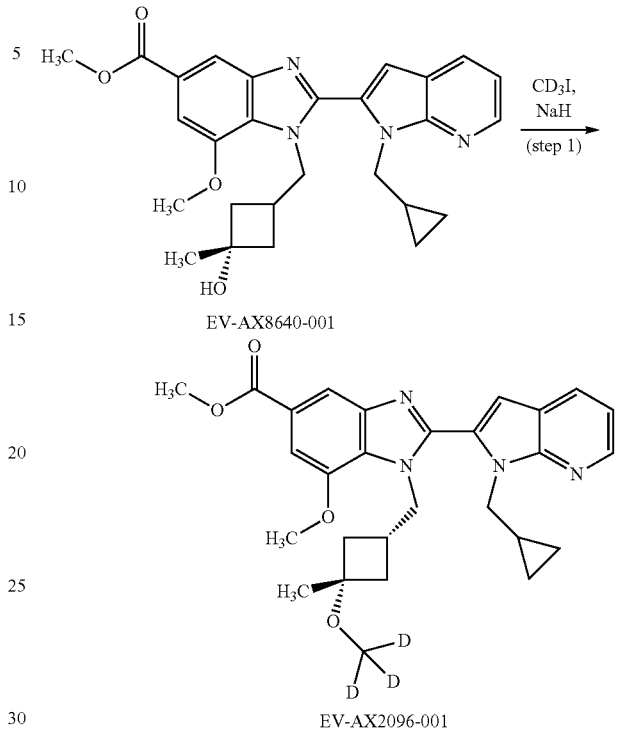

EV-AX8640-001

CD$_3$I, NaH
(step 1)

EV-AX2096-001

Methyl 2-[1-(cyclopropylmethyl)-1H-pyrrolo[2,3-b]pyridin-2-yl]-7-methoxy-1-{[(1r,3s)-3-($^2$H$_3$)methoxy-3-methylcyclobutyl]methyl}-1H-1,3-benzodiazole-5-carboxylate EV-AX2096-001—step 1

To a stirred solution of methyl 2-[1-(cyclopropylmethyl)-1H-pyrrolo[2,3-b]pyridin-2-yl]-7-methoxy-1-{[(1r,3s)-3-hydroxy-3-methylcyclobutyl]methyl}-1H-1,3-benzodiazole-5-carboxylate (EV-AX8640-001, 85%, 250 mg, 0.45 mmol) in DMF (2.0 ml) was added sodium hydride (60%, 36 mg, 0.90 mmol). The resulting mixture was stirred at room temperature for 10 minutes and iodo($^2$H$_3$)methane (CAS 865-50-9, 84 μl, 1.34 mmol) was added. The reaction mixture was stirred at room temperature for 4.5 h and concentrated in vacuo. The residue was partitioned between EtOAc (20 ml) and water (15 ml). The aqueous layer was re-extracted with EtOAc (2×10 ml) and the combined organics were washed with water (10 ml), saturated aqueous sodium chloride (10 ml), dried over sodium sulfate and concentrated in vacuo. The resulting material was purified by flash column chromatography (0-50% EtOAc/heptane) to obtain 184 mg (75%) of methyl 2-[1-(cyclopropylmethyl)-1H-pyrrolo[2,3-b]pyridin-2-yl]-7-methoxy-1-{[(1r,3s)-3-(2H-3-)methoxy-3-methylcyclobutyl]methyl}-1H-1,3-benzodiazole-5-carboxylate EV-AX2096-001 as a pale yellow solid. LCMS (method D): retention time 1.43 min, M/z=492 (M+1).

(1R,4R,7R)-2-{2-[6-(Difluoromethyl)-1-ethyl-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AW5368-001 (EOAI3460286) II-189 was synthesised according to the procedures described in Scheme 3 via synthesis of methyl 2-[6-(difluoromethyl)-1-ethyl-1H-pyrrolo[2,3-b]pyridin-2-yl]-7-methoxy-1-methyl-1H-1,3-benzodiazole-5-carboxylate EV-AW5361-001 described in Scheme 3.9:

-1-methyl-1H-1,3-benzodiazole-5-carboxylate EV-AW5353-002 as a white solid. LCMS (method D): retention time 1.34 min, M/z=391 (M+1).

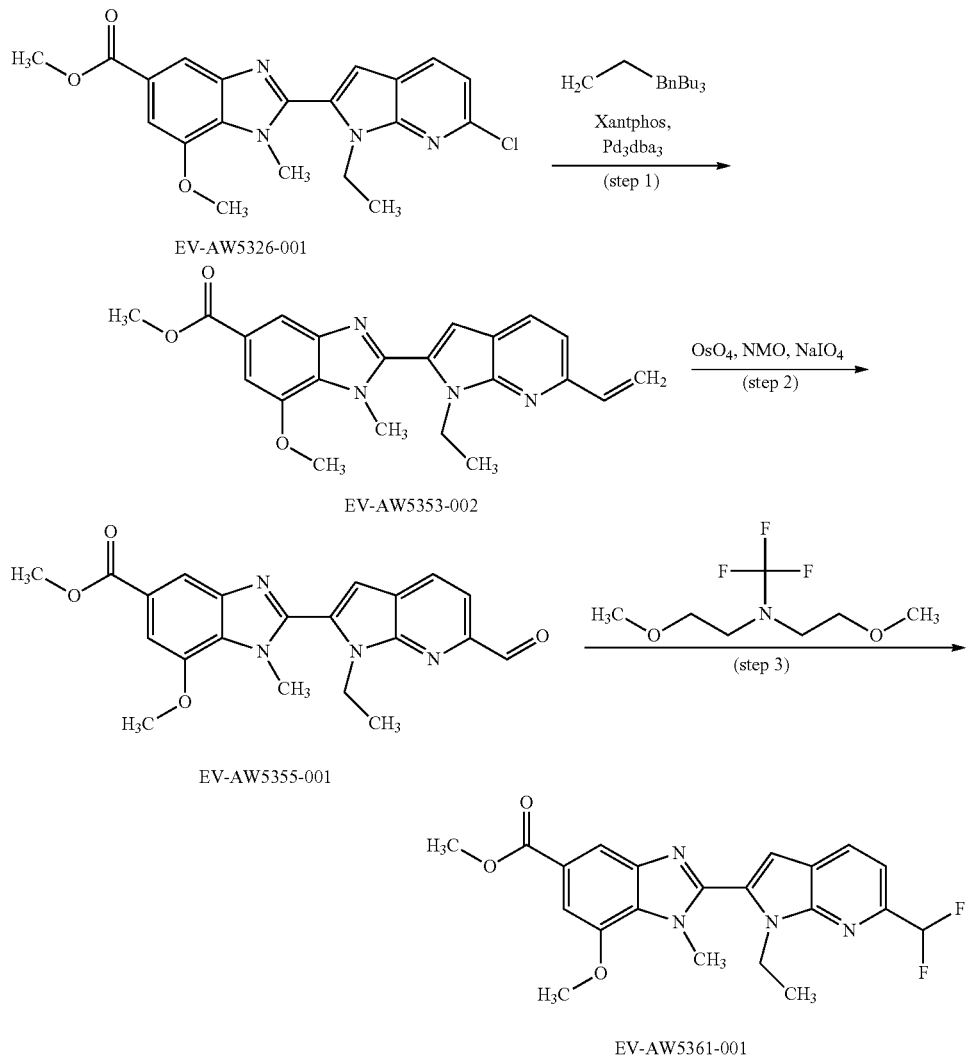

Scheme 3.9

Methyl 2-{6-ethenyl-1-ethyl-1H-pyrrolo[2,3-b]pyridin-2-yl}-7-methoxy-1-methyl-1H-1,3-benzodiazole-5-carboxylate EV-AW5353-002—step 1

To a solution of methyl 2-{6-chloro-1-ethyl-1H-pyrrolo[2,3-b]pyridin-2-yl}-7-methoxy-1-methyl-1H-1,3-benzodiazole-5-carboxylate (EV-AW5326-001, 500 mg, 1.25 mmol) in dioxane (10 ml) was added tributyl(ethenyl)stannane (477 mg, 1.50 mmol). The reaction mixture was purged with nitrogen for 15 min then Xantphos (54 mg, 0.04 mmol) and Pd$_2$dba$_3$ (29 mg, 0.03 mmol) were added. The resulting mixture was stirred at 110° C. for 16 h. The reaction was concentrated in vacuo and the crude residue was purified by flash column chromatography (0-50% EtOAc/heptane) to obtain 340 mg (66%) of methyl 2-{6-ethenyl-1-ethyl-1H-pyrrolo[2,3-b]pyridine-2-yl}-7-methoxy

Methyl 2-{-ethyl-6-formyl-1H-pyrrolo[2,3-b]pyridin-2-yl}-7-methoxy-1-methyl-1H-1,3-benzodiazole-5-carboxylate EV-AW5355-001—step 2

To a solution of methyl 2-{6-ethenyl-1-ethyl-1H-pyrrolo[2,3-b]pyridin-2-yl}-7-methoxy-1-methyl-1H-1,3-benzodiazole-5-carboxylate (EV-AW5353-002, 89%, 470 mg, 1.07 mmol) in THF:water (2:1, 9 ml) were added t-butanol (0.10 ml), 4-methylmorpholine 4-oxide (188 mg, 1.61 mmol) and OsO$_4$ (0.10 ml in water, 0.02 mmol). The reaction was stirred at room temperature for 5 h, NaIO$_4$ (687 mg, 3.20 mmol) was added and stirring at room temperature was continued for 16 h. The reaction mixture was filtered through a pad of celite and washed with EtOAc. The filtrate was diluted with water (20 ml) and extracted with EtOAc (3×20 ml). The combined organic extracts were washed with saturated aqueous sodium chloride, dried over sodium sulfate, filtered and concentrated in vacuo. The crude residue was purified by flash column chromatography (0-40% EtOAc/heptane) to obtain 270 mg (62%) of methyl 2-{1-ethyl-6-formyl-1H-pyrrolo[2,3-b]pyridin-2-yl}-7-methoxy-1-methyl-1H-1,3-benzodiazole-5-carboxylate EV-AW5355-001 as a yellow solid. LCMS (method D): retention time 1.24 min, M/z=393 (M+1).

Methyl 2-[6-(difluoromethyl)-1-ethyl-1H-pyrrolo[2,3-b]pyridin-2-yl]-7-methoxy-1-methyl-1H-1,3-benzodiazole-5-carboxylate EV-AW5361-001—step 3

To a solution of methyl 2-{1-ethyl-6-formyl-1H-pyrrolo[2,3-b]pyridin-2-yl}-7-methoxy-1-methyl-1H-1,3-benzodiazole-5-carboxylate (200 mg, 0.50 mmol) in DCM (10 ml) was added 2-methoxy-N-(2-methoxyethyl)-N-(trifluorolambda-4-sulfanyl)ethanamine (CAS, 202289-38-1, 0.45 ml, 1.24 mmol) at room temperature. The reaction mixture was stirred at 45° C. for 16 h, cooled down to room temperature and poured onto ice/water. The aqueous layer was neutralised with saturated sodium bicarbonate and extracted with DCM (3×20 ml). The combined organic extracts were dried over sodium sulfate, filtered and concentrated in vacuo. The crude residue was purified by flash column chromatography (0-40% EtOAc/heptane) to obtain 105 mg (49%) of methyl 2-[6-(difluoromethyl)-1-ethyl-1H-pyrrolo[2,3-b]pyridin-2-yl]-7-methoxy-1-methyl-1H-1,3-benzodiazole-5-carboxylate EV-AW5361-001 as a white solid. LCMS (method D): retention time 1.33 min, M/z=415 (M+1).

(1R,4R,7R)-2-{2-[6-(difluoromethoxy)-1-ethyl-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AW9564-001 (EOAI3460927) I-200 was synthesised according to the procedures described in Scheme 3 via synthesis of methyl 6-(difluoromethoxy)-1-ethyl-1H-pyrrolo[2,3-b]pyridine-2-carboxylate EV-AW9553-001 described in Scheme 3.10:

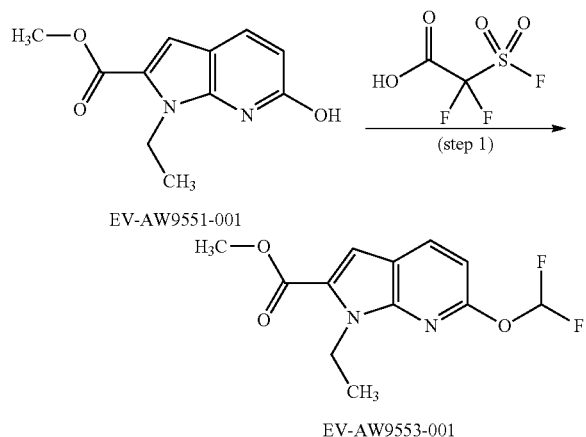

2,2-Difluoro-2-(fluorosulfonyl)acetic acid (CAS 1717-59-5, 912 mg, 5.12 mmol) was added to a stirred suspension of benzyl N-[(3S,4R)-1-{2-[1-(cyclopropylmethyl)-1H-pyrrolo[2,3-b]pyridin-2-yl]-7-methoxy-1-methyl-1H-1,3-benzodiazole-5-carbonyl}-4-hydroxypiperidin-3-yl]carbamate (EV-AW9553-001 synthesised according to Scheme 3.18, 451 mg, 2.05 mmol) and sodium sulfate (291 mg, 2.05 mmol) in acetonitrile (10 ml). The resulting mixture was stirred at room temperature for 16 h. The reaction crude was concentrated in vacuo and the residue was purified by flash column chromatography (0-60% EtOAc/heptane) to obtain 327 mg (59%) of methyl 6-(difluoromethoxy)-1-ethyl-1H-pyrrolo[2,3-b]pyridine-2-carboxylate EV-AW9553-001 as an off-white solid. LCMS (method D): retention time 1.30 min, M/z=271 (M+1).

(1R,4R,7R)-2-{2-[7-(Cyclopropylmethyl)-2-methyl-7H-pyrrolo[2,3-d]pyrimidin-6-yl]-7-methoxy-1-methyl-1H-1,3-benzodiazole-5-carbonyl}-2-azabicyclo[2.2.1]heptan-7-amine EV-AX1665-002 (EOAI3460929) I-202 was synthesised according to the procedures described in Scheme 3 via synthesis of methyl 2-[7-(cyclopropylmethyl)-2-methyl-7H-pyrrolo[2,3-d]pyrimidin-6-yl]-7-methoxy-1-methyl-1H-1,3-benzodiazole-5-carboxylate EV-AX1646-002 described in Scheme 3.11:

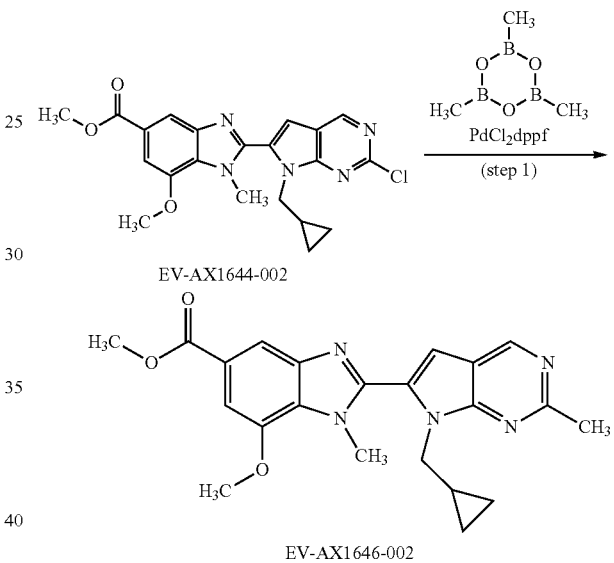

To a solution of methyl 2-[2-chloro-7-(cyclopropylmethyl)-7H-pyrrolo[2,3-d]pyrimidin-6-yl]-7-methoxy-1-methyl-1H-1,3-benzodiazole-5-carboxylate (EV-AX1644-002, 134 mg, 0.31 mmol) in DME (5 ml) were added potassium carbonate (87 mg, 0.63 mmol), PdCl₂dppf (26 mg, 0.03 mmol) and trimethylboroxin (3.5M in THF, 0.36 ml, 1.26 mmol). The reaction mixture was stirred at 100° C. for 15 h. The solvent was removed in vacuo and the crude residue was purified by flash column chromatography (0-100% EtOAc/heptane then 0-40% methanol/EtOAc) to obtain 94 mg (70%) of methyl 2-[7-(cyclopropylmethyl)-2-methyl-7H-pyrrolo[2,3-d]pyrimidin-6-yl]-7-methoxy-1-methyl-1H-1,3-benzodiazole-5-carboxylate EV-AX1646-002 as an off-white solid. LCMS (method D): retention time 1.05 min, M/z=406 (M+1).

2-(2-{5-[(1R,4R,7R)-7-Amino-2-azabicyclo[2.2.1]heptane-2-carbonyl]-7-methoxy-1-methyl-1H-1,3-benzodiazol-2-yl}-1-(cyclopropylmethyl)-1H-pyrrolo[2,3-b]pyridin-6-yl)propan-2-ol EV-AW6283-001 (EOAI3461372) I-210 was synthesised according to the procedures described in Scheme 3 via synthesis of methyl 1-(cyclopropylmethyl)-6-(2-hydroxypropan-2-yl)-1H-pyrrolo[2,3-b]pyridine-2-carboxylate EV-AW6273-002 described in Scheme 3.12:

Scheme 3.12

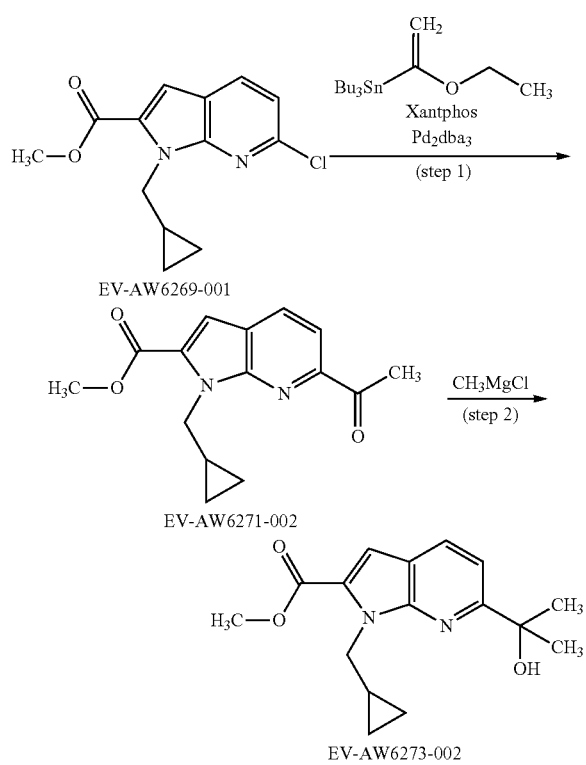

Methyl 6-acetyl-1-(cyclopropylmethyl)-1H-pyrrolo[2,3-b]pyridine-2-carboxylate EV-AW6271-002—step 1

To a solution of methyl 6-chloro-1-(cyclopropylmethyl)-1H-pyrrolo[2,3-b]pyridine-2-carboxylate (EV-AW6269-001, 90%, 1.16 g, 3.93 mmol) in anhydrous dioxane (3 ml) were added tributyl(1-ethoxyethenyl)stannane (1.59 ml, 4.71 mmol), Xantphos (0.17 g, 0.29 mmol) and Pd₂dba₃ (0.09 g, 0.10 mmol). The reaction mixture was stirred at 90° C. for 17 h. The solvent was removed in vacuo and 1M HCl (50 ml) and DCM (50 ml) were added to the residue. The biphasic mixture was stirred for 20 minutes then the organic layer was separated and concentrated in vacuo. The crude residue was purified by flash column chromatography (0-10% EtOAc/heptane) to obtain 0.512 g (47%) of methyl 6-acetyl-1-(cyclopropylmethyl)-1H-pyrrolo[2,3-b]pyridine-2-carboxylate EV-AW6271-002 as an off-white solid. LCMS (method D): retention time 1.40 min, M/z=273 (M+1).

Methyl 1-(cyclopropylmethyl)-6-(2-hydroxypropan-2-yl)-1H-pyrrolo[2,3-b]pyridine-2-carboxylate EV-AW6273-002—step 2

Methylmagnesium chloride (3M in THF, 642 μl) was added drop-wise to a stirred solution of methyl 6-acetyl-1-(cyclopropylmethyl)-1H-pyrrolo[2,3-b]pyridine-2-carboxylate (EV-AW6271-002, 510 mg, 1.84 mmol) in anhydrous THF (5 ml) at −78° C. The reaction was stirred at −78° C. for 2.5 h. Further methylmagnesium chloride (3M in THF, 61 μl) was added at −78° C. and stirring was continued for 30 minutes. The reaction was quenched with water (20 ml) and THF was removed in vacuo. 1M HCl was added to the aqueous layer until pH 3. The aqueous layer was extracted with EtOAc (2×30 ml). The combined extracts dried over sodium sulfate, filtered and concentrated in vacuo. The crude residue was purified by flash column chromatography (0-35% EtOAc/heptane) to obtain 410 mg (76%) of methyl 1-(cyclopropylmethyl)-6-(2-hydroxypropan-2-yl)-1H-pyrrolo[2,3-b]pyridine-2-carboxylate EV-AW6273-002 as an off-white solid. LCMS (method D): retention time 1.23 min, M/z=289 (M+1).

(1R,4R,7R)-2-{2-[1-(cyclopropylmethyl)-1H-pyrrolo[2,3-b]pyridin-2-yl]-1-(2-methanesulfonylethyl)-7-methoxy-1H-1,3-benzodiazole-5-carbonyl}-2-azabicyclo[2.2.1]heptan-7-amine EV-AY0021-001 (EOAI3461556) I-214 was synthesised according to the procedures described in Scheme 3 via synthesis of methyl 2-[1-(cyclopropylmethyl)-1H-pyrrolo[2,3-b]pyridin-2-yl]-1-(2-methanesulfonylethyl)-7-methoxy-1H-1,3-benzodiazole-5-carboxylate EV-AY0016-001 described in Scheme 3.13.

(1R,4R,7R)-2-{2-[1-(Cyclopropylmethyl)-1H-pyrrolo[2,3-b]pyridin-2-yl]-1-(2-methanesulfinylethyl)-7-methoxy-1H-1,3-benzodiazole-5-carbonyl}-2-azabicyclo[2.2.1]heptan-7-amine EV-AY0020-001 (EOAI3461555) I-213 was synthesised according to the procedures described in Scheme 3 via synthesis of methyl 2-[1-(cyclopropylmethyl)-1H-pyrrolo[2,3-b]pyridin-2-yl]-1-(2-methanesulfinylethyl)-7-methoxy-1H-1,3-benzodiazole-5-carboxylate EV-AY0014-001 described in Scheme 3.13.

Scheme 3.13

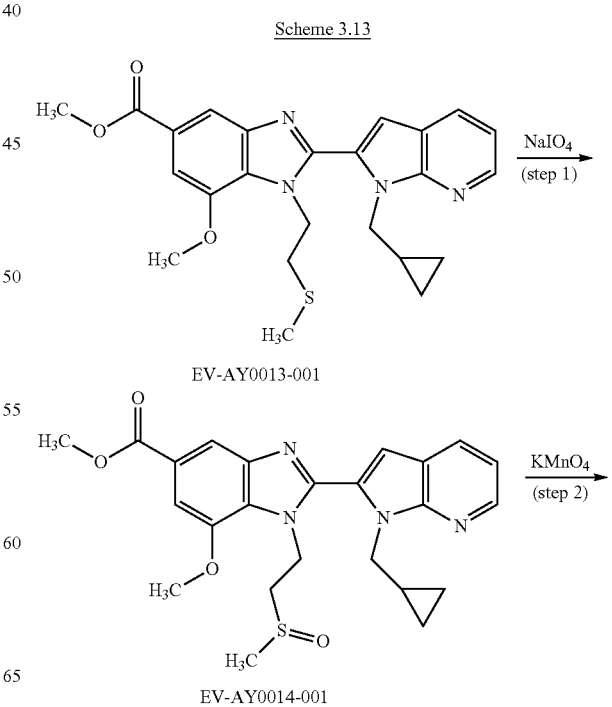

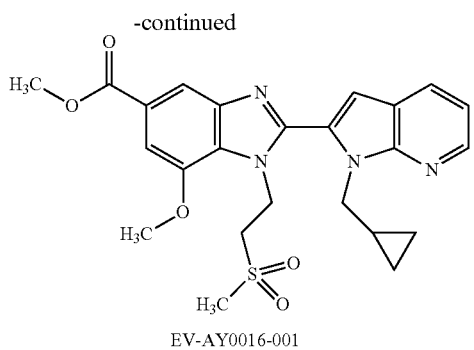

EV-AY0016-001

Methyl 2-[1-(cyclopropylmethyl)-1H-pyrrolo[2,3-b]pyridin-2-yl]-1-(2-methanesulfinylethyl)-7-methoxy-1H-1,3-benzodiazole-5-carboxylate EV-AY0014-001—step 1

To a stirred solution of methyl 2-[1-(cyclopropylmethyl)-1H-pyrrolo[2,3-b]pyridin-2-yl]-7-methoxy-1-[2-(methylsulfanyl)ethyl]-1H-1,3-benzodiazole-5-carboxylate (EV-AY0013-001, 260 mg, 0.52 mmol) in methanol (8 ml) and water (2 ml) was added NaIO$_4$ (122 mg, 0.57 mmol). The reaction was stirred at room temperature for 18 h. The solvent was removed in vacuo and the residue was partitioned between EtOAc (20 ml) and water (50 ml). The aqueous layer was extracted further with EtOAc (2×20 ml). The combined organics were washed with saturated aqueous sodium chloride (20 ml), dried over sodium sulfate, filtered and evaporated under reduced pressure. The residue was purified by flash column chromatography (0-50% EtOAc/heptane then 1-10% Methanol/DCM) to obtain 220 mg (91%) of methyl 2-[1-(cyclopropylmethyl)-1H-pyrrolo[2,3-b]pyridin-2-yl]-1-(2-methanesulfinylethyl)-7-methoxy-1H-1,3-benzodiazole-5-carboxylate EV-AY0014-001 as a red foam. LCMS (method D): retention time 1.08 min, M/z=467 (M+1).

Methyl 2-[1-(cyclopropylmethyl)-1H-pyrrolo[2,3-b]pyridin-2-yl]-1-(2-methanesulfonylethyl)-7-methoxy-1H-1,3-benzodiazole-5-carboxylate EV-AY0016-001—step 2

To a stirred solution of methyl 2-[1-(cyclopropylmethyl)-1H-pyrrolo[2,3-b]pyridin-2-yl]-1-(2-methanesulfinylethyl)-7-methoxy-1H-1,3-benzodiazole-5-carboxylate (EV-AY0014-001, 135 mg, 0.29 mmol) in Methanol (40 ml) was added KMnO$_4$ (50 mg, 0.32 mmol). The reaction was stirred at room temperature for 15 minutes. The reaction was quenched by the addition of saturated aqueous sodium bisulfate (20 ml). The mixture was filtered through Kieselguhr and the filtrate was concentrated in vacuo. The residue was diluted in EtOAc (20 ml) and water (50 ml) and the aqueous layer was extracted with EtOAc (2×20 ml). The combined organics were washed with saturated aqueous sodium chloride (20 ml), dried over sodium sulfate, filtered and evaporated under reduced pressure to obtain 115 mg (81%) of methyl 2-[1-(cyclopropylmethyl)-1H-pyrrolo[2,3-b]pyridin-2-yl]-1-(2-methanesulfonylethyl)-7-methoxy-1H-1,3-benzodiazole-5-carboxylate EV-AY0016-001 as a brown solid. LCMS (method D): retention time 1.15 min, M/z=483 (M+1).

Rac-[(2R,5S)-5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4303-001 (EOAI3462115) I-220 and rac-[(2R,5R)-5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4304-001 (EOAI3462116) I-221 were obtained from the Boc-deprotection of rac-tert-butyl N-[(3R,6S)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-001 and rac-tert-butyl N-[(3R,6R)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-002 respectively following the procedures described in Schemes 3 and 3.14:

Scheme 3.14

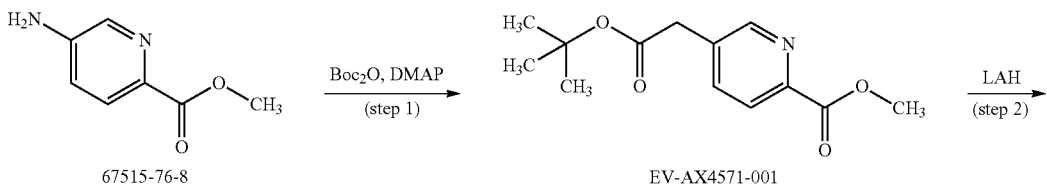

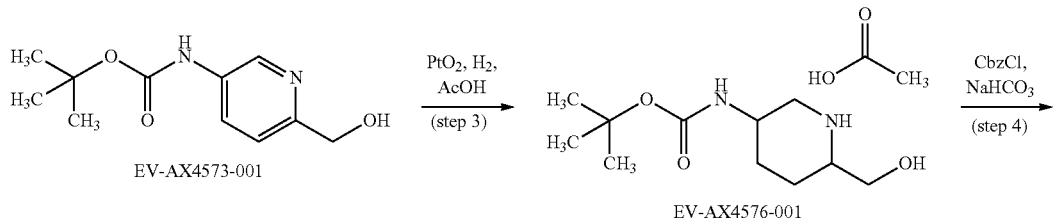

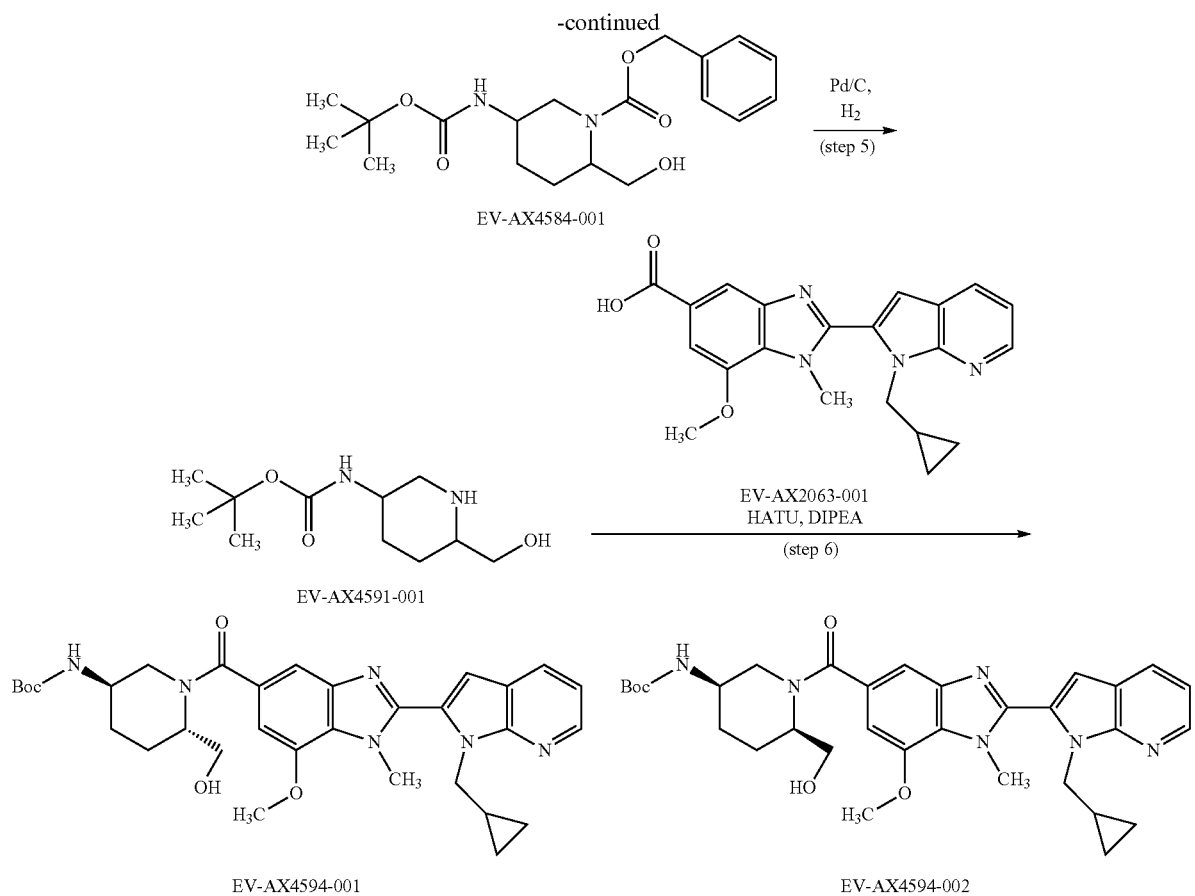

Methyl 5-{[(tert-butoxy)carbonyl]amino}pyridine-2-carboxylate EV-AX4571-001—step 1

To a stirred solution of methyl 5-aminopyridine-2-carboxylate (CAS 67515-76-8, 1.8 g, 11.83 mmol) in DCM (40 ml) under an atmosphere of nitrogen was added di-tert-butyl dicarbonate (2.84 g, 13.01 mmol) and N,N-dimethylpyridin-4-amine (0.14 g, 1.18 mmol) and the reaction was stirred at room temperature for 5 h. The reaction mixture was filtered (rinsing the filter with DCM), the filtrate was diluted with DCM (100 ml) and washed with water (2×100 ml). The organic layer was dried with sodium sulfate, filtered and concentrated in vacuo to obtain 2.73 g (60%) of methyl 5-{[(tert-butoxy)carbonyl]amino}pyridine-2-carboxylate EV-AX4571-001 as an off-white solid. LCMS (method D): retention time 1.01 min, M/z=253 (M+1).

Tert-butyl N-[6-(hydroxymethyl)pyridin-3-yl]carbamate EV-AX4573-001—step 2

To a stirred solution of methyl 5-{[(tert-butoxy)carbonyl]amino}pyridine-2-carboxylate (EV-AX4571-001, 2.73 g, 10.82 mmol) in THF (60 ml) at 0° C. under an atmosphere of nitrogen was added 4M lithium tetrahydridoaluminate(1-) in diethyl ether (4.1 ml) drop-wise, the reaction was allowed to warm to room temperature and stirred for a further 12 h. The reaction was quenched by addition of THF:water (9:1, 15 ml), followed by 10% sodium hydroxide (10 ml) and then water (10 ml). The reaction mixture was then filtered through a pad of Kieselguhr, rinsing with THF (3×50 ml). The filtrate was concentrated in vacuo and the crude was purified by flash column chromatography (50-100% EtOAc/heptane then 0-10% Methanol/EtOAc) to obtain 1.50 g (60%) of tert-butyl N-[6-(hydroxymethyl)pyridin-3-yl]carbamate EV-AX4573-001 as an off-white solid. LCMS (method D): retention time 0.70 min, M/z=224 (M+1).

Acetic acid tert-butyl N-[6-(hydroxymethyl)piperidin-3-yl]carbamate EV-AX4576-001—step 3

To a pressure vessel was added a solution of tert-butyl N-[6-(hydroxymethyl)pyridin-3-yl]carbamate (EV-AX4573-001, 1.50 g, 6.69 mmol) in ethanol (25 ml) and Acetic acid (1.5 ml). $PtO_2$ (266 mg, 1.17 mmol) was added and the pressure vessel was purged with nitrogen before the reaction was sealed and stirred under a hydrogen atmosphere (55 psi, 3.75 atm) at 65° C. for 16 h. The reaction mixture was filtered through a pad of Kieselguhr and concentrated in vacuo to obtain 2.40 g (99%) of acetic acid tert-butyl N-[6-(hydroxymethyl)piperidin-3-yl]carbamate EV-AX4576-001 as an orange oil. No LCMS data.

Benzyl 5-{[(tert-butoxy)carbonyl]amino}-2-(hydroxymethyl)piperidine-1-carboxylate EV-AX4584-001—step 4

To a stirred solution of acetic acid tert-butyl N-[6-(hydroxymethyl)piperidin-3-yl]carbamate (EV-AX4576-001, 70%, 2.00 g, 4.82 mmol) in THF (40 ml) and water (12 ml) at 0° C. was added sodium bicarbonate (1.22 g, 14.47 mmol) and benzyl carbonochloridate (0.62 ml, 4.34 mmol). The reaction mixture was stirred at 0° C. for 15 minutes, the solution was allowed to warm to room temperature and stirring was continued for 4 h. The reaction mixture was diluted with water (10 ml) and extracted with EtOAc (3×5 ml). The combined organics were dried over magnesium sulfate, filtered and concentrated in vacuo. The crude was purified by flash column chromatography (40-100% EtOAc/heptane) to obtain 1.40 g (80%) of benzyl 5-{[(tert-butoxy)carbonyl]amino}-2-(hydroxymethyl)piperidine-1-carboxylate EV-AX4584-001 as a white solid. LCMS (method D): retention time 1.12 min, M/z=387 (M+23).

Tert-butyl N-[6-(hydroxymethyl)piperidin-3-yl]carbamate EV-AX4591-001—step 5

To solution of benzyl 5-{[(tert-butoxy)carbonyl]amino}-2-(hydroxymethyl)piperidine-1-carboxylate (EV-AX4584-001, 1.40 g, 3.84 mmol) in ethanol (20 ml) was added palladium on carbon (5%, 0.82 g, 0.38 mmol) and the reaction mixture was stirred for 14 h at room temperature under a hydrogen atmosphere. The mixture was filtered through a pad of Kieselguhr (washing with Methanol) and the filtrate was concentrated in vacuo to obtain 0.82 g (93%) of tert-butyl N-[6-(hydroxymethyl)piperidin-3-yl]carbamate EV-AX4591-001 as a colourless oil. LCMS (method D): retention time 1.20 min, M/z=231 (M+1).

Rac-tert-butyl N-[(3R,6S)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-001 and rac-tert-butyl N-[(3R,6R)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-002—step 6

To a stirred solution of 2-[1-(cyclopropylmethyl)-1H-pyrrolo[2,3-b]pyridin-2-yl]-7-methoxy-1-methyl-1H-1,3-benzodiazole-5-carboxylic acid (EV-AX2063-001, 200 mg, 0.53 mmol) in DMF (5 ml) were added DIPEA (463 µl, 2.66 mmol), HATU (222 mg, 0.58 mmol) and tert-butyl N-[6-(hydroxymethyl)piperidin-3-yl]carbamate (EV-AX4591-001, 122 mg, 0.53 mmol) at room temperature. The reaction mixture was stirred for 1 h and concentrated in vacuo. The crude was purified by preparative HPLC (acidic) to obtain 2 products:

70 mg (22%) of rac-tert-butyl N-[(3R,6S)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-001 as an off-white solid. LCMS (method D): retention time 1.18 min, M/z=589 (M+1).

220 mg (70%) of rac-tert-butyl N-[(3R,6R)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-002 as an off-white solid. LCMS (method D): retention time 1.19 min, M/z=589 (M+1).

[(2S,5R)-5-Amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4308-001 (EOAI3462646) I-226 and [(2R,5S)-5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4309-001 (EOAI3462647) I-227 were both obtained from chiral resolution of rac-tert-butyl N-[(3R,6S)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-001 followed by Boc-deprotection as described in Scheme 3. The absolute configuration of both products was arbitrarily assigned.

[(2R,5R)-5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4310-001 (EOAI3462648) I-228 and [(2S,5S)-5-amino-1-{2-[1-(cyclopropylmethyl)-1H-pyrrolo[2,3-b]pyridin-2-yl]-7-methoxy-1-methyl-1H-1,3-benzodiazole-5-carbonyl}piperidin-2-yl]methanol EV-AY4311-001 (EOAI3462649) I-229 were both obtained from chiral resolution of rac-tert-butyl N-[(3R,6R)-1-{2-[1-(cyclopropylmethyl)-1H-pyrrolo[2,3-b]pyridin-2-yl]-7-methoxy-1-methyl-1H-1,3-benzodiazole-5-carbonyl}-6-(hydroxymethyl)piperidin-3-yl]carbamate EV-AX4594-002 followed by Boc-deprotection as described in Scheme 3. The absolute configuration of both products was arbitrarily assigned.

(1R,4R,7R)-2-{2-[7-(cyclopropylmethyl)-2-methoxy-7H-pyrrolo[2,3-d]pyrimidin-6-yl]-7-methoxy-1-methyl-1H-1,3-benzodiazole-5-carbonyl}-2-azabicyclo[2.2.]heptan-7-amine EV-AX5554-001 (EOAI3468827) I-239 was synthesised according to procedures described in Scheme 3 via synthesis of methyl 7-(cyclopropylmethyl)-2-methoxy-7H-pyrrolo[2,3-d]pyrimidine-6-carboxylate EV-AX5535-006 described in Scheme 3.15:

Scheme 3.15

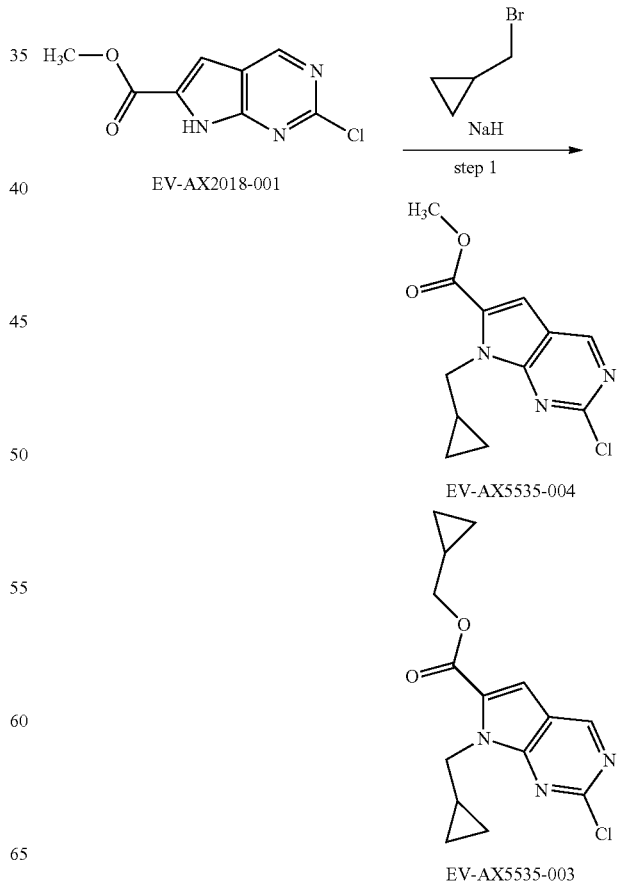

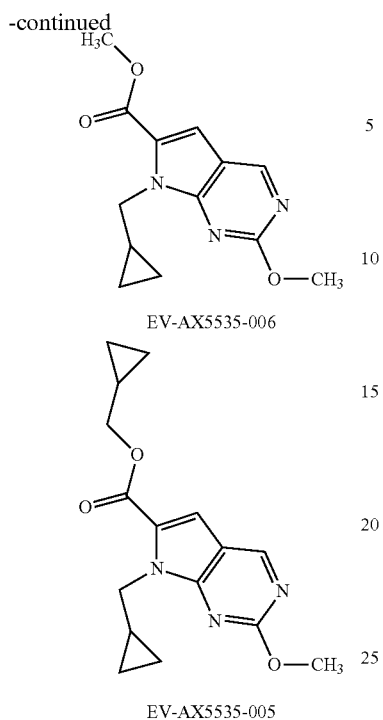

EV-AX5535-006

EV-AX5535-005

Methyl 7-(cyclopropylmethyl)-2-methoxy-7H-pyrrolo[2,3-d]pyrimidine-6-carboxylate EV-AX5535-006—step 1

To s stirred solution of methyl 2-chloro-7H-pyrrolo[2,3-d]pyrimidine-6-carboxylate (EV-AX2018-001, 1.00 g, 4.68 mmol) in anhydrous DMF (20 ml) at 0° C. was added sodium hydride (60%, 0.28 g, 7.02 mmol) portion-wise over 1 minute. (Bromomethyl)cyclopropane (680 µl, 7.01 mmol) was added at 0° C. after 30 minutes. The reaction was allowed to warm to room temperature and stirred for 60 h. The reaction mixture was concentrated in vacuo and the resulting residue partitioned between EtOAc (50 ml) and water (30 ml). The layers were separated and the organic phase washed with 0.5M HCl (30 ml) and saturated aqueous sodium chloride (30 ml). The organic layer was dried over magnesium sulfate, filtered and concentrated under reduced pressure. The crude was purified by flash column chromatography (5-40% EtOAc/heptane) to obtain 4 products:

113 mg (8%) of cyclopropylmethyl 2-chloro-7-(cyclopropylmethyl)-7H-pyrrolo[2,3-d]pyrimidine-6-carboxylate EV-AX5535-003 as an off-white powder. LCMS (method D): retention time 1.38 min, M/z=306/308 (M+1).

256 mg (20%) of methyl 2-chloro-7-(cyclopropylmethyl)-7H-pyrrolo[2,3-d]pyrimidine-6-carboxylate EV-AX5535-004 as an off-white crystalline solid. LCMS (method D): 1.24 min, M/z=266/268 (M+1).

93 mg (6%) of cyclopropylmethyl 7-(cyclopropylmethyl)-2-methoxy-7H-pyrrolo[2,3-d]pyrimidine-6-carboxylate EV-AX5535-005 as a yellow gum. LCMS (method D): retention time 1.32 min, M/z=302 (M+1).

197 mg (16%) of methyl 7-(cyclopropylmethyl)-2-methoxy-7H-pyrrolo[2,3-d]pyrimidine-6-carboxylate EV-AX5535-006 as a yellow crystalline solid. LCMS (method D): retention time 1.20 min, M/z=262 (M+1).

(1R,4R,7R)-2-{2-[1-(cyclopropylmethyl)-6-fluoro-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AX4151-006 (EOAI3476815) I-269 was synthesised following the procedures described in Scheme 3 via synthesis of 1-(cyclopropylmethyl)-6-fluoro-1H-pyrrolo[2,3-b]pyridine-2-carboxylic acid EV-AX4144-003 described in Scheme 3.16:

Scheme 3.16

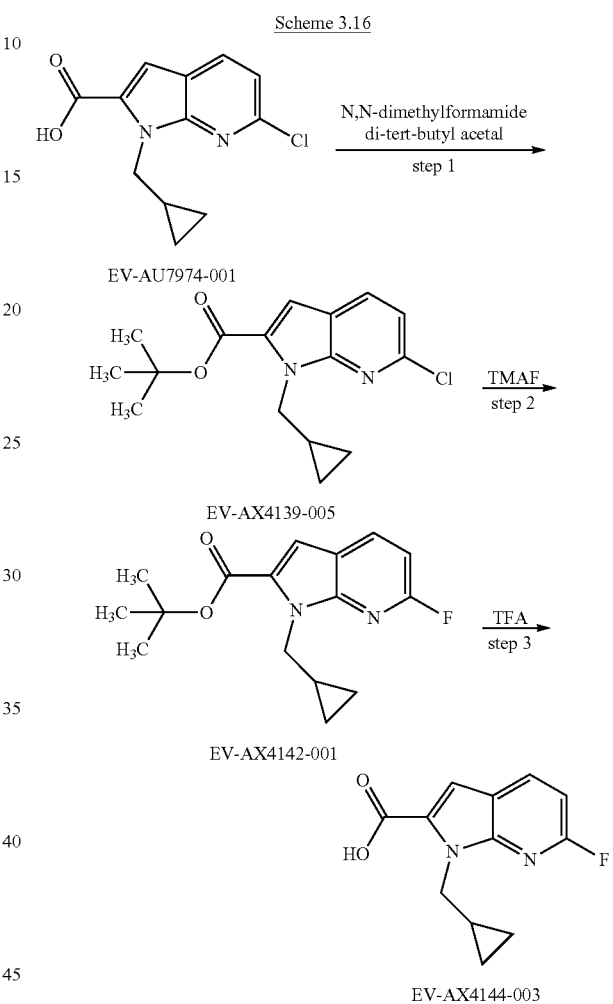

Tert-butyl 6-chloro-1-(cyclopropylmethyl)-1H-pyrrolo[2,3-b]pyridine-2-carboxylate EV-AX4139-001—step 1

A stirred suspension of 6-chloro-1-(cyclopropylmethyl)-1H-pyrrolo[2,3-b]pyridine-2-carboxylic acid (EV-AU7974-001, 500 mg, 1.99 mmol) in toluene (30 ml) was heated to 85° C. before N,N-dimethylformamide di-tert-butyl acetal (2.0 ml, 8.34 mmol) was added drop-wise. The reaction was stirred at 85° C. for 2 h and further N,N-dimethylformamide di-tert-butyl acetal (2.0 ml, 8.34 mmol) was added. Stirring was continued at 85° C. for 18 h then at 100° C. for 3 h. After cooling, the reaction mixture was diluted with EtOAc (200 ml), washed with saturated aqueous sodium chloride (50 ml), dried over magnesium sulfate, filtered and concentrated in vacuo. The crude was purified by flash column chromatography (0-10% EtOAc/heptane) to obtain 366 mg (60%) of tert-butyl 6-chloro-1-(cyclopropylmethyl)-1H-pyrrolo[2, 3-b]pyridine-2-carboxylate EV-AX4139-005 as a colourless oil. LCMS (method D): retention time 1.66 min, M/z=307/309 (M+1)

Tert-butyl 1-(cyclopropylmethyl)-6-fluoro-1H-pyrrolo[2,3-b]pyridine-2-carboxylate EV-AX4142-001—step 2

To a stirred solution of tert-butyl 6-chloro-1-(cyclopropylmethyl)-1H-pyrrolo[2,3-b]pyridine-2-carboxylate (EV-AX4139-005, 366 mg, 1.19 mmol) in DMF (5 ml) was added tetramethylammonium fluoride (CAS 373-68-2, 250 mg, 2.68 mmol) and the mixture was stirred at 80° C. for 18 h. After cooling, the reaction mixture was partitioned among DCM (200 ml), water (100 ml) and saturated aqueous sodium chloride (100 ml). The organic layer was separated, further washed with saturated aqueous sodium chloride (50 ml), dried over magnesium sulfate, filtered and concentrated in vacuo. The crude material was purified by flash column chromatography (0-10% EtOAc/heptane) to obtain 112 mg (32%) of tert-butyl 1-(cyclopropylmethyl)-6-fluoro-1H-pyrrolo[2,3-b]pyridine-2-carboxylate EV-AX4142-001 as a colourless oil. LCMS (method D): retention time 1.61 min, M/z=291 (M+1).

1-(Cyclopropylmethyl)-6-fluoro-1H-pyrrolo[2,3-b]pyridine-2-carboxylic acid EV-AX4144-003—step 3

A solution of tert-butyl 1-(cyclopropylmethyl)-6-fluoro-1H-pyrrolo[2,3-b]pyridine-2-carboxylate (EV-AX4142-001, 100 mg, 0.34 mmol) in TFA (2.0 ml, 26.2 mmol) was stirred at room temperature for 3 h. After concentration in vacuo the residue was taken up in DCM and concentrated to give 80 mg (89%) of 1-(cyclopropylmethyl)-6-fluoro-1H-pyrrolo[2,3-b]pyridine-2-carboxylic acid EV-AX4144-003 as a yellow solid. LCMS (method D): retention time 1.15 min, M/z=235 (M+1).

(1R,4R,7R)-2-{2-[1-(cyclopropylmethyl)-6-(oxan-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AY7194-001 (EOAI3477013) I-275 was synthesised according to the procedures described in Scheme 3 via synthesis of ethyl 1-(cyclopropylmethyl)-6-(oxan-4-yl)-1H-pyrrolo[2,3-b]pyridine-2-carboxylate EV-AY7184-001 described in Scheme 3.17:

Scheme 3.17

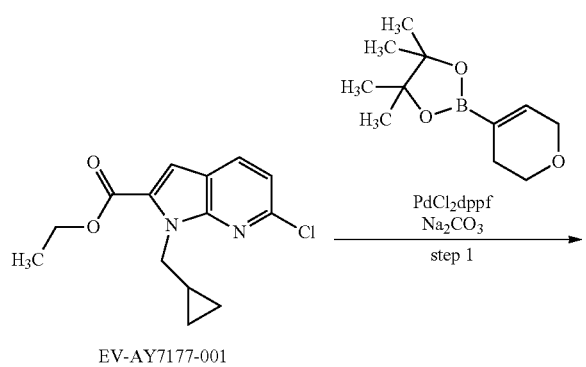

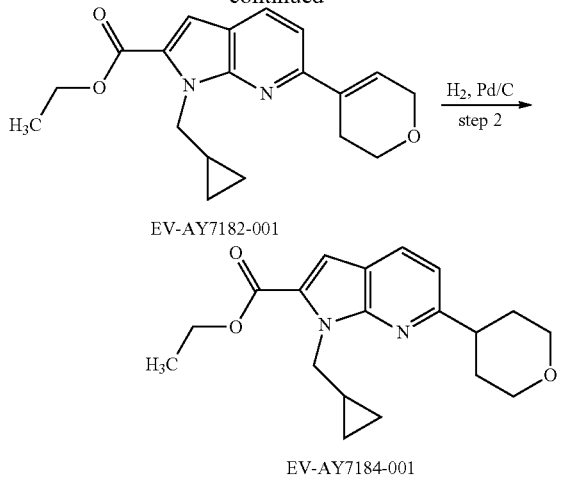

Ethyl 1-(cyclopropylmethyl)-6-(3,6-dihydro-2H-pyran-4-yl)-1H-pyrrolo[2,3-b]pyridine-2-carboxylate EV-AY7182-001—step 1

Ethyl 6-chloro-1-(cyclopropylmethyl)-1H-pyrrolo[2,3-b]pyridine-2-carboxylate (EV-AY7177-001, 90%, 950 mg, 3.07 mmol) and 2-(3,6-dihydro-2H-pyran-4-yl)-4,4,5,5-tetramethyl-1,3,2-dioxaborolane (CAS 287944-16-5, 709 mg, 3.37 mmol) were dissolved in THF: toluene (4:1, 10 ml) and 2M sodium carbonate (3.07 ml) was added. The reaction mixture was purged with nitrogen for 5 minutes and Pd(dppf)Cl$_2$ (449 mg, 0.61 mmol) was added. The reaction mixture was stirred at 100° C. for 4 h, cooled down to room temperature and concentrated in vacuo. The resulting residue was dissolved in EtOAc (20 ml) and washed with water (2×10 ml) and saturated aqueous sodium chloride (10 ml). The organic layer was dried over sodium sulfate and concentrated in vacuo. The crude material was purified by flash column chromatography (0-50% EtOAc/heptane) to obtain 587 mg (56%) of ethyl 1-(cyclopropylmethyl)-6-(3,6-dihydro-2H-pyran-4-yl)-1H-pyrrolo[2,3-b]pyridine-2-carboxylate EV-AY7182-001 as an orange oil. LCMS (method D): 1.52 min, M/z=327 (M+1).

Ethyl 1-(cyclopropylmethyl)-6-(oxan-4-yl)-1H-pyrrolo[2,3-b]pyridine-2-carboxylate EV-AY7184-001—step 2

To stirred solution of ethyl 1-(cyclopropylmethyl)-6-(3,6-dihydro-2H-pyran-4-yl)-1H-pyrrolo[2,3-b]pyridine-2-carboxylate (EV-AY7182-001, 587 mg, 1.71 mmol) in EtOAc:Ethanol (1:1, 30 ml) was added Pd/C (10%, 91 mg, 0.09 mmol). The reaction was placed under a hydrogen atmosphere and stirred at room temperature for 18 h. The reaction was filtered through a pad of Kieselguhr and washed through with methanol (30 ml). The filtrate was concentrated in vacuo to obtain 516 mg (83%) of ethyl 1-(cyclopropylmethyl)-6-(oxan-4-yl)-1H-pyrrolo[2,3-b]pyridine-2-carboxylate EV-AY7184-001 as an off-white powder. LCMS (method D): retention time 1.51 min, M/z=329 (M+1).

(1R,4R,7R)-2-{2-[1-(cyclopropylmethyl)-6-($^2$H$_3$)methoxy-1H-pyrrolo[2,3-b]pyridin-2-yl]-1-methyl-1H-1,3-benzodiazole-5-carbonyl}-2-azabicyclo[2.2.1]heptan-7-amine EV-AZ5120-001 (EOAI3478073) I-285 was synthesised following the procedures described in Scheme 3 via synthesis of methyl 1-(cyclopropylmethyl)-6-($^2$H$_3$)methoxy-1H-pyrrolo[2,3-b]pyridine-2-carboxylate EV-AZ5103-001 described in Scheme 3.18:

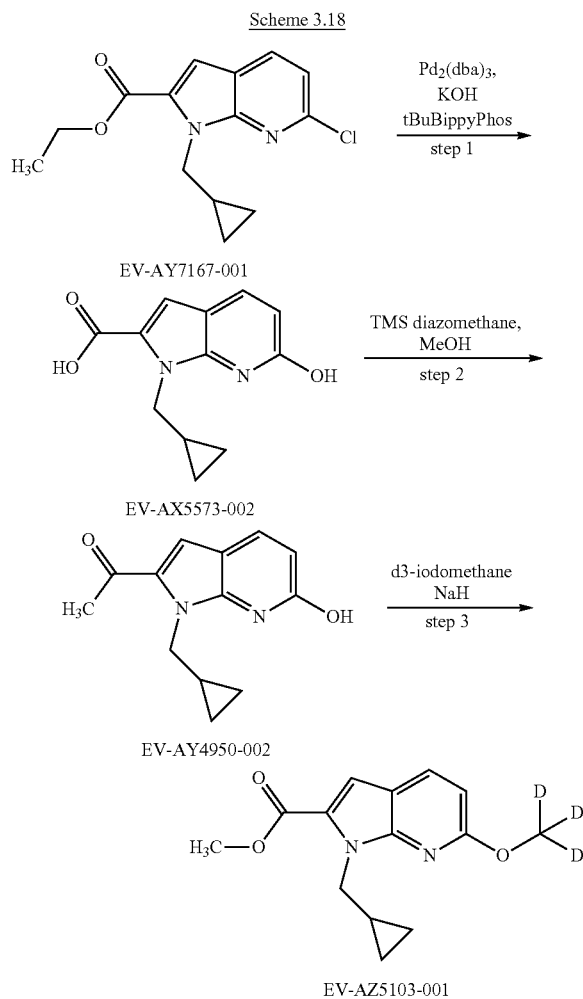

1-(cyclopropylmethyl)-6-hydroxy-1H-pyrrolo[2,3-b]pyridine-2-carboxylic acid EV-AX5573-002—step 1

Ethyl 6-chloro-1-(cyclopropylmethyl)-1H-pyrrolo[2,3-b]pyridine-2-carboxylate (EV-AY7167-001, 90%, 1.45 g, 4.68 mmol), Pd$_2$(dba)$_3$ (214 mg, 0.23 mmol), $^t$Bu-BippyPhos (237 mg, 0.47 mmol) and potassium hydroxide (788 mg, 14.0 mmol) were combined in dioxane (7 ml) and water (7 ml) in a pressure tube. The reaction mixture was purged with nitrogen for 5 minutes then the vessel was sealed and heated at 70° C. for 1.5 h. The reaction mixture was cooled down to room temperature and filtered through a glass fibre filter paper. The filtrate was partitioned between water (10 ml) and EtOAc (30 ml). The aqueous layer was acidified to pH 5 with 2M HCl and the resulting precipitate was filtered and dried to obtain 0.80 g (62%) of 1-(cyclopropylmethyl)-6-hydroxy-1H-pyrrolo[2,3-b]pyridine-2-carboxylic acid EV-AX5573-002 as an off-white powder. LCMS (method D): retention time 0.95 min, M/z=233 (M+1).

Methyl 1-(cyclopropylmethyl)-6-hydroxy-1H-pyrrolo[2,3-b]pyridine-2-carboxylate EV-AY4950-002—step 2

To a stirred suspension of 1-(cyclopropylmethyl)-6-hydroxy-1H-pyrrolo[2,3-b]pyridine-2-carboxylic acid (EV-AX5573-002, 73%, 550 mg, 1.73 mmol) in anhydrous toluene (6 ml) and anhydrous methanol (2 ml, 49.44 mmol) under an atmosphere of nitrogen was added 2M (diazomethyl)(trimethyl)silane (1.73 ml in diethylether). The resulting mixture was stirred at room temperature for 1.5 h. Acetic acid (~0.7 ml) was added until the bright yellow colour disappeared. The reaction mixture was concentrated in vacuo and triturated with DCM (5 ml). The solid was filtered off and dried to afford 131 mg (28%) of 1-(cyclopropylmethyl)-6-hydroxy-1H-pyrrolo[2,3-b]pyridine-2-carboxylic acid EV-AY4950-001 as a pale beige solid. LCMS (method D): retention time 1.13 min, M/z=247 (M+1).

Methyl 1-(cyclopropylmethyl)-6-($^2$H$_3$)methoxy-1H-pyrrolo[2,3-b]pyridine-2-carboxylate EV-AZ5013-001—step 3

To a stirred solution of 1-(cyclopropylmethyl)-6-hydroxy-1H-pyrrolo[2,3-b]pyridine-2-carboxylic acid (EV-AY4950-001, 100 mg, 0.40 mmol) in DMF (30 ml) was added sodium hydride (60%, 32 mg, 0.80 mmol). The reaction was stirred at room temperature for 10 minutes then iodo($^2$H$_3$)methane (74 µl, 1.19 mmol) was added. The reaction mixture was stirred at room temperature for 17 h, diluted with EtOAc (20 ml), washed with water (2×20 ml) and saturated aqueous sodium chloride (10 ml). The organic phase was dried and concentrated in vacuo to obtain methyl 1-(cyclopropylmethyl)-6-($^2$H$_3$)methoxy-1H-pyrrolo[2,3-b]pyridine-2-carboxylate EV-AZ5013-001 (85 mg, 75%) as a yellow powder. LCMS (method D): retention time 1.36 min, M/z=264 (M+1).

(1R,4R,7R)-2-{2-[1-(cyclopropylmethyl)-3-fluoro-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AZ5131-001 (EOAI3478196) I-292 was synthesised according to the procedures described in Scheme 3 via synthesis of ethyl 1-(cyclopropylmethyl)-3-fluoro-1H-pyrrolo[2,3-b]pyridine-2-carboxylate EV-AZ5111-001 described in Scheme 3.19:

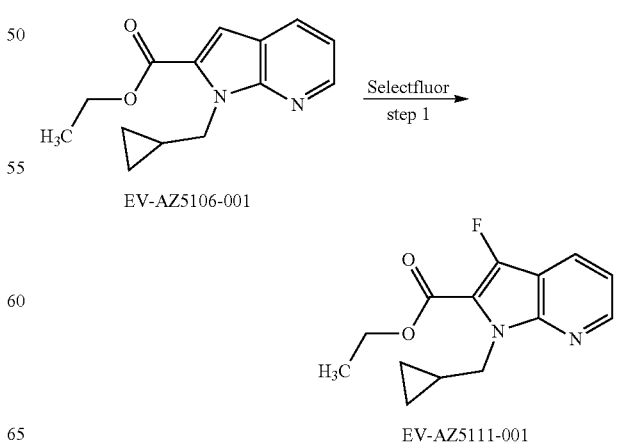

Ethyl 1-(cyclopropylmethyl)-3-fluoro-1H-pyrrolo[2,3-b]pyridine-2-carboxylate EV-AZ5111-001—step 1

To a stirred solution of ethyl 1-(cyclopropylmethyl)-1H-pyrrolo[2,3-b]pyridine-2-carboxylate (EV-AZ5106-001, 1.00 g, 4.09 mmol) in DMF (20 ml) was added Selectfluor® (CAS 140681-55-6, 1.45 g, 4.09 mmol). The resulting mixture was stirred at room temperature for 60 h. The reaction mixture was concentrated in vacuo and the residue was dissolved in EtOAc (20 ml) and washed with water (3×20 ml). The organic phase was dried over sodium sulfate and concentrated in vacuo. The crude was purified by flash column chromatography (0-50% DCM/heptane) to obtain 245 mg (22%) of ethyl 1-(cyclopropylmethyl)-3-fluoro-1H-pyrrolo[2,3-b]pyridine-2-carboxylate EV-AZ5111-001 as a yellow oil. LCMS (method D): retention time 1.33 min, M/z=263 (M+1).

(1R,4R,7R)-2-{2-[1-(cyclopropylmethyl)-4-fluoro-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AY4588-001 (EOAI3478689) I-294 was synthesised following procedures described in Scheme 3 via synthesis of tert-butyl 1-(cyclopropylmethyl)-4-fluoro-1H-pyrrolo[2,3-b]pyridine-2-carboxylate EV-AX4168-003 described in Scheme 3.16 and 3.20:

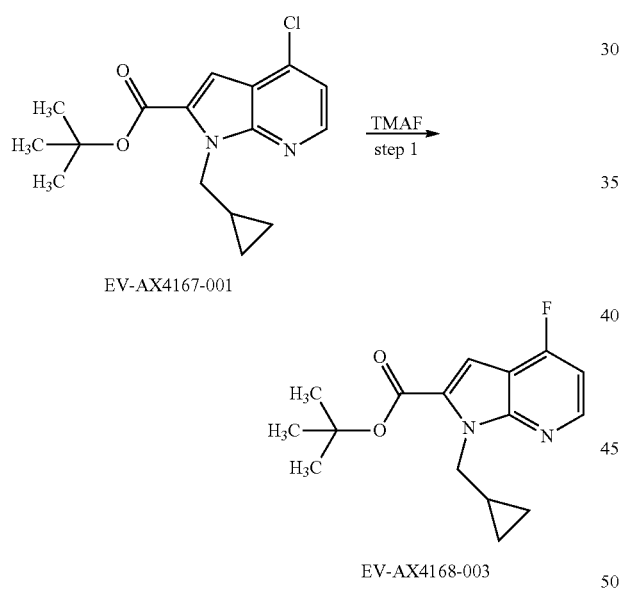

Scheme 3.20

EV-AX4167-001

TMAF
step 1

EV-AX4168-003

Tert-butyl 1-(cyclopropylmethyl)-4-fluoro-1H-pyrrolo[2,3-b]pyridine-2-carboxylate EV-AX4168-003—step 1

To a stirred solution of tert-butyl 4-chloro-1-(cyclopropylmethyl)-1H-pyrrolo[2,3-b]pyridine-2-carboxylate (EV-AX4167-001, 820 mg, 2.67 mmol) in anhydrous DMF (10 ml) was added tetramethylammonium fluoride (500 mg, 5.36 mmol) and the mixture was stirred at 80° C. for 18 h. The reaction mixture was partitioned between DCM (200 ml) and saturated aqueous sodium bicarbonate (200 ml). The aqueous layer was washed with DCM (2×100 ml) and the combined organics were washed with saturated aqueous sodium chloride (100 ml), dried over magnesium sulfate, filtered and concentrated in vacuo. The crude material was purified by flash column chromatography (0-10% EtOAc/heptane) to obtain 401 mg (52%) of tert-butyl 1-(cyclopropylmethyl)-4-fluoro-1H-pyrrolo[2,3-b]pyridine-2-carboxylate EV-AX4168-003 as a colourless oil. LCMS (method D): retention time 1.48 min, M/z=291 (M+1).

(1R,4R,7R)-2-{2-[1-(cyclopropylmethyl)-6-(morpholin-4-yl)-1H-pyrrolo[2,3-b]pyridin-2-yl]-7-methoxy-1-methyl-1H-1,3-benzodiazole-5-carbonyl}-2-azabicyclo[2.2.1]heptan-7-amine EV-AX5592-001 (EOAI3478190) I-287 was synthesised according to the procedures described in Scheme 3 via synthesis of ethyl 1-(cyclopropylmethyl)-6-(morpholin-4-yl)-1H-pyrrolo[2,3-b]pyridine-2-carboxylate EV-AZ2525-001 described in Scheme 3.21:

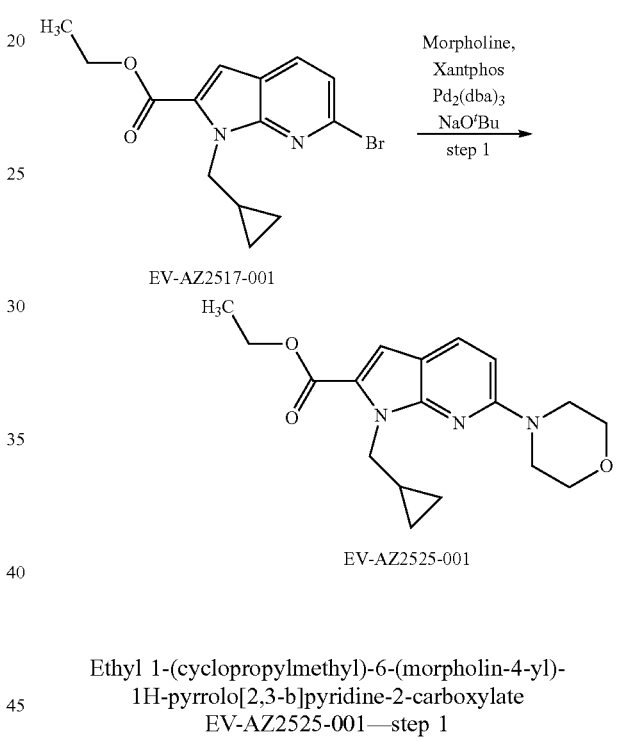

Scheme 3.21

EV-AZ2517-001

Morpholine,
Xantphos
Pd$_2$(dba)$_3$
NaO$^t$Bu
step 1

EV-AZ2525-001

Ethyl 1-(cyclopropylmethyl)-6-(morpholin-4-yl)-1H-pyrrolo[2,3-b]pyridine-2-carboxylate EV-AZ2525-001—step 1

Morpholine (74 µl, 0.86 mmol), Pd$_2$(dba)$_3$ (33 mg, 0.04 mmol), Xantphos (41 mg, 0.07 mmol) and sodium tert butoxide (103 mg, 1.07 mmol) were added to a pressure tube containing a nitrogen-purged solution of ethyl 6-bromo-1-(cyclopropylmethyl)-1H-pyrrolo[2,3-b]pyridine-2-carboxylate (EV-AZ2517-001, 231 mg, 0.71 mmol) in toluene (6 ml). The pressure tube was sealed under a nitrogen environment. The reaction mixture was heated at 110° C. for 2 h, cooled down to room temperature, diluted with water (10 ml) and extracted with EtOAc (3×10 ml). The combined organic layers were washed with saturated aqueous sodium chloride (10 ml), dried over magnesium sulfate, filtered and concentrated in vacuo. The crude was purified by flash column chromatography (0-20% EtOAc/heptane) to obtain 60 mg (25%) of ethyl 1-(cyclopropylmethyl)-6-(morpholin-4-yl)-1H-pyrrolo[2,3-b]pyridine-2-carboxylate EV-AZ2525-001 as a yellow solid. LCMS (method D): retention time 1.35 min, M/z=330 (M+1).

Scheme 4
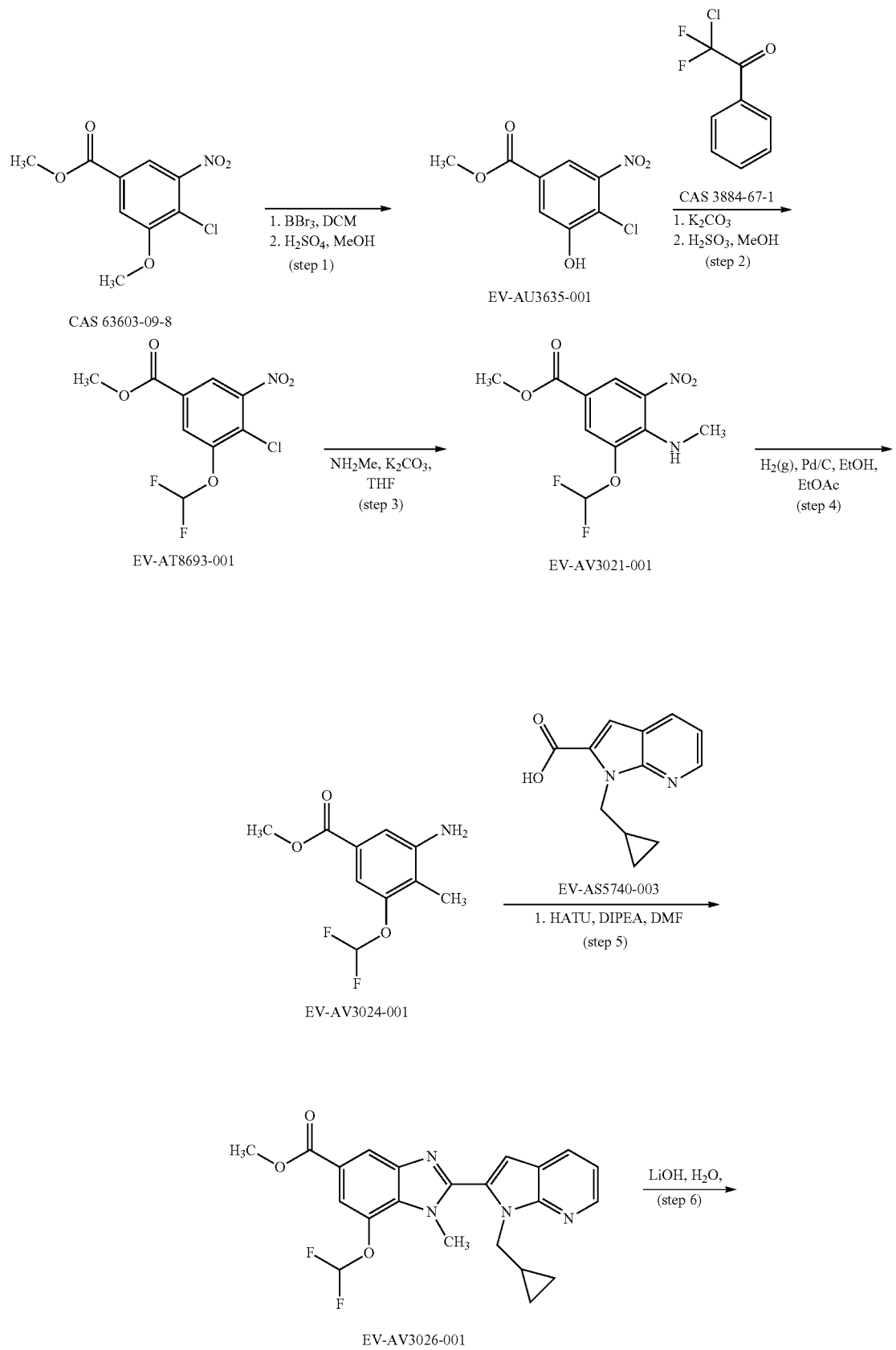

-continued
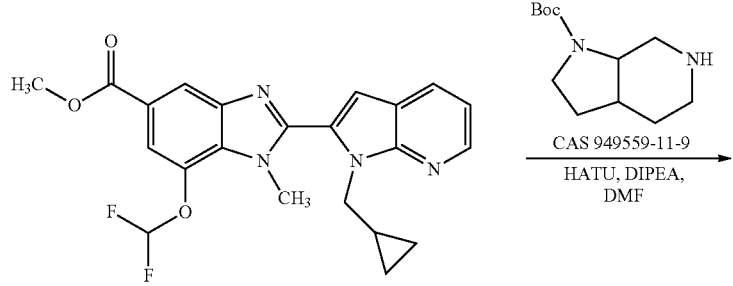
EV-AV3032-001
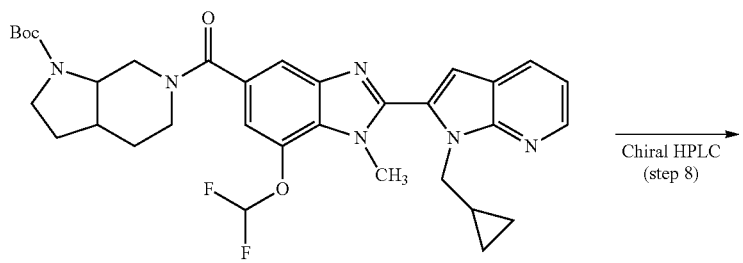
EV-AV3033-001
Chiral HPLC
(step 8)
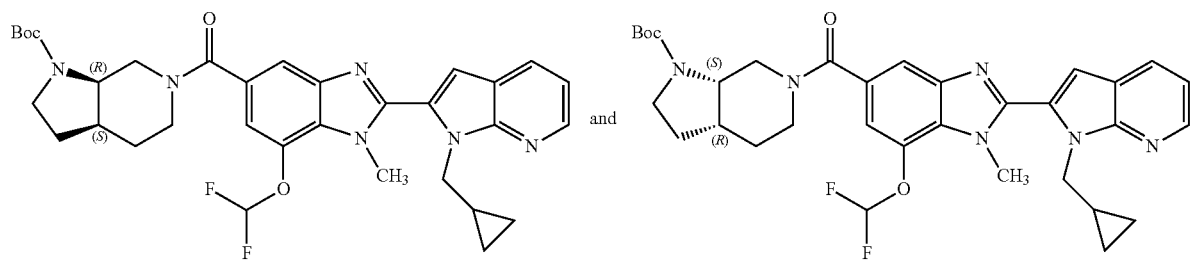
EV-AV3033-002 and EV-AV3033-003
HCl
(Step 9)
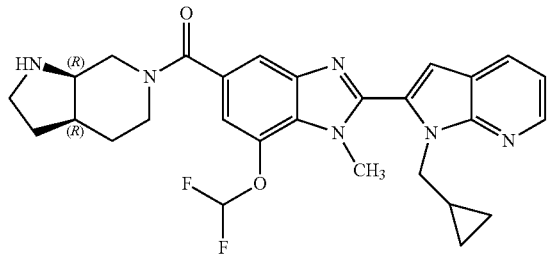
EV-AV3043-001
(EOAI3452073)
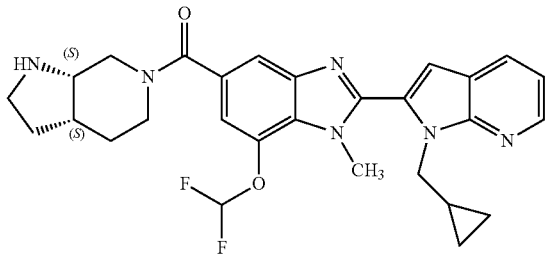
EV-AV3044-001
(EOAI3452074)

Synthesis of 5-[(3aR,7aR)-octahydro-1H-pyrrolo[2,3-c]pyridine-6-carbonyl]-2-[1-(cyclopropylmethyl)-1H-pyrrolo[2,3-b]pyridin-2-yl]-7-(difluoromethoxy)-1-methyl-1H-1,3-benzodiazole hydrochloride EV-AV3043-001 (EOAI3452073, absolute stereochemistry arbitrarily assigned) I-24

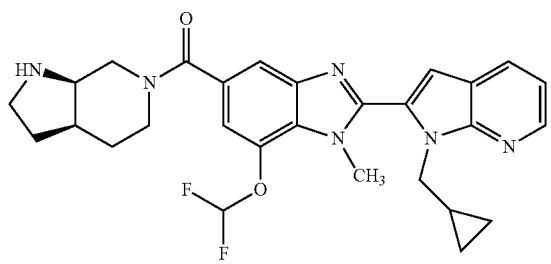

I-24

Methyl 4-chloro-3-hydroxy-5-nitrobenzoate EV-AU3635-002—step 1

Please note: reaction carried out in duplicate under identical set of conditions. The crudes from each reaction were combined after methanol quench as described below.

To a stirred solution of methyl 4-chloro-3-methoxy-5-nitrobenzoate (CAS 63603-09-8, 5.00 g, 20.4 mmol) in anhydrous DCM (20 ml) at 0° C. under nitrogen was added BBr$_3$ (1M in DCM, 40.71 ml, 2.81 mmol) drop wise over 20 minutes. The reaction mixtures were stirred at 0° C. for 30 minutes and then allowed to warm to room temperature and stirred for 15 h. The reaction mixtures were cooled to 0° C., quenched carefully with methanol, combined and concentrated in vacuo. The residue was dissolved in methanol (300 ml), concentrated sulfuric acid (10 drops) was added and the reaction mixture stirred at 75° C. for 5 h. The cooled mixture was concentrated in vacuo and to the residue was added water (50 ml) and saturated NaHCO$_3$ (50 mL) carefully to achieve a basic pH. The suspension was sonicated for 15 minutes and stirred for a further 30 minutes before the resultant solid was collected and dried under vacuum filtration. The solid was washed with water (25 ml) and dried to afford 8.14 g (82.9%) of methyl 4-chloro-3-hydroxy-5-nitrobenzoate EV-AU3635-002 as a light brown powder. LCMS (method D): retention time 1.1 min, M/z=230 (M+1).

Methyl 4-chloro-3-(difluoromethoxy)-5-nitrobenzoate EV-AT8693-001—step 2

Please note: reaction carried out in triplicate under identical set of conditions. The crudes from each reaction were combined for work-up as described below.

To a solution of methyl 4-chloro-3-hydroxy-5-nitrobenzoate (EV-AU3635-002, 333 mg, 4.32 mmol) and potassium carbonate (7.17 g, 155.4 mmol) in acetonitrile: water (1:1, 20 ml) in a pressure tube was added 2-chloro-2,2-difluoro-1-phenylethanone (1.06 ml, 21.6 mmol). The vessel was sealed and heated at 80° C. for 16 h. The cooled reaction mixtures were combined and partitioned between EtOAc (200 ml) and 2M HCl (aq). The aqueous fraction (at ~pH5) was back-extracted with more EtOAc (2×100 ml). The combined organics were dried over sodium sulfate, filtered and concentrated in vacuo. The residue was dissolved in methanol (150 ml), concentrated sulfuric acid (3 drops) was added and the reaction stirred at 75° C. for 40 h. The cooled mixture was concentrated in vacuo and to the residue was added saturated NaHCO$_3$ carefully to achieve a basic pH. The aqueous layer was extracted with EtOAc (3×100 ml) and the combined organics were dried over sodium sulfate, filtered and concentrated in vacuo. The crude residue was purified by flash column chromatography (0-20% EtOAc/heptane) to obtain 775 mg (60%) of methyl 4-chloro-3-(difluoromethoxy)-5-nitrobenzoate EV-AT8693-001 as a yellow solid. LCMS (method D): retention time 1.20 min, no mass ion observed.

Methyl 3-(difluoromethoxy)-4-(methylamino)-5-nitrobenzoate EV-AV3021-001—step 3

To a stirred solution of methyl 4-chloro-3-(difluoromethoxy)-5-nitrobenzoate (EV-AT8693-001, 400 mg, 1.34 mmol) in THF (10 ml) was added K$_2$CO$_3$ (1.29 g, 9.35 mmol) and methanamine (2.0M in THF, 1 ml, 2.00 mmol). The reaction mixture was stirred at room temperature for 24 h, concentrated in vacuo and partitioned between EtOAc (30 ml) and 1M HCl (15 ml). The organic fraction was washed with more 1M HCl (15 ml), saturated aqueous sodium chloride (10 ml), dried over sodium sulfate, filtered and concentrated in vacuo to obtain methyl 3-(difluoromethoxy)-4-(methylamino)-5-nitrobenzoate EV-AV3021-001 (370 mg, 88%) as an orange powder. LCMS (method D): retention time 1.17 min, M/z=277 (M+1).

Methyl 3-amino-5-(difluoromethoxy)-4-(methylamino)benzoate EV-AV3024-001—step 4

To a stirred solution methyl 3-(difluoromethoxy)-4-(methylamino)-5-nitrobenzoate (EV-AV3021-001, 370 mg, 1.18 mmol) in EtOAc: EtOH (1:1 20 ml) under nitrogen was added 10% Pd/C (62.7 mg, 0.06 mmol) and the resulting mixture was stirred at room temperature under an atmosphere of hydrogen for 16 h. The reaction mixture was filtered through Kieselguhr and the filter cake was washed through with EtOAc. The filtrate was concentrated in vacuo to obtain 296 mg (93%) of methyl 3-amino-5-(difluoromethoxy)-4-(methylamino)benzoate EV-AV3024-001 as a pale brown powder. LCMS (method D): retention time 0.97 min, M/z=247 (M+1).

Methyl 2-[1-(cyclopropylmethyl)-1H-pyrrolo[2,3-b]pyridin-2-yl]-7-(difluoromethoxy)-1-methyl-1H-1,3-benzodiazole-5-carboxylate EV-AV3026-001—step 5

To a stirred solution of 1-(cyclopropylmethyl)-1H-pyrrolo[2,3-b]pyridine-2-carboxylic acid (EV-AS5740-003 synthesised according to Scheme 1, step 1, 139 mg, 0.55 mmol) in DMF (5 ml) was added DIPEA (0.08 ml, 0.47 mmol) followed by HATU (177 mg, 0.47 mmol) at 0° C. The resulting mixture was stirred at 0° C. for 10 minutes, methyl 3-amino-5-(difluoromethoxy)-4-(methylamino)benzoate (EV-AV3024-001, 150 mg, 0.55 mmol) was added and the reaction mixture was stirred at room temperature for 16 h. The reaction mixture was then stirred at 50° C. for 22 h and then concentrated in vacuo. The crude residue was dissolved in acetic acid (3 ml) and heated in a sealed tube at 80° C. for 2 h. The solvent was removed in vacuo and the remaining material was purified by flash column chromatography (0-70% EtOAc/heptane) to obtain 131 mg (48%) of methyl 2-[1-(cyclopropylmethyl)-1H-pyrrolo[2,3-b]pyridin-2-yl]-7-(difluoromethoxy)-1-methyl-1H-1,3-benzodiazole-5-carboxylate EV-AV3026-001 as a pale brown powder white powder. LCMS (method D): retention time 1.29 min, M/z=427 (M+1).

2-[1-(Cyclopropylmethyl)-1H-pyrrolo[2,3-b]pyridin-2-yl]-7-(difluoromethoxy)-1-methyl-1H-1,3-benzodiazole-5-carboxylic acid EV-AV3032-001—step 6

To a stirred solution of methyl 2-[1-(cyclopropylmethyl)-1H-pyrrolo[2,3-b]pyridin-2-yl]-7-(difluoromethoxy)-1-methyl-1H-1,3-benzodiazole-5-carboxylate (EV-AV3026-001, 131 mg, 0.26 mmol) in THF: MeOH (4 ml: 1 ml) was added 2M lithium hydroxide (528 µl, 1.06 mmol) and the reaction mixture was stirred at 40° C. for 16 h. The reaction mixture was concentrated in vacuo, suspended in water (2 ml) and acidified to pH 2 using 2M HCl. The resulting suspension was stirred for 10 minutes and the resultant precipitate was collected by vacuum filtration and dried to obtain 108 mg (97%) of 2-[1-(cyclopropylmethyl)-1H-pyrrolo[2,3-b]pyridin-2-yl]-7-(difluoromethoxy)-1-methyl-1H-1,3-benzodiazole-5-carboxylic acid EV-AV3032-001 as an orange powder. LCMS (method D): retention time 1.15 min, M/z=413 (M+1).

Tert-butyl 6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-001—step 7

To a solution of 2-[1-(cyclopropylmethyl)-1H-pyrrolo[2,3-b]pyridin-2-yl]-7-(difluoromethoxy)-1-methyl-1H-1,3-benzodiazole-5-carboxylic acid (EV-AV3032-001, 108 mg, 0.26 mmol) in DMSO (2 ml), at 0° C. was added HATU (117.1 mg, 0.31 mmol) and DIPEA (87.87 µl, 0.51 mmol). The reaction mixture was stirred for 10 minutes, tert-butyl octahydro-1H-pyrrolo[2,3-c]pyridine-1-carboxylate (CAS 949559-11-9, 61 mg, 0.27 mmol) was added and the reaction mixture was stirred at room temperature for 16 h. The reaction mixture was diluted with water (1 ml) and purified by preparative HPLC (basic method) to obtain 125 mg (79%) of tert-butyl 6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-001 as a white powder. LCMS (method A): retention time 3.96 min, M/z=621 (M+1).

Chiral HPLC to obtain tert-butyl (3aS,7aR)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-002 and tert-butyl (3aR,7aS)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-003—step 8

125 mg of tert-butyl 6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-001 was dissolved in methanol and then purified by chiral HPLC (method G) to obtain 47.6 mg (27%) of tert-butyl (3aS,7aR)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-002 and 50.1 mg (29%) of tert-butyl (3aS,7aS)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate EV-AV3033-003 both as colourless gums (absolute stereochemistry arbitrarily assigned).

EV-AV3033-002 Chiral purity (UV, 254 nm): 100%, retention time: 5.46 min (method I)
EV-AV3033-003 Chiral purity (UV, 254 nm): 100%, retention time: 7.87 min (method I)

5-[(3aR,7aR)-octahydro-1H-pyrrolo[2,3-c]pyridine-6-carbonyl]-2-[1-(cyclopropylmethyl)-1H-pyrrolo[2,3-b]pyridin-2-yl]-7-(difluoromethoxy)-1-methyl-1H-1,3-benzodiazole hydrochloride EV-AV3043-001 (EOAI3452073, absolute stereochemistry arbitrarily assigned) I-24—step 9

Tert-butyl (3aS,7aR)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate (EV-AV3033-002, 47.6 mg, 0.07 mmol) was dissolved in 1.25M HCl in EtOH (1 ml) and stirred at 40° C. for 6 h. The reaction mixture was concentrated under vacuum, dissolved in water (2 ml) and freeze dried to obtain 29 mg (71%) of 5-[(3aR,7aR)-octahydro-1H-pyrrolo[2,3-c]pyridine-6-carbonyl]-2-[1-(cyclopropylmethyl)-1H-pyrrolo[2,3-b]pyridin-2-yl]-7-(difluoromethoxy)-1-methyl-1H-1,3-benzodiazole hydrochloride EV-AV3043-001 (I-24) as a yellow powder. LCMS (method A): retention time 2.23 min, M/z=521 (M+1).

5-[(3aR,7aS)-octahydro-1H-pyrrolo[2,3-c]pyridine-6-carbonyl]-2-[1-(cyclopropylmethyl)-1H-pyrrolo[2,3-b]pyridin-2-yl]-7-(difluoromethoxy)-1-methyl-1H-1,3-benzodiazole hydrochloride EV-AV3044-001 (EOAI3452074, absolute stereochemistry arbitrarily assigned) I-25—step 9

Tert-butyl (3aS,7aS)-6-{2-[1-(cyclopropylmethyl)-1H-pyrrolo[2,3-b]pyridin-2-yl]-7-(difluoromethoxy)-1-methyl-1H-1,3-benzodiazole-5-carbonyl}-octahydro-1H-pyrrolo[2,3-c]pyridine-1-carboxylate (EV-AV3033-003, 50.1 mg, 0.08 mmol) was dissolved in 1.25M HCl in EtOH (1 ml) and stirred at 40° C. for 6 h. The reaction mixture was concentrated under vacuum, dissolved in water (2 ml) and freeze dried to obtain 37 mg (87%) of 5-[(3aR,7aS)-octahydro-1H-pyrrolo[2,3-c]pyridine-6-carbonyl]-2-[1-(cyclopropylmethyl)-1H-pyrrolo[2,3-b]pyridin-2-yl]-7-(difluoromethoxy)-1-methyl-1H-1,3-benzodiazole hydrochloride EV-AV3044-001 (I-25) as a yellow powder. LCMS (method A): retention time 2.26 min, M/z=521 (M+1).

Scheme 5

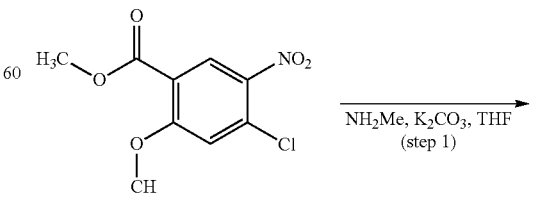

CAS 109069-75-2

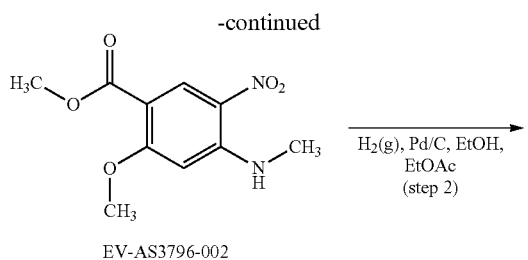

EV-AS3796-002

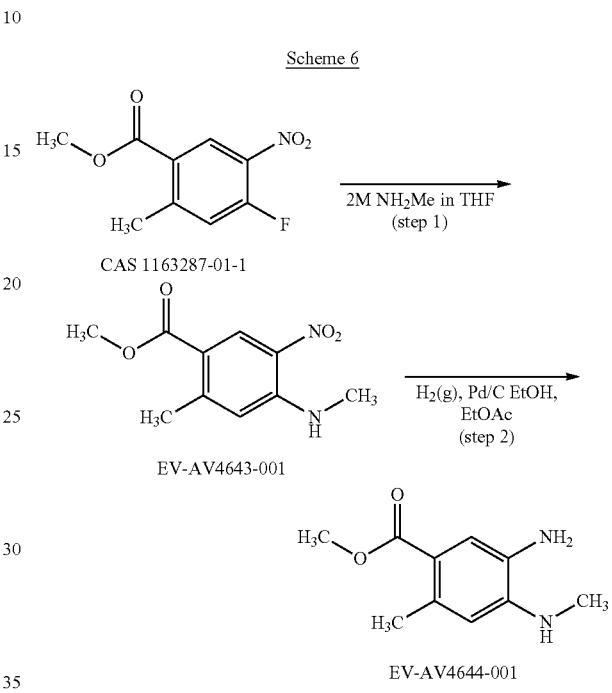

Methyl 2-methoxy-4-(methylamino)-5-nitrobenzoate EV-AS3796-002—step 1

To a solution of methyl 4-chloro-2-methoxy-5-nitrobenzoate (CAS 109069-75-2, 1.50 g, 6.11 mmol) in DMF (15 ml) at 0° C. was added methylamine (2.0M in THF, 3.66 ml, 7.33 mmol), the resulting reaction mixture was allowed to warm to room temperature and stirred for 20 h. Potassium carbonate (1.01 g, 7.33 mmol) was added and the reaction mixture stirred at room temperature for 1 h before more methylamine (2.0M in THF, 3.66 ml, 7.33 mmol) was added. The reaction was stirred at room temperature for a further 5 h. The reaction mixture was concentrated in vacuo and the crude residue was purified using by flash column chromatography (0-100% EtOAc/heptane followed by 50% EtOAc/methanol) to obtain 905 mg (56%) of methyl 2-methoxy-4-(methylamino)-5-nitrobenzoate EV-AS3796-002 as a yellow powder. LCMS (method D): retention time 1.04 min, M/z=241 (M+1).

Methyl 5-amino-2-methoxy-4-(methylamino)benzoate EV-AS3799-003—step 2

To a stirred solution of methyl 2-methoxy-4-(methylamino)-5-nitrobenzoate (EV-AS3796-002, 905 mg, 3.77 mmol) in ethanol: EtOAc (1:2, 60 ml) under nitrogen was added Pd/C (10%, 200 mg, 0.19 mmol) and the reaction mixture was stirred under an atmosphere of hydrogen for 5.5 h. The reaction mixture was filtered through Kieselguhr and the filter cake was washed through with EtOAc, ethanol and DCM. The filtrate was concentrated in vacuo and the residue was dissolved in DCM: ethanol (6:1, 70 ml). Pd/C (10%, 200 mg, 0.19 mmol) was added under nitrogen and the reaction mixture was stirred under an atmosphere of hydrogen for 6.5 h. The reaction mixture was filtered through Kieselguhr and the filter cake was washed through with ethanol and DCM. The filtrate was concentrated in vacuo and the residue was dissolved in DCM: ethanol (1:1, 120 mL). Pd/C (10%, 200 mg, 0.19 mmol) was added under nitrogen and the reaction mixture was stirred under an atmosphere of hydrogen for 22 h. The reaction mixture was filtered through Kieselguhr and the filter cake was washed through with ethanol and DCM. The filtrate was concentrated in vacuo to obtain 656 mg (76%) of methyl 5-amino-2-methoxy-4-(methylamino)benzoate EV-AS3799-003 as a dark brown powder. LCMS (method A): retention time 0.90 min, M/z=211 (M+1).

EV-AS3799-003 was used to synthesise (3R)-1-{2-[1-(cyclopropylmethyl)-1H-pyrrolo[2,3-b]pyridin-2-yl]-6-methoxy-1-methyl-1H-1,3-benzodiazole-5-carbonyl}piperidin-3-amine hydrochloride EV-AV3612-001 (EOAI3447040) I-68 according to the procedures described in Scheme 1.

Methyl 2-methyl-4-(methylamino)-5-nitrobenzoate EV-AV4643-001—step 1

To a stirred solution of methyl 4-fluoro-2-methyl-5-nitrobenzoate (CAS 1163287-01-1, 1.00 g, 4.69 mmol) in THF (12 ml) was added methylamine (2.0M in THF, 5.4 ml, 10.8 mmol) and the reaction mixture was stirred at room temperature for 10 minutes. The reaction mixture was partitioned between ethyl acetate (250 ml) and saturated aqueous NaHCO$_3$ (100 ml). The organic extract was washed with water (100 ml), dried over sodium sulfate, filtered and concentrated in vacuo to obtain 1.07 g (quantitative) of methyl 2-methyl-4-(methylamino)-5-nitrobenzoate EV-AV4643-001 as a yellow powder. LCMS (method D): retention time 1.14 min, M/z=225 (M+1).

Methyl 5-amino-2-methyl-4-(methylamino)benzoate EV-AV4644-001—step 2

To a stirred solution of methyl 2-methyl-4-(methylamino)-5-nitrobenzoate (EV-AV4643-001, 1.07 g, 4.77 mmol) in ethanol (100 ml) under nitrogen was added 10% Pd/C (102 mg, 0.048 mmol) and the resulting mixture was stirred at room temperature under an atmosphere of hydrogen for 16 h. The reaction mixture was filtered through glass fibre sinter and the filtrate was concentrated in vacuo to obtain 1.02 g (98%) of methyl 5-amino-2-methyl-4-(methylamino)benzoate EV-AV4644-001 as a light brown crystalline solid. LCMS (method D): retention time 0.77 min, M/z=195 (M+1).

Methyl 5-amino-2-methyl-4-(methylamino)benzoate EV-AV4644-001 was used to synthesise (3R)-1-{2-[1-(cyclopropylmethyl)-1H-pyrrolo[2,3-b]pyridin-2-yl]-1,6-dimethyl-1H-1,3-benzodiazole-5-carbonyl}piperidin-3-amine hydrochloride EV-AV4649-001 (EOAI3454825) I-103 according to the procedures described in Scheme 2.

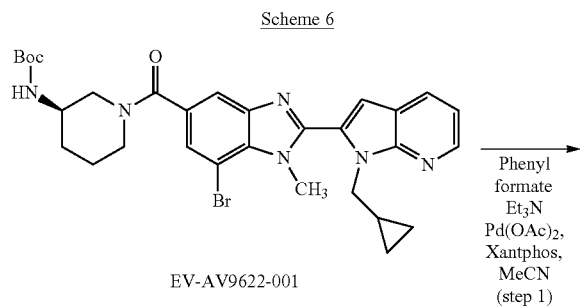

Scheme 6

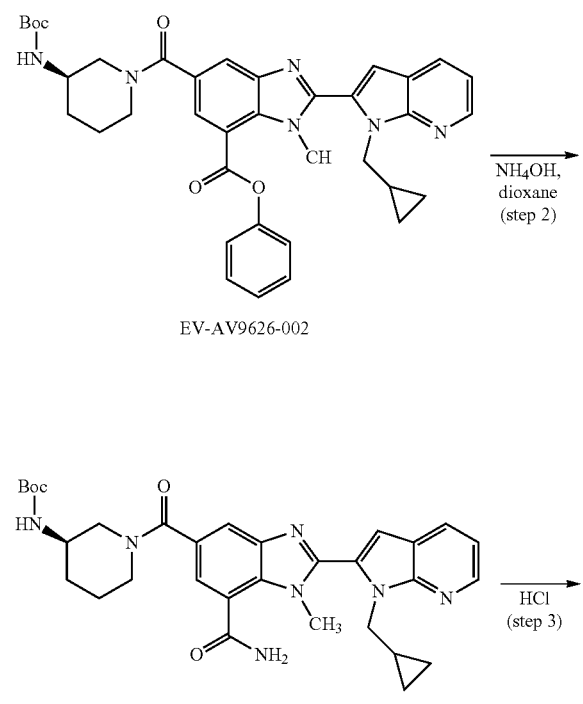

Synthesis of 5-[(3R)-3-aminopiperidine-1-carbonyl]-2-[1-(cyclopropylmethyl)-1H-pyrrolo[2,3-b]pyridin-2-yl]-1-methyl-1H-1,3-benzodiazole-7-carboxamide hydrochloride EV-AV9635-001 (EOAI3455108) I-112

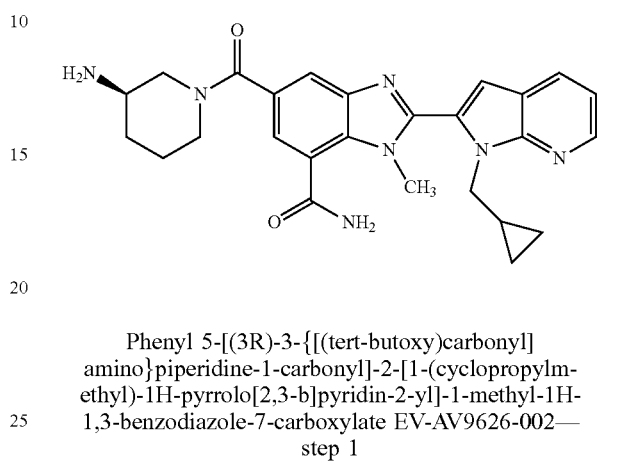

Phenyl 5-[(3R)-3-{[(tert-butoxy)carbonyl]amino}piperidine-1-carbonyl]-2-[1-(cyclopropylmethyl)-1H-pyrrolo[2,3-b]pyridin-2-yl]-1-methyl-1H-1,3-benzodiazole-7-carboxylate EV-AV9626-002—step 1

A solution of Pd(OAc)$_2$ (6 mg, 0.03 mmol) and Xantphos (30 mg, 0.05 mmol) in acetonitrile (20 ml) in a pressure tube was de-gassed for 5 minutes and tert-butyl N-[(3R)-1-{7-bromo-2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AV9622-001, synthesised according to Scheme 1, 520 mg, 0.86 mmol), phenyl formate (0.19 ml, 1.71 mmol) and triethylamine (0.24 ml, 1.71 mmol) were added. The reaction vessel was sealed and heated to 80° C. for 4 h. The cooled reaction mixture was diluted with EtOAc and washed with water. The organic fraction was dried over sodium sulfate, filtered and concentrated in vacuo. The crude residue was purified by flash column chromatography (0-100% EtOAc) to obtain 220 mg (39%) of phenyl 5-[(3R)-3-{[(tert-butoxy)carbonyl]amino}piperidine-1-carbonyl]-2-[1-(cyclopropylmethyl)-1H-pyrrolo[2,3-b]pyridin-2-yl]-1-methyl-1H-1,3-benzodiazole-7-carboxylate EV-AV9626-002 as a beige solid. LCMS (method D): retention time 1.35 min, M/z=649 (M+1).

Tert-butyl N-[(3R)-1-{7-carbamoyl-2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AV9632-002—step 2

To a solution of phenyl 5-[(3R)-3-{[(tert-butoxy)carbonyl]amino}piperidine-1-carbonyl]-2-[1-(cyclopropylmethyl)-1H-pyrrolo[2,3-b]pyridin-2-yl]-1-methyl-1H-1,3-benzodiazole-7-carboxylate (EV-AV9626-002, 110 mg, 0.17 mmol) in dioxane (5 ml) in a pressure tube was added ammonium hydroxide (35% w/w, 0.1 ml, 2.54 mmol). The vessel was sealed and heated at 50° C. 2.5 h. More ammonium hydroxide (35% w/w, 0.5 ml) was added and the vessel was sealed and heated at 50° C. for 17 h. More ammonium hydroxide (35% w/w, 0.5 ml) was added and the vessel was sealed and heated at 50° C. for a further 23 h. The reaction mixture was concentrated in vacuo, re-dissolved in DCM and washed with 5% NaOH (aq). The organic fraction was passed through a phase separator cartridge and concentrated in vacuo. The crude residue was purified by preparative HPLC (basic method) to obtain 75 mg (77%) of tert-butyl N-[(3R)-1-{7-carbamoyl-2-[1-(cyclopropylmethyl)-1H-pyrrolo[2,3-b]pyridin-2-yl]-1-methyl-1H-1,3-benzodiazole-5-carbonyl}piperidin-3-yl]carbamate EV-AV9632-002 an off-white powder. LCMS (method D): retention time 1.08 min, M/z=572 (M+1).

5-[(3R)-3-aminopiperidine-1-carbonyl]-2-[1-(cyclopropylmethyl)-1H-pyrrolo[2,3-b]pyridin-2-yl]-1-methyl-1H-1,3-benzodiazole-7-carboxamide hydrochloride EV-AV9635-001 (I-112)—step 3

To tert-butyl N-[(3R)-1-{7-carbamoyl-2-[1-(cyclopropylmethyl)-1H-pyrrolo[2,3-b]pyridin-2-yl]-1-methyl-1H-1,3-benzodiazole-5-carbonyl}piperidin-3-yl]carbamate (EV-AV9632-002, 75 mg, 0.13 mmol) was added 1.25 M HCl in ethanol (3 ml) and the reaction mixture was stirred at 40° C. for 1.5 h. The reaction mixture was concentrated in vacuo and the residue was freeze-dried from water (3 mL) to obtain 57.6 mg (84%) of 5-[(3R)-3-aminopiperidine-1-carbonyl]-2-[1-(cyclopropylmethyl)-1H-pyrrolo[2,3-b]pyridin-2-yl]-1-methyl-1H-1,3-benzodiazole-7-carboxamide hydrochloride EV-AV9635-001 (I-112) as an off-white powder. LCMS (method A): retention time 1.53 min, M/z=472 (M+1).

Special Cases

2-[7-(Cyclopropylmethyl)-7H-pyrrolo[2,3-d]pyrimidin-6-yl]-1-methyl-5-{octahydro-1H-pyrrolo[2,3-c]pyridine-6-carbonyl}-1H-1,3-benzodiazole EV-AQ4191-002 (EOAI3434971) I-9 was synthesised according to the procedures described in Scheme 1, 2-[7-(cyclopropylmethyl)-7H-pyrrolo[2,3-d]pyrimidin-6-yl]-7-methoxy-1-methyl-5-{octahydro-1H-pyrrolo[2,3-c]pyridine-6-carbonyl}-1H-1,3-benzodiazole EV-AS1566-001 (EOAI3435740) I-15, 5-[(3aR,7aR)-octahydro-1H-pyrrolo[2,3-c]pyridine-6-carbonyl]-2-[7-(cyclopropylmethyl)-7H-pyrrolo[2,3-d]pyrimidin-6-yl]-7-methoxy-1-methyl-1H-1,3-benzodiazole EV-AS1590-001 (EOAI3437977) I-12 and 5-[(3aS,7aS)-octahydro-1H-pyrrolo[2,3-c]pyridine-6-carbonyl]-2-[7-(cyclopropylmethyl)-7H-pyrrolo[2,3-d]pyrimidin-6-yl]-7-methoxy-1-methyl-1H-1,3-benzodiazole EV-AS1591-001 (EOAI3437978) I-4 were synthesised according to the procedures described in Scheme 2 via synthesis of methyl 7H-pyrrolo[2,3-d]pyrimidine-6-carboxylate EV-AQ1970-001 described in Scheme 7:

Additional methanol (15 ml) was added to aid dissolution, the mixture was cooled to 0° C. and further thionyl dichloride (0.56 ml, 7.66 mmol) was added dropwise under an atmosphere of nitrogen. The mixture was heated again to reflux for 3 h and evaporated to dryness to obtain 0.66 g (quantitative) of methyl 7H-pyrrolo[2,3-d]pyrimidine-6-carboxylate EV-AQ1970-001 as a pink powder. LCMS (method J): retention time 1.02 min, M/z=178 (M+1).

(3R)-1-{2-[1-(Cyclopropylmethyl)-6-methoxy-1H-pyrrolo[2,3-b]pyridin-2-yl]-1-methyl-1H-1,3-benzodiazole-5-carbonyl}piperidin-3-amine EV-AU3631-001 (EOAI3447868) I-70 was synthesised according to the procedures described in Scheme 1, (3R)-1-{2-[1-(cyclopropylmethyl)-6-methoxy-1H-pyrrolo[2,3-b]pyridin-2-yl]-1-(2,2-difluoroethyl)-7-methoxy-1H-1,3-benzodiazole-5-carbonyl}piperidin-3-amine EV-AV3086-001 (EOAI3454400) I-94 and (3R)-1-{2-[1-(cyclopropylmethyl)-6-methoxy-1H-pyrrolo[2,3-b]pyridin-2-yl]-7-methoxy-1-methyl-1H-1,3-benzodiazole-5-carbonyl}piperidin-3-amine EV-AV4830-003 (EOAI3454405) I-33 were synthesised according to the procedures described in Scheme 2, (3R)-1-{2-[1-(cyclopropylmethyl)-6-methoxy-1H-pyrrolo[2,3-b]pyridin-2-yl]-7-(difluoromethoxy)-1-methyl-1H-1,3-benzodiazole-5-carbonyl}piperidin-3-amine EV-AV3852-001 (EOAI3454816) I-104 and (3R,5R)-1-{2-[1-(cyclopropylmethyl)-6-methoxy-1H-pyrrolo[2,3-b]pyridin-2-yl]-7-(difluoromethoxy)-1-methyl-1H-1,3-benzodiazole-5-carbonyl}-5-fluoropiperidin-3-amine EV-AV4849-001 (EOAI3455105) I-109 were synthesised according to the procedures described in Scheme 3 via synthesis of ethyl 6-methoxy-1H-pyrrolo[2,3-b]pyridine-2-carboxylate EV-AU3621-002 described in Scheme 8:

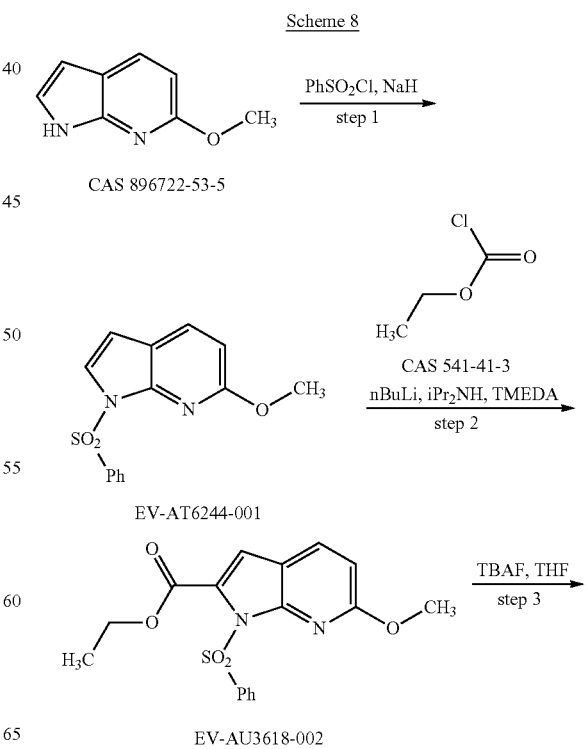

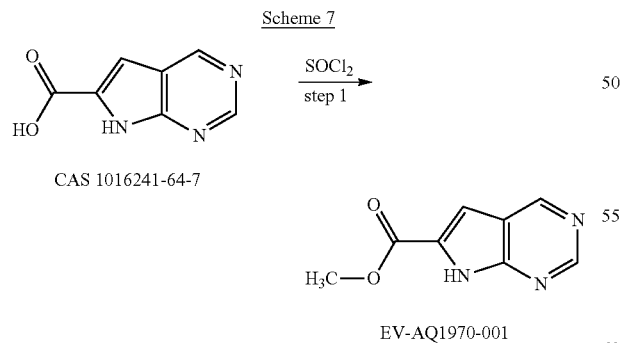

To a stirred suspension of 7H-pyrrolo[2,3-d]pyrimidine-6-carboxylic acid (CAS 1016241-64-7, 0.50 g, 3.06 mmol) in methanol (10 ml) at 0° C. was added thionyl dichloride (0.56 ml, 7.66 mmol) dropwise under an atmosphere of nitrogen. The resulting mixture was allowed to warm to room temperature and then heated up to reflux for 24 h.

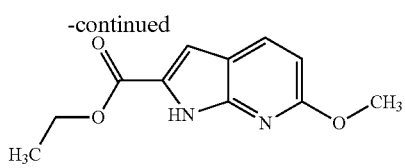

EV-AU3621-002

1-(Benzenesulfonyl)-6-methoxy-1H-pyrrolo[2,3-b]pyridine EV-AT6244-001—step 1

To a stirred solution of 6-methoxy-1H-pyrrolo[2,3-b]pyridine (CAS 896722-53-5, 300 mg, 2.02 mmol) in THF (15 ml) at 0° C. was added sodium hydride (60%, 121 mg, 3.04 mmol) portion-wise under an atmosphere of nitrogen. The resulting mixture was stirred at 0° C. for 30 minutes before the addition of benzenesulfonyl chloride (0.31 ml, 2.44 mmol). The mixture was stirred at room temperature for 2 h. The reaction mixture was poured onto water (20 ml) and extracted with EtOAc (3×10 ml). The combined organic layers were washed with saturated aqueous sodium chloride (20 ml), dried over sodium sulfate, filtered and concentrated in vacuo to afford 607 mg (97.7%) of 1-(benzenesulfonyl)-6-methoxy-1H-pyrrolo[2,3-b]pyridine EV-AT6244-001 as a beige solid. LCMS (method D): retention time 1.26 min, M/z=289 (M+1).

Ethyl 1-(benzenesulfonyl)-6-methoxy-1H-pyrrolo[2,3-b]pyridine-2-carboxylate EV-AU3618-002—step 2

To a stirred solution of diisopropylamine (0.15 ml, 1.04 mmol) in anhydrous THF (5 ml) at −78° C. was added n-butyllithium (2.5M in hexanes, 0.37 ml, 0.94 mmol) drop-wise over 10 minutes under an atmosphere of nitrogen. The resulting mixture was stirred for 30 minutes, warmed to room temperature and stirred for 1 h. The mixture was then diluted with anhydrous THF (5 ml) and cooled to −30° C. A solution of 1-(benzenesulfonyl)-6-methoxy-1H-pyrrolo[2,3-b]pyridine (EV-AT6244-001, 200 mg, 0.69 mmol) and TMEDA (0.16 ml, 1.04 mmol) in anhydrous THF (10 ml) was added via cannula over 20 minutes. The resulting mixture was stirred between −30° C. and −20° C. for 2.5 h. Ethyl chloroformate (CAS 541-41-3, 0.20 ml, 2.08 mmol) was added drop-wise over 10 minutes, the mixture was stirred at −30° C. for 2 h before warming to room temperature over 16 h. The reaction mixture was cooled to 0° C. and quenched with water (15 ml). The aqueous layer was extracted with DCM (3×15 ml), the combined layers were washed with water (3×10 ml), dried over sodium sulfate, filtered and concentrated in vacuo. The crude product was purified by flash column chromatography (0-100% EtOAc/heptane) to obtain 93 mg (36.5%) of ethyl 1-(benzenesulfonyl)-6-methoxy-1H-pyrrolo[2,3-b]pyridine-2-carboxylate EV-AU3618-002 as an off-white solid. LCMS (method D): retention time 1.31 min, M/z=361 (M+1).

Note: the reaction was repeated to obtain an additional batch of ethyl 1-(benzenesulfonyl)-6-methoxy-1H-pyrrolo[2,3-b]pyridine-2-carboxylate (165 mg, 29.6%, EV-AU3619-002) which was combined with EV-AU3618-002 to carry out step 3.

Ethyl 6-methoxy-1H-pyrrolo[2,3-b]pyridine-2-carboxylate EV-AU3621-002—step 3

To a stirred solution of ethyl 1-(benzenesulfonyl)-6-methoxy-1H-pyrrolo[2,3-b]pyridine-2-carboxylate (EV-AU3618-002 and EV-AU3619-002, 84%, 258 mg, 0.60 mmol) in THF (10 ml) was added TBAF (1M in THF, 0.78 ml, 0.78 mmol) and the mixture was stirred at 70° C. for 30 minutes. The reaction mixture was concentrated to around 1/4 volume and purified by flash column chromatography (0-100% EtOAc/heptane) to obtain 95 mg (71.7%) of ethyl 6-methoxy-1H-pyrrolo[2,3-b]pyridine-2-carboxylate EV-AU3621-002 as an off-white powder. LCMS (method D): retention time 1.14 min, M/z=221 (M+1).

Scheme 9

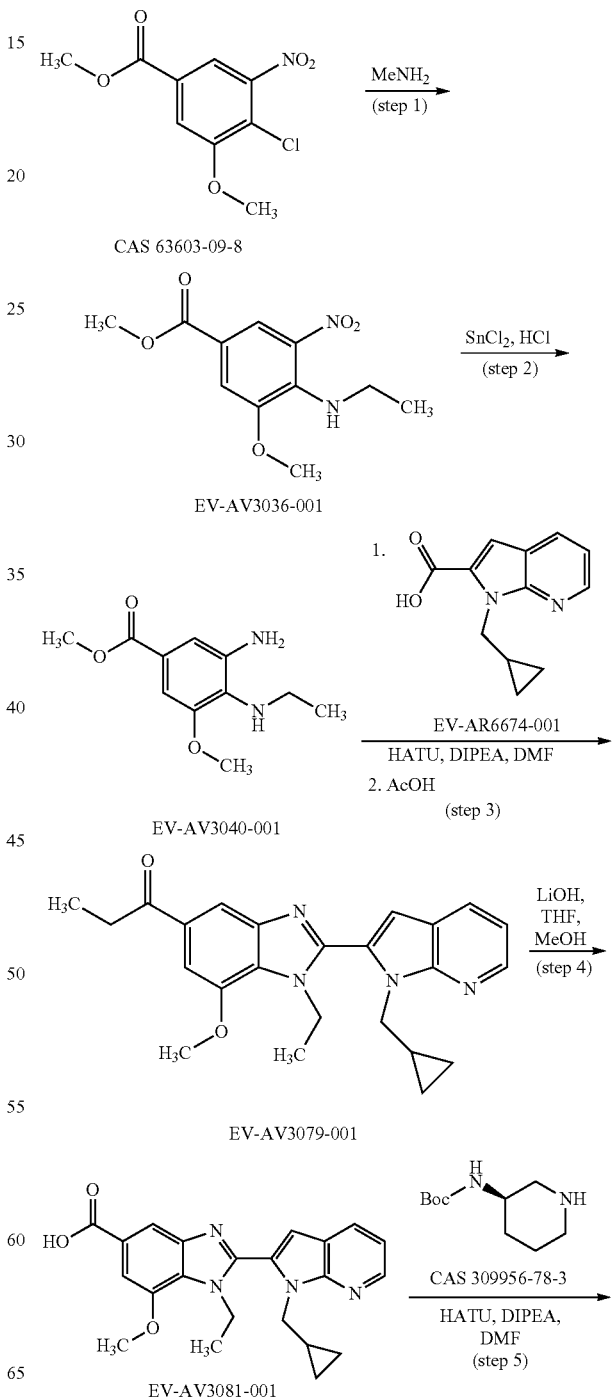

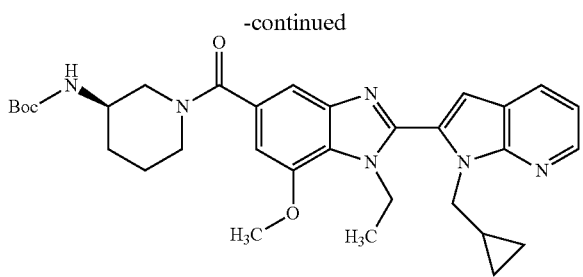

EV-AV3083-001

| HCl
(step 6)

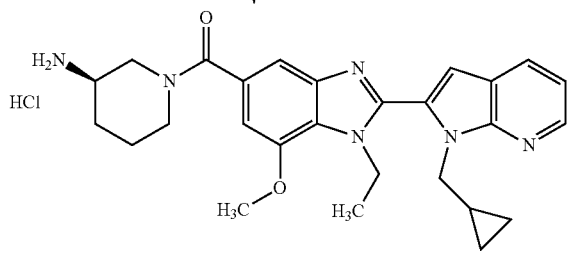

EV-AV3085-001

Synthesis of 1 (3R)-1-{2-[1-(cyclopropylmethyl)-1H-pyrrolo[2,3-b]pyridin-2-yl]-1-ethyl-7-methoxy-1H-1,3-benzodiazole-5-carbonyl}piperidin-3-amine EV-AV3085-001 (EOAI3449644) I-119

I-119

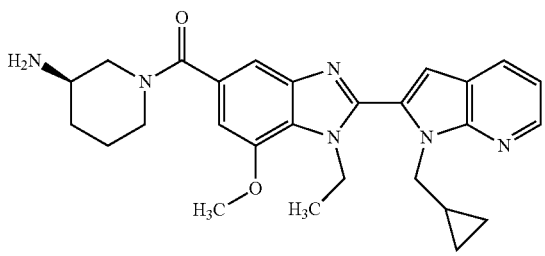

Methyl 4-(ethylamino)-3-methoxy-5-nitrobenzoate EV-AV3036-001—step 1

Ethylamine (2M in THF, 18.3 ml) and potassium carbonate (21.1 g, 152.7 mmol) were added to a stirred solution of methyl 4-chloro-3-methoxy-5-nitrobenzoate (CAS 63603-09-8, 7.50 g, 30.5 mmol) in THF (100 ml). The reaction mixture was stirred at 50° C. for 16 h then at 60° C. for 7 h. Further potassium carbonate (21.1 g, 152.7 mmol) and ethylamine (2M in THF, 7.63 ml) were added and the stirring was continued at room temperature for 60 h. The volatiles were removed in vacuo and the resulting residue was diluted with EtOAc (150 ml), washed with water (2×50 ml) and saturated aqueous sodium chloride (50 ml). The organic layer was dried over sodium sulfate, filtered and concentrated in vacuo to obtain 6.88 g (85%) of methyl 4-(ethyl-amino)-3-methoxy-5-nitrobenzoate EV-AV3036-001 as an orange powder. LCMS (method D): retention time 1.21 min, M/z=255 (M+1).

Methyl 3-amino-4-(ethylamino)-5-methoxybenzoate EV-AV3040-001—step 2

SnCl$_2$ (19.7 g, 103.9 mmol) and 2M HCl (52 ml) were added to a stirred suspension of methyl 4-(ethylamino)-3-methoxy-5-nitrobenzoate (EV-AV3036-001, 6.88 g, 26.0 mmol) in ethanol (150 ml). The reaction mixture was stirred with reflux for 1 h and the volatiles were removed in vacuo. The resulting residue was basified with 5M aqueous sodium hydroxide (50 ml) then diluted with EtOAc (150 ml) and stirred for 15 minutes. The mixture was then filtered through Kieselguhr and the filter was washed with EtOAc. The organic phase of the filtrate was separated and washed with saturated aqueous sodium chloride (50 ml). The organic layer was dried over sodium sulfate and concentrated in vacuo to obtain 4.20 g (71%) of methyl 3-amino-4-(ethylamino)-5-methoxybenzoate EV-AV3040-001 as a brown powder. LCMS (method D): retention time 0.70 min, M/z=225 (M+1).

Methyl 2-[1-(cyclopropylmethyl)-1H-pyrrolo[2,3-b]pyridin-2-yl]-1-ethyl-7-methoxy-1H-1,3-benzodiazole-5-carboxylate EV-AV3079-001—step 3

To a solution of 1-(cyclopropylmethyl)-1H-pyrrolo[2,3-b]pyridine-2-carboxylic acid (EV-AR6674-001, synthesised according to Scheme 1, step 1, 300 mg, 1.36 mmol) in DMF (5 ml) at 0° C. were added HATU (620 mg, 1.63 mmol) and DIPEA (0.47 ml, 2.72 mmol). The mixture was stirred at 0° C. for 10 minutes then 3-amino-4-(ethylamino)-5-methoxybenzoate (EV-AV3040-001, 311 mg, 1.36 mmol). was added. The mixture was heated to 50° C. and stirred for 3 h. The solvent was removed in vacuo, the residue was dissolved in acetic acid (3 ml) and heated in a sealed tube at 80° C. for 2 h. The solvent was removed in vacuo and the crude material was purified by flash column chromatography (0-100% EtOAc/heptane) to obtain 488 mg (76%) of methyl 2-[1-(cyclopropylmethyl)-1H-pyrrolo[2,3-b]pyridin-2-yl]-1-ethyl-7-methoxy-1H-1,3-benzodiazole-5-carboxylate EV-AV3079-001 as a yellow powder. LCMS (method D): retention time 1.31 min, M/z=405 (M+1).

2-[1-(Cyclopropylmethyl)-1H-pyrrolo[2,3-b]pyridin-2-yl]-1-ethyl-7-methoxy-1H-1,3-benzodiazole-5-carboxylic acid EV-AV3081-001—step 4

Methyl 2-[1-(cyclopropylmethyl)-1H-pyrrolo [2,3-b]pyridin-2-yl]-1-ethyl-7-methoxy-1H-1,3-benzodiazole-5-carboxylate (EV-AV3079-001, 488 mg, 1.04 mmol) was dissolved in THF/Methanol (4 ml/1 ml) and 2M aqueous lithium hydroxide (5.19 ml) was added. The mixture was stirred at 40° C. for 16 h and the solvent was removed in vacuo. The resulting residue was dissolved in water (2 ml) and acidified to pH 2 using 2M HCl. The mixture was stirred at room temperature for 10 minutes, the precipitate formed was filtered under vacuum and dried to give 350 mg (80%) of 2-[1-(cyclopropylmethyl)-1H-pyrrolo[2,3-b]pyridin-2-yl]-1-ethyl-7-methoxy-1H-1,3-benzodiazole-5-carboxylic acid EV-AV3081-001 as a white powder. LCMS (method D): retention time 1.14 min, M/z=391 (M+1).

Tert-butyl N-(1-{2-[1-(cyclopropylmethyl)-1H-pyrrolo[2,3-b]pyridin-2-yl]-1-ethyl-7-methoxy-1H-1,3-benzodiazole-5-carbonyl}piperidin-3-yl)carbamate EV-AV3083-001—step 5

HATU (217 mg, 0.57 mmol) and DIPEA (163 µl, 0.95 mmol) were added to a stirred solution of 2-[1-(cyclopropylmethyl)-1H-pyrrolo[2,3-b]pyridin-2-yl]-1-ethyl-7-methoxy-1H-1,3-benzodiazole-5-carboxylic acid (EV-AV3081-001, 200 mg, 0.48 mmol) in DMSO (2 ml) at 0° C. The reaction mixture was stirred at 0° C. for 10 minutes then tert-butyl tert-butyl N-[(3R)-piperidin-3-yl]carbamate (CAS 309956-78-3, 100 mg, 0.50 mmol) was added. The mixture was allowed to warm up to room temperature and stirred for 20 minutes. The crude was purified by preparative HPLC (basic method) to obtain 211 mg (74%) of tert-butyl N-(1-{2-[1-(cyclopropylmethyl)-1H-pyrrolo [2,3-b]pyridin-2-yl]-1-ethyl-7-methoxy-1H-1,3-benzodiazole-5-carbonyl}piperidin-3-yl)carbamate EV-AV3083-001 as a white powder. LCMS (method D): retention time 1.25 min, M/z=573 (M+1).

(3R)-1-{2-[1-(Cyclopropylmethyl)-1H-pyrrolo[2,3-b]pyridin-2-yl]-1-ethyl-7-methoxy-1H-1,3-benzodiazole-5-carbonyl}piperidin-3-amine EV-AV3085-001 (EOAI3449644)—step 6

Tert-butyl N-(1-{2-[1-(cyclopropylmethyl)-1H-pyrrolo[2,3-b]pyridin-2-yl]-1-ethyl-7-methoxy-1H-1,3-benzodiazole-5-carbonyl}piperidin-3-yl)carbamate (EV-AV3083-001, 210 mg, 0.35 mmol) was dissolved in DCM (2 ml) and 2M HCl in diethyl ether (2 ml) was added. The reaction mixture was stirred at room temperature for 2 h and the solvent was removed in vacuo. The residue was re-dissolved in water/acetonitrile (2 ml/0.5 ml), concentrated in vacuo and further dried to give 147 mg (81%) of (3R)-1-{2-[1-(cyclopropylmethyl)-1H-pyrrolo[2,3-b]pyridin-2-yl]-1-ethyl-7-methoxy-1H-1,3-benzodiazole-5-carbonyl}piperidin-3-amine hydrochloric acid EV-AV3085-001 as a yellow powder. LCMS (method A): retention time 2.19 min, M/z=473 (M+1).

(1S,4R,6S,7R)-7-Amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-ol EV-AW5575-001 (EOAI3459241) I-162 was synthesised according to the procedures described in Scheme 3 via synthesis of tert-butyl N-[(1S,4R,6S,7R)-6-hydroxy-2-azabicyclo[2.2.1]heptan-7-yl]carbamate EV-AW5569-001 described in Scheme 10:

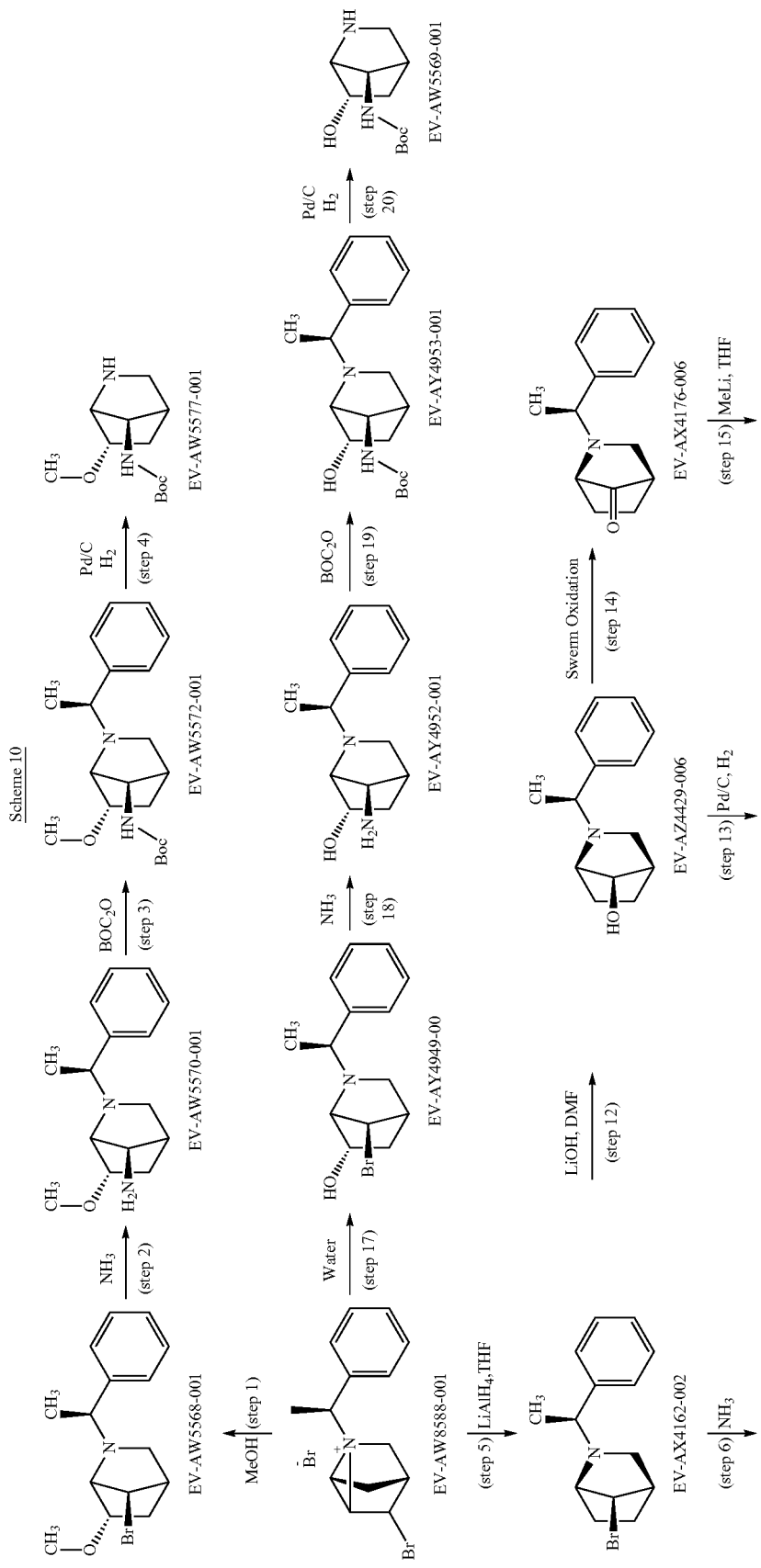

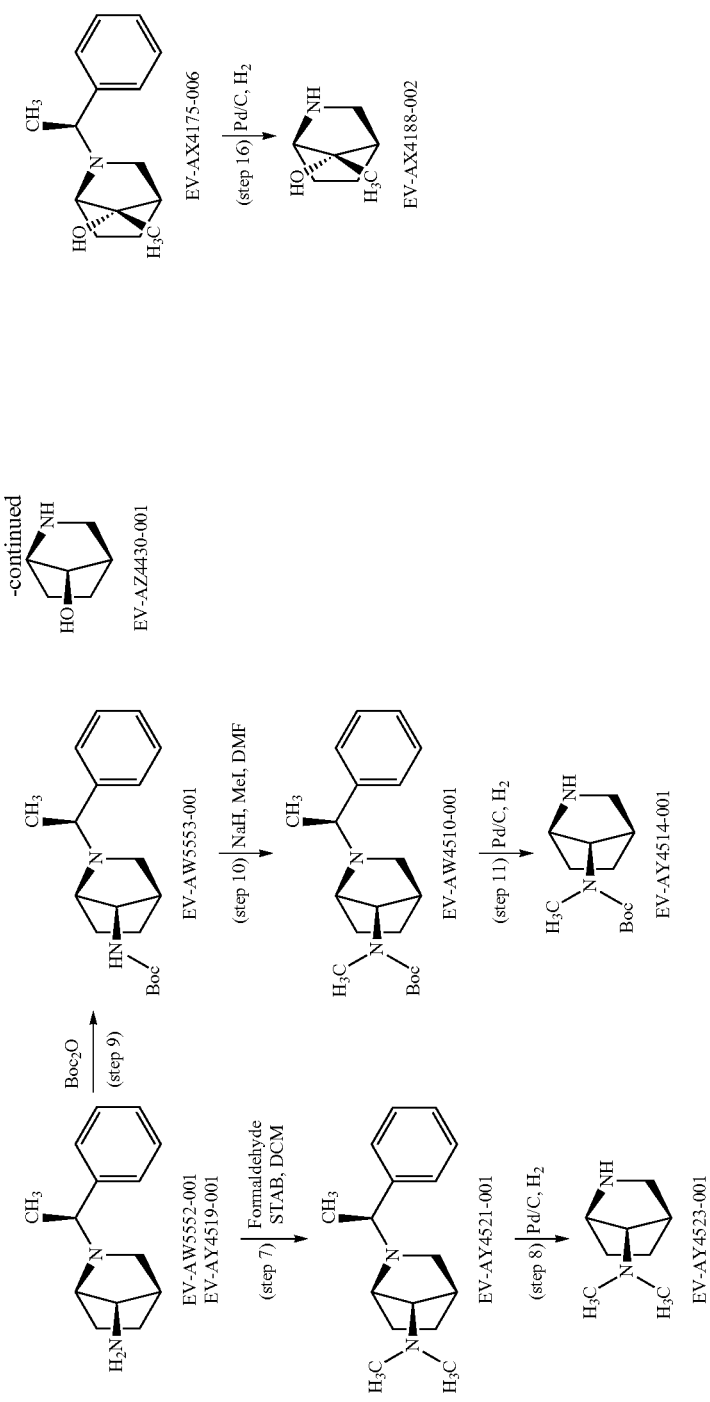

-continued
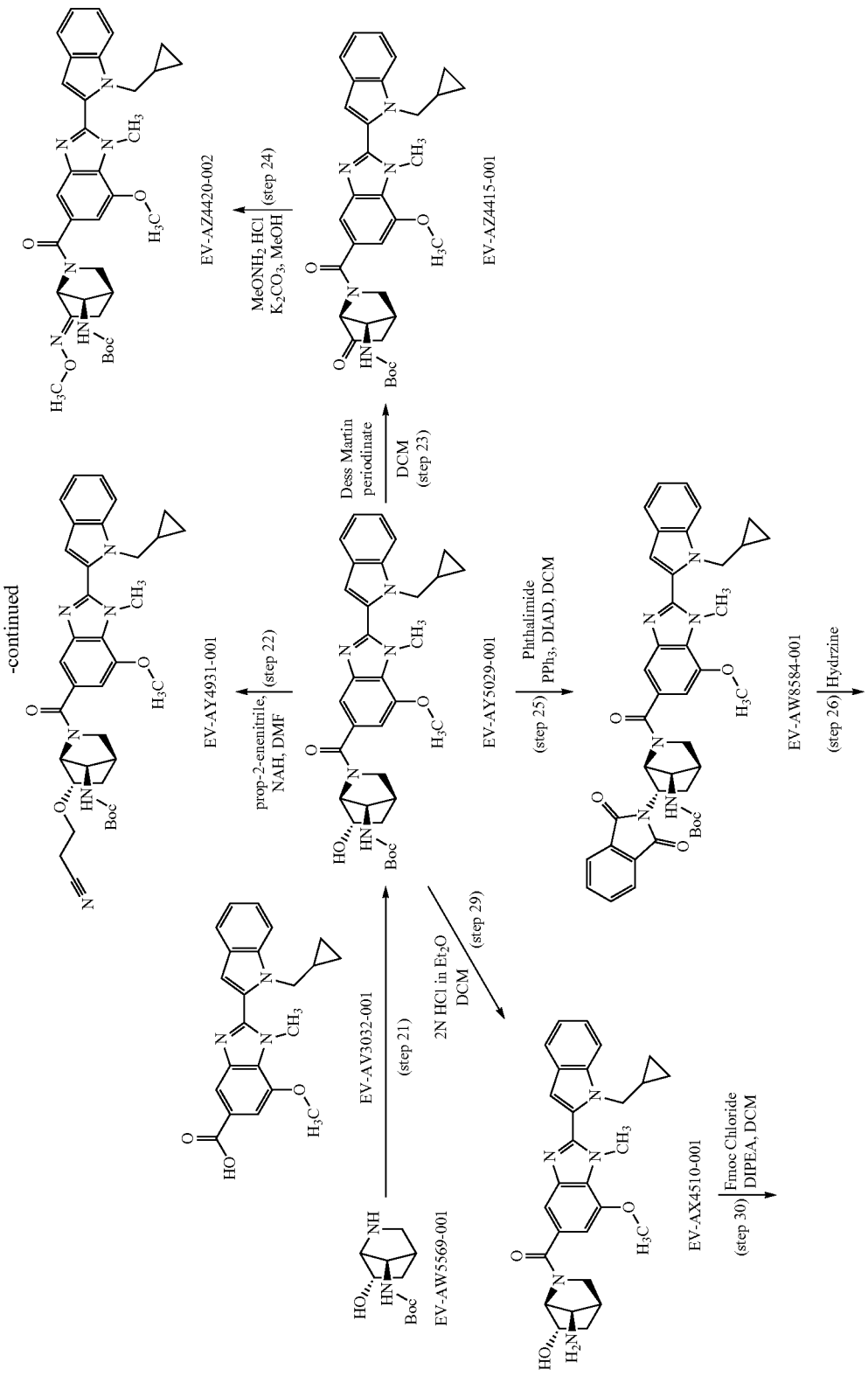

-continued
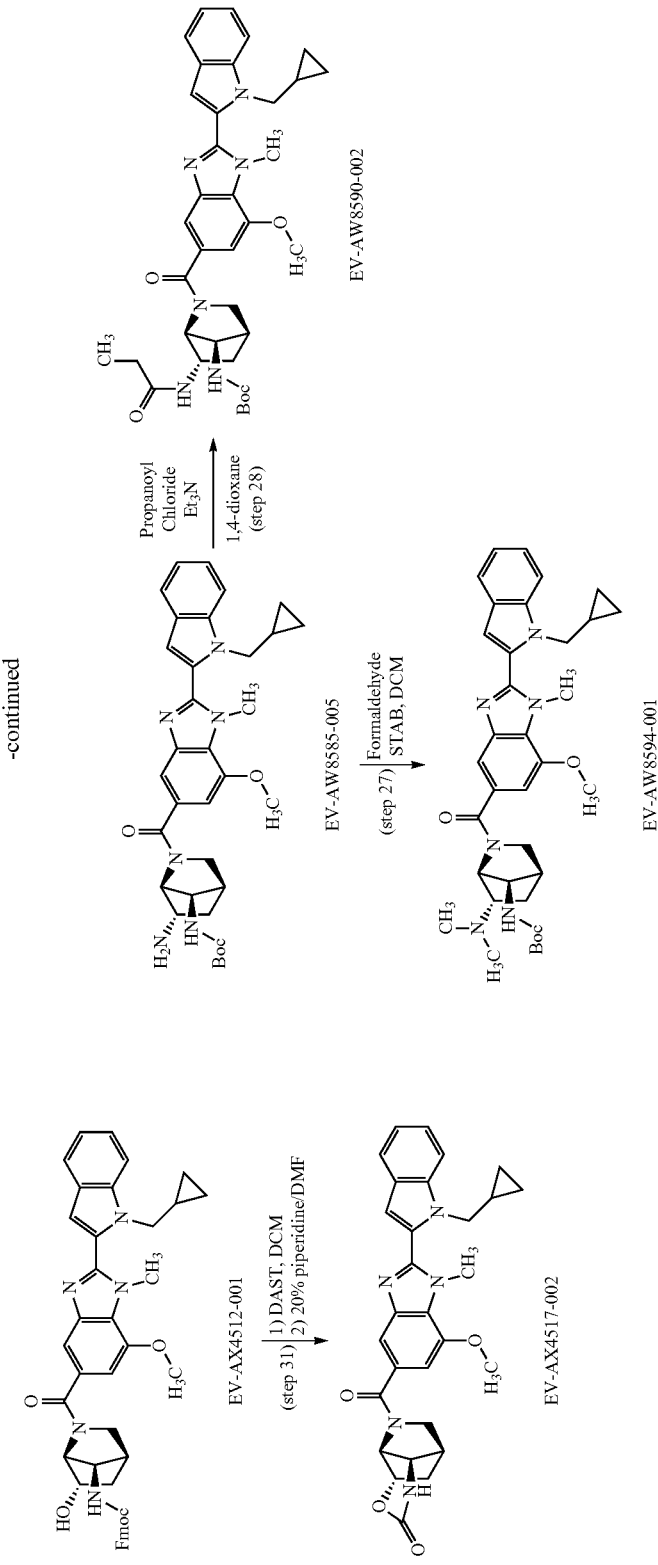

(1S,4R,6S,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-6-methoxy-2-azabicyclo[2.2.1]heptan-7-amine EV-AW5584-001 (EOAI3459405) I-167 was synthesised according to the procedures described in Scheme 3 via synthesis of tert-butyl N-[(1S,4R,6S,7R)-6-methoxy-2-azabicyclo[2.2.1]heptan-7-yl]carbamate EV-AW5577-001 described in Scheme 10.

(1R,4R,6S,7R)-7-bromo-6-methoxy-2-[(1S)-1-phenylethyl]-2-azabicyclo[2.2.1]heptane EV-AW5568-001—step 1 (Scheme 10)

(4R,6R)-3-bromo-1-[(1S)-1-phenylethyl]-1-azatricyclo[2.2.1.0]heptan-1-ium bromide (EV-AW8588-001, 1.00 g, 3.58 mmol) was dissolved in Methanol: acetonitrile (1:1, 40 ml) and the resulting suspension was heated to 65° C. for 12 h. The reaction was concentrated in vacuo and purified by flash column chromatography (0-30% EtOAc/heptane) to afford 0.85 g (98%) of (1R,4R,6S,7R)-7-bromo-6-methoxy-2-[(1S)-1-phenylethyl]-2-azabicyclo[2.2.1]heptane EV-AW5568-001 as an orange oil. LCMS (method D): retention time 0.73 min, M/z=312 (M+1).

(1S,4R,6S,7R)-6-methoxy-2-[(1S)-1-phenylethyl]-2-azabicyclo[2.2.1]heptan-7-amine EV-AW5570-001—step 2 (Scheme 10)

To (1R,4R,6S,7R)-7-bromo-6-methoxy-2-[(1S)-1-phenylethyl]-2-azabicyclo[2.2.1]heptane (EV-AW5568-001, 0.84 g, 2.71 mmol) was added 7M ammonia in methanol (7.74 ml). The solution was stirred for 2 h at 80° C. The reaction mixture was concentrated in vacuo to afford 0.82 g (98%) of (1S,4R,6S,7R)-6-methoxy-2-[(1S)-1-phenylethyl]-2-azabicyclo[2.2.1]heptan-7-amine EV-AW5570-001 as an orange solid. LCMS (method D): retention time 0.27 min, M/z=247 (M+1).

Tert-butyl N-[(1S,4R,6S,7R)-6-methoxy-2-[(1S)-1-phenylethyl]-2-azabicyclo[2.2.1]heptan-7-yl]carbamate EV-AW5572-001—step 3 (Scheme 10)

The title compound was synthesised from (1S,4R,6S,7R)-6-methoxy-2-[(1S)-1-phenylethyl]-2-azabicyclo[2.2.1]heptan-7-amine (EV-AW5570-001) according to the procedure described in Scheme 10 step 19. LCMS (method D): retention time 0.86 min, M/z=347 (M+1).

Tert-butyl N-[(1S,4R,6S,7R)-6-methoxy-2-azabicyclo[2.2.1]heptan-7-yl]carbamate EV-AW5577-001—step 4 (Scheme 10)

The title compound was synthesised from tert-butyl N-[(1S,4R,6S,7R)-6-methoxy-2-[(1S)-1-phenylethyl]-2-azabicyclo[2.2.1]heptan-7-yl]carbamate (EV-AW5572-001) according to the procedure described in Scheme 10 step 20. $^1$H NMR (500 MHz, Chloroform-d) δ 5.78-5.48 (m, 1H), 3.94 (d, J=7.6 Hz, 1H), 3.49 (d, J=6.1 Hz, 1H), 3.34 (s, 3H), 3.22 (s, 1H), 2.99 (d, J=9.2 Hz, 1H), 2.47 (d, J=9.5 Hz, 1H), 2.41 (s, 1H), 1.90 (dd, J=13.5, 7.1 Hz, 1H), 1.75-1.63 (m, 2H), 1.44 (s, 9H). No LCMS data.

(1R,4R,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-N-methyl-2-azabicyclo[2.2.1]heptan-7-amine EV-AY4518-001 (EOAI3462944) I-237 was synthesised according to the procedures described in Scheme 3 via synthesis of tert-butyl N-[(1R,4R,7R)-2-azabicyclo[2.2.1]heptan-7-yl]-N-methylcarbamate EV-AY4514-001 described in Scheme 10.

(1R,4R,7R)-7-bromo-2-[(1S)-1-phenylethyl]-2-azabicyclo[2.2.1]heptane EV-AX4162-002—step 5 (Scheme 10)

To a solution of (4R,6R)-3-bromo-1-[(1S)-1-phenylethyl]-1-azatricyclo[2.2.1.0]heptan-1-ium bromide (EV-AW8588-001, 3.10 g, 8.63 mmol) in anhydrous THF (60 ml) was added 4M lithium aluminium hydride in diethyl ether (2.5 ml, 10 mmol) at −10 to −15° C. The mixture was stirred at −10 to −15° C. for 2 h and quenched with saturated aqueous sodium bicarbonate (60 ml). The mixture was added to water (200 ml) and extracted with ethyl acetate (4×100 ml). The combined extracts were washed with saturated aqueous sodium chloride (100 ml), dried over magnesium sulfate, filtered and concentrated in vacuo to give 2.11 g (87%) of (1R,4R,7R)-7-bromo-2-[(1S)-1-phenylethyl]-2-azabicyclo[2.2.1]heptane EV-AX4162-002 as a brown oil. LCMS (method D): retention time 0.81 min, M/z=279.95/281.85 (M+1).

(1R,4R,7R)-2-[(1S)-1-Phenylethyl]-2-azabicyclo[2.2.1]heptan-7-amine EV-AW5552-001—step 6 (Scheme 10)

The title compound was synthesised from (1R,4R,7R)-7-bromo-2-[(1S)-1-phenylethyl]-2-azabicyclo[2.2.1]heptane (EV-AX4162-002) according to the procedure described in Scheme 10 step 2. LCMS (method D): retention time 0.20 min, M/z=217 (M+1).

Tert-butyl N-[(1R,4R,7R)-2-[(1S)-1-phenylethyl]-2-azabicyclo[2.2.1]heptan-7-yl]carbamate EV-AW5553-001—step 9 (Scheme 10)

The title compound was synthesised from (1R,4R,7R)-2-[(1S)-1-phenylethyl]-2-azabicyclo[2.2.1]heptan-7-amine (EV-AW5552-001) according to the procedure described in Scheme 10 step 19. LCMS (method D): retention time 0.83 min, M/z=317 (M+1).

Tert-butyl N-methyl-N-[(1R,4R,7R)-2-[(1S)-1-phenylethyl]-2-azabicyclo[2.2.1]heptan-7-yl]carbamate EV-AY4510-001—step 10 (Scheme 10)

To a stirred solution of tert-butyl N-[(1R,4R,7R)-2-[(1S)-1-phenylethyl]-2-azabicyclo[2.2.1]heptan-7-yl]carbamate (EV-AW5553-001, 100 mg, 0.32 mmol) in DMF (2 ml) under an atmosphere of nitrogen was added sodium hydride (60%, 15 mg, 0.38 mmol) followed by iodomethane (39 μL, 0.63 mmol). The reaction mixture was stirred at room temperature for 16 h, diluted with water (30 ml) and extracted with EtOAc (2×30 ml). The combined organic extracts were dried over sodium sulfate, filtered and concentrated in vacuo to obtain 110 mg (quantitative) of tert-butyl N-methyl-N-[(1R,4R,7R)-2-[(1S)-1-phenylethyl]-2-azabicyclo[2.2.1]heptan-7-yl]carbamate EV-AY4510-001 as a colourless viscous oil. LCMS (method D): retention time 1.06 min, M/z=331 (M+1).

Tert-butyl N-[(1R,4R,7R)-2-azabicyclo[2.2.1]heptan-7-yl]-N-methylcarbamate EV-AY4514-001—step 11 (Scheme 10)

The title compound was synthesised from tert-butyl N-methyl-N-[(1R,4R,7R)-2-[(1S)-1-phenylethyl]-2-azabicyclo[2.2.1]heptan-7-yl]carbamate (EV-AY4510-001) according to the procedure described in Scheme 10 step 20. ¹H NMR (500 MHz, Methanol-d4) δ 4.56 (s, 1H), 4.33 (s, 1H), 3.61 (s, 1H), 3.22 (d, J=10.9 Hz, 1H), 2.98 (d, J=11.1 Hz, 1H), 2.92-2.87 (m, 3H), 2.82 (s, 1H), 1.98-1.83 (m, 2H), 1.81-1.72 (m, 1H), 1.63-1.56 (m, 1H), 1.48 (s, 9H). No LCMS data.

(1R,4R,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-N,N-dimethyl-2-azabicyclo[2.2.1]heptan-7-amine EV-AY4524-001 (EOAI3468840) I-243 was synthesised according to the procedures described in Scheme 3 via synthesis of tert-butyl N-[(1R,4R,7R)-2-azabicyclo[2.2.1]heptan-7-yl]-N-methylcarbamate EV-AY4523-001 described in Scheme 10:

(1R,4R,7R)—N,N-dimethyl-2-[(1S)-1-phenylethyl]-2-azabicyclo[2.2.1]heptan-7-amine EV-AY4521-001—step 7 (Scheme 10)

To a stirred solution of (1R,4R,7R)-2-[(1 S)-1-phenylethyl]-2-azabicyclo[2.2.1]heptan-7-amine dihydrochloride (EV-AY4519-001, 210 mg, 0.73 mmol) (synthesised in Scheme 10, step 6) in DCM (10 ml) under an atmosphere of nitrogen was added an aqueous solution of formaldehyde (37%, 0.27 ml, 3.63 mmol) followed by STAB (923 mg, 4.36 mmol). The reaction mixture was stirred at room temperature for 16 h, diluted with water (30 ml) and extracted with EtOAc (2×30 ml). The combined organic extracts were dried over sodium sulfate, filtered and concentrated in vacuo to obtain 189 mg (quantitative) of (1R,4R,7R)—N,N-dimethyl-2-[(1S)-1-phenylethyl]-2-azabicyclo[2.2.1]heptan-7-amine (EV-AY4521-001) as a colourless viscous oil. ¹H NMR (500 MHz, DMSO-d₆) δ 7.39-7.12 (m, 6H), 3.57 (s, 1H), 3.01 (s, 1H), 2.84 (s, 1H), 2.31-2.12 (m, 3H), 2.07-1.95 (m, 6H), 1.67 (s, 2H), 1.36 (s, 1H), 1.23-1.12 (m, 3H). No LCMS data.

Tert-butyl N-[(1R,4R,7R)-2-azabicyclo[2.2.1]heptan-7-yl]-N-methylcarbamate EV-AY4523-001—step 8 (Scheme 10)

The title compound was synthesised from (1R,4R,7R)—N,N-dimethyl-2-[(1S)-1-phenylethyl]-2-azabicyclo[2.2.1]heptan-7-amine (EV-AY4521-001) according to the procedure described in Scheme 10 step 20. ¹H NMR (500 MHz, DMSO-d₆) δ 2.41 (s, 1H), 2.12 (dt, J=9.8, 3.0 Hz, 1H), 1.79 (d, J=9.8 Hz, 1H), 1.49 (s, 1H), 1.47-1.37 (m, 7H), 1.10-0.99 (m, 2H), 0.71-0.61 (m, 1H), 0.58-0.48 (m, 1H). No LCMS data.

3-{[(1S,4R,6S,7R)-7-Amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]oxy}propanenitrile EV-AY4932-001 (EOAI3472707) I-256 was synthesised according to the procedures described in Scheme 3 via synthesis of tert-butyl N-[(1 S,4R,6S,7R)-6-(2-cyanoethoxy)-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AY4931-001 described in Scheme 10. The final deprotection was performed according to the procedures described in Scheme 1.

Tert-butyl N-[(1S,4R,6S,7R)-6-(2-cyanoethoxy)-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AY4931-001—step 22 (Scheme 10)

To a stirred solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 120 mg, 0.18 mmol) in DMF (3 ml) at 0° C. was added sodium hydride (60%, 7.8 mg, 0.20 mmol). The reaction was stirred for 5 minutes then prop-2-enenitrile (12 μl, 0.18 mmol) was added. The reaction was stirred at room temperature for 2 h. The solvent was removed in vacuo and the residue was partitioned between EtOAc (10 ml) and water (10 ml). The aqueous layer was extracted with EtOAc (2×5 ml) and the combined organics were washed with water (5 ml), dried over sodium sulfate and concentrated in vacuo. The crude was purified by preparative HPLC (acidic method) to obtain 80 mg (67%) of tert-butyl N-[(1S,4R,6S,7R)-6-(2-cyanoethoxy)-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AY4931-001 as a colourless oil. LCMS (method D): retention time 1.28 min, M/z=640 (M+1).

2-{[(1 S,4R,6S,7R)-7-Amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]oxy}acetonitrile EV-AY4925-001 (EOAI3470051) I-246 was synthesised according to the procedure described in Scheme 10 step 22 using bromoacetonitrile. The final deprotection was performed according to the procedures described in Scheme 1. LCMS (method A): retention time 2.05 min, M/z=526 (M+1).

1S,4R,6E,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-6-(methoxyimino)-2-azabicyclo[2.2.1]heptan-7-amine EV-AZ4422-001 (EOAI3482317) I-307 was synthesised according to the N-Boc deprotection procedure described in Scheme 3 via synthesis of N-[(1 S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(methoxyimino)-2-azabicyclo[2.2.1]heptan-7-yl]carbamate EV-AZ4420-002 described in Scheme 10:

Tert-butyl N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-oxo-2-azabicyclo[2.2.1]heptan-7-yl]carbamate EV-AZ4415-001—step 23 (Scheme 10)

To a solution of tert-butyl N-[(1 S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 490 mg, 0.84 mmol) in DCM (10 ml) at 0° C. was added Dess-Martin periodinane (710 mg, 1.67 mmol) and the reaction was allowed to warm to room temperature. The reaction mixture was stirred for 24 h, quenched with saturated aqueous sodium thiosulfate (10 ml) and extracted with DCM (3×20 ml). The combined organic layers were dried over sodium sulfate, filtered and concentrated in vacuo. The remaining residue was purified by preparative HPLC (acidic method) to afford 471 mg (89%) of tert-butyl N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-oxo-2-azabicyclo[2.2.1]heptan-7-yl]carbamate EV-AZ4415-001 as a white solid. LCMS (method D): retention time 1.25 min, M/z=585 (M+1).

N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(methoxyimino)-2-azabicyclo[2.2.1]heptan-7-yl]carbamate EV-AZ4420-002—step 24 (Scheme 10)

To a suspension of tert-butyl N-[(1S,4R,7R)-2-{2-[1-(cyclopropylmethyl)-1H-pyrrolo[2,3-b]pyridin-2-yl]-7- methoxy-1-methyl-1H-1,3-benzodiazole-5-carbonyl}-6-oxo-2-azabicyclo[2.2.1]heptan-7-yl]carbamate (EV-AZ4415-001, 50 mg, 0.08 mmol) in methanol (1 ml) was added O-methylhydroxylamine HCl (6.7 mg, 0.08 mmol) and sodium bicarbonate (6.6 mg, 0.08 mmol). The reaction was heated at 65° C. for 15 h before cooling to room temperature. Further O-methylhydroxylamine HCl (6.7 mg, 0.08 mmol) and sodium bicarbonate (6.6 mg, 0.08 mmol) were added after 2 h and the reaction was continued at 65° C. for an additional 6 h. The temperature was reduced to 60° C. and the reaction was stirred for 16 h. The reaction mixture was cooled to room temperature and the solvent was removed in vacuo. The resulting yellow oil was purified by preparative HPLC (acidic method) to afford 12 mg (26%) of N-[(1S,4R,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(methoxyimino)-2-azabicyclo[2.2.1]heptan-7-yl]carbamate EV-AZ4420-002 as a white solid. LCMS (method D): retention time 1.30 min, M/z=614 (M+1).

(1R,4R,6S,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptane-6,7-diamine EV-AY5019-001, (EOAI3469927) I-245 was synthesised according to the procedures described in Scheme 3 via synthesis of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AW8585-005 described in Scheme 10.

Tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate EV-AW8584-001—step 25 (Scheme 10)

DIAD (107 µl, 0.51 mmol) was added to a stirred solution of triphenylphosphane (134 mg, 0.51 mmol) in anhydrous THF (5 ml) under an atmosphere of nitrogen at 0° C. The reaction was stirred at 0° C. for 5 minutes then a solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AY5029-001, 200 mg, 0.34 mmol) in anhydrous THF (5 ml) was added followed by 1H-isoindole-1,3(2H)-dione (41 µl, 0.34 mmol). The reaction mixture was stirred at room temperature for 18 h, concentrated in vacuo and purified by flash column chromatography (0-100% EtOAc/heptane) to obtain 138 mg (48%) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate EV-AW8584-001 as a white foam. LCMS (method D): retention time 1.28 min, M/z=716 (M+1).

Tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AW8585-005—step 26 (Scheme 10)

To a solution of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(1,3-dioxo-2,3-dihydro-1H-isoindol-2-yl)-2-azabicyclo[2.2.1]heptan-7-yl]carbamate (EV-AW8584-001, 134 mg, 0.19 mmol) in DCM (3 ml) was added hydrazine hydrate (1:1) (27 µl, 0.56 mmol). The reaction mixture was stirred at room temperature for 45 minutes and at 50° C. for 18 h, filtered and the filtrate was concentrated in vacuo. EtOAc (10 ml) was added to the residue and the mixture was stirred for 5 minutes then filtered. The filtrate was concentrated in vacuo and purified by flash column chromatography (20-100% EtOAc/heptane) to obtain 75 mg (63%) of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate EV-AW8585-005 as a white foam. LCMS (method D): retention time 1.05 min, M/z=586 (M+1).

(1S,4R,6S,7R)-2-{2-[1-(Cyclopropylmethyl)-1H-pyrrolo[2,3-b]pyridin-2-yl]-7-methoxy-1-methyl-1H-1,3-benzodiazole-5-carbonyl}-N6,N6-dimethyl-2-azabicyclo[2.2.1]heptane-6,7-diamine EV-AW8596-002 (EOAI3476814) I-268 was synthesised according to the procedures described in Scheme 3 via synthesis of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(dimethylamino)-2-azabicyclo[2.2.1]heptan-7-yl]carbamate EV-AW8594-001 as described in Scheme 10.

Tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(dimethylamino)-2-azabicyclo[2.2.1]heptan-7-yl]carbamate EV-AW8594-001—step 27 (Scheme 10)

To a stirred mixture of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate (EV-AW8585-005, 80 mg, 0.12 mmol) in DCM (1 ml) at room temperature was added 3M formaldehyde solution (37% in WATER, 10 µl). The reaction mixture was stirred for 15 minutes then sodium tris(acetato-kappaO)(hydrido)borate (1-) (37 mg, 0.18 mmol) was added. The reaction was continued for 17 h. Additional sodium tris(acetato-kappaO)(hydrido)borate(1-) (37 mg, 0.18 mmol) was added and the reaction continued for 2 h. The solvent was removed in vacuo and the residue was purified by preparative HPLC (acidic method) to afford 20 mg (28%) of tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-(dimethylamino)-2-azabicyclo[2.2.1]heptan-7-yl]carbamate EV-AW8594-001 as a white solid. LCMS (method D): retention time 1.16 min, M/z=614 (M+1).

N-[(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-yl]propanamide EV-AW8592-002 (EOAI3476589) I-264 was synthesised according to the procedures described in Scheme 3 via synthesis of tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-propanamido-2-azabicyclo[2.2.1]heptan-7-yl]carbamate EV-AW8590-002 as described in Scheme 10.

Tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-propanamido-2-azabicyclo[2.2.1]heptan-7-yl]carbamate EV-AW8590-002—step 28 (Scheme 10)

To a stirred solution of tert-butyl N-[(1R,4R,6S,7R)-6-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]carbamate (EV-AW8585-005, 62 mg, 0.10 mmol) in dioxane (3 ml) was added triethylamine (16 µl, 0.12 mmol) followed by propanoyl chloride (10 µl, 0.12 mmol). The reaction mixture was stirred at room temperature for 30 minutes. The reaction mixture was concentrated in vacuo and purified by preparative HPLC (acidic method) to afford 34 mg (50%) of tert-butyl N-[(1R,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-propanamido-2-azabicyclo[2.2.1]heptan-7-yl]carbamate EV-AW8590-002 as a white solid. LCMS (method D): 1.19 min, M/z=642 (M+1).

(1S,2R,8R)-10-{2-[1-(Cyclopropylmethyl)-1H-pyrrolo[2,3-b]pyridin-2-yl]-7-methoxy-1-methyl-1H-1,3-benzodiazole-5-carbonyl}-5-oxa-3,10-diazatricyclo[4.4.0.0$^{2,8}$]decan-4-one EV-AX4517-002 (EOAI3460130) I-187 was synthesised according to the procedures described in Scheme 10:

(1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-ol EV-AX4510-001—step 29 (Scheme 10)

The title compound was synthesised from tert-butyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate EV-AY5029-001 according to the procedures described in Scheme 9 step 6. LCMS (method D): retention time 0.92 min, M/z=487.15 (M+1).

9H-Fluoren-9-ylmethyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate EV-AX4513-001—step 30 (Scheme 10)

To a solution of (1S,4R,6S,7R)-7-amino-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-6-ol (EV-AX4510-001, 112 mg, 0.21 mmol) in DCM (2 ml) were added DIPEA (0.11 ml, 0.64 mmol) and FMOC chloride (83 mg, 0.32 mmol) at 0° C. The resulting mixture was stirred at 0° C. for 2 h, saturated aqueous sodium bicarbonate (1 ml) was added and the aqueous layer was extracted with DCM (2×1 ml). The combined organic fractions were dried over sodium sulphate, filtered and concentrated in vacuo. The crude was purified by preparative HPLC (acidic method) to obtain 47 mg (31%) of 9H-fluoren-9-ylmethyl N-[(1 S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate EV-AX4513-001 as a white solid. LCMS (method D): retention time 1.33 min, M/z=409.4 (M+1).

(1S,2R,8R)-10-{2-[1-(cyclopropylmethyl)-H-pyrrolo[2,3-b]pyridin-2-yl]-7-methoxy-1-methyl-1H-1,3-benzodiazole-5-carbonyl}-5-oxa-3,10-diazatricyclo[4.4.0.0$^{2,8}$]decan-4-one EV-AX4517-002—step 31 (Scheme 10)

To a solution of 9H-fluoren-9-ylmethyl N-[(1S,4R,6S,7R)-2-{2-[1-(cyclopropylmethyl)-1H-pyrrolo[2,3-b]pyridin-2-yl]-7-methoxy-1-methyl-1H-1,3-benzodiazole-5-carbonyl}-6-hydroxy-2-azabicyclo[2.2.1]heptan-7-yl]carbamate (EV-AX4513-001, 46 mg, 0.06 mmol) in DCM (1 ml) was added N-ethyl-N-(trifluoro-lambda-4-1-sulfanyl)ethanamine (34 µl, 0.26 mmol) at −78° C. under atmosphere of nitrogen and the reaction was stirred at −78° C. for 1 h. The reaction was warmed up to room temperature and stirred for a further 12 h. Saturated aqueous sodium bicarbonate (5 ml) was added and the aqueous layer was extracted with DCM (2×5 ml). The combined organic extracts were dried over sodium sulfate, filtered and concentrated in vacuo. The resulting residue was dissolved in 20% piperidine in DMF (2 ml) and the solution stirred at room temperature under an atmosphere of nitrogen for 2 h. The reaction mixture was concentrated in vacuo and purified by preparative HPLC (basic method) to obtain 16 mg (55%) of (1 S,2R,8R)-10-{2-[1-(cyclopropylmethyl)-1H-pyrrolo[2,3-b]pyridin-2-yl]-7-methoxy-1-methyl-1H-1,3-benzodiazole-5-carbonyl}-5-oxa-3,10-diazatricyclo[4.4.0.0$^{2,8}$]decan-4-one EV-AX4517-002 as a white solid. LCMS (method A): retention time 2.90 min, M/z=513.2 (M+1).

N-[(7R)-2-{2-[1-(Cyclopropylmethyl)-1H-pyrrolo[2,3-b]pyridin-2-yl]-7-methoxy-1-methyl-H-1,3-benzodiazole-5-carbonyl}-2-azabicyclo[2.2.1]heptan-7-yl]ethanimidamide EV-AZ7933-001 (EOAI3669061) I-340 was synthesised according to the procedures described in Scheme 10.1:

Scheme 10.1

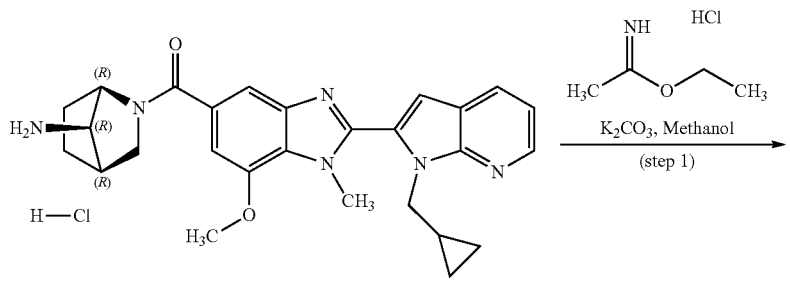

EV-AU9363-001

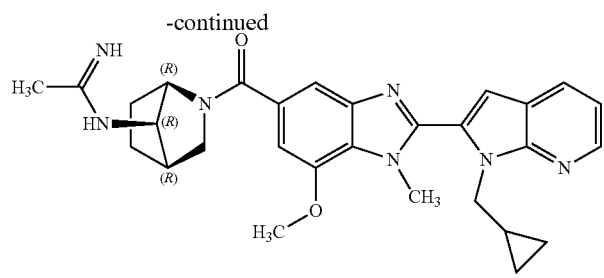

EV-AZ7933-001

N-[(7R)-2-{2-[1-(Cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]ethanimidamide EV-AZ7933-001—step 1

To a stirred solution of (7R)-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-amine hydrochloride (EV-AU9363-001 synthesised according to the procedures described in Scheme 3, 140 mg, 0.28 mmol) in Methanol (5 ml), was added potassium carbonate (153 mg, 1.10 mmol) and the reaction mixture was stirred at room temperature for 24 h. The mixture was filtered and the filtrate was concentrated in vacuo. The residue was purified by prep HPLC (basic method initially followed by re-purification with acidic method) to obtain 27 mg (18%) of N-[(7R)-2-{2-[1-(cyclopropylmethyl)-1H-pyrrolo[2,3-b]pyridin-2-yl]-7-methoxy-1-methyl-1H-1,3-benzodiazole-5-carbonyl}-2-azabicyclo[2.2.1]heptan-7-yl]ethanimidamide formate salt EV-AZ7933-001 as a white powder. LCMS (method A): retention time 2.05 min, M/z=512.3 (M+1).

The following compounds were synthesised according to procedures described above:

| Structure | # | Mol Wt | LCMS T_ret | M/z (+) | LCMS Method | Salt | Salt Stoichoimetry |
|---|---|---|---|---|---|---|---|
| (structure) | I-1 | 428.529 | 1.64 min | 429 | A | TFA | 1 |
| (structure) | I-2 | 453.579 | 2.19 min | 454 | A | HCl | 1 |
| (structure) | I-3 | 458.555 | 1.83 min | 459 | A | HCl | 1 |
| (structure) | I-4 | 485.581 | 1.53 min | 486 | A | TFA | 1 |

-continued

| # | Structure | Mol Wt | LCMS T$_{ret}$ | M/z (+) | LCMS Method | Salt | Salt Stoichiometry |
|---|---|---|---|---|---|---|---|
| I-5 | 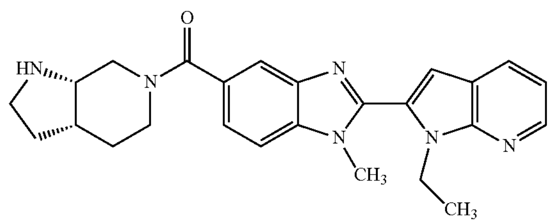 [SMILES: CCn1c(-c2nc3cc(C(=O)N4CC[C@@H]5CCN[C@@H]5C4)ccc3n2C)cc2cccnc21] | 428.529 | 1.65 min | 429 | A | N/A | N/A |
| I-6 | 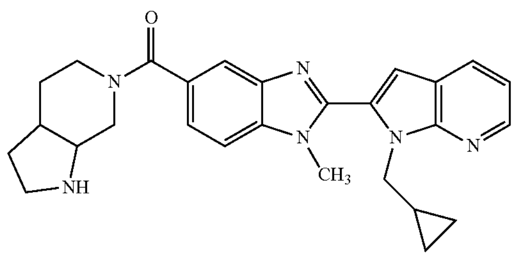 [SMILES: Cn1c(-c2cc3cccnc3n2CC2CC2)nc2cc(C(=O)N3CCC4CCNC4C3)ccc21] | 454.567 | 1.83 min | 455 | A | N/A | N/A |
| I-7 | 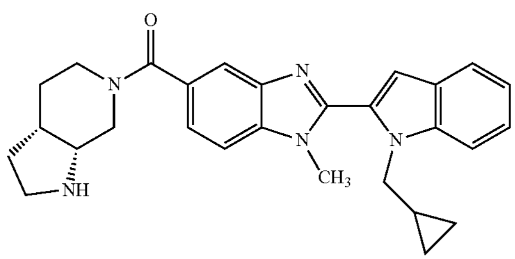 [SMILES: Cn1c(-c2cc3ccccc3n2CC2CC2)nc2cc(C(=O)N3CC[C@H]4CCN[C@H]4C3)ccc21] | 453.579 | 2.17 min | 454 | A | HCl | 1 |

-continued
| # | Structure | Mol Wt | LCMS T_ret | M/z (+) | LCMS Method | Salt | Salt Stoichiometry |
|---|---|---|---|---|---|---|---|
| I-8 | 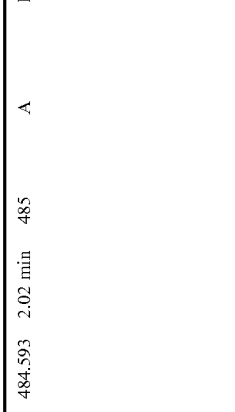 | 484.593 | 2.02 min | 485 | A | HCl | 1 |
| I-9 | 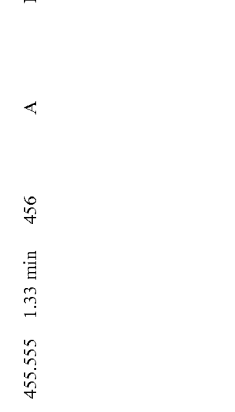 | 455.555 | 1.33 min | 456 | A | N/A | N/A |
| I-10 | 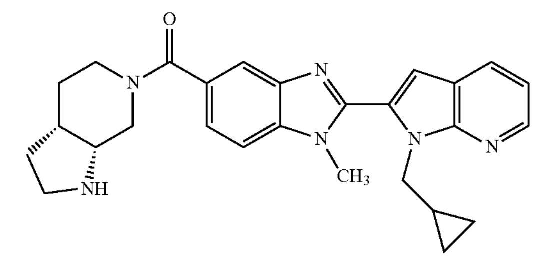 [SMILES: Cn1c(-c2cc3cccnc3n2CC2CC2)nc2cc(C(=O)N3CC[C@H]4CCN[C@H]4C3)ccc21] | 454.567 | 2.64 min | 455 | B | HCl | 1 |

-continued

| # | Structure | Mol Wt | LCMS $T_{ret}$ | M/z (+) | LCMS Method | Salt | Salt Stoichoimetry |
|---|---|---|---|---|---|---|---|
| I-11 | 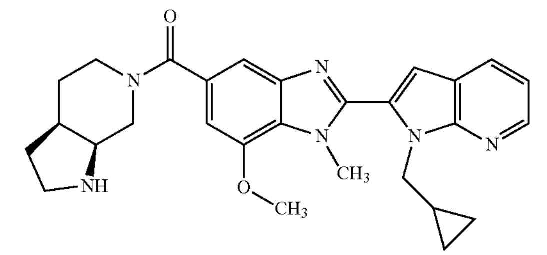 [SMILES: COc1cc(C(=O)N2CC[C@@H]3CCN[C@@H]3C2)cc2nc(-c3cc4cccnc4n3CC3CC3)n(C)c12] | 484.593 | 2.01 min | 485 | A | HCl | 1 |
| I-12 | 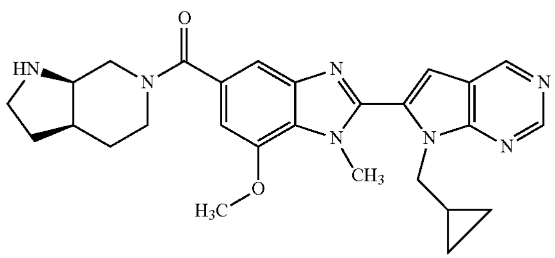 [SMILES: COc1cc(C(=O)N2CC[C@H]3CCN[C@H]3C2)cc2nc(-c3cc4cncnc4n3CC3CC3)n(C)c12] | 485.581 | 1.52 min | 486 | A | TFA | 1 |
| I-13 | 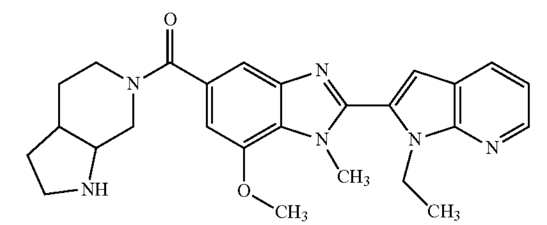 [SMILES: CCn1c(-c2nc3cc(C(=O)N4CCC5CCNC5C4)cc(OC)c3n2C)cc2cccnc21] | 458.555 | 1.80 min | 459 | A | HCl | 1 |
| I-14 | 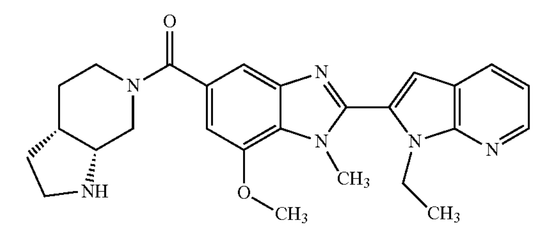 | 458.555 | 1.82 min | 459 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-15 | 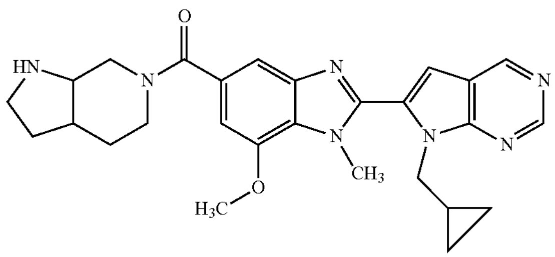 [SMILES: COc1cc(C(=O)N2CCC3CCNC3C2)cc2nc(-c3cc4cncnc4n3CC3CC3)n(C)c12] | 485.581 | 1.52 min | 486 | A | N/A | N/A |
| I-16 | 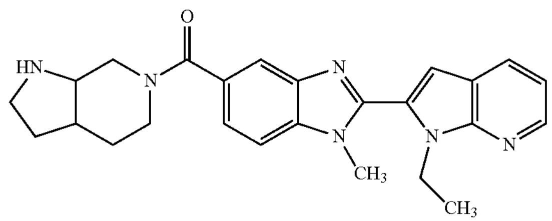 | 428.529 | 1.64 min | 429 | A | TFA | 1 |
| I-17 | 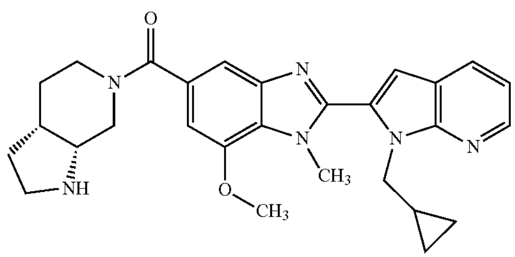 | 484.593 | 2.03 min | 485 | A | HCl | 1 |
| I-18 | 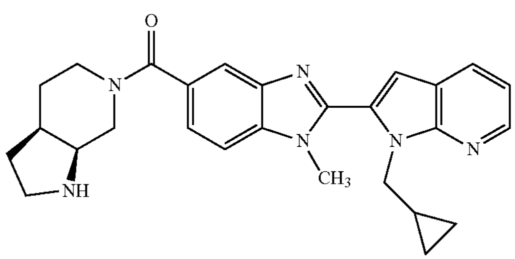 [SMILES: Cn1c(-c2cc3cccnc3n2CC2CC2)nc2cc(C(=O)N3CC[C@@H]4CCN[C@@H]4C3)ccc21] | 454.567 | 2.71 min | 455 | B | HCl | 1 |

-continued

| Structure | # | Mol Wt | LCMS T$_{ret}$ | M/z (+) | LCMS Method | Salt | Salt Stoichiometry |
|---|---|---|---|---|---|---|---|
| 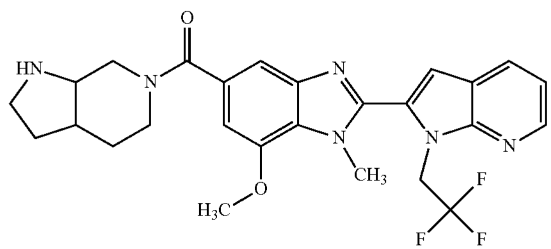 [SMILES: COc1cc(C(=O)N2CCC3CCNC3C2)cc2nc(-c3cc4cccnc4n3CC(F)(F)F)n(C)c12] | I-19 | 512.527 | 2.12 min | 513 | A | HCl | 1 |
| 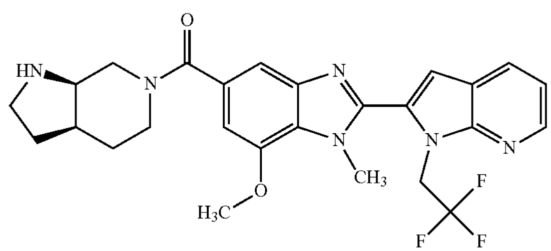 [SMILES: COc1cc(C(=O)N2CC[C@H]3CCN[C@H]3C2)cc2nc(-c3cc4cccnc4n3CC(F)(F)F)n(C)c12] | I-20 | 512.527 | 2.11 min | 513 | A | HCl | 1 |
| 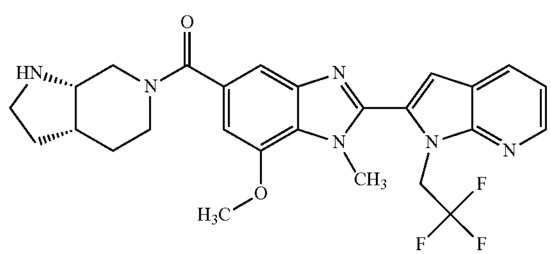 [SMILES: COc1cc(C(=O)N2CC[C@@H]3CCN[C@@H]3C2)cc2nc(-c3cc4cccnc4n3CC(F)(F)F)n(C)c12] | I-21 | 512.527 | 2.11 min | 513 | A | HCl | 1 |

| # | Structure | Mol Wt | LCMS T$_{ret}$ | M/z (+) | LCMS Method | Salt | Salt Stoichiometry |
|---|---|---|---|---|---|---|---|
| I-22 | 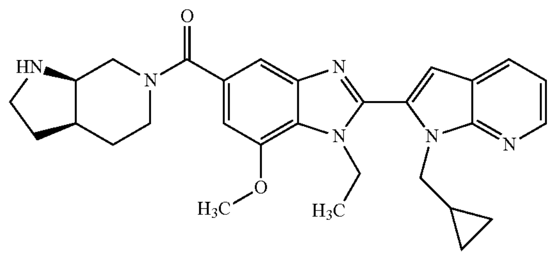 [SMILES: CCn1c(-c2cc3cccnc3n2CC2CC2)nc2cc(C(=O)N3CC[C@H]4CCN[C@H]4C3)cc(OC)c21] | 498.619 | 2.26 min | 499 | A | HCl | 1 |
| I-23 | 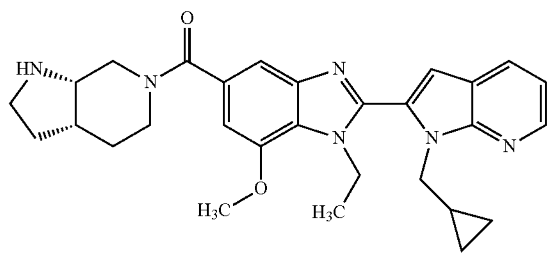 [SMILES: CCn1c(-c2cc3cccnc3n2CC2CC2)nc2cc(C(=O)N3CC[C@@H]4CCN[C@@H]4C3)cc(OC)c21] | 498.619 | 2.26 min | 499 | A | HCl | 1 |
| I-24 | 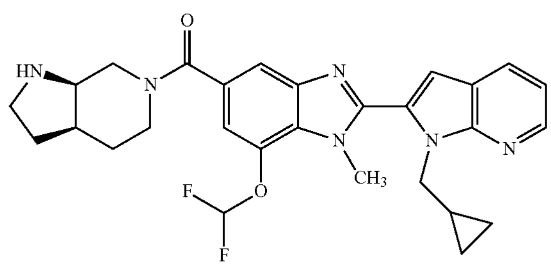 [SMILES: Cn1c(-c2cc3cccnc3n2CC2CC2)nc2cc(C(=O)N3CC[C@H]4CCN[C@H]4C3)cc(OC(F)F)c21] | 520.574 | 2.23 min | 521 | A | HCl | 1 |

-continued

| # | Structure | Mol Wt | LCMS T_ret | M/z (+) | LCMS Method | Salt | Salt Stoichiometry |
|---|---|---|---|---|---|---|---|
| I-25 | 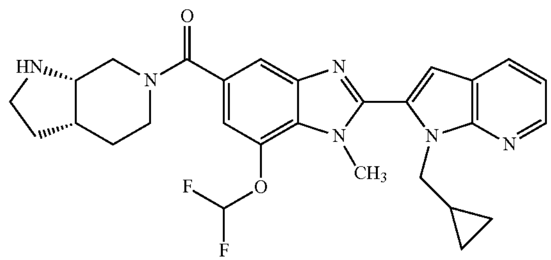 [SMILES: Cn1c(-c2cc3cccnc3n2CC2CC2)nc2cc(C(=O)N3CC[C@@H]4CCN[C@@H]4C3)cc(OC(F)F)c21] | 520.574 | 2.26 min | 521 | A | HCl | 1 |
| I-26 | 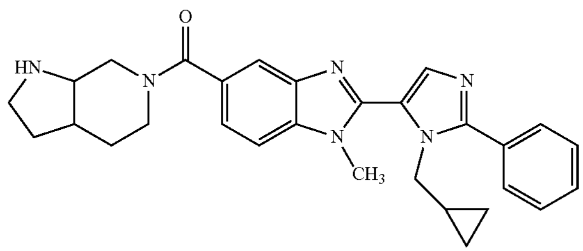 [SMILES: Cn1c(-c2cnc(-c3ccccc3)n2CC2CC2)nc2cc(C(=O)N3CCC4CCNC4C3)ccc21] | | 1.42 min | 481 | A | HCl | 1 |
| I-27 | 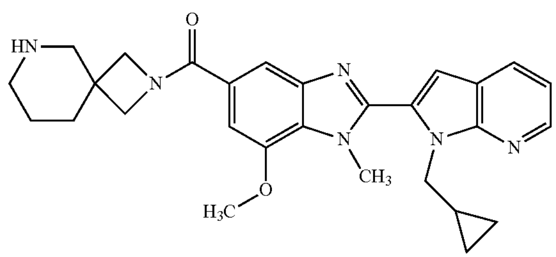 [SMILES: COc1cc(C(=O)N2CC3(CCCNC3)C2)cc2nc(-c3cc4cccnc4n3CC3CC3)n(C)c12] | | 2.09 min | 485 | A | | |

-continued

| # | Structure | Mol Wt | LCMS $T_{ret}$ | M/z (+) | LCMS Method | Salt | Salt Stoichiometry |
|---|---|---|---|---|---|---|---|
| I-28 | 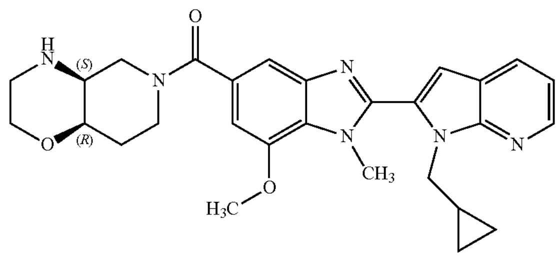 | | 2.11 min | 501 | A | | |
| I-29 | 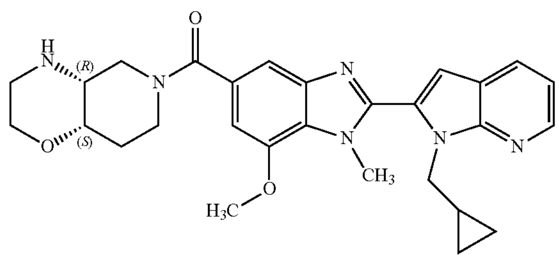 | | 2.11 min | 501 | A | | |
| I-30 | 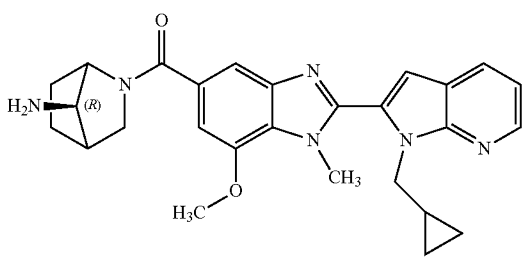 | | 1.97 min | 471 | A | HCl | 1 |

-continued

| # | Structure | Mol Wt | LCMS T$_{ret}$ | LCMS M/z (+) | LCMS Method | Salt | Salt Stoichiometry |
|---|---|---|---|---|---|---|---|
| I-31 | 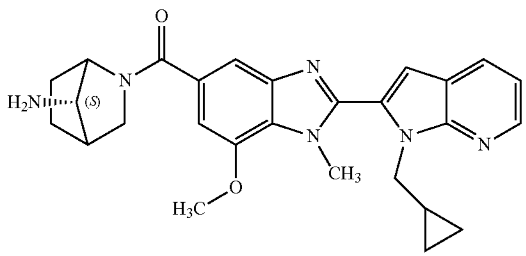 | | 1.96 min | 471 | A | HCl | 1 |
| I-32 | 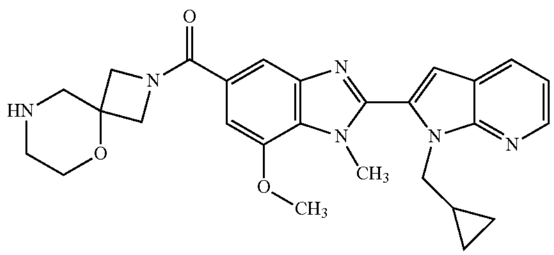 [SMILES: COc1cc(C(=O)N2CC3(CNCCO3)C2)cc2nc(-c3cc4cccnc4n3CC3CC3)n(C)c12] | | 2.07 min | 487 | A | HCl | 1 |
| I-33 | 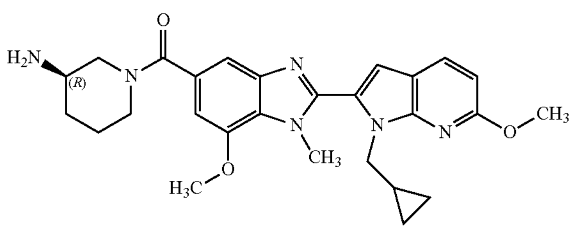 | | 2.41 min | 489 | A | | |
| I-34 | 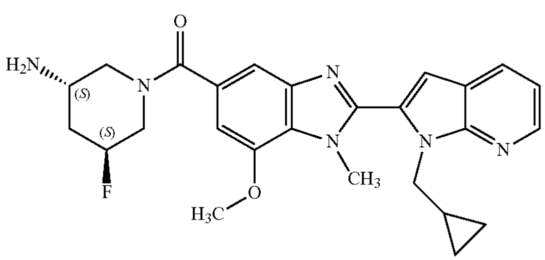 | | 2.08 min | 477 | A | HCl | 1 |

-continued

| # | Structure | Mol Wt | LCMS T_ret | M/z (+) | LCMS Method | Salt | Salt Stoichiometry |
|---|---|---|---|---|---|---|---|
| I-35 | 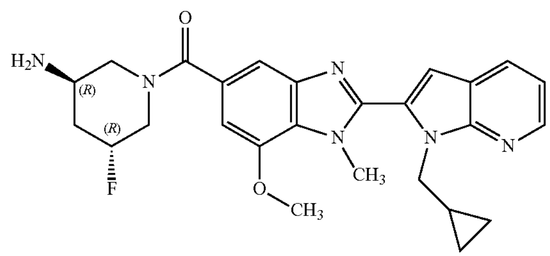 | | 2.04 min | 477 | A | HCl | 1 |
| I-36 | 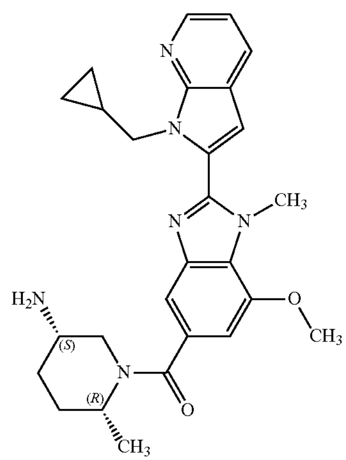 | | 3.02 min | 473 | C | HCl | 1 |
| I-37 | 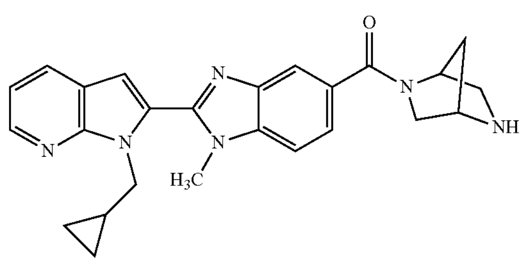 [SMILES: Cn1c(-c2cc3cccnc3n2CC2CC2)nc2cc(C(=O)N3CC4CC3CN4)ccc21] | | 1.70 min | 427 | A | HCl | 1 |

-continued

| Structure | # | Mol Wt | LCMS T_ret | M/z (+) | LCMS Method | Salt | Salt Stoichiometry |
|---|---|---|---|---|---|---|---|
| 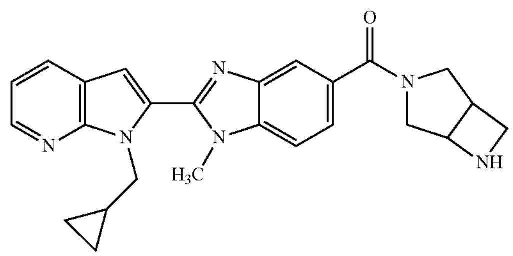 [SMILES: Cn1c(-c2cc3cccnc3n2CC2CC2)nc2cc(C(=O)N3CC4CNC4C3)ccc21] | I-38 | | 1.68 min | 427 | A | HCl | 1 |
| 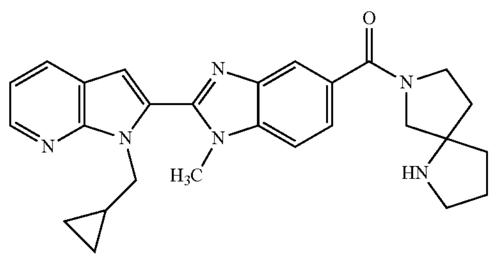 [SMILES: Cn1c(-c2cc3cccnc3n2CC2CC2)nc2cc(C(=O)N3CCC4(CCCN4)C3)ccc21] | I-39 | | 1.77 min | 455 | A | HCl | 1 |
| 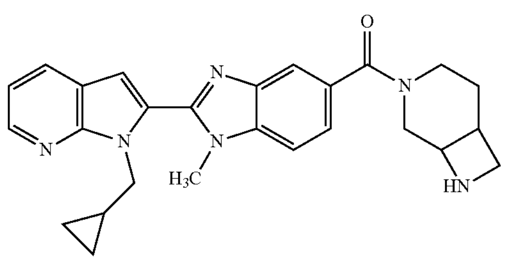 [SMILES: Cn1c(-c2cc3cccnc3n2CC2CC2)nc2cc(C(=O)N3CCC4CNC4C3)ccc21] | I-40 | | 1.76 min | 441 | A | | |

-continued

| # | Structure | Mol Wt | LCMS T$_{ret}$ | LCMS M/z (+) | LCMS Method | Salt | Salt Stoichiometry |
|---|---|---|---|---|---|---|---|
| I-41 | 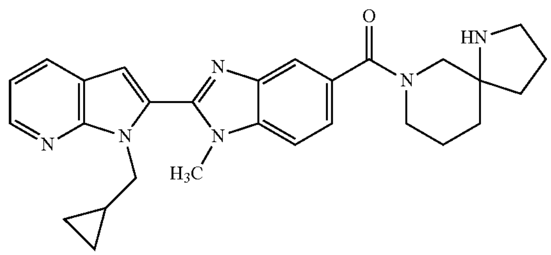 [SMILES: Cn1c(-c2cc3cccnc3n2CC2CC2)nc2cc(C(=O)N3CCCC4(CCCN4)C3)ccc21] | | 1.87 min | 469 | A | | |
| I-42 | 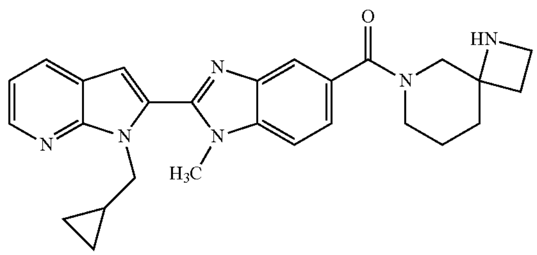 [SMILES: Cn1c(-c2cc3cccnc3n2CC2CC2)nc2cc(C(=O)N3CCCC4(CCN4)C3)ccc21] | | 2.72 min | 455 | C | | |
| I-43 | 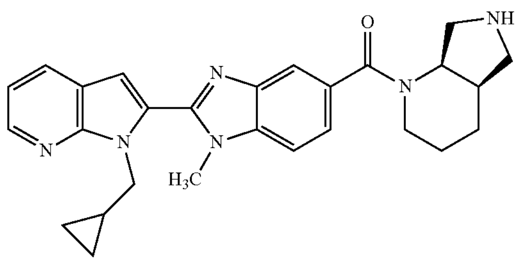 [SMILES: Cn1c(-c2cc3cccnc3n2CC2CC2)nc2cc(C(=O)N3CCC[C@@H]4CNC[C@@H]43)ccc21] | | 1.87 min | 455 | A | TFA | 1 |

-continued

| # | Structure | Mol Wt | LCMS T$_{ret}$ | M/z (+) | LCMS Method | Salt | Salt Stoichiometry |
|---|---|---|---|---|---|---|---|
| I-44 | 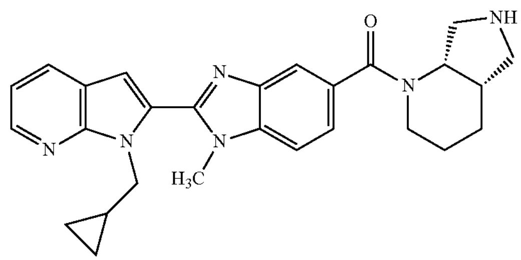 [SMILES: Cn1c(-c2cc3cccnc3n2CC2CC2)nc2cc(C(=O)N3CCC[C@H]4CNC[C@H]43)ccc21] | | 1.88 min | 455 | A | TFA | 1 |
| I-45 | 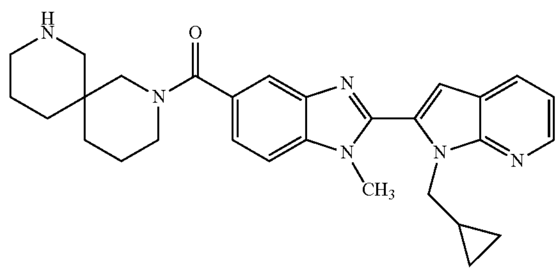 [SMILES: Cn1c(-c2cc3cccnc3n2CC2CC2)nc2cc(C(=O)N3CCCC4(CCCNC4)C3)ccc21] | | 2.00 min | 483 | A | TFA | 1 |
| I-46 | 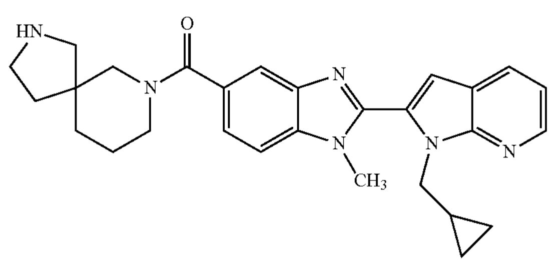 [SMILES: Cn1c(-c2cc3cccnc3n2CC2CC2)nc2cc(C(=O)N3CCCC4(CCNC4)C3)ccc21] | | 1.93 min | 469 | A | TFA | 1 |

| # | Structure | Mol Wt | LCMS T$_{ret}$ | M/z (+) | LCMS Method | Salt | Salt Stoichiometry |
|---|---|---|---|---|---|---|---|
| I-47 | 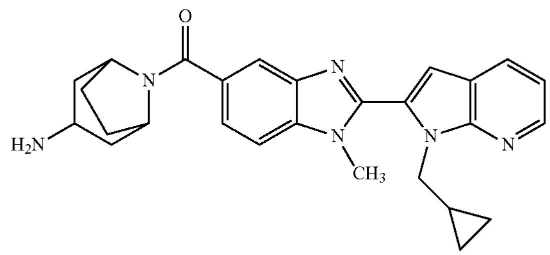 [SMILES: Cn1c(-c2cc3cccnc3n2CC2CC2)nc2cc(C(=O)N3C4CCC3CC(N)C4)ccc21] | | 1.81 min | 455 | A | TFA | 1 |
| I-48 | 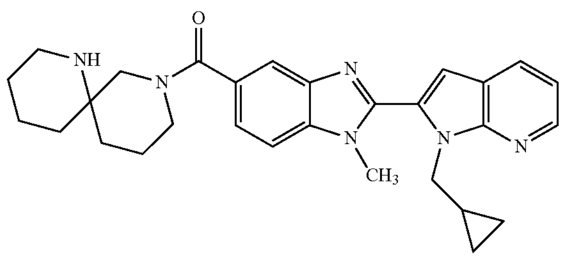 [SMILES: Cn1c(-c2cc3cccnc3n2CC2CC2)nc2cc(C(=O)N3CCCC4(CCCCN4)C3)ccc21] | | 1.94 min | 483 | A | TFA | 1 |
| I-49 | 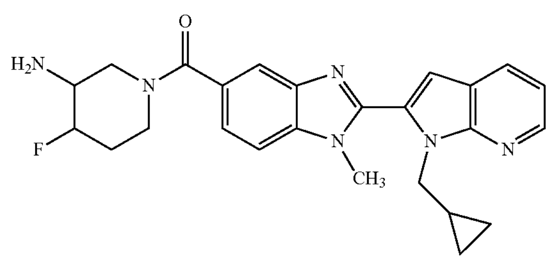 [SMILES: Cn1c(-c2cc3cccnc3n2CC2CC2)nc2cc(C(=O)N3CCC(F)C(N)C3)ccc21] | | 1.82 min | 447 | A | TFA | 1 |

-continued

| # | Structure | Mol Wt | LCMS T$_{ret}$ | M/z (+) | LCMS Method | Salt | Salt Stoichiometry |
|---|---|---|---|---|---|---|---|
| I-50 | 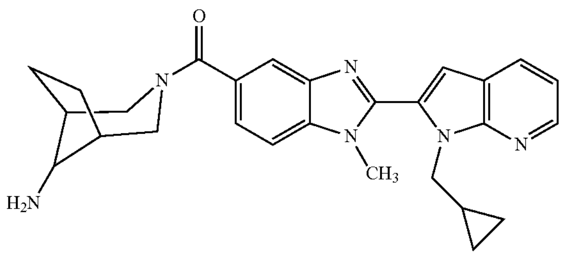 [SMILES: Cn1c(-c2cc3cccnc3n2CC2CC2)nc2cc(C(=O)N3CC4CCC(C3)C4N)ccc21] | | 1.83 min | 455 | A | TFA | 1 |
| I-51 | 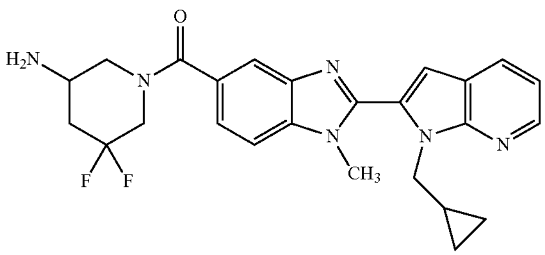 [SMILES: Cn1c(-c2cc3cccnc3n2CC2CC2)nc2cc(C(=O)N3CC(N)CC(F)(F)C3)ccc21] | | 1.94 min | 465 | A | | |
| I-52 | 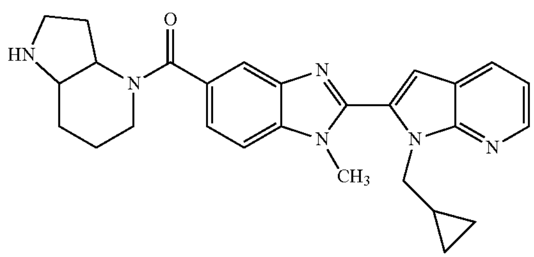 [SMILES: Cn1c(-c2cc3cccnc3n2CC2CC2)nc2cc(C(=O)N3CCCC4NCCC43)ccc21] | | 1.84 min | 455 | A | HCl | 1 |

-continued

| # | Structure | Mol Wt | LCMS T$_{ret}$ | M/z (+) | LCMS Method | Salt | Salt Stoichoimetry |
|---|---|---|---|---|---|---|---|
| I-53 | 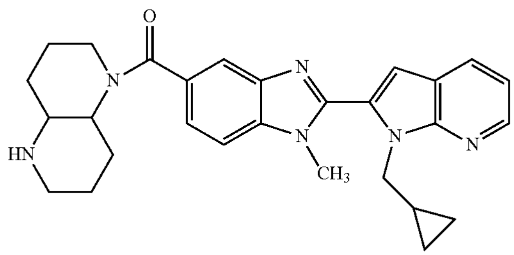 [SMILES: Cn1c(-c2cc3cccnc3n2CC2CC2)nc2cc(C(=O)N3CCCC4NCCCC43)ccc21] | | 2.76 min | 469 | C | TFA | 1 |
| I-54 | 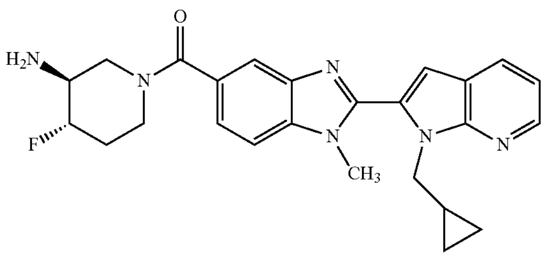 [SMILES: Cn1c(-c2cc3cccnc3n2CC2CC2)nc2cc(C(=O)N3CC[C@H](F)[C@@H](N)C3)ccc21] | | 3.05 min | 447 | C | TFA | 1 |
| I-55 | 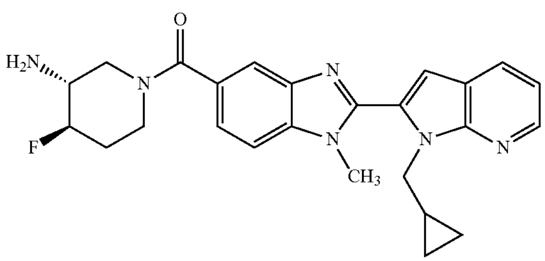 [SMILES: Cn1c(-c2cc3cccnc3n2CC2CC2)nc2cc(C(=O)N3CC[C@@H](F)[C@H](N)C3)ccc21] | | 3.08 min | 447 | C | TFA | 1 |

-continued

| # | Structure | Mol Wt | LCMS T$_{ret}$ | M/z (+) | LCMS Method | Salt | Salt Stoichiometry |
|---|---|---|---|---|---|---|---|
| I-56 | 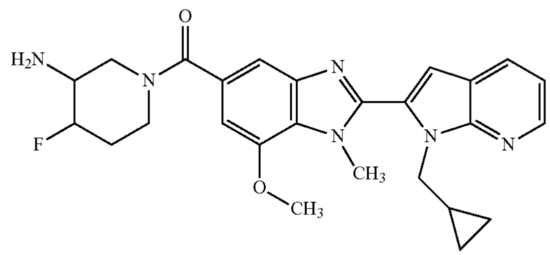 [SMILES: COc1cc(C(=O)N2CCC(F)C(N)C2)cc2nc(-c3cc4cccnc4n3CC3CC3)n(C)c12] | | 2.03 min | 477 | A | HCl | 1 |
| I-57 | 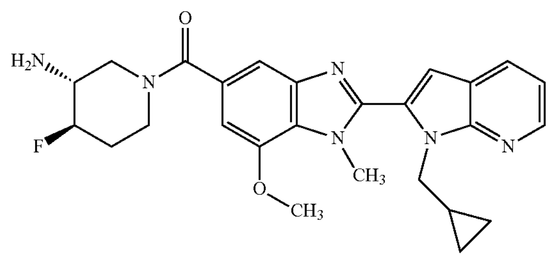 [SMILES: COc1cc(C(=O)N2CC[C@@H](F)[C@H](N)C2)cc2nc(-c3cc4cccnc4n3CC3CC3)n(C)c12] | | 2.03 min | 477 | A | | |
| I-58 | 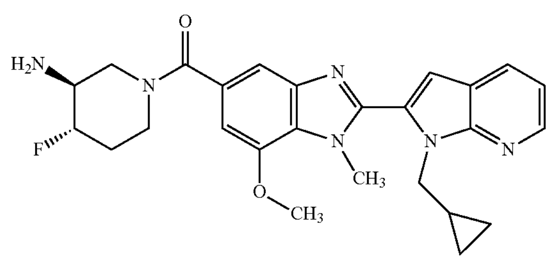 [SMILES: COc1cc(C(=O)N2CC[C@H](F)[C@@H](N)C2)cc2nc(-c3cc4cccnc4n3CC3CC3)n(C)c12] | | 2.04 min | 477 | A | | |

-continued

| # | Structure | Mol Wt | LCMS T_ret | M/z (+) | LCMS Method | Salt | Salt Stoichiometry |
|---|---|---|---|---|---|---|---|
| I-59 | 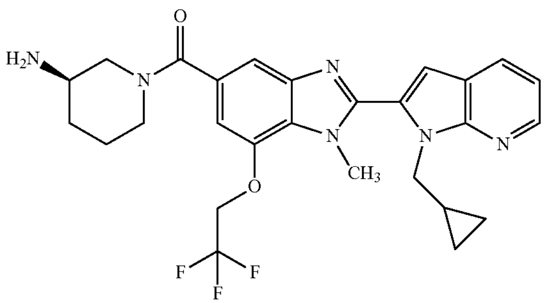 [SMILES: Cn1c(-c2cc3cccnc3n2CC2CC2)nc2cc(C(=O)N3CCC[C@@H](N)C3)cc(OCC(F)(F)F)c21] | | 2.35 min | 527 | A | HCl | 1 |
| I-60 | 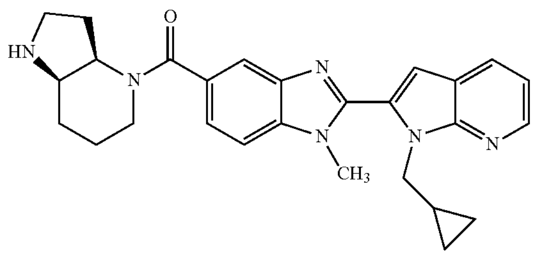 [SMILES: Cn1c(-c2cc3cccnc3n2CC2CC2)nc2cc(C(=O)N3CCC[C@H]4NCC[C@H]43)ccc21] | | 1.85 min | 455 | A | HCl | 1 |
| I-61 | 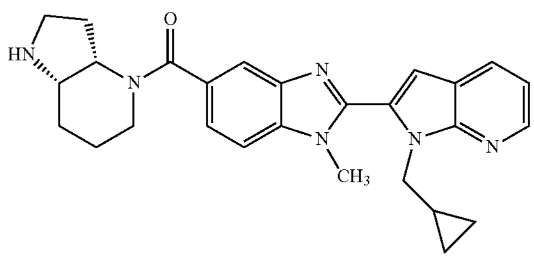 [SMILES: Cn1c(-c2cc3cccnc3n2CC2CC2)nc2cc(C(=O)N3CCC[C@@H]4NCC[C@@H]43)ccc21] | | 1.85 min | 455 | A | HCl | 1 |

| Structure | # | Mol Wt | LCMS $T_{ret}$ | M/z (+) | LCMS Method | Salt | Salt Stoichiometry |
|---|---|---|---|---|---|---|---|
| 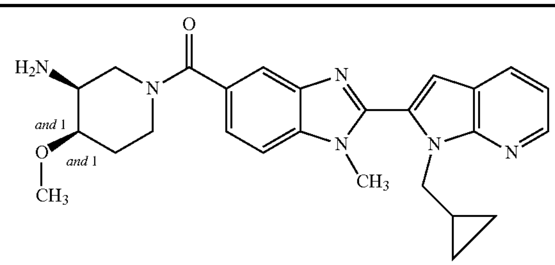 | I-62 | | 1.86 min | 459 | A | TFA | 1 |
| 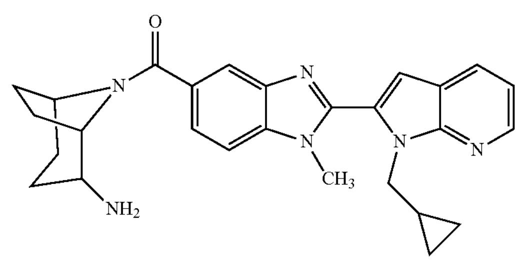 [SMILES: Cn1c(-c2cc3cccnc3n2CC2CC2)nc2cc(C(=O)N3C4CCC(N)C3CC4)ccc21] | I-63 | | 1.97 min | 455 | A | | |
| 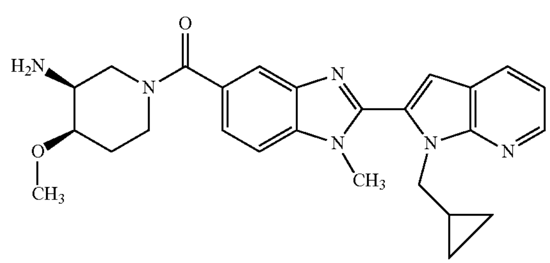 [SMILES: CO[C@@H]1CCN(C(=O)c2ccc3c(c2)nc(-c2cc4cccnc4n2CC2CC2)n3C)C[C@@H]1N] | I-64 | | 1.86 min | 459 | A | TFA | 1 |

-continued

| # | Structure | Mol Wt | LCMS T_ret | M/z (+) | LCMS Method | Salt | Salt Stoichiometry |
|---|---|---|---|---|---|---|---|
| I-65 | 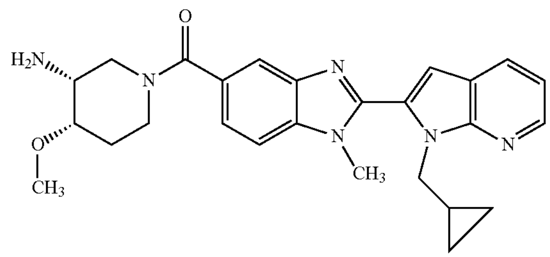 [SMILES: CO[C@H]1CCN(C(=O)c2ccc3c(c2)nc(-c2cc4cccnc4n2CC2CC2)n3C)C[C@H]1N] | | 1.86 min | 459 | A | HCl | 1 |
| I-66 | 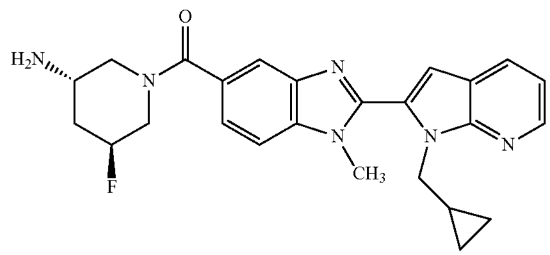 [SMILES: Cn1c(-c2cc3cccnc3n2CC2CC2)nc2cc(C(=O)N3C[C@@H](N)C[C@H](F)C3)ccc21] | | 1.84 min | 447 | A | HCl | 1 |
| I-67 | 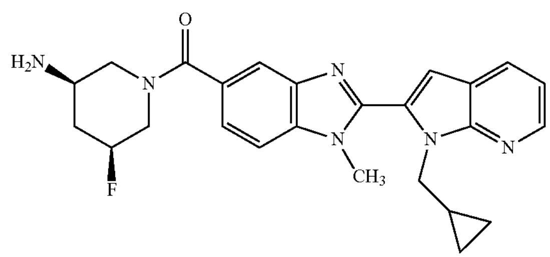 [SMILES: Cn1c(-c2cc3cccnc3n2CC2CC2)nc2cc(C(=O)N3C[C@H](N)C[C@H](F)C3)ccc21] | | 1.77 min | 447 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-68 | 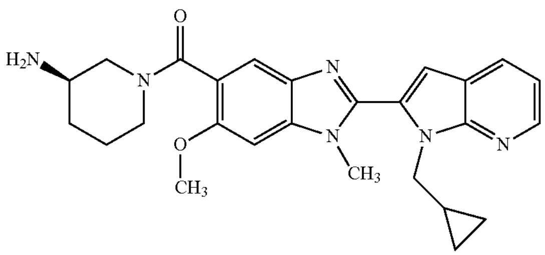 [SMILES: COc1cc2c(cc1C(=O)N1CCC[C@@H](N)C1)nc(-c1cc3cccnc3n1CC1CC1)n2C] | | 1.80 min | 459 | A | HCl | 1 |
| I-69 | 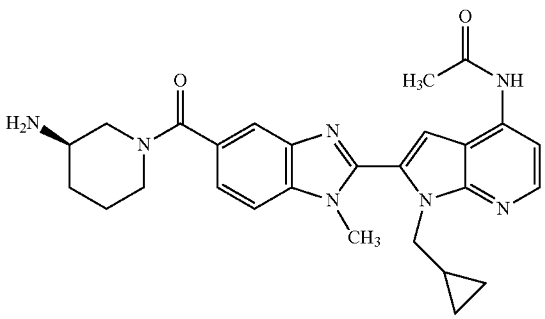 [SMILES: CC(=O)Nc1ccnc2c1cc(-c1nc3cc(C(=O)N4CCC[C@@H](N)C4)ccc3n1C)n2CC1CC1] | | 1.56 min | 486 | A | HCl | 1 |
| I-70 | 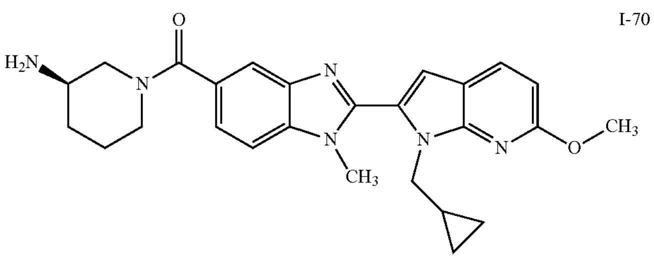 | | 2.27 min | 459 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-71 | 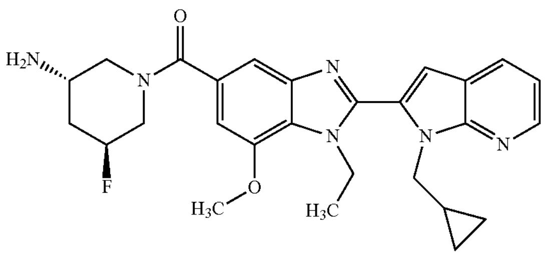 [SMILES: CCn1c(-c2cc3cccnc3n2CC2CC2)nc2cc(C(=O)N3C[C@@H](N)C[C@H](F)C3)cc(OC)c21] | | 2.22 min | 491 | A | HCl | 1 |
| I-72 | 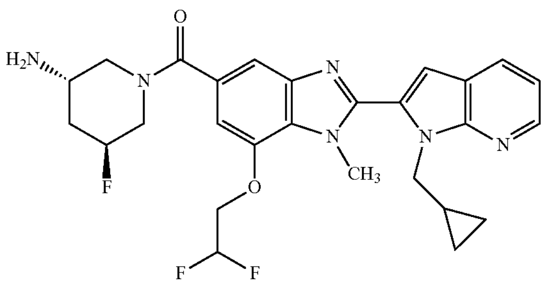 [SMILES: Cn1c(-c2cc3cccnc3n2CC2CC2)nc2cc(C(=O)N3C[C@@H](N)C[C@H](F)C3)cc(OCC(F)F)c21] | | 2.23 min | 527 | A | HCl | 1 |
| I-73 | 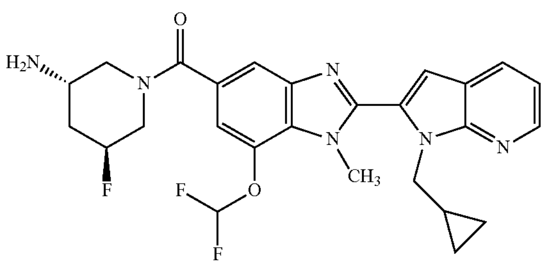 [SMILES: Cn1c(-c2cc3cccnc3n2CC2CC2)nc2cc(C(=O)N3C[C@@H](N)C[C@H](F)C3)cc(OC(F)F)c21] | | 2.25 min | 513 | A | HCl | 1 |

-continued

| # | Structure | Mol Wt | LCMS T_ret | M/z (+) | LCMS Method | Salt | Salt Stoichiometry |
|---|---|---|---|---|---|---|---|
| I-74 | 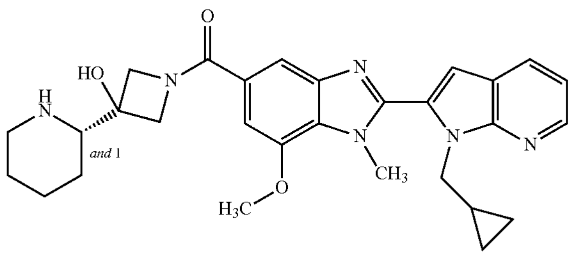 [SMILES: COc1cc(C(=O)N2CC(O)([C@@H]3CCCCN3)C2)cc2nc(-c3cc4cccnc4n3CC3CC3)n(C)c12] | | 2.11 min | 515 | A | | |
| I-75 | 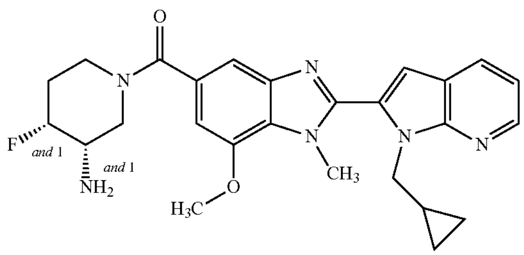 [SMILES: COc1cc(C(=O)N2CC[C@@H](F)[C@@H](N)C2)cc2nc(-c3cc4cccnc4n3CC3CC3)n(C)c12] | | 2.02 min | 477 | A | | |
| I-76 | 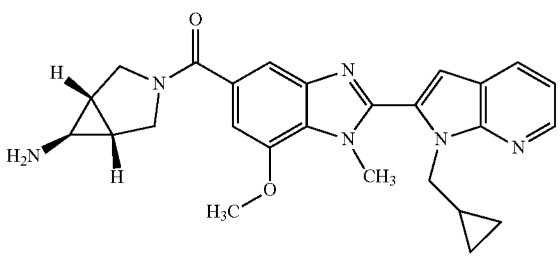 [SMILES: COc1cc(C(=O)N2C[C@@H]3[C@@H](N)[C@@H]3C2)cc2nc(-c3cc4cccnc4n3CC3CC3)n(C)c12] | | 1.94 min | 457 | A | HCl | 1 |

-continued

| # | Structure | Mol Wt | LCMS $T_{ret}$ | M/z (+) | LCMS Method | Salt | Salt Stoichiometry |
|---|---|---|---|---|---|---|---|
| I-77 | 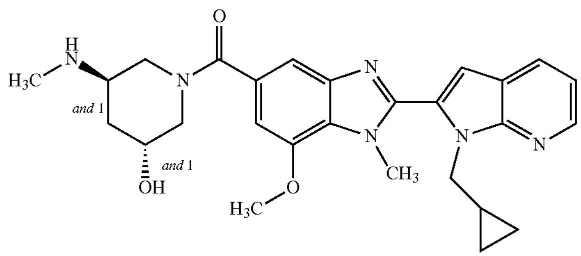 [SMILES: CN[C@@H]1C[C@@H](O)CN(C(=O)c2cc(OC)c3c(c2)nc(-c2cc4cccnc4n2CC2CC2)n3C)C1] | | 1.93 min | 489 | A | HCl | 1 |
| I-80 | 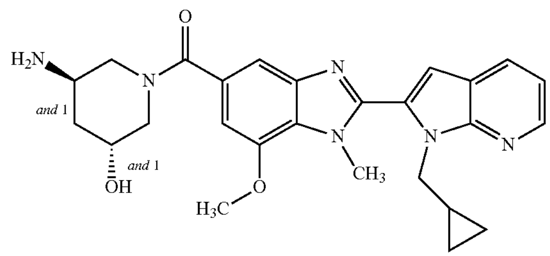 [SMILES: COc1cc(C(=O)N2C[C@H](N)C[C@@H](O)C2)cc2nc(-c3cc4cccnc4n3CC3CC3)n(C)c12] | | 1.91 min | 475 | A | | |
| I-81 | 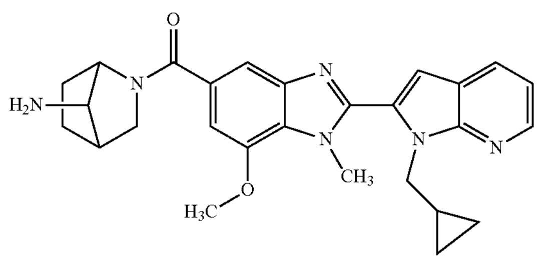 [SMILES: COc1cc(C(=O)N2CC3CCC2C3N)cc2nc(-c3cc4cccnc4n3CC3CC3)n(C)c12] | | 2.02 min | 471 | A | HCl | 1 |

-continued

| # | Structure | Mol Wt | LCMS $T_{ret}$ | M/z (+) | LCMS Method | Salt | Salt Stoichoimetry |
|---|---|---|---|---|---|---|---|
| I-82 | 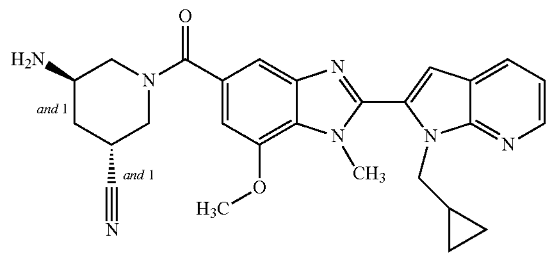 [SMILES: COc1cc(C(=O)N2C[C@H](N)C[C@@H](C#N)C2)cc2nc(-c3cc4cccnc4n3CC3CC3)n(C)c12] | | 2.08 min | 484 | A | TFA | 1 |
| I-83 | 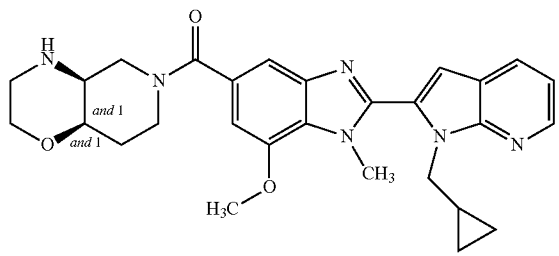 [SMILES: COc1cc(C(=O)N2CC[C@H]3OCCN[C@H]3C2)cc2nc(-c3cc4cccnc4n3CC3CC3)n(C)c12] | | 2.11 min | 501 | A | HCl | 1 |
| I-84 | 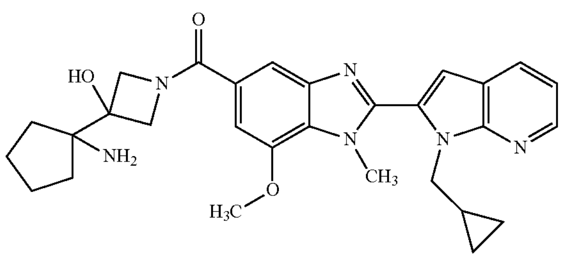 [SMILES: COc1cc(C(=O)N2CC(O)(C3(N)CCCC3)C2)cc2nc(-c3cc4cccnc4n3CC3CC3)n(C)c12] | | 2.07 min | 515 | A | HCO$_2$H | 1 |

-continued

| # | Structure | Mol Wt | LCMS $T_{ret}$ | M/z (+) | LCMS Method | Salt | Salt Stoichoimetry |
|---|---|---|---|---|---|---|---|
| I-85 | 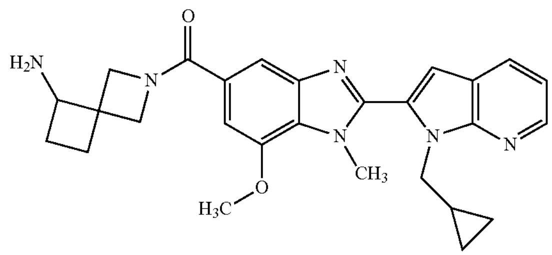 [SMILES: COc1cc(C(=O)N2CC3(CCC3N)C2)cc2nc(-c3cc4cccnc4n3CC3CC3)n(C)c12] | | 2.05 min | 471 | A | TFA | 1 |
| I-86 | 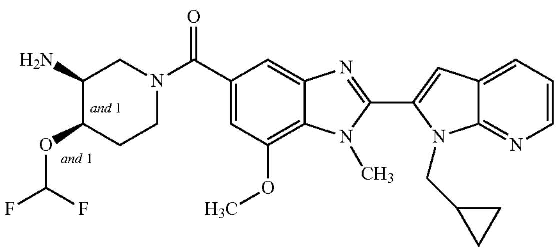 [SMILES: COc1cc(C(=O)N2CC[C@@H](OC(F)F)[C@@H](N)C2)cc2nc(-c3cc4cccnc4n3CC3CC3)n(C)c12] | | 2.20 min | 525 | A | HCl | 1 |
| I-87 | 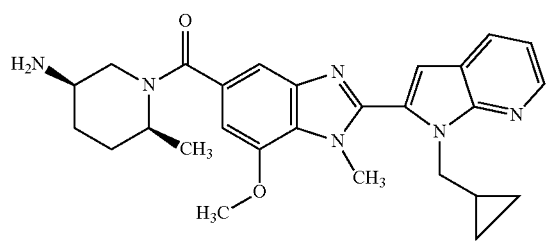 [SMILES: COc1cc(C(=O)N2C[C@H](N)CC[C@@H]2C)cc2nc(-c3cc4cccnc4n3CC3CC3)n(C)c12] | | 3.03 min | 473 | C | HCl | 1 |
| I-88 | 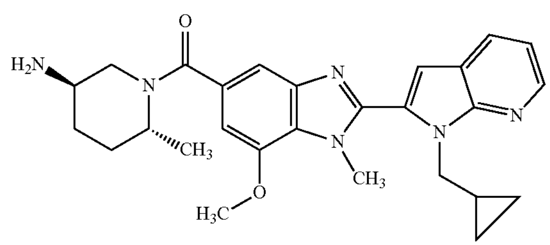 [SMILES: COc1cc(C(=O)N2C[C@H](N)CC[C@H]2C)cc2nc(-c3cc4cccnc4n3CC3CC3)n(C)c12] | | 3.04 min | 473 | C | HCl | 1 |

| # | Structure | Mol Wt | LCMS T_ret | M/z (+) | LCMS Method | Salt | Salt Stoichiometry |
|---|---|---|---|---|---|---|---|
| I-89 | 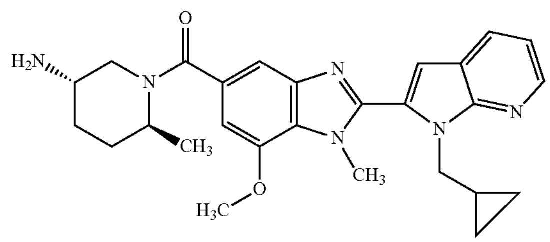 [SMILES: COc1cc(C(=O)N2C[C@@H](N)CC[C@@H]2C)cc2nc(-c3cc4cccnc4n3CC3CC3)n(C)c12] | | 3.04 min | 473 | C | HCl | 1 |
| I-90 | 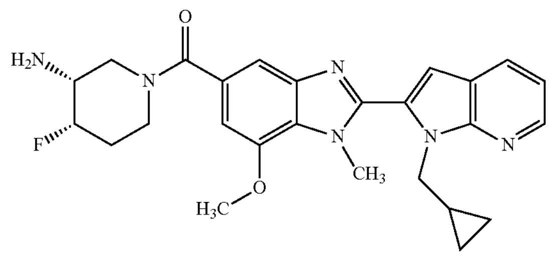 [SMILES: COc1cc(C(=O)N2CC[C@H](F)[C@H](N)C2)cc2nc(-c3cc4cccnc4n3CC3CC3)n(C)c12] | | 2.99 min | 477 | C | | |
| I-91 | 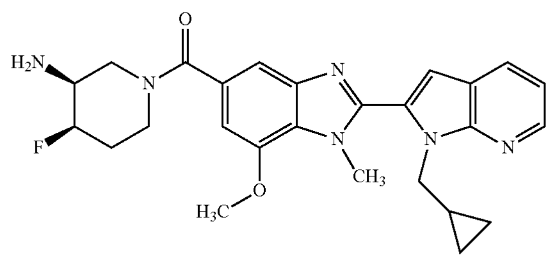 [SMILES: COc1cc(C(=O)N2CC[C@@H](F)[C@@H](N)C2)cc2nc(-c3cc4cccnc4n3CC3CC3)n(C)c12] | | 3.01 min | 477 | C | | |

-continued
| # | Structure | Mol Wt | LCMS $T_{ret}$ | M/z (+) | LCMS Method | Salt | Salt Stoichiometry |
|---|---|---|---|---|---|---|---|
| I-92 | 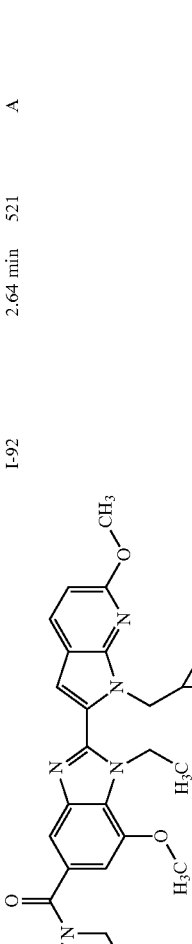 | | 2.64 min | 521 | A | HCl | 1 |
| I-93 | 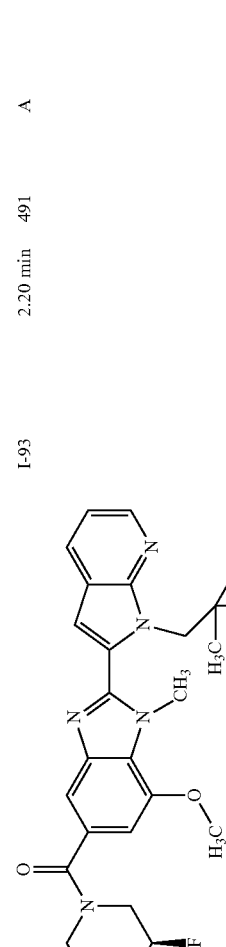 | | 2.20 min | 491 | A | HCl | 1 |
| I-94 | 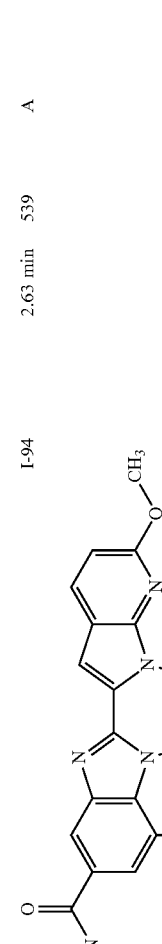 | | 2.63 min | 539 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-95 | 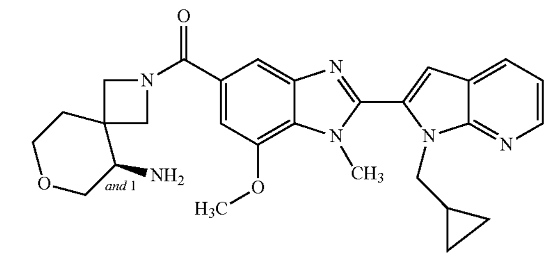 [SMILES: COc1cc(C(=O)N2CC3(CCOC[C@@H]3N)C2)cc2nc(-c3cc4cccnc4n3CC3CC3)n(C)c12] | | 2.06 min | 501 | A | | |
| I-96 | 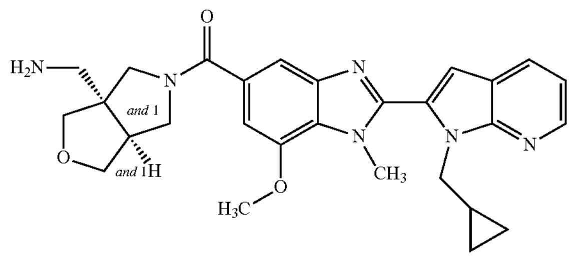 [SMILES: COc1cc(C(=O)N2C[C@H]3COC[C@@]3(CN)C2)cc2nc(-c3cc4cccnc4n3CC3CC3)n(C)c12] | | 2.01 min | 501 | A | | |
| I-97 | 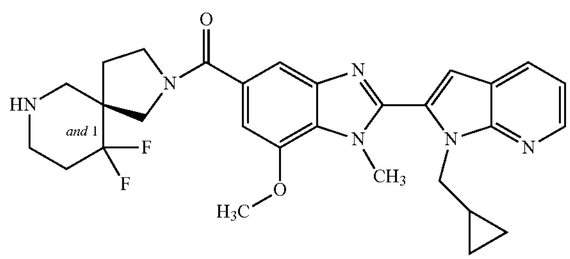 [SMILES: COc1cc(C(=O)N2CC[C@]3(CNCCC3(F)F)C2)cc2nc(-c3cc4cccnc4n3CC3CC3)n(C)c12] | | 2.22 min | 535 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-98 | 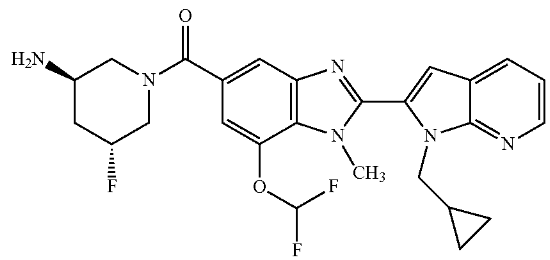 [SMILES: Cn1c(-c2cc3cccnc3n2CC2CC2)nc2cc(C(=O)N3C[C@H](N)C[C@@H](F)C3)cc(OC(F)F)c21] | | 2.26 min | 513 | A | HCl | 1 |
| I-99 | 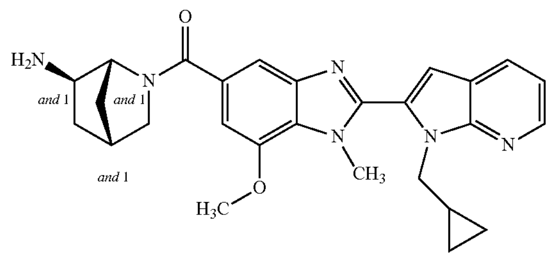 [SMILES: COc1cc(C(=O)N2C[C@@H]3C[C@@H](N)[C@H]2C3)cc2nc(-c3cc4cccnc4n3CC3CC3)n(C)c12] | | 2.07 min | 471 | A | | |
| I-100 | 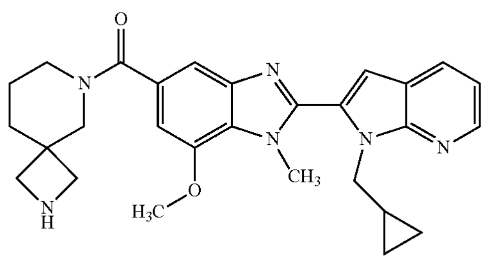 [SMILES: COc1cc(C(=O)N2CCCC3(CNC3)C2)cc2nc(-c3cc4cccnc4n3CC3CC3)n(C)c12] | | 2.12 min | 485 | A | | |

| # | Structure | Mol Wt | LCMS $T_{ret}$ | M/z (+) | LCMS Method | Salt | Salt Stoichiometry |
|---|---|---|---|---|---|---|---|
| I-101 | 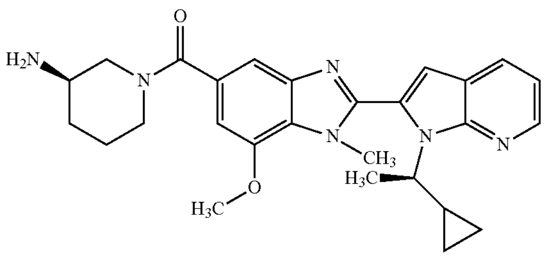 [SMILES: COc1cc(C(=O)N2CCC[C@@H](N)C2)cc2nc(-c3cc4cccnc4n3[C@H](C)C3CC3)n(C)c12] | | 2.25 min | 473 | A | HCl | 1 |
| I-102 | 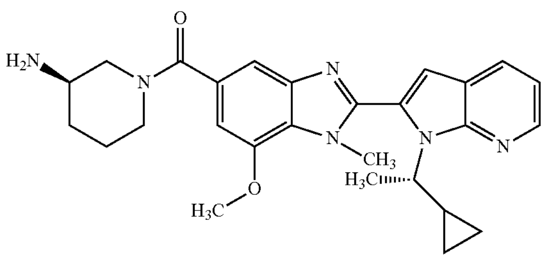 [SMILES: COc1cc(C(=O)N2CCC[C@@H](N)C2)cc2nc(-c3cc4cccnc4n3[C@@H](C)C3CC3)n(C)c12] | | 2.26 min | 473 | A | HCl | 1 |
| I-103 | 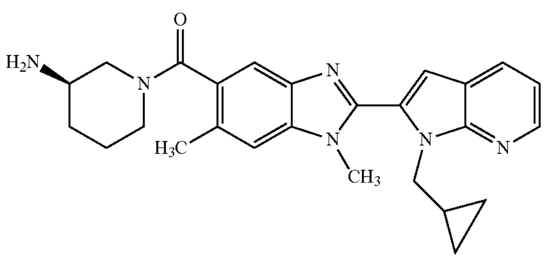 [SMILES: Cc1cc2c(cc1C(=O)N1CCC[C@@H](N)C1)nc(-c1cc3cccnc3n1CC1CC1)n2C] | | 1.86 min | 443 | A | HCl | 1 |

-continued

| # | Structure | Mol Wt | LCMS T$_{ret}$ | M/z (+) | LCMS Method | Salt | Salt Stoichiometry |
|---|---|---|---|---|---|---|---|
| I-104 | 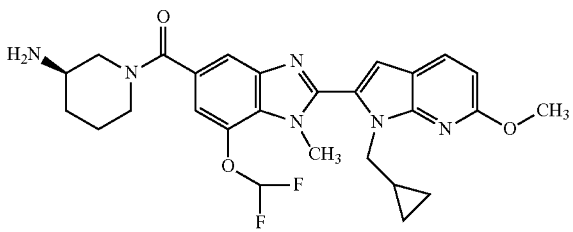 [SMILES: COc1ccc2cc(-c3nc4cc(C(=O)N5CCC[C@@H](N)C5)cc(OC(F)F)c4n3C)n(CC3CC3)c2n1] | | 2.66 min | 525 | A | HCl | 1 |
| I-105 | 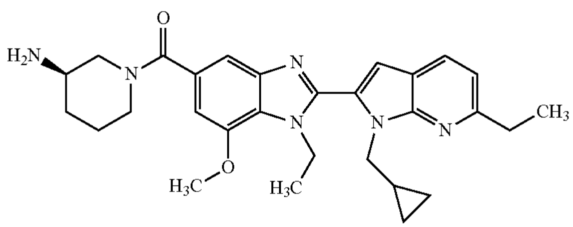 [SMILES: CCc1ccc2cc(-c3nc4cc(C(=O)N5CCC[C@@H](N)C5)cc(OC)c4n3CC)n(CC3CC3)c2n1] | | 2.62 min | 501 | A | HCl | 1 |
| I-106 | 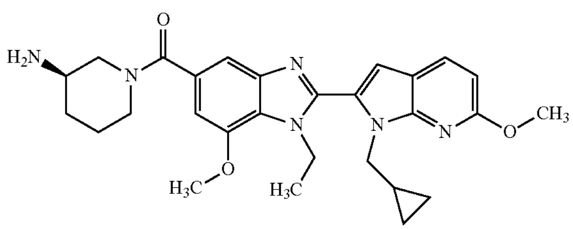 [SMILES: CCn1c(-c2cc3ccc(OC)nc3n2CC2CC2)nc2cc(C(=O)N3CCC[C@@H](N)C3)cc(OC)c21] | | 2.59 min | 503 | A | HCl | 1 |
| I-107 | 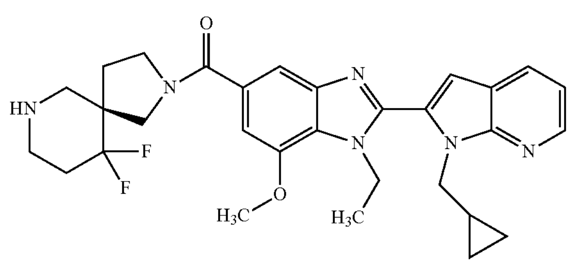 [SMILES: CCn1c(-c2cc3cccnc3n2CC2CC2)nc2cc(C(=O)N3CC[C@]4(CNCCC4(F)F)C3)cc(OC)c21] | | 2.21 min | 535 | A | | |

-continued

| # | Structure | Mol Wt | LCMS T_ret | M/z (+) | LCMS Method | Salt | Salt Stoichiometry |
|---|---|---|---|---|---|---|---|
| I-108 | 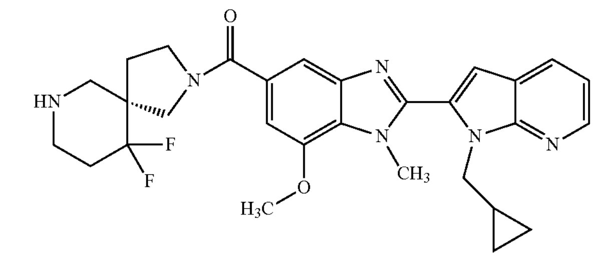 [SMILES: COc1cc(C(=O)N2CC[C@@]3(CNCCC3(F)F)C2)cc2nc(-c3cc4cccnc4n3CC3CC3)n(C)c12] | | 2.22 min | 535 | A | | |
| I-109 | 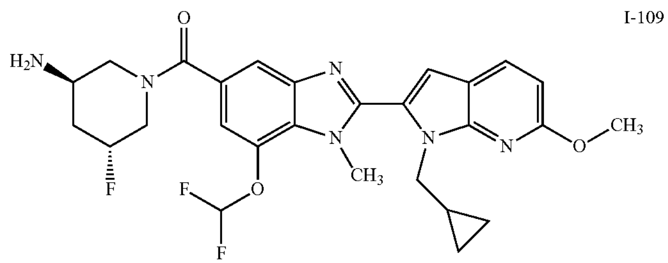 | | 2.68 min | 543 | A | HCl | 1 |
| I-110 | 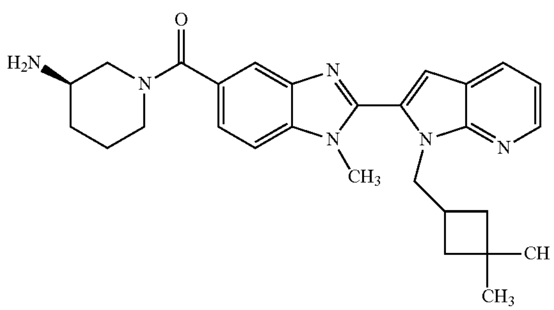 [SMILES: Cn1c(-c2cc3cccnc3n2CC2CC(C)(C)C2)nc2cc(C(=O)N3CCC[C@@H](N)C3)ccc21] | | 3.18 min | 473 | H | HCl | 1 |

-continued
| # | Structure | Mol Wt | LCMS T_ret | M/z (+) | LCMS Method | Salt | Salt Stoichiometry |
|---|---|---|---|---|---|---|---|
| I-111 | 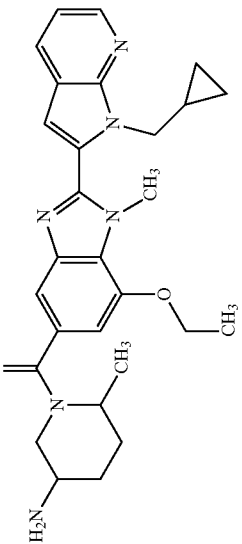 | | 2.33 min | 487 | A | HCl | 1 |
| I-112 | 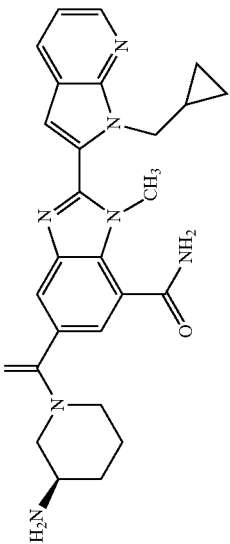 | | 1.53 min | 472 | A | HCl | 1 |
| I-113 | 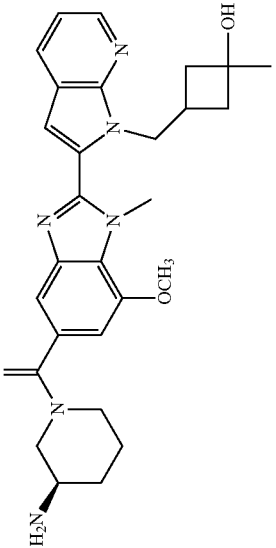 | 502.608 | 1.85 min | 503 | A | HCl | 1 |

-continued
| # | Structure | Mol Wt | LCMS $T_{ret}$ | M/z (+) | LCMS Method | Salt | Salt Stoichiometry |
|---|---|---|---|---|---|---|---|
| I-114 | 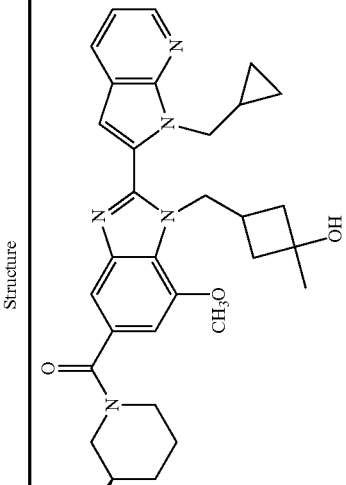 | 542.6718 | 1.92 min | 543 | A | HCl | 1 |
| I-115 | 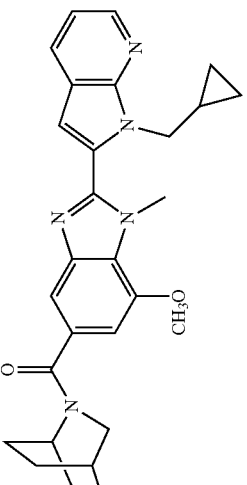 | 484.5927 | 2.08 min | 485.2 | A | | |
| I-116 | 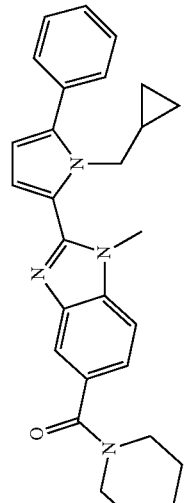 | 479.62 | 2.20 min | 480 | A | | |
| I-117 | 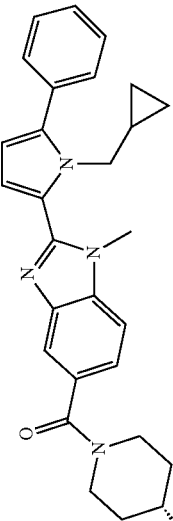 | 479.62 | 2.21 min | 480 | A | | |

-continued

| # | Structure | Mol Wt | LCMS $T_{ret}$ | M/z (+) | LCMS Method | Salt | Salt Stoichoimetry |
|---|---|---|---|---|---|---|---|
| I-119 | 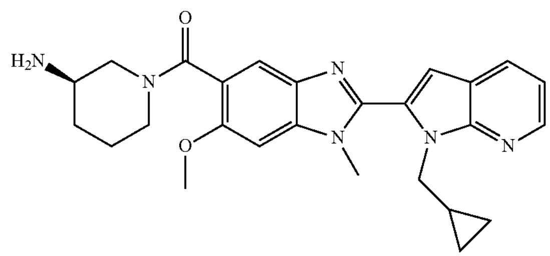 [SMILES: COc1cc2c(cc1C(=O)N1CCC[C@@H](N)C1)nc(-c1cc3cccnc3n1CC1CC1)n2C] | 472.582 | 2.19 min | 473 | A | Hydrochloric acid | 1 |
| I-121 | 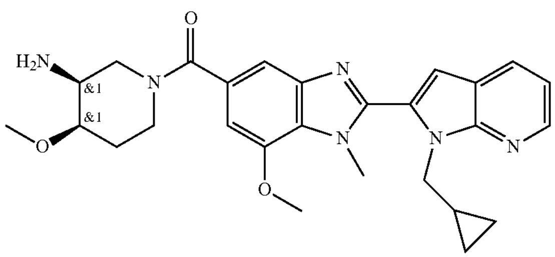 [SMILES: COc1cc(C(=O)N2CC[C@@H](OC)[C@@H](N)C2)cc2nc(-c3cc4cccnc4n3CC3CC3)n(C)c12] | 488.5814 | 2.10 min | 489 | A | Hydrochloric acid | 1 |
| I-122 | 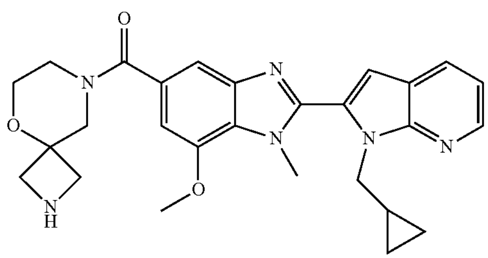 [SMILES: COc1cc(C(=O)N2CCOC3(CNC3)C2)cc2nc(-c3cc4cccnc4n3CC3CC3)n(C)c12] | 486.5655 | 2.04 min | 487 | A | Hydrochloric acid | 1 |

-continued

| # | Structure | Mol Wt | LCMS $T_{ret}$ | M/z (+) | LCMS Method | Salt | Salt Stoichiometry |
|---|---|---|---|---|---|---|---|
| I-123 | 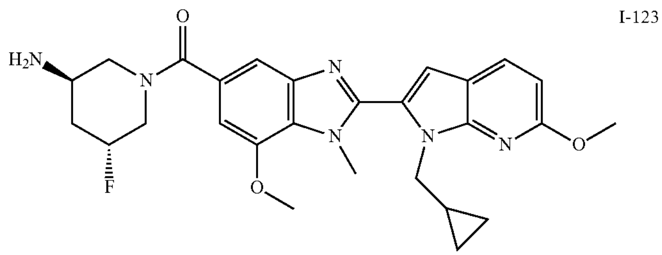 | 506.5718 | 2.53 min | 507 | A | | |
| I-124 | 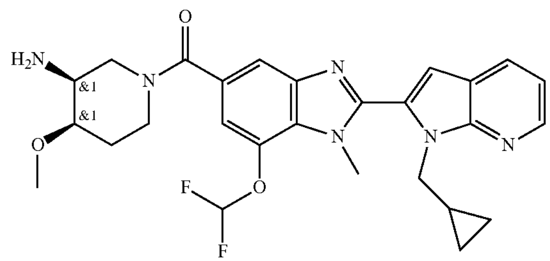 [SMILES: CO[C@@H]1CCN(C(=O)c2cc(OC(F)F)c3c(c2)nc(-c2cc4cccnc4n2CC2CC2)n3C)C[C@@H]1N] | 524.5623 | 2.30 min | 525 | A | Hydrochloric acid | 1 |
| I-125 | 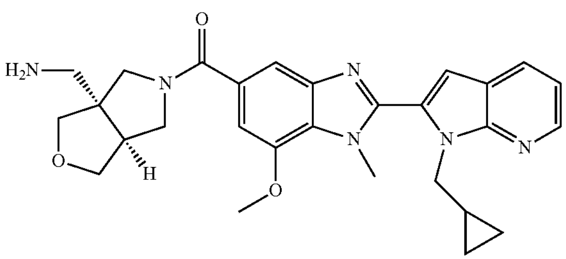 [SMILES: COc1cc(C(=O)N2C[C@H]3COC[C@@]3(CN)C2)cc2nc(-c3cc4cccnc4n3CC3CC3)n(C)c12] | 500.5921 | 2.01 min | 501 | A | | |

-continued

| # | Structure | Mol Wt | LCMS T$_{ret}$ | M/z (+) | LCMS Method | Salt | Salt Stoichiometry |
|---|---|---|---|---|---|---|---|
| I-126 | 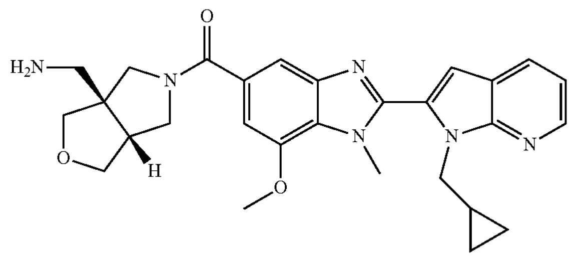 [SMILES: COc1cc(C(=O)N2C[C@@H]3COC[C@]3(CN)C2)cc2nc(-c3cc4cccnc4n3CC3CC3)n(C)c12] | 500.5921 | 1.98 min | 501 | A | | |
| I-127 | 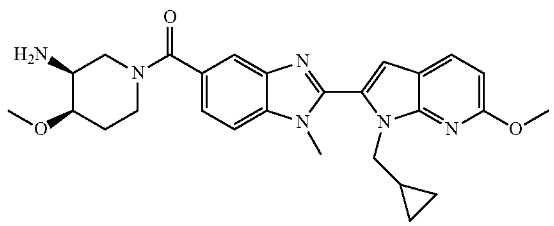 | 488.5814 | 2.38 min | 489 | A | Hydrochloric acid | 1 |
| I-128 | 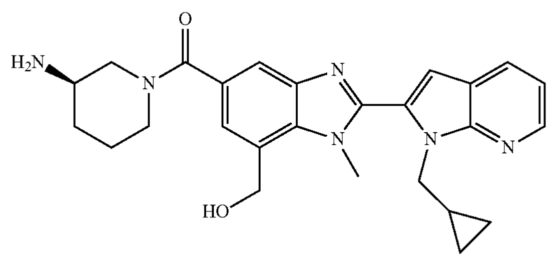 [SMILES: Cn1c(-c2cc3cccnc3n2CC2CC2)nc2cc(C(=O)N3CCC[C@@H](N)C3)cc(CO)c21] | 458.5554 | 1.66 min | 459 | A | Hydrochloric acid | 1 |

-continued

| # | Structure | Mol Wt | LCMS T_ret | M/z (+) | LCMS Method | Salt | Salt Stoichiometry |
|---|---|---|---|---|---|---|---|
| I-129 | 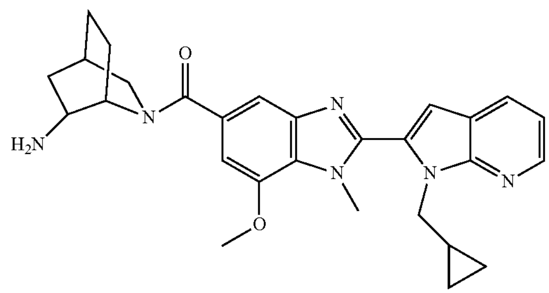 [SMILES: COc1cc(C(=O)N2CC3CCC2C(N)C3)cc2nc(-c3cc4cccnc4n3CC3CC3)n(C)c12] | 484.5927 | 2.06 min | 485 | A | | |
| I-130 | 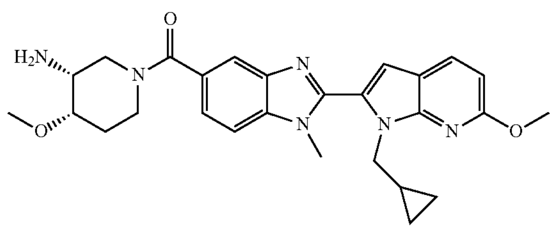 | 488.5814 | 3.39 min | 489 | H | | |
| I-131 | 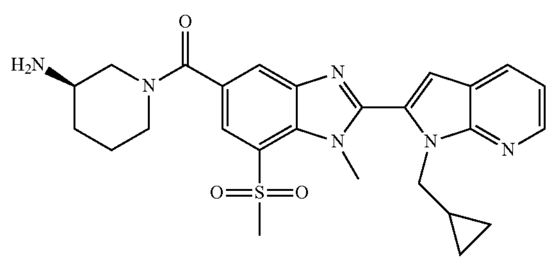 [SMILES: Cn1c(-c2cc3cccnc3n2CC2CC2)nc2cc(C(=O)N3CCC[C@@H](N)C3)cc(S(C)(=O)=O)c21] | 506.62 | 1.96 min | 507 | A | Hydrochloric acid | 1 |

-continued

| Structure | # | Mol Wt | LCMS T$_{ret}$ | M/z (+) | LCMS Method | Salt | Salt Stoichiometry |
|---|---|---|---|---|---|---|---|
| 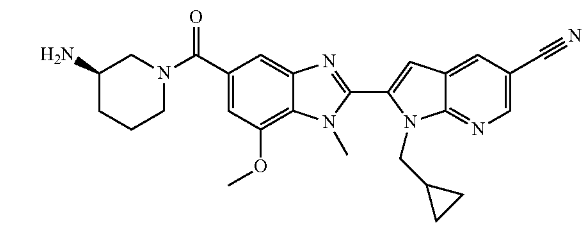 [SMILES: COc1cc(C(=O)N2CCC[C@@H](N)C2)cc2nc(-c3cc4cc(C#N)cnc4n3CC3CC3)n(C)c12] | I-132 | 483.5649 | 2.13 min | 484 | A | Hydrochloric acid | 1 |
| 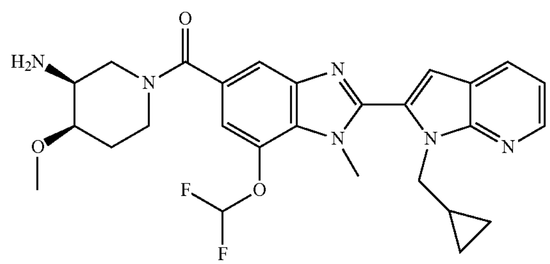 [SMILES: CO[C@@H]1CCN(C(=O)c2cc(OC(F)F)c3c(c2)nc(-c2cc4cccnc4n2CC2CC2)n3C)C[C@@H]1N] | I-133 | 524.5623 | 2.24 min | 525 | A | Hydrochloric acid | 1 |
| 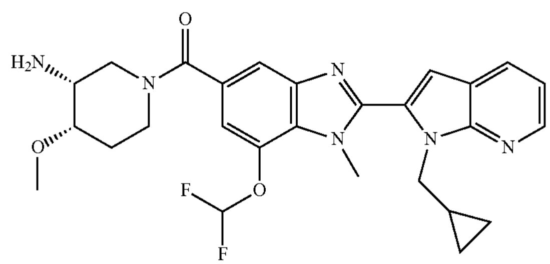 [SMILES: CO[C@H]1CCN(C(=O)c2cc(OC(F)F)c3c(c2)nc(-c2cc4cccnc4n2CC2CC2)n3C)C[C@H]1N] | I-134 | 524.5623 | 2.23 min | 525 | A | Hydrochloric acid | 1 |
| 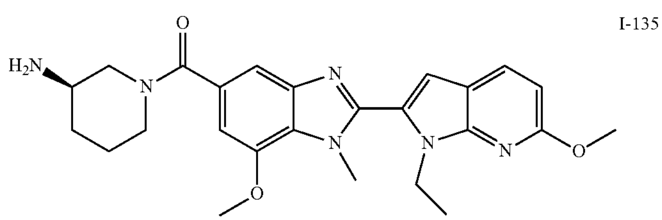 | I-135 | 462.5441 | 2.32 min | 463 | A | | |

-continued

| # | Structure | Mol Wt | LCMS T$_{ret}$ | M/z (+) | LCMS Method | Salt | Salt Stoichoimetry |
|---|---|---|---|---|---|---|---|
| I-136 | 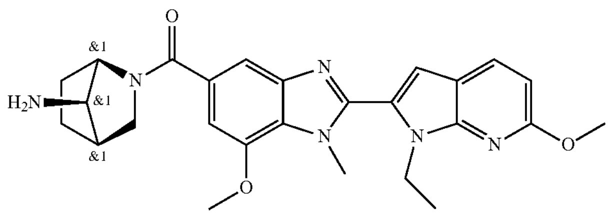 [SMILES: CCn1c(-c2nc3cc(C(=O)N4C[C@H]5CC[C@@H]4[C@@H]5N)cc(OC)c3n2C)cc2ccc(OC)nc21] | 474.5548 | 2.26 min | 475 | A | Hydrochloric acid | 1 |
| I-137 | 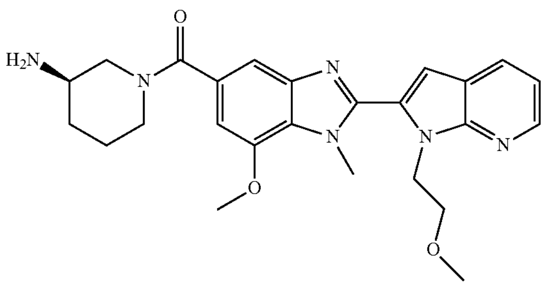 [SMILES: COCCn1c(-c2nc3cc(C(=O)N4CCC[C@@H](N)C4)cc(OC)c3n2C)cc2cccnc21] | 462.5441 | 1.78 min | 463 | A | Hydrochloric acid | 1 |
| I-138 | 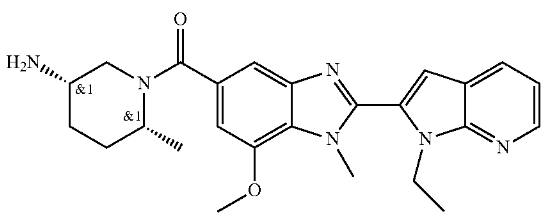 [SMILES: CCn1c(-c2nc3cc(C(=O)N4C[C@@H](N)CC[C@H]4C)cc(OC)c3n2C)cc2cccnc21] | 446.5447 | 1.93 min | 447 | A | Hydrochloric acid | 1 |
| I-139 | 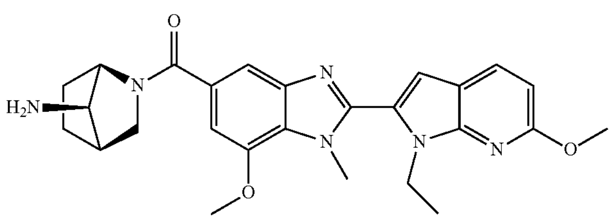 [SMILES: CCn1c(-c2nc3cc(C(=O)N4C[C@H]5CC[C@@H]4[C@@H]5N)cc(OC)c3n2C)cc2ccc(OC)nc21] | 474.5548 | 2.24 min | 475 | A | Hydrochloric acid | 1 |

-continued
| # | Structure | Mol Wt | LCMS $T_{ret}$ | M/z (+) | LCMS Method | Salt | Salt Stoichiometry |
|---|---|---|---|---|---|---|---|
| I-140 | 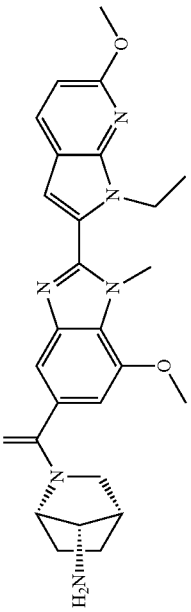 | 474.5548 | 2.24 min | 475 | A | Hydrochloric acid | 1 |
| I-141 | 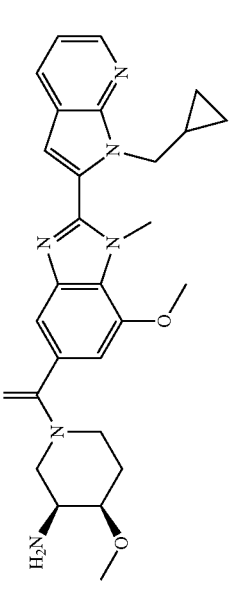 | 488.5814 | 2.11 min | 489 | A | Hydrochloric acid | 1 |
| I-142 | 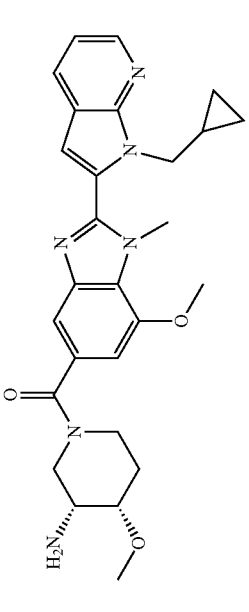 | 488.5814 | 2.12 min | 489 | A | Hydrochloric acid | 1 |
| I-143 | 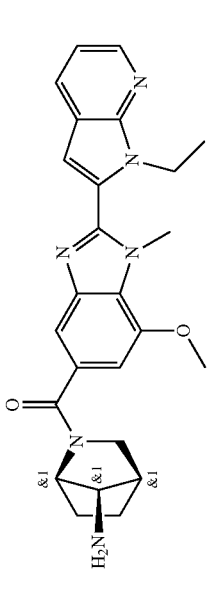 | 444.5288 | 1.82 min | 445 | A | Hydrochloric acid | 1 |

-continued

| # | Structure | Mol Wt | LCMS $T_{ret}$ | M/z (+) | LCMS Method | Salt | Salt Stoichiometry |
|---|---|---|---|---|---|---|---|
| I-144 | 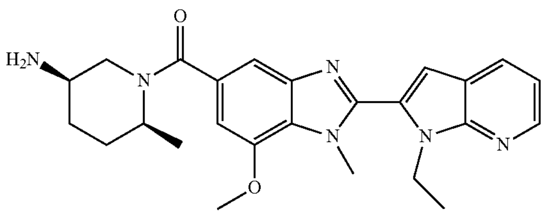 [SMILES: CCn1c(-c2nc3cc(C(=O)N4C[C@H](N)CC[C@@H]4C)cc(OC)c3n2C)cc2cccnc21] | 446.5447 | 1.94 min | 447 | A | Hydrochloric acid | 1 |
| I-145 | 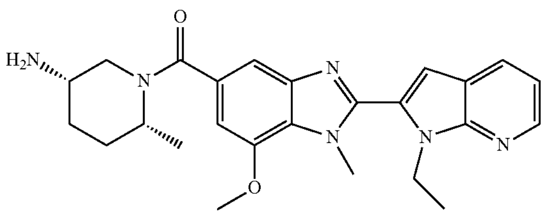 [SMILES: CCn1c(-c2nc3cc(C(=O)N4C[C@@H](N)CC[C@H]4C)cc(OC)c3n2C)cc2cccnc21] | 446.5447 | 1.95 min | 447 | A | Hydrochloric acid | 1 |
| I-146 | 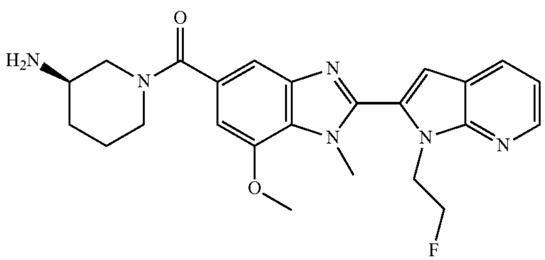 [SMILES: COc1cc(C(=O)N2CCC[C@@H](N)C2)cc2nc(-c3cc4cccnc4n3CCF)n(C)c12] | 450.5086 | 2.70 min | 451 | H | Hydrochloric acid | 1 |
| I-147 | 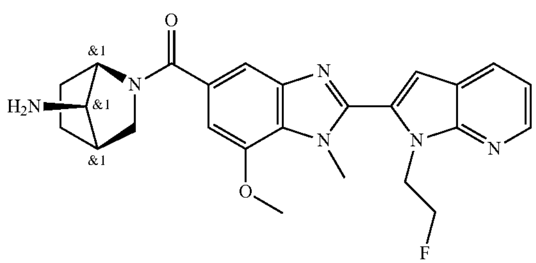 [SMILES: COc1cc(C(=O)N2C[C@H]3CC[C@@H]2[C@@H]3N)cc2nc(-c3cc4cccnc4n3CCF)n(C)c12] | 462.5193 | 1.81 min | 463 | A | Hydrochloric acid | 1 |

-continued

| Structure | # | Mol Wt | LCMS T_ret | M/z (+) | LCMS Method | Salt | Salt Stoichiometry |
|---|---|---|---|---|---|---|---|
| 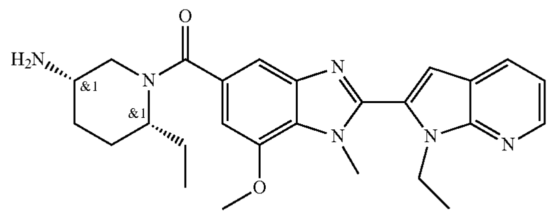 [SMILES: CC[C@@H]1CC[C@H](N)CN1C(=O)c1cc(OC)c2c(c1)nc(-c1cc3cccnc3n1CC)n2C] | I-148 | 460.5713 | 2.05 min | 461 | A | Hydrochloric acid | 1 |
| 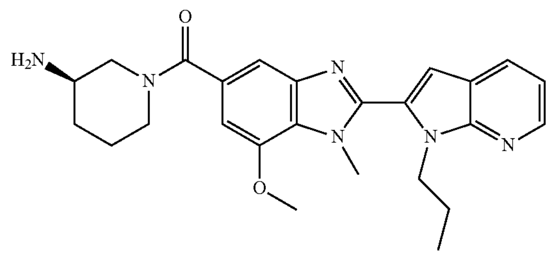 [SMILES: CCCn1c(-c2nc3cc(C(=O)N4CCC[C@@H](N)C4)cc(OC)c3n2C)cc2cccnc21] | I-149 | 446.5447 | 1.96 min | 447 | A | Hydrochloric acid | 1 |
| 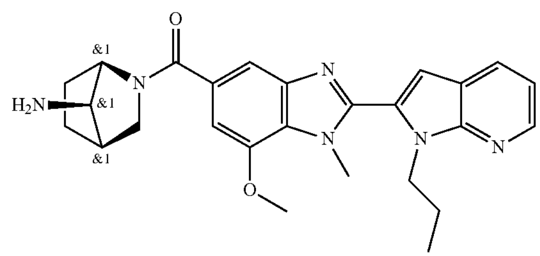 [SMILES: CCCn1c(-c2nc3cc(C(=O)N4C[C@H]5CC[C@@H]4[C@@H]5N)cc(OC)c3n2C)cc2cccnc21] | I-150 | 458.5554 | 1.93 min | 459 | A | Hydrochloric acid | 1 |
| 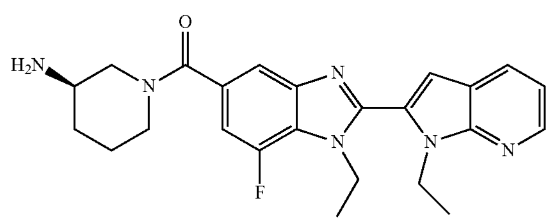 [SMILES: CCn1c(-c2nc3cc(C(=O)N4CCC[C@@H](N)C4)cc(F)c3n2CC)cc2cccnc21] | I-151 | 434.5092 | 1.97 min | 435 | A | Hydrochloric acid | 1 |

-continued

| # | Structure | Mol Wt | LCMS T_ret | M/z (+) | LCMS Method | Salt | Salt Stoichiometry |
|---|---|---|---|---|---|---|---|
| I-152 | 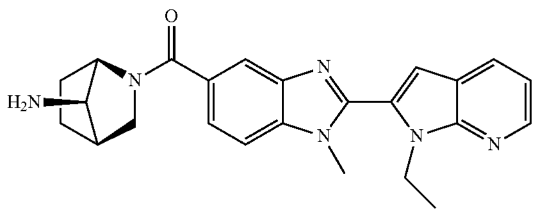 [SMILES: CCn1c(-c2nc3cc(C(=O)N4C[C@H]5CC[C@@H]4[C@@H]5N)ccc3n2C)cc2cccnc21] | 414.5028 | 1.58 min | 415 | A | Hydrochloric acid | 1 |
| I-153 | 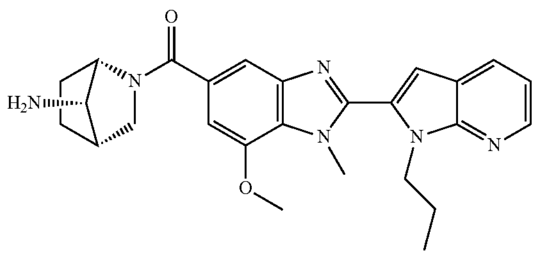 [SMILES: CCCn1c(-c2nc3cc(C(=O)N4C[C@@H]5CC[C@H]4[C@H]5N)cc(OC)c3n2C)cc2cccnc21] | 458.5554 | 1.91 min | 459 | A | Hydrochloric acid | 1 |
| I-154 | 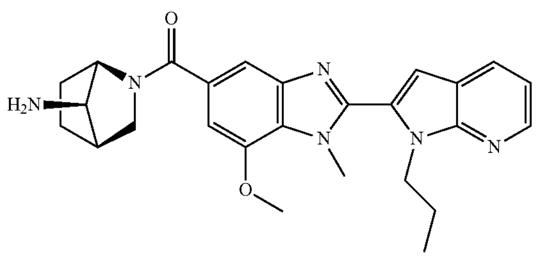 [SMILES: CCCn1c(-c2nc3cc(C(=O)N4C[C@H]5CC[C@@H]4[C@@H]5N)cc(OC)c3n2C)cc2cccnc21] | 458.5554 | 1.92 min | 459 | A | Hydrochloric acid | 1 |

-continued

| # | Structure | Mol Wt | LCMS T$_{ret}$ | M/z (+) | LCMS Method | Salt | Salt Stoichoimetry |
|---|---|---|---|---|---|---|---|
| I-155 | 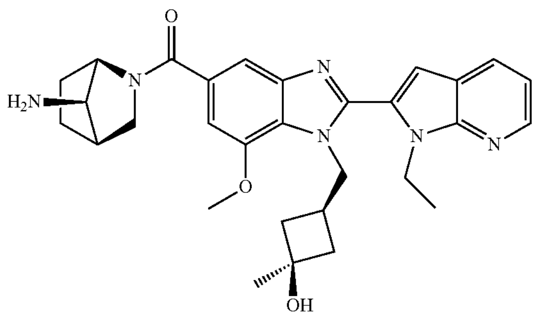 [SMILES: CCn1c(-c2nc3cc(C(=O)N4C[C@H]5CC[C@@H]4[C@@H]5N)cc(OC)c3n2C[C@H]2C[C@@](C)(O)C2)cc2cccnc21] | 528.6452 | 1.72 min | 529 | A | Hydrochloric acid | 1 |
| I-156 | 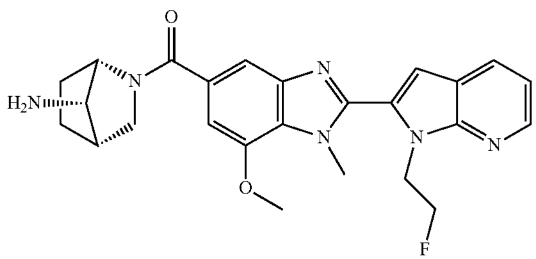 [SMILES: COc1cc(C(=O)N2C[C@@H]3CC[C@H]2[C@H]3N)cc2nc(-c3cc4cccnc4n3CCF)n(C)c12] | 462.5193 | 1.78 min | 463 | A | Hydrochloric acid | 1 |
| I-157 | 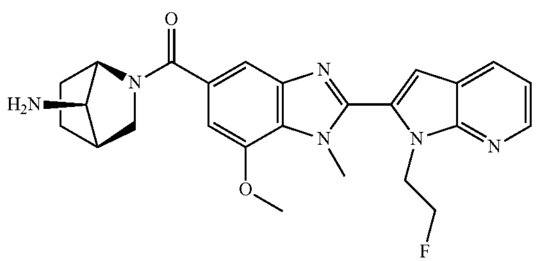 [SMILES: COc1cc(C(=O)N2C[C@H]3CC[C@@H]2[C@@H]3N)cc2nc(-c3cc4cccnc4n3CCF)n(C)c12] | 462.5193 | 1.79 min | 463 | A | Hydrochloric acid | 1 |

-continued

| Structure | # | Mol Wt | LCMS $T_{ret}$ | M/z (+) | LCMS Method | Salt | Salt Stoichiometry |
|---|---|---|---|---|---|---|---|
| 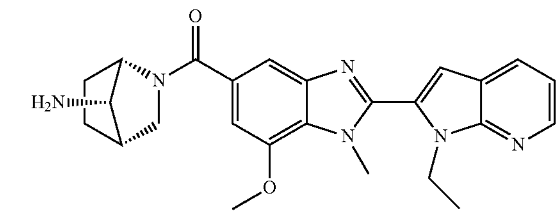 [SMILES: CCn1c(-c2nc3cc(C(=O)N4C[C@@H]5CC[C@H]4[C@H]5N)cc(OC)c3n2C)cc2cccnc21] | I-158 | 444.5288 | 1.80 min | 445 | A | Hydrochloric acid | 1 |
| 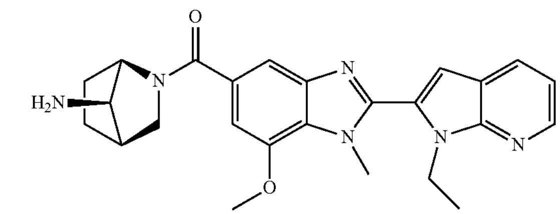 [SMILES: CCn1c(-c2nc3cc(C(=O)N4C[C@H]5CC[C@@H]4[C@@H]5N)cc(OC)c3n2C)cc2cccnc21] | I-159 | 444.5288 | 1.80 min | 445 | A | Hydrochloric acid | 1 |
| 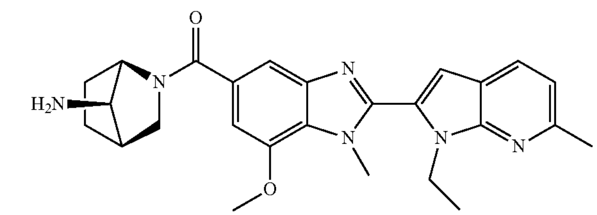 [SMILES: CCn1c(-c2nc3cc(C(=O)N4C[C@H]5CC[C@@H]4[C@@H]5N)cc(OC)c3n2C)cc2ccc(C)nc21] | I-160 | 458.5554 | 1.89 min | 459 | A | Hydrochloric acid | 1 |
| 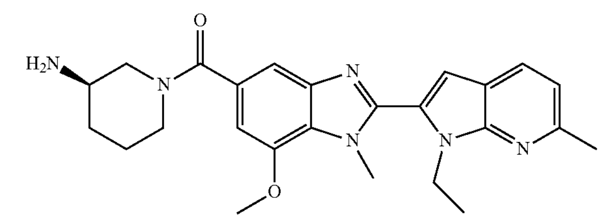 [SMILES: CCn1c(-c2nc3cc(C(=O)N4CCC[C@@H](N)C4)cc(OC)c3n2C)cc2ccc(C)nc21] | I-161 | 446.5447 | 1.94 min | 447 | A | Hydrochloric acid | 1 |

| # | Structure | Mol Wt | LCMS T_ret | M/z (+) | LCMS Method | Salt | Salt Stoichiometry |
|---|---|---|---|---|---|---|---|
| I-162 | 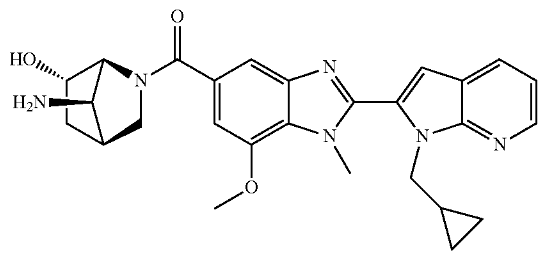 [SMILES: COc1cc(C(=O)N2C[C@H]3C[C@H](O)[C@@H]2[C@@H]3N)cc2nc(-c3cc4cccnc4n3CC3CC3)n(C)c12] | 486.5655 | 1.96 min | 487 | A | Hydrochloric acid | 1 |
| I-163 | 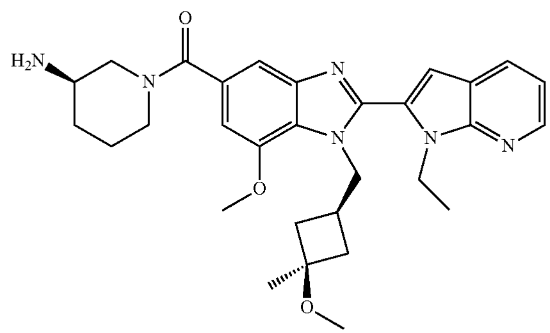 [SMILES: CCn1c(-c2nc3cc(C(=O)N4CCC[C@@H](N)C4)cc(OC)c3n2C[C@H]2C[C@@](C)(OC)C2)cc2cccnc21] | 530.6611 | 2.14 min | 531 | A | Hydrochloric acid | 1 |
| I-164 | 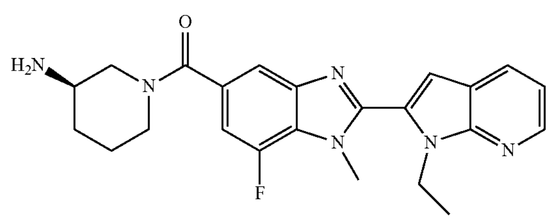 [SMILES: CCn1c(-c2nc3cc(C(=O)N4CCC[C@@H](N)C4)cc(F)c3n2C)cc2cccnc21] | 420.4826 | 1.72 min | 421 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-165 | 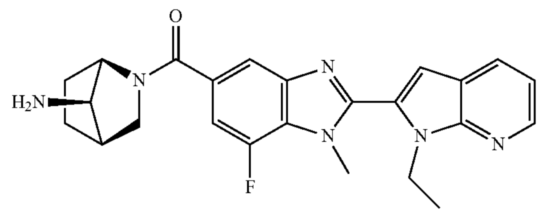 [SMILES: CCn1c(-c2nc3cc(C(=O)N4C[C@H]5CC[C@@H]4[C@@H]5N)cc(F)c3n2C)cc2cccnc21] | 432.4933 | 1.78 min | 433 | A | Hydrochloric acid | 1 |
| I-166 | 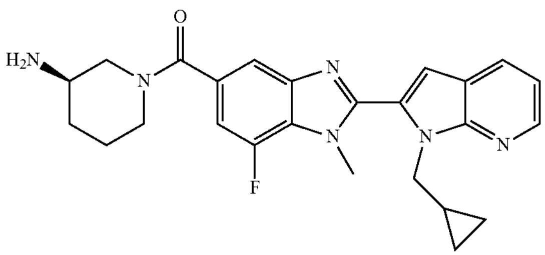 [SMILES: Cn1c(-c2cc3cccnc3n2CC2CC2)nc2cc(C(=O)N3CCC[C@@H](N)C3)cc(F)c21] | 446.5199 | 2.05 min | 447 | A | Hydrochloric acid | 1 |
| I-167 | 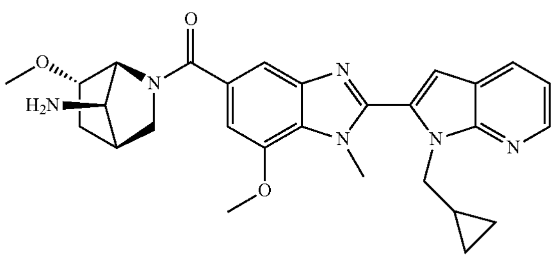 [SMILES: COc1cc(C(=O)N2C[C@H]3C[C@H](OC)[C@@H]2[C@@H]3N)cc2nc(-c3cc4cccnc4n3CC3CC3)n(C)c12] | 500.5921 | 2.07 min | 501 | A | Hydrochloric acid | 1 |

-continued

| Structure | # | Mol Wt | LCMS T$_{ret}$ | M/z (+) | LCMS Method | Salt | Salt Stoichiometry |
|---|---|---|---|---|---|---|---|
| 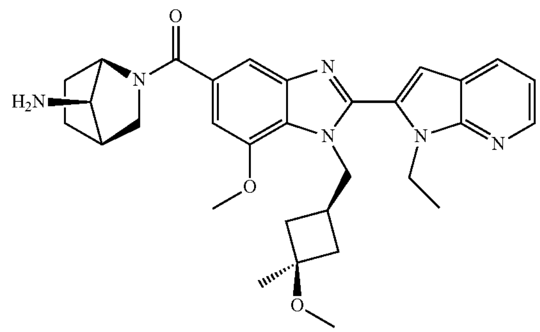 [SMILES: CCn1c(-c2nc3cc(C(=O)N4C[C@H]5CC[C@@H]4[C@@H]5N)cc(OC)c3n2C[C@H]2C[C@@](C)(OC)C2)cc2cccnc21] | I-168 | 542.6718 | 2.09 min | 543 | A | Hydrochloric acid | 1 |
| 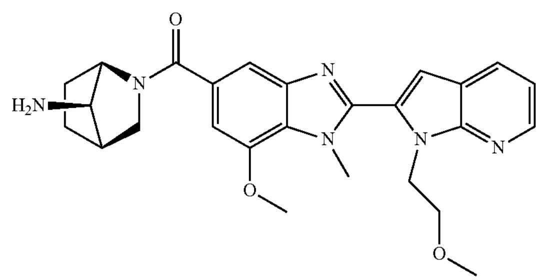 [SMILES: COCCn1c(-c2nc3cc(C(=O)N4C[C@H]5CC[C@@H]4[C@@H]5N)cc(OC)c3n2C)cc2cccnc21] | I-169 | 474.5548 | 1.75 min | 475 | A | Hydrochloric acid | 1 |
| 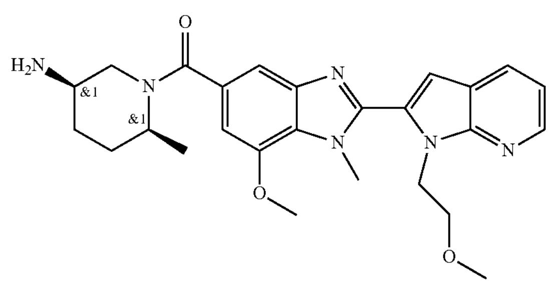 [SMILES: COCCn1c(-c2nc3cc(C(=O)N4C[C@H](N)CC[C@@H]4C)cc(OC)c3n2C)cc2cccnc21] | I-170 | 476.5707 | 1.87 min | 477 | A | Hydrochloric acid | 1 |

-continued

| Structure | # | Mol Wt | LCMS T_ret | M/z (+) | LCMS Method | Salt | Salt Stoichiometry |
|---|---|---|---|---|---|---|---|
| 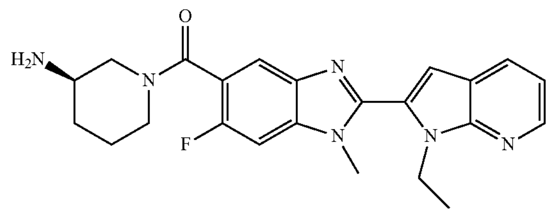 [SMILES: CCn1c(-c2nc3cc(C(=O)N4CCC[C@@H](N)C4)c(F)cc3n2C)cc2cccnc21] | I-171 | 420.4826 | 1.70 min | 421 | A | | |
| 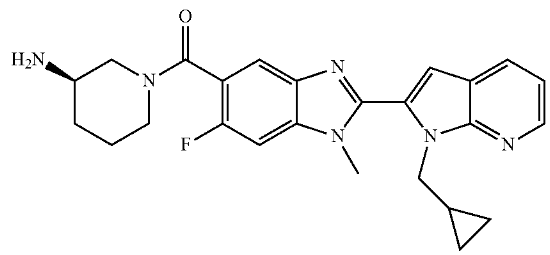 [SMILES: Cn1c(-c2cc3cccnc3n2CC2CC2)nc2cc(C(=O)N3CCC[C@@H](N)C3)c(F)cc21] | I-172 | 446.5199 | 1.92 min | 447 | A | Hydrochloric acid | 1 |
| 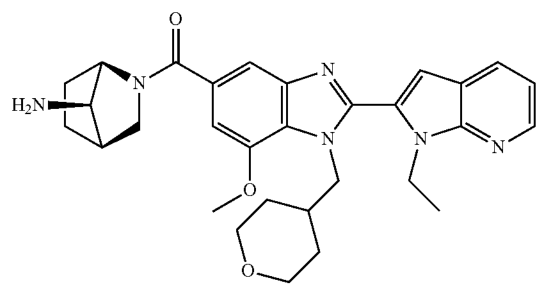 [SMILES: CCn1c(-c2nc3cc(C(=O)N4C[C@H]5CC[C@@H]4[C@@H]5N)cc(OC)c3n2CC2CCOCC2)cc2cccnc21] | I-173 | 528.6452 | 1.85 min | 529 | A | Hydrochloric acid | 1 |

-continued

| Structure | # | Mol Wt | LCMS T_ret | M/z (+) | LCMS Method | Salt | Salt Stoichoimetry |
|---|---|---|---|---|---|---|---|
| 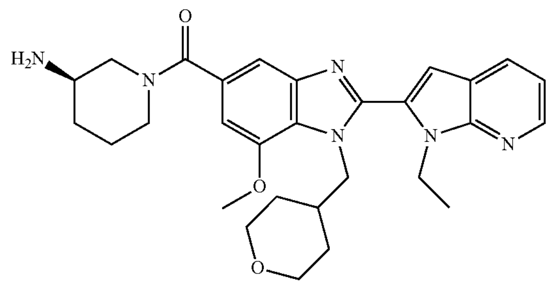 [SMILES: CCn1c(-c2nc3cc(C(=O)N4CCC[C@@H](N)C4)cc(OC)c3n2CC2CCOCC2)cc2cccnc21] | I-174 | 516.6345 | 1.90 min | 517 | A | Hydrochloric acid | 1 |
| 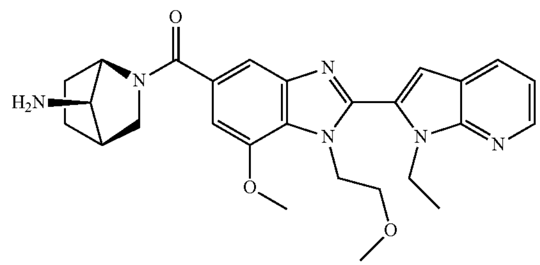 [SMILES: CCn1c(-c2nc3cc(C(=O)N4C[C@H]5CC[C@@H]4[C@@H]5N)cc(OC)c3n2CCOC)cc2cccnc21] | I-175 | 488.5814 | 1.83 min | 489 | A | Hydrochloric acid | 1 |
| 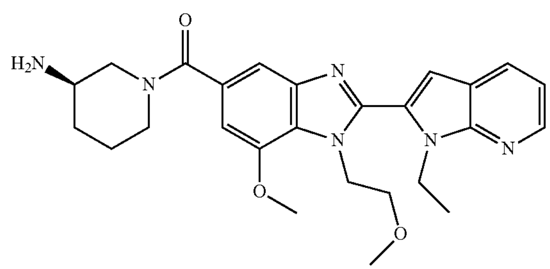 [SMILES: CCn1c(-c2nc3cc(C(=O)N4CCC[C@@H](N)C4)cc(OC)c3n2CCOC)cc2cccnc21] | I-176 | 476.5707 | 1.87 min | 477 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-177 | 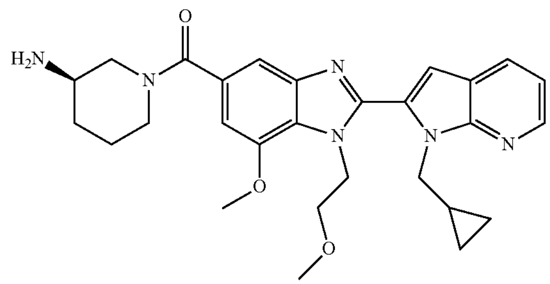 [SMILES: COCCn1c(-c2cc3cccnc3n2CC2CC2)nc2cc(C(=O)N3CCC[C@@H](N)C3)cc(OC)c21] | 502.608 | 2.08 min | 503 | A | Hydrochloric acid | 1 |
| I-178 | 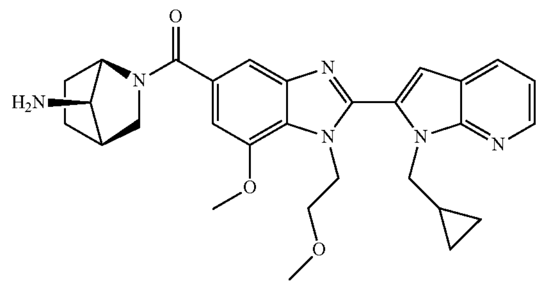 [SMILES: COCCn1c(-c2cc3cccnc3n2CC2CC2)nc2cc(C(=O)N3C[C@H]4CC[C@@H]3[C@@H]4N)cc(OC)c21] | 514.6187 | 2.05 min | 515 | A | Hydrochloric acid | 1 |
| I-179 | 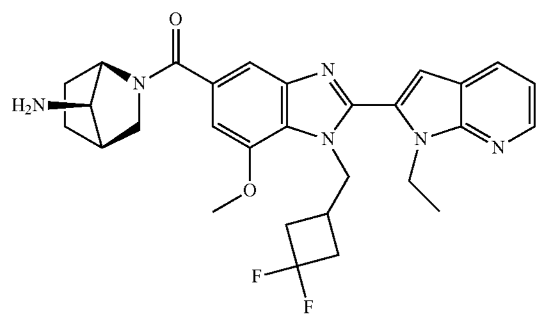 [SMILES: CCn1c(-c2nc3cc(C(=O)N4C[C@H]5CC[C@@H]4[C@@H]5N)cc(OC)c3n2CC2CC(F)(F)C2)cc2cccnc21] | 534.6002 | 2.18 min | 535 | A | Hydrochloric acid | 1 |

-continued

| # | Structure | Mol Wt | LCMS $T_{ret}$ | M/z (+) | LCMS Method | Salt | Salt Stoichoimetry |
|---|---|---|---|---|---|---|---|
| I-180 | 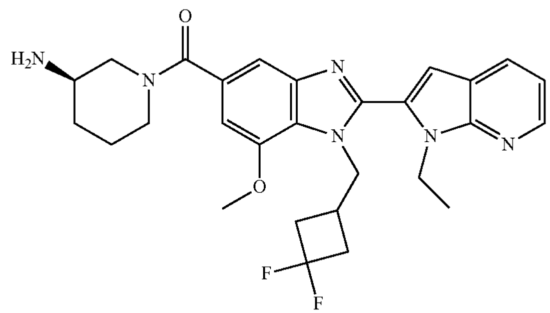 [SMILES: CCn1c(-c2nc3cc(C(=O)N4CCC[C@@H](N)C4)cc(OC)c3n2CC2CC(F)(F)C2)cc2cccnc21] | 522.5895 | 2.20 min | 523 | A | Hydrochloric acid | 1 |
| I-181 | 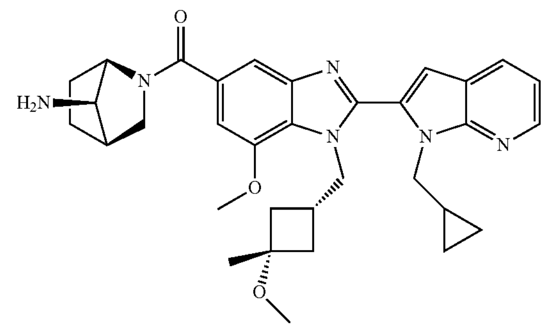 [SMILES: COc1cc(C(=O)N2C[C@H]3CC[C@@H]2[C@@H]3N)cc2nc(-c3cc4cccnc4n3CC3CC3)n(C[C@H]3C[C@@](C)(OC)C3)c12] | 568.7091 | 2.27 min | 569 | A | Hydrochloric acid | 1 |
| I-182 | 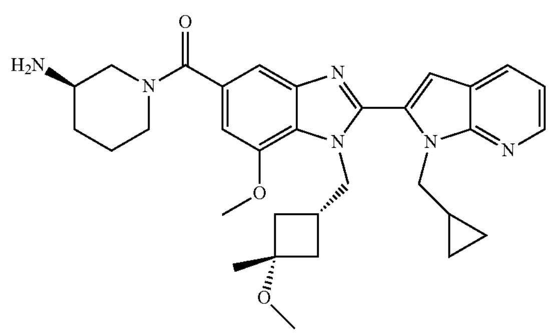 [SMILES: COc1cc(C(=O)N2CCC[C@@H](N)C2)cc2nc(-c3cc4cccnc4n3CC3CC3)n(C[C@H]3C[C@@](C)(OC)C3)c12] | 556.6984 | 2.25 min | 557 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-183 | 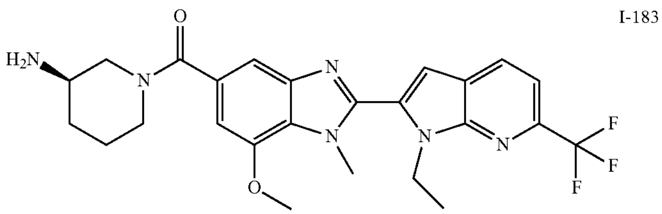 | 512.5268 | 2.42 min | 513 | A | Hydrochloric acid | 1 |
| I-184 | 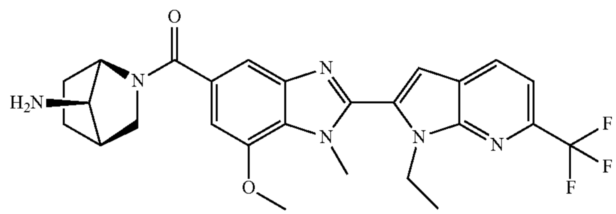 [SMILES: CCn1c(-c2nc3cc(C(=O)N4C[C@H]5CC[C@@H]4[C@@H]5N)cc(OC)c3n2C)cc2ccc(C(F)(F)F)nc21] | 500.5161 | 2.51 min | 501 | A | Hydrochloric acid | 1 |
| I-185 | 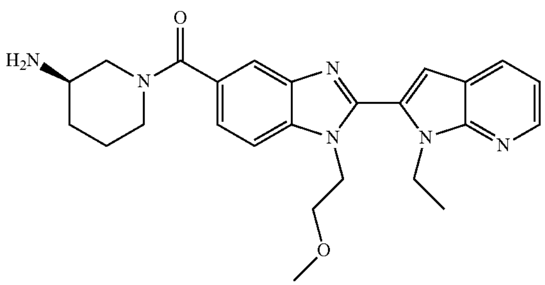 [SMILES: CCn1c(-c2nc3cc(C(=O)N4CCC[C@@H](N)C4)ccc3n2CCOC)cc2cccnc21] | 446.5447 | 1.71 min | 447 | A | Hydrochloric acid | 1 |
| I-186 | 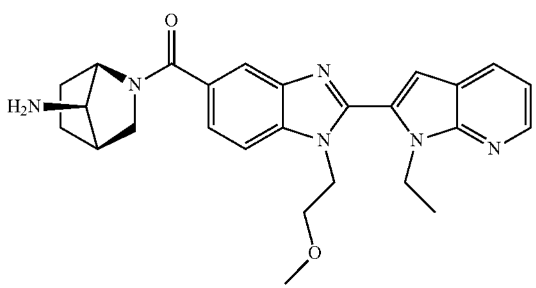 [SMILES: CCn1c(-c2nc3cc(C(=O)N4C[C@H]5CC[C@@H]4[C@@H]5N)ccc3n2CCOC)cc2cccnc21] | 458.5554 | 1.66 min | 459 | A | Hydrochloric acid | 1 |

-continued
| # | Structure | Mol Wt | LCMS T_ret | M/z (+) | LCMS Method | Salt | Salt Stoichiometry |
|---|---|---|---|---|---|---|---|
| I-187 | 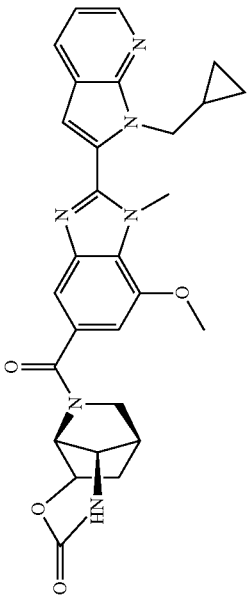 | 512.5597 | 2.90 min | 513 | A | | |
| I-188 | 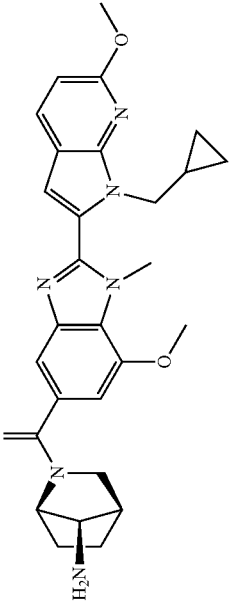 | 500.5921 | 2.37 min | 501 | A | | 1 |
| I-189 | 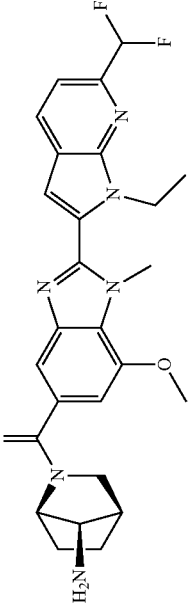 | 494.5363 | 2.26 min | 495 | A | | |

-continued

| # | Structure | Mol Wt | LCMS T$_{ret}$ | M/z (+) | LCMS Method | Salt | Salt Stoichiometry |
|---|---|---|---|---|---|---|---|
| I-190 | 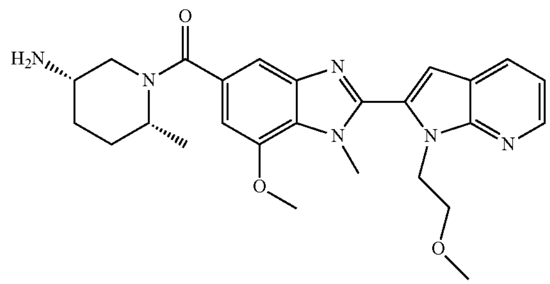 [SMILES: COCCn1c(-c2nc3cc(C(=O)N4C[C@@H](N)CC[C@H]4C)cc(OC)c3n2C)cc2cccnc21] | 476.5707 | 1.86 min | 477 | A | Hydrochloric acid | 1 |
| I-191 | 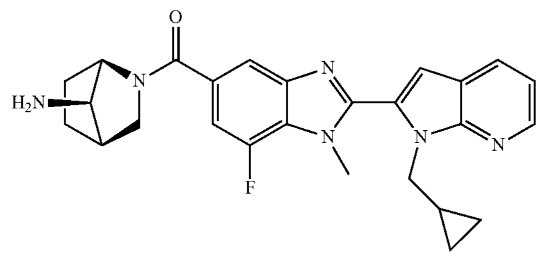 [SMILES: Cn1c(-c2cc3cccnc3n2CC2CC2)nc2cc(C(=O)N3C[C@H]4CC[C@@H]3[C@@H]4N)cc(F)c21] | 458.5306 | 1.98 min | 459 | A | Hydrochloric acid | 1 |
| I-192 | 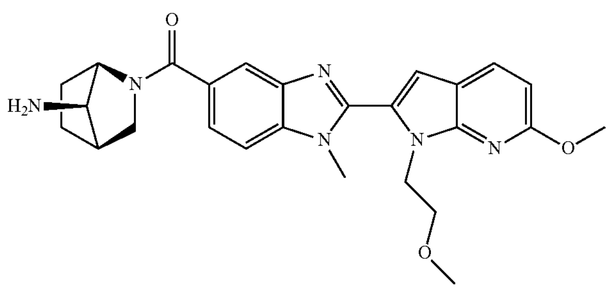 [SMILES: COCCn1c(-c2nc3cc(C(=O)N4C[C@H]5CC[C@@H]4[C@@H]5N)ccc3n2C)cc2ccc(OC)nc21] | 474.5548 | 1.88 min | 475 | A | Hydrochloric acid | 1 |

-continued
| # | Structure | Mol Wt | LCMS $T_{ret}$ | M/z (+) | LCMS Method | Salt | Salt Stoichiometry |
|---|---|---|---|---|---|---|---|
| I-193 | 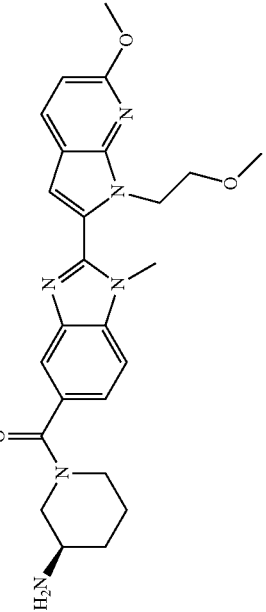 | 462.5441 | 1.91 min | 463 | A | Hydrochloric acid | 1 |
| I-194 | 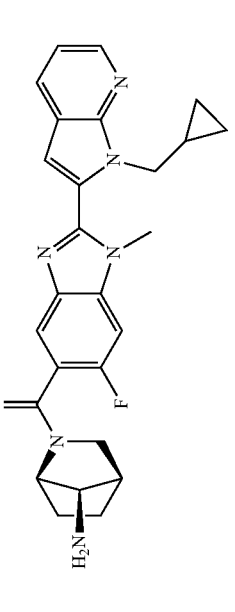 | 458.5306 | 1.86 min | 459 | A | Hydrochloric acid | 1 |
| I-195 | 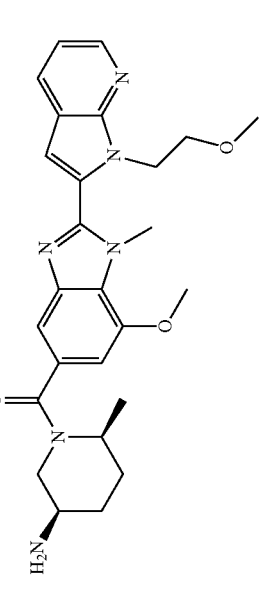 | 476.5707 | 1.88 min | 477 | A | Hydrochloric acid | 1 |

-continued

| # | Structure | Mol Wt | LCMS T$_{ret}$ | M/z (+) | LCMS Method | Salt | Salt Stoichoimetry |
|---|---|---|---|---|---|---|---|
| I-196 | 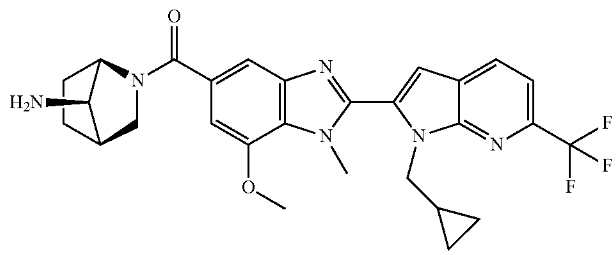 [SMILES: COc1cc(C(=O)N2C[C@H]3CC[C@@H]2[C@@H]3N)cc2nc(-c3cc4ccc(C(F)(F)F)nc4n3CC3CC3)n(C)c12] | 538.5641 | 2.65 min | 539.2 | A | Hydrochloric acid | 1 |
| I-197 | 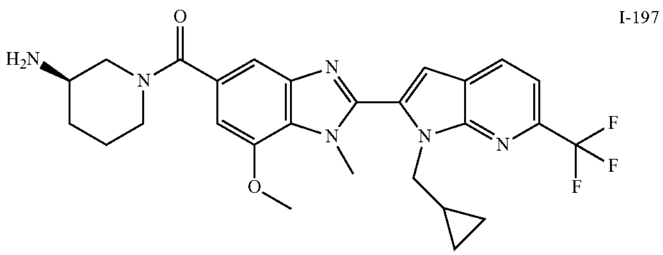 | 526.5534 | 2.69 min | 527.2 | A | Hydrochloric acid | 1 |
| I-198 | 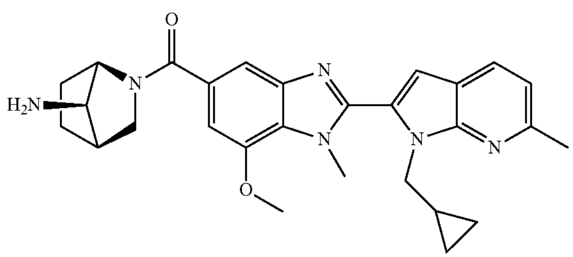 [SMILES: COc1cc(C(=O)N2C[C@H]3CC[C@@H]2[C@@H]3N)cc2nc(-c3cc4ccc(C)nc4n3CC3CC3)n(C)c12] | 484.5927 | 2.14 min | 485.1 | A | Hydrochloric acid | 1 |

-continued

| # | Structure | Mol Wt | LCMS $T_{ret}$ | M/z (+) | LCMS Method | Salt | Salt Stoichoimetry |
|---|---|---|---|---|---|---|---|
| I-199 | 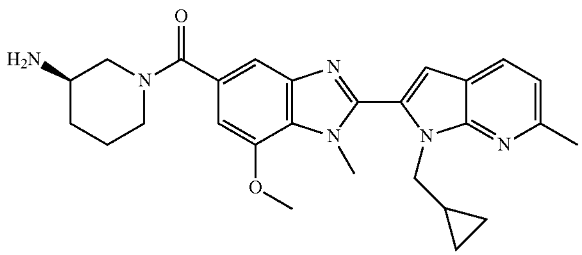 [SMILES: COc1cc(C(=O)N2CCC[C@@H](N)C2)cc2nc(-c3cc4ccc(C)nc4n3CC3CC3)n(C)c12] | 472.582 | 2.19 min | 473.2 | A | Hydrochloric acid | 1 |
| I-200 | 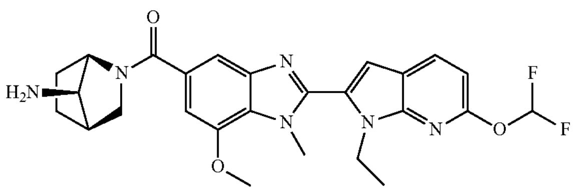 [SMILES: CCn1c(-c2nc3cc(C(=O)N4C[C@H]5CC[C@@H]4[C@@H]5N)cc(OC)c3n2C)cc2ccc(OC(F)F)nc21] | 510.5357 | 2.46 min | 511.2 | A | Hydrochloric acid | 1 |
| I-201 | 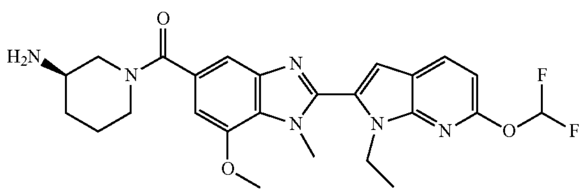 [SMILES: CCn1c(-c2nc3cc(C(=O)N4CCC[C@@H](N)C4)cc(OC)c3n2C)cc2ccc(OC(F)F)nc21] | 498.525 | 2.52 min | 499.2 | A | Hydrochloric acid | 1 |
| I-202 | 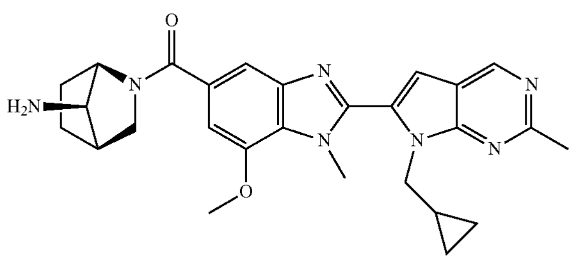 [SMILES: COc1cc(C(=O)N2C[C@H]3CC[C@@H]2[C@@H]3N)cc2nc(-c3cc4cnc(C)nc4n3CC3CC3)n(C)c12] | 485.5807 | 1.37 min | 486.1 | A | Hydrochloric acid | 1 |

-continued

| # | Structure | Mol Wt | LCMS T$_{ret}$ | LCMS M/z (+) | LCMS Method | Salt | Salt Stoichiometry |
|---|---|---|---|---|---|---|---|
| I-203 | 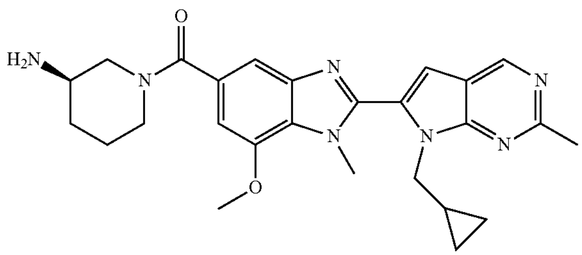 [SMILES: COc1cc(C(=O)N2CCC[C@@H](N)C2)cc2nc(-c3cc4cnc(C)nc4n3CC3CC3)n(C)c12] | 473.57 | 1.38 min | 474.2 | A | Hydrochloric acid | 1 |
| I-204 | 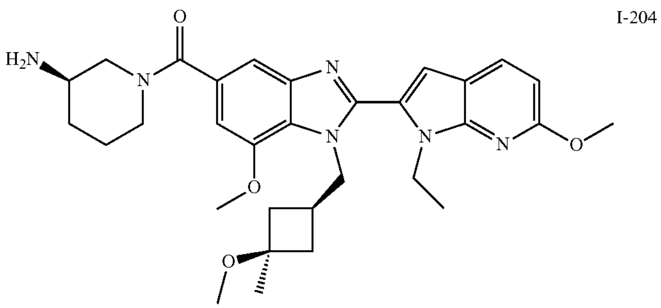 | 560.6871 | 2.56 min | 561.3 | A | Hydrochloric acid | 1 |
| I-205 | 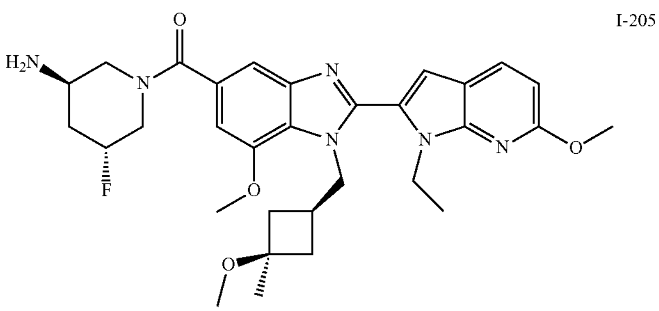 | 578.6776 | 2.58 min | 579.2 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-206 | 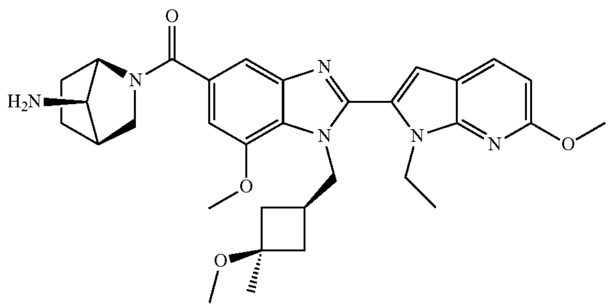 [SMILES: CCn1c(-c2nc3cc(C(=O)N4C[C@H]5CC[C@@H]4[C@@H]5N)cc(OC)c3n2C[C@H]2C[C@@](C)(OC)C2)cc2ccc(OC)nc21] | 572.6978 | 2.52 min | 573.2 | A | Hydrochloric acid | 1 |
| I-207 | 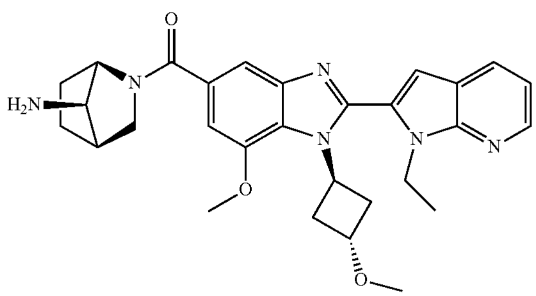 [SMILES: CCn1c(-c2nc3cc(C(=O)N4C[C@H]5CC[C@@H]4[C@@H]5N)cc(OC)c3n2[C@H]2C[C@H](OC)C2)cc2cccnc21] | 514.6187 | 1.92 min | 515.2 | A | Hydrochloric acid | 1 |
| I-208 | 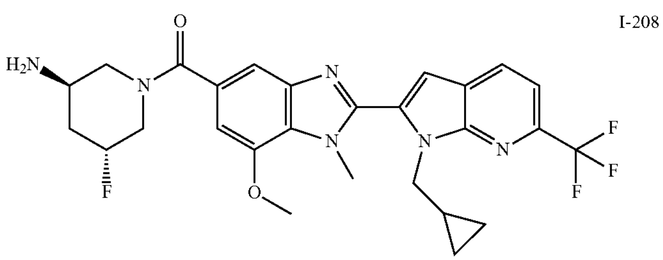 | 544.5438 | 2.70 min | 545.2 | A | Hydrochloric acid | 1 |

-continued

| # | Structure | Mol Wt | LCMS T$_{ret}$ | LCMS M/z (+) | LCMS Method | Salt | Salt Stoichoimetry |
|---|---|---|---|---|---|---|---|
| I-209 | 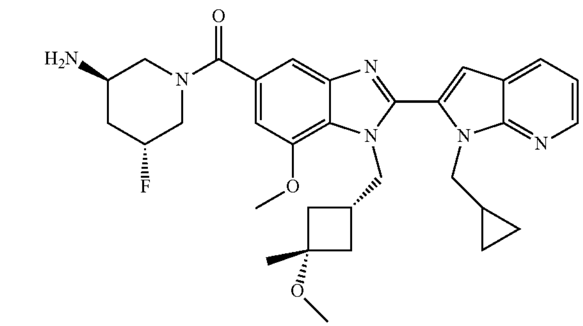 [SMILES: COc1cc(C(=O)N2C[C@H](N)C[C@@H](F)C2)cc2nc(-c3cc4cccnc4n3CC3CC3)n(C[C@H]3C[C@@](C)(OC)C3)c12] | 574.6889 | 2.35 min | 575.2 | A | Hydrochloric acid | 1 |
| I-210 | 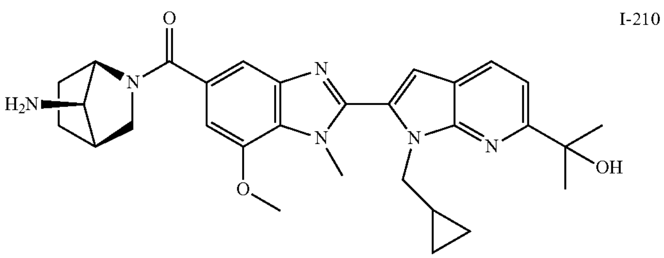 | 528.6452 | 2.17 min | 529.2 | A | Hydrochloric acid | 1 |
| I-211 | 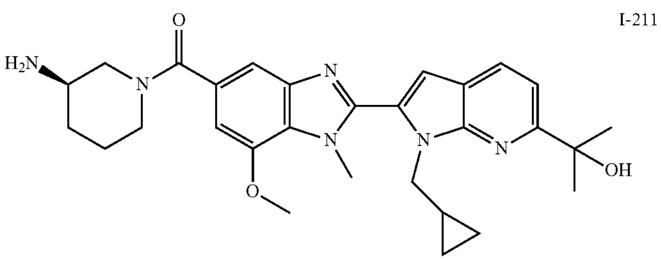 | 516.6345 | 2.22 min | 517.2 | A | Hydrochloric acid | 1 |

-continued
| # | Structure | Mol Wt | LCMS T_ret | M/z (+) | LCMS Method | Salt | Salt Stoichiometry |
|---|---|---|---|---|---|---|---|
| I-212 | 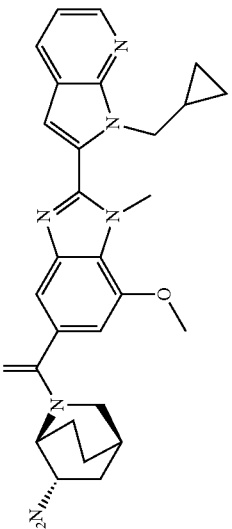 | 484.5927 | 2.08 min | 485.2 | A | | |
| I-213 | 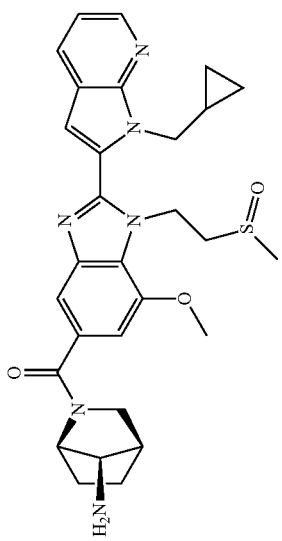 | 546.684 | 2.18 min | 547.4 | H | Formic acid | 1 |
| I-214 | 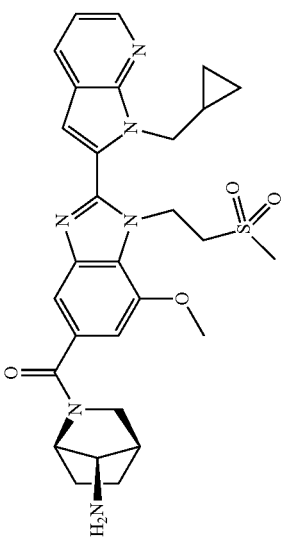 | 562.683 | 1.73 min | 563.2 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-215 | 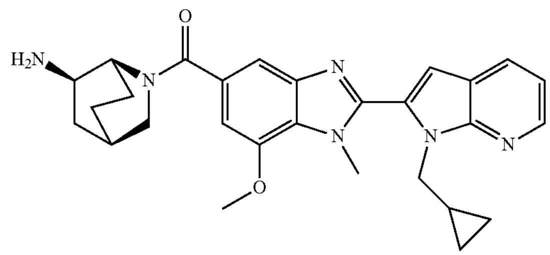 [SMILES: COc1cc(C(=O)N2C[C@@H]3CC[C@H]2[C@H](N)C3)cc2nc(-c3cc4cccnc4n3CC3CC3)n(C)c12] | 484.5927 | 2.10 min | 485.2 | A | | |
| I-216 | 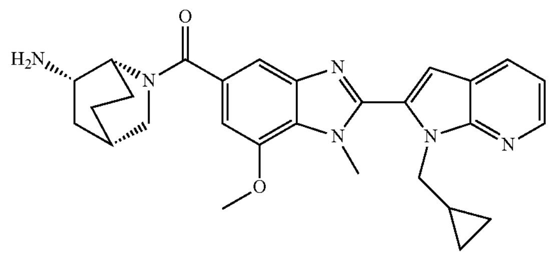 [SMILES: COc1cc(C(=O)N2C[C@H]3CC[C@@H]2[C@@H](N)C3)cc2nc(-c3cc4cccnc4n3CC3CC3)n(C)c12] | 484.5927 | 2.13 min | 485.2 | A | | |
| I-217 | 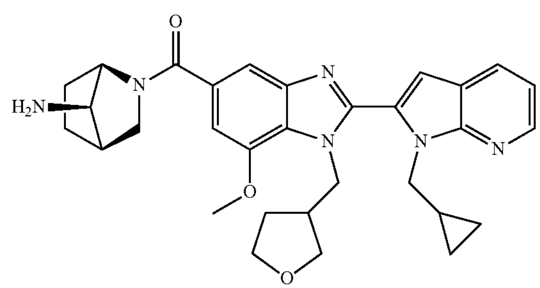 [SMILES: COc1cc(C(=O)N2C[C@H]3CC[C@@H]2[C@@H]3N)cc2nc(-c3cc4cccnc4n3CC3CC3)n(CC3CCOC3)c12] | 540.6559 | 3.69 min | 541.3 | B | Hydrochloric acid | 1 |

-continued

| # | Mol Wt | LCMS T_ret | M/z (+) | LCMS Method | Salt | Salt Stoichiometry |
|---|---|---|---|---|---|---|
| I-218 | 514.6187 | 2.79 min | 515.4 | H | Hydrochloric acid | 1 |
| I-219 | 540.6559 | 2.18 min | 541.4 | A | Hydrochloric acid | 1 |
| I-220 | 488.5814 | 3.81 min | 489.1 | C | | |

-continued

| # | Structure | Mol Wt | LCMS T$_{ret}$ | M/z (+) | LCMS Method | Salt | Salt Stoichiometry |
|---|---|---|---|---|---|---|---|
| I-221 | 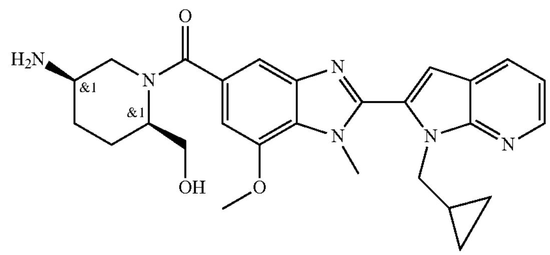 [SMILES: COc1cc(C(=O)N2C[C@H](N)CC[C@@H]2CO)cc2nc(-c3cc4cccnc4n3CC3CC3)n(C)c12] | 488.5814 | 1.92 min | 489.4 | A | Hydrochloric acid | 1 |
| I-222 | 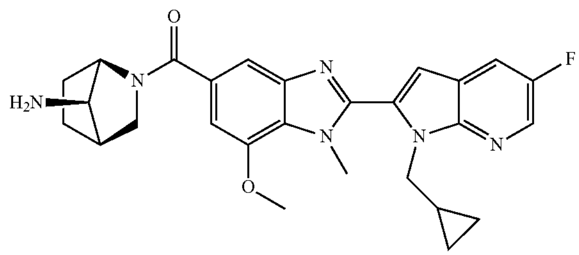 [SMILES: COc1cc(C(=O)N2C[C@H]3CC[C@@H]2[C@@H]3N)cc2nc(-c3cc4cc(F)cnc4n3CC3CC3)n(C)c12] | 488.5566 | 2.22 min | 489.3 | A | Hydrochloric acid | 1 |
| I-223 | 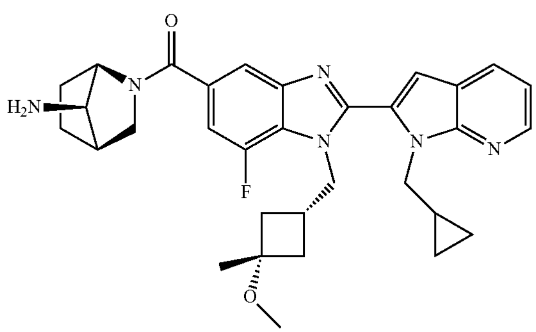 [SMILES: CO[C@]1(C)C[C@H](Cn2c(-c3cc4cccnc4n3CC3CC3)nc3cc(C(=O)N4C[C@H]5CC[C@@H]4[C@@H]5N)cc(F)c32)C1] | 556.6736 | 2.30 min | 557.5 | A | | |

-continued
| # | Structure | Mol Wt | LCMS $T_{ret}$ | M/z (+) | LCMS Method | Salt | Salt Stoichoimetry |
|---|---|---|---|---|---|---|---|
| I-224 | 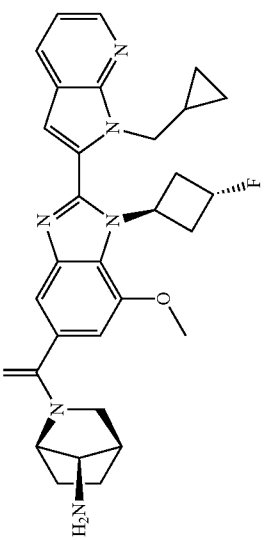 | 528.6204 | 2.20 min | 529.3 | A | Hydrochloric acid | 1 |
| I-225 | 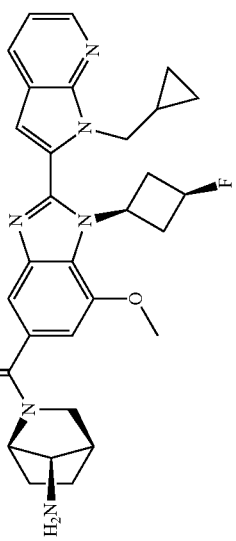 | 528.6204 | 2.21 min | 529.3 | A | Hydrochloric acid | 1 |
| I-226 | 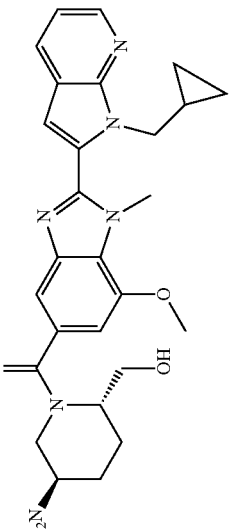 | 488.5814 | 1.86 min | 489.3 | A | Hydrochloric acid | 1 |

-continued

| # | Structure | Mol Wt | LCMS T_ret | LCMS M/z (+) | LCMS Method | Salt | Salt Stoichiometry |
|---|---|---|---|---|---|---|---|
| I-227 | 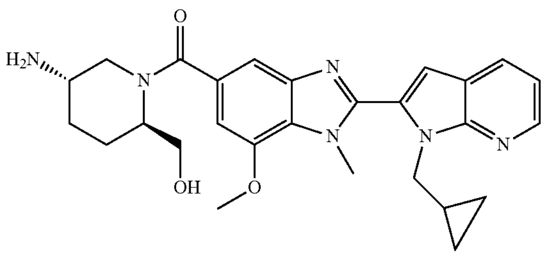 [SMILES: COc1cc(C(=O)N2C[C@@H](N)CC[C@@H]2CO)cc2nc(-c3cc4cccnc4n3CC3CC3)n(C)c12] | 488.5814 | 1.85 min | 489.3 | A | Hydrochloric acid | 1 |
| I-228 | 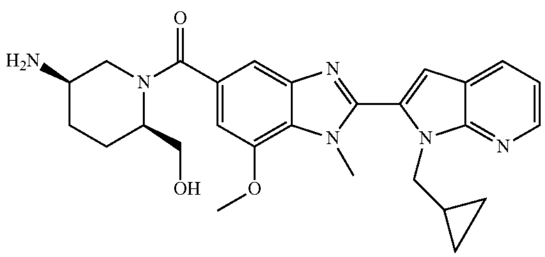 [SMILES: COc1cc(C(=O)N2C[C@H](N)CC[C@@H]2CO)cc2nc(-c3cc4cccnc4n3CC3CC3)n(C)c12] | 488.5814 | 1.91 min | 489.3 | A | Hydrochloric acid | 1 |
| I-229 | 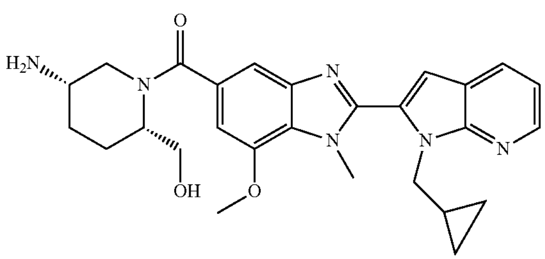 [SMILES: COc1cc(C(=O)N2C[C@@H](N)CC[C@H]2CO)cc2nc(-c3cc4cccnc4n3CC3CC3)n(C)c12] | 488.5814 | 1.90 min | 489.3 | A | Hydrochloric acid | 1 |

-continued
| # | Structure | Mol Wt | LCMS $T_{ret}$ | M/z (+) | LCMS Method | Salt | Salt Stoichiometry |
|---|---|---|---|---|---|---|---|
| I-230 | 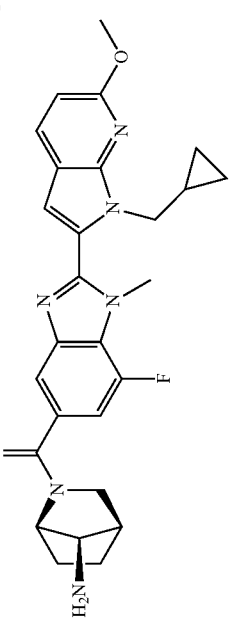 | 488.5566 | 2.46 min | 489.3 | A | Hydrochloric acid | 1 |
| I-231 | 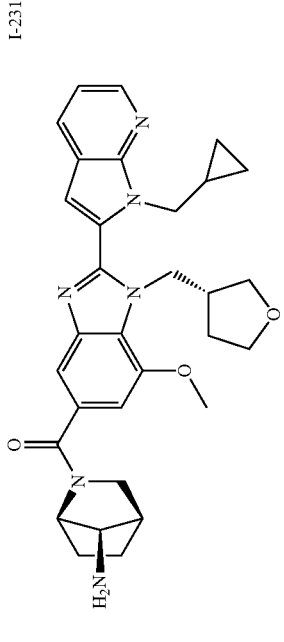 | 540.6559 | 1.99 min | 541.3 | A | Hydrochloric acid | 1 |
| I-232 | 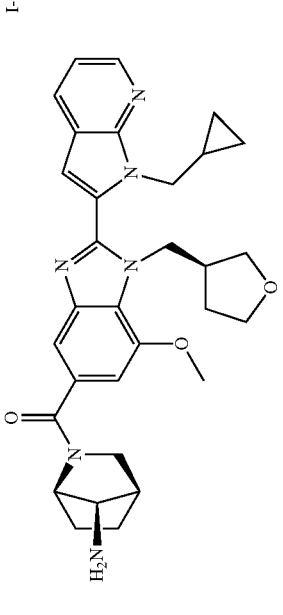 | 540.6559 | 1.98 min | 541.3 | A | | 1 |

-continued
| # | Structure | Mol Wt | LCMS $T_{ret}$ | M/z (+) | LCMS Method | Salt | Salt Stoichoimetry |
|---|---|---|---|---|---|---|---|
| I-233 | 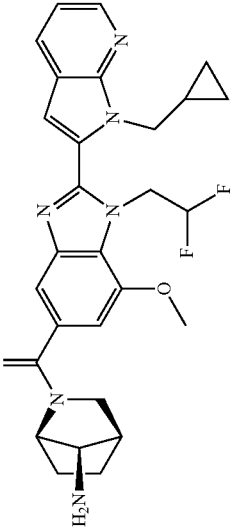 | 520.5736 | 2.18 min | 521.3 | A | | 1 |
| I-234 | 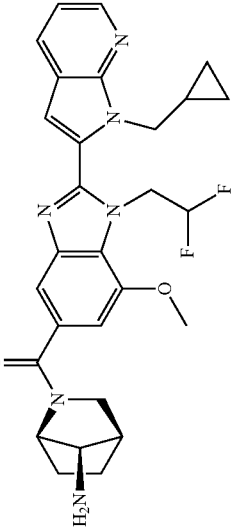 | 494.5363 | 1.97 min | 495.3 | A | Hydrochloric acid | 1 |
| I-235 | 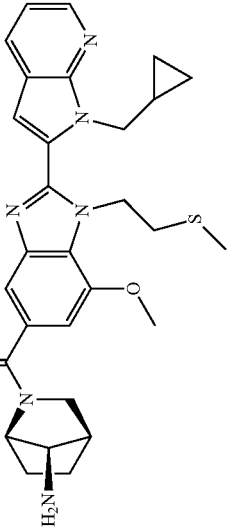 | 530.684 | 2.28 min | 531.3 | A | Formic acid | 0.5 |

-continued

| # | Mol Wt | LCMS $T_{ret}$ | M/z (+) | LCMS Method | Salt | Salt Stoichiometry |
|---|---|---|---|---|---|---|
| I-236 | 554.6825 | 2.16 min | 555.3 | A | Hydrochloric acid | 1 |
| I-237 | 484.5927 | 2.06 min | 485.3 | A | Hydrochloric acid | 1 |
| I-238 | 571.7276 | 2.26 min | 572.4 | H | | |

-continued
| # | Structure | Mol Wt | LCMS T$_{ret}$ | M/z (+) | LCMS Method | Salt | Salt Stoichiometry |
|---|---|---|---|---|---|---|---|
| I-239 | 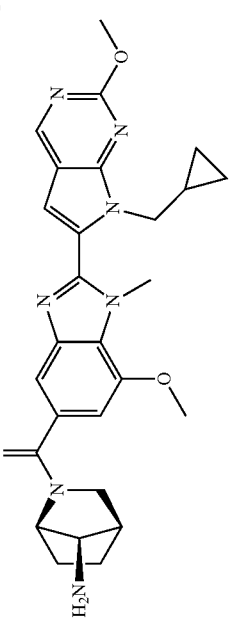 | 501.5801 | 1.87 min | 502.3 | A | Hydrochloric acid | 1 |
| I-240 | 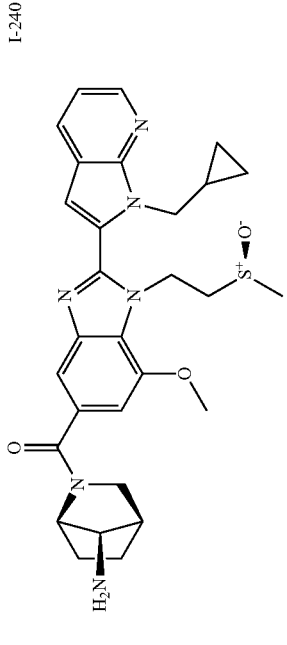 | 546.684 | 2.20 min | 547.4 | A | Formic acid | 0.5 |
| I-241 | 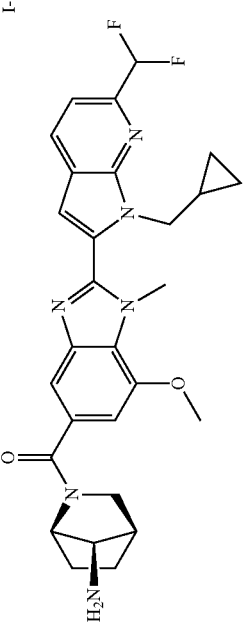 | 520.5736 | 2.39 min | 521.3 | A | Hydrochloric acid | 1 |

-continued

| Structure | # | Mol Wt | LCMS $T_{ret}$ | LCMS M/z (+) | LCMS Method | Salt | Salt Stoichiometry |
|---|---|---|---|---|---|---|---|
| 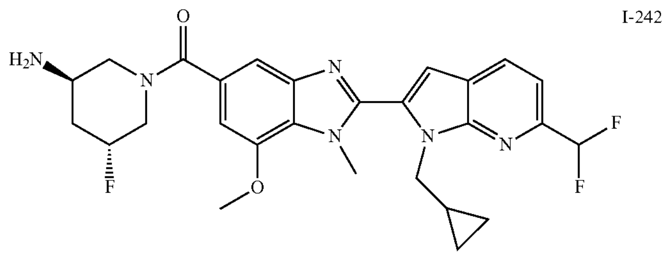 | I-242 | 526.5534 | 2.48 min | 527.2 | A | Hydrochloric acid | 1 |
| 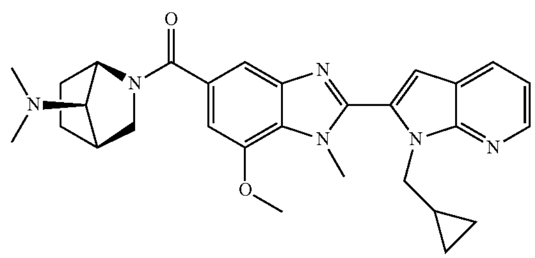 [SMILES: COc1cc(C(=O)N2C[C@H]3CC[C@@H]2[C@@H]3N(C)C)cc2nc(-c3cc4cccnc4n3CC3CC3)n(C)c12] | I-243 | 498.6193 | 3.58 min | 499.4 | H | Hydrochloric acid | 1 |
| 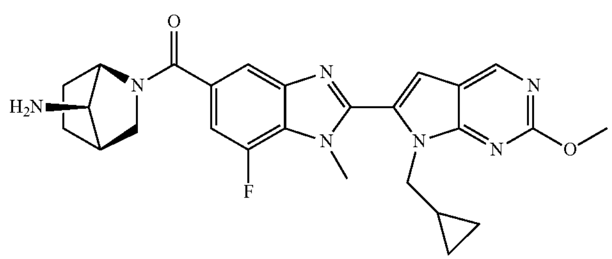 [SMILES: COc1ncc2cc(-c3nc4cc(C(=O)N5C[C@H]6CC[C@@H]5[C@@H]6N)cc(F)c4n3C)n(CC3CC3)c2n1] | I-244 | 489.5446 | 1.85 min | 490.3 | A | Hydrochloric acid | 1 |

-continued
| # | Structure | Mol Wt | LCMS T$_{ret}$ | M/z (+) | LCMS Method | Salt | Salt Stoichiometry |
|---|---|---|---|---|---|---|---|
| I-245 | 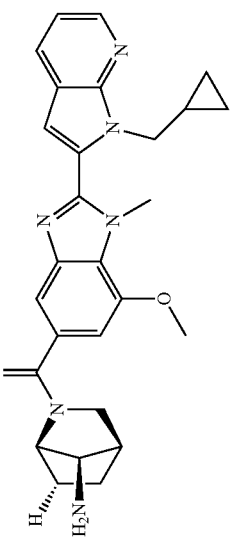 | 485.5807 | 2.02 min | 486.3 | A | | |
| I-246 | 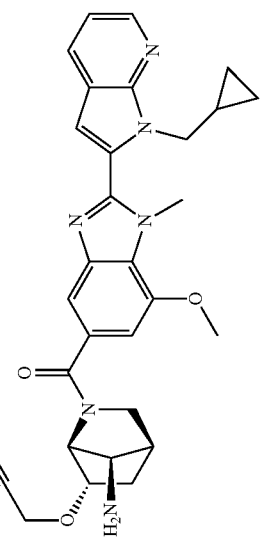 | 525.6015 | 2.05 min | 526.3 | A | Trifluoroacetic acid | 1 |
| I-247 | 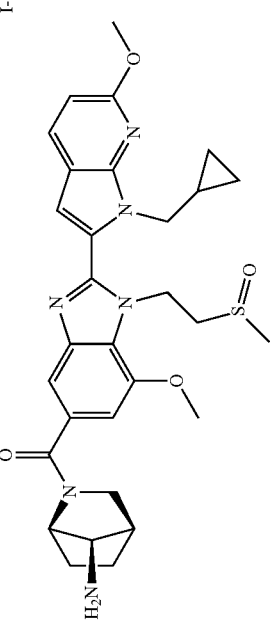 | 576.71 | 1.96 min | 577.3 | A | Hydrochloric acid | 1 |

| # | Structure | Mol Wt | LCMS T$_{ret}$ | LCMS M/z (+) | LCMS Method | Salt | Salt Stoichiometry |
|---|---|---|---|---|---|---|---|
| I-248 | 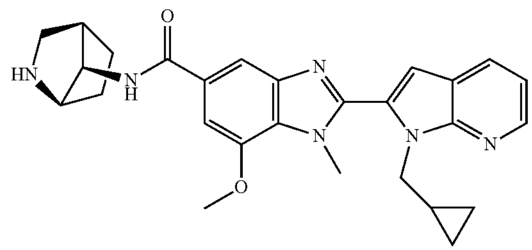 [SMILES: COc1cc(C(=O)N[C@@H]2[C@@H]3CC[C@H]2NC3)cc2nc(-c3cc4cccnc4n3CC3CC3)n(C)c12] | 470.5661 | 2.14 min | 471.3 | A | | |
| I-249 | 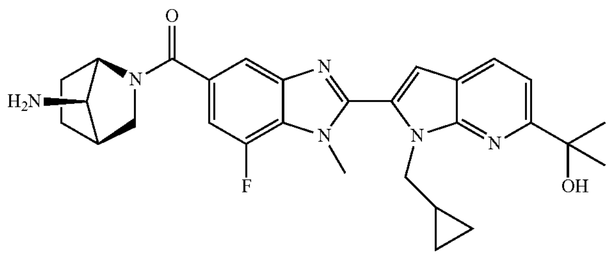 [SMILES: Cn1c(-c2cc3ccc(C(C)(C)O)nc3n2CC2CC2)nc2cc(C(=O)N3C[C@H]4CC[C@@H]3[C@@H]4N)cc(F)c21] | 516.6097 | 2.19 min | 517.3 | A | | |
| I-250 | 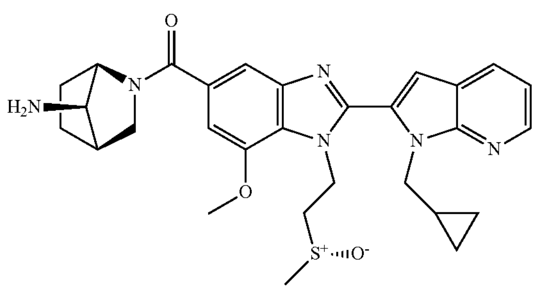 [SMILES: COc1cc(C(=O)N2C[C@H]3CC[C@@H]2[C@@H]3N)cc2nc(-c3cc4cccnc4n3CC3CC3)n(CC[S@@+](C)[O-])c12] | 546.684 | 1.55 min | 547.2 | A | Formic acid | 0.5 |

-continued

| # | Structure | Mol Wt | LCMS T$_{ret}$ | M/z (+) | LCMS Method | Salt | Salt Stoichiometry |
|---|---|---|---|---|---|---|---|
| I-251 | 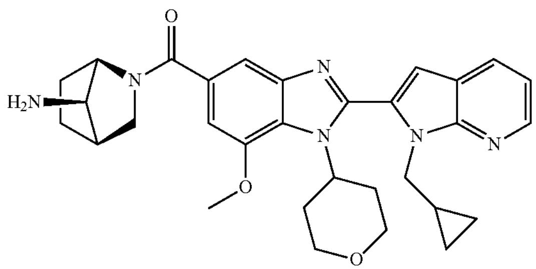 [SMILES: COc1cc(C(=O)N2C[C@H]3CC[C@@H]2[C@@H]3N)cc2nc(-c3cc4cccnc4n3CC3CC3)n(C3CCOCC3)c12] | 540.6559 | 2.00 min | 541.3 | A | Hydrochloric acid | 1 |
| I-252 | 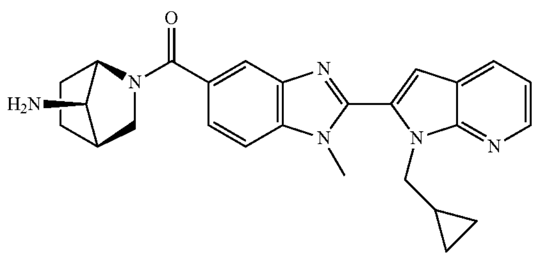 [SMILES: Cn1c(-c2cc3cccnc3n2CC2CC2)nc2cc(C(=O)N3C[C@H]4CC[C@@H]3[C@@H]4N)ccc21] | 440.5401 | 1.79 min | 441.3 | A | Hydrochloric acid | 1 |
| I-253 | 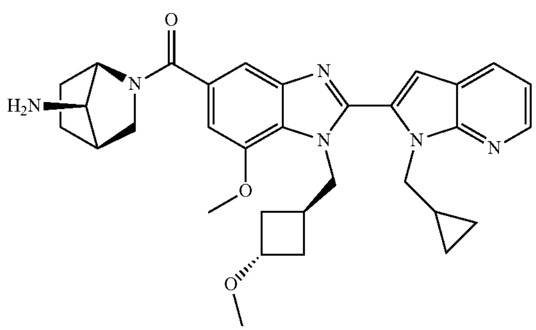 [SMILES: COc1cc(C(=O)N2C[C@H]3CC[C@@H]2[C@@H]3N)cc2nc(-c3cc4cccnc4n3CC3CC3)n(C[C@H]3C[C@H](OC)C3)c12] | 554.6825 | 2.19 min | 555.3 | A | Hydrochloric acid | 1 |

-continued

| # | Structure | Mol Wt | LCMS T_ret | LCMS M/z (+) | LCMS Method | Salt | Salt Stoichiometry |
|---|---|---|---|---|---|---|---|
| I-254 | 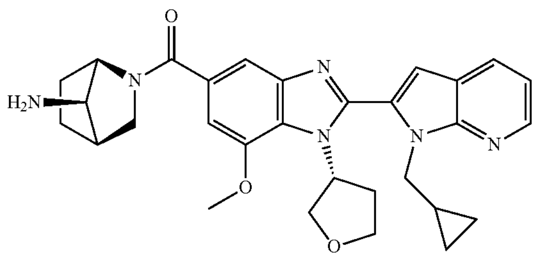 [SMILES: COc1cc(C(=O)N2C[C@H]3CC[C@@H]2[C@@H]3N)cc2nc(-c3cc4cccnc4n3CC3CC3)n([C@@H]3CCOC3)c12] | 526.6294 | 2.79 min | 527.4 | H | Hydrochloric acid | 1 |
| I-255 | 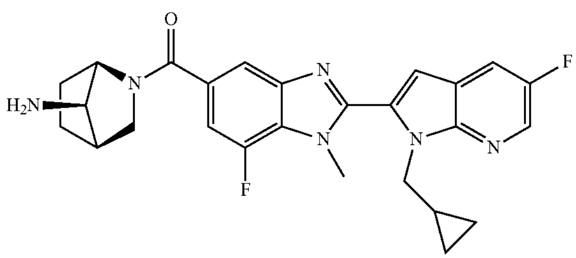 [SMILES: Cn1c(-c2cc3cc(F)cnc3n2CC2CC2)nc2cc(C(=O)N3C[C@H]4CC[C@@H]3[C@@H]4N)cc(F)c21] | 476.521 | 2.14 min | 477.3 | A | Hydrochloric acid | 1 |
| I-256 | 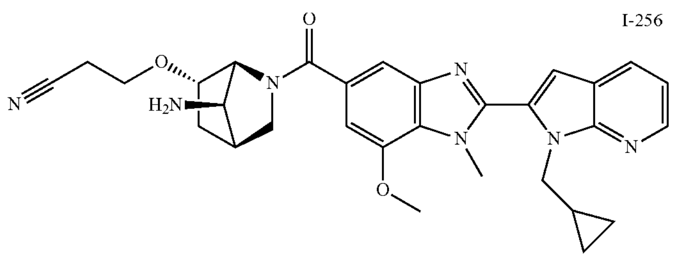 [SMILES: COc1cc(C(=O)N2C[C@H]3C[C@H](OCCC#N)[C@@H]2[C@@H]3N)cc2nc(-c3cc4cccnc4n3CC3CC3)n(C)c12] | 539.6281 | 3.29 min | 540.2 | C | | |

-continued

| # | Structure | Mol Wt | LCMS T$_{ret}$ | M/z (+) | LCMS Method | Salt | Salt Stoichoimetry |
|---|---|---|---|---|---|---|---|
| I-257 | 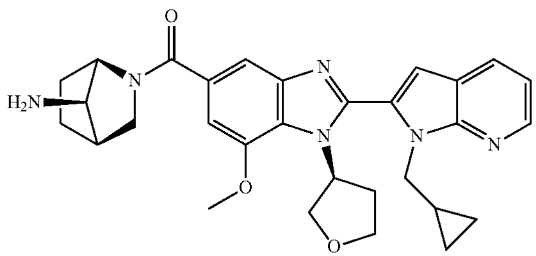 [SMILES: COc1cc(C(=O)N2C[C@H]3CC[C@@H]2[C@@H]3N)cc2nc(-c3cc4cccnc4n3CC3CC3)n([C@H]3CCOC3)c12] | 526.6294 | 2.79 min | 527.4 | H | Hydrochloric acid | 1 |
| I-258 | 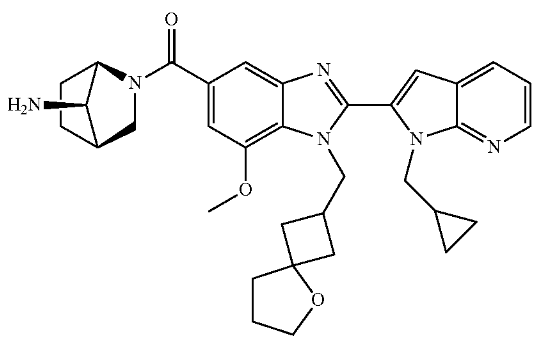 [SMILES: COc1cc(C(=O)N2C[C@H]3CC[C@@H]2[C@@H]3N)cc2nc(-c3cc4cccnc4n3CC3CC3)n(CC3CC4(CCCO4)C3)c12] | 580.7198 | 2.18 min | 581.3 | A | Hydrochloric acid | 1 |
| I-259 | 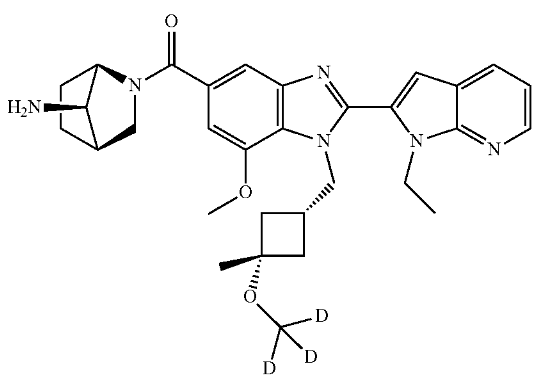 [SMILES: [2H]C([2H])([2H])O[C@]1(C)C[C@H](Cn2c(-c3cc4cccnc4n3CC)nc3cc(C(=O)N4C[C@H]5CC[C@@H]4[C@@H]5N)cc(OC)c32)C1] | 545.6903 | 2.00 min | 546.4 | A | Hydrochloric acid | 1 |

-continued

| # | Structure | Mol Wt | LCMS $T_{ret}$ | M/z (+) | LCMS Method | Salt | Salt Stoichiometry |
|---|---|---|---|---|---|---|---|
| I-260 | 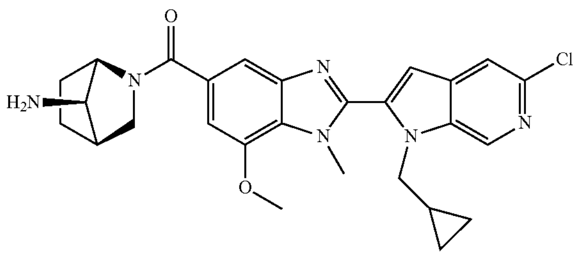 [SMILES: COc1cc(C(=O)N2C[C@H]3CC[C@@H]2[C@@H]3N)cc2nc(-c3cc4cc(Cl)ncc4n3CC3CC3)n(C)c12] | 505.011 | 2.04 min | 505.3 | A | Hydrochloric acid | 1 |
| I-261 | 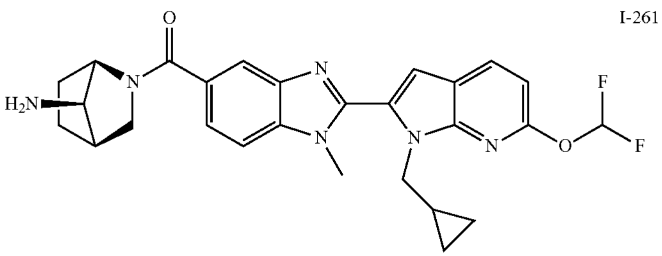 | 506.547 | 2.34 min | 507.3 | A | Hydrochloric acid | 1 |
| I-262 | 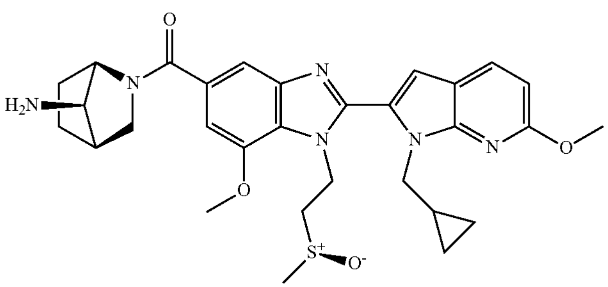 [SMILES: COc1ccc2cc(-c3nc4cc(C(=O)N5C[C@H]6CC[C@@H]5[C@@H]6N)cc(OC)c4n3CC[S@+](C)[O-])n(CC3CC3)c2n1] | 576.71 | 1.90 min | 577.3 | A | | |

-continued

| # | Mol Wt | LCMS $T_{ret}$ | M/z (+) | LCMS Method | Salt | Salt Stoichiometry |
|---|---|---|---|---|---|---|
| I-263 | 576.71 | 1.90 min | 577.3 | A | | |
| I-264 | 541.644 | 1.97 min | 542.3 | A | Hydrochloric acid | 1 |
| I-265 | 470.5661 | 1.10 min | 471.4 | A | | |

-continued
| # | Structure | Mol Wt | LCMS $T_{ret}$ | M/z (+) | LCMS Method | Salt | Salt Stoichiometry |
|---|---|---|---|---|---|---|---|
| I-266 | 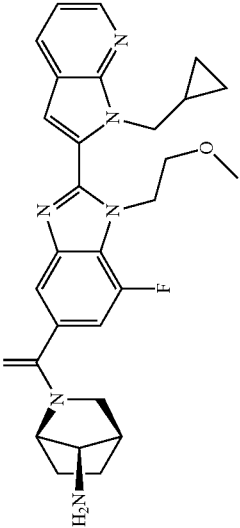 | 502.5831 | 2.00 min | 503.4 | A | | |
| I-267 | 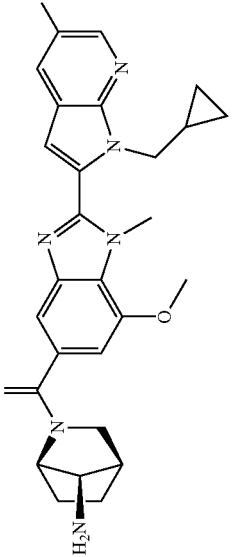 | 505.011 | 2.36 min | 505.3 | A | Hydrochloric acid | 1 |
| I-268 | 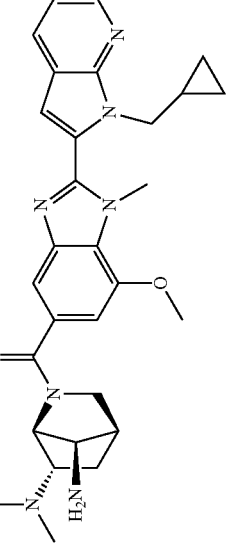 | 513.6339 | 1.99 min | 514.3 | A | Hydrochloric acid | 2 |

-continued

| # | Structure | Mol Wt | LCMS T$_{ret}$ | LCMS M/z (+) | LCMS Method | Salt | Salt Stoichiometry |
|---|---|---|---|---|---|---|---|
| I-269 | 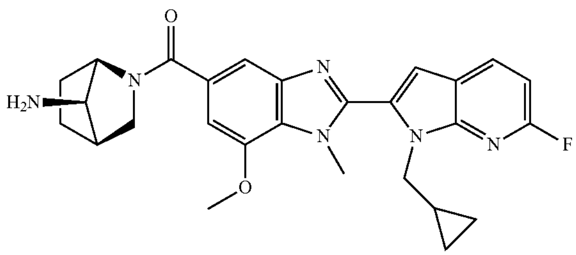 [SMILES: COc1cc(C(=O)N2C[C@H]3CC[C@@H]2[C@@H]3N)cc2nc(-c3cc4ccc(F)nc4n3CC3CC3)n(C)c12] | 488.5566 | 3.26 min | 489.4 | H | Hydrochloric acid | 1 |
| I-270 | 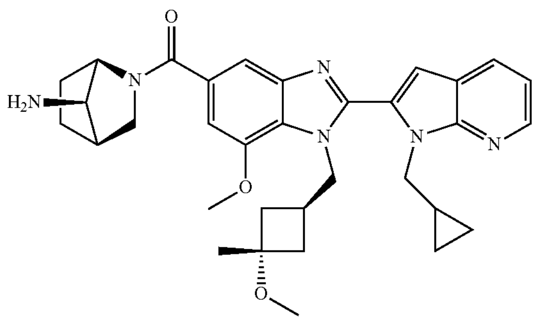 [SMILES: COc1cc(C(=O)N2C[C@H]3CC[C@@H]2[C@@H]3N)cc2nc(-c3cc4cccnc4n3CC3CC3)n(C[C@H]3C[C@](C)(OC)C3)c12] | 568.7091 | 2.19 min | 569.5 | A | Hydrochloric acid | 1 |
| I-271 | 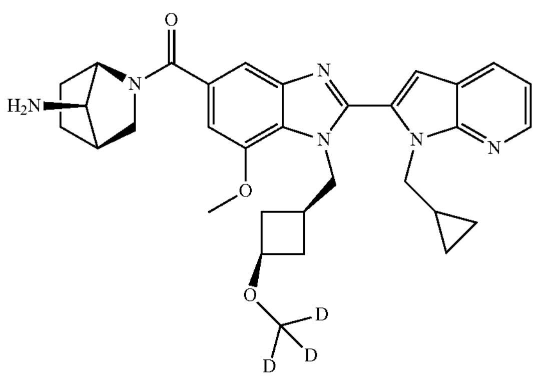 [SMILES: [2H]C([2H])([2H])O[C@H]1C[C@@H](Cn2c(-c3cc4cccnc4n3CC3CC3)nc3cc(C(=O)N4C[C@H]5CC[C@@H]4[C@@H]5N)cc(OC)c32)C1] | 557.701 | 2.12 min | 558.4 | H | | |

-continued

| # | Structure | Mol Wt | LCMS T_ret | M/z (+) | LCMS Method | Salt | Salt Stoichoimetry |
|---|---|---|---|---|---|---|---|
| I-272 | 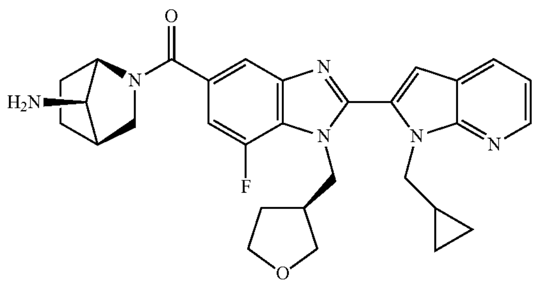 [SMILES: N[C@@H]1[C@@H]2CC[C@H]1N(C(=O)c1cc(F)c3c(c1)nc(-c1cc4cccnc4n1CC1CC1)n3C[C@@H]1CCOC1)C2] | 528.6204 | 2.86 min | 529.4 | H | Hydrochloric acid | 1 |
| I-273 | 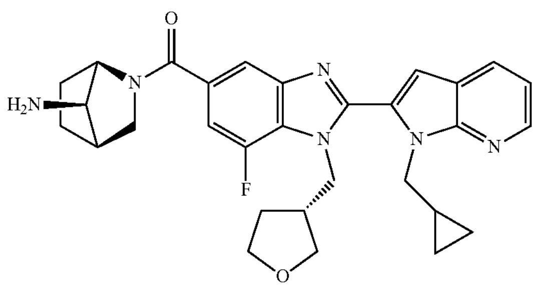 [SMILES: N[C@@H]1[C@@H]2CC[C@H]1N(C(=O)c1cc(F)c3c(c1)nc(-c1cc4cccnc4n1CC1CC1)n3C[C@H]1CCOC1)C2] | 528.6204 | 2.86 min | 529.5 | H | Hydrochloric acid | 1 |
| I-274 | 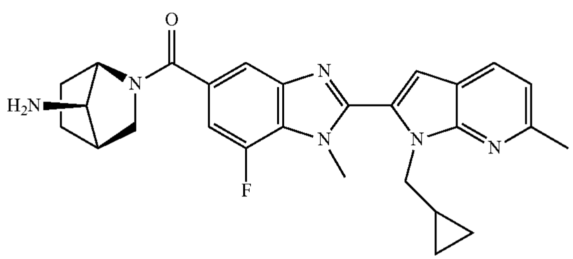 [SMILES: Cc1ccc2cc(-c3nc4cc(C(=O)N5C[C@H]6CC[C@@H]5[C@@H]6N)cc(F)c4n3C)n(CC3CC3)c2n1] | 472.5572 | 2.12 min | 473.3 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-275 | 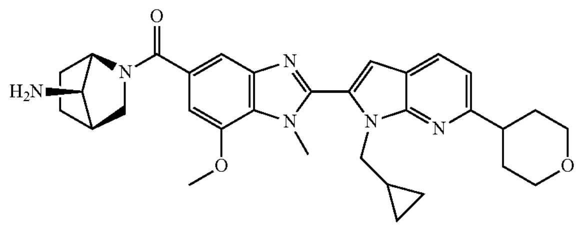 [SMILES: COc1cc(C(=O)N2C[C@H]3CC[C@@H]2[C@@H]3N)cc2nc(-c3cc4ccc(C5CCOCC5)nc4n3CC3CC3)n(C)c12] | 554.6825 | 3.41 min | 555.4 | H | Hydrochloric acid | 1 |
| I-276 | 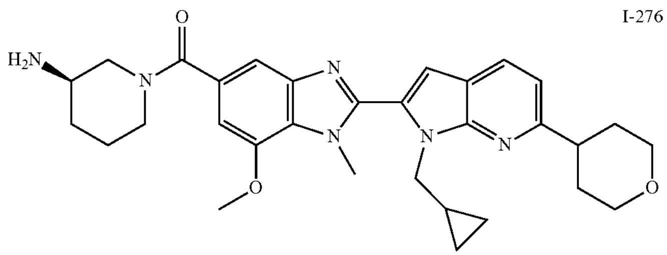 | 542.6718 | 3.66 min | 543.5 | H | Hydrochloric acid | 1 |
| I-277 | 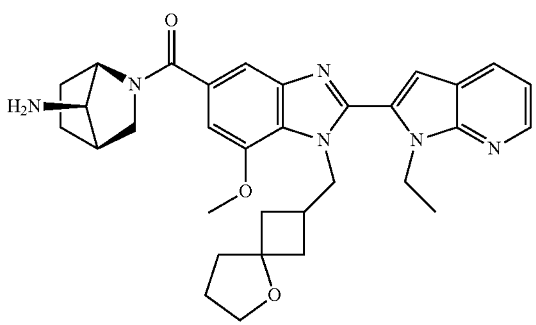 [SMILES: CCn1c(-c2nc3cc(C(=O)N4C[C@H]5CC[C@@H]4[C@@H]5N)cc(OC)c3n2CC2CC3(CCCO3)C2)cc2cccnc21] | 554.6825 | 2.03 min | 555.4 | A | Hydrochloric acid | 1 |

-continued

| # | Structure | Mol Wt | LCMS T_ret | LCMS M/z (+) | LCMS Method | Salt | Salt Stoichoimetry |
|---|---|---|---|---|---|---|---|
| I-278 | 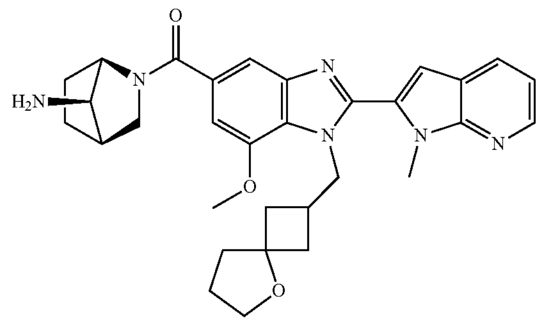 [SMILES: COc1cc(C(=O)N2C[C@H]3CC[C@@H]2[C@@H]3N)cc2nc(-c3cc4cccnc4n3C)n(CC3CC4(CCCO4)C3)c12] | 540.6559 | 1.93 min | 541.4 | A | Hydrochloric acid | 1 |
| I-279 | 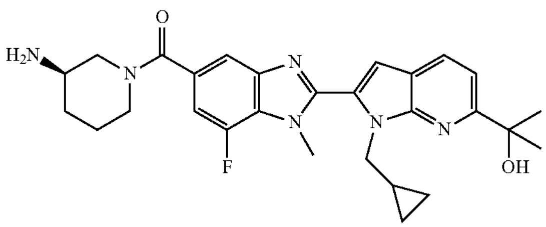 [SMILES: Cn1c(-c2cc3ccc(C(C)(C)O)nc3n2CC2CC2)nc2cc(C(=O)N3CCC[C@@H](N)C3)cc(F)c21] | 504.599 | 3.28 min | 505.4 | H | Hydrochloric acid | 1 |
| I-280 | 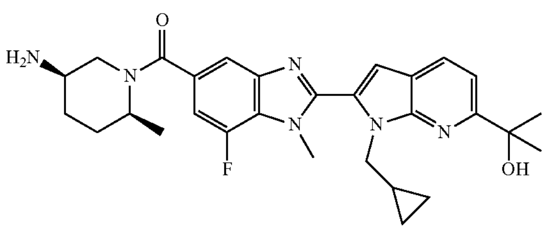 [SMILES: C[C@H]1CC[C@@H](N)CN1C(=O)c1cc(F)c2c(c1)nc(-c1cc3ccc(C(C)(C)O)nc3n1CC1CC1)n2C] | 518.6256 | 3.41 min | 519.4 | H | Hydrochloric acid | 1 |

-continued

| # | Structure | Mol Wt | LCMS T_ret | M/z (+) | LCMS Method | Salt | Salt Stoichiometry |
|---|---|---|---|---|---|---|---|
| I-281 | 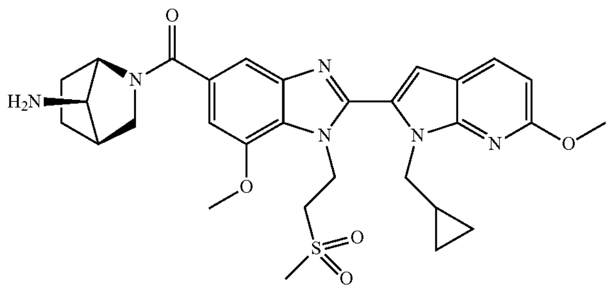 [SMILES: COc1ccc2cc(-c3nc4cc(C(=O)N5C[C@H]6CC[C@@H]5[C@@H]6N)cc(OC)c4n3CCS(C)(=O)=O)n(CC3CC3)c2n1] | 592.709 | 3.03 min | 593.4 | H | Hydrochloric acid | 1 |
| I-282 | 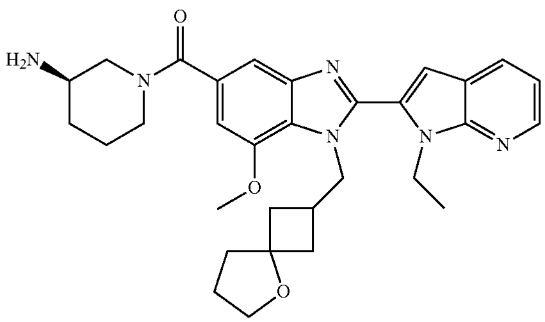 [SMILES: CCn1c(-c2nc3cc(C(=O)N4CCC[C@@H](N)C4)cc(OC)c3n2CC2CC3(CCCO3)C2)cc2cccnc21] | 542.6718 | 2.05 min | 543.4 | A | | |
| I-283 | 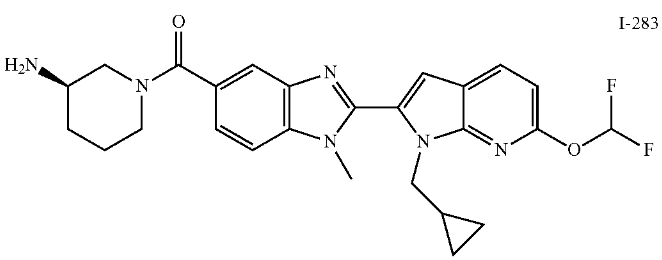 | 494.5363 | 2.39 min | 595.4 | A | Hydrochloric acid | 1 |

-continued
| # | Structure | Mol Wt | LCMS $T_{ret}$ | LCMS M/z (+) | LCMS Method | Salt | Salt Stoichoi-metry |
|---|---|---|---|---|---|---|---|
| I-284 | 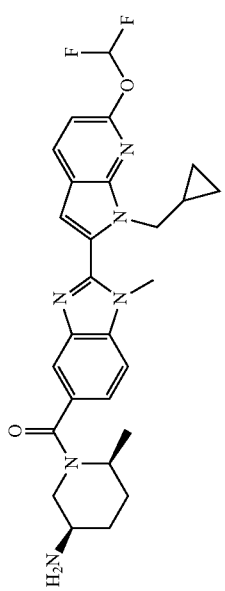 | 508.5629 | 2.46 min | 509.4 | A | Hydrochloric acid | 1 |
| I-285 | 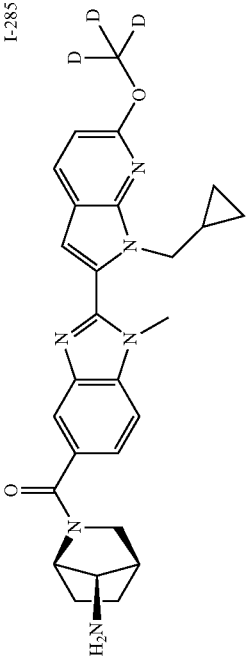 | 473.5846 | 3.28 min | 474.4 | H | Hydrochloric acid | 1 |
| I-286 | 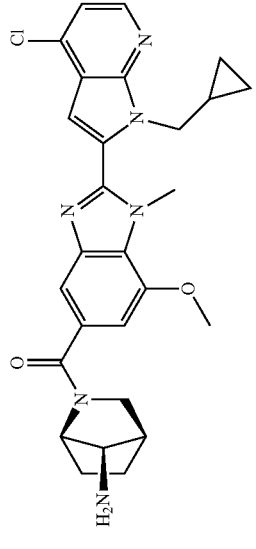 | 505.011 | 3.42 min | 505.4 | H | Hydrochloric acid | 1 |
| I-287 | 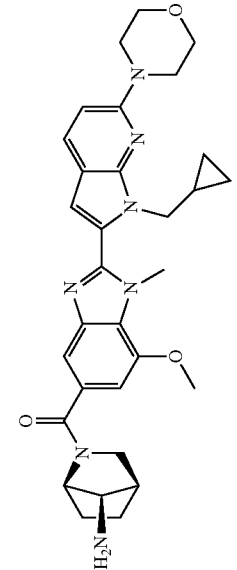 | 555.6706 | 2.22 min | 556.3 | A | Hydrochloric acid | 1 |

-continued
| # | Structure | Mol Wt | LCMS $T_{ret}$ | M/z (+) | LCMS Method | Salt | Salt Stoichiometry |
|---|---|---|---|---|---|---|---|
| I-288 | 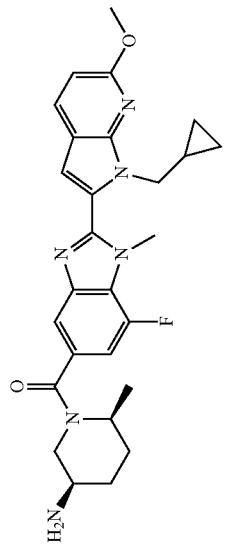 | 490.5724 | 2.52 min | 491.4 | A | Hydrochloric acid | 1 |
| I-289 | 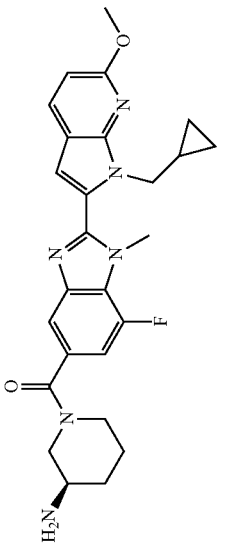 | 476.5459 | 2.43 min | 477.3 | A | Hydrochloric acid | 1 |
| I-290 | 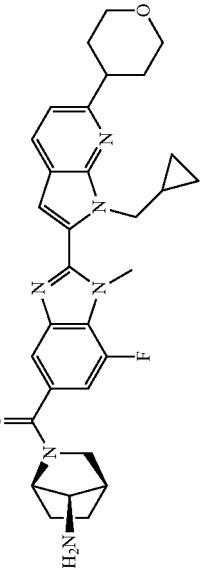 | 542.647 | 2.33 min | 543.3 | A | Hydrochloric acid | 1 |
| I-291 | 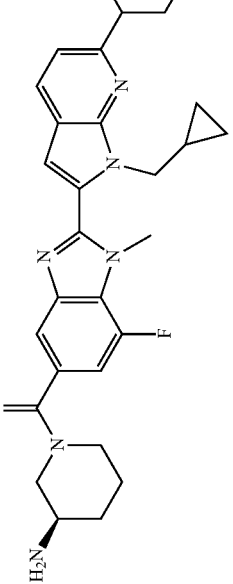 | 530.6363 | 2.35 min | 531.3 | A | Hydrochloric acid | 1 |

| # | Structure | Mol Wt | LCMS $T_{ret}$ | M/z (+) | LCMS Method | Salt | Salt Stoichoimetry |
|---|---|---|---|---|---|---|---|
| I-292 | 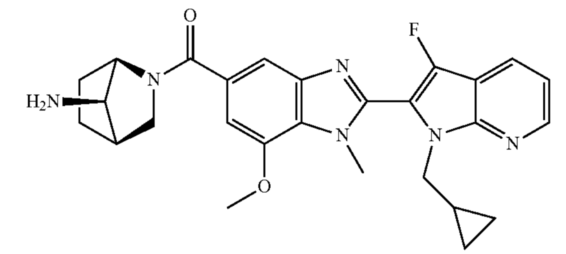 [SMILES: COc1cc(C(=O)N2C[C@H]3CC[C@@H]2[C@@H]3N)cc2nc(-c3c(F)c4cccnc4n3CC3CC3)n(C)c12] | 488.5566 | 2.12 min | 489.3 | A | Hydrochloric acid | 1 |
| I-293 | 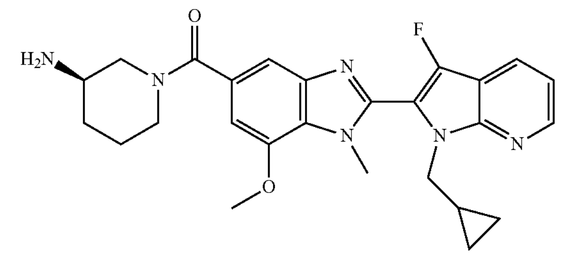 [SMILES: COc1cc(C(=O)N2CCC[C@@H](N)C2)cc2nc(-c3c(F)c4cccnc4n3CC3CC3)n(C)c12] | 476.5459 | 2.18 min | 477.4 | A | Hydrochloric acid | 1 |
| I-294 | 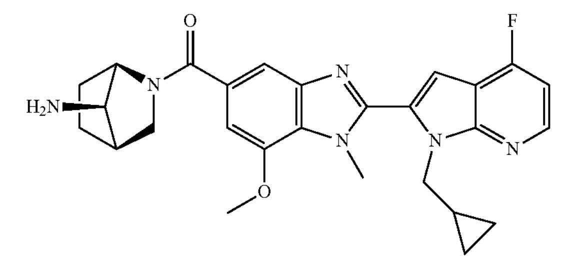 | 488.5566 | 2.10 min | 489.3 | A | Hydrochloric acid | 1 |
| I-295 | 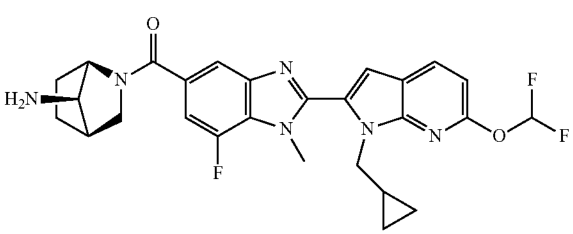 [SMILES: Cn1c(-c2cc3ccc(OC(F)F)nc3n2CC2CC2)nc2cc(C(=O)N3C[C@H]4CC[C@@H]3[C@@H]4N)cc(F)c21] | 524.5375 | 3.63 min | 525.3 | H | Hydrochloric acid | 1 |

-continued

| # | Structure | Mol Wt | LCMS T$_{ret}$ | M/z (+) | LCMS Method | Salt | Salt Stoichoimetry |
|---|---|---|---|---|---|---|---|
| I-296 | 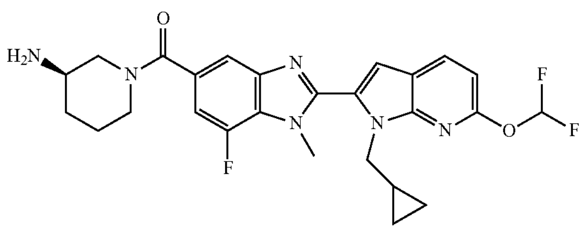 [SMILES: Cn1c(-c2cc3ccc(OC(F)F)nc3n2CC2CC2)nc2cc(C(=O)N3CCC[C@@H](N)C3)cc(F)c21] | 512.5268 | 2.49 min | 513.3 | A | Hydrochloric acid | 1 |
| I-297 | 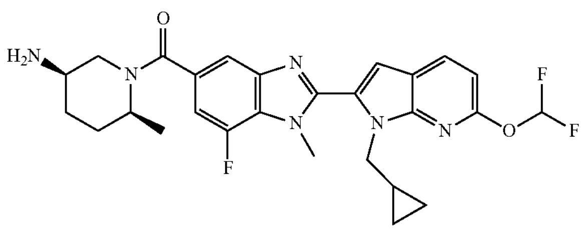 [SMILES: C[C@H]1CC[C@@H](N)CN1C(=O)c1cc(F)c2c(c1)nc(-c1cc3ccc(OC(F)F)nc3n1CC1CC1)n2C] | 526.5534 | 2.61 min | 527.3 | A | Hydrochloric acid | 1 |
| I-298 | 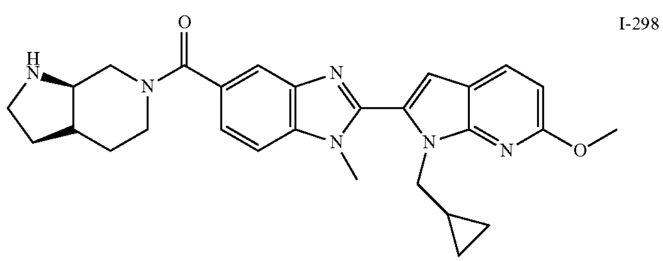 | 484.5927 | 2.27 min | 485.4 | A | | |
| I-299 | 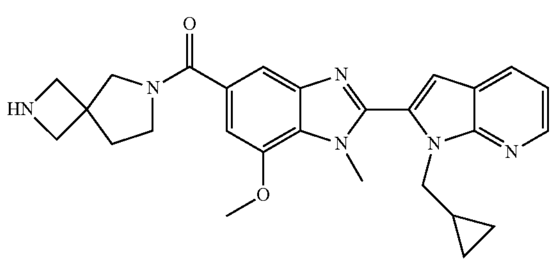 [SMILES: COc1cc(C(=O)N2CCC3(CNC3)C2)cc2nc(-c3cc4cccnc4n3CC3CC3)n(C)c12] | 470.5661 | 1.90 min | 471.4 | A | | |

-continued

| # | Structure | Mol Wt | LCMS T$_{ret}$ | M/z (+) | LCMS Method | Salt | Salt Stoichoimetry |
|---|---|---|---|---|---|---|---|
| I-300 | 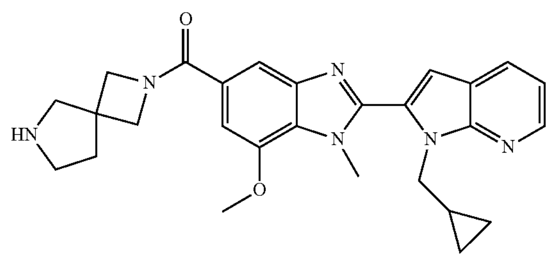 [SMILES: COc1cc(C(=O)N2CC3(CCNC3)C2)cc2nc(-c3cc4cccnc4n3CC3CC3)n(C)c12] | 470.5661 | 1.98 min | 471.4 | A | Trifluoroacetic acid | 1 |
| I-301 | 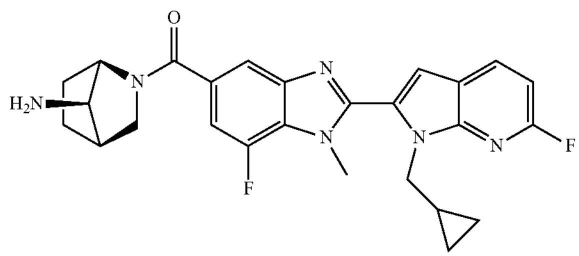 [SMILES: Cn1c(-c2cc3ccc(F)nc3n2CC2CC2)nc2cc(C(=O)N3C[C@H]4CC[C@@H]3[C@@H]4N)cc(F)c21] | 476.521 | 2.15 min | 477.4 | A | Hydrochloric acid | 1 |
| I-302 | 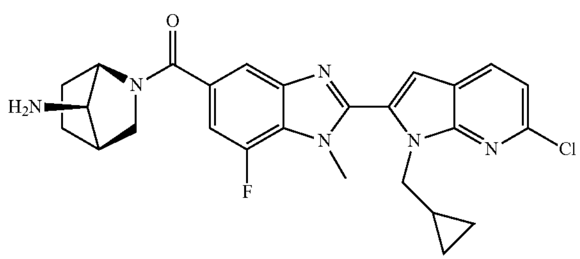 [SMILES: Cn1c(-c2cc3ccc(Cl)nc3n2CC2CC2)nc2cc(C(=O)N3C[C@H]4CC[C@@H]3[C@@H]4N)cc(F)c21] | 492.976 | 2.31 min | 493.3 | A | Hydrochloric acid | 1 |

-continued

| # | Structure | Mol Wt | LCMS T_ret | M/z (+) | LCMS Method | Salt | Salt Stoichiometry |
|---|---|---|---|---|---|---|---|
| I-303 | 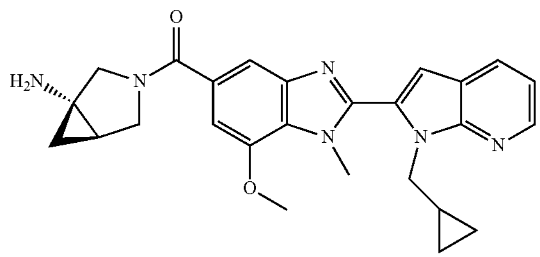 [SMILES: COc1cc(C(=O)N2C[C@H]3C[C@@]3(N)C2)cc2nc(-c3cc4cccnc4n3CC3CC3)n(C)c12] | 456.5395 | 1.94 min | 457.4 | A | Hydrochloric acid | 1 |
| I-304 | 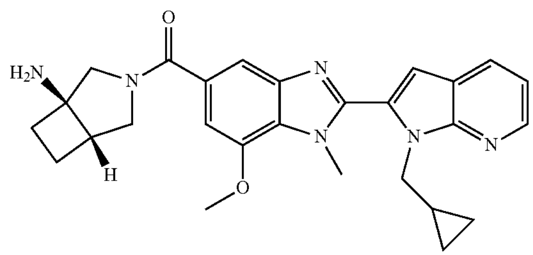 [SMILES: COc1cc(C(=O)N2C[C@@H]3CC[C@]3(N)C2)cc2nc(-c3cc4cccnc4n3CC3CC3)n(C)c12] | 470.5661 | 2.00 min | 471.3 | A | | |
| I-305 | 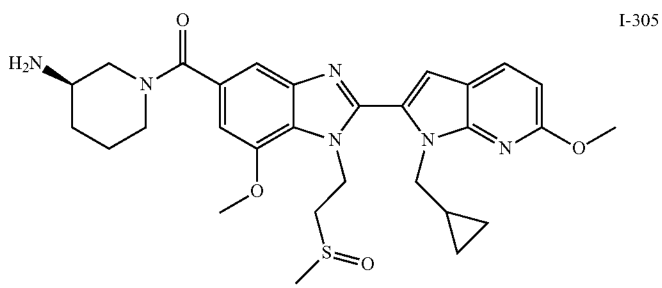 | 564.699 | 2.77 min | 565.4 | H | | |

-continued

| # | Structure | Mol Wt | LCMS T$_{ret}$ | LCMS M/z (+) | LCMS Method | Salt | Salt Stoichoiometry |
|---|---|---|---|---|---|---|---|
| I-306 | 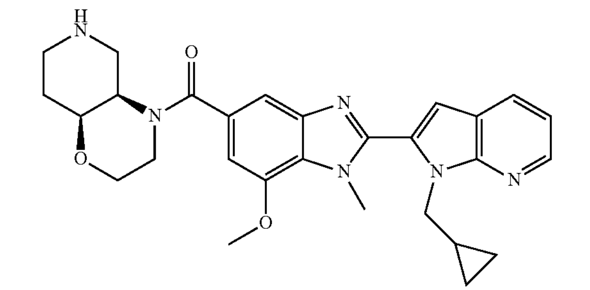 [SMILES: COc1cc(C(=O)N2CCO[C@H]3CCNC[C@H]32)cc2nc(-c3cc4cccnc4n3CC3CC3)n(C)c12] | 500.5921 | 2.06 min | 501.3 | A | Hydrochloric acid | 1 |
| I-307 | 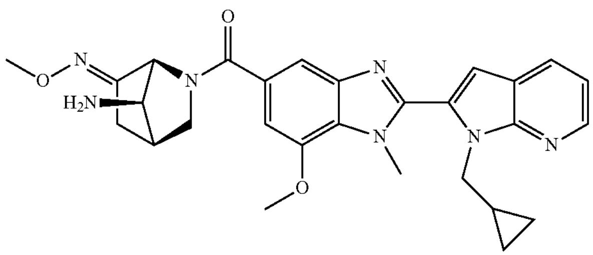 [SMILES: CO/N=C1\C[C@@H]2CN(C(=O)c3cc(OC)c4c(c3)nc(-c3cc5cccnc5n3CC3CC3)n4C)[C@H]1[C@@H]2N] | 513.5908 | 2.08 min | 514.3 | A | Hydrochloric acid | 1 |
| I-308 | 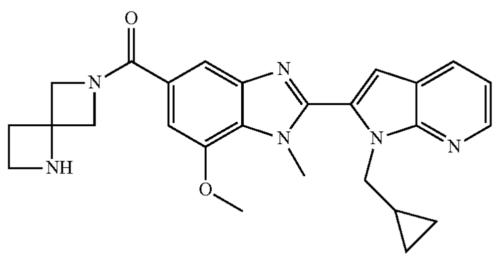 [SMILES: COc1cc(C(=O)N2CC3(CCN3)C2)cc2nc(-c3cc4cccnc4n3CC3CC3)n(C)c12] | 456.5395 | 1.96 min | 457.3 | A | | |

-continued

| # | Structure | Mol Wt | LCMS $T_{ret}$ | M/z (+) | LCMS Method | Salt | Salt Stoichiometry |
|---|---|---|---|---|---|---|---|
| I-309 | 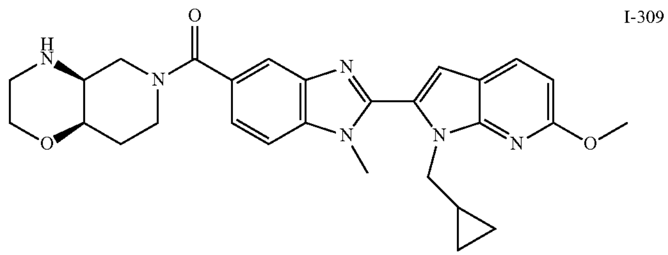 | 500.5921 | 2.27 min | 501.4 | A | | |
| I-310 | 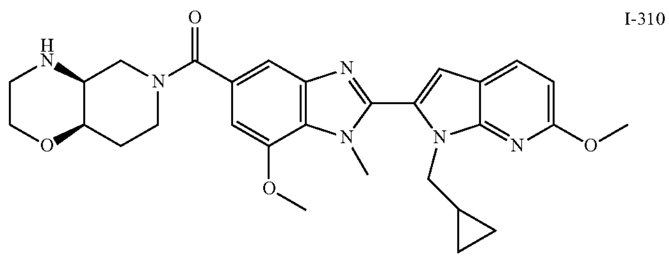 | 530.6181 | 2.47 min | 531.4 | A | | |
| I-311 | 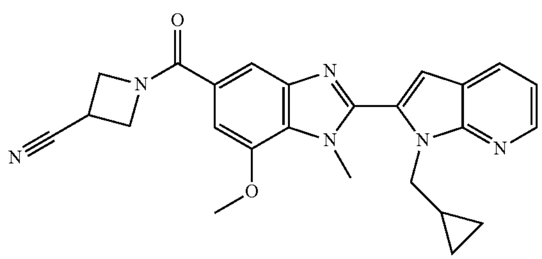 [SMILES: COc1cc(C(=O)N2CC(C#N)C2)cc2nc(-c3cc4cccnc4n3CC3CC3)n(C)c12] | 440.4971 | 3.20 min | 441.3 | H | | |

-continued

| # | Structure | Mol Wt | LCMS T$_{ret}$ | M/z (+) | LCMS Method | Salt | Salt Stoichiometry |
|---|---|---|---|---|---|---|---|
| I-312 | 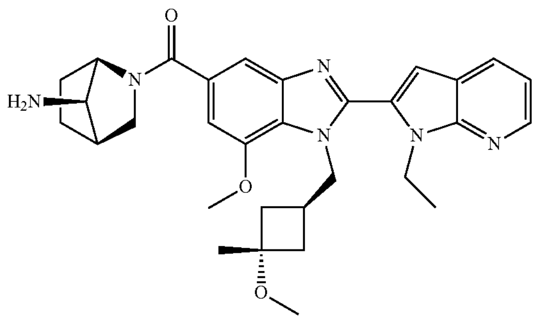 [SMILES: CCn1c(-c2nc3cc(C(=O)N4C[C@H]5CC[C@@H]4[C@@H]5N)cc(OC)c3n2C[C@H]2C[C@](C)(OC)C2)cc2cccnc21] | 542.6718 | 2.03 min | 543.4 | A | Hydrochloric acid | 1 |
| I-313 | 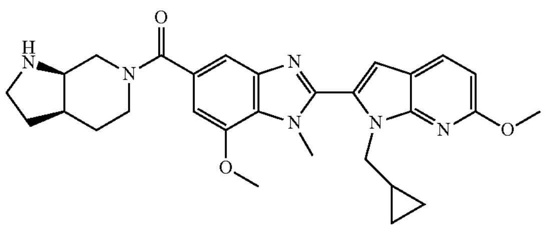 [SMILES: COc1ccc2cc(-c3nc4cc(C(=O)N5CC[C@H]6CCN[C@H]6C5)cc(OC)c4n3C)n(CC3CC3)c2n1] | 514.6187 | 2.41 min | 515.3 | A | | |
| I-314 | 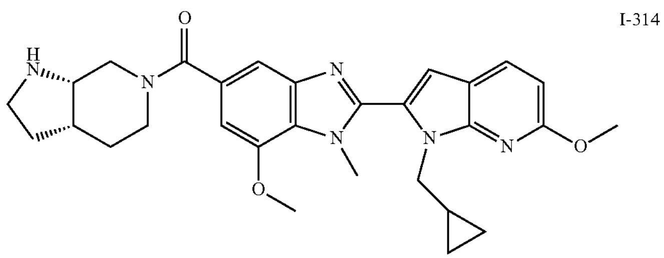 | 514.6187 | 2.42 min | 515.3 | A | | |

-continued

| # | Structure | Mol Wt | LCMS $T_{ret}$ | M/z (+) | LCMS Method | Salt | Salt Stoichoimetry |
|---|---|---|---|---|---|---|---|
| I-315 | 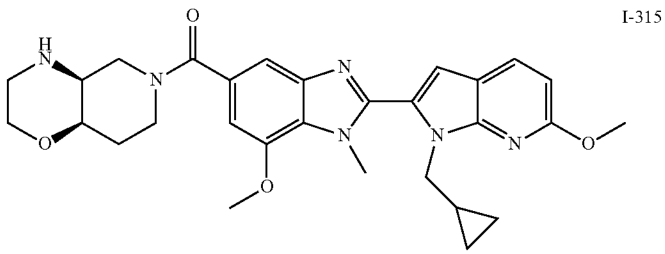 | 530.6181 | 2.43 min | 531.4 | A | | |
| I-316 | 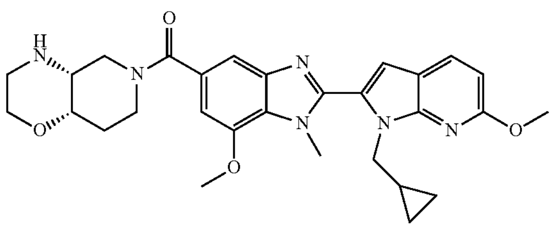 [SMILES: COc1ccc2cc(-c3nc4cc(C(=O)N5CC[C@@H]6OCCN[C@@H]6C5)cc(OC)c4n3C)n(CC3CC3)c2n1] | 530.6181 | 2.47 min | 531.3 | A | | |
| I-317 | 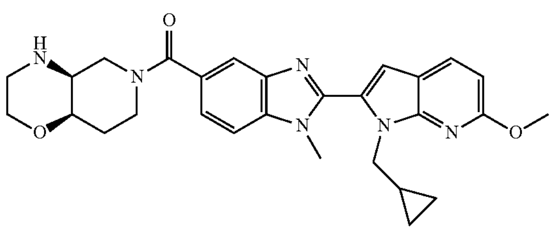 [SMILES: COc1ccc2cc(-c3nc4cc(C(=O)N5CC[C@H]6OCCN[C@H]6C5)ccc4n3C)n(CC3CC3)c2n1] | 500.5921 | 2.27 min | 501.3 | A | | |

-continued

| # | Structure | Mol Wt | LCMS $T_{ret}$ | LCMS M/z (+) | LCMS Method | Salt | Salt Stoichiometry |
|---|---|---|---|---|---|---|---|
| I-318 | 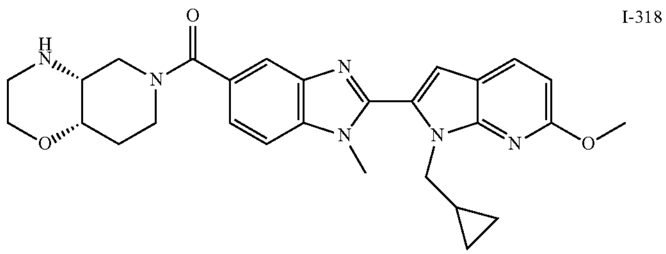 | 500.5921 | 2.27 min | 501.3 | A | | |
| I-319 | 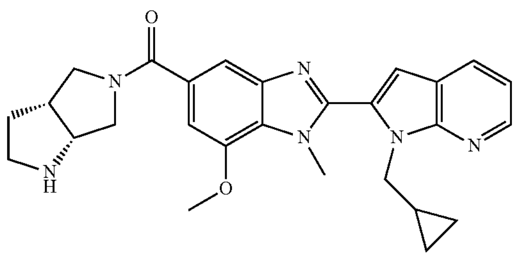 [SMILES: COc1cc(C(=O)N2C[C@H]3CCN[C@H]3C2)cc2nc(-c3cc4cccnc4n3CC3CC3)n(C)c12] | 470.5661 | 1.93 min | 471.3 | A | Hydrochloric acid | 1 |
| I-320 | 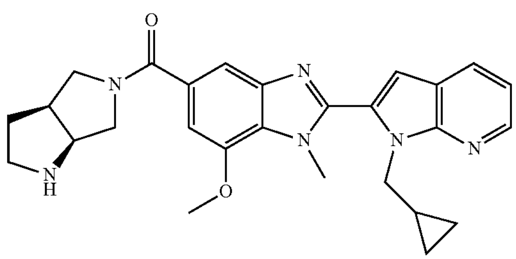 [SMILES: COc1cc(C(=O)N2C[C@@H]3CCN[C@@H]3C2)cc2nc(-c3cc4cccnc4n3CC3CC3)n(C)c12] | 470.5661 | 1.94 min | 471.3 | A | | |

-continued

| # | Structure | Mol Wt | LCMS T_ret | M/z (+) | LCMS Method | Salt | Salt Stoichiometry |
|---|---|---|---|---|---|---|---|
| I-321 | 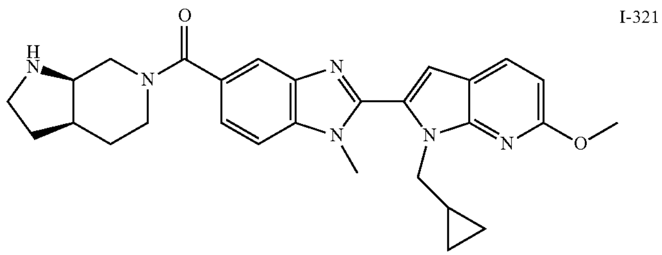 | 484.5927 | 2.26 min | 485.3 | A | Hydrochloric acid | 1 |
| I-322 | 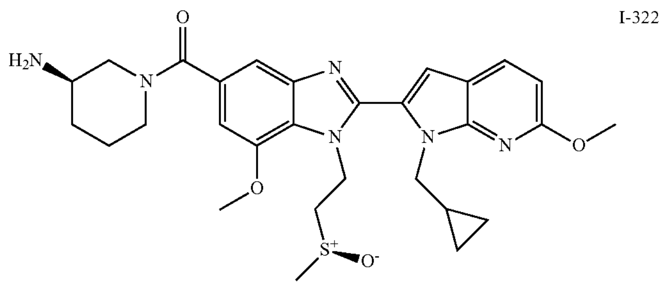 | 564.699 | 1.93 min | 565.3 | A | | |
| I-323 | 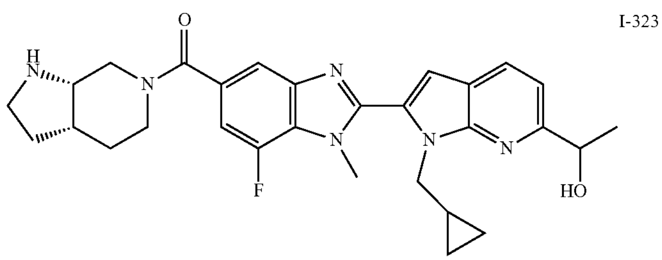 | 530.6363 | 2.10 min | 531.3 | A | Hydrochloric acid | 1 |

-continued

| # | Structure | Mol Wt | LCMS T$_{ret}$ | M/z (+) | LCMS Method | Salt | Salt Stoichiometry |
|---|---|---|---|---|---|---|---|
| I-324 | 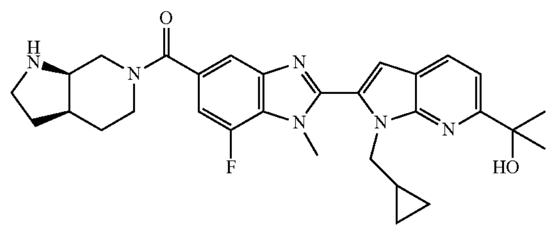 [SMILES: Cn1c(-c2cc3ccc(C(C)(C)O)nc3n2CC2CC2)nc2cc(C(=O)N3CC[C@H]4CCN[C@H]4C3)cc(F)c21] | 530.6363 | 2.11 min | 531.3 | A | Hydrochloric acid | 1 |
| I-325 | 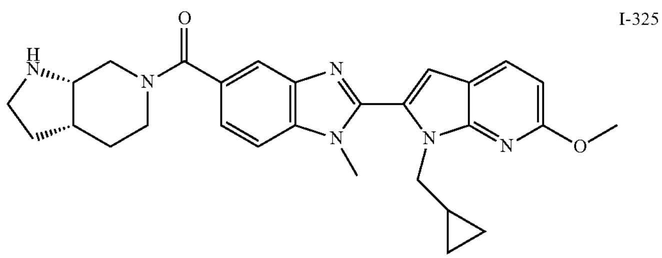 | 484.5927 | 2.24 min | 485.3 | A | Hydrochloric acid | 1 |
| I-326 | 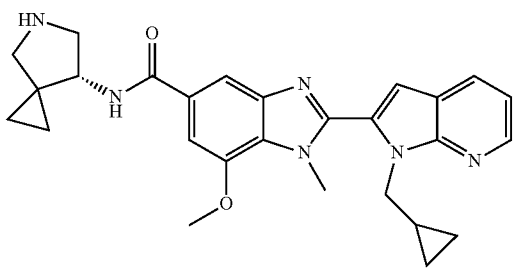 [SMILES: COc1cc(C(=O)N[C@H]2CNCC23CC3)cc2nc(-c3cc4cccnc4n3CC3CC3)n(C)c12] | 470.5661 | 2.12 min | 471.3 | A | | |

| # | Mol Wt | LCMS $T_{ret}$ | M/z (+) | LCMS Method | Salt | Salt Stoichiometry |
|---|---|---|---|---|---|---|
| I-327 | 564.699 | 1.93 min | 565.3 | A | | |
| I-328 | 546.6357 | 3.54 min | 547.3 | C | | |
| I-329 | 546.6357 | 3.56 min | 547.3 | C | | |

-continued

| # | Structure | Mol Wt | LCMS $T_{ret}$ | LCMS M/z (+) | LCMS Method | Salt | Salt Stoichiometry |
|---|---|---|---|---|---|---|---|
| I-330 | 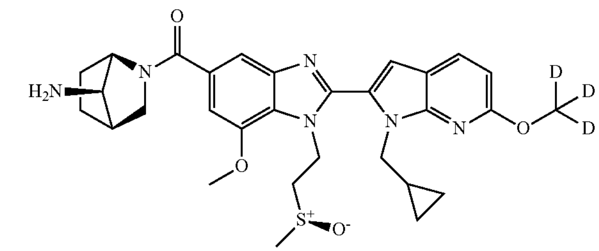 [SMILES: [2H]C([2H])([2H])Oc1ccc2cc(-c3nc4cc(C(=O)N5C[C@H]6CC[C@@H]5[C@@H]6N)cc(OC)c4n3CC[S@+](C)[O-])n(CC3CC3)c2n1] | 579.728 | 2.70 min | 580.4 | H | | |
| I-331 | 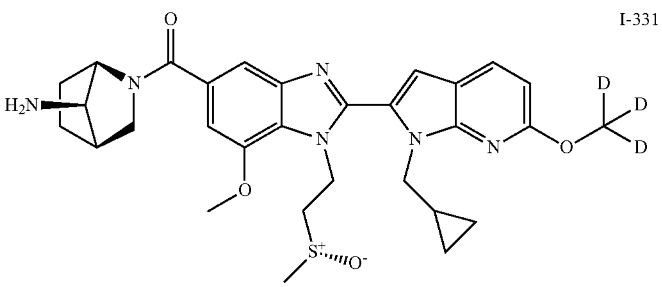 | 579.728 | 2.70 min | 580.4 | H | | |
| I-332 | 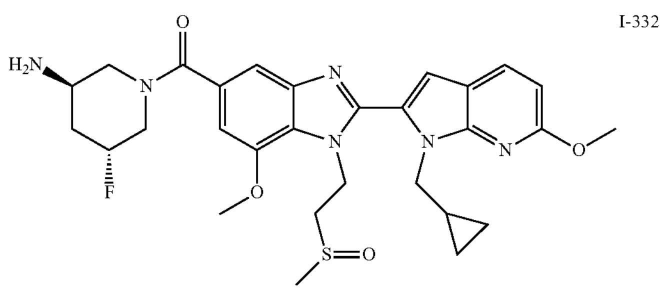 | 582.689 | 1.93 min | 583.2 | A | Trifluoroacetic acid | 1 |

-continued

| # | Structure | Mol Wt | LCMS $T_{ret}$ | M/z (+) | LCMS Method | Salt | Salt Stoichiometry |
|---|---|---|---|---|---|---|---|
| I-333 | 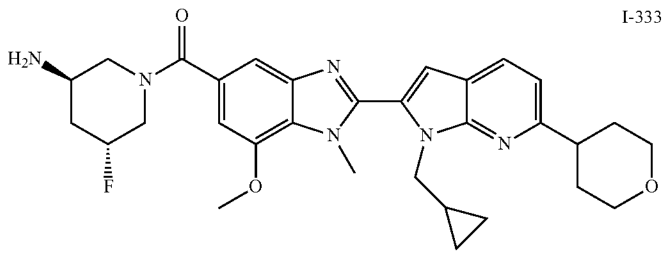 | 560.6623 | 2.34 min | 561.3 | A | Hydrochloric acid | 1 |
| I-334 | 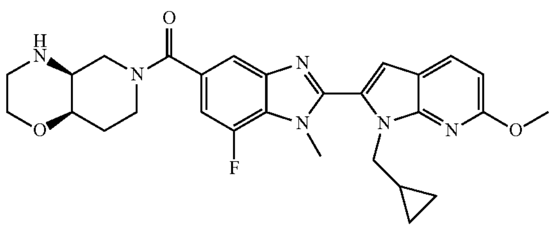 [SMILES: COc1ccc2cc(-c3nc4cc(C(=O)N5CC[C@H]6OCCN[C@H]6C5)cc(F)c4n3C)n(CC3CC3)c2n1] | 518.5825 | 2.44 min | 519.3 | A | | |
| I-335 | 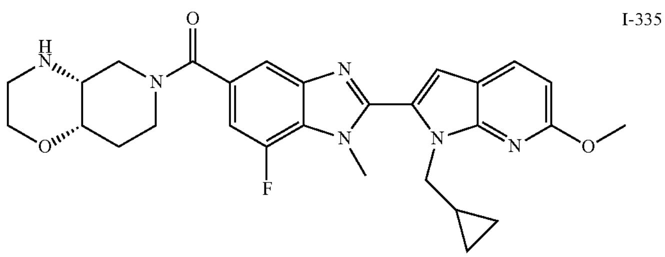 | 518.5825 | 2.44 min | 519.3 | A | | |
| I-336 | 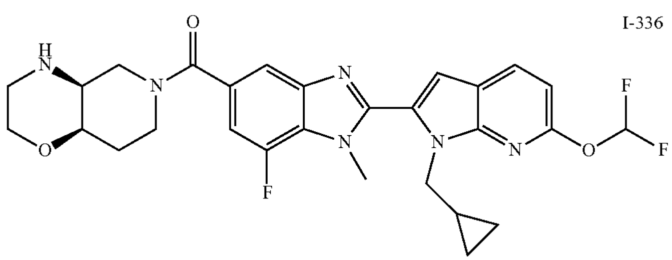 [SMILES: Cn1c(-c2cc3ccc(OC(F)F)nc3n2CC2CC2)nc2cc(C(=O)N3CC[C@H]4OCCN[C@H]4C3)cc(F)c21] | 554.5635 | 2.53 min | 555.2 | A | | |

| # | Structure | Mol Wt | LCMS T$_{ret}$ | M/z (+) | LCMS Method | Salt | Salt Stoichoimetry |
|---|---|---|---|---|---|---|---|
| I-337 | 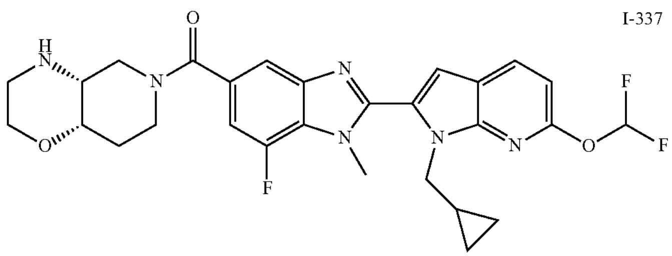 [SMILES: Cn1c(-c2cc3ccc(OC(F)F)nc3n2CC2CC2)nc2cc(C(=O)N3CC[C@@H]4OCCN[C@@H]4C3)cc(F)c21] | 554.5635 | 2.53 min | 555.2 | A | | |
| I-338 | 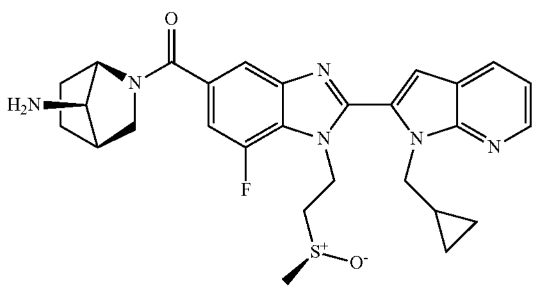 [SMILES: C[S@+]([O-])CCn1c(-c2cc3cccnc3n2CC2CC2)nc2cc(C(=O)N3C[C@H]4CC[C@@H]3[C@@H]4N)cc(F)c21] | 534.648 | 1.48 min | 535.2 | A | | |
| I-339 | 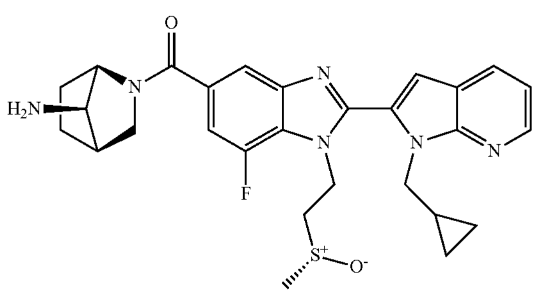 [SMILES: C[S@@+]([O-])CCn1c(-c2cc3cccnc3n2CC2CC2)nc2cc(C(=O)N3C[C@H]4CC[C@@H]3[C@@H]4N)cc(F)c21] | 534.648 | 1.49 min | 535.2 | A | | |

-continued

| # | Structure | Mol Wt | LCMS T$_{ret}$ | M/z (+) | LCMS Method | Salt | Salt Stoichiometry |
|---|---|---|---|---|---|---|---|
| I-340 | 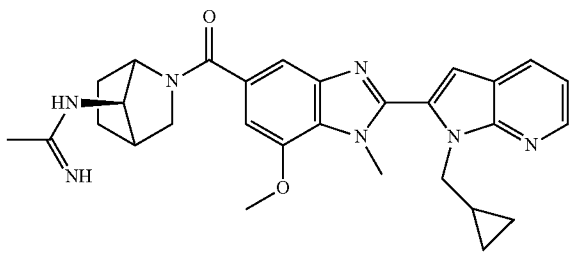 [SMILES: COc1cc(C(=O)N2CC3CCC2[C@@H]3NC(C)=N)cc2nc(-c3cc4cccnc4n3CC3CC3)n(C)c12] | 511.618 | 2.05 min | 512.3 | A | Formic acid | 1 |
| I-341 | 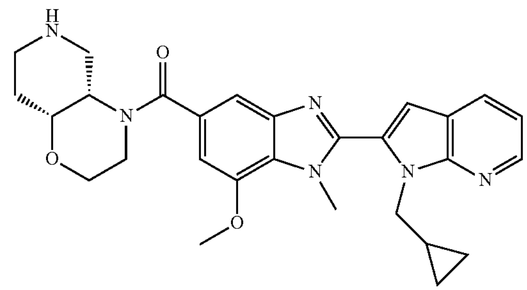 [SMILES: COc1cc(C(=O)N2CCO[C@@H]3CCNC[C@@H]32)cc2nc(-c3cc4cccnc4n3CC3CC3)n(C)c12] | 500.5921 | 2.03 min | 501.3 | A | | |
| I-342 | 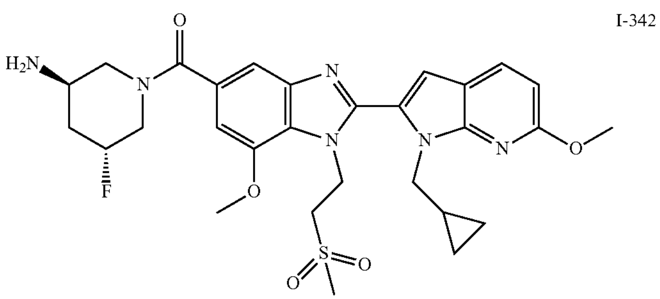 | 598.689 | 2.12 min | 599.3 | A | Trifluoroacetic acid | 1 |

-continued

| # | Structure | Mol Wt | LCMS $T_{ret}$ | M/z (+) | LCMS Method | Salt | Salt Stoichiometry |
|---|---|---|---|---|---|---|---|
| I-343 | 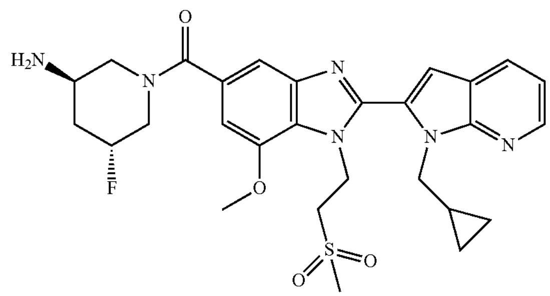 [SMILES: COc1cc(C(=O)N2C[C@H](N)C[C@@H](F)C2)cc2nc(-c3cc4cccnc4n3CC3CC3)n(CCS(C)(=O)=O)c12] | 568.663 | 2.12 min | 569.3 | A | | |
| I-344 | 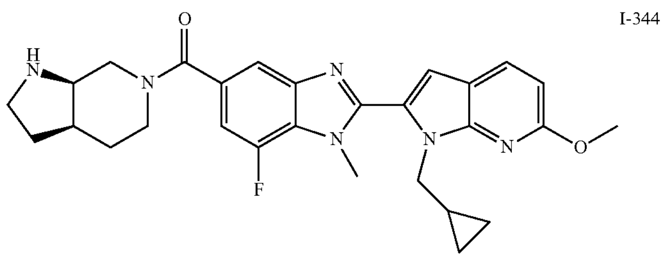 | 502.5831 | 2.40 min | 503.3 | A | | |
| I-345 | 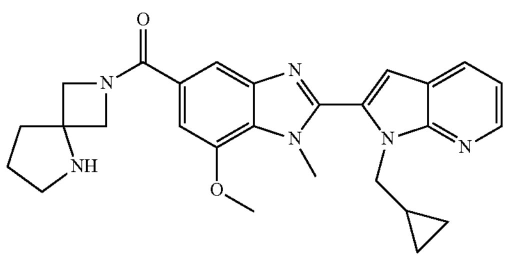 [SMILES: COc1cc(C(=O)N2CC3(CCCN3)C2)cc2nc(-c3cc4cccnc4n3CC3CC3)n(C)c12] | 470.5661 | 2.01 min | 471.3 | A | | |

| # | Structure | Mol Wt | LCMS $T_{ret}$ | M/z (+) | LCMS Method | Salt | Salt Stoichiometry |
|---|---|---|---|---|---|---|---|
| I-346 | 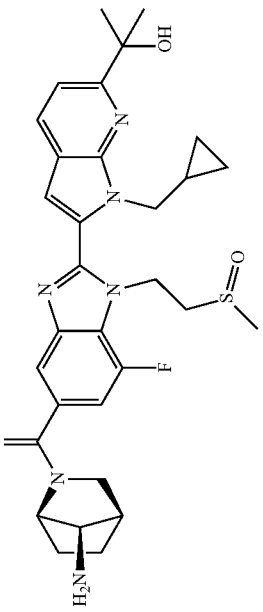 | 592.727 | 1.69 min | 593.4 | A | | |
| I-347 | 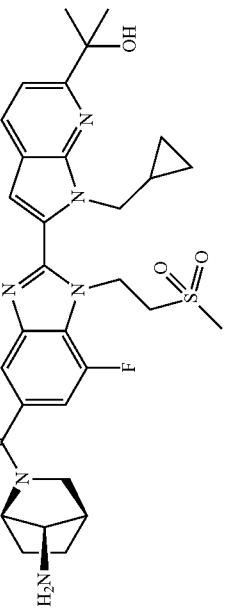 | 608.727 | 1.86 min | 609.3 | A | | |
| I-348 | 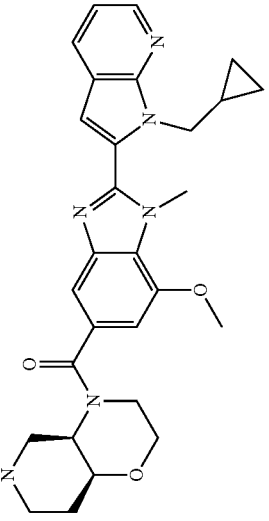 | 500.5921 | 2.01 min | 501.3 | A | | |

I-349

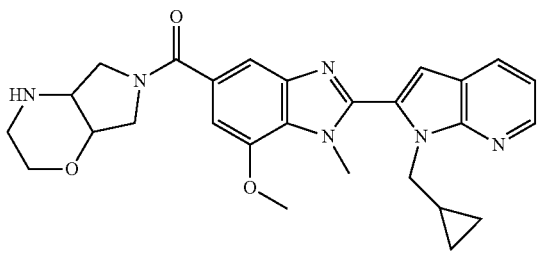

(2-(1-(cyclopropylmethyl)-1H-pyrrolo[2,3-b]pyridin-2-yl)-7-methoxy-1-methyl-1H-benzo[d]imidazol-5-yl)((cis)-hexahydropyrrolo[3,4-b][1,4]oxazin-6(2H)-yl)methanone. I-349 Note: Starting material was the cis-racemate.

Prepared in a similar manner to Scheme 1. Mol wt=486.57; LC/MS Ret. Time=1.19 min. (Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm)). M/Z (+)=487.12; Salt=freebase.

Chiral HPLC to obtain (2-(1-(cyclopropylmethyl)-1H-pyrrolo[2,3-b]pyridin-2-yl)-7-methoxy-1-methyl-1H-benzo[d]imidazol-5-yl)((4aR,7aS)-hexahydropyrrolo[3,4-b][1,4]oxazin-6(2H)-yl)methanone and (2-(1-(cyclopropylmethyl)-1H-pyrrolo[2,3-b]pyridin-2-yl)-7-methoxy-1-methyl-1H-benzo[d]imidazol-5-yl)((4aS,7aR)-hexahydropyrrolo[3,4-b][1,4]oxazin-6(2H)-yl)methanone. Note: Starting material was the cis-racemate. Absolute stereochemistry arbitrarily assigned.

Prepared in a similar manner to Scheme 1. (2-(1-(cyclopropylmethyl)-1H-pyrrolo[2,3-b]pyridin-2-yl)-7-methoxy-1-methyl-1H-benzo[d]imidazol-5-yl)((cis)-hexahydropyrrolo[3,4-b][1,4]oxazin-6(2H)-yl)methanone was dissolved in ethanol and then purified by chiral HPLC (Chiralcel OD 21×250 mm 10 u, wavelength: 254, Flow Rate: 15 ml/min, Solvent A: 100% Heptane, Solvent B: 100% Ethanol, Isocratic Collection by UV, % B: 35) to obtain 25.7 mg (50.4%) of (2-(1-(cyclopropylmethyl)-1H-pyrrolo[2,3-b]pyridin-2-yl)-7-methoxy-1-methyl-1H-benzo[d]imidazol-5-yl)((4aR,7aS)-hexahydropyrrolo[3,4-b][1,4]oxazin-6(2H)-yl)methanone as Isomer A and 25.4 mg (97.0%) of (2-(1-(cyclopropylmethyl)-1H-pyrrolo[2,3-b]pyridin-2-yl)-7-methoxy-1-methyl-1H-benzo[d]imidazol-5-yl)((4aS,7aR)-hexahydropyrrolo[3,4-b][1,4]oxazin-6(2H)-yl)methanone as Isomer (absolute stereochemistry arbitrarily assigned).

Isomer A I-350 Chiral purity (UV, 254 nm): 100%, retention time: 17.36 min (Chiralcel OD 21×250 mm 10 u, wavelength: 254, Flow Rate: 15 ml/min, Solvent A: 100% Heptane, Solvent B: 100% Ethanol, Isocratic Collection by UV, % B: 35). Salt=freebase.

I-351

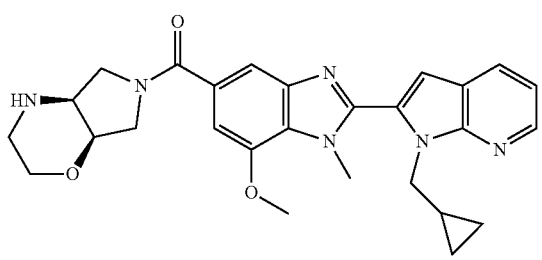

Isomer B I-351 Chiral purity (UV, 254 nm): 100%, retention time: 27.17 min (Chiralcel OD 21×250 mm 10 u, wavelength: 254, Flow Rate: 15 ml/min, Solvent A: 100% Heptane, Solvent B: 100% Ethanol, Isocratic Collection by UV, % B: 35). Salt=freebase.

LC-MS Condition for Schemes 9 and 10:

Column: Waters Acquity SDS

Mobile Phase: Solvent A: water

Solvent B: Acetonitrile

Gradient Range: Linear gradient of 2% to 98% solvent B over 1 minutes ("min"), with 0.5 minute ("min") hold at 98% B.

Gradient Time: 1 min

Analysis Time: 1.7 min

Detector: Ultraviolet ("UV") visualization at 254 nanometers ("nm")

Tert-butyl ((3R,6S)-1-(2-(1-(cyclopropylmethyl)-6-methoxy-1H-pyrrolo[2,3-b]pyridin-2-yl)-1-methyl-1H-benzo[d]imidazole-5-carbonyl)-6-methylpiperidin-3-yl)carbamate. I-352 Prepared using Scheme 11.

I-350

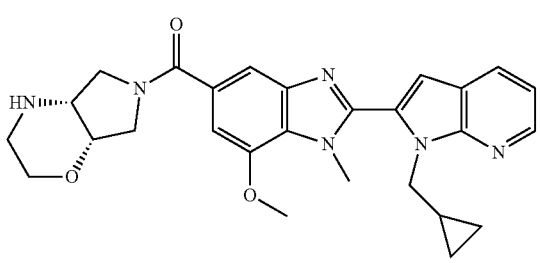

I-352

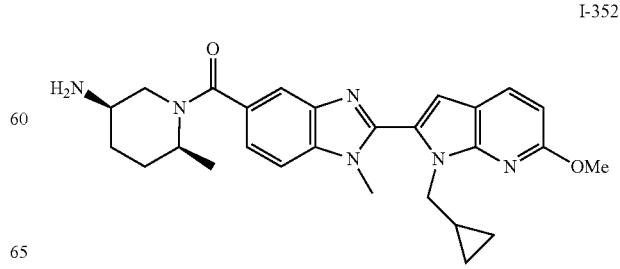

Scheme 11

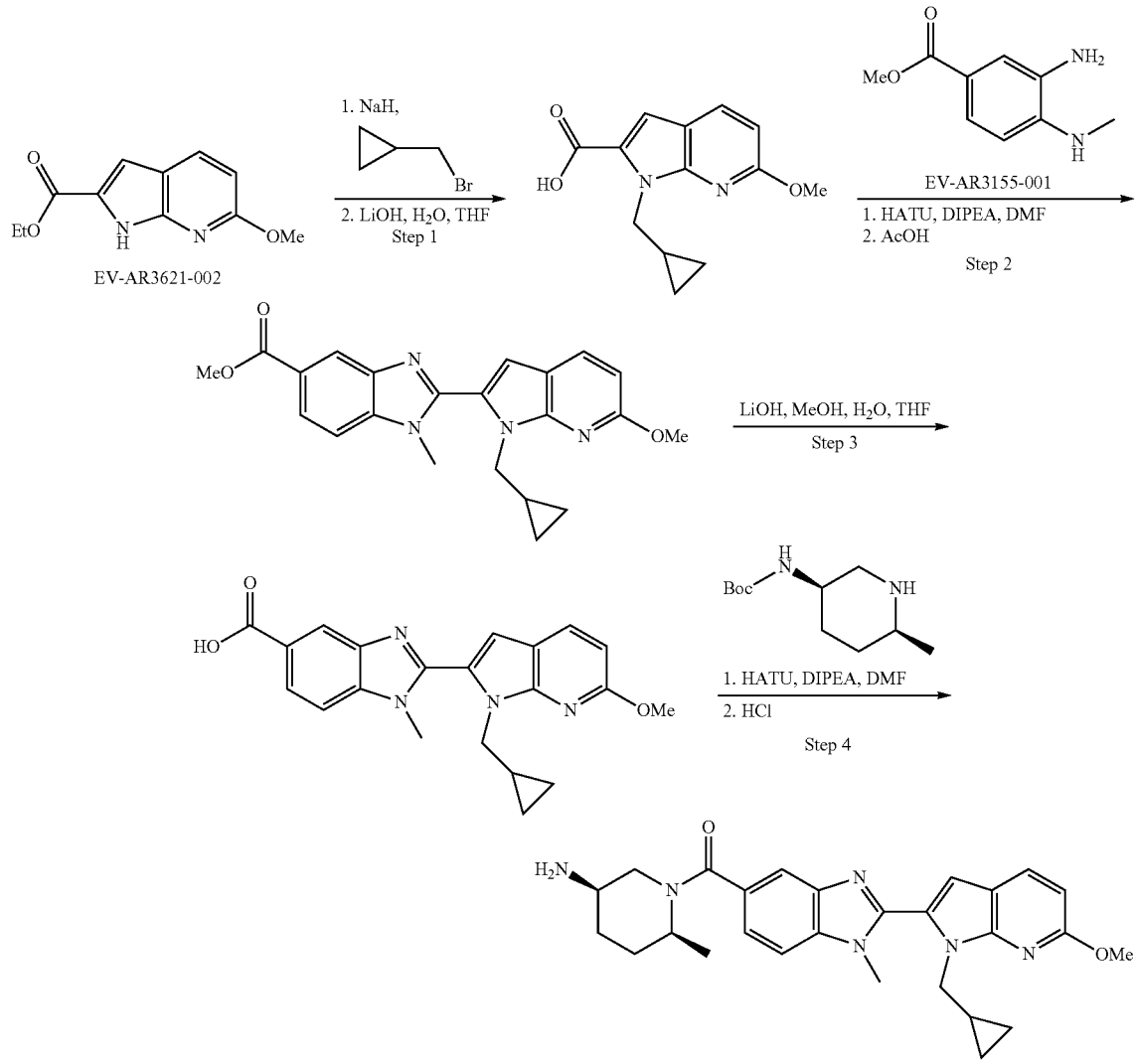

Methyl 2-(1-(cyclopropylmethyl)-6-methoxy-1H-pyrrolo[2,3-b]pyridin-2-yl)-1-methyl-1H-indole-5-carboxylate—Step 2

1-(cyclopropylmethyl)-6-methoxy-1H-pyrrolo[2,3-b]pyridine-2-carboxylic acid (5 g, 20.30 mmol) (prepared from EV-AR3621-002 following Scheme 2) was combined with 1-[bis(dimethylamino)methylene]-1H-1,2,3-triazolo[4,5-b]pyridinium 3-oxide hexafluorophosphate (HATU, 7.72 g, 20.30 mmol) and N,N-Diisopropylethylamine (DIPEA, 3.90 mL, 22.33 mmol) in dimethylformamide (DMF, 80 mL). The reaction was stirred for 15 minutes and then methyl 3-amino-4-(methylamino)benzoate EV-AR3155-001 (4.02 g, 22.33 mmol) was added to the reaction. The reaction was stirred at room temperature for 2 hours. Upon completion of the reaction the solvent was removed in vacuo. To the residue was added acetic acid (AcOH, 120 mL) and the vessel was warmed to 70° C. and stirred for 3 hours. The solvent was removed and the reaction was purified using automated chromatography, the product came off the column at 40% ethyl acetate in hexane, yielding methyl 2-(1-(cyclopropylmethyl)-6-methoxy-1H-pyrrolo[2,3-b]pyridin-2-yl)-1-methyl-1H-benzo[d]imidazole-5-carboxylate (6.9 g, 17.67 mmol, 87% yield). LCMS: retention time 0.95 min, M/z=391.0 (M+1).

2-(1-(cyclopropylmethyl)-6-methoxy-1H-pyrrolo[2,3-b]pyridin-2-yl)-1-methyl-1H-benzo[d]imidazole-5-carboxylic acid—Step 3

To a solution of methyl 2-(1-(cyclopropylmethyl)-6-methoxy-1H-pyrrolo[2,3-b]pyridin-2-yl)-1-methyl-1H-benzo[d]imidazole-5-carboxylate (500 mg, 1.281 mmol) in THF (7 mL) and methanol (3.50 mL) was added water (3.50 mL) and a solution of lithium hydroxide monohydrate in water (3 M, 1.281 mL, 3.84 mmol). After 30 minutes, the starting material crushed out of the solution, additional THF (9 mL) was added and the reaction was stirred overnight. The reaction was concentrated in vacuo and then neutralized with hydrochloric acid (1 M in water, 3.84 mL, 3.84 mmol). Water was added to the suspension and after sonication the suspension was filtered and the solid air dried to provide the product 2-(1-(cyclopropylmethyl)-6-methoxy-1H-pyrrolo[2,3-b]pyridin-2-yl)-1-methyl-1H-benzo[d]imidazole-5-carboxylic acid (470 mg, 1.249 mmol, 98% yield). LCMS: retention time 0.85 min, M/z=376.8 (M+1).

Tert-butyl ((3R,6S)-1-(2-(1-(cyclopropylmethyl)-6-methoxy-1H-pyrrolo[2,3-b]pyridin-2-yl)-1-methyl-1H-benzo[d]imidazole-5-carbonyl)-6-methylpiperidin-3-yl)carbamate, I-352—Step 4

2-(1-(cyclopropylmethyl)-6-methoxy-1H-pyrrolo[2,3-b]pyridin-2-yl)-1-methyl-1H-benzo[d]imidazole-5-carboxylic acid (30 mg, 0.080 mmol), tert-butyl ((3R,6S)-6-methylpiperidin-3-yl)carbamate (25.6 mg, 0.120 mmol), HATU (36.4 mg, 0.096 mmol) and DIPEA (0.042 mL, 0.239 mmol) were combined in DMF (1 mL) and the reaction stirred for 30 minutes. Upon the completion of amide formation (as measured by LCMS), HCl (4 M in dioxane, 1 mL, 4 mmol) was added to the reaction. The reaction was warmed to 50° C. and stirred for 3 hours. The reaction was cooled to room temperature, filtered and then purified using preparative HPLC to provide ((2S,5R)-5-amino-2-methylpiperidin-1-yl)(2-(1-(cyclopropylmethyl)-6-methoxy-1H-pyrrolo[2,3-b]pyridin-2-yl)-1-methyl-1H-benzo[d]imidazol-5-yl)methanone, I-352, (22.6 mg, 0.047 mmol, 59.4% yield, 99% purity) LCMS: retention time 0.73 min, M/z=472.9 (M+1).

1H NMR (500 MHz, DMSO-d6) Shift 8.04-8.00 (m, 1H), 7.78-7.72 (m, 2H), 7.40-7.33 (m, 1H), 7.11-7.02 (m, 2H), 6.72-6.63 (m, 1H), 4.54-4.42 (m, 2H), 4.01-3.96 (m, 3H), 3.96-3.91 (m, 3H), 3.03-2.91 (m, 1H), 1.95-1.82 (m, 1H), 1.79-1.68 (m, 2H), 1.66-1.51 (m, 1H), 1.26-1.13 (m, 4H), 0.36-0.29 (m, 2H), 0.25-0.19 (m, 2H)

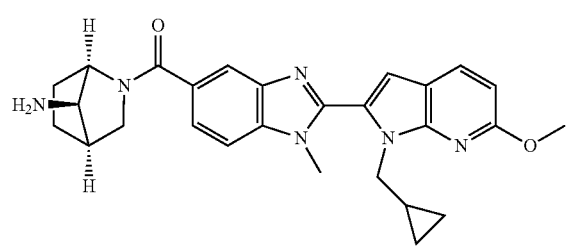

I-353

((1R,4R,7R)-7-amino-2-azabicyclo[2.2.1]heptan-2-yl)(2-(1-(cyclopropylmethyl)-6-methoxy-1H-pyrrolo[2,3-b]pyridin-2-yl)-1-methyl-1H-benzo[d]imidazol-5-yl)methanone, I-353

Following the procedure in Scheme 11 afforded I-353 (95% yield, 97% purity). LCMS: retention time 0.71 min, M/z=470.9 (M+1). (several signals appear hidden under water peak)$^1$H NMR (500 MHz, DMSO-d6) δ 8.02 (br d, J=8.25 Hz, 2H), 7.81 (s, 1H), 7.67-7.78 (m, 1H), 7.42-7.55 (m, 1H), 7.12-7.33 (m, 1H), 7.07 (br s, 2H), 6.68 (d, J=8.41 Hz, 1H), 4.41-4.59 (m, 2H), 3.97 (br s, 3H), 3.94 (s, 3H), 3.08-3.28 (m, 1H), 2.66 (br s, 1H), 1.79-2.04 (m, 3H), 1.55-1.72 (m, 1H), 1.09-1.28 (m, 1H), 0.31 (br d, J=7.83 Hz, 2H), 0.22 (br s, 2H).

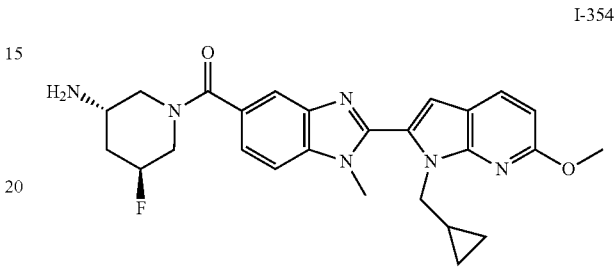

I-354

((3S,5S)-3-amino-5-fluoropiperidin-1-yl)(2-(1-(cyclopropylmethyl)-6-methoxy-1H-pyrrolo[2,3-b]pyridin-2-yl)-1-methyl-1H-benzo[d]imidazol-5-yl)methanone Following the procedure in Scheme 11 afforded I-354 (90% yield, 96% purity). LCMS: retention time 0.72 min, M/z=476.9 (M+1).

1H NMR (500 MHz, DMSO-d6) Shift 8.03-7.96 (m, 1H), 7.80-7.70 (m, 2H), 7.44-7.36 (m, 1H), 7.06-7.02 (m, 1H), 6.71-6.60 (m, 1H), 4.56-4.36 (m, 2H), 4.01-3.94 (m, 3H), 3.94-3.89 (m, 3H), 3.48-3.33 (m, 1H), 3.07-2.87 (m, 1H), 2.42-2.28 (m, 1H), 1.93-1.72 (m, 1H), 1.21-1.04 (m, 1H), 0.35-0.24 (m, 2H), 0.22-0.08 (m, 2H)

((2S,5R)-5-amino-2-methylpiperidin-1-yl)(2-(1-(cyclopropylmethyl)-6-methoxy-1H-pyrrolo[2,3-b]pyridin-2-yl)-7-methoxy-1-methyl-1H-benzo[d]imidazol-5-yl)methanone. I 355 Prepared according to Scheme 12.

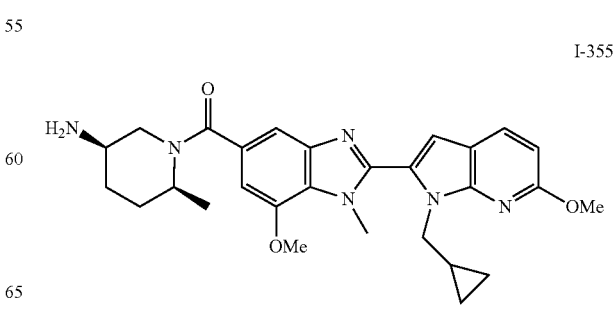

I-355

Scheme 12

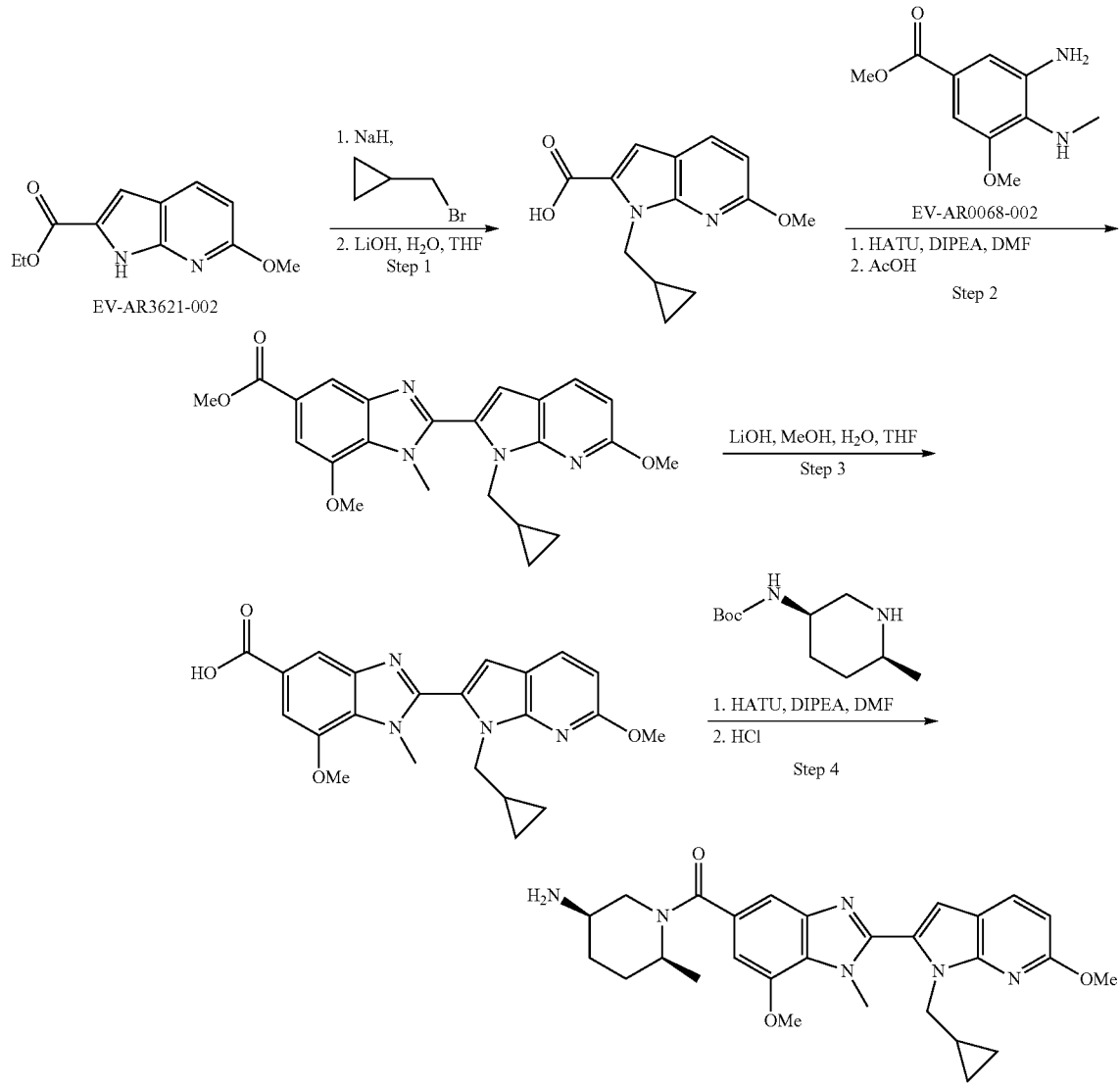

Methyl 2-(1-(cyclopropylmethyl)-6-methoxy-1H-pyrrolo[2,3-b]pyridin-2-yl)-7-methoxy-1-methyl-1H-benzo[d]imidazole-5-carboxylate—Step 2

1-(cyclopropylmethyl)-6-methoxy-1H-pyrrolo[2,3-b]pyridine-2-carboxylic acid (5 g, 20.30 mmol), HATU (7.72 g, 20.30 mmol) and DIPEA (10.64 ml, 60.9 mmol) were added to DMF (80 ml). The reaction was stirred for 15 minutes at room temperature at which point methyl 3-amino-5-methoxy-4-(methylamino)benzoate HCl salt (5.51 g, 22.33 mmol) was added and the reaction was stirred overnight. The solvent was removed under vacuum and AcOH (120 mL) was added to the residue. The reaction was stirred at 70° C. for 4 hours and then the AcOH was removed in vacuo and the crude product was absorbed onto celite and purified using automated chromatography to provide methyl 2-(1-(cyclopropylmethyl)-6-methoxy-1H-pyrrolo[2,3-b]pyridin-2-yl)-7-methoxy-1-methyl-1H-benzo[d]imidazole-5-carboxylate (6.5 g, 15.46 mmol, 76% yield). LCMS: retention time 0.98 min, M/z=421.0 (M+1).

2-(1-(cyclopropylmethyl)-6-methoxy-1H-pyrrolo[2,3-b]pyridin-2-yl)-7-methoxy-1-methyl-1H-benzo[d]imidazole-5-carboxylic acid—Step 3

Methyl 2-(1-(cyclopropylmethyl)-6-methoxy-1H-pyrrolo[2,3-b]pyridin-2-yl)-7-methoxy-1-methyl-1H-benzo[d]imidazole-5-carboxylate (500 mg, 1.189 mmol) was dissolved in THF (10 mL), MeOH (5.00 mL) and water (2.500 mL), and a solution of lithium hydroxide in water (3M, 1.189 mL, 3.57 mmol) was added to the reaction. Additional THF was added until the reaction was homogenous. The reaction was stirred at room temperature for two days. The reaction was concentrated under vacuum and HCl in water (1 M, 3.6 mL, 3.6 mmol) was added to adjust the pH to about 6. The resulting solid was collected via to provide the product 2-(1-(cyclopropylmethyl)-6-methoxy-1H-pyrrolo[2,3-b]pyridin-2-yl)-7-methoxy-1-methyl-1H-benzo[d]imidazole-5-carboxylic acid (435 mg, 1.07 mmol, 90% yield). LCMS: retention time 0.89 min, M/z=406.8 (M+1).

((2S,5R)-5-amino-2-methylpiperidin-1-yl)(2-(1-(cyclopropylmethyl)-6-methoxy-1H-pyrrolo[2,3-b]pyridin-2-yl)-7-methoxy-1-methyl-1H-benzo[d]imidazol-5-yl)methanone, I-355—Step 4

Follow the procedure Step 4 in Scheme 12 to make ((2S,5R)-5-amino-2-methylpiperidin-1-yl)(2-(1-(cyclopropylmethyl)-6-methoxy-1H-pyrrolo[2,3-b]pyridin-2-yl)-7-methoxy-1-methyl-1H-benzo[d]imidazol-5-yl)methanone, I-355, (68.7% yield, 100% Purity). LCMS: retention time 0.76 min, M/z=502.9 (M+1).

1H NMR (500 MHz, DMSO-d6) Shift 8.03-7.98 (m, 1H), 7.28-7.22 (m, 1H), 7.01-6.94 (m, 1H), 6.83-6.77 (m, 1H), 6.70-6.61 (m, 1H), 4.48-4.38 (m, 2H), 4.17-4.06 (m, 3H), 4.00-3.96 (m, 3H), 3.96-3.93 (m, 3H), 2.70-2.62 (m, 1H), 2.56-2.52 (m, 3H), 1.90-1.88 (m, 2H), 1.76-1.62 (m, 2H), 1.58-1.39 (m, 2H), 1.26-1.12 (m, 4H), 0.38-0.27 (m, 2H), 0.25-0.14 (m, 2H)

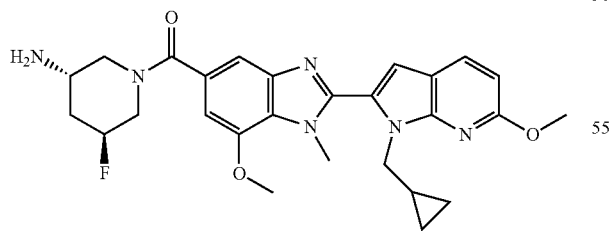

((3S,5S)-3-amino-5-fluoropiperidin-1-yl)(2-(1-(cyclopropylmethyl)-6-methoxy-1H-pyrrolo[2,3-b]pyridin-2-yl)-7-methoxy-1-methyl-1H-benzo[d]imidazol-5-yl)methanone. I-356

Following the procedure in Scheme 12 afforded ((3S,5S)-3-amino-5-fluoropiperidin-1-yl)(2-(1-(cyclopropylmethyl)-6-methoxy-1H-pyrrolo[2,3-b]pyridin-2-yl)-7-methoxy-1-methyl-1H-benzo[d]imidazol-5-yl)methanone, I-356, (56.7% yield, 99% Purity). LCMS: retention time 0.75 min, M/z=506.9 (M+1).

1H NMR (500 MHz, DMSO-d6) Shift 8.06-7.96 (m, 1H), 7.36-7.25 (m, 1H), 7.01-6.93 (m, 1H), 6.87-6.79 (m, 1H), 6.70-6.61 (m, 1H), 4.44-4.37 (m, 2H), 4.14-4.08 (m, 3H), 4.01-3.95 (m, 3H), 3.95-3.92 (m, 3H), 3.54-3.43 (m, 1H), 3.31-3.21 (m, 1H), 3.06-2.96 (m, 1H), 2.23-2.10 (m, 1H), 1.94-1.84 (m, 2H), 1.65-1.43 (m, 1H), 1.21-1.06 (m, 1H), 0.37-0.24 (m, 2H), 0.23-0.11 (m, 2H)

Scheme 13

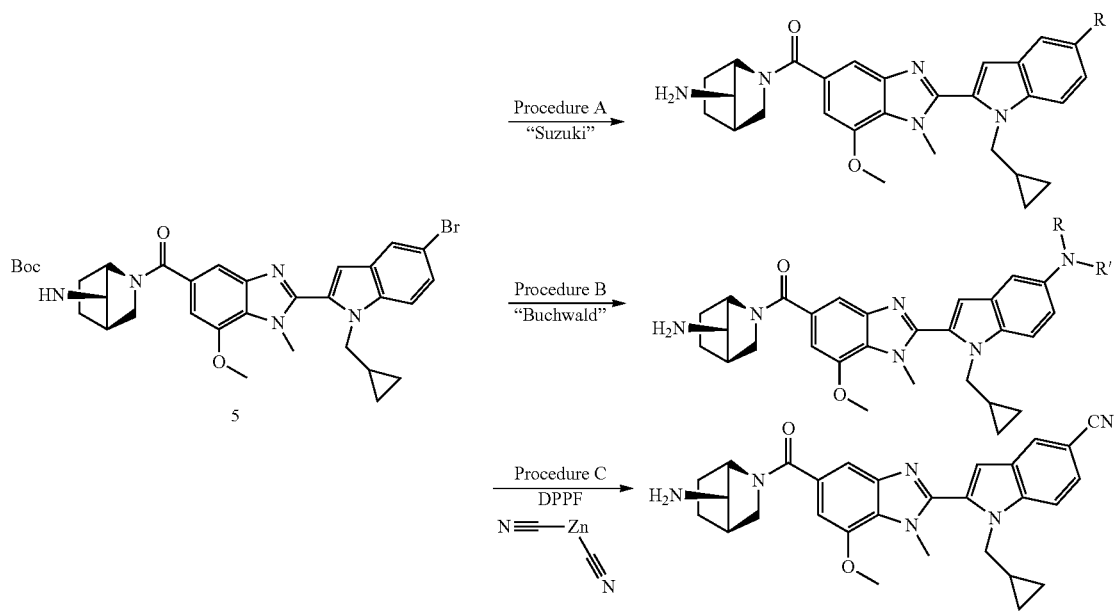

Tert-butyl ((1S,4R)-2-(2-(5-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate: 5 Prepared using Scheme 13.1

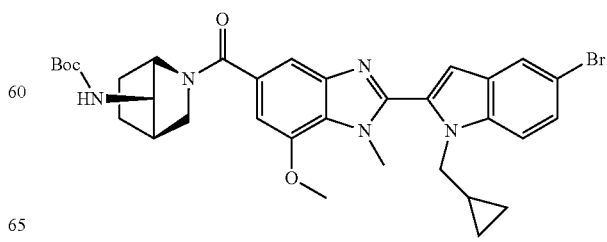

Scheme 13.1

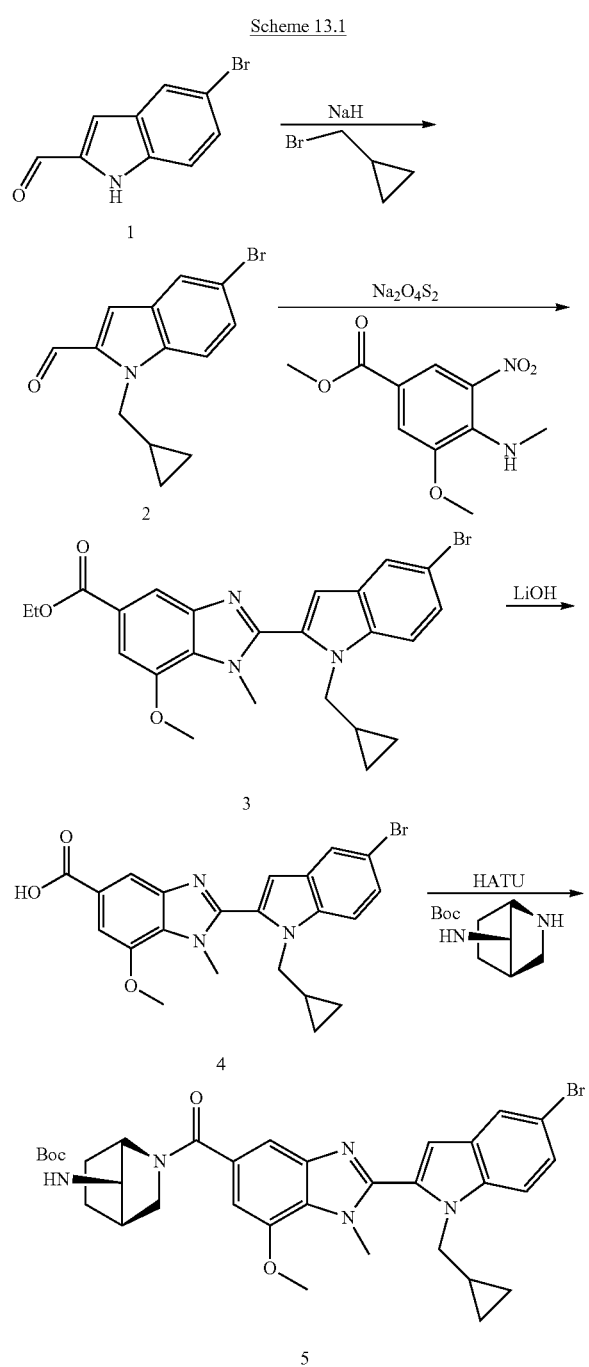

5-bromo-1-(cyclopropylmethyl)-1H-indole-2-carbaldehyde: 2

A cold (0° C.) solution of commercially available 5-bromo-1H-indole-2-carbaldehyde 1 (1 g, 4.46 mmol), in DMF was treated with NaH (0.196 g, 4.91 mmol) portion wise. The reaction was then stirred at 0° C. for an additional 30 min. (bromomethyl)cyclopropane (0.723 g, 5.36 mmol) was then added, and the ice bath was removed. After 14 hrs, the reaction was quenched with H$_2$O (2 mL) then diluted with EtOAc and extracted with H$_2$O, brine, dried (MgSO$_4$) and concentrated to give an orange wax. The wax was then purified by Biotage (80 g col, 0-60% EtOAc/hexanes, 12 CV) to give desired product, 800 mg (64%), as a lt. yellow oil, LCMS (method A): retention time 2.18 min, M/z=280.10 (M+2).

Methyl-2-(5-bromo-1-(cyclopropylmethyl)-1H-indol-2-yl)-7-methoxy-1-methyl-1H-benzo[d]imidazole-5-carboxylate: 3

A suspension of 5-bromo-1-(cyclopropylmethyl)-1H-indole-2-carbaldehyde 2 (2.2 g, 7.91 mmol), and methyl-3-methoxy-4-(methylamino)-5-nitrobenzoate (WO 2014/015905 A1, intermediate 23) (1.900 g, 7.91 mmol), in ethanol (30 mL) was treated with a solution of sodium hydrosulfite (4.13 g, 23.73 mmol) in H$_2$O (10 mL) in one portion. The reaction was then heated to reflux for 18 hrs. After which time the reaction was diluted with DCM (150 ml) dried, MgSO$_4$, and concentrated to give an orange solid. The solid was purified by Biotage (80 g col, 0-30% EtOAc/hexanes, 12 CV) to give, 1 g of recovered aldehyde, 1.4 g of recovered nitro compound. Along with 430 mg (12%) desired product, as a yellow solid, LCMS (method A): retention time 2.25 min, M/z=470.20 (M+2).

2-(5-bromo-1-(cyclopropylmethyl)-1H-indol-2-yl)-7-methoxy-1-methyl-1H-benzo[d]imidazole-5-carboxylic acid: 4

A room temperature solution of methyl 2-(5-bromo-1-(cyclopropylmethyl)-1H-indol-2-yl)-7-methoxy-1-methyl-1H-benzo[d]imidazole-5-carboxylate 3 (1.1 g, 2.349 mmol) in THF (15 mL) was treated with a solution of LiOH (0.225 g, 9.39 mmol) in H$_2$O (6 mL). The reaction was then heated to reflux for 1.5 hrs. The suspension was cooled with Ice, then made acidic with 1N HCl (approx. 25 ml). The resulting red solid was filtered off, washed with H$_2$O, and dried (High Vac). The solid was then taken into EtOAc/DCM and dried again with MgSO$_4$, filtered, then concentrated to give a red solid. 940 mg (88%), LCMS (method A): retention time 1.27 min, M/z=456.20 (M+2).

tert-butyl((1S,4R)-2-(2-(5-bromo-1-(cyclopropylmethyl)-1H-indol-2-yl)-7-methoxy-1-methyl-1H-benzo[d]imidazole-5-carbonyl)-2-azabicyclo[2.2.2.1]heptan-7-yl)carbamate: 5

A room temperature solution of 2-(5-bromo-1-(cyclopropylmethyl)-1H-indol-2-yl)-7-methoxy-1-methyl-1H-benzo[d]imidazole-5-carboxylic acid 4 (940 mg, 2.069 mmol), DIEA (0.542 mL, 3.10 mmol) in DCM (50 mL) was treated with HATU (865 mg, 2.276 mmol) in one portion. tert-Butyl (1R, 4R, 7R)-2-azabicyclo[2.2.1]heptan-7-ylcarbamate (483 mg, 2.276 mmol) was added and stirring was continued for 18 hrs. The reaction was diluted with DCM, and washed with H$_2$O, Sat. Bicarb, brine, dried (MgSO$_4$) and concentrated to give an orange oil. The oil was then purified by Biotage (80 g col, 50-90% EtOAc/Hexanes, 12 CV, then 90% EtOAc/Hexanes, 2 CV) to give desired product, as a lt. orange oil, 1.07 g (80%), LCMS (method A): retention time 1.09 min, M/z=649.50 (M+1). M/z=650.13 (M+2).

Procedure A

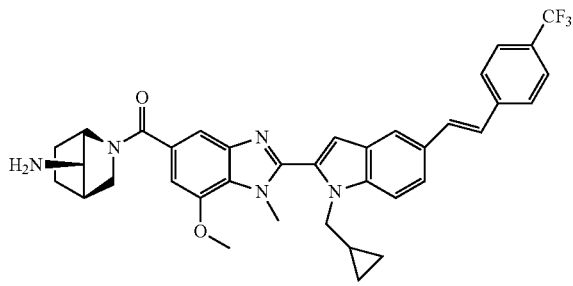

((1S,4R)-7-amino-2-azabicyclo[2.2.1]heptan-2-yl)
(2-(1-(cyclopropylmethyl)-5-((E)-4-(trifluoromethyl)
styryl)-1H-indol-2-yl)-7-methoxy-1-methyl-1H-
benzo[d]imidazol-5-yl)methanone, I-361

A suspension of tert-butyl ((1S,4R)-2-(2-(5-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate 5 (50 mg, 0.077 mmol), (E)-(4-(trifluoromethyl)styryl)boronic acid (16.65 mg, 0.077 mmol), and an aqueous solution (0.5M) of potassium phosphate tribasic (0.925 mL, 0.463 mmol) in THF (5 mL) was added 2-dicyclohexylphosphino-2',6'-di-I-propoxy-1,1'-biphenyl (21.58 mg, 0.046 mmol) and palladium(II) chloride (2.73 mg, 0.015 mmol) in one portion. The resulting reddish suspension was heated to 80° C. for 4 hrs. The reaction was diluted with EtOAc washed with H₂O, brine, dried (MgSO₄) and concentrated to give a light orange wax. The wax was clean enough by LCMS (MW=739) to carry on to the deprotection step. The wax was taken into DCM (2 mL) then treated with 4M HCl (0.5 mL, 2.000 mmol) (4M in Dioxane). After 1 hr, the reaction was concentrated, taken into DCM and filtered, dried (MgSO₄), concentrated, then purified, 32 mg in 2 ml DMF. The crude material was purified via preparative LC/MS: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-90% B over 19 minutes, then a 4-minute hold at 100% B; Flow: 20 mL/min. Fractions containing the desired product were combined and dried via centrifugal evaporation. The yield of the product was 20.3 mg, (34% yield) and its estimated purity by LCMS analysis was 100%. LCMS (method B): retention time 2.42 min, M/z=640.14 (M+1).

Procedure B

I-374

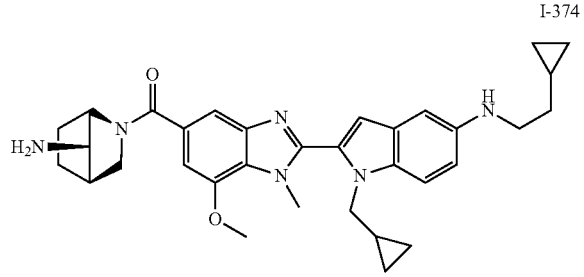

((1S,4R)-7-amino-2-azabicyclo[2.2.1]heptan-2-yl)
(2-(5-((2-cyclopropylethyl)amino)-1-(cyclopropylmethyl)-1H-indol-2-yl)-7-methoxy-1-methyl-1H-
benzo[d]imidazol-5-yl)methanone, I-374

A suspension of 5 (50 mg, 0.077 mmol), 2-cyclopropylethanamine (6.56 mg, 0.077 mmol), X-PHOS (7.35 mg, 0.015 mmol), in toluene (15 mL) was degassed for 15 min with nitrogen. Pd₂(dba)₃ (7.06 mg, 7.71 μmol) and sodium tert-butoxide (14.82 mg, 0.154 mmol) were then added and the suspension was heated to 80° C. for 4 hrs. The reaction was cooled, diluted with EtOAc, then washed with H₂O, brine, dried (MgSO₄) and concentrated to give a tan wax. The wax was shown by LCMS to contain desired product by LCMS (MW=652) which was then deprotected directly.

The material was taken into DCM (0.5 mL) then treated with HCl (0.5 mL, 2 mmol, 4M in dioxane). After 1 hr the reaction was concentrated, then evaporated from DCM (2×). The crude material was dissolved in MeOH (filtered) and evaporated to give a red solid: 37 mg. The crude material was purified via preparative LC/MS: Column: XBridge C18, 19×200 mm, 5-μm particle size; mobile phase A: 5:95 acetonitrile: water with 10-mM ammonium acetate; mobile phase B: 95:5 acetonitrile: water with 10-mM ammonium acetate; Gradient: 35-75% B over 20 minutes, then a 7-minute hold at 100% B; flow: 20 mL/min. Fractions containing the desired product were combined and dried via centrifugal evaporation. The yield of the product was 10.9 mg, (16%) and its estimated purity by LCMS analysis was 98%. LCMS (method B): retention time 1.84 min, M/z=553.26 (M+1).

Procedure C

I-370

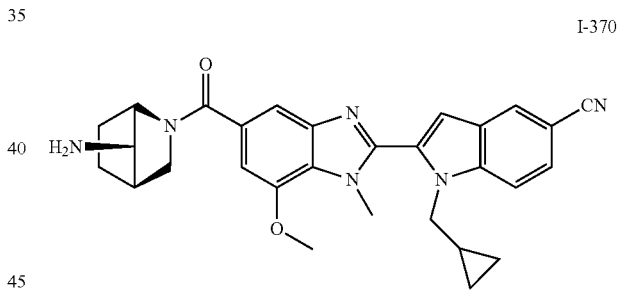

Step 1: tert-butyl ((1S,4R)-2-(2-(5-cyano-1-(cyclopropylmethyl)-1H-indol-2-yl)-7-methoxy-1-methyl-1H-benzo[d]imidazole-5-carbonyl)-2-azabicyclo
[2.2.1]heptan-7-yl)carbamate A suspension of tert-butyl ((1S,4R)-2-(2-(5-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate (100 mg, 0.154 mmol) 5, zinc cyanide(18.10 mg, 0.154 mmol), Pd₂dba₃ (7.06 mg, 7.71 μmol) and DPPF (10.26 mg, 0.019 mmol) in DMF (4 mL) and water (0.4 mL) was heated to 120° C. for 18 hrs. Additional zinc cyanide (18.10 mg, 0.154 mmol), Pd₂dba₃ (7.06 mg, 7.71 mol) and DPPF (10.26 mg, 0.019 mmol) were added, and stirring at 120° C. was continued for 4 hrs. The reaction was cooled, diluted with EtOAc, washed with H₂O, sat. bicarb, dried (MgSO₄) and concentrated to give a black wax. The wax was purified by Biotage (40 g col, 20-100% EtOAc/Hexanes, 12 CV then 100% EtOAc for 4 CV) to give desired product as a light yellow wax: 89 mg (97% yield), LCMS (method A): retention time min 2.11 min, M/z=595.65 (M+1).

Step 2: 2-(5-((1S,4R)-7-amino-2-azabicyclo[2.2.1] heptane-2-carbonyl)-7-methoxy-1-methyl-1H-benzo [d]imidazol-2-yl)-1-(cyclopropylmethyl)-1H-indole-5-carbonitrile, I-370

A solution of tert-butyl ((1S,4R)-2-(2-(5-cyano-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate (35 mg, 0.059 mmol) in DCM (1 mL) was treated with HCl (0.5 ml, 2 mmol, 4M in dioxane) dropwise. After 1 hr the reaction was concentrated then sequentially dissolved in DCM and concentrated (2x). The crude material was dissolved in MeOH (filtered) and evaporated to give a red solid, 22 mg which was dissolved in 1.5 ml of DMF and purified via preparative LC/MS: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. Fractions containing the desired product were combined and dried via centrifugal evaporation. The yield of the product was 14.4 mg (38% yield), and its estimated purity by LCMS analysis was 100%. LCMS (method B): retention time min 1.81 min, M/z=495.07 (M+1).

All 6 substituted -1H-indol-2yl compounds were made from tert-butyl ((1S,4R)-2-(2-(6-bromo-1-(cyclopropylmethyl)-1H-indol-2-yl)-7-methoxy-1-methyl-1H-benzo[d] imidazole-5-carbonyl)-2-azabicyclo[2.2.1]heptan-7-yl)carbamate 6 using the same procedures as described for the 5-substituted compounds (Scheme 13).

HPLC Methods for Schemes 13 and 14
Method A
(low pH Shimadzu 3 min method)
Column: Waters Acquity UPLC BEH dC18, 2.1 mm×50 mm, 1.7 μm column
Flow rate: 0.6 ml/min
Mobile Phase: A, TFA (aqueous) 0.05% and B, TFA (acetonitrile) 0.05%
Injection Vol: 3 μl
Temp.: 40° C.
Detection: 220 nm (nominal)
Gradient—0-100% B
Method B
Column: Water Xbridge C18, 2.1 mm×50 mm, 1.7 μm column
Flow rate: 0.6 ml/min
Mobile Phase: acetonitrile:water with 10 mM ammonium acetate; Mobile Phase B: 95:5 acetonitrile:water with 10 mM ammonium acetate; Temperature:

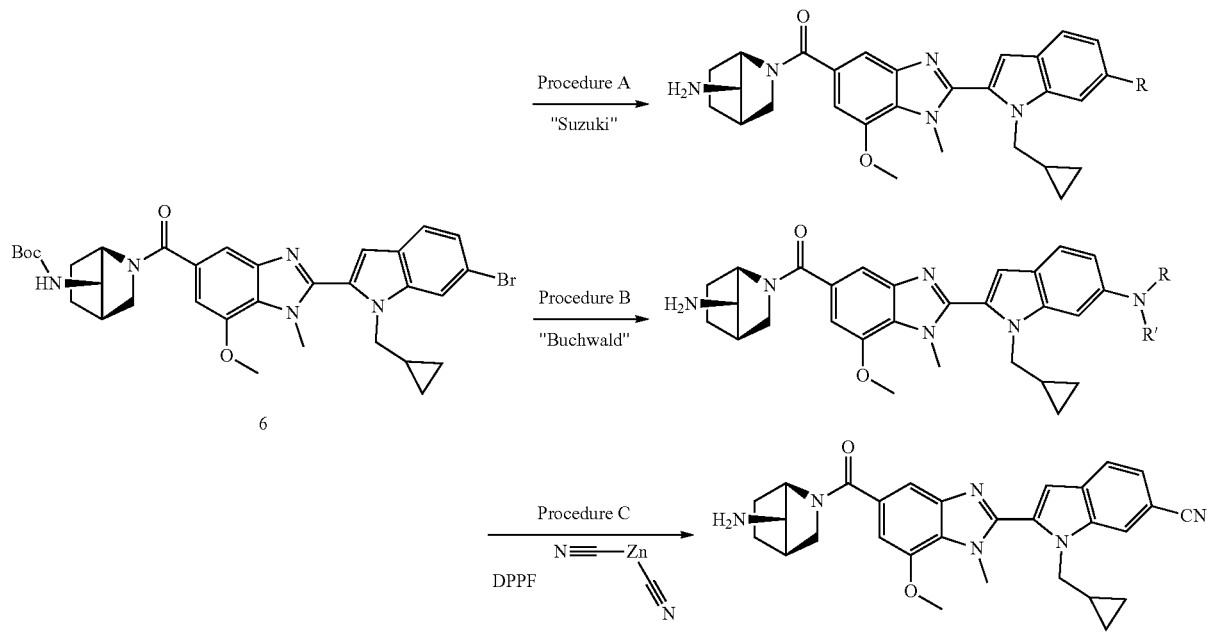

Scheme 14

Tert-butyl ((1 S,4R)-2-(2-(6-bromo-1-(cyclopropylmethyl)-1H-indol-2-yl)-7-methoxy-1-methyl-1H-benzo[d]imidazole-5-carbonyl)-2-azabicyclo[2.2.1] heptan-7-yl)carbamate 6

The bromide was made as described in Scheme 13.1 starting from the commercially available 6-bromo-1H-indole-2-carbaldehyde to give an orange wax, LCMS (method A): retention time 1.29 min, M/z=650.30 (M+2).

50° C.; Gradient: 0% B to 100% B over 3 min, then a 0.75 min hold at 100% B
Injection Vol: 3 μl
Temp.: 40° C.
Detection: 220 nm (nominal)

The following compounds were prepared using Method A, B, or C as described in Schemes 13 and 14:

| Structure | # | Method | Mol Wt | LCMS T_ret | M/z (+) | LCMS Method | Salt | Salt Stoichiometry |
|---|---|---|---|---|---|---|---|---|
| 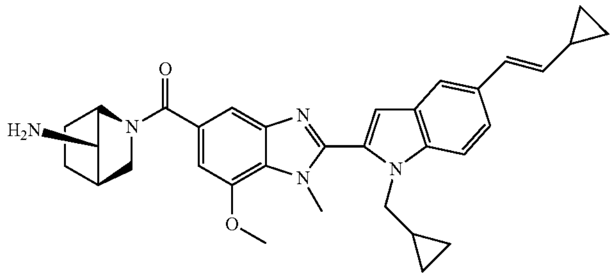 | I-357 | A | 535.679 | 2.11 min | 536.19 | B | | |
| 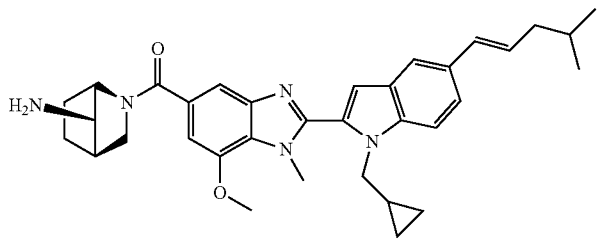 | I-358 | A | 551.722 | 2.39 min | 552.15 | B | | |
| 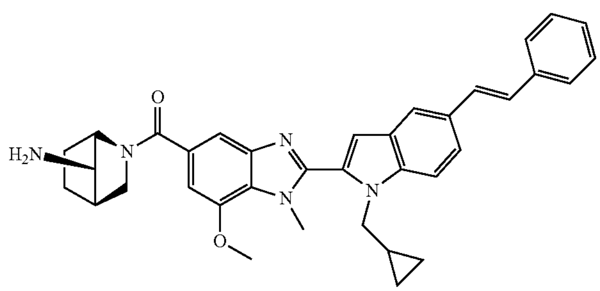 | I-359 | A | 571.71 | 2.16 min | 572.13 | B | | |
| 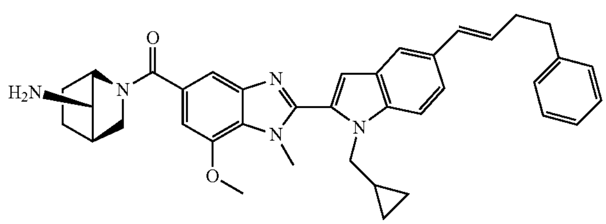 | I-360 | A | 599.764 | 2.25 min | 600.40 | A | TFA | 1 |
| 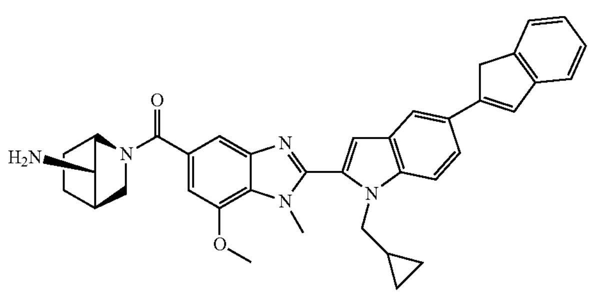 | I-362 | A | 583.722 | 2.21 min | 584.12 | B | | |
| 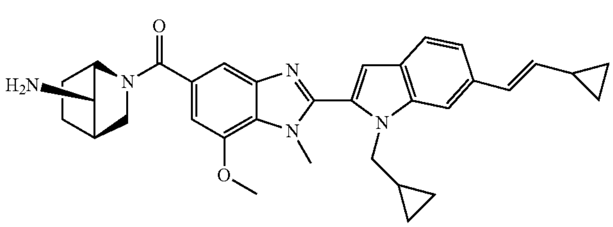 | I-363 | A | 535.679 | 2.04 min | 536.24 | B | | |

-continued
| Structure | # | Method | Mol Wt | LCMS T_ret | M/z (+) | LCMS Method | Salt | Salt Stoichiometry |
|---|---|---|---|---|---|---|---|---|
| 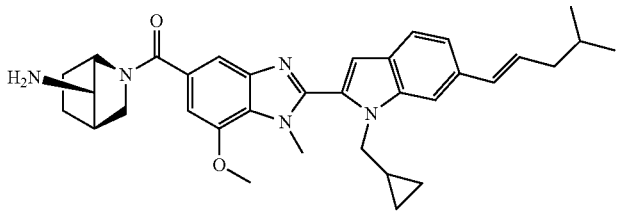 | I-364 | A | 551.722 | 2.35 min | 552.26 | B | | |
| 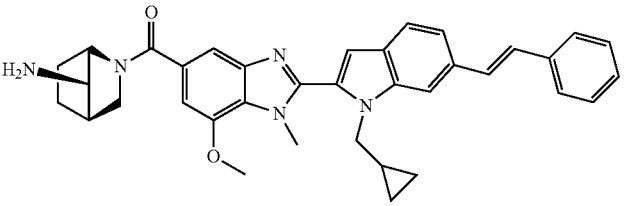 | I-365 | A | 571.711 | 2.16 min | 572.25 | B | | |
| 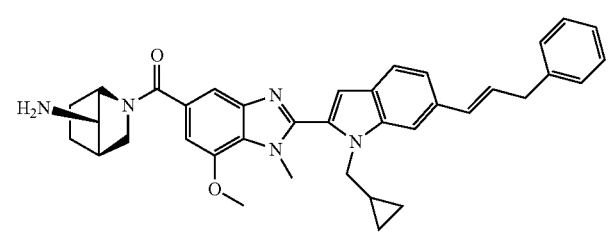 | I-366 | A | 585.738 | 2.57 min | 586.10 | B | | |
| 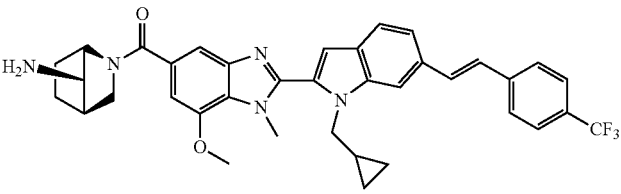 | I-367 | A | 639.709 | 2.36 min | 640.24 | B | | |
| 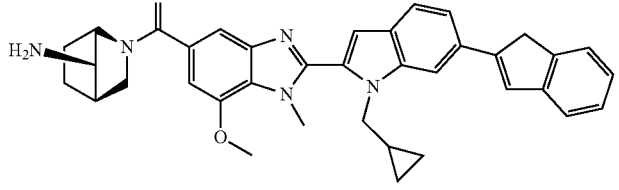 | I-368 | A | 583.722 | 2.19 min | 584.24 | B | | |
| 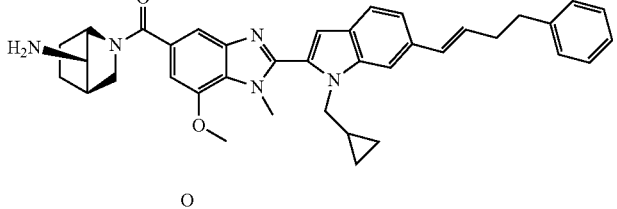 | I-369 | A | 599.764 | 2.65 min | 600.12 | B | | |
| 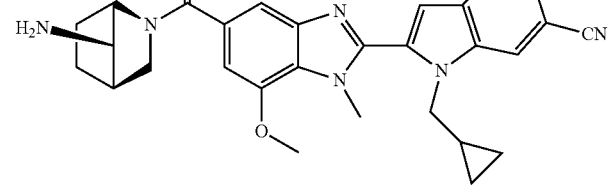 | I-371 | C | 494.588 | 0.91 min | 495.30 | A | TFA | 1 |

| Structure | # | Method | Mol Wt | LCMS $T_{ret}$ | M/z (+) | LCMS Method | Salt | Salt Stoichiometry |
|---|---|---|---|---|---|---|---|---|
| 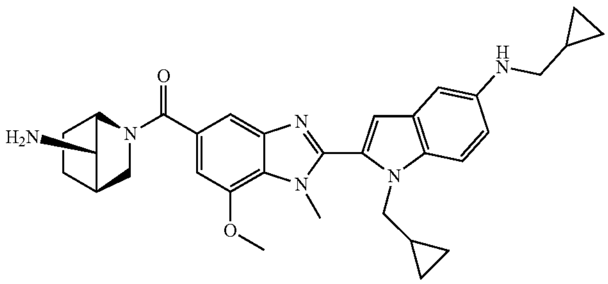 | I-372 | B | 538.683 | 1.19 min | 539.22 | A | TFA | 1 |
| 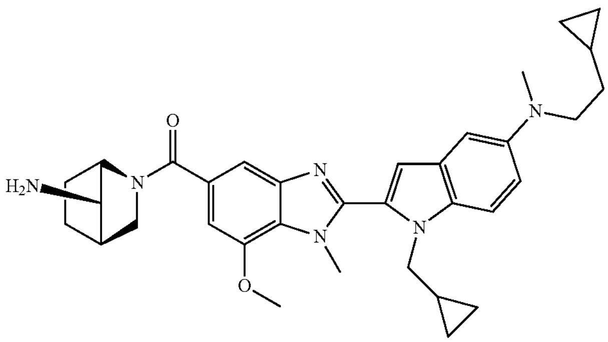 | I-373 | B | 566.736 | 2.20 min | 567.22 | B | | |
| 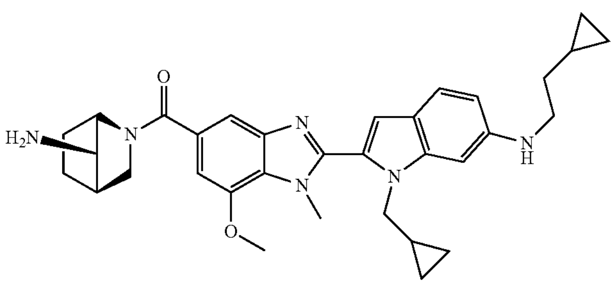 | I-375 | B | 552.710 | 2.17 min | 553.12 | B | | |
| 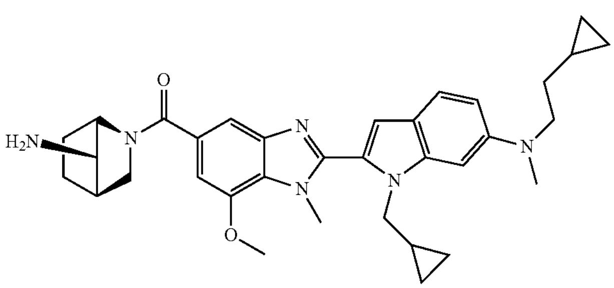 | I-376 | B | 556.736 | 1.31 min | 567.30 | A | | |

Biological Assays

Compounds of the present invention were assayed as inhibitors of PAD4 using the assay protocol described below.

Compounds were solubilised in 100% DMSO to achieve 100 mM final compound concentration. Compound stock solutions were stored at RT. A series of dilutions were prepared in DMSO and mixed 8 times with 20 μL mixing volume. Final assay conditions were as follows:

Reaction volume: 20 μl

Assay buffer (as aforementioned): 100 mM Tris-HCl (pH 7.6), 2 mM DTT, 1 mM CaCl$_2$ Final concentrations:
100 nM hPAD4 enzyme
50 μM (8-fold sub-$K_m$) substrate peptide
0.5% DMSO
Total incubation time: 65 mins at 37° C.
Stop solution: 40 μl 5% TCA in ACN 0.25 μL of compound solution was added to 10 μL of 200 nM PAD4 in assay buffer (100 mM Tris-HCl pH 7.6, 2 mM DTT). After 5 mins, 10 μL of 100 μM of substrate in buffer (100 mM Tris-HCl pH 7.6, 2 mM DTT, 2 mM CaCl$_2$) was added and the reaction incubated for 60 mins at 37° C. The enzymatic reaction was quenched by addition of 40 μl of 5%

TCA in ACN (1.7% TCA final concentration) stop solution. Arginine containing substrate and citrulline containing product (+1 Da mass shift) were subjected to solid phase extraction on Agilent RapidFire (RF) 300 system and detected on a coupled, triple quadrupole Agilent 6460 QQQ mass spectrometry (MS) device under application of multiple reaction monitoring (MRM) for quantitation.

IC50 Determinations Against PAD Isozymes

The IC50 for a given test compound was measured using a mass spec assay which detected the citrullinated product of BAEE after reaction with phenylglyoxal. Test compounds were dissolved in 100% DMSO and 0.125 uL were delivered to a 384 well REMP polypropylene plate prior to the addition of enzyme. The enzyme and the compound were pre-incubated for 30 mins at 37° C. and the reaction was initiated by the addition of the BAEE substrate such that the final concentration in each assay well was equal to the Km value for BAEE at saturating calcium concentration (250 uM). The buffer used for the reaction contained 25 mM Hepes pH 7.5, 5 mM NaCl, 1 mM DTT, 0.01% Chaps, 0.2 mg/mL BSA and either 50 uM or 1 mM $CaCl_2$ which corresponds the one-fifth of the $K_{0.5}$ for $Ca^{2+}$ or 20×$K_{0.5}$ for $Ca^{2+}$, respectively, as measured at 10-fold Km of BAEE. A typical enzyme concentration used was 5 nM in the final reaction and the total reaction volume was 25 uL. The reaction was allowed to proceed for 1.5 hours at 37° C. after the addition of BAEE before being quenched with 15 ul of 6.1 N TCA and 35 ul of 8.5 mM phenylglyoxal. The final concentration of phenyl glyoxal was 4 mM. The mixture was allowed to incubate for an additional 30 mins at 37° C. with agitation to allow complete modification of the citrullinated product by phenyl glyoxal. The quenched reaction plate was centrifuged at 5000×g for 3 minutes and an equal volume of methanol containing an internal standard (phenylglyoxal modified citrulline) was added to each well. The contents were transferred to a new 384-well REMP plate for rapidfire MS analysis.

Samples were loaded on to the RapidFire RF300 system (Agilent) wherein they were first sipped for 1000 ms and then directly loaded to a C18 separations cartridge using a mixture of acetonitrile containing 0.01% formic acid for 3000 ms desalting. The flow rate of the mobile phase was 1.5 ml/min. Once the samples were eluted from the cartridge, a mobile phase of acetonitrile containing 0.01% formic acid was used to move the samples into the mass spectrometer for 4000 ms at a flow rate of 1.25 ml/min. Sciex API4000 triple quadrupole mass spectrometer (Applied Biosystems) equipped with ESI was used to analyze the peptidyl citrulline and internal standard ions. MRM transition of product and internal standard were monitored at m/z 424.5 to 350.4 and m/z 293 to 247, respectively. The dwell time for each transition was set at 200 ms, and the ESI voltage was used at 5500 V with a source temperature of 400° C. Extracted ion peaks for each transition were integrated using the rapidfire integrator software. Peak area was normalized against the internal standard.

For IC50 determinations, compounds were 3-fold serially diluted in DMSO and tested at 11 different concentrations. Peak area ratios were calculated by dividing peak area of analyte with peak area of internal standard. The peak area ratio from the DMSO control and the no enzyme background were used to calculate percent inhibition occurring at each concentration of inhibitor, and the IC50 was calculated using the following equation $$Y = A + \frac{(B - A)}{1 + \left(\frac{C}{x}\right)^D}$$

where Y=% inhibition at each inhibitor concentration, A=minimal Y value, B=maximal Y value, C=log IC50, D=hill slope, and x=concentration of inhibitor.

Table 2, below, shows the activity of selected compounds of this invention in the PAD4 assays described above. The compound numbers correspond to the compound numbers in Table 1. Compounds having an activity designated as "A" provided an $IC_{50} \leq 1$ µM; compounds having an activity designated as "B" provided an $IC_{50}$ of 1.0-5.0 µM; compounds having an activity designated as "C" provided an $IC_{50}$ of 5.0-10.0 µM; and compounds having an activity designated as "D" provided an $IC_{50}$ of $\geq 10.0$ µM. The term $pIC_{50} = -\log(IC_{50})$. Compounds having an activity designated as "E" provided a $pIC_{50} \leq 4$; compounds having an activity designated as "F" provided a $pIC_{50}$ of 4.0-5.0; compounds having an activity designated as "G" provided a $pIC_{50}$ of 5.0-6.0; and compounds having an activity designated as "H" provided a $pIC_{50}$ of $\geq 6$. "NA" stands for "not assayed."

TABLE 2

PAD4 Activity

| Compound # | hPAD4 RFMS $IC_{50}$ µM | hPAD4 RFMS $pIC_{50}$ | mPAD4 RFMS $IC_{50}$ µM | mPAD4 RFMS $pIC_{50}$ |
|---|---|---|---|---|
| I-1 | D | F | NA | NA |
| I-2 | D | F | NA | NA |
| I-3 | B | G | NA | NA |
| I-4 | D | F | NA | NA |
| I-5 | D | F | NA | NA |
| I-6 | B | G | NA | NA |
| I-7 | A | H | NA | NA |
| I-8 | A | H | NA | NA |
| I-9 | C | G | D | F |
| I-10 | B | G | C | G |
| I-11 | A | H | A | H |
| I-12 | B | G | D | F |
| I-13 | B | G | NA | NA |
| I-14 | D | F | NA | NA |
| I-15 | C | G | NA | NA |
| I-16 | C | G | NA | NA |
| I-17 | D | F | D | F |
| I-18 | D | F | D | F |
| I-19 | B | G | C | G |
| I-20 | D | F | NA | NA |
| I-21 | B | G | B | G |
| I-22 | D | F | D | F |
| I-23 | A | H | B | G |
| I-24 | D | F | D | F |
| I-25 | B | G | B | G |
| I-26 | D | F | D | E |
| I-27 | B | G | B | G |
| I-28 | A | H | A | H |
| I-29 | C | F | C | G |
| I-30 | D | F | D | F |
| I-31 | A | H | A | H |
| I-32 | D | E | D | F |
| I-33 | A | H | A | H |
| I-34 | A | H | A | H |
| I-35 | A | H | A | H |
| I-36 | A | H | A | H |
| I-37 | D | E | NA | NA |
| I-38 | D | E | NA | NA |
| I-39 | D | F | NA | NA |
| I-40 | D | F | NA | NA |
| I-41 | D | F | NA | NA |
| I-42 | D | E | NA | NA |

TABLE 2-continued

PAD4 Activity

| Compound # | hPAD4 RFMS IC$_{50}$ μM | hPAD4 RFMS pIC$_{50}$ | mPAD4 RFMS IC$_{50}$ μM | mPAD4 RFMS pIC$_{50}$ |
|---|---|---|---|---|
| I-43 | D | E | NA | NA |
| I-44 | D | E | NA | NA |
| I-45 | D | E | NA | NA |
| I-46 | D | E | NA | NA |
| I-47 | D | E | NA | NA |
| I-48 | D | F | NA | NA |
| I-49 | C | G | NA | NA |
| I-50 | D | E | NA | NA |
| I-51 | D | F | NA | NA |
| I-52 | D | F | D | F |
| I-53 | D | E | NA | NA |
| I-54 | C | G | D | F |
| I-55 | D | F | D | F |
| I-56 | B | G | B | G |
| I-57 | B | G | NA | NA |
| I-58 | D | F | NA | NA |
| I-59 | B | G | A | H |
| I-60 | D | F | NA | NA |
| I-61 | D | E | NA | NA |
| I-62 | B | G | C | G |
| I-63 | D | F | NA | NA |
| I-64 | B | G | C | G |
| I-65 | D | F | D | F |
| I-66 | A | G | B | G |
| I-67 | D | F | NA | NA |
| I-68 | C | G | D | F |
| I-69 | A | G | D | F |
| I-70 | A | H | A | H |
| I-71 | B | G | A | H |
| I-72 | B | G | A | H |
| I-73 | B | G | A | H |
| I-74 | D | F | D | F |
| I-75 | B | G | B | G |
| I-76 | D | F | D | F |
| I-77 | D | F | D | F |
| I-80 | C | G | B | G |
| I-81 | A | H | A | H |
| I-82 | D | F | D | F |
| I-83 | B | G | B | G |
| I-84 | D | F | D | F |
| I-85 | D | F | D | F |
| I-86 | A | H | A | H |
| I-87 | A | H | A | H |
| I-88 | D | F | C | G |
| I-89 | D | F | D | F |
| I-90 | B | G | B | G |
| I-91 | A | H | A | H |
| I-92 | B | G | A | H |
| I-93 | B | G | B | G |
| I-94 | A | H | A | H |
| I-95 | D | F | D | F |
| I-96 | D | F | D | F |
| I-97 | D | F | D | F |
| I-98 | A | H | A | H |
| I-99 | D | E | D | E |
| I-100 | D | E | D | E |
| I-101 | B | G | B | G |
| I-102 | A | G | B | G |
| I-103 | D | F | D | F |
| I-104 | A | H | A | H |
| I-105 | A | H | A | H |
| I-106 | A | H | A | H |
| I-107 | D | F | D | F |
| I-108 | D | F | D | F |
| I-109 | A | H | A | H |
| I-110 | B | G | D | F |
| I-111 | B | G | A | H |
| I-112 | C | G | B | G |
| I-113 | B | G | C | G |
| I-114 | A | H | A | H |
| I-115 | A | H | A | H |
| I-116 | D | F | NA | NA |
| I-117 | B | G | D | F |
| I-119 | A | H | A | H |
| I-121 | A | H | A | H |
| I-122 | D | E/F | D | E |
| I-123 | A | H | A | H |
| I-124 | D | F | C | G |
| I-125 | D | F | D | F |
| I-126 | D | F | D | F |
| I-127 | B | G | B | G |
| I-128 | B | G | B | G |
| I-129 | B | G | B | G |
| I-130 | A | H | B | G |
| I-131 | C | G | D | F |
| I-132 | A | H | B | G |
| I-133 | D | F | B | G |
| I-134 | B | G | A | H |
| I-135 | A | H | A | H |
| I-136 | A | H | A | H |
| I-137 | B | G | B | G |
| I-138 | A | H | A | H |
| I-139 | A | H | A | H |
| I-140 | C | G | D | F |
| I-141 | A | H | A | H |
| I-142 | B | G | B | G |
| I-143 | A | H | A | H |
| I-146 | B | G | A | H |
| I-149 | A | H | A | H |
| I-151 | B | G | C | G |
| I-152 | B | G | C | G |
| I-154 | A | H | A | H |
| I-155 | A | H | A | H |
| I-157 | B | G | B | G |
| I-159 | A | H | A | H |
| I-160 | A | H | A | H |
| I-161 | A | H | A | H |
| I-162 | A | H | B | G |
| I-163 | B | G | A | H |
| I-164 | B | G | C | G |
| I-165 | B | G | B | G |
| I-166 | A | H | B | G |
| I-167 | B | G | NA | NA |
| I-168 | A | H | NA | NA |
| I-169 | A | H | NA | NA |
| I-170 | B | G | NA | NA |
| I-171 | C | G | C | G |
| I-172 | B | G | B | G |
| I-173 | A | H | B | G |
| I-174 | B | G | B | G |
| I-175 | A | H | B | G |
| I-176 | B | G | B | G |
| I-177 | B | G | A | H |
| I-178 | A | H | A | H |
| I-179 | A | H | B | G |
| I-180 | B | G | A | H |
| I-181 | A | H | A | H |
| I-182 | A | H | A | H |
| I-183 | A | H | A | H |
| I-184 | A | H | A | H |
| I-185 | C | G | D | F |
| I-186 | B | G | D | F |
| I-187 | D | F | D | F |
| I-188 | A | H | A | H |
| I-189 | A | H | A | H |
| I-190 | B | G | B | G |
| I-191 | A | H | B | G |
| I-192 | A | H | C | G |
| I-193 | B | G | B | G |
| I-194 | B | G | C | G |
| I-195 | C | G | B | G |
| I-196 | A | H | A | H |
| I-197 | A | H | A | H |
| I-198 | A | H | A | H |
| I-199 | A | H | A | H |
| I-200 | A | H | A | H |
| I-201 | A | H | A | H |
| I-202 | A | H | B | G |

TABLE 2-continued

PAD4 Activity

| Compound # | hPAD4 RFMS IC$_{50}$ μM | hPAD4 RFMS pIC$_{50}$ | mPAD4 RFMS IC$_{50}$ μM | mPAD4 RFMS pIC$_{50}$ |
|---|---|---|---|---|
| I-203 | A | H | B | G |
| I-204 | A | H | A | H |
| I-205 | A | H | A | H |
| I-206 | A | H | A | H |
| I-207 | C | G | B | G |
| I-208 | A | H | A | H |
| I-209 | A | H | A | H |
| I-210 | A | H | A | H |
| I-211 | A | H | A | H |
| I-212 | D | F | D | F |
| I-213 | A | H | A | H |
| I-214 | A | H | B | G |
| I-215 | D | E/F | D | E/F |
| I-216 | D | F | D | F |
| I-217 | A | H | A | H |
| I-218 | B | G | B | G |
| I-219 | A | H | B | G |
| I-220 | D | E/F | D | E/F |
| I-221 | D | F | B | G |
| I-222 | A | H | A | H |
| I-223 | A | H | A | H |
| I-224 | A | H | A | H |
| I-225 | A | H | A | H |
| I-226 | D | E/F | D | E/F |
| I-227 | D | F | D | E/F |
| I-228 | C | G | B | G |
| I-229 | D | F | C | G |
| I-230 | A | H | A | H |
| I-231 | A | H | A | H |
| I-232 | A | H | A | H |
| I-233 | A | H | A | H |
| I-234 | A | H | B | G |
| I-235 | A | H | A | H |
| I-236 | A | H | A | H |
| I-237 | D | F | D | F |
| I-238 | A | H | A | H |
| I-352 | A | H | | |
| I-353 | A | H | | |
| I-354 | A | H | | |
| I-355 | A | H | | |
| I-356 | A | H | | |
| I-357 | A | H | | |
| I-358 | A | H | | |
| I-359 | A | H | | |
| I-360 | A | H | | |
| I-361 | A | H | | |
| I-362 | A | H | | |
| I-363 | A | H | | |
| I-364 | A | H | | |
| I-365 | A | H | | |
| I-366 | A | H | | |
| I-367 | A | H | | |
| I-368 | A | H | | |
| I-369 | A | H | | |
| I-371 | A | H | | |
| I-372 | B | G/H | | |
| I-373 | B | G | | |
| I-374 | A | H | | |
| I-375 | A | H | | |
| I-376 | A | H | | |

We claim:
1. A compound of formula I':

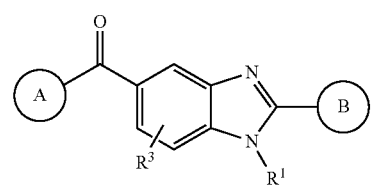

or a pharmaceutically acceptable salt thereof, wherein:
Ring A is

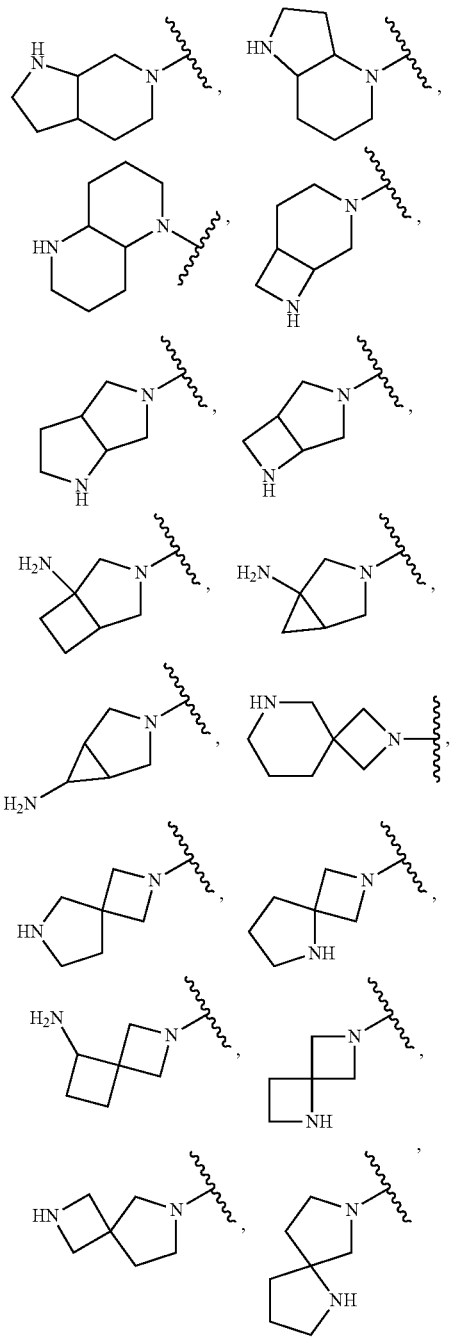

537
-continued
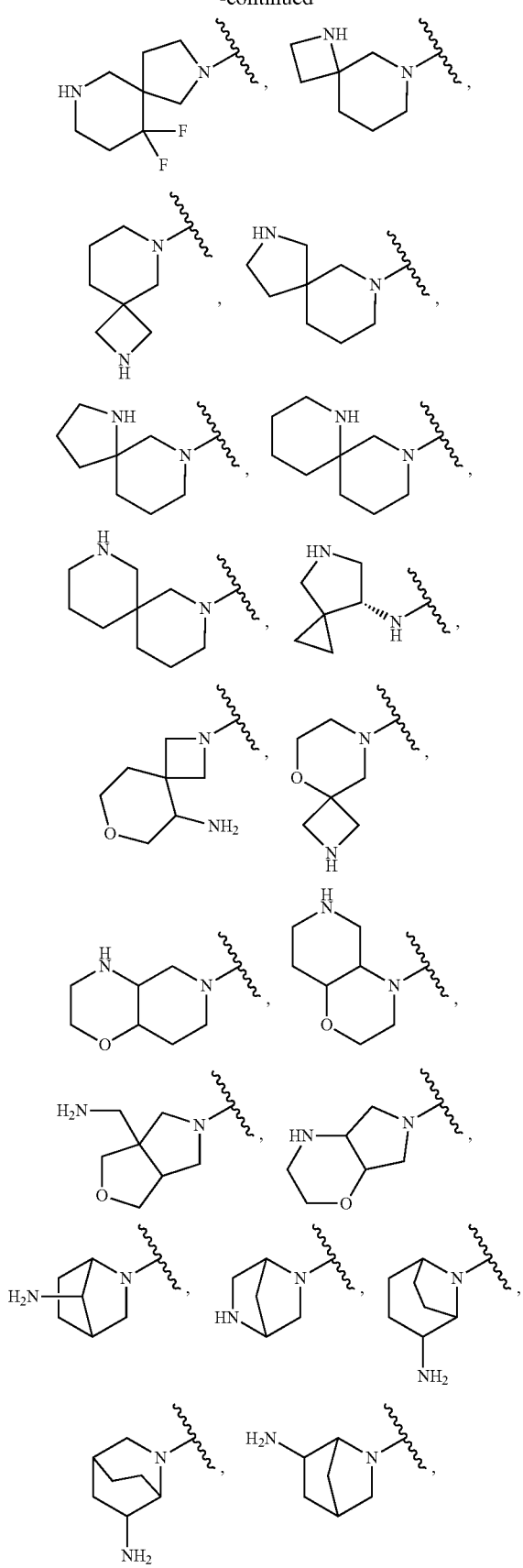
538
-continued
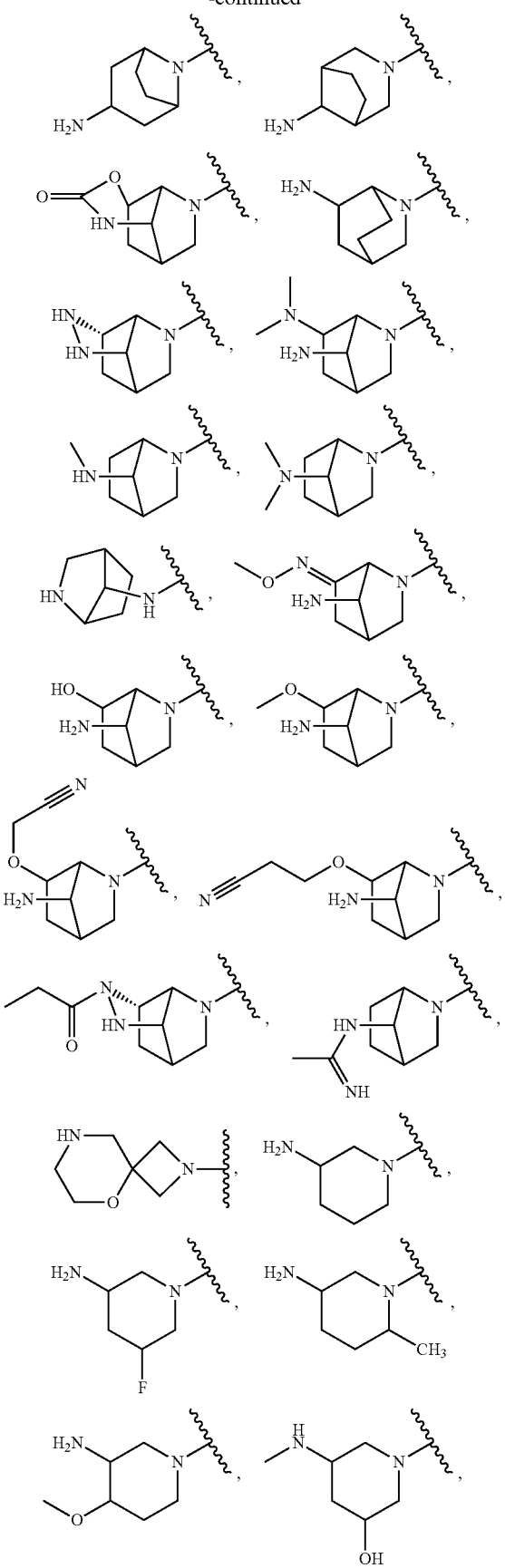

-continued

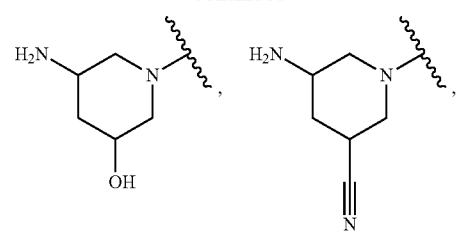

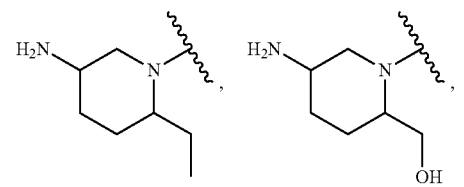

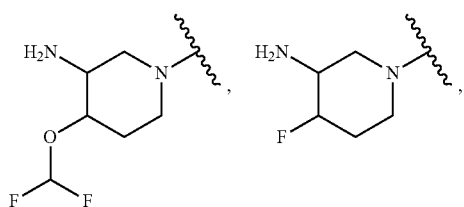

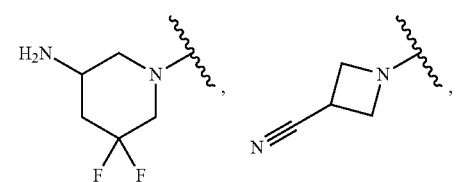

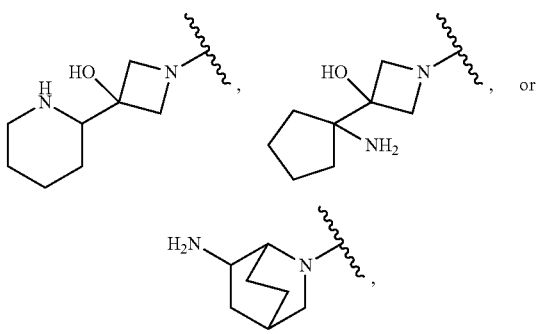

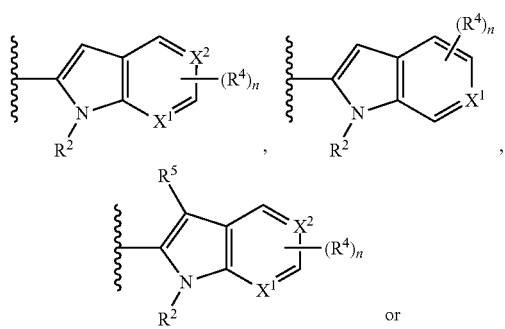

wherein:
Ring A is optionally substituted with 1-4 groups selected from fluorine, —CN, —OR, or $C_{1-6}$ aliphatic optionally substituted with 1-3 fluorine atoms;
Ring B is

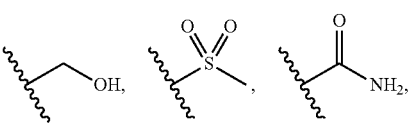

-continued

[structure with $X^1$, $(R^4)_n$, $R^2$]

$R^1$ is hydrogen, —CN, —OR,

[tetrahydrofuran, tetrahydropyran, tetrahydrofuranyl-methyl structures]

[tetrahydropyranylmethyl, spiro, thiomethyl structures]

[sulfoxide, sulfone, cyclobutyl-OCD$_3$ structures]

[methyl cyclobutyl-OCD$_3$ structure]

or $C_{1-6}$ aliphatic optionally substituted with 1-4 groups selected from fluorine, —CN, or —OR;

$R^2$ is hydrogen or $C_{1-10}$ aliphatic optionally substituted with 1-5 groups selected from fluorine, —CN, or —OR;

each of $X^1$ and $X^2$ is independently selected from N or $C(R^4)$;

$R^3$ is halogen, —CN, —R,

[—CH$_2$CH$_2$OH, —SO$_2$CH$_3$, —C(O)NH$_2$ structures]

or —OR;

each $R^4$ is independently halogen, —CN, —R,

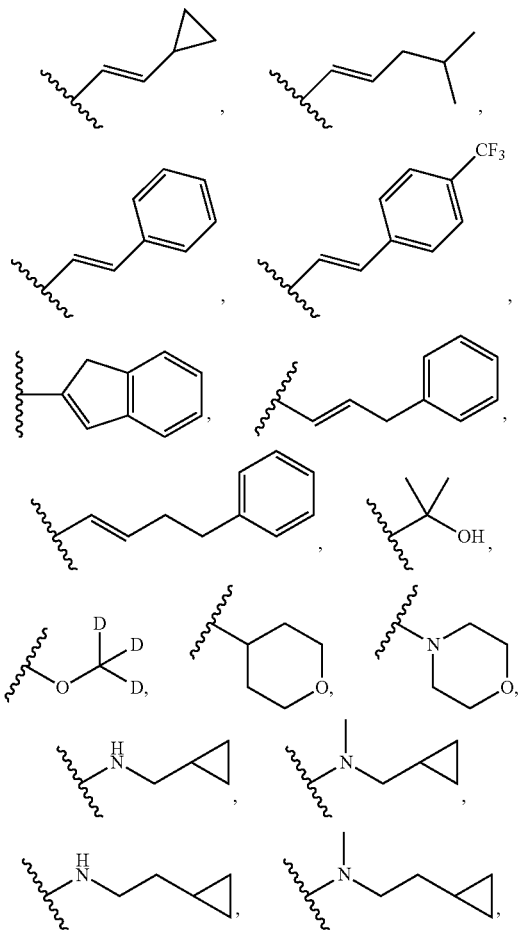

or —OR;

$R^5$ is hydrogen or halogen;

n is 0-4; and each R is independently hydrogen or $C_{1-6}$ aliphatic optionally substituted with 1-3 fluorine atoms provided that Ring A is not

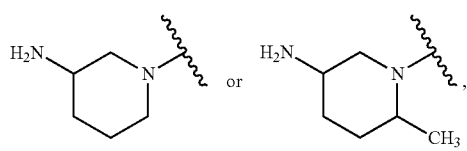

when $R^1$ is $C_{1-6}$ aliphatic optionally substituted with —OR; Ring A is not

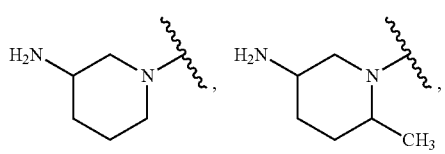

-continued

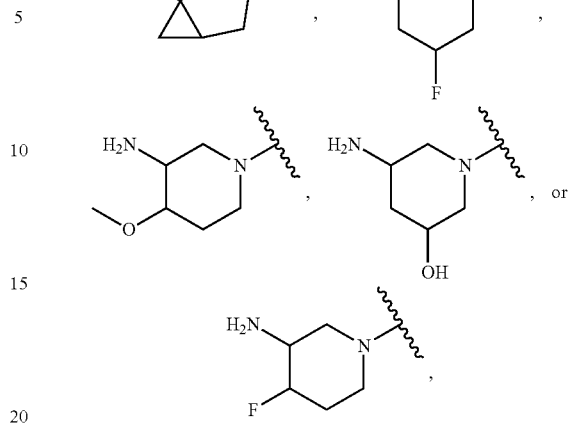

when $X^1$ is $C(R^4)$.

2. The compound according to claim 1, wherein Ring A is

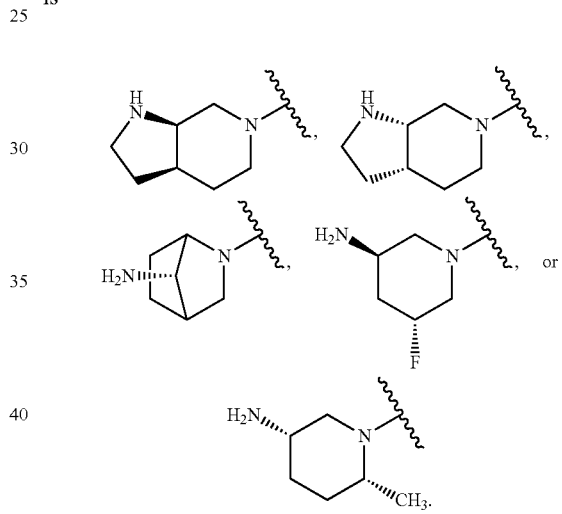

3. The compound according to claim 1, wherein Ring A is

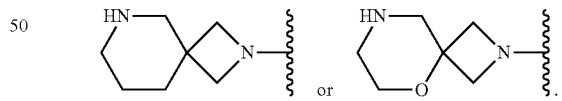

4. The compound according to 1, wherein $R^1$ is methyl, ethyl, or propyl.

5. The compound according to claim 1, wherein $R^2$ is $C_{1-10}$ aliphatic, optionally substituted with 1-5 fluorine atoms.

6. The compound according to claim 5, wherein $R^2$ is methyl, ethyl, or —CH$_2$— cyclopropyl.

7. The compound according to claim 5, wherein $R^2$ is $C_{1-10}$ aliphatic, substituted with 1-5 fluorine atoms.

8. The compound according to claim 7, wherein $R^2$ is —CH$_2$CF$_3$.

9. The compound according to claim 1, wherein both of $X^1$ and $X^2$ are N.

10. The compound according to claim 1, wherein $X^1$ is N, and $X^2$ is CH.

11. The compound according to claim 1, wherein $X^1$ is CH, and $X^2$ is N.

12. The compound according to claim 1, wherein both of $X^1$ and $X^2$ are CH.

13. The compound according to claim 1, wherein $R^4$ is $C_{1-6}$ aliphatic or —OR.

14. The compound according to claim 13, wherein $R^4$ is ethyl or —OCH$_3$.

15. A pharmaceutically acceptable composition comprising the compound according to claim 1, and a pharmaceutically acceptable carrier, adjuvant, or vehicle.

16. The composition according to claim 15, in combination with an additional therapeutic agent.

17. A method of inhibiting PAD4 in a subject or in a biological sample comprising the step of contacting the PAD4 with a compound according to claim 1.

18. A method of treating a PAD4-mediated disease, disorder, or condition selected from the group consisting of acute lymphocytic leukemia, ankylosing spondylitis, cancer, chronic lymphocytic leukemia, colitis, lupus, rheumatoid arthritis, multiple sclerosis, and ulcerative colitis, in a subject having a PAD4-mediated disease, disorder, or condition, comprising the step of administering to said subject the composition according to claim 15.

19. The method according to claim 18, wherein the PAD4-mediated disease, disorder, or condition is selected from rheumatoid arthritis, systemic lupus erythematosus, cutaneous lupus erythematosis, ulcerative colitis, and cancer.

20. A compound selected from

I-10
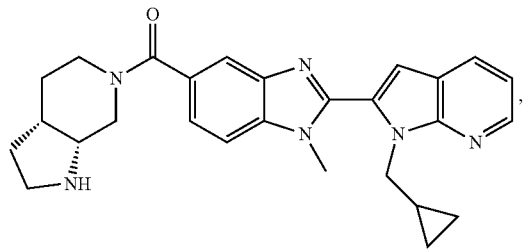
I-11
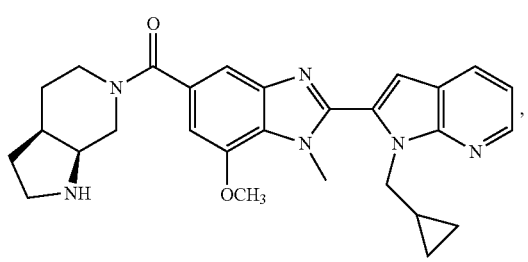
I-12
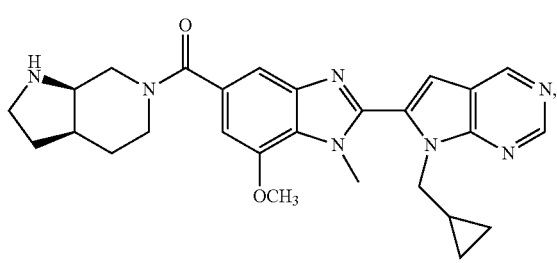
I-13
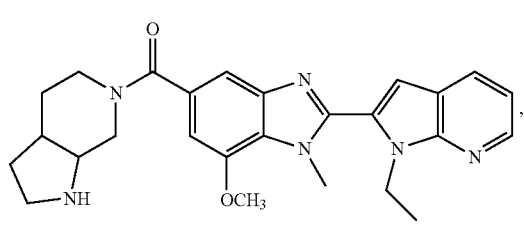
I-14
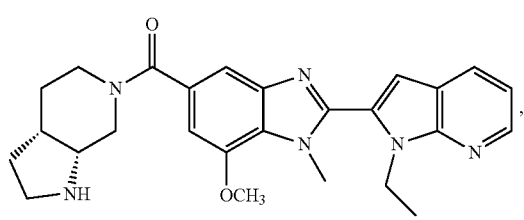
I-15
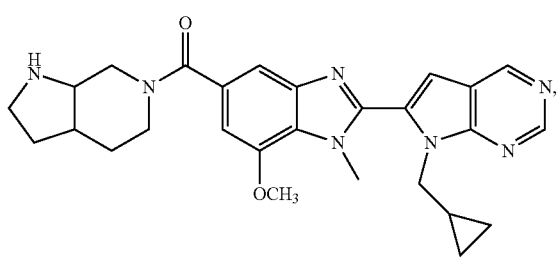
I-16
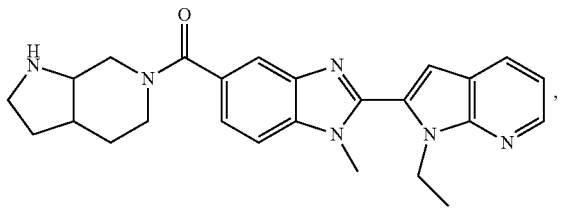
I-17
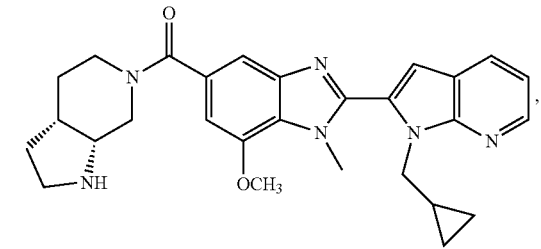
I-18
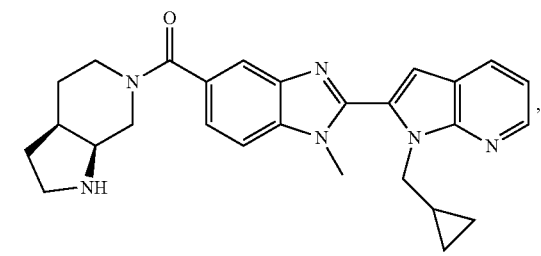
I-19
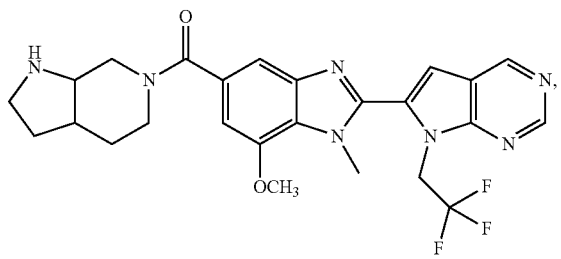
I-20
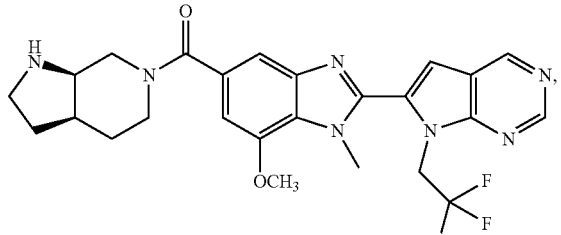
I-21
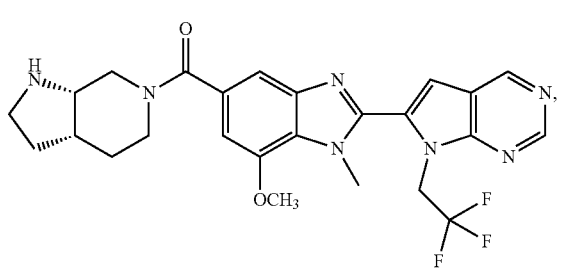

I-22
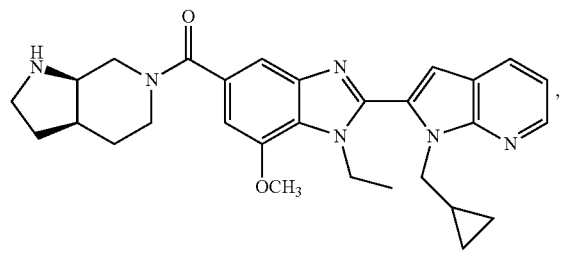
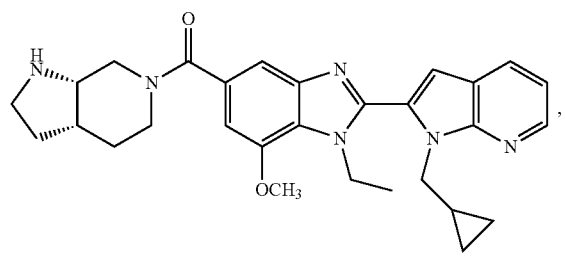
I-24
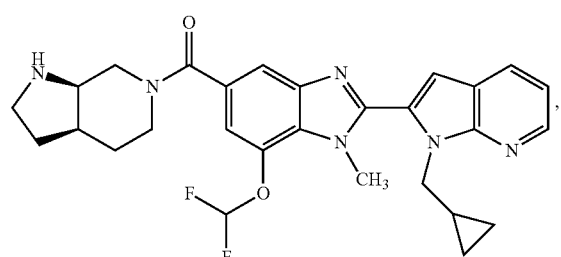
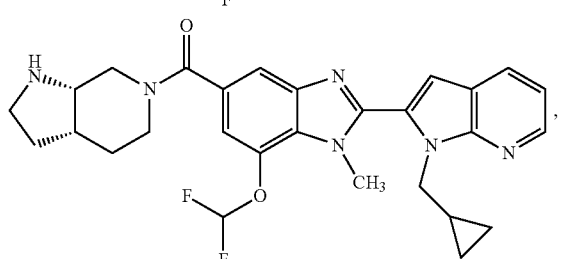
I-26
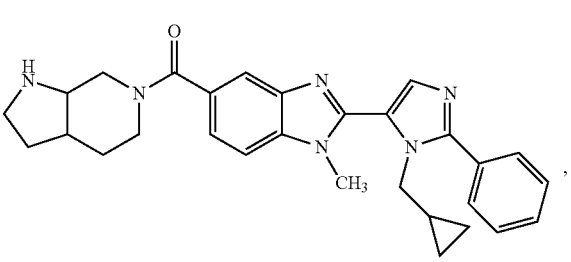
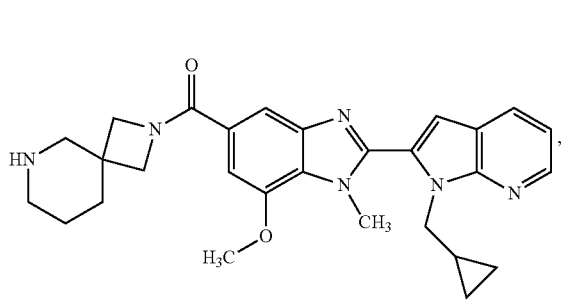
I-28
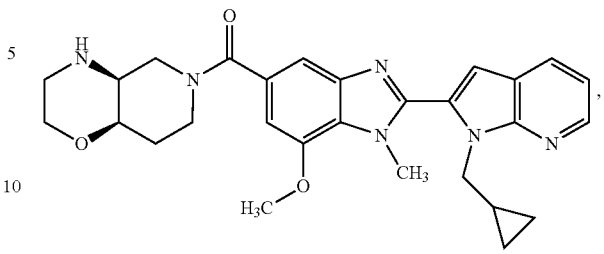
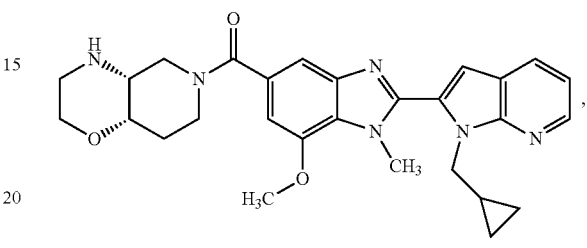
I-30
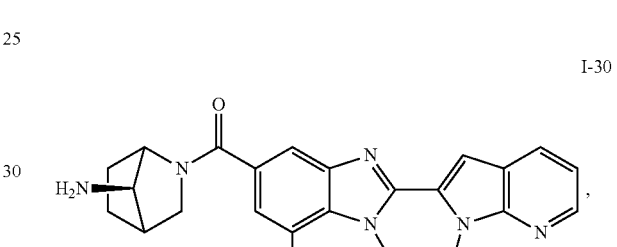
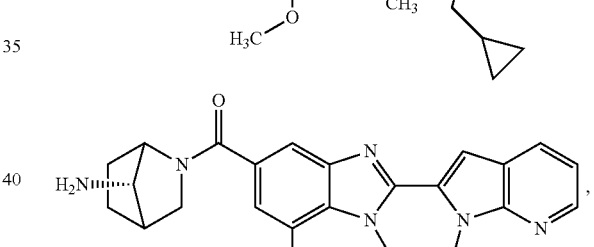
I-32
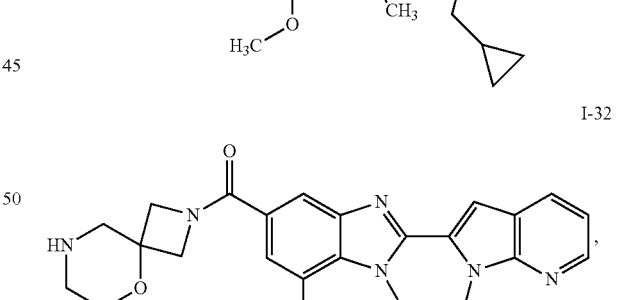
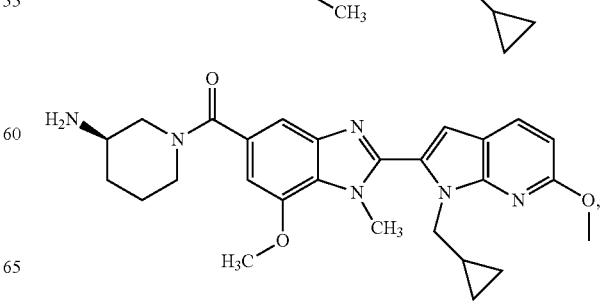

-continued
I-34
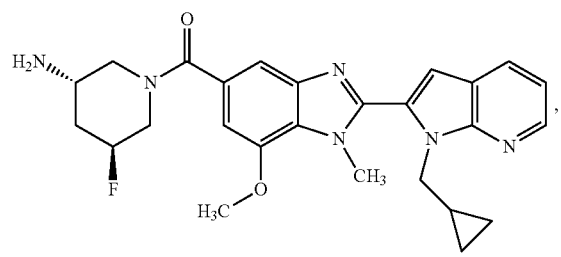
I-35
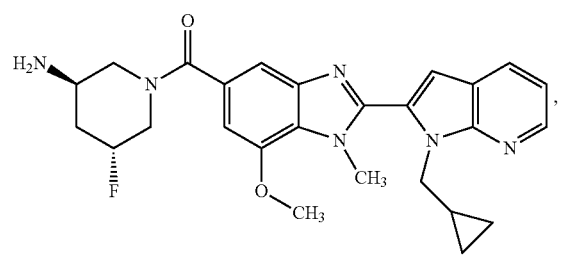
I-36
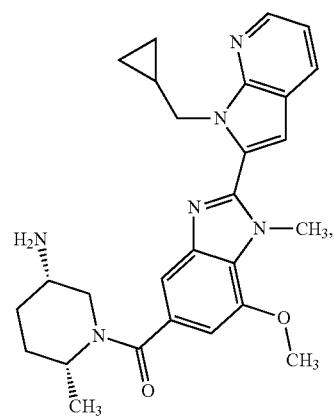
I-37
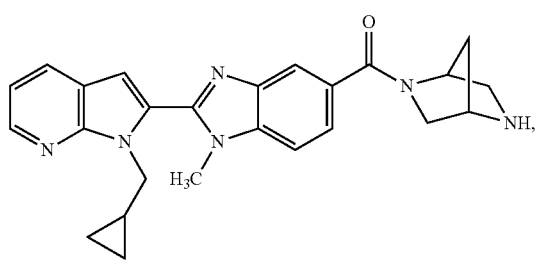
I-38
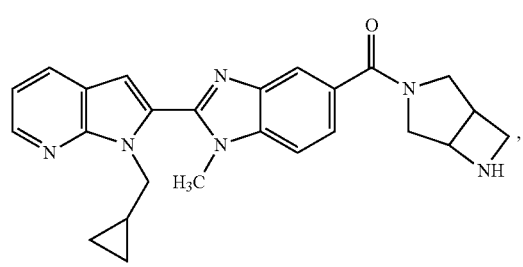
-continued
I-39
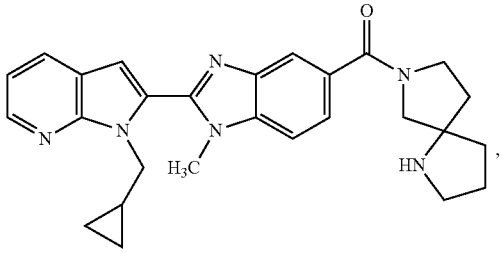
I-40
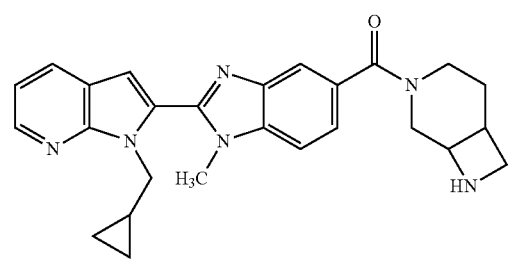
I-41
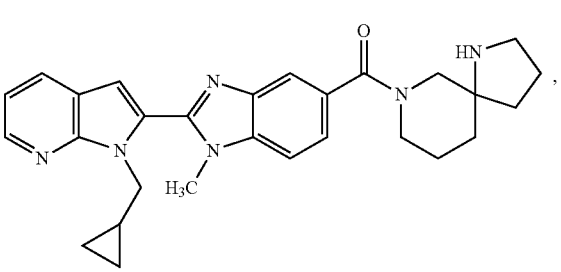
I-42
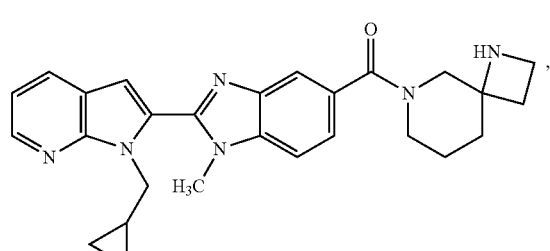
I-44
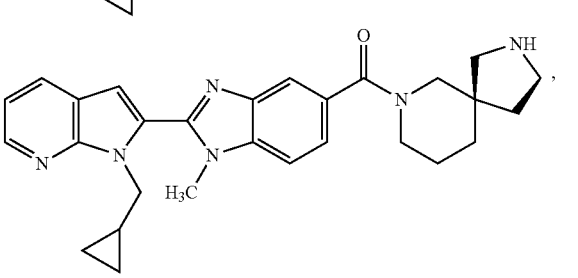

I-45
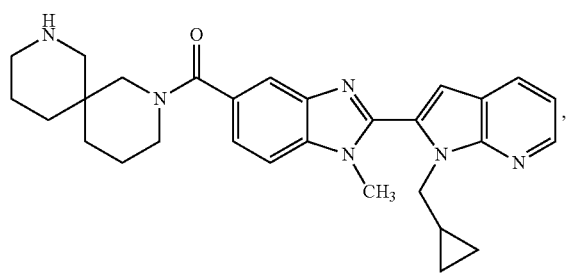
I-46
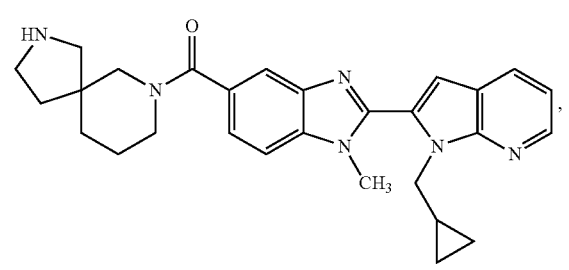
I-47
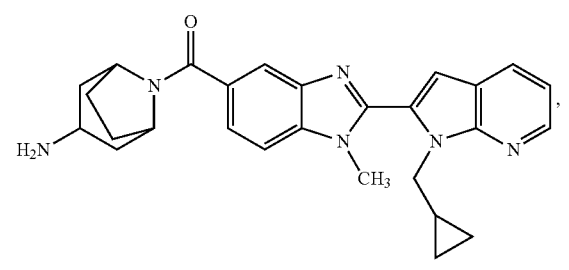
I-48
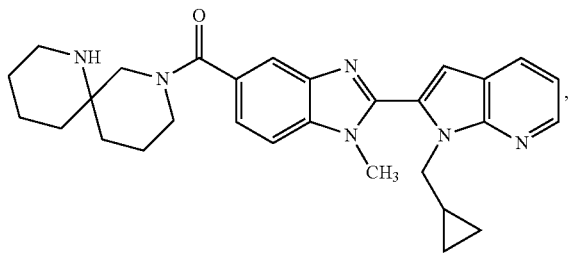
I-49
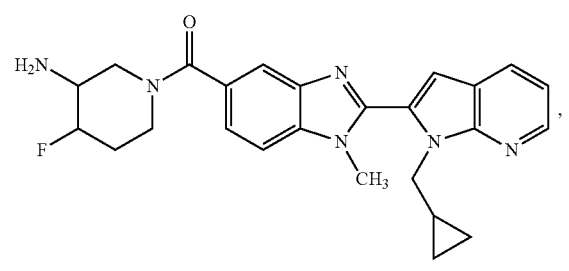
I-50
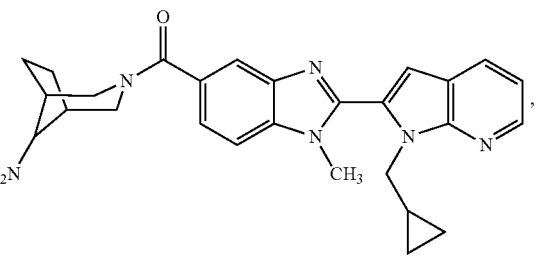
I-51
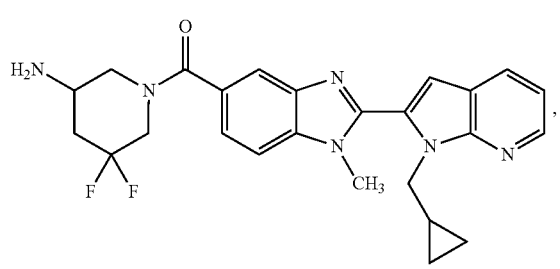
I-52
I-54

I-55
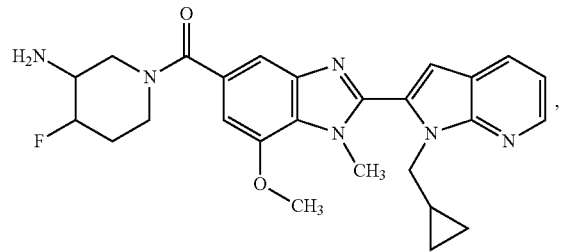
I-58
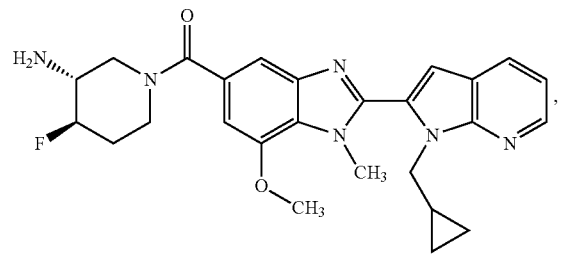
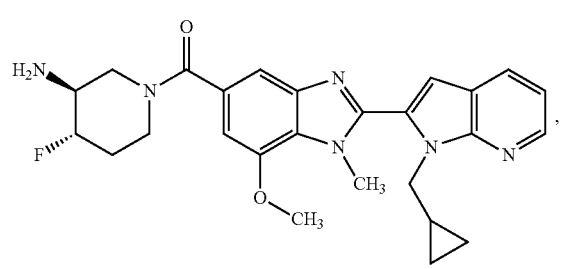
I-60
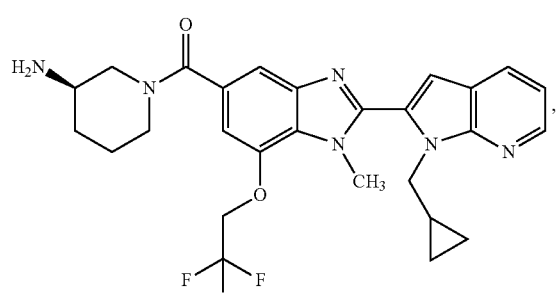
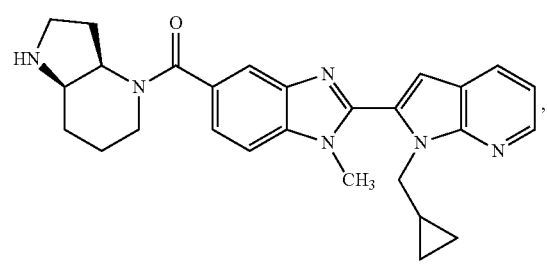
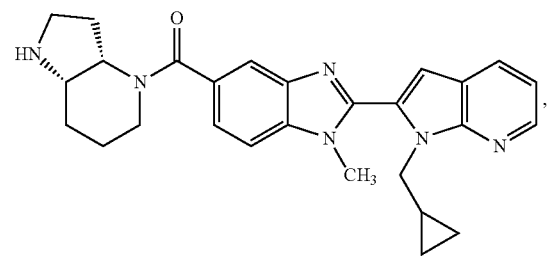
I-62
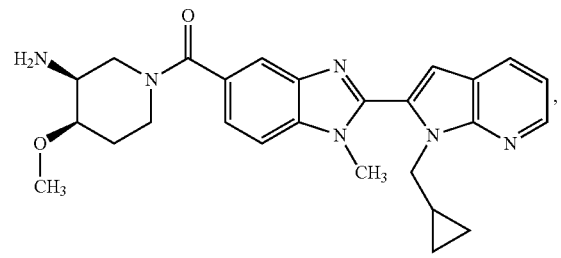
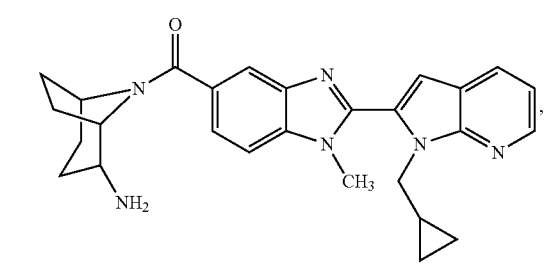
I-64
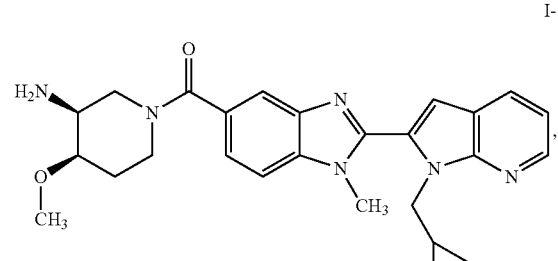
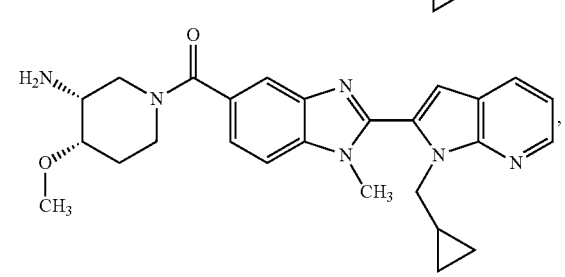
I-66
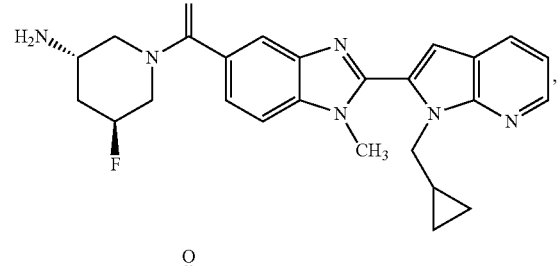
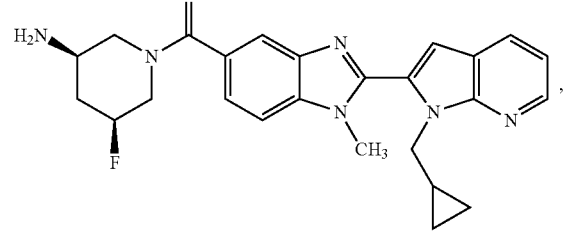

I-68
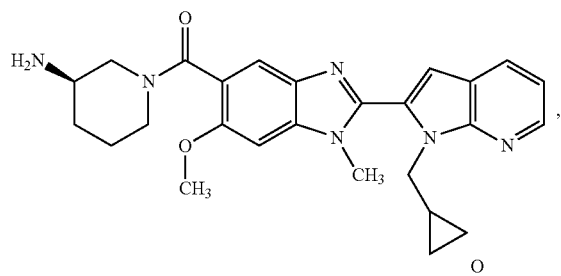
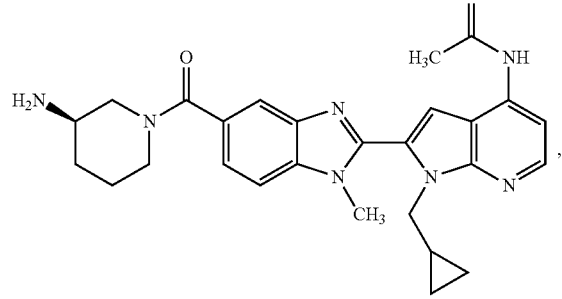
I-70
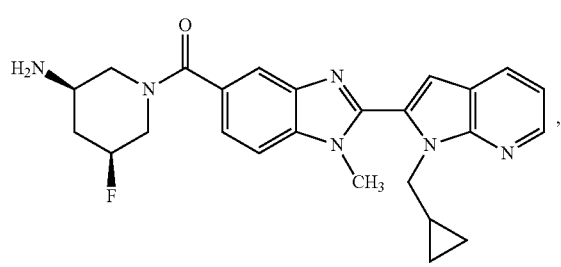
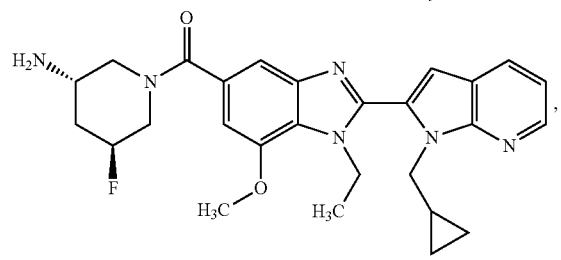
I-72
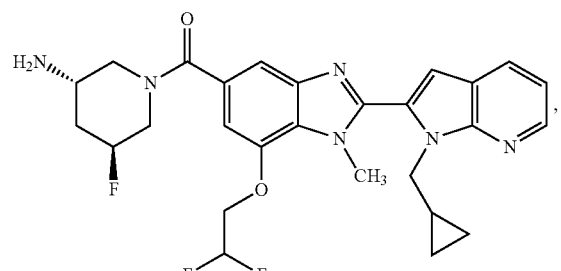
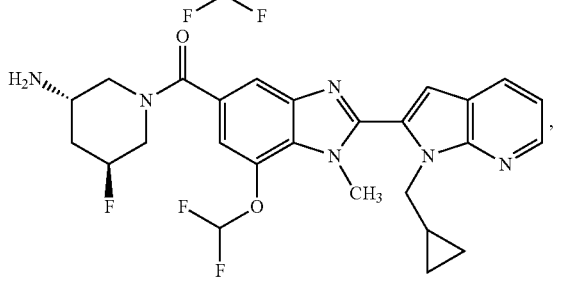
I-74
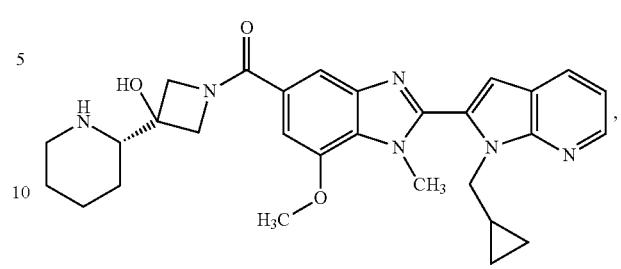
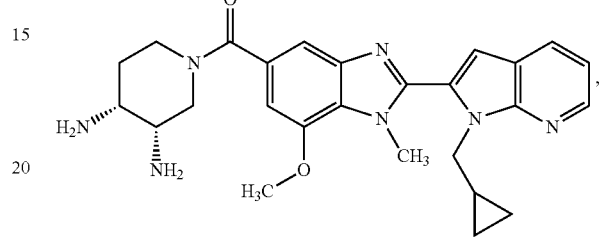
I-76
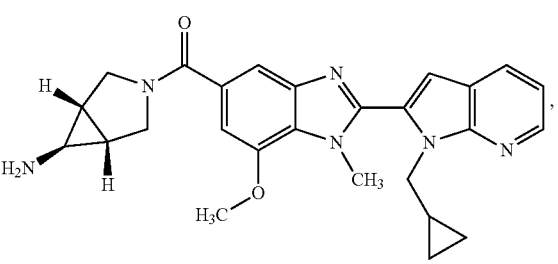
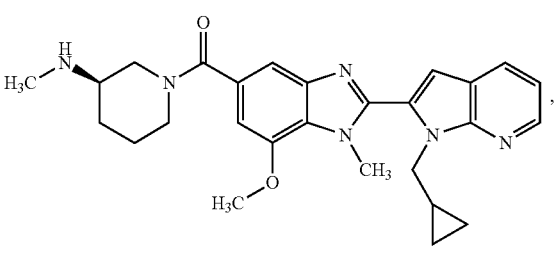
I-80
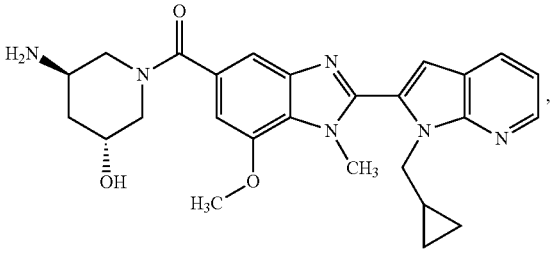
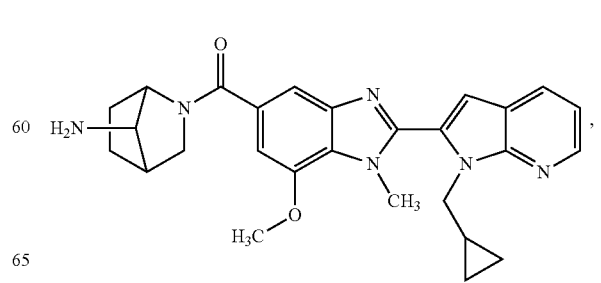

I-82
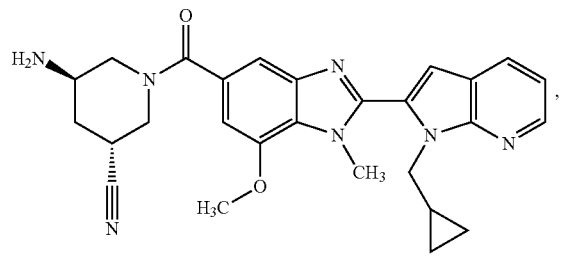
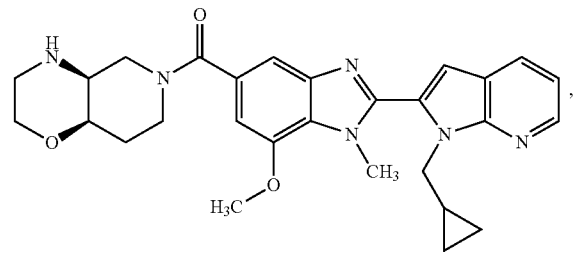
I-83
I-86
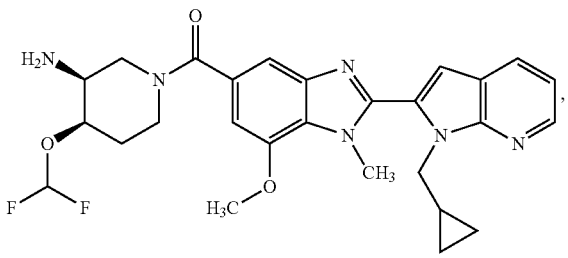
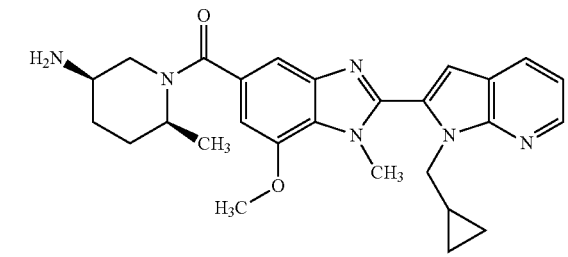
I-88
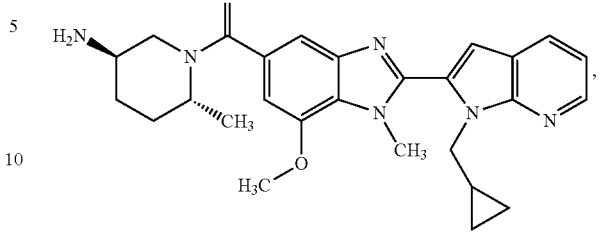
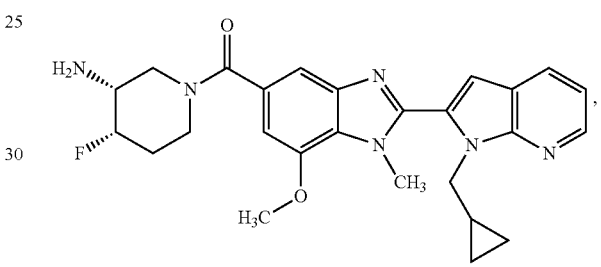
I-90
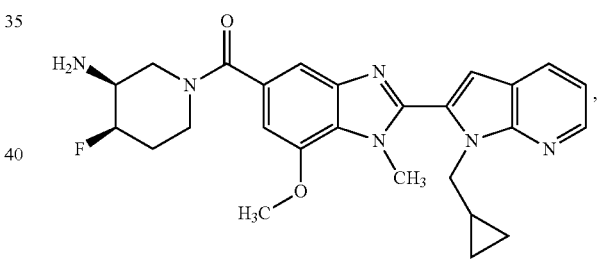
I-92
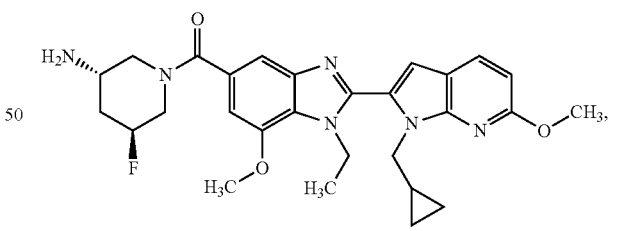
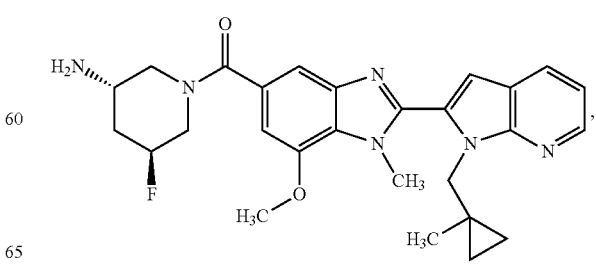

I-94
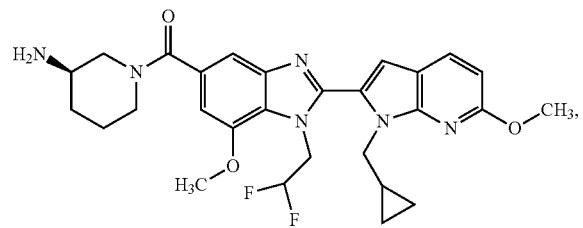
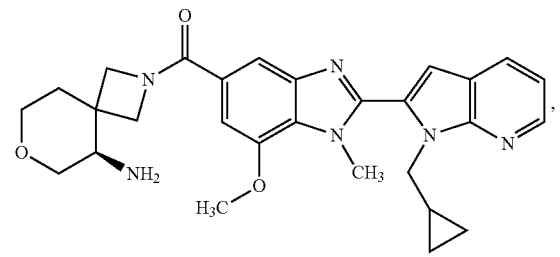
I-96
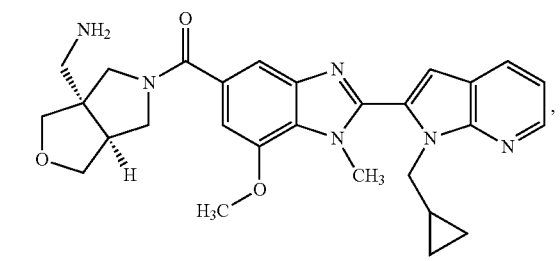
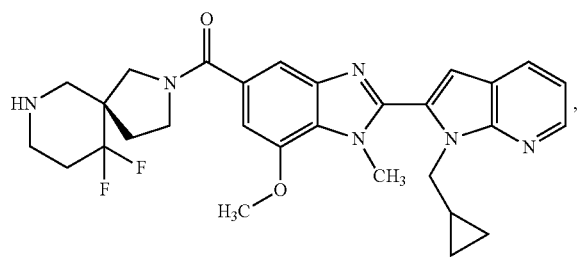
I-98
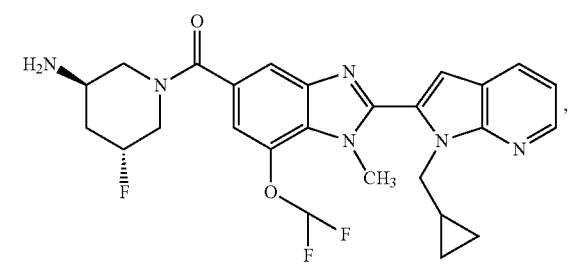
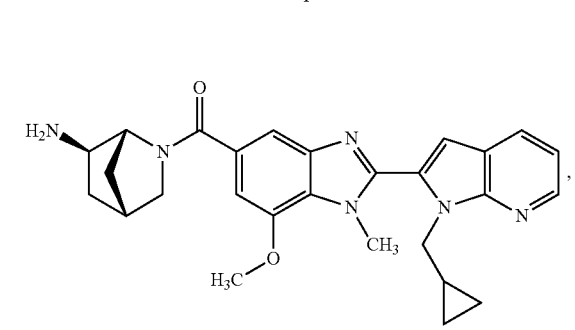
I-99
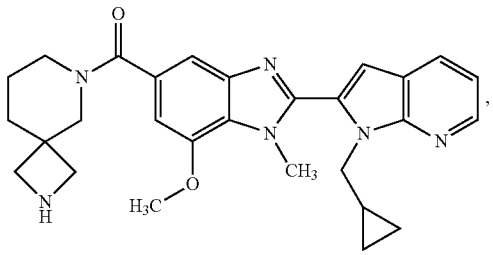
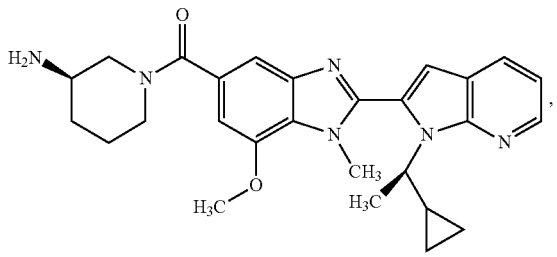
I-102
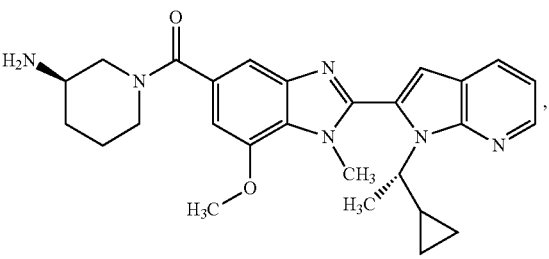
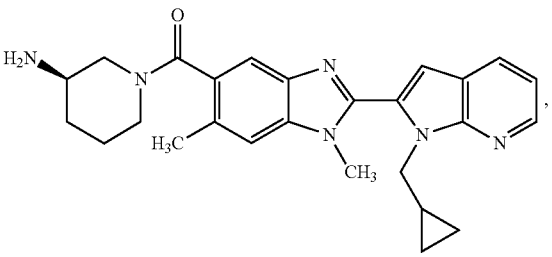
I-104
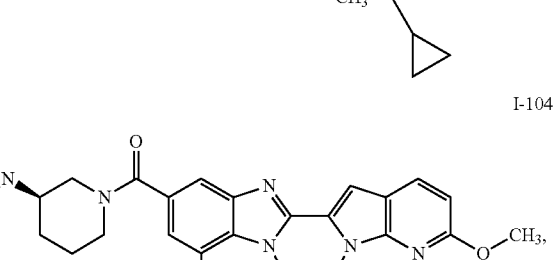
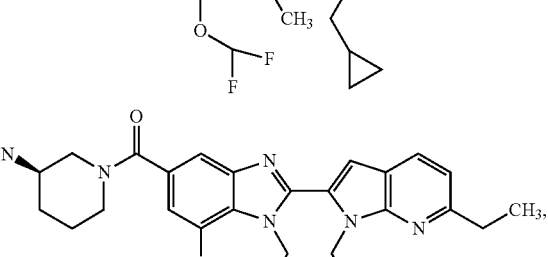

I-106
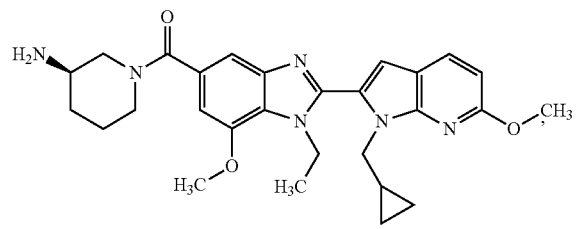
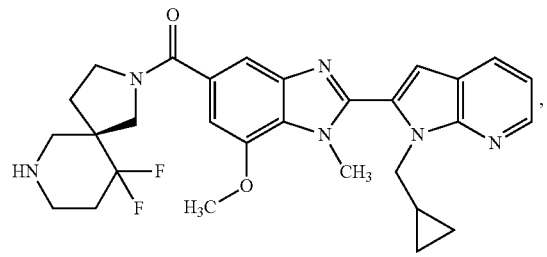
I-108
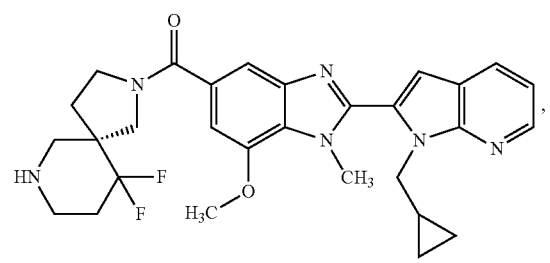
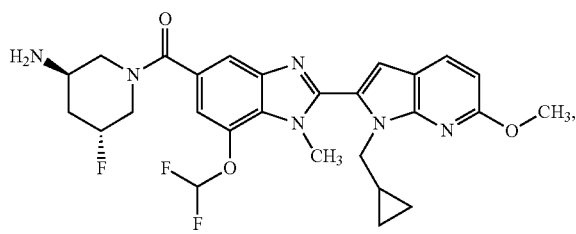
I-110
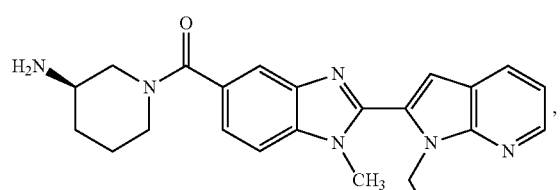
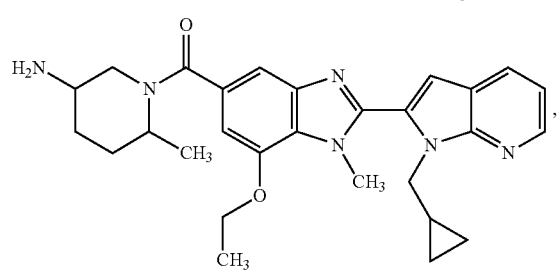
I-111
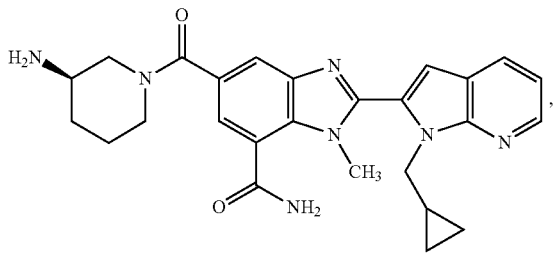
I-113
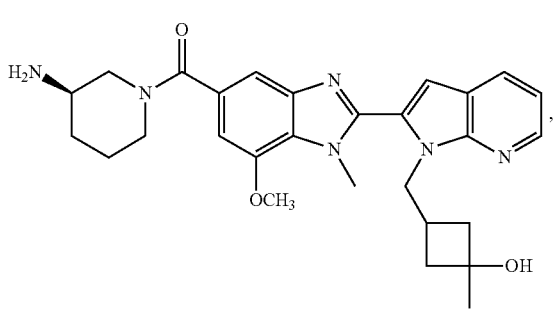
I-114
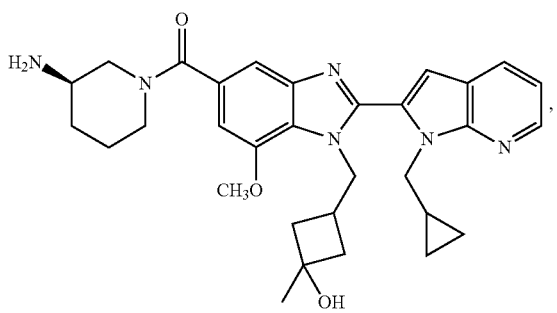
I-115
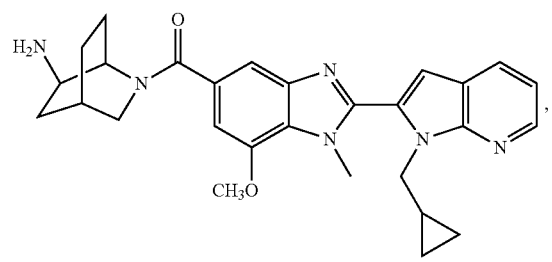
I-116

I-117
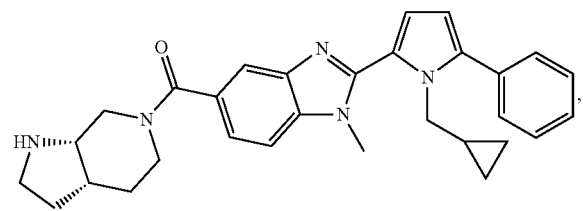
I-119
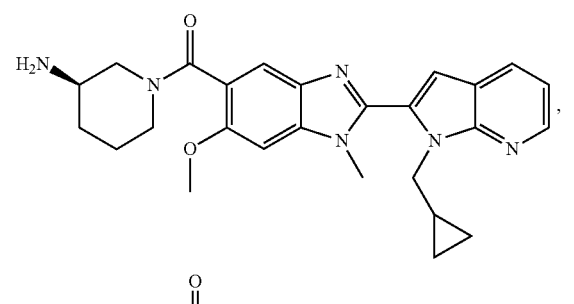
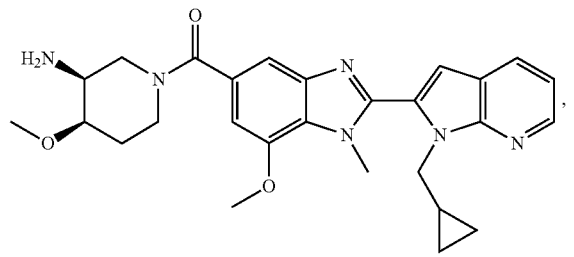
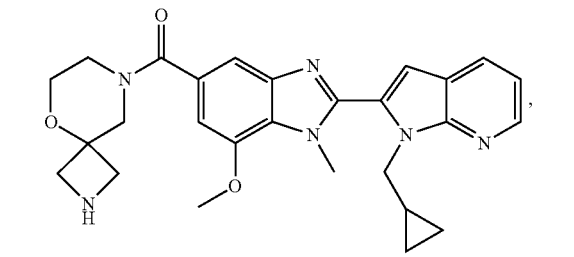
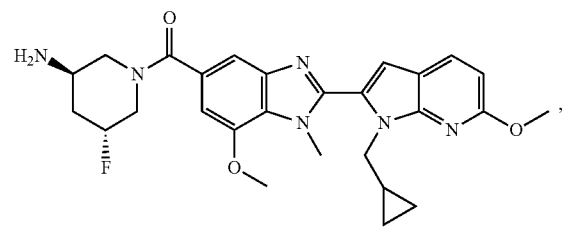
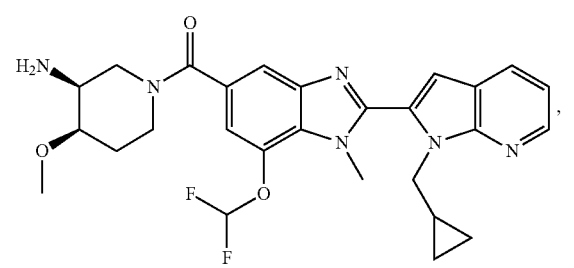
I-125
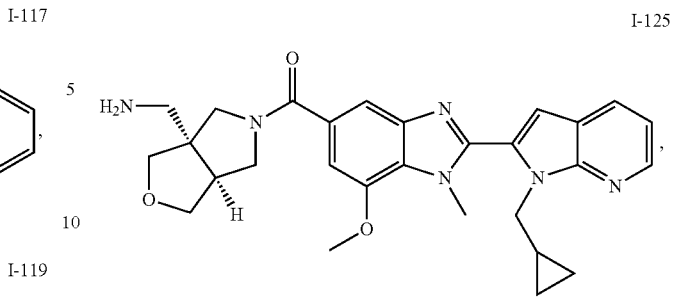
I-126
I-129
I-130

-continued

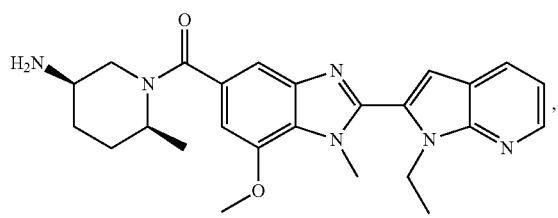
I-145
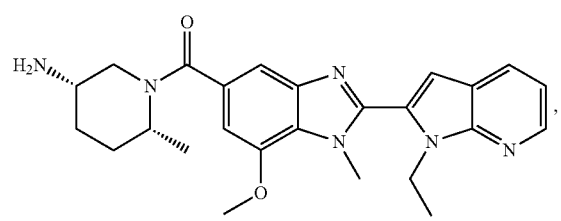
I-146
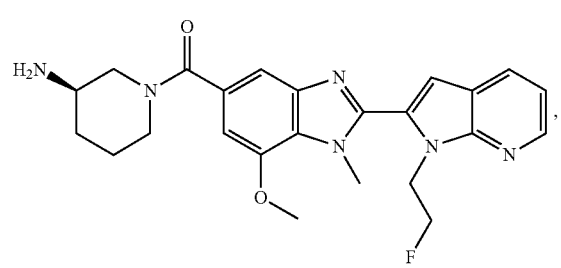
I-148
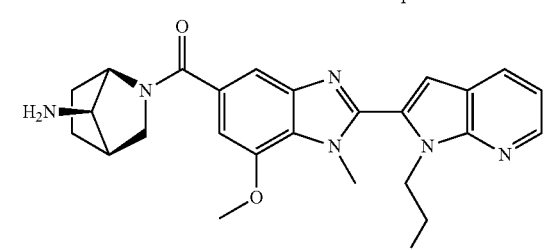
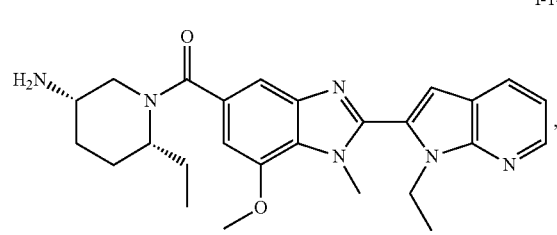
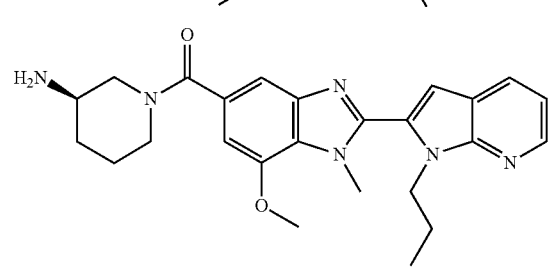
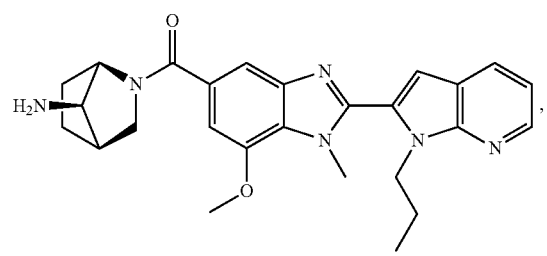
I-151
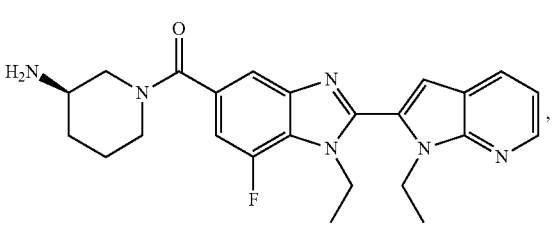
I-152
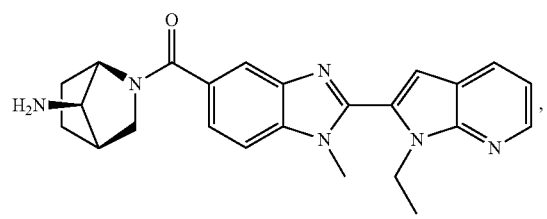
I-153
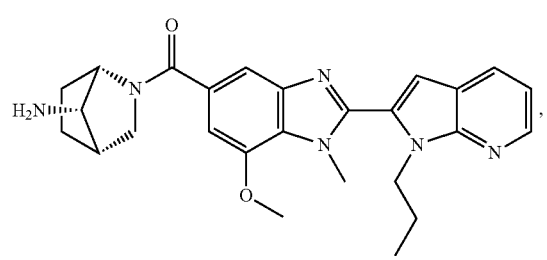
I-154
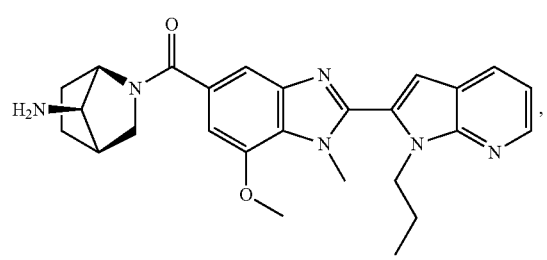
I-155
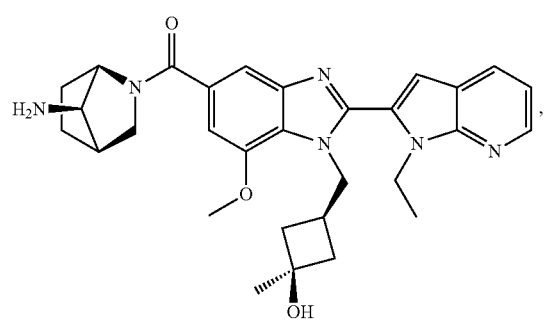

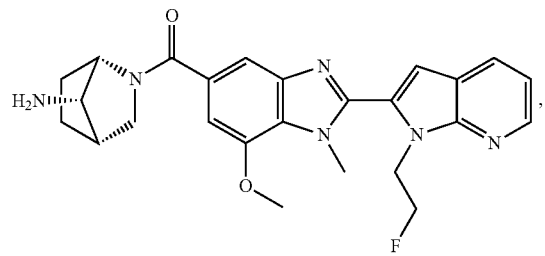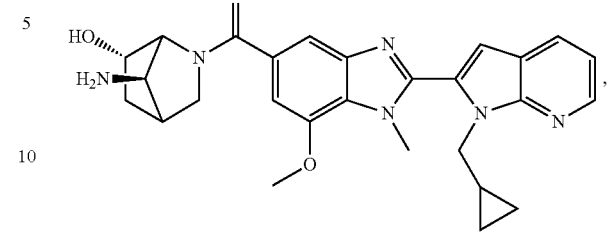

I-167
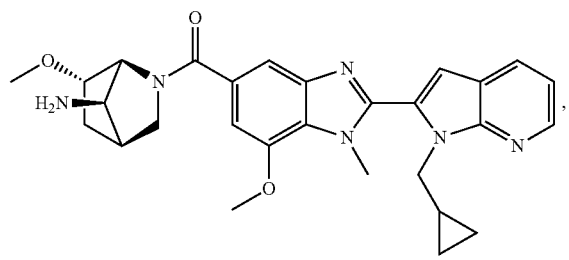
I-168
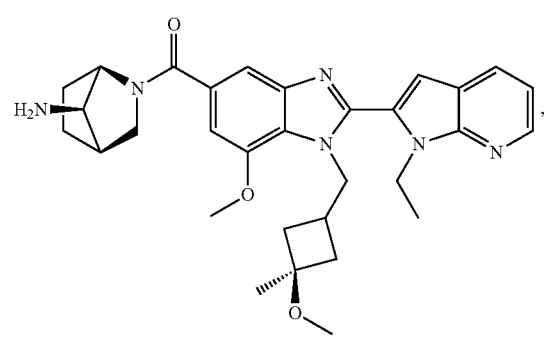
I-169
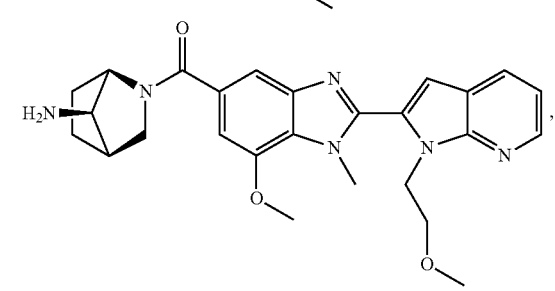
I-170
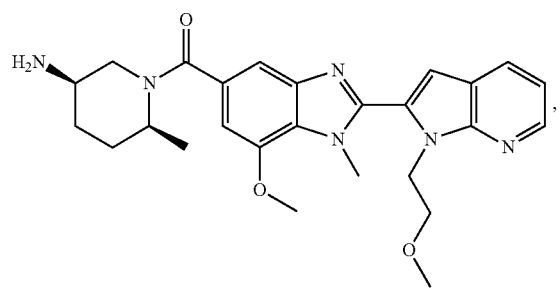
I-171
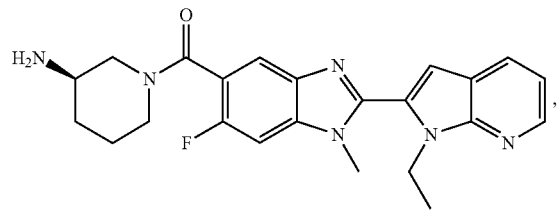
I-172
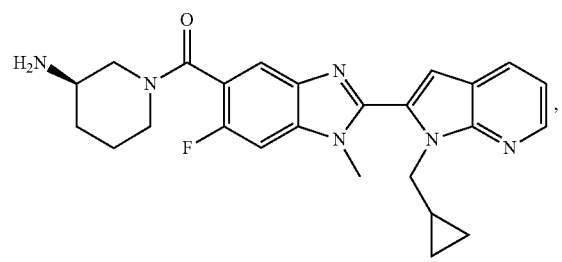
I-173
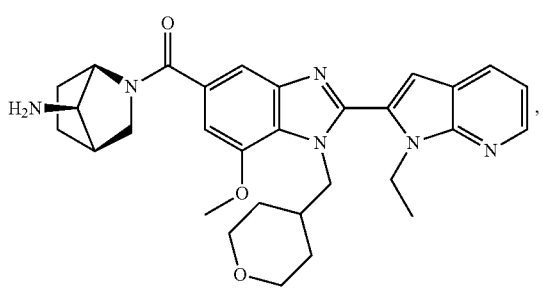
I-174
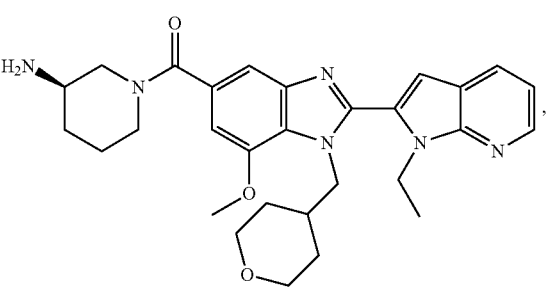
I-175
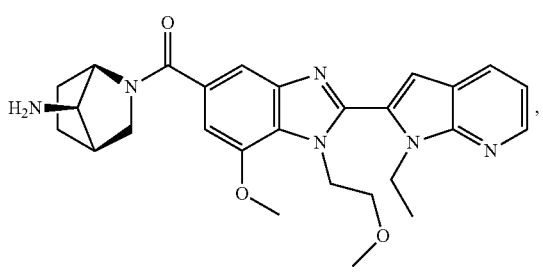
I-176
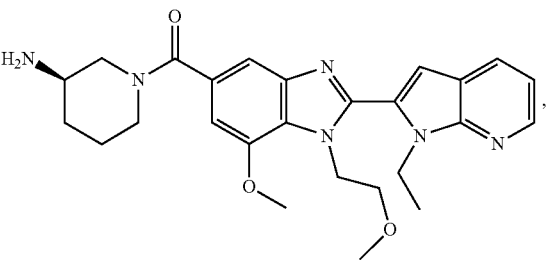

-continued
I-177
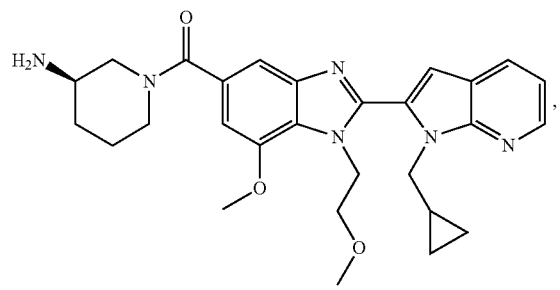
I-178
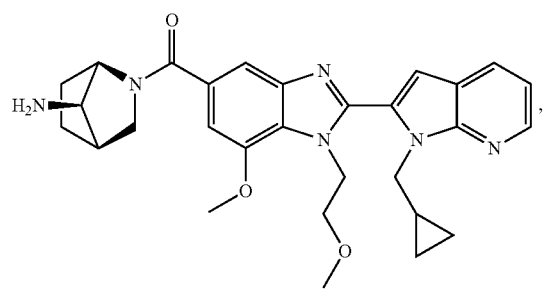
I-179
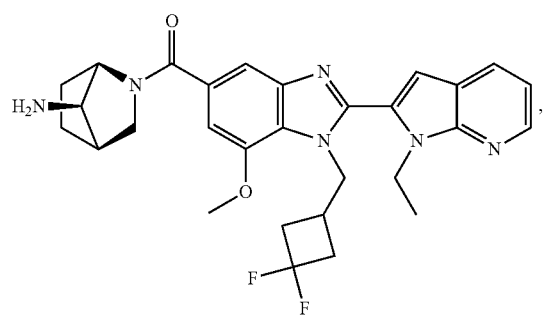
I-180
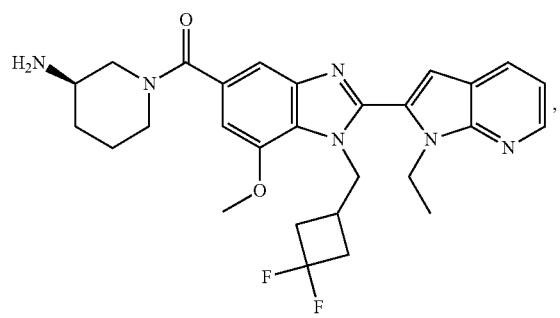
I-181
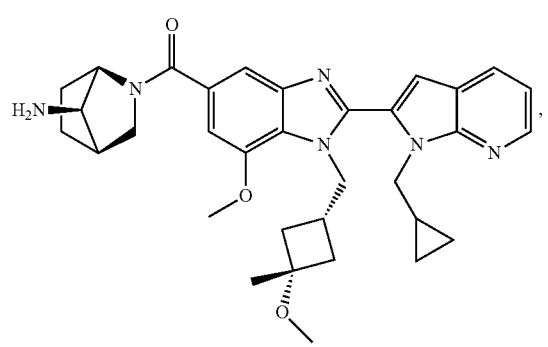
-continued
I-182
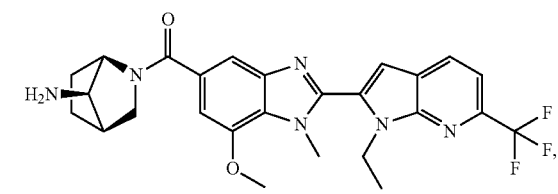
I-183
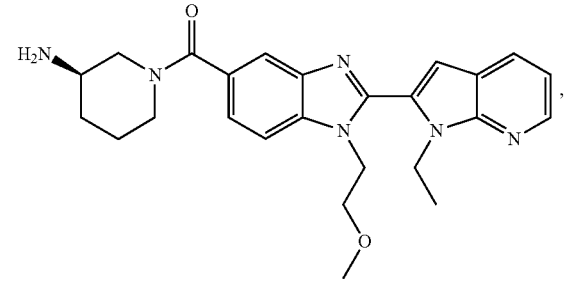
I-184
I-185
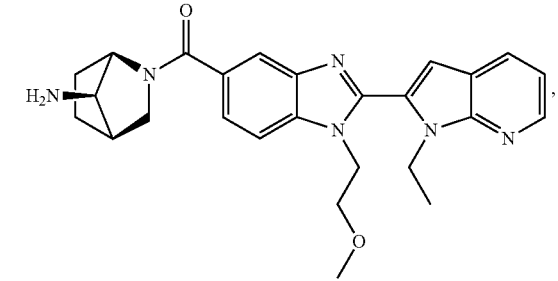
I-186

I-187
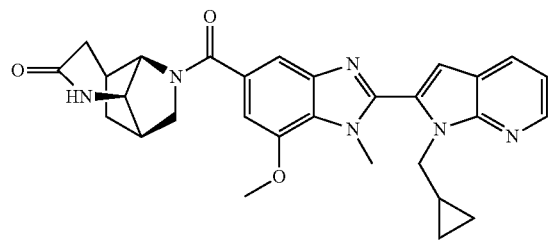
I-188
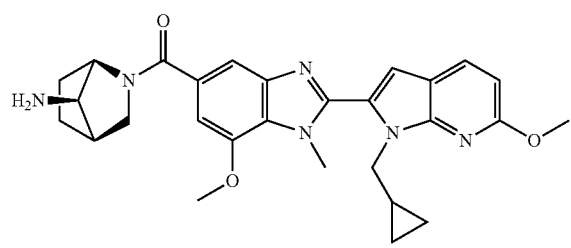
I-189
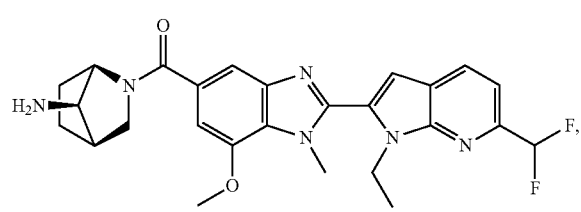
I-190
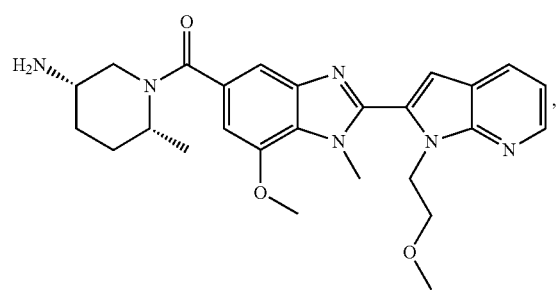
I-191
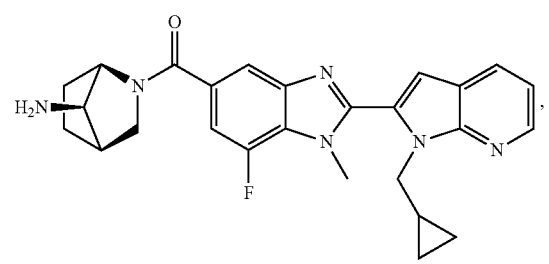
I-192
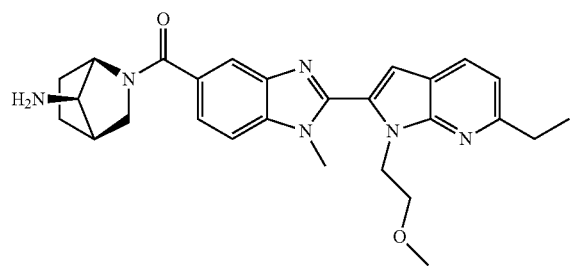
I-193
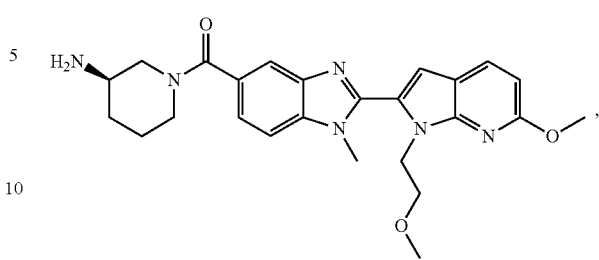
I-194
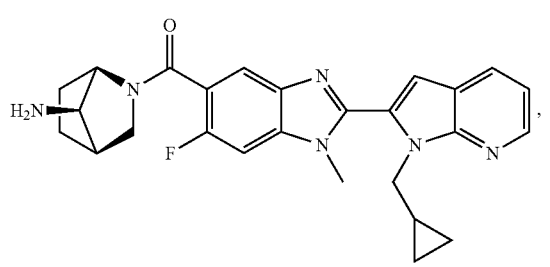
I-195
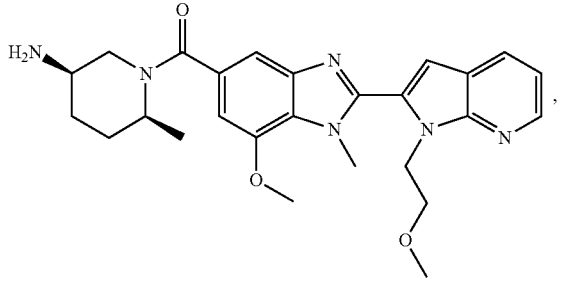
I-196
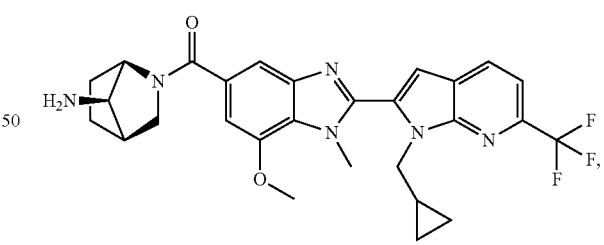
I-197
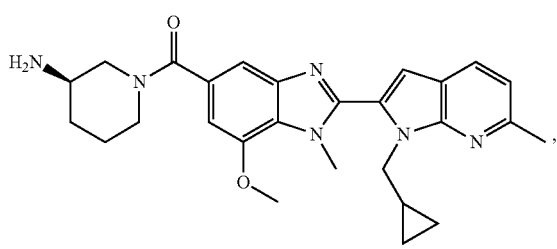

I-198
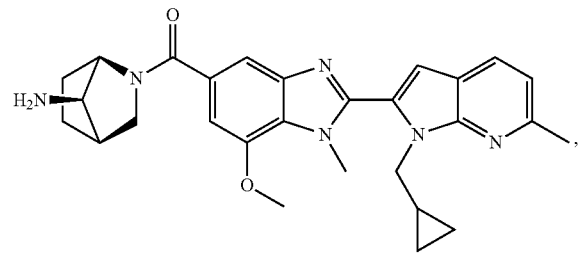
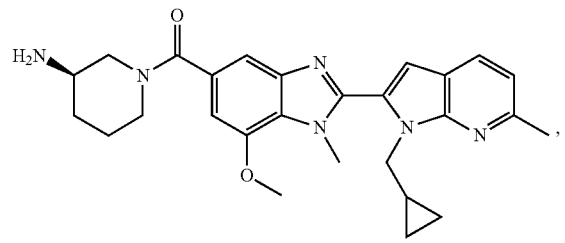
I-201
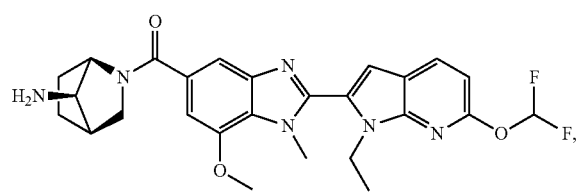
I-202
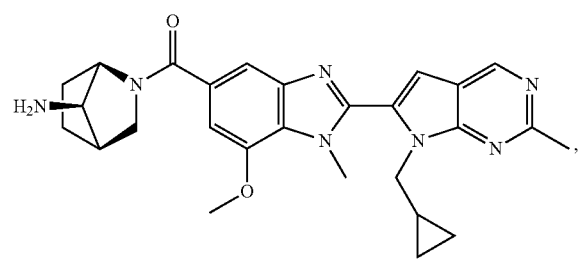
I-203
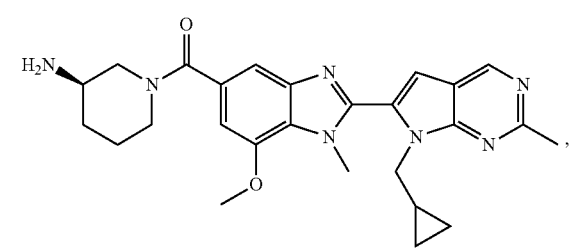
I-204
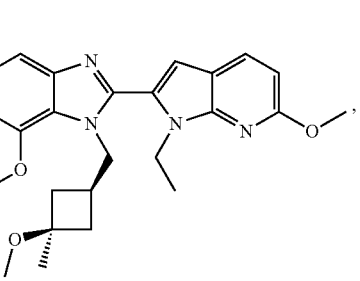
I-205
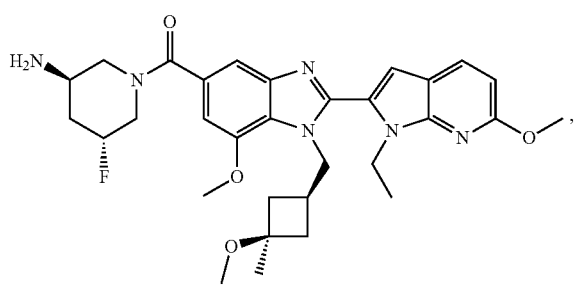
I-206
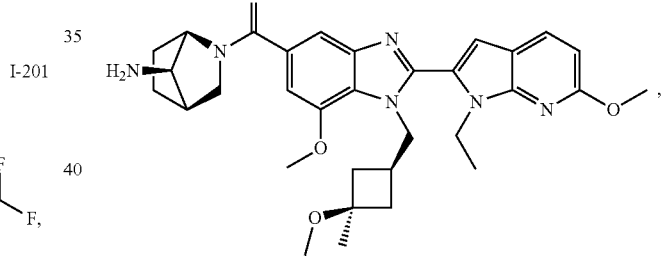
I-207
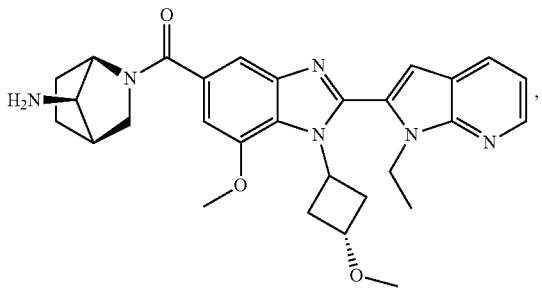
I-208

-continued
I-209
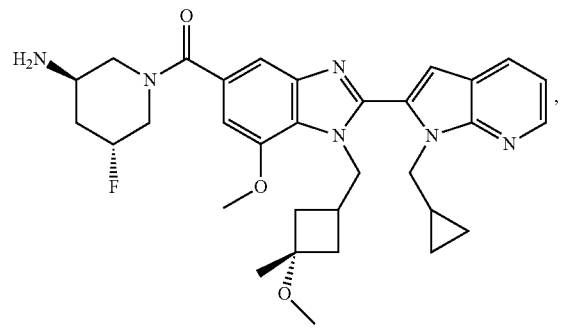
I-210
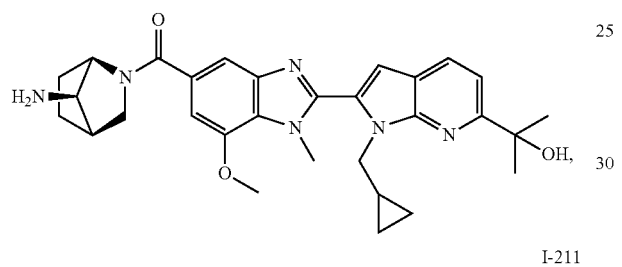
I-211
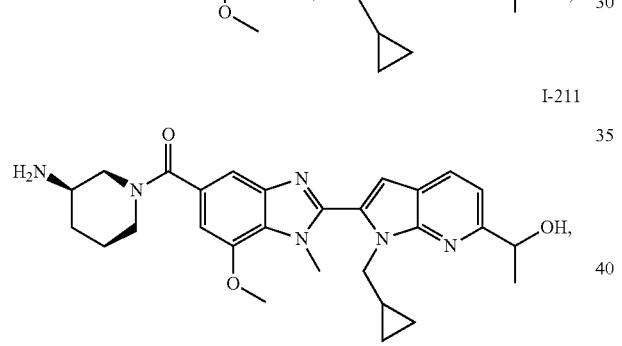
I-212
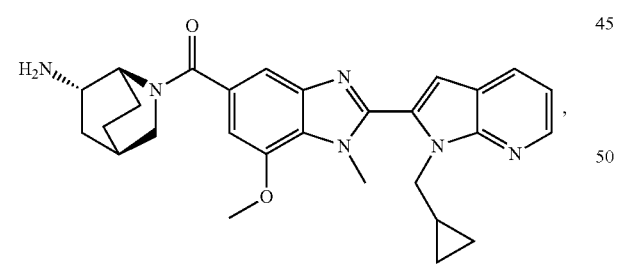
I-213
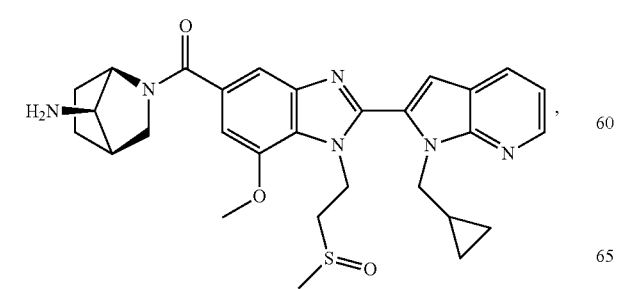
-continued
I-214
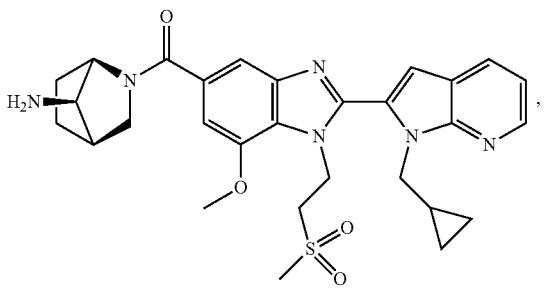
I-215
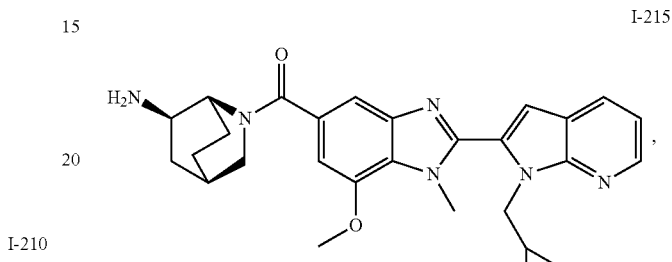
I-216
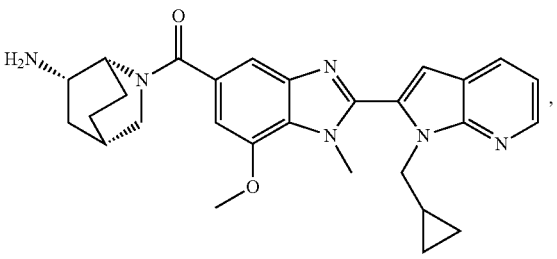
I-217
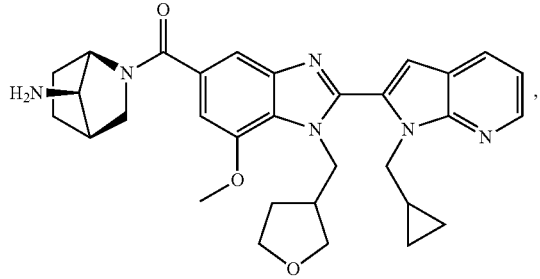
I-218
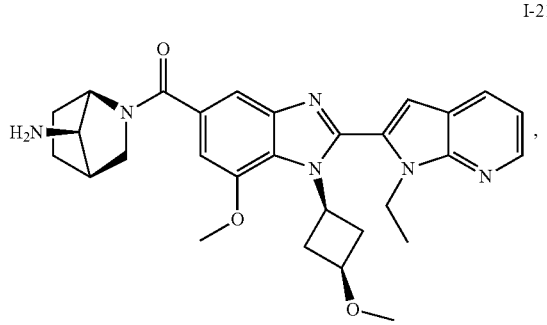

581
-continued
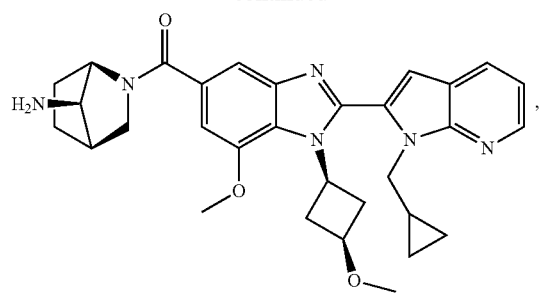
I-220
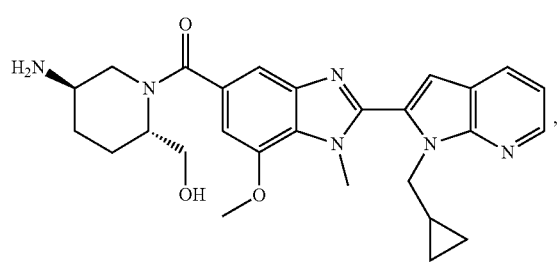
I-221
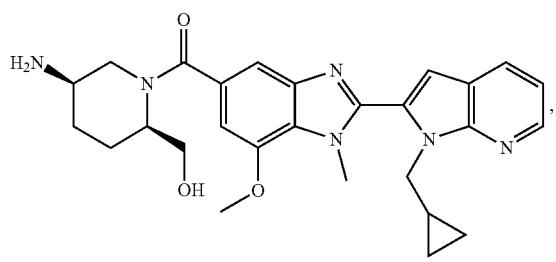
I-222
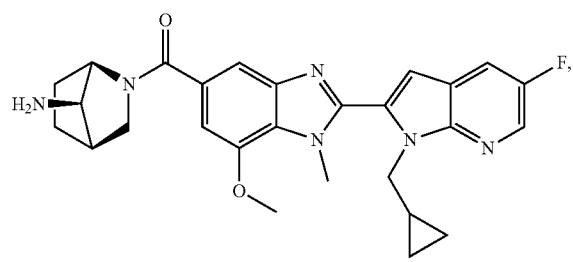
I-223
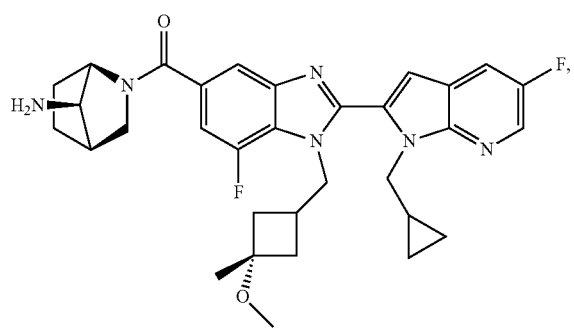
582
-continued
I-224
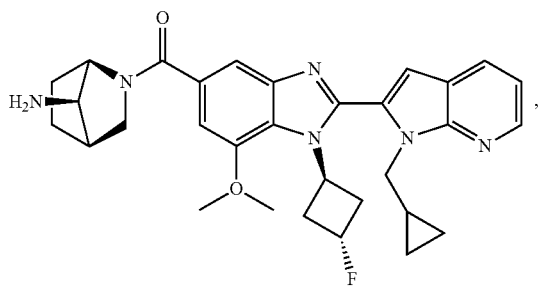
I-225
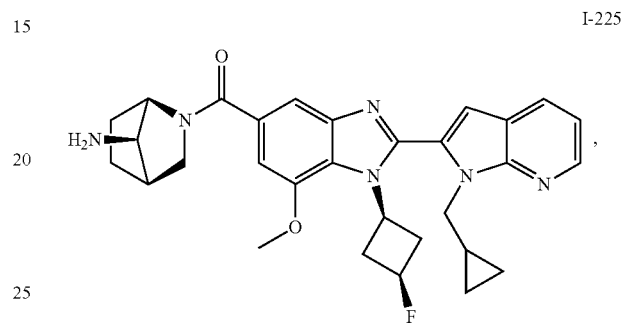
I-226
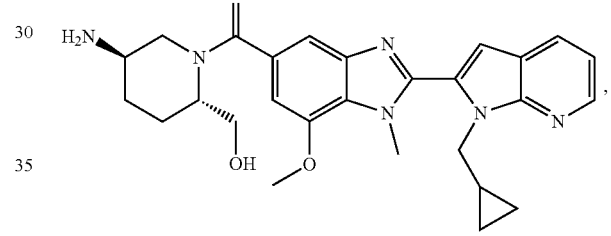
I-227
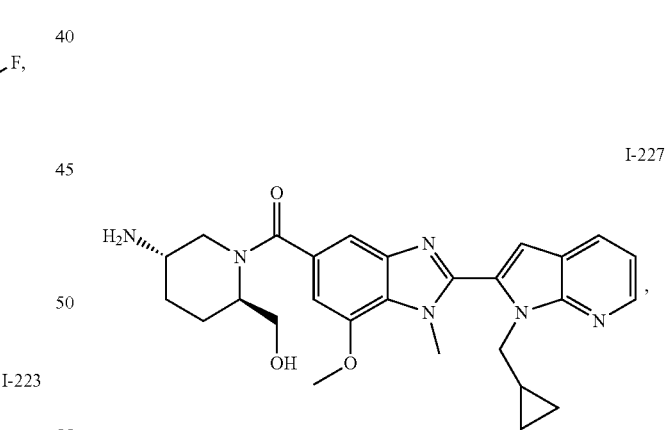
I-228
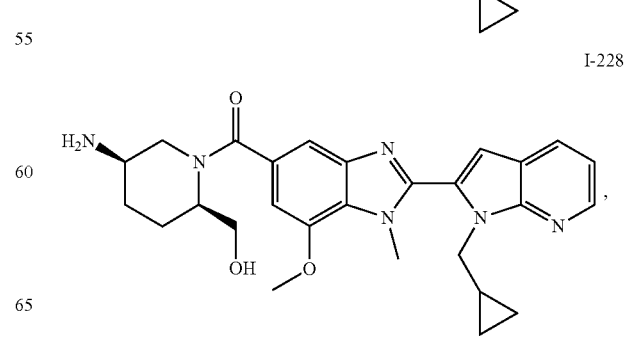

I-229
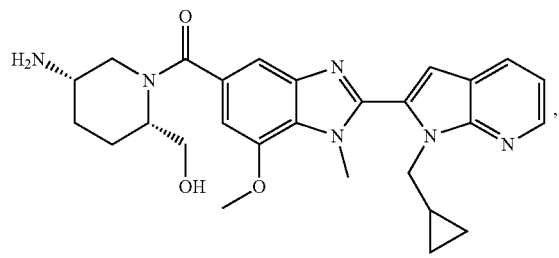
I-234
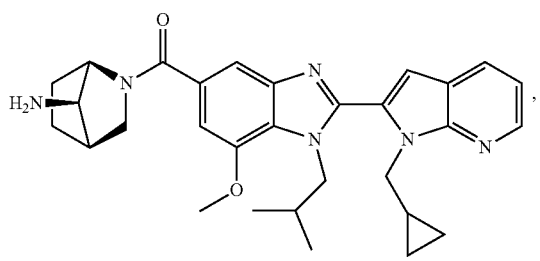
I-230
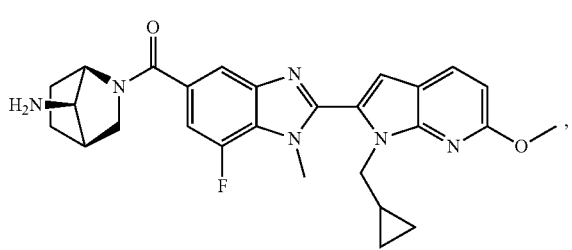
I-235
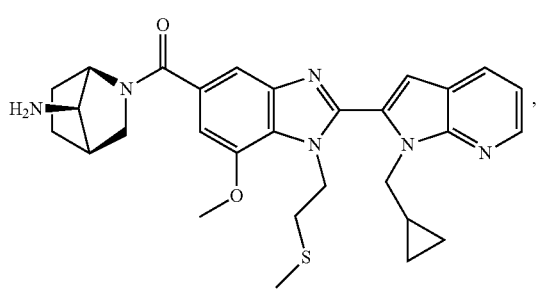
I-231
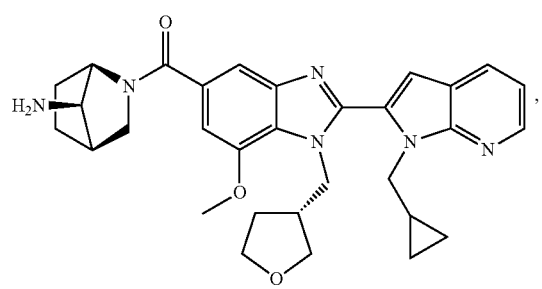
I-236
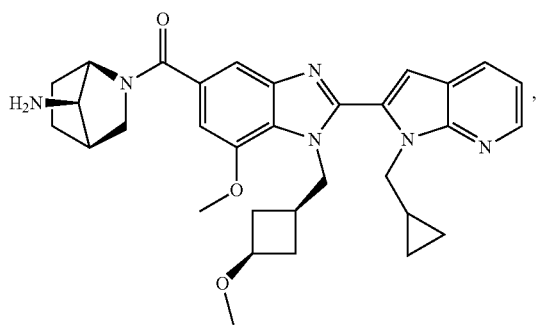
I-232
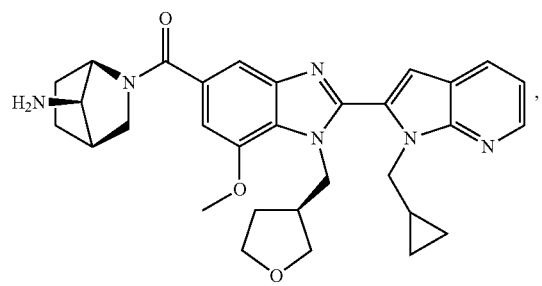
I-237
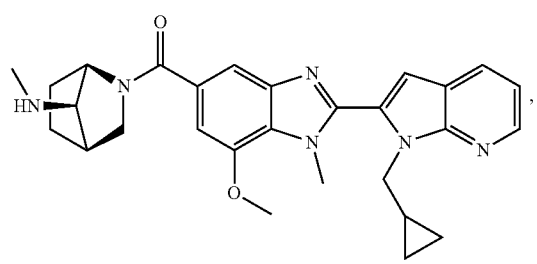
I-233
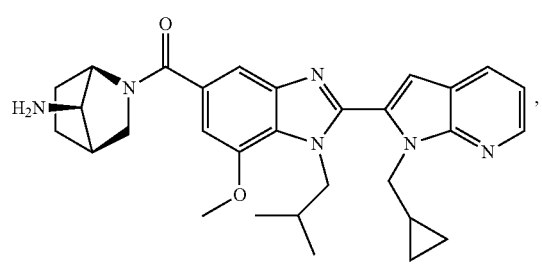
I-238
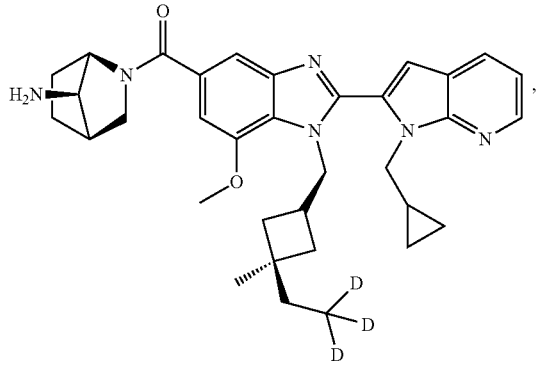

I-239
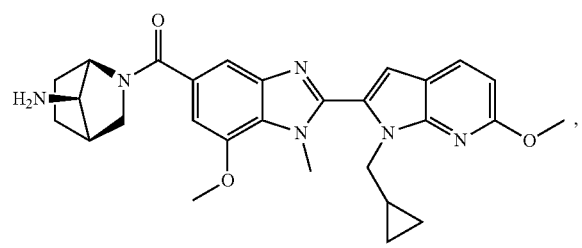
I-240
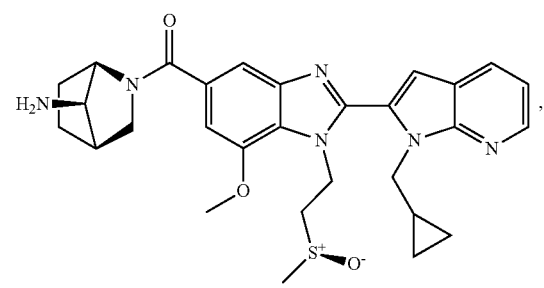
I-241
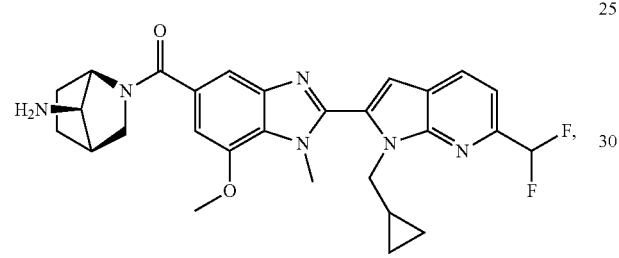
I-242
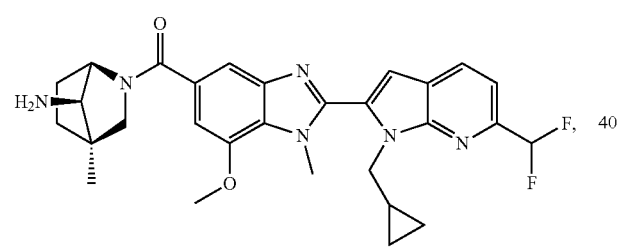
I-243
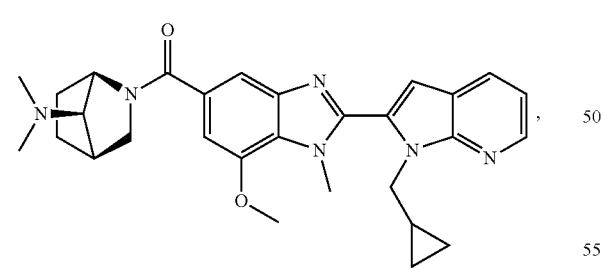
I-244
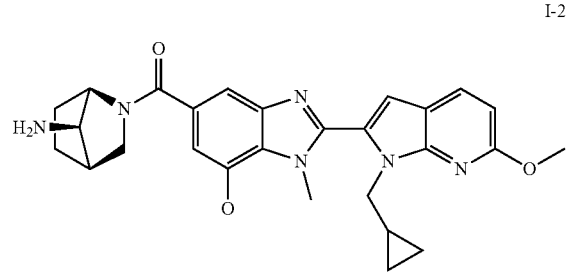
I-245
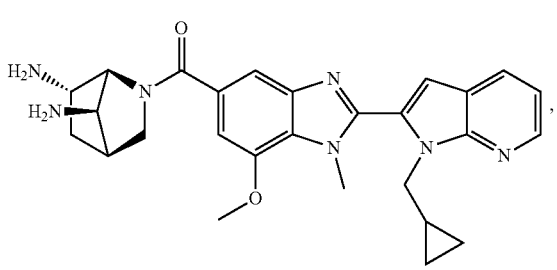
I-246
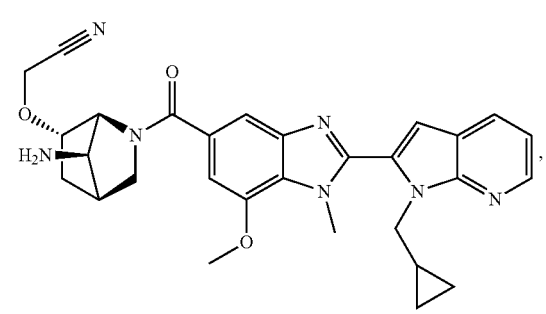
I-247
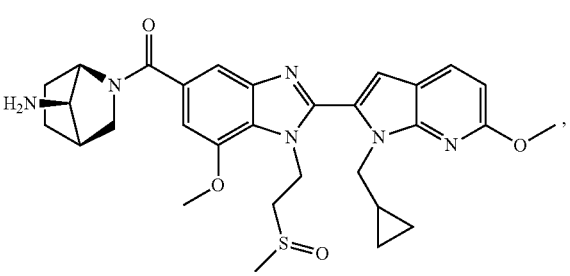
I-248
I-249
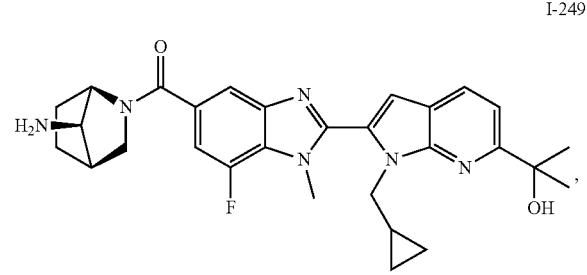

I-250
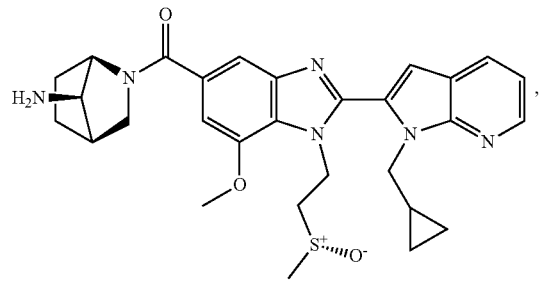
I-251
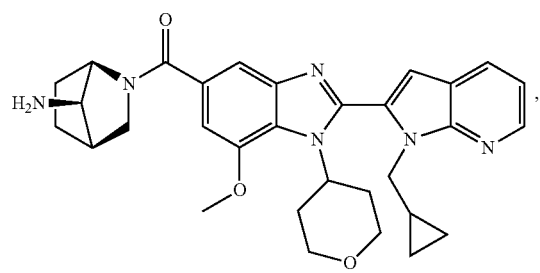
I-252
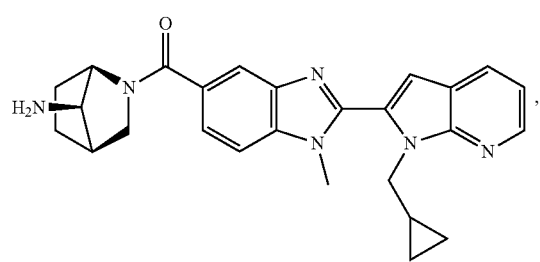
I-253
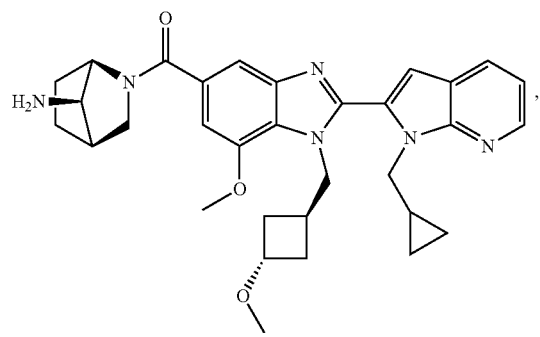
I-254
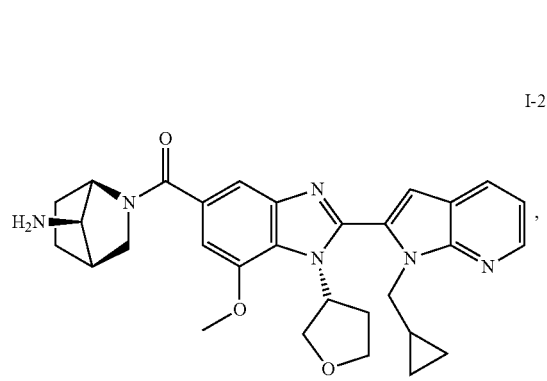
I-255
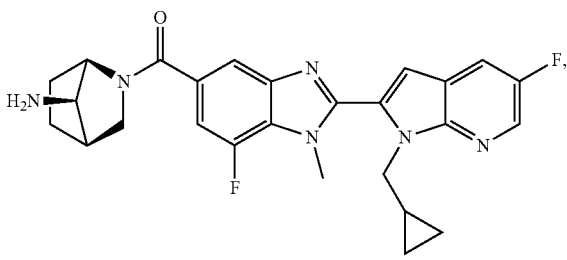
I-256
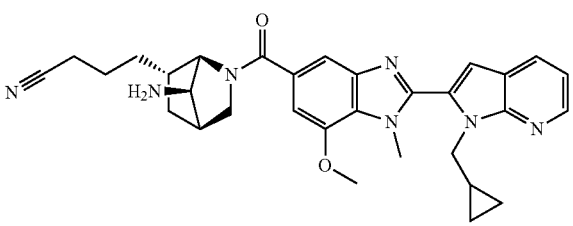
I-257
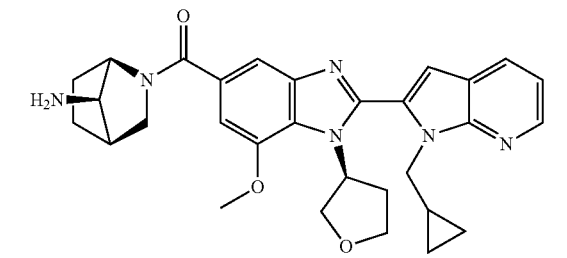
I-258
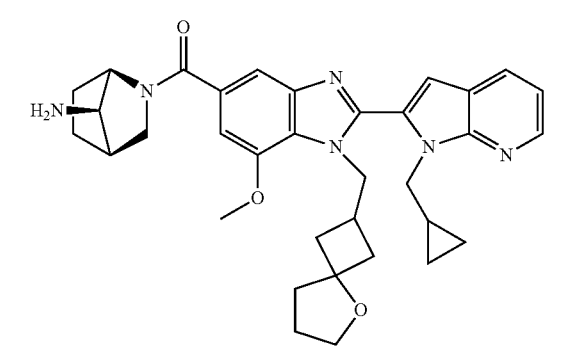
I-259
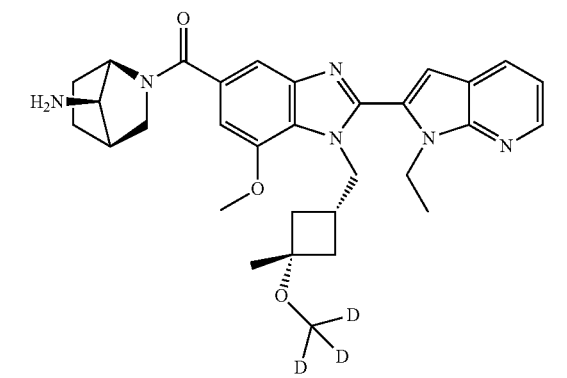

-continued
I-260
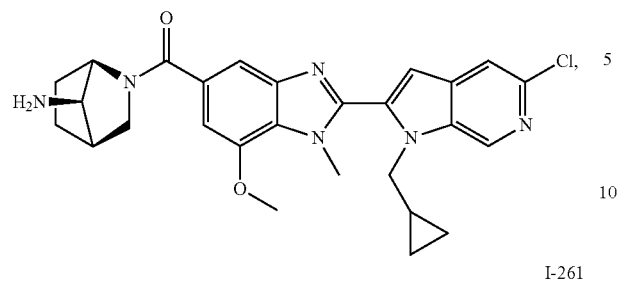
I-266
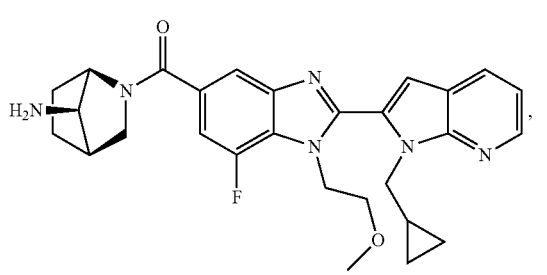
I-261
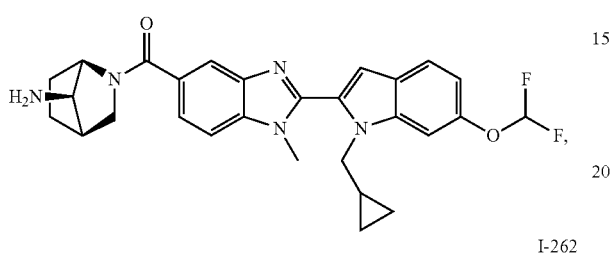
I-267
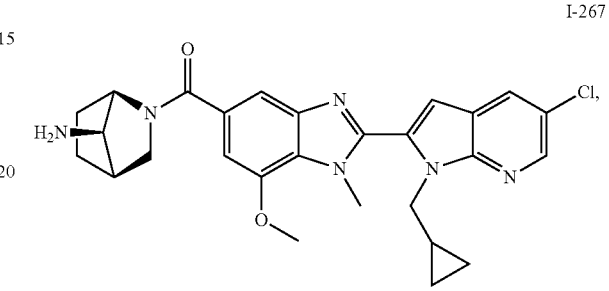
I-262
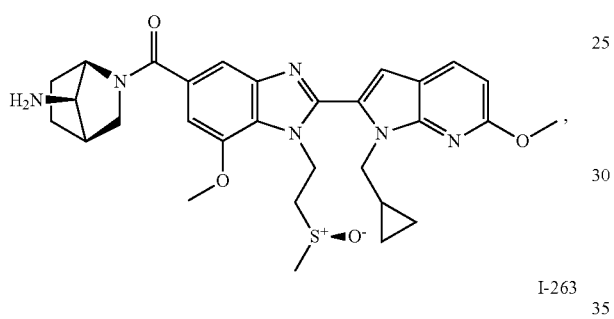
I-268
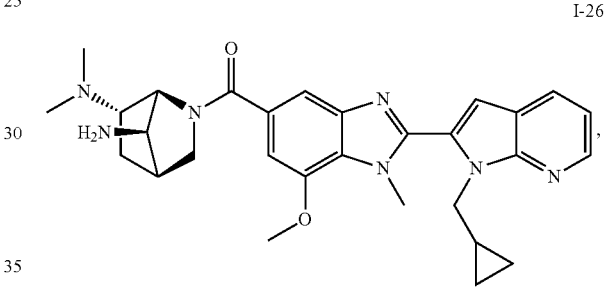
I-263
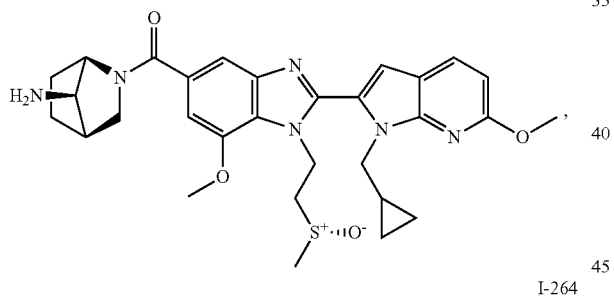
I-269
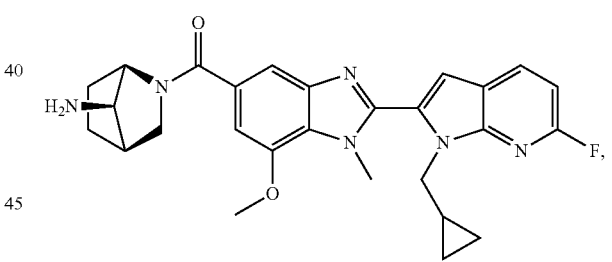
I-264
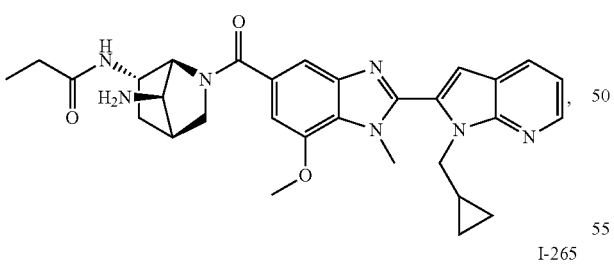
I-270
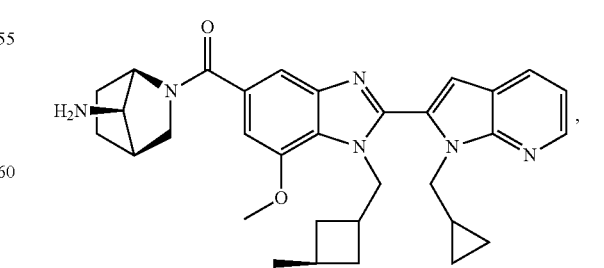
I-265
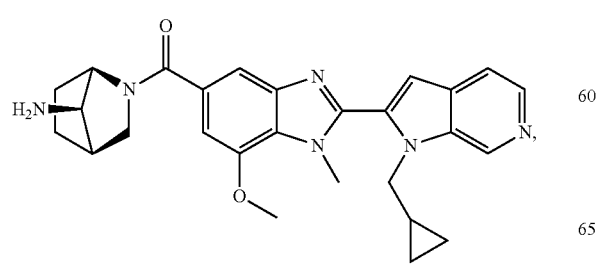

I-271
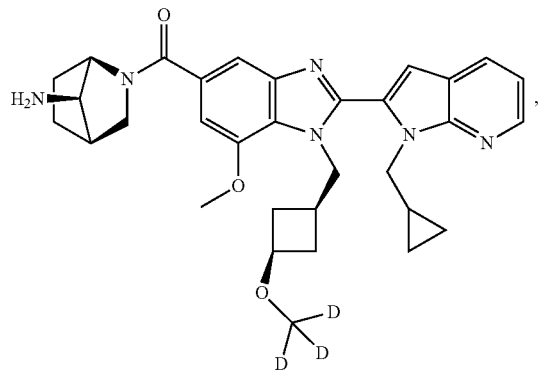
I-272
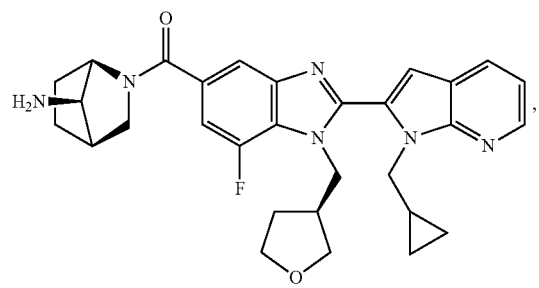
I-273
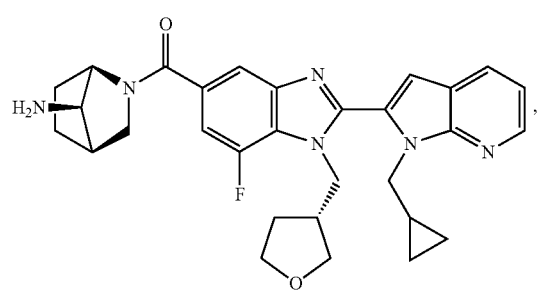
I-274
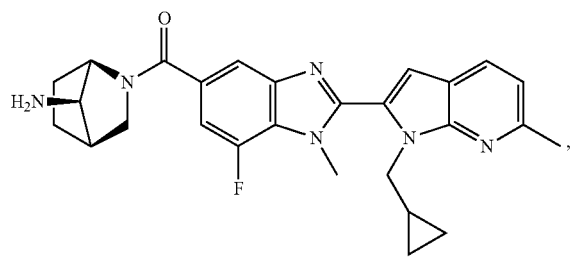
I-275
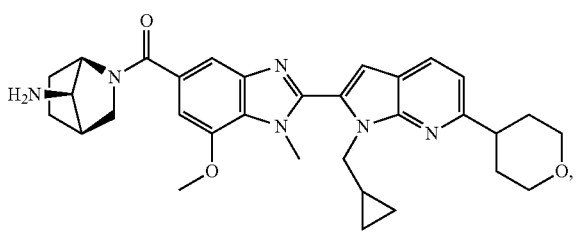
I-276
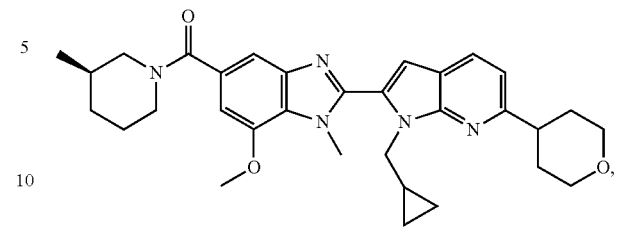
I-277
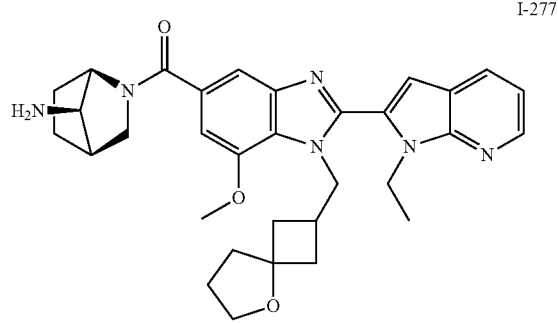
I-278
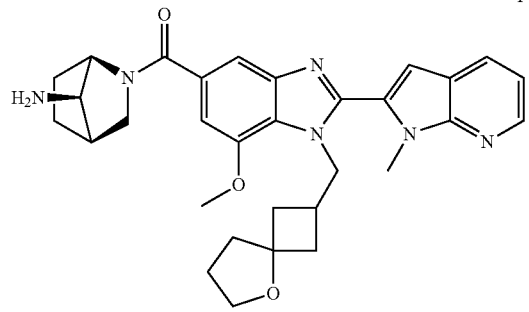
I-279
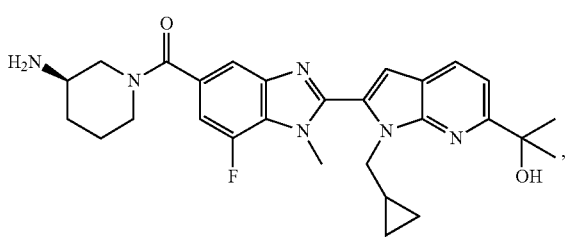
I-280
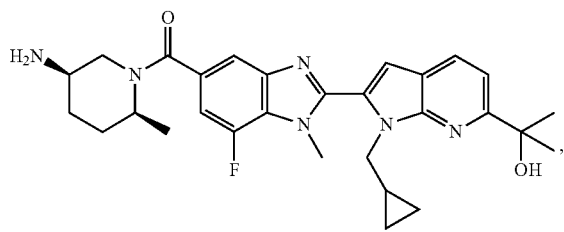

I-281
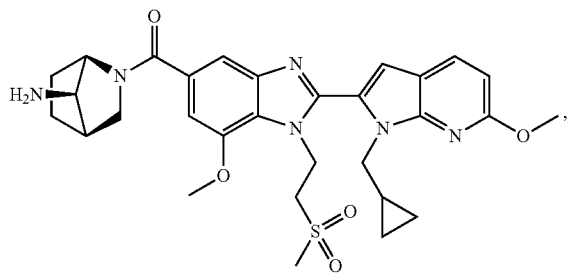
I-282
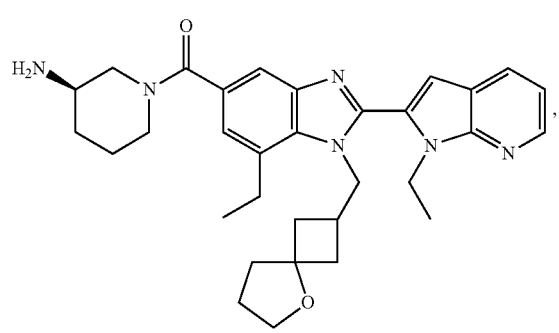
I-283
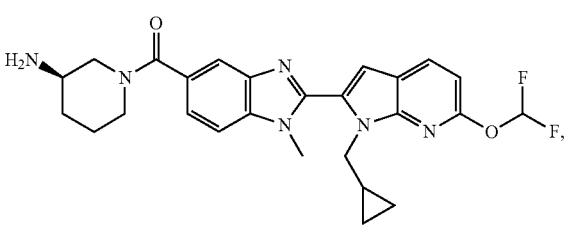
I-284
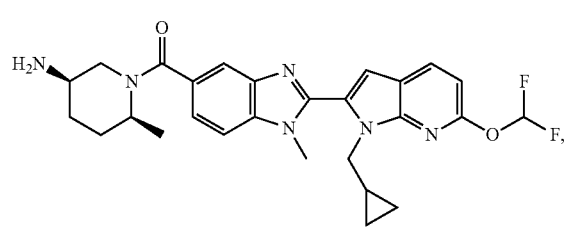
I-285
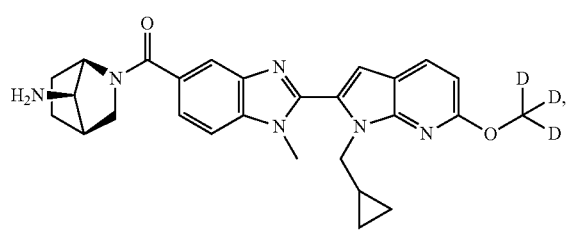
I-286
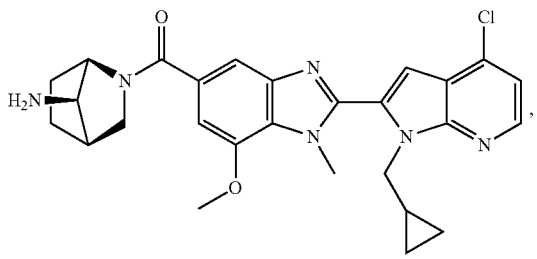
I-287
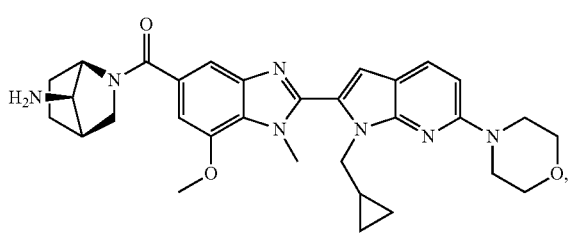
I-288
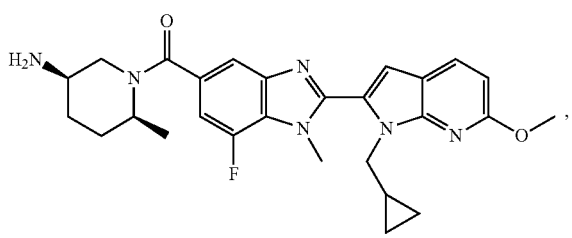
I-289
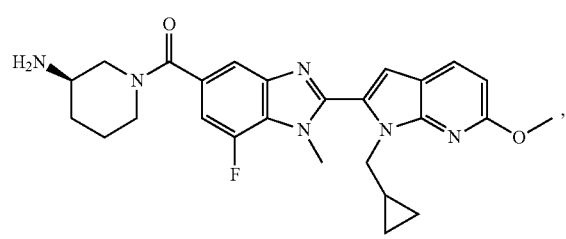
I-290
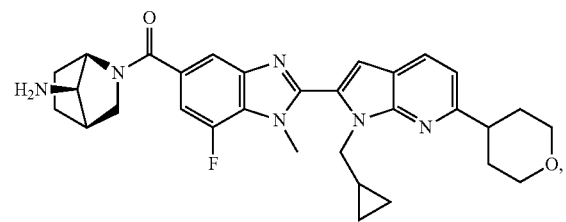
I-291
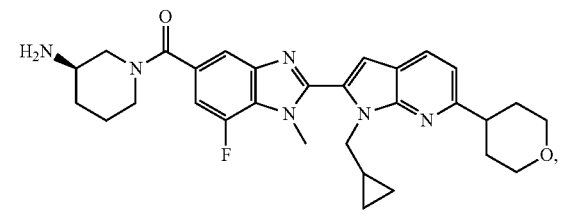

I-292
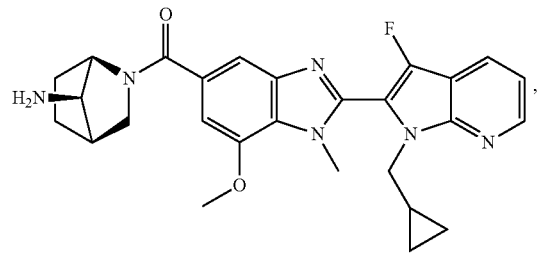
I-293
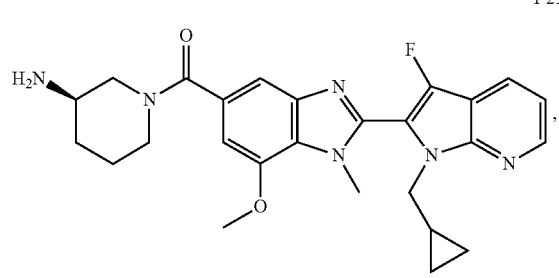
I-294
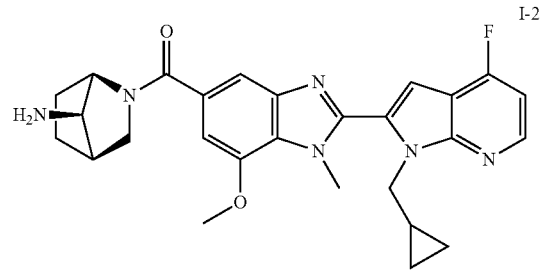
I-295
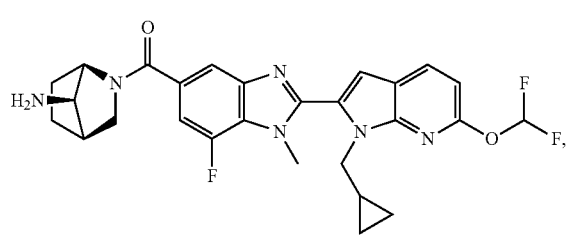
I-296
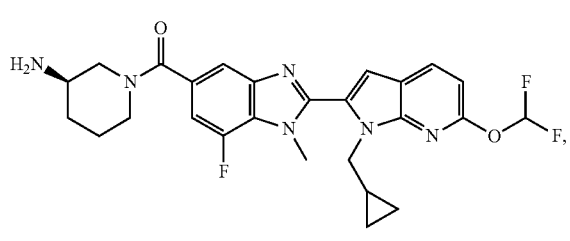
I-297
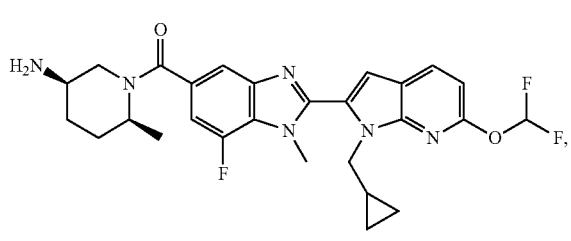
I-298
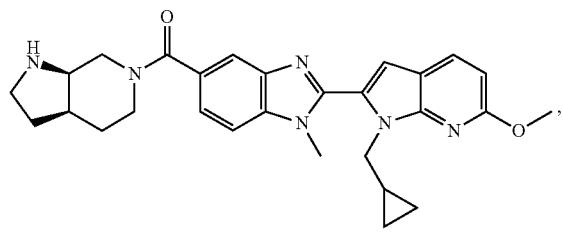
I-299
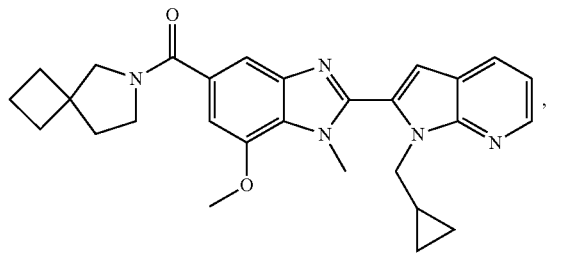
I-300
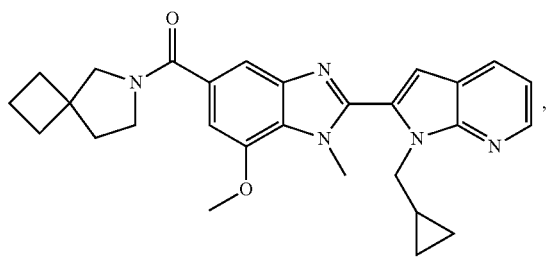
I-301
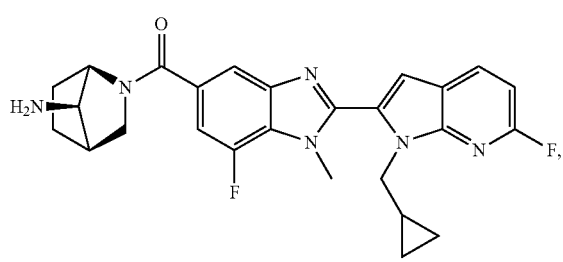
I-302
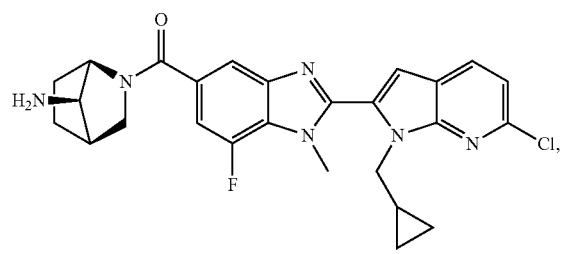
I-303
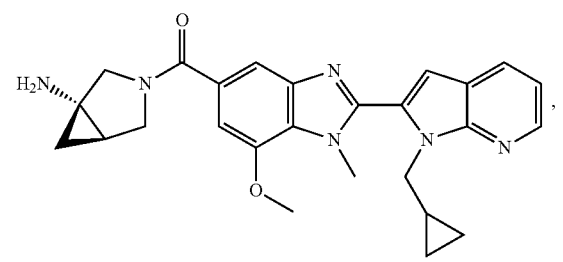

-continued
I-304
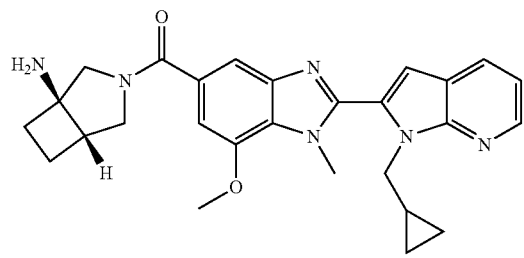
I-305
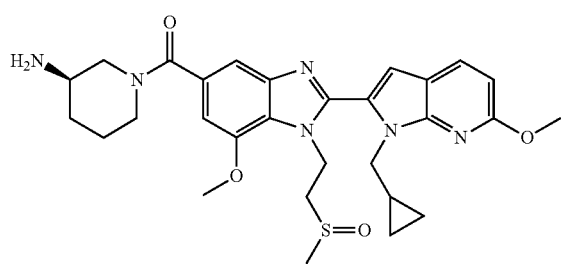
I-306
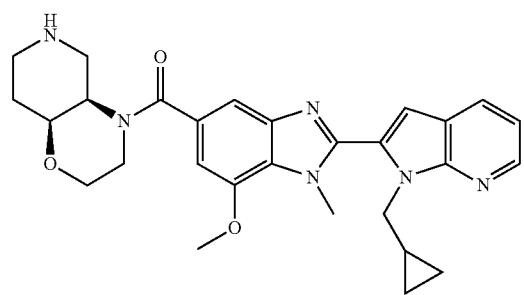
I-307
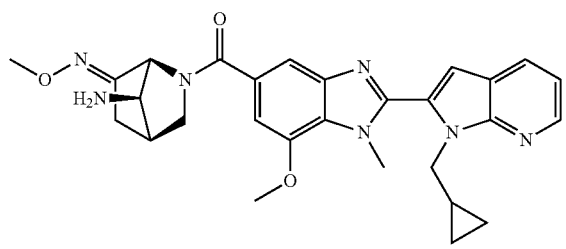
I-308
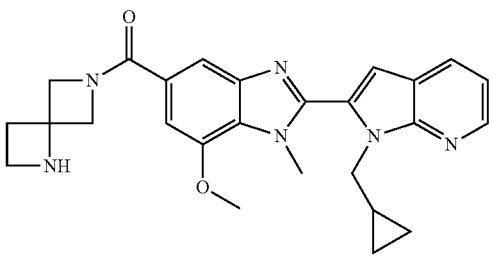
-continued
I-315
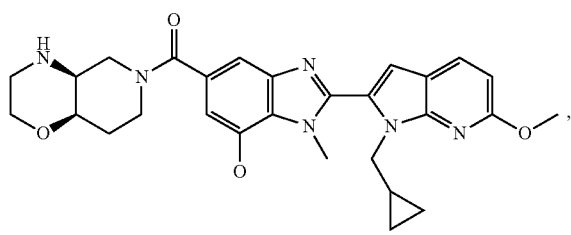
I-309
I-310
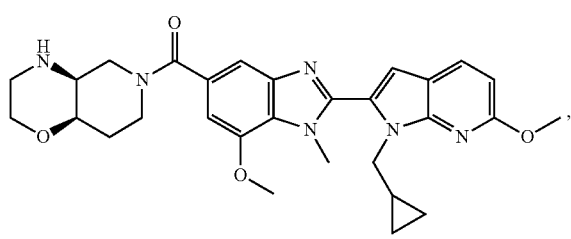
I-311
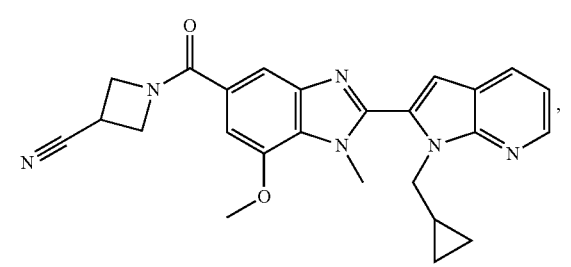
I-312
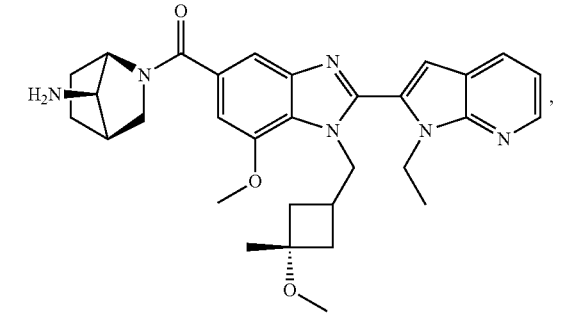
I-313
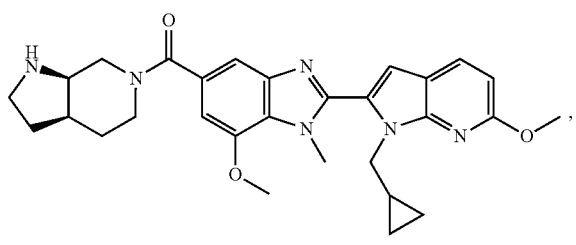

I-314 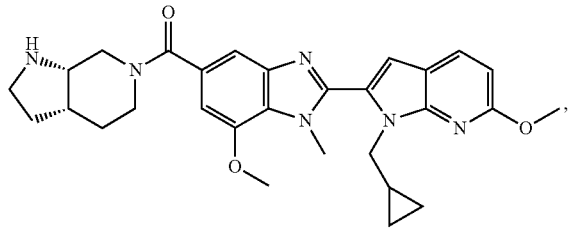
I-315 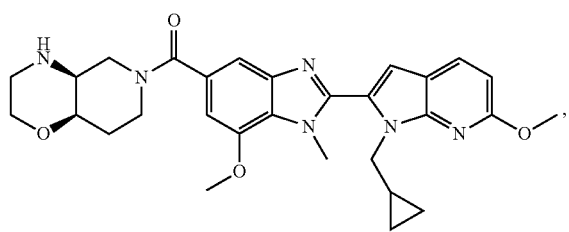
I-316 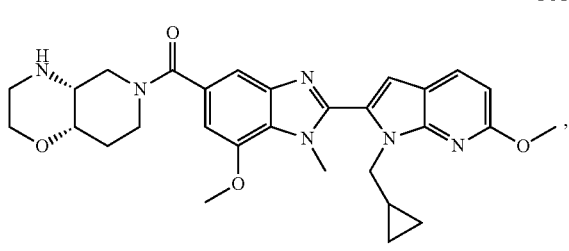
I-317 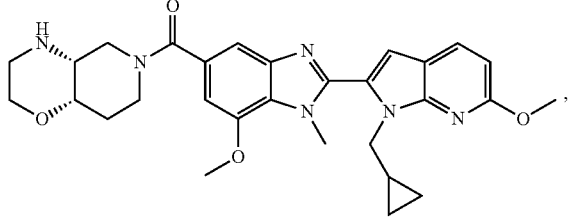
I-318 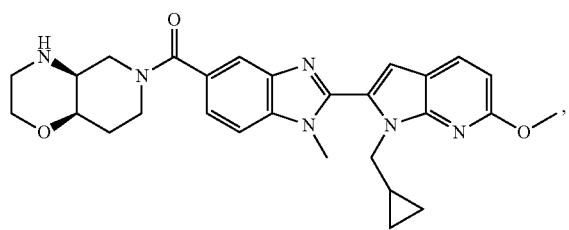
I-319 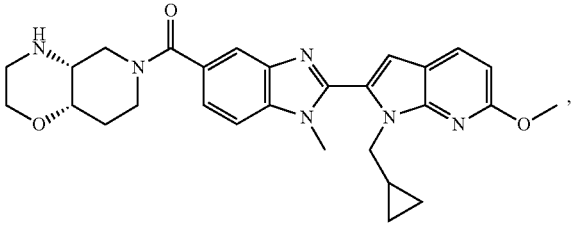
I-320 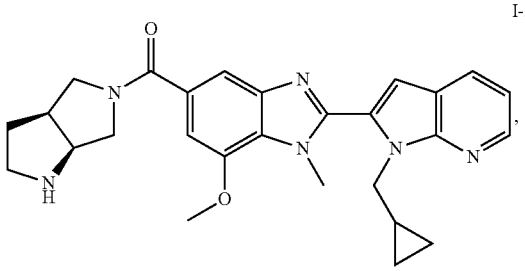
I-321 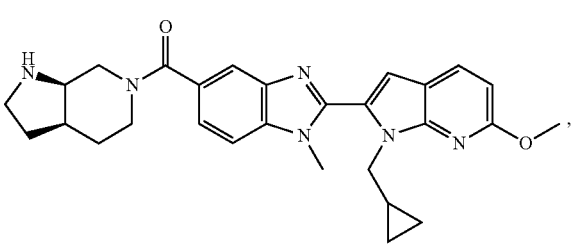
I-322 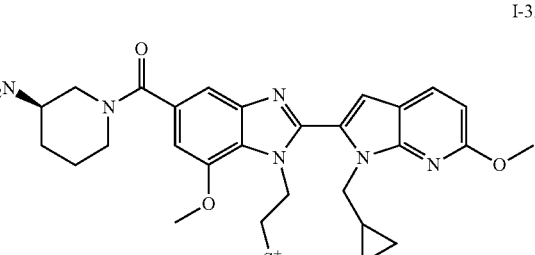
I-323 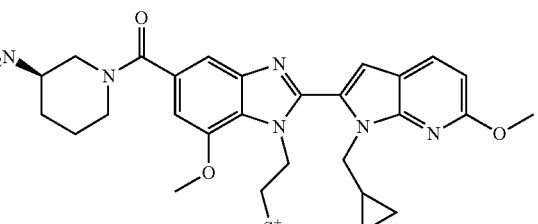
I-324 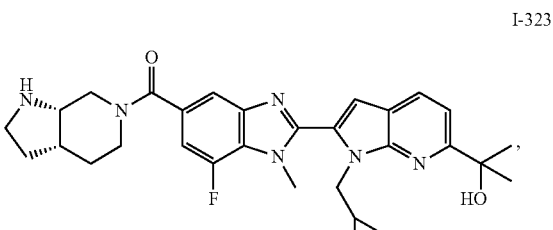
I-325 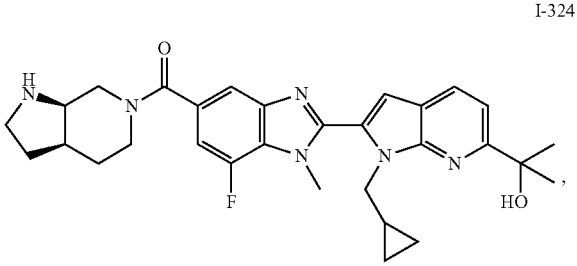

601
-continued
I-326
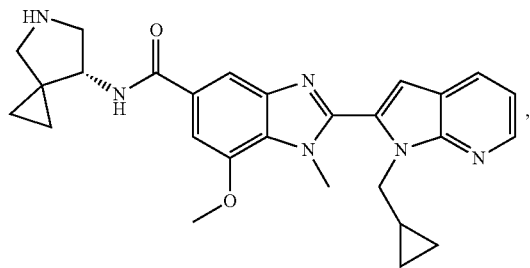
I-327
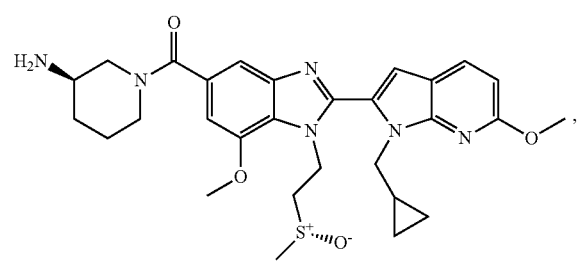
I-328
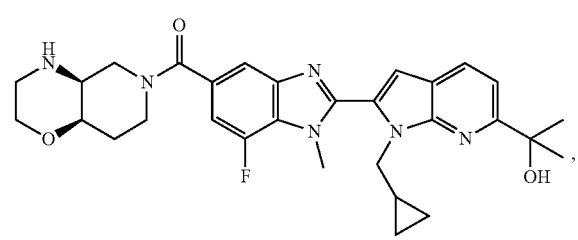
I-329
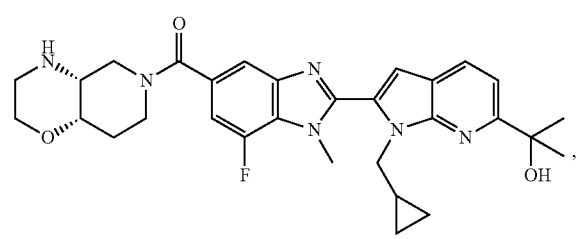
I-330
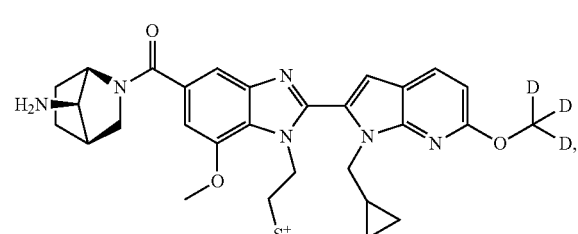
I-331
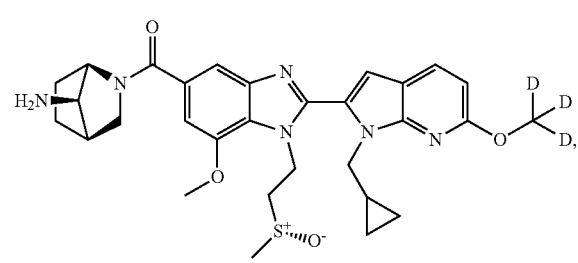
602
-continued
I-332
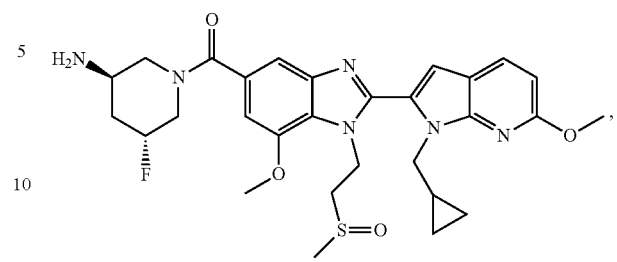
I-333
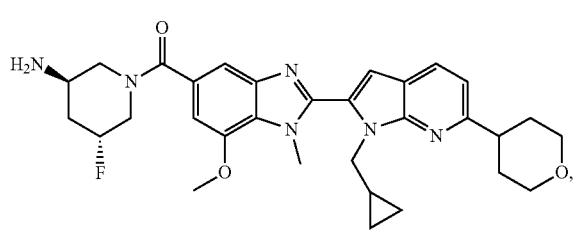
I-334
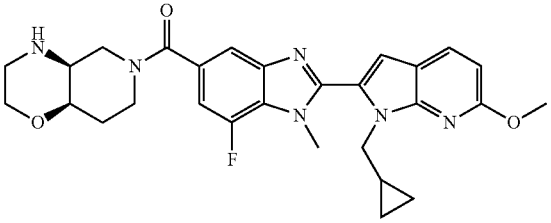
I-335
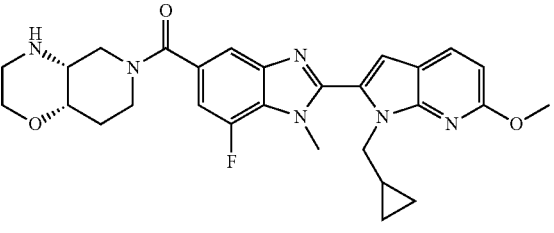
I-336
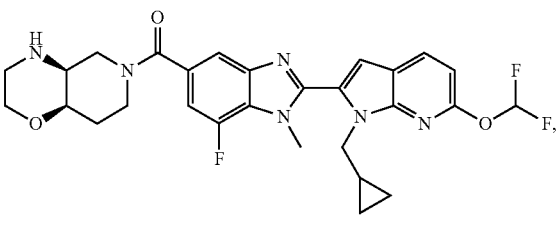
I-337
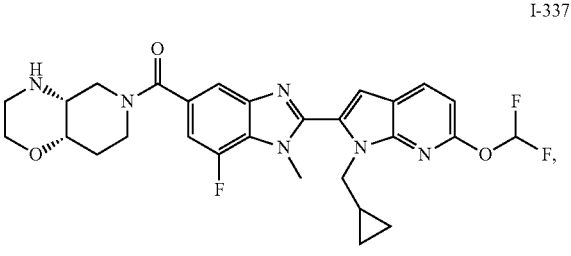

I-338
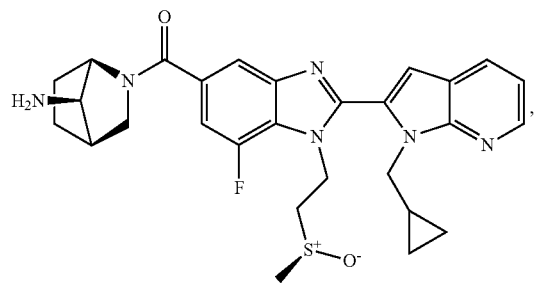
I-339
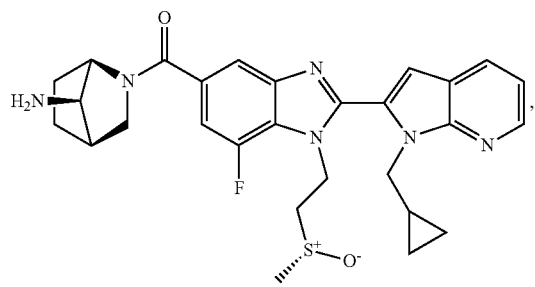
I-340
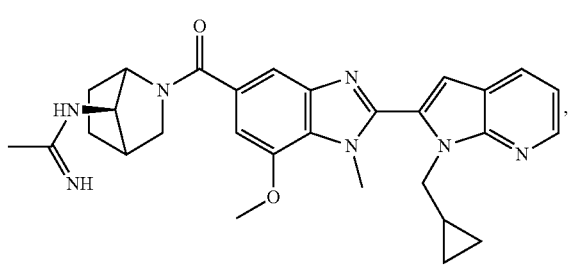
I-341
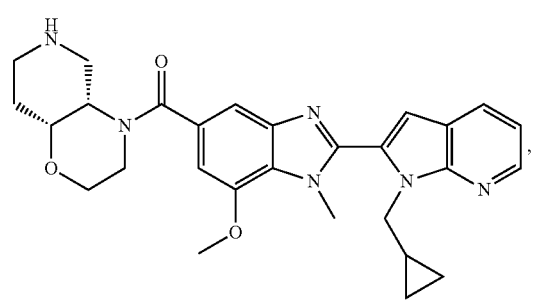
I-342
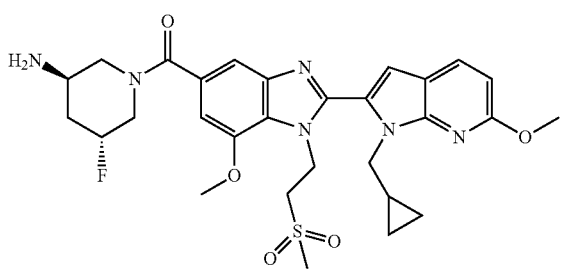
I-343
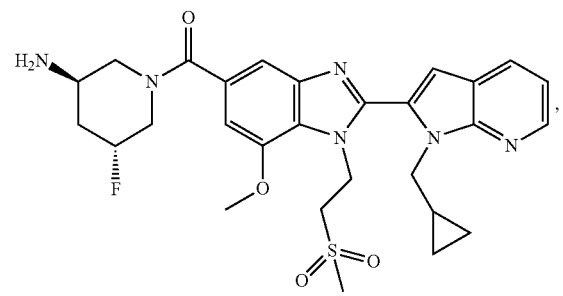
I-344
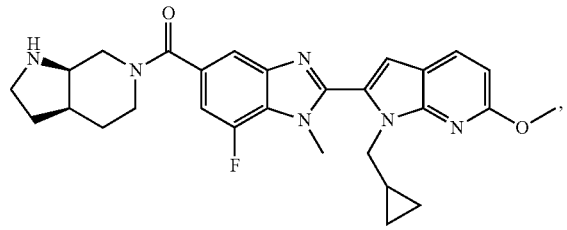
I-345
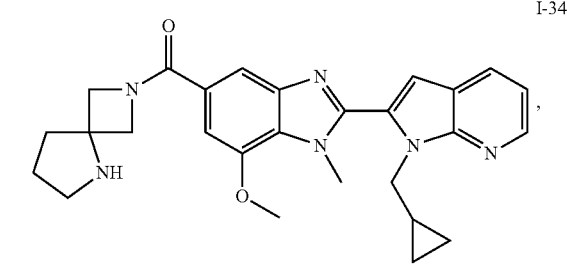
I-346
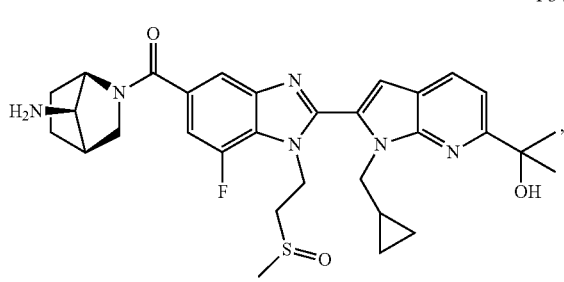
I-347
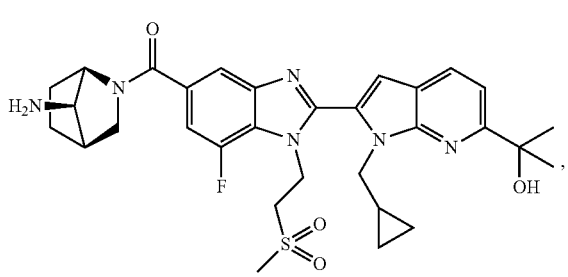

605
-continued
I-348
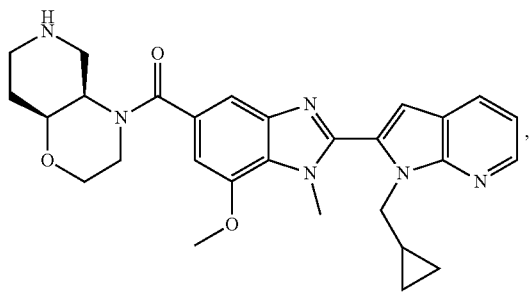
I-349
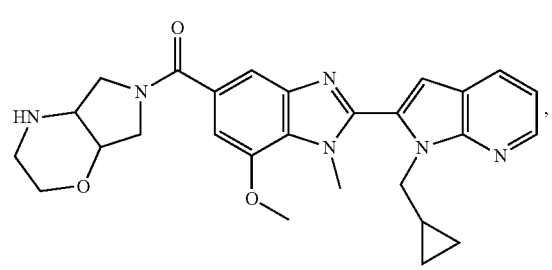
I-350
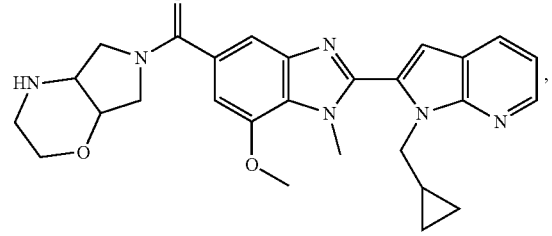
I-351
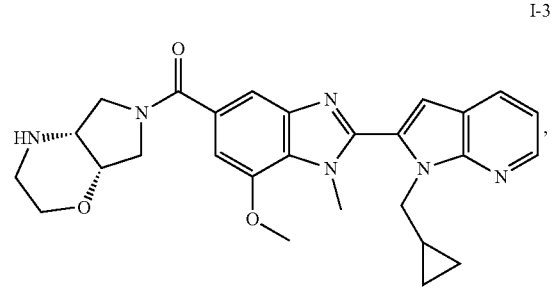
I-352
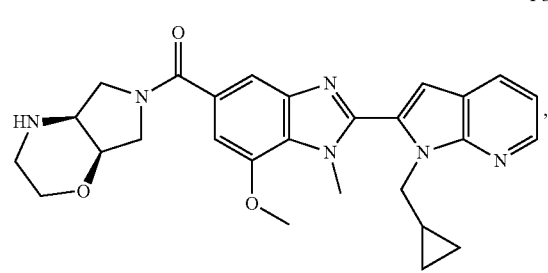
606
-continued
I-353
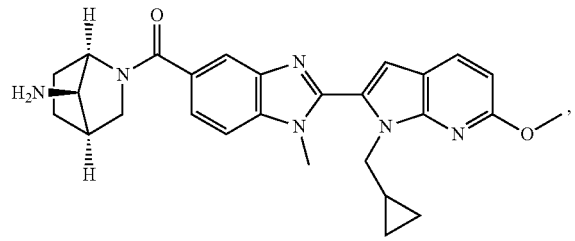
I-354
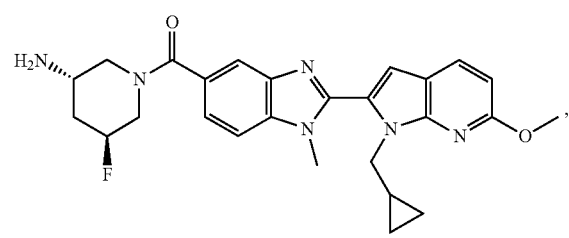
I-355
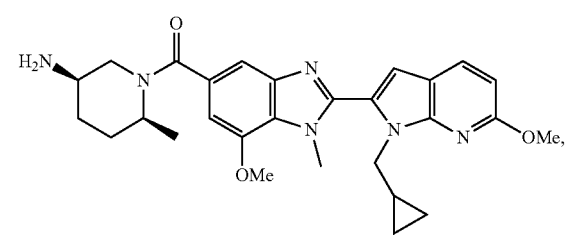
I-356
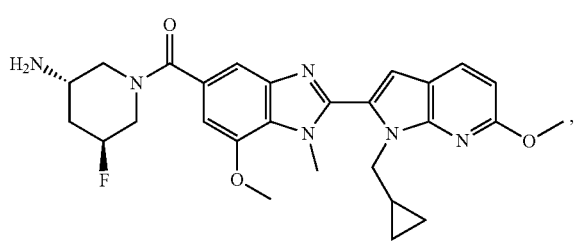
I-357
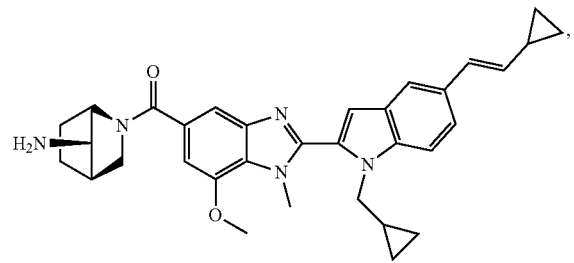
I-358
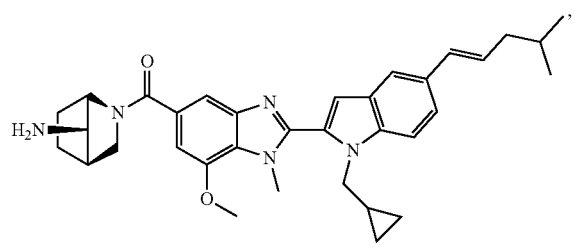

I-359
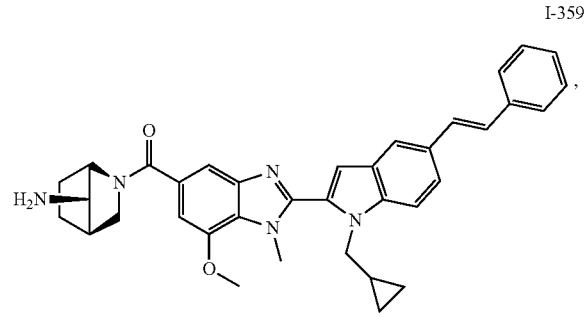
I-365
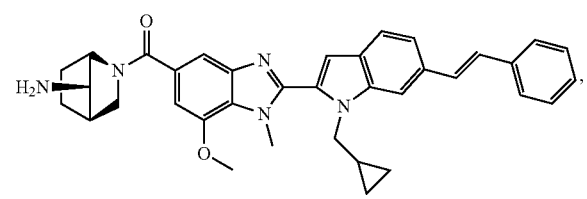
I-360
I-366
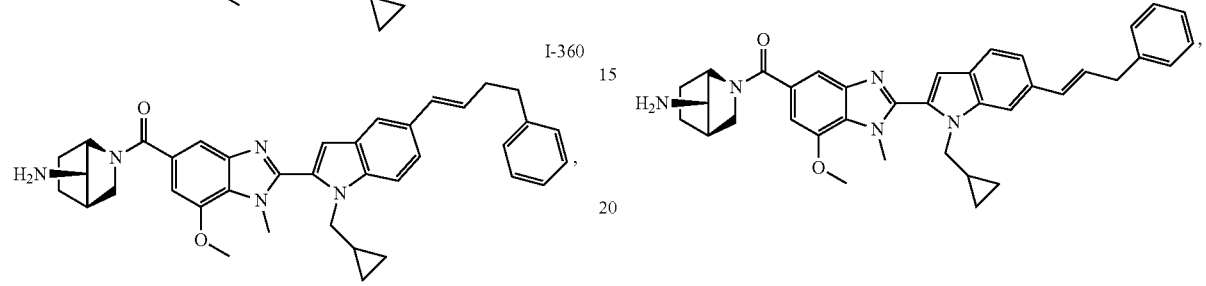
I-361
I-367
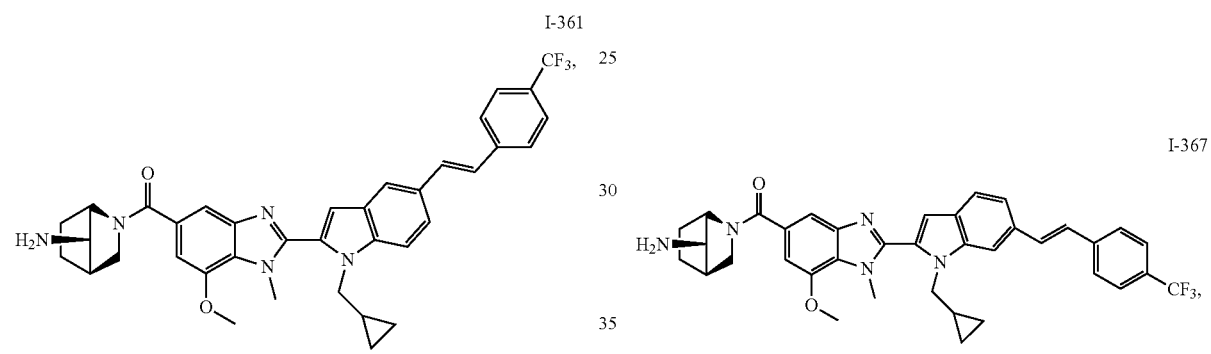
I-362
I-368
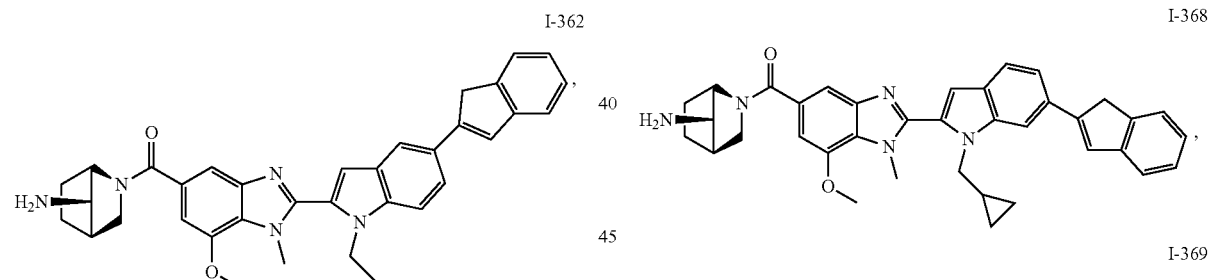
I-363
I-369
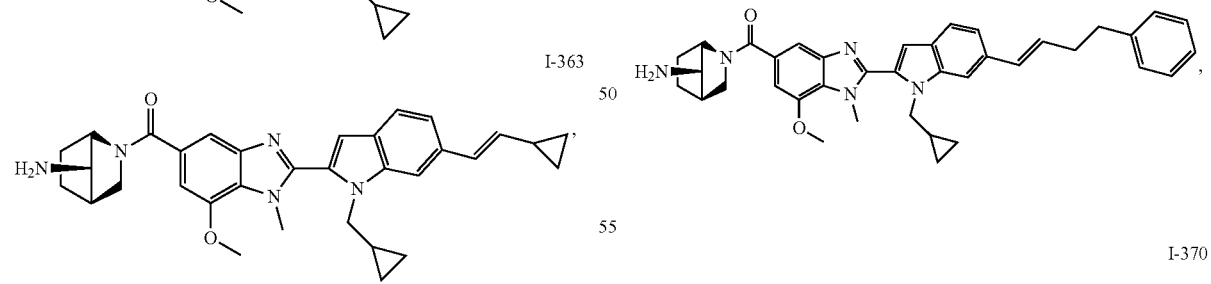
I-364
I-370
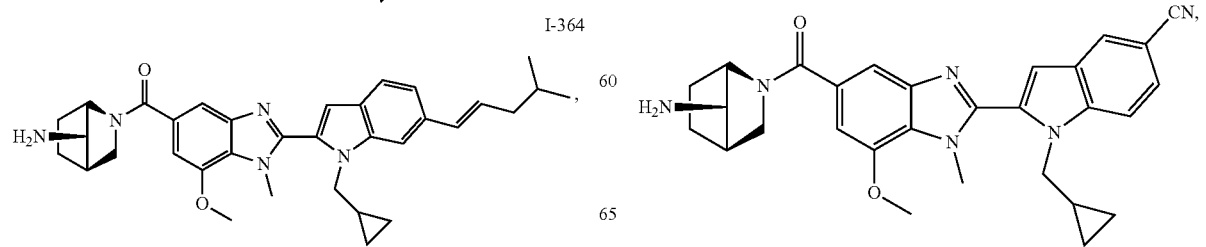

I-371
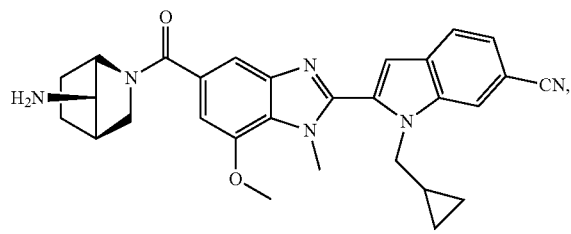
I-372
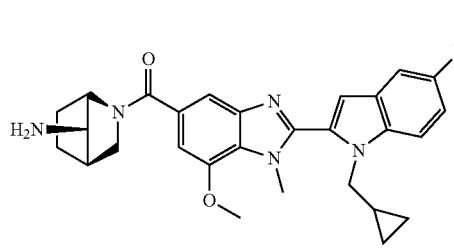
I-373
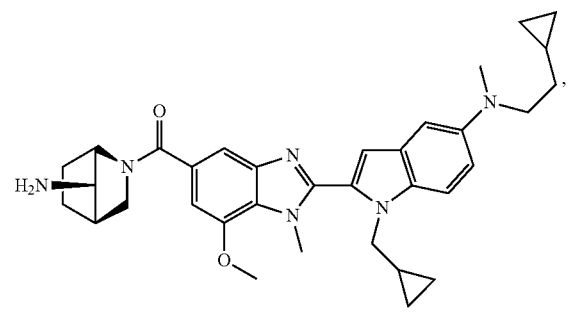
I-374
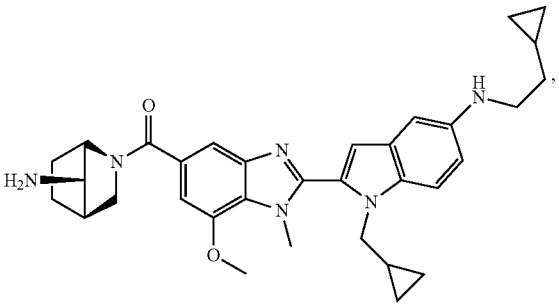
I-375
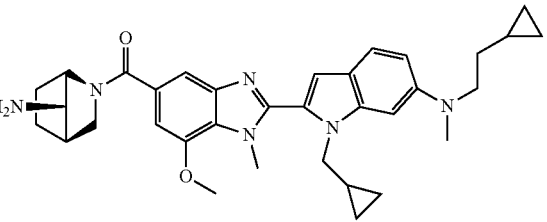
or
I-376
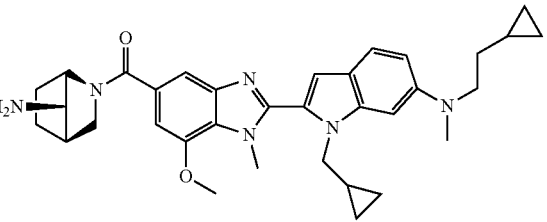
or a pharmaceutically acceptable salt thereof.
* * * * *